United States Patent
Bonjouklian et al.

(10) Patent No.: US 6,743,794 B2
(45) Date of Patent: Jun. 1, 2004

(54) METHODS AND COMPOUNDS FOR INHIBITING MRP1

(75) Inventors: Rosanne Bonjouklian, Zionsville, IN (US); Jeffrey Daniel Cohen, Indianapolis, IN (US); Joseph Michael Gruber, Brownsburg, IN (US); Douglas Webb Johnson, Zionsville, IN (US); Louis Nickolaus Jungheim, Indianapolis, IN (US); Julian Stanley Kroin, Indianapolis, IN (US); Peter Ambrose Lander, Indianapolis, IN (US); Ho-Shen Lin, Indianapolis, IN (US); Mark Christopher Lohman, Boulder, CO (US); Brian Stephen Muehl, Greenwood, IN (US); Bryan Hurst Norman, Indianapolis, IN (US); Vinod Francis Patel, Acton, MA (US); Michael Enrico Richett, Indianapolis, IN (US); Kenneth Jeff Thrasher, Indianapolis, IN (US); Sreenivasarao Vepachedu, Palo Alto, CA (US); Wesley Todd White, Indianapolis, IN (US); Yongping Xie, Naperville, IL (US); Jeremy Schulenburg York, Indianapolis, IN (US); Brandon Lee Parkhurst, Indianapolis, IN (US); Qiupang Wang, Hamden, CT (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/130,800

(22) PCT Filed: Dec. 11, 2000

(86) PCT No.: PCT/US00/32443

§ 371 (c)(1),
(2), (4) Date: May 21, 2002

(87) PCT Pub. No.: WO01/46199

PCT Pub. Date: Jun. 28, 2002

(65) Prior Publication Data

US 2003/0100576 A1 May 29, 2003

Related U.S. Application Data

(60) Provisional application No. 60/171,373, filed on Dec. 22, 1999, provisional application No. 60/226,076, filed on Aug. 17, 2000, and provisional application No. 60/234,539, filed on Sep. 22, 2000.

(51) Int. Cl.$^7$ .............. A61K 31/496; A61K 31/4745; C07D 498/04; A61P 35/00

(52) U.S. Cl. ............. 514/253.03; 514/293; 514/232.8; 514/255.05; 514/228.5; 514/256; 544/126; 544/60; 544/405; 544/333; 544/361; 546/83; 546/82

(58) Field of Search .................. 546/83, 82; 544/126, 544/60, 405, 333, 361; 514/293, 232.8, 255.05, 253.03, 228.5, 256

(56) References Cited

FOREIGN PATENT DOCUMENTS

| WO | WO97/34897 A | 9/1997 |
|---|---|---|
| WO | WO99/51227 A | 10/1999 |
| WO | WO99/51228 A | 10/1999 |
| WO | WO99/51236 A | 10/1999 |

OTHER PUBLICATIONS

Germann UA et al. Anti–Cancer Drugs. 1997, 8:141–155.*
Lawrence DS et al. J. Med. Chem. 2001, 44: 594–601.*
Marbeuf–Gueye C et al. Molecular Pharmacology. 1998, 53:141–147.*

* cited by examiner

*Primary Examiner*—Evelyn Mei Huang
(74) *Attorney, Agent, or Firm*—Tina M. Tucker; Elizabeth McGraw

(57) ABSTRACT

The present invention further relates to a method of inhibiting MRP1 in a mammal which comprises administering to a mammal in need thereof an effective amount of a compound of formula (I).

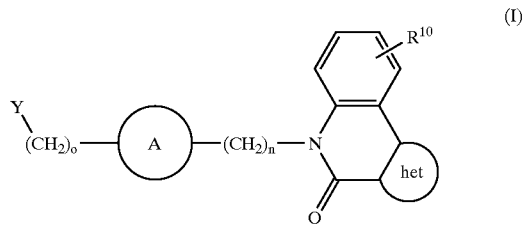

39 Claims, No Drawings

METHODS AND COMPOUNDS FOR INHIBITING MRP1

This application is the U.S. National Stage filing of PCT/US00/32443, filed Dec. 11, 2000, which claims the benefit of U.S. Provisional Applications Serial Nos. 60/171,373, filed on Dec. 22, 1999; No. 60/226,076, filed on Aug. 17, 2000; and No. 60/234,539, filed on Sep. 22, 2000.

BACKGROUND

Along with surgery and radiotherapy, chemotherapy continues to be an effective therapy for many cancers. In fact, several types of cancer, such as Hodgkin's disease, large cell lymphoma, acute lymphocytic leukemia, testicular cancer and early stage breast cancer, are now considered to be curable by chemotherapy. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", Cancer Research, 54:5902–5910, 1994. Doxorubicin, daunorubicin, epirubicin, vincristine, paclitaxel, mitoxantrone, melphalan, and etoposide are substrates of MRP1, i.e., MRP1 can bind to these oncolytics and redistribute them away from their site of action, the nucleus, and out of the cell. Id. and Marquardt, D., and Center, M. S., Cancer Research, 52:3157, 1992.

Doxorubicin, daunorubicin, and epirubicin are members of the anthracycline class of oncolytics. They are isolates of various strains of Streptomyces and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to coadminister an agent that is a selective inhibitor of that protein. It is, therefore, desirable to provide compounds that are selective inhibitors of MDR1 or MRP1.

SUMMARY OF THE INVENTION

The present invention relates to a compound of formula:

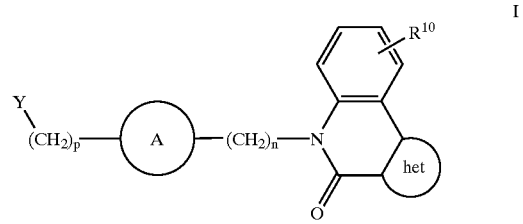

where:
A is a $C_3$–$C_8$ cycloalkyl, optionally substituted 1–3 times with a $C_1$–$C_4$ alkyl;

het is a five (5) membered heterocyclic ring comprising N and a second heteroatom selected from N, O, or S;

wherein the non-fused carbon atom of the heteroaryl ring may be optionally substituted with $R^b$: $C_1$–$C_6$ alkyl, optionally substituted aryl, optionally substituted heterocycle, an amino acid ester, $CH_2OH$, $CH_2O$-heterocycle, halo, $CH_2N_3$, $CH_2SR^1$, $CH_2NR^4R^6$, $OR^1$, $SR^{13}$, $S(CH_2)_k$-phenyl, or $NR^4R^6$; provided that when het is pyrazole or imidazole, the saturated nitrogen of the het ring may be optionally substituted with $R^a$: $C_1$–$C_4$ alkyl;

k is 0, 1, 2, 3, or 4;

n is 0, 1, or 2;

p is 0 or 1;

q is 0, 1, or 2;

r is 0, 1, or 2;

t is 0, 1, 2, 3, or 4;

u is 0, 1, 2, 3, or 4;

Y is —E—C(O)$R^3$, —E—CH=CH$R^{13}$, —E—C(OH)$R^{13}$, —E—N$R^4R^5$, —E—O$R^2$, —E—S(O)$_qR^{13}$, —E—SO$_2$N$R^4R^6$, —C($R^{11}$)=N$R^6$, or an optionally substituted heterocycle;

E is a bond or —C($R^{11}$)($R^{11}$)—;

$R^1$ is independently at each occurrence hydrogen or $C_1$–$C_6$ alkyl;

$R^2$ is independently at each occurrence hydrogen, $C_1$–$C_6$ alkyl, optionally substituted $C_3$–$C_8$ cycloalkyl, optionally substituted ($C_1$–$C_4$ alkyl)-aryl, optionally substituted aryl, or optionally substituted heterocycle, C(O)-aryl, or $(CH_2)_2NR^4R^5$;

$R^3$ is independently at each occurrence hydrogen, $C_1$–$C_6$ alkyl, optionally substituted $C_3$–$C_8$ cycloalkyl, optionally substituted ($C_1$–$C_4$ alkyl)-aryl, optionally substituted aryl, optionally substituted heterocycle, $OR^{13}$, or $NR^4R^6$;

$R^4$ is independently at each occurrence hydrogen, $C_1$–$C_6$ alkyl, optionally substituted ($C_1$–$C_6$ alkyl)-aryl, optionally substituted aryl, or $R^4$ and $R^5$, $R^6$, $R^{6'}$ combine to form =$CR^1R^{14}$;

$R^5$ is independently at each occurrence hydrogen, $C_1$–$C_6$ alkyl, $C_1$–$C_4$ alkoxy, optionally substituted heterocycle, optionally substituted $C_3$–$C_8$ cycloalkyl, optionally substituted $C_6$–$C_{10}$ bicycloalkyl; optionally substituted ($C_1$–$C_4$ alkyl)-aryl, optionally substituted aryl, optionally substituted ($C_1$–$C_4$ alkyl)-heterocycle, $C(O)C(O)R^{13}$, $C(O)R^7$, $CH_2R^7$, $SO_2R^8$, a moiety of the formula

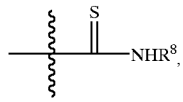

or $R^4$ and $R^5$, together with the nitrogen to which they are attached, combine to form an optionally substituted N-heterocycle;

$R^6$ is independently at each occurrence hydrogen, $C_1$–$C_6$ alkyl, $C_1$–$C_4$ alkoxy, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted ($C_1$–$C_4$ alkyl)-heterocycle, optionally substituted heterocycle, or $R^4$ and $R^6$, together with the nitrogen to which they are attached, combine to form an optionally substituted N-heterocycle;

$R^{6'}$ is independently at each occurrence hydrogen, $C_1$–$C_6$ alkyl, $C_1$–$C_4$ alkoxy, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted ($C_1$–$C_4$ alkyl)-heterocycle, optionally substituted heterocycle, ($C_1$–$C_4$ alkyl)-$OR^{13}$:
wherein the ($C_1$–$C_4$ alkyl) of the ($C_1$–$C_4$ alkyl)-$OR^{13}$ may be optionally substituted from 1 to 2 times with $C_1$–$C_4$ alkyl, optionally substituted aryl, optionally substituted heterocycle;

or $R^4$ and $R^{6'}$, together with the nitrogen to which they are attached, combine to form an optionally substituted N-heterocycle;

$R^7$ is independently at each occurrence optionally substituted $C_1$–$C_6$ alkyl, $C_1$–$C_6$ alkoxy, ($C_1$–$C_4$ alkoxy)-aryl, ($C_1$–$C_4$ alkoxy)-heterocycle, ($C_1$–$C_4$ alkoxy)-SiCH$_3$, optionally substituted ($C_3$–$C_8$ cycloalkyl), optionally substituted ($C_1$–$C_4$ alkyl)-($C_3$–$C_8$ cycloalkyl), optionally substituted ($C_1$–$C_4$ alkyl)-aryl, optionally substituted aryl, diphenylmethyl, optionally substituted ($C_1$–$C_4$ alkyl)-CO-aryl, optionally substituted CO-aryl, optionally substituted ($C_1$–$C_4$ alkyl)-heterocycle, optionally substituted CH=CH-heterocycle, optionally substituted phenoxy, optionally substituted heterocycle, optionally substituted ($C_1$–$C_4$ alkyl)-phenoxy, $(CH_2)_tS(O)_rR^1$, $(CH_2)_tC(R^{12})(R^9)N(R^{16})(R^{15})$, $(CH_2)_tC(R^{12})(R^9)O(R^{17})$, $(CH_2)_tC(R^{12})(R^9)S(R^{17})$, or $NR^4R^{6'}$;

$R^8$ is independently at each occurrence optionally substituted $C_1$–$C_6$ alkyl, optionally substituted aryl, optionally substituted ($C_1$–$C_4$ alkyl)-aryl, optionally substituted ($C_1$–$C_4$ alkyl)-heterocycle, or optionally substituted heterocycle;

$R^9$ is independently at each occurrence hydrogen, optionally substituted $C_1$–$C_6$ alkyl, optionally substituted $C_3$–$C_8$ cycloalkyl, optionally substituted ($C_1$–$C_4$ alkyl)-aryl, optionally substituted aryl, optionally substituted heterocycle, $(CH_2)_u$-($C_1$–$C_6$ alkoxy), optionally substituted $(CH_2)_u$—O—(C3–C8 cycloalkyl), optionally substituted $(CH_2)_u$-($C_1$–$C_4$ alkoxy)-aryl, optionally substituted $(CH_2)_u$—O-aryl, optionally substituted $(CH_2)_u$—O-heterocycle, ($C_1$–$C_4$ alkyl)-$CO_2$-($C_1$–$C_6$ alkyl), optionally substituted ($C_1$–$C_4$ alkyl)-$CO_2$-($C_3$–$C_8$ cycloalkyl), optionally substituted ($C_1$–$C_4$ alkyl)-$CO_2$-($C_1$–$C_4$ alkyl)-aryl, optionally substituted ($C_1$–$C_4$ alkyl)-$CO_2$-aryl, optionally substituted ($C_1$–$C_4$ alkyl)-$CO_2$-heterocycle, or $R^9$ and $R^{12}$ can combine to form a $C_3$–$C_8$ cycloalkyl;

$R^{10}$ is 0 to 4 substituents from the aryl ring independently at each occurrence hydrogen, halo, $C(O)R^3$, cyano, optionally substituted heterocycle, optionally substituted aryl, C≡C—$R^1$, $C_1$–$C_4$ alkoxy, ($C_1$–$C_4$ alkyl)-phenyl, $NR^{19}R^{20}$, or $C_2$–$C_6$ alkenyl;

$R^{11}$ is independently at each occurrence hydrogen, $C_1$–$C_6$ alkyl, optionally substituted heterocycle, optionally substituted ($C_1$–$C_4$ alkyl)-heterocycle, optionally substituted aryl, or optionally substituted ($C_1$–$C_4$ alkyl)-aryl;

$R^{12}$ is independently at each occurrence hydrogen, optionally substituted $C_1$–$C_6$ alkyl, optionally substituted C3–C8 cycloalkyl, optionally substituted ($C_1$–$C_4$ alkyl)-aryl, optionally substituted aryl, optionally substituted ($C_1$–$C_4$ alkyl)-heterocycle or optionally substituted heterocycle;

$R^{13}$ is independently at each occurrence hydrogen, optionally substituted $C_1$–$C_6$ alkyl, optionally substituted $C_3$–$C_8$ cycloalkyl, optionally substituted ($C_1$–$C_4$ alkyl)-aryl, optionally substituted aryl, $CO_2CH_2CO_2CH_2CH_3$, or optionally substituted heterocycle;

$R^{14}$ is independently at each occurrence $C_1$–$C_6$ alkyl or optionally substituted ($C_1$–$C_4$ alkyl)-aryl;

$R^{15}$ is independently at each occurrence hydrogen, $C_1$–$C_6$ alkyl, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted ($C_1$–$C_4$ alkyl)-heterocycle, optionally substituted heterocycle, $C(O)OR^{13}$, $SO_2R^8$, $C(O)R^{18}$, or a moiety of the formula

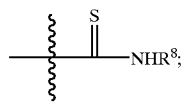

$R^{16}$ is independently at each occurrence hydrogen, optionally substituted $C_1$–$C_6$ alkyl, optionally substituted aryl, optionally substituted heterocycle, $SO_2R^8$, or —$COR^8$; or $R^{16}$ and $R^{15}$, together with the nitrogen to which they are attached, combine to form an optionally substituted N-heterocycle;

$R^{17}$ is independently at each occurrence hydrogen, optionally substituted $C_1$–$C_6$ alkyl, optionally substituted $C_3$–$C_8$ cycloalkyl, optionally substituted ($C_1$–$C_4$ alkyl)-aryl, optionally substituted aryl, $COR^{18}$, optionally substituted heterocycle, optionally substituted ($C_1$–$C_4$ alkyl)-heterocycle, optionally substituted $C_1$–$C_6$ alkoxy, optionally substituted ($C_1$–$C_4$ alkoxy)- aryl, optionally substituted ($C_1$–$C_4$ alkoxy)-heterocycle, ($C_1$–$C_4$ alkyl)-N($R^1$)($R^1$), or an amino acid ester;

$R^{18}$ is independently at each occurrence hydrogen, optionally substituted $C_1$–$C_6$ alkyl, optionally substituted $C_3$–$C_8$ cycloalkyl, optionally substituted ($C_1$–$C_4$ alkyl)-aryl, optionally substituted aryl, optionally substituted heterocycle, ($C_1$–$C_4$ alkyl)-NHCO$_2$-($C_1$–$C_4$ alkyl), or optionally substituted ($C_1$–$C_4$ alkyl)-heterocycle;

$R^{19}$ is independently at each occurrence hydrogen, or optionally substituted $C_1$–$C_6$ alkyl;

$R^{20}$ is independently at each occurrence hydrogen, optionally substituted $C_1$–$C_6$ alkyl, CH$_2$OH, CO—($C_1$–$C_4$ alkyl); or a pharmaceutical salt thereof.

The present invention further relates to a method of inhibiting MRP1 in a mammal which comprises administering to a mammal in need thereof an effective amount of a compound of formula I.

In another embodiment, the present invention relates to a method of inhibiting a resistant neoplasm, or a neoplasm susceptible to resistance in a mammal which comprises administering to a mammal in need thereof an effective amount of a compound of formula I in combination with an effective amount of an oncolytic agent.

The present invention also relates to a pharmaceutical formulation comprising a compound of formula I in combination with one or more oncolytics, pharmaceutical carriers, diluents, or excipients therefor.

DETAILED DESCRIPTION OF THE INVENTION

The current invention concerns the discovery that compounds of formula I are selective inhibitors of multidrug resistant protein (MRP1), and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell. Additionally, these terms refer to (repeat to redistribute) an MRP1 substrate away from the substrate's site of action.

As used herein, the term "effective amount of a compound of formula I" refers to an amount of a compound of the present invention which is capable of inhibiting MRP1. The term "effective amount of an oncolytic agent" refers to an amount of oncolytic agent capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm, which is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm, which is "susceptible to resistance", is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytic agents where at least one oncolytic agent is a substrate of MRP1. A "substrate of MRP1" is an oncolytic that binds to MRP1 and is redistributed away from the oncolytic's site of action (the nucleus of the neoplasm) and out of the cell, thus, rendering the therapy less effective. Preferred oncolytic agents are camptosar, vinorelbine, mitoxantrone, doxorubicin, daunorubicin, epirubicin, vincristine, and etopsoside.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight, branched, or cyclic saturated hydrocarbon containing from 1 to 6 carbon atoms. Additionally, the term "$C_1$–$C_6$ alkyl" includes $C_1$–$C_4$ alkyl groups and $C_3$–$C_6$ cycloalkyls. The term "$C_1$–$C_6$ alkyl" includes, but is not limited to, cyclopentyl, pentyl, hexyl, cyclohexyl, and the like.

The term "$C_3$–$C_8$ cycloalkyl" refers to cyclopropyl, cyclobutyl, cyclopentyl, cyclohexyl, cycloheptyl, and cyclooctyl. The term "$C_5$–$C_7$ cycloalkyl" refers to cyclopentyl, cyclohexyl, and cycloheptyl.

The term "$C_6$–$C_{10}$ bicycloalkyl" refers to bicyclo-[2.1.1]hexanyl, [2.2.1]heptanyl, [3.2.1]octanyl, [2.2.2]octanyl, [3.2.2]nonanyl, [3.3.1]nonanyl, [3.3.2]decanyl, and [4.3.1]decanyl ring systems; and benzofused ring systems including 1,2,3,4-tetrahydronaphthalene, indane, 1,2-dihydrocyclobuta[1,2-a]benzene, and hydrocyclopropa[1,2-a]benzene.

The terms "optionally substituted $C_1$–$C_4$ alkyl" and "optionally substituted $C_1$–$C_6$ alkyl" refers to a $C_1$–$C_4$ alkyl or $C_1$–$C_6$ alkyl, respectively, unsubstituted or substituted from 1 to 3 times with halo, $C_1$–$C_4$ alkanol, NH$_2$, or hydroxy.

The terms "$C_1$–$C_4$ alkoxy" and "$C_1$–$C_6$ alkoxy" refer to moieties of the formula O—($C_1$–$C_4$ alkyl) and O—($C_1$–$C_6$ alkyl) respectively.

The term "optionally substituted $C_3$–$C_8$ cycloalkyl" refers to a $C_3$–$C_8$ cycloalkyl unsubstituted or substituted once with a phenyl, substituted phenyl, hydroxy, or CO$_2$R$^1$ group.

The terms "optionally substituted ($C_1$–$C_4$ alkyl)-($C_3$–$C_8$ cycloalkyl)" refers to optionally substituted $C_3$–$C_8$ cycloalkyl linked through an optionally substituted $C_1$–$C_4$ alkyl.

The term "optionally substituted O—($C_3$–$C_8$ cycloalkyl)" refers to an optionally substituted $C_3$–$C_8$ cycloalkyl linked through an oxygen atom.

The term "optionally substituted $C_6$–$C_{10}$ bicycloalkyl" refers to a $C_6$–$C_{10}$ bicycloalkyl unsubstituted or substituted once with a phenyl, substituted phenyl, or CO$_2$R$^1$ group.

The term "halo" or "halide" refers to fluoro, chloro, bromo, and iodo.

The term "aryl" refers to phenyl, and naphthyl.

The term "optionally substituted aryl" refers to a phenyl and naphthyl group, respectively, unsubstituted or substituted from 1 to 5 times independently with $C_1$–$C_6$ alkyl, $C_1$–$C_4$ alkoxy, halo, hydroxy, trifluoromethyl, phenyl, phenoxy, $SO_2R^1$, $OR^{11}$; $NR^4R^5$, $SO_2N(R^{13})_2$, NH-Pg, $C_1$–$C_6$ alkoxy, benzyloxy, $C(O)R^{13}$, $C_5$–$C_7$ cycloalkyl, trifluoromethoxy, $SR^1$, cyano, or nitro.

The term "optionally substituted ($C_1$–$C_4$ alkyl)-aryl" refers to optionally substituted aryl linked through an optionally substituted $C_1$–$C_4$ alkyl.

The term "optionally substituted O-aryl" refers to an optionally substituted aryl linked through an oxygen atom.

The term "optionally substituted phenoxy" refers to a phenoxy group unsubstituted or substituted from 1 to 3 times independently with $C_1$–$C_6$ alkyl, halo, hydroxy, trifluoromethyl, $NR^4R^6$, $SO_2N(R^{13})_2$, NH-Pg, $C_1$–$C_6$ alkoxy, benzyloxy, $C(O)R^{13}$, $C_5$–$C_7$ cycloalkyl, trifluoromethoxy, cyano, or nitro.

The term "optionally substituted ($C_1$–$C_4$ alkyl)-phenoxy" refers to unsubstituted or substituted phenoxy linked through an optionally substituted $C_1$–$C_4$ alkyl.

The term "heterocycle" is taken to mean stable unsaturated and saturated 3 to 6 membered rings containing from 1 to 4 heteroatoms selected from the group consisting of nitrogen, oxygen and sulfur, said rings being optionally benzofused. All of these rings may be substituted with up to three substituents independently selected from the group consisting of halo, $C_1$–$C_4$ alkoxy, $C_1$–$C_4$ alkyl, cyano, nitro, hydroxy, —S(O)m-($C_1$–$C_4$ alkyl) and —S(O)$_m$-phenyl where m is 0, 1 or 2. Saturated rings include, for example, pyrrolidinyl, azetidine, piperidinyl, piperazinyl, tetrahydrofuryl, oxazolidinyl, morpholino, dioxanyl, pyranyl, and the like. Benzofused saturated rings include indolinyl, 1,2,3,4-tetrahydroquinolinyl, 1,2,3,4-tetrahydroisoquinolinyl and the like. Unsaturated rings include furyl, thienyl, pyridinyl, pyrrolyl, N-methylpyrrolyl, oxazolyl, isoxazolyl, pyrazolyl, imidazolyl, triazolyl, oxadiazolyl, thiadiazolyl, thiazolyl, pyrimidinyl, pyrazinyl, thiophenyl, pyridazinyl, and the like. Benzofused unsaturated rings include isoquinolinyl, benzoxazolyl, benzthiazolyl; quinolinyl, benzofuranyl, thionaphthyl, furanopyridine, cinnolinyl, thiophenopyridine, indolyl and the like.

The term "heteroaryl" is taken to mean an unsaturated or benzofused unsaturated heterocycle as defined in the previous paragraph.

The term "optionally substituted heterocycle" refers to a heterocyclic ring unsubstituted or substituted 1 or 3 times independently with a $C_1$–$C_6$ alkyl, halo, benzyl, optionally substituted phenyl, $SR^1$, $C_1$–$C_4$ alkoxy, $CO_2R^1$, nitro, cyano, ($C_1$–$C_4$ alkyl)-cyano, heterocycle, $NR^{19}R^{20}$, $COR^{12}$, $C_1$–$C_6$ alkanol, benzyloxy, phenoxy, trifluoromethyl. Heterocyclic rings may be additionally substituted 1 or 2 times with an oxo group.

The term "optionally substituted O-heterocycle" refers to an optionally substituted heterocycle linked through an oxygen atom.

The term "optionally substituted ($C_1$–$C_4$ alkyl)-heterocycle" refers to optionally substituted heterocycle linked through an optionally substituted $C_1$–$C_4$ alkyl.

The term "N-heterocycle" refers to a nitrogen containing heterocycle linked through a nitrogen atom.

The term "optionally substituted N-heterocycle" refers to a N-heterocycle, optionally substituted 1 or 3 times independently with a $C_1$–$C_6$ alkyl, halo, benzyl, optionally substituted phenyl, $SR^1$, $C_1$–$C_4$ alkoxy, $CO_2R^1$, nitro, cyano, ($C_1$–$C_4$ alkyl)-cyano, heterocycle, $NR^{19}R^{20}$, $COR^{12}$, $C_1$–$C_6$ alkanol, benzyloxy, phenoxy, trifluoromethyl; and additionally substituted 1 or 2 times with an oxo group.

The term "amino acid ester" as used in this specification refers to an amino acid, where the carboxy group is substituted with a $C_1$–$C_6$ alkyl or benzyl group. That is, the alkyl group when taken together with the carboxy group forms a $C_1$–$C_6$ alkyl ester. A skilled artisan would appreciate that some amino acids have two carboxy groups that may be substituted with a $C_1$–$C_6$ alkyl group, for example, aspartic acid and glutamic acid. This invention contemplates the possibility of amino acid mono- or diesters in these circumstances.

The term "amino acid" refers to a chemical unit made up of both a basic amino group and an acidic carboxyl group. Examples of amino acids include alanine, asparagine, cysteine, glutamine, glycine, isoleucine, leucine, methionine, phenylalanine, proline, serine, threonine, tryptophan, tyrosine, valine, aspartic acid, glutaric acid, arginine, histidine, and lysine.

The term "protecting group" (Pg) refers to an amino protecting group or a hydroxy protecting group. The species of protecting group will be evident from whether the "Pg" group is attached to a nitrogen atom (amino protecting group) or attached to an oxygen atom (hydroxy protecting group).

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reaction (s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, "Protective Groups in Organic Synthesis", John Wiley and Sons, New York, N.Y., 1991, Chapter 7 hereafter referred to as "*Greene*". A preferred amino protecting group is t-butyloxycarbonyl.

The term "hydroxy protecting group" denotes a group understood by one skilled in the organic chemical arts of the type described in Chapter 2 of *Greene*. Representative hydroxy protecting groups include, for example, ether groups including methyl and substituted methyl ether groups such as methyl ether, methoxymethyl ether, methylthiomethyl ether, tert-buylthiomethyl ether, (phenyldimethylsilyl) methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)-ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorobenzyl ether; and alkylsilyl ether groups such as trimethyl-triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono-, di-, and trichloroacetate esters, phenoxyacetate ester, and p-chlorophenoxyacetate and the like. The species of hydroxy protecting group employed is not critical so long as the derivatized hydroxy group is stable to the conditions of subsequent reaction(s) on other positions of the intermediate molecule and can be selectively removed at the appropriate point without disrupting the remainder of the molecule including any other hydroxy protecting group(s).

The term "carbonyl activating group" refers to a substituent of a carbonyl that increases the susceptibility of that carbonyl to nucleophilic addition. Such groups include, but are not limited to, alkoxy, aryloxy, nitrogen containing unsaturated heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenylsulfonate, and the like; and halides especially chloride, bromide, or iodide.

The term "carbonyl activating reagent" refers to a reagent that converts the carbonyl of a carboxylic acid group to one that is more prone to nucleophilic addition and includes, but is not limited to, such reagents as those found in "The Peptides", Gross and Meienhofer, Eds., Academic Press (1979), Ch. 2 and M. Bodanszky, "Principles of Peptide Synthesis", $2^{nd}$ Ed., Springer-Verlag Berlin Heidelberg, 1993, hereafter referred to as "*The Peptides*" and "*Peptide Synthesis*" respectively. Specifically, carbonyl activating reagents include thionyl bromide, thionyl chloride, oxalyl chloride, and the like; alcohols such as nitrophenol, pentachlorophenol, and the like; amines such as N-hydroxy-N-methoxyamine and the like; acid halides such as acetic, formic, methanesulfonic, ethanesulfonic, benzenesulfonic, or p-tolylsulfonic acid halide, and the like; and compounds such as 1,1'-carbonyldiimidazole, benzotriazole, imidazole, N-hydroxysuccinimide, dicyclohexylcarbodiimide, and the like.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D.C., "Pharmaceutical Salts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

The term "acid addition salt" refers to a salt of a compound of formula I prepared by reaction of a compound of formula I with a mineral or organic acid. For exemplification of pharmaceutical acid addition salts see, e.g., Berge, S. M, Bighley, L. D., and Monkhouse, D.C., *J. Pharm. Sci.*, 66:1, 1977. Since compounds of this invention can be basic in nature, they accordingly react with any of a number of inorganic and organic acids to form pharmaceutical acid addition salts.

The pharmaceutical acid addition salts of the invention are typically formed by reacting the compound of formula I with an equimolar or excess amount of acid. The reactants are generally combined in a mutual solvent such as diethylether, tetrahydrofuran, methanol, ethanol, isopropanol, benzene, and the like. The salts normally precipitate out of solution within about one hour to about ten days and can be isolated by filtration or other conventional methods.

Acids commonly employed to form acid addition salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycolate, tartrate, methanesulfonate, propanesulfonate, 1,5-naphthalene-disulfonate, naphthalene-1-sulfonate, naphthalene-2-sulfonate, mandelate and the like.

The term "base addition salt" refers to a salt of a compound of formula I prepared by reaction of a compound of formula I with a mineral or organic base. For exemplification of pharmaceutical base addition salts see, e.g., Berge, S. M, Bighley, L. D., and Monkhouse, D.C., *J. Pharm. Sci.*, 66:1, 1977. This invention also contemplates pharmaceutical base addition salts of compounds of formula I. The skilled artisan would appreciate that some compounds of formula I may be acidic in nature and accordingly react with any of a number of inorganic and organic bases to form pharmaceutical base addition salts. Examples of pharmaceutical base addition salts are the ammonium, lithium, potassium, sodium, calcium, magnesium, methylamino, diethylamino, ethylene diamino, cyclohexylamino, and ethanolamino salts, and the like of a compound of formula I.

While all of the compounds of the present invention are useful, certain of the compounds are particularly interesting and are preferred. The following listing sets out several groups of preferred compounds. It will be understood that each of the listings may be combined with other listings to create additional groups of preferred embodiments.

i. A is $C_5$–$C_6$ cycloalkyl;
ii. A is cyclopentyl;
iii. A is cyclohexyl;
iv. $R^b$ is $C_1$–$C_6$ alkyl;
v. $R^b$ is methyl;
vi. $R^b$ is halo;
vii. n is 0:
viii. n is 1;
ix. p is 0;
x. p is 1;
xi. Y is —E—C(O)$R^3$, —E—NR$^4$R$^5$, or an optionally substituted heterocycle;
xii. Y is —E—C(O)$R^3$;
xiii. Y is —E—NR$^4$R$^5$;

xiv. Y is an optionally substituted heterocycle;
xv. E is a bond;
xvi. When Y is —E—C(O)R$^3$, R$^3$ is OR$^{13}$, or NR$^4$R$^6$;
xvii. When Y is —E—C(O)R$^3$, R$^3$ is OR$^{13}$, R$^{13}$ is optionally substituted C$_1$–C$_6$ alkyl;
xviii. When Y is —E—C(O)R$^3$, R$^3$ is OR$^{13}$, R$^{13}$ is methyl;
xix. When Y is —E—C(O)R$^3$, R$^3$ is OR$^{13}$, R$^{13}$ is optionally substituted (C$_1$–C$_4$ alkyl)-aryl;
xx. When Y is —E—C(O)R$^3$, R$^3$ is OR$^{13}$ and R$^{13}$ is benzyl;
xxi. When Y is —E—C(O)R$^3$, R$^3$ is OR$^{13}$ and R$^{13}$ is optionally substituted aryl;
xxii. When Y is —E—C(O)R$^3$, R$^3$ is OR$^{13}$ and R$^{13}$ is phenyl;
xxiii. When Y is —E—C(O)R$^3$, R$^3$ is NR$^4$R$^6$ and R4 is hydrogen;
xxiv. When Y is —E—C(O)R$^3$, R$^3$ is NR$^4$R$^6$, R4 is hydrogen, and R$^6$ is C$_1$–C$_6$ alkyl, optionally substituted C$_3$–C$_8$ cycloalkyl, optionally substituted C$_6$–C$_{10}$ bicycloalkyl, optionally substituted (C$_1$–C$_4$ alkyl)-aryl, optionally substituted aryl, optionally substituted (C$_1$–C$_4$ alkyl)-heterocycle, or optionally substituted heterocycle;
xxv. When Y is —E—C(O)R$^3$, R$^3$ is NR$^4$R$^6$, R$^4$ and R$^6$, together with the nitrogen to which they are attached, combine to form an optionally substituted N-heterocycle;
xxvi. When Y is —E—NR$^4$R$^5$, R$^4$ is hydrogen;
xxvii. When Y is —E—NR$^4$R$^5$, R$^4$ is hydrogen, and R$^5$ is C(O)R$^7$;
xxviii. When Y is —E—NR$^4$R$^5$, R$^4$ is hydrogen, and R$^5$ is C(O)R$^7$, R$^7$ is C$_1$–C$_6$ alkoxy, optionally substituted (C$_3$–C$_8$ cycloalkyl), optionally substituted (C$_1$–C$_4$ alkyl)-(C$_3$–C$_8$ cycloalkyl), optionally substituted (C$_1$–C$_4$ alkyl)-aryl, optionally substituted aryl, diphenylmethyl, optionally substituted (C$_1$–C$_4$ alkyl)-CO-aryl, optionally substituted CO-aryl, optionally substituted (C$_1$–C$_4$ alkyl)-heterocycle, optionally substituted heterocycle, (CH$_2$)$_t$C(R$^{12}$)(R$^9$)N(R$^{16}$)(R$^{15}$), or (CH$_2$)$_t$C(R$^{12}$)(R$^9$)O(R$^{17}$);
xxix. When Y is —E—NR$^4$R$^5$, R$^4$ is hydrogen, R$^5$ is C(O)R$^7$, and R$^7$ is (CH$_2$)$_t$C(R$^{12}$)(R$^9$)N(R$^{16}$)(R$^{15}$);
xxx. When Y is —E—NR$^4$R$^5$, R$^4$ is hydrogen, R$^5$ is C(O)R$^7$, R$^7$ is (CH$_2$)$_t$C(R$^{12}$)(R$^9$)N(R$^{16}$)(R$^{15}$), R$^{12}$ is hydrogen, and R$^9$ is phenyl;
xxxi. When Y is —E—NR$^4$R$^5$, R$^4$ is hydrogen, R$^5$ is C(O)R$^7$, R$^7$ is (CH$_2$)$_t$C(R$^{12}$)(R$^9$)N(R$^{16}$)(R$^{15}$), R$^{12}$ is hydrogen, R$^9$ is phenyl, and R16 is hydrogen, then R$^{15}$ is hydrogen, C$_1$–C$_6$ alkyl, optionally substituted C$_3$–C$_8$ cycloalkyl, optionally substituted C$_6$–C$_{10}$ bicycloalkyl, optionally substituted (C$_1$–C$_4$ alkyl)-aryl, optionally substituted aryl, optionally substituted (C$_1$–C$_4$ alkyl)-heterocycle, optionally substituted heterocycle, C(O)OR$^{13}$, SO$_2$R$^8$, or C(O)R$^{18}$;
xxxii. When Y is —E—NR$^4$R$^5$, R$^4$ is hydrogen, R$^5$ is C(O)R$^7$, R$^7$ is (CH$_2$)$_t$C(R$^{12}$)(R$^9$)N(R$^{16}$)(R$^{15}$), R$^{12}$ is hydrogen, R$^9$ is phenyl, and R16 is hydrogen, then R15 is optionally substituted phenyl;
xxxiii. When Y is —E—NR$^4$R$^5$, R$^4$ is hydrogen, R$^5$ is C(O)R$^7$, R$^7$ is (CH$_2$)$_t$C(R$^{12}$)(R$^9$)N(R$^{16}$)(R$^{15}$), R$^{12}$ is hydrogen, R$^9$ is phenyl, and R16 is hydrogen, then R15 is optionally substituted heterocycle
xxxiv. When Y is —E—NR$^4$R$^5$, R$^4$ is hydrogen, R$^5$ is C(O)R$^7$, R$^7$ is (CH$_2$)$_t$C(R$^{12}$)(R$^9$)N(R$^{16}$)(R$^{15}$), R$^{12}$ is hydrogen, and R$^9$ is phenyl, then R$^{16}$ and R$^{15}$, together with the nitrogen to which they are attached, combine to form an optionally substituted N-heterocycle; .
xxxv. When Y is —E—NR$^4$R$^5$, R$^4$ and R$^5$, together with the nitrogen to which they are attached, combine to form an optionally substituted N-heterocycle;
xxxvi. R$^4$ is hydrogen
xxxvii. R$^4$ is C$_1$–C$_6$ alkyl;
xxxviii. R$^5$ is hydrogen;
xxxix. R$^5$ is optionally substituted heterocycle;
xl. R$^5$ is optionally substituted C$_6$–C$_{10}$ bicycloalkyl;
xli. R$^5$ is optionally substituted (C$_1$–C$_4$ alkyl)-aryl;
xlii. R$^5$ is SO$_2$R$^8$;
xliii. R$^5$ is a moiety of the formula $$\begin{array}{c}\xi \\ \xi \\ \xi\end{array}\!\!\!\overset{\displaystyle S}{\underset{\displaystyle \|}{-}}\!\!\!-NHR^8;$$

xliv. R$^6$ is hydrogen;
xlv. R$^6$ is C$_1$–C$_6$ alkyl;
xlvi. R$^6$ is optionally substituted C$_3$–C$_8$ cycloalkyl;
xlvii. R$^6$ is optionally substituted C$_6$–C$_{10}$ bicycloalkyl;
xlviii. R$^6$ is optionally substituted (C$_1$–C$_4$ alkyl)-aryl;
xlix. R$^6$ is optionally substituted aryl;
l. R$^6$ is optionally substituted (C$_1$–C$_4$ alkyl)-heterocycle;
li. R$^6$ is optionally substituted heterocycle;
lii. R$^{6'}$ is C$_1$–C$_6$ alkyl;
liii. R$^{6'}$ is optionally substituted C$_3$–C$_8$ cycloalkyl;
liv. R$^{6'}$ is optionally substituted C$_6$–C$_{10}$ bicycloalkyl;
lv. R$^{6'}$ is optionally substituted (C$_1$–C$_4$ alkyl)-aryl;
lvi. R$^{6'}$ is optionally substituted aryl;
lvii. R$^7$ is optionally substituted C$_1$–C$_6$ alkyl;
lviii. R$^7$ is C$_1$–C$_6$ alkoxy;
lix. R$^7$ is (C$_1$–C$_4$ alkoxy)-aryl;
lx. R$^7$ is optionally substituted (C$_3$–C$_8$ cycloalkyl);
lxi. R$^7$ is optionally substituted (C$_1$–C$_4$ alkyl)-(C$_3$–C$_8$ cycloalkyl);
lxii. R$^7$ is optionally substituted (C$_1$–C$_4$ alkyl)-aryl;
lxiii. R$^7$ is optionally substituted aryl;
lxiv. R$^7$ is diphenylmethyl;
lxv. R$^7$ is optionally substituted (C$_1$–C$_4$ alkyl)-CO-aryl;
lxvi. R$^7$ is optionally substituted CO-aryl;
lxvii. R$^7$ is optionally substituted (C$_1$–C$_4$ alkyl)-heterocycle;
lxviii. R$^7$ is optionally substituted phenoxy;
lxix. R$^7$ is optionally substituted heterocycle;
lxx. R$^7$ is (CH$_2$)$_s$S(O)$_r$R$^1$;
lxxi. R$^7$ is (CH$_2$)$_t$C(R$^{12}$)(R$^9$)N(R$^{16}$)(R$^{15}$);
lxxii. R$^7$ is (CH$_2$)$_t$C(R$^{12}$)(R$^9$)O(R$^{17}$);
lxxiii. R$^7$ is (CH$_2$)$_t$C(R$^{12}$)(R$^9$)S(R$^{17}$);
lxxiv. R$^7$ is NR$^4$R$^{6'}$;
lxxv. R$^8$ is optionally substituted C$_1$–C$_6$ alkyl;
lxxvi. R$^8$ is optionally substituted aryl;
lxxvii. R$^8$ is optionally substituted (C$_1$–C$_4$ alkyl)-aryl;
lxxviii. R$^9$ is hydrogen;
lxxix. R$^9$ is optionally substituted C$_1$–C$_6$ alkyl;
lxxx. R$^9$ is optionally substituted C$_3$–C$_8$ cycloalkyl;
lxxxi. R$^9$ is optionally substituted aryl;
lxxxii. R$^9$ is optionally substituted heterocycle;
lxxxiii. R$^9$ is optionally substituted (CH$_2$)$_u$-(C$_1$–C$_4$ alkoxy)-aryl;
lxxxiv. R9 and R$^{12}$ combine to form a C$_3$–C$_8$ cycloalkyl;
lxxxv. R$^{10}$ is 1 to 4 substituents selected from the group consisting of hydrogen, halo, cyano, optionally substituted heterocycle, or NR$^{19}$R$^{20}$;
lxxxvi. R$^{10}$ is monosubstituted with chloro;
lxxxvii. R$^{10}$ is monosubstituted with cyano;
lxxxviii. R$^{10}$ is monosubstituted with NH$_2$;
lxxxix. R$^{11}$ is hydrogen;
xc. R$^{12}$ is hydrogen;
xci. R$^{12}$ is optionally substituted C$_1$–C$_6$ alkyl;
xcii. R$^{12}$ is optionally substituted aryl;
xciii. R$^{13}$ is hydrogen;

xciv. $R^{13}$ is optionally substituted $C_1$–$C_6$ alkyl;
xcv. $R^{13}$ is optionally substituted ($C_1$–$C_4$ alkyl)-aryl;
xcvi. $R^{13}$ is optionally substituted aryl;
xcvii. $R^{13}$ is $CO_2CH_2CO_2CH_2CH_3$;
xcviii. $R^{15}$ is hydrogen;
xcix. $R^{15}$ is $C_1$–$C_6$;
c. $R^{15}$ is optionally substituted $C_6$–$C^{10}$ bicycloalkyl;
ci. $R^{15}$ is optionally substituted aryl;
cii. $R^{15}$ is optionally substituted heterocycle;
ciii. $R^{15}$ is $C(O)OR^{13}$;
civ. $R^{15}$ is $SO_2R^8$;
cv. $R^{15}$ is $C(O)R^{18}$;
cvi. $R^{16}$ is hydrogen;
cvii. $R^{16}$ is optionally substituted $C_1$–$C_6$ alkyl;
cviii. $R^{16}$ and $R^{15}$, together with the nitrogen to which they are attached, combine to form an optionally substituted N-heterocycle;
cix. $R^{17}$ is hydrogen;
cx. $R^{17}$ is optionally substituted $C_1$–$C_6$ alkyl,
cxi. $R^{17}$ is optionally substituted aryl;
cxii. $R^{17}$ is optionally substituted heterocycle;
cxiii. $R^{18}$ is hydrogen;
cxiv. $R^{18}$ is optionally substituted $C_1$–$C_6$ alkyl;
cxv. $R^{18}$ is optionally substituted aryl;
cxvi. $R^{18}$ is optionally substituted heterocycle;
cxvii. $R^{18}$ is ($C_1$–$C_4$ alkyl)-$NHCO_2$—($C_1$–$C_4$ alkyl);
cxviii. $R^{19}$ is hydrogen;
cxix. $R^{19}$ is optionally substituted $C_1$–$C_6$ alkyl;
cxx. $R^{20}$ is hydrogen;
cxxi. $R^{20}$ is optionally substituted $C_1$–$C_6$ alkyl;
cxxii. $R^{20}$ is $CH_2OH$;
cxxiii. $R^{20}$ is CO—($C_1$–$C_4$ alkyl);

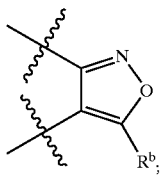

cxxiv. Het is

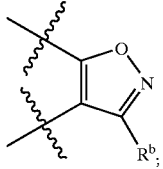

cxxv. Het is

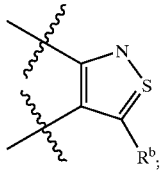

cxxvi. Het is

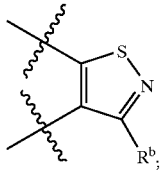

cxxvii. Het is

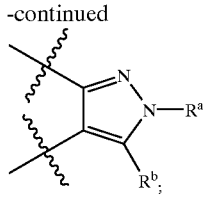

cxxviii. Het is

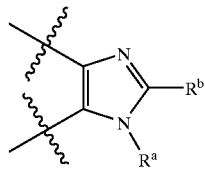

cxxix. Het is

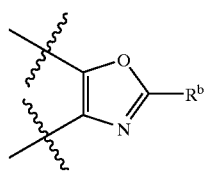

cxxx. Het is cxxxi. $R^b$ is chloro;
cxxxii. $R^a$ is hydrogen;
cxxxiii. $R^a$ is t-butyl;
cxxxiv. The compound is a pharmaceutical salt; and
cxxxv. The compound is the hydrochloride salt.

The following group, including the racemic trans and cis, and the isolated enantiomers, is illustrative of compounds contemplated within the scope of this invention:

a) N-[3-(9-Chloro-3-methyl-4-oxo-5H-isoxazolo[4,3-c]quinolin-5-yl)-cyclohexyl]-2-hydroxy-acetamide
b) N-[3-(9-Chloro-3-methyl-4-oxo-5H-isoxazolo[4,3-c]quinolin-5-yl)-cyclohexyl]-2-hydroxy-3-methyl-butyramide
c) N-[3-(9-Chloro-3-methyl-4-oxo-5H-isoxazolo[4,3-c]quinolin-5-yl)-cyclohexyl]-3-hydroxy-3-phenyl-propionamide
d) N-[3-(9-Chloro-3-methyl-4-oxo-5H-isoxazolo[4,3-c]quinolin-5-yl)-cyclohexyl]-3-hydroxy-3-phenyl-propionamide
e) N-[3-(9-Chloro-3-methyl-4-oxo-5H-isoxazolo[4,3-c]quinolin-5-yl)-cyclohexyl]-2-hydroxy-3-methyl-butyramide
f) 1-Hydroxy-cyclopropanecarboxylic acid [3-(9-chloro-3-methyl-4-oxo-5H-isoxazolo[4,3-c]quinolin-5-yl)-cyclohexyl]-amide
g) {[3-(9-Chloro-3-methyl-4-oxo-5H-isoxazolo[4,3-c]quinolin-5-yl)-cyclohexylcarbamoyl]-methyl}-methyl-carbamic acid tert-butyl ester
h) N-[3-(9-Chloro-3-methyl-4-oxo-5H-isoxazolo[4,3-c]quinolin-5-yl)-cyclohexyl]-2-methylamino-acetamide hydrochloride
i) N-[3-(9-Chloro-3-methyl-4-oxo-5H-isoxazolo[4,3-c]quinolin-5-yl)-cyclohexyl]-2-dimethylamino-acetamide
j) {1-[3-(9-Chloro-3-methyl-4-oxo-5H-isoxazolo[4,3-c]quinolin-5-yl)-cyclohexylcarbamoyl]-1-methyl-ethyl}-carbamic acid tert-butyl ester
k) 2-Amino-N-[3-(9-chloro-3-methyl-4-oxo-5H-isoxazolo[4,3-c]quinolin-5-yl)-cyclohexyl]-2-methyl-propionamide hydrochloride
l) {[3-(9-Chloro-3-methyl4-oxo-5H-isoxazolo[4,3-c]quinolin-5-yl)-cyclohexylcarbamoyl]-methyl }-carbamic acid tert-butyl ester m) 2-Amino-N-[3-(9-chloro-3-methyl-4-oxo-5H-isoxazolo[4,3-c]quinolin-5-yl)-cyclohexyl]-acetamide hydrochloride
n) 2-Hydroxy-hexanoic acid [3-(9-chloro-3-methyl-4-oxo-5H-isoxazolo[4,3-c]quinolin-5-yl)-cyclohexyl]-amide
o) N-[3-(9-Chloro-3-methyl-4-oxo-5H-isoxazolo[4,3-c]quinolin-5-yl)-cyclohexyl]-2-hydroxy-benzamide
p) 4-{[3-(9-Chloro-3-methyl-4-oxo-5H-isoxazolo[4,3-c]quinolin-5-yl)-cyclohexylcarbamoyl]-phenyl-methyl}-piperazine-1-carboxylic acid tert-butyl ester
q) N-[3-(9-Chloro-3-methyl-4-oxo-5H-isoxazolo[4,3-c]quinolin-5-yl)-cyclohexyl]-2-phenyl-2-piperazin-1-yl-acetamide dihydrochloride
r) {[3-(9-Chloro-3-methyl-4-oxo-5H-isoxazolo[4,3-c]quinolin-5-yl)-cyclohexylcarbamoyl]-phenyl-methyl}-methyl-carbamic acid tert-butyl ester
s) N-[3-(9-Chloro-3-methyl-4-oxo-5H-isoxazolo[4,3-c]quinolin-5-yl)-cyclohexyl]-2-methylamino-2-phenyl-acetamide hydrochloride
t) N-[3-(9-Chloro-3-methyl-4-oxo-5H-isoxazolo[4,3-c]quinolin-5-yl)-cyclohexyl]-2-[4-(2-hydroxy-ethyl)-piperazin-1-yl]-2-phenyl-acetamide
u) N-[3-(9-Chloro-3-methyl-4-oxo-5H-isoxazolo[4,3-c]quinolin-5-yl)-cyclohexyl]-2-phenyl-2-(4-pyridin-2-yl-piperazin-1-yl)-acetamide
v) N-[3-(9-Chloro-3-methyl-4-oxo-5H-isoxazolo[4,3-c]quinolin-5-yl)-cyclohexyl]-2-piperidin-1-yl-acetamide
w) N-[3-(9-Chloro-3-methyl-4-oxo-5H-isoxazolo[4,3-c]quinolin-5-yl)-cyclohexyl]-2-(4-methyl-piperazin-1-yl)-acetamide
x) N-[3-(9-Chloro-3-methyl-4-oxo-5H-isoxazolo[4,3-c]quinolin-5-yl)-cyclohexyl]-2-diethylamino-acetarmide
y) 2-Chloro-N-[3-(9-chloro-3-methyl-4-oxo-5H-isoxazolo[4,3-c]quinolin-5-yl)-cyclohexylmethyl]-6-methoxy-isonicotinamide
z) 3-(9-Chloro-3-methyl4-oxo-5H-isoxazolo[4,3-c]quinolin-5-yl)-cyclohexanecarboxylic acid (2-hydroxy-1-phenyl-ethyl)-amide
aa) 3-(9-Chloro-3-methyl-4-oxo-5H-isoxazolo[4,3-c]quinolin-5-yl)-cyclohexanecarboxylic acid (2-hydroxy-1-phenyl-ethyl)-amide
bb) N-[3-(9-Chloro-3-methyl-4-oxo-5H-isoxazoto[4,3-c]quinolin-5-yl)-cyclohexyl]-2-(methyl-phenyl-amino)-acetamide
cc) N-[3-(9-Chloro-3-methyl-4-oxo-5H-isoxazolo[4,3-c]quinolin-5-yl)-cyclohexyl]-2-phenyl-2-(pyridin-3-yloxy)-acetamide
dd) N-[3-(9-Chloro-3-methyl-4-oxo-5H-isoxazolo[4,3-c]quinolin-5-yl)-cyclohexyl]-2(pyridin-3-yloxy)-acetamide
ee) {1-[3-(9-Chloro-3-methyl-4-oxo-5H-isoxazolo[4,3-c]quinolin-5-yl)-cyclohexylcarbamoyl]-cyclohexyl}-carbamic acid tert-butyl ester.
ff) 1-Amino-cyclohexanecarboxylic acid [3-(9-chloro-3-methyl-4-oxo-5H-isoxazolo[4,3-c]quinolin-5-yl)-cyclohexyl]-amide hydrochloride
gg) N-[3-(9-Chloro-3-methyl-4-oxo-5H-isoxazolo[4,3-c]quinolin-5-yl)-cyclohexyl]-2-morpholin-4-yl-acetamide
hh) N-[3-(9-Chloro-3-methyl-4-oxo-5H-isoxazolo[4,3-c]quinolin-5-yl)-cyclohexyl]-2-(4-hydroxy-piperidin-1-yl)-acetamide
ii) N-[3-(9-Chloro-3-methyl-4-oxo-5H-isoxazolo[4,3-c]quinolin-5-yl)-cyclohexyl]-2-(pyridin-2-yloxy)-acetamide
jj) N-[3-(9-Chloro-3-methyl-4-oxo-5H-isoxazolo[4,3-c]quinolin-5-yl)-cyclohexyl]-2-(pyridin-4-yloxy)-acetamide
kk) N-[3-(9-Chloro-3-methyl-4-oxo-5H-isoxazolo[4,3-c]quinolin-5-yl)-cyclohexyl]-2-(pyridin-4-ylsulfanyl)-acetamide
ll) {[3-(9-Chloro-3-methyl-4-oxo-5H-isoxazolo[4,3-c]quinolin-5-yl)-cyclohexylcarbamoyl]-cyclohexyl-methyl}-carbamic acid tert-butyl ester
mm) 2-Amino-N-[3-(9-chloro-3-methyl-4-oxo-5H-isoxazolo[4,3-c]quinolin-5-yl)-cyclohexyl]-2-cyclohexyl-acetamide hydrochloride
nn) 2-Amino-N-[3-(9-chloro-3-methyl-4-oxo-5H-isoxazolo[4,3-c]quinolin-5-yl)-cyclohexyl]-2-cyclohexyl-acetamide hydrochloride
oo) {[3-(9-Chloro-3-methyl4-oxo-5H-isoxazolo[4,3-c]quinolin-5-yl)-cyclohexylcarbamoyl]-cyclohexyl-methyl}-carbamic acid tert-butyl ester
pp) thieno[3,2-b]pyridine-2-carboxylic acid [3-(9-chloro-3-methyl-4-oxo-5H-isoxazolo[4,3-c]quinolin-5-yl)-cyclohexyl]-amide
qq) N-[3-(9-Chloro-3-methyl-4-oxo-5H-isoxazolo[4,3-c]quinolin-5-yl)-cyclohexyl]-2-(2-chloro-pyridin-4-yloxy)-acetamide
rr) N-[3-(9-Chloro-3-methyl-4-oxo-5H-isoxazolo[4,3-c]quinolin-5-yl)-cyclohexyl]-2-(quinolin-3-yloxy)-acetamide
ss) 2-tert-Butylamino-N-[3-(9-chloro-3-methyl-4-oxo-5H-isoxazolo[4,3-c]quinolin-5-yl)-cyclohexyl]-acetamide
tt) N-[3-(9-Chloro-3-methyl-4-oxo-5H-isoxazolo[4,3-c]quinolin-5-yl)-cyclohexyl]-2-(pyridin-2-ylsulfanyl)-acetamide
uu) (2-aminoindan-2-yl)-N-[3-(9-chloro-3-methyl-4-oxo-5H-isoxazolo[4,3-c]quinolin-5-yl))cyclohexyl]carboxamide
vv) N-[3-(9-Chloro-3-methyl-4-oxo-5H-isoxazolo[4,3-c]quinolin-5-yl)-cyclohexyl]-2-dimethylamino-2-cyclohexylpropionamide
ww) N-[3-(9-Chloro-3-methyl-4-oxo-5H-isoxazolo[4,3-c]quinolin-5-yl)-cyclohexyl]-2-dimethylamino-2-(3-chlorophenyl)-propionamide
xx) N-[3-(9-Chloro-3-methyl-4-oxo-5H-isoxazolo[4,3-c]quinolin-5-yl)-cyclohexyl]-2-dimethylamino-2-pyrid-1-yl-propionamide
yy) N-[3-(9-Chloro-3-methyl-4-oxo-5H-isoxazolo[4,3-c]quinolin-5-yl)-cyclohexyl]-2-dimethylamino-2-fur-3-yl-propionanide
zz) N-[3-(9-Chloro-3-methyl-4-oxo-5H-isoxazolo[4,3-c]quinolin-5-yl)-cyclohexyl]-2-(2-chlorophenyl)amino-2-(3-chlorophenyl)-propionamnide
aaa) N-[3-(9-Chloro-3-methyl-4-oxo-5H-isoxazolo[4,3-c]quinolin-5-yl)-cyclohexyl]-2-diphenylamino-2-phenylpropionarnide
bbb) N-[3-(9-Chloro-3-methyl-4-oxo-5H-isoxazolo[4,3-c]quinolin-5-yl)-cyclobutyl]-2-hydroxy-acetamide
ccc) N-[3-(9-Chloro-3-methyl-4-oxo-5H-isoxazolo[4,3-c]quinolin-5-yl)-cyclopentyl]-2-hydroxy-3-methyl-butyramide
ddd) N-[3-(9-Chloro-3-methyl-4-oxo-5H-isoxazolo[4,3-c]quinolin-5-yl)-cycloheptyl]-3-hydroxy-3-phenyl-propionamide
eee) N-[3-(9-Chloro-3-methyl-4-oxo-5H-isoxazolo[4,3-c]quinolin-5-yl)-cyclobutyl]-3-hydroxy-3-phenyl-propionamide
fff) N-[3-(9-Chloro-3-methyl-4-oxo-5H-isoxazolo[4,3-c]quinolin-5-yl)-cyclopentyl]-2-hydroxy-3-methyl-butyramide
ggg) 1-Hydroxy-cyclopropanecarboxylic acid [3-(9-chloro-3-methyl-4-oxo-5H-isoxazolo[4,3-c]quinolin-5-yl)-cycloheptyl]-amide
hhh) {[3-(9-Chloro-3-methyl-4-oxo-5H-isoxazolo[4,3-c]quinolin-5-yl)-cyclopentylcarbamoyl]-methyl }-methyl-carbamic acid tert-butyl ester iii) N-[3-(9-Chloro-3-methyl-4-oxo-5H-isoxazolo[4,3-c]quinolin-5-yl)-cyclopentyl]-2-methylamino-acetamide hydrochloride jjj) N-[3-(9-Chloro-3-methyl-4-oxo-5H-isoxazolo[4,3-c]quinolin-5-yl)-cyclopentyl]-2-dimethylamino-acetamide kkk) {1-[3-(9-Chloro-3-methyl-4-oxo-H-isoxazolo[4,3-c]quinolin-5-yl)-cyclopentylcarbamoyl]-1-methyl-ethyl}-carbamic acid tert-butyl ester lll) 2-Amino-N-[3-(9-chloro-3-methyl-4-oxo-5H-isoxazolo[4,3-c]quinolin-5-yl)-cyclopentyl]-2-methyl-propionamide hydrochloride mmm) {[3-(9-Chloro-3-methyl4-oxo-5H-isoxazolo[4,3-c]quinolin-5-yl)-cyclopentylcarbamoyl]-methyl}-carbamic acid tert-butyl ester nnn) 2-Amino-N-[3-(9-chloro-3-methyl-4-oxo-5H-isoxazolo[4,3-c]quinolin-5-yl)-cyclopentyl]-acetamide hydrochloride ooo) 2-Hydroxy-hexanoic acid [3-(9-chloro-3-methyl-4-oxo-5H-isoxazolo[4,3-c]quinolin-5-yl)-cyclopentyl]-amide ppp) N-[3-(9-Chloro-3-methyl-4-oxo-5H-isoxazolo[4,3-c]quinolin-5-yl)-cyclopentyl]-2-hydroxy-benzamide qqq) 4-{[3-(9-Chloro-3-methyl-4-oxo-5H-isoxazolo[4,3-c]quinolin-5-yl)-cyclopentylcarbamoyl]-phenyl-methyl}-piperazine-1-carboxylic acid tert-butyl ester rrr) N-[3-(9-Chloro-3-methyl-4-oxo-5H-isoxazolo[4,3-c]quinolin-5-yl)-cyclopentyl]-2-phenyl-2-piperazin-1-yl-acetamide dihydrochloride sss) {[3(9-Chloro-3-methyl-4-oxo-5H-isoxazolo[4,3-c]quinolin-5-yl)-cyclopentylcarbamoyl]-phenyl-methyl}-methyl-carbamic acid tert-butyl ester ttt) N-[3-(9-Chloro-3-methyl-4-oxo-5H-isoxazolo[4,3-c]quinolin-5-yl)-cyclopentyl]-2-methylamino-2-phenyl-acetamide hydrochloride uuu) N-[3-(9-Chloro-3-methyl-4-oxo-5H-isoxazolo[4,3-c]quinolin-5-yl)-cyclopentyl]-2-[4-(2-hydroxy-ethyl)-piperazin-1-yl]-2-phenyl-acetamide vvv) N-[3-(9-Chloro-3-methyl-4-oxo-5H-isoxazolo[4,3-c]quinolin-5-yl)-cyclopentyl]-2-phenyl-2-(4-pyridin-2-yl-piperazin-1-yl)-acetamide www) N-[3-(9-Chloro-3-methyl-4-oxo-5H-isoxazolo[4,3-c]quinolin-5-yl)-cyclopentyl]-2-piperidin-1-yl-acetamide xxx) N-[3-(9-Chloro-3-methyl-4-oxo-5H-isoxazolo[4,3-c]quinolin-5-yl)-cyclopentyl]-2-(4-methyl-piperazin-1-yl)-acetamide yyy) N-[3-(9-Chloro-3-methyl-4-oxo-5H-isoxazolo[4,3-c]quinolin-5-yl)-cyclopentyl]-2-diethylamino-acetamide zzz) 2-Chloro-N-[3-(9-chloro-3-methyl-4-oxo-5H-isoxazolo[4,3-c]quinolin-5-yl)-cyclopentylmethyl]-6-methoxy-isonicotinamide aaaa) 3-(9-Chloro-3-methyl-4-oxo-5H-isoxazolo[4,3-c]quinolin-5-yl)-cyclohexanecarboxylic acid (2-hydroxy-1-phenyl-ethyl)-amide bbbb) 3-(9-Chloro-3-methyl-4-oxo-5H-isoxazolo[4,3-c]quinolin-5-yl)-cyclohexanecarboxylic acid (2-hydroxy-1-phenyl-ethyl)-amide cccc) N-[3-(9-Chloro-3-methyl-4-oxo-5H-isoxazolo[4,3-c]quinolin-5-yl)-cyclopentyl]-2-(methyl-phenyl-amino)-acetamide dddd) N-[3-(9-Chloro-3-methyl-4-oxo-5H-isoxazolo[4,3-c]quinolin-5-yl)-cyclopentyl]-2-phenyl-2-(pyridin-3-yloxy)-acetamide eeee) N-[3-(9-Chloro-3-methyl-4-oxo-5H-isoxazolo[4,3-c]quinolin-5-yl)-cyclopentyl]-2-(pyridin-3-yloxy)-acetamide ffff) {1-[3-(9-Chloro-3-methyl-4-oxo-5H-isoxazolo[4,3-c]quinolin-5-yl)-cyclopentylcarbamoyl]-cyclopentyl}-carbamic acid tert-butyl ester.

gggg) 1-Amino-cyclohexanecarboxylic acid [3-(9-chloro-3-methyl4-oxo-5H-isoxazolo[4,3-c]quinolin-5-yl)-cyclopentyl]-amide hydrochloride hhhh) N-[3-(9-Chloro-3-methyl-4-oxo-5H-isoxazolo[4,3-c]quinolin-5-yl)-cyclopentyl]-2-morpholin-4-yl-acetamide iiii) N-[3-(9-Chloro-3-methyl-4-oxo-5H-isoxazolo[4,3-c]quinolin-5-yl)-cyclopentyl]-2-(4-hydroxy-piperidin-1-yl)-acetamide jjjj) N-[3-(9-Chloro-3-methyl-4-oxo-5H-isoxazolo[4,3-c]quinolin-5-yl)-cyclopentyl]-2-(pyridin-2-yloxy)-acetamide kkkk) N-[3-(9-Chloro-3-methyl-4-oxo-5H-isoxazolo[4,3-c]quinolin-5-yl)-cyclopentyl]-2-(pyridin-4-yloxy)-acetamide llll) N-[3-(9-Chloro-3-methyl-4-oxo-5H-isoxazolo[4,3-c]quinolin-5-yl)-cyclopentyl]-2-(pyridin-4-ylsulfanyl)-acetamide mmmm) {[3-(9-Chloro-3-methyl-4-oxo-5H-isoxazolo[4,3-c]quinolin-5-yl)-cyclopentylcarbamoyl]-cyclohexyl-methyl}-carbamic acid tert-butyl ester nnnn) 2-Amino-N-[3-(9-chloro-3-methyl-4-oxo-5H-isoxazolo[4,3-c]quinolin-5-yl)-cyclopentyl]-2-cyclohexyl-acetamide hydrochloride oooo) 2-Amino-N-[3-(9-chloro-3-methyl-4-oxo-5H-isoxazolo[4,3-c]quinolin-5-yl)-cyclohexyl]-2-cyclopentyl-acetamide hydrochloride pppp) {[3-(9-Chloro-3-methyl-4-oxo-5H-isoxazolo[4,3-c]quinolin-5-yl)-cyclopentylcarbamoyl]-cyclohexyl-methyl}-carbamic acid tert-butyl ester qqqq) thieno[3,2-b]pyridine-2-carboxylic acid[3-(9-chloro-3-methyl4-oxo-5H-isoxazolo[4,3-c]quinolin-5-yl)-cyclopentyl]-amide rrrr) N-[3-(9-Chloro-3-methyl-4-oxo-5H-isoxazolo[4,3-c]quinolin-5-yl)-cyclopentyl]-2-(2-chloro-pyridin-4-yloxy)-acetamide ssss) N-[3-(9-Chloro-3-methyl-4-oxo-5H-isoxazolo[4,3-c]quinolin-5-yl)-cyclopentyl]-2-(quinolin-3-yloxy)-acetamide tttt) 2-tert-Butylmino-N-[3-(9-chloro-3-methyl-4-oxo-5H-isoxazolo[4,3-c]quinolin-5-yl)-cyclopentyl]-acetamide uuuu) N-[3-(9-Chloro-3-methyl-4-oxo-5H-isoxazolo[4,3-c]quinolin-5-yl)-cyclopentyl]-2-(pyridin-2-ylsulfanyl)-acetamide vvvv) (2-aminoindan-2-yl)-N-[3-(9-chloro-3-methyl-4-oxo-5H-isoxazolo[4,3-c]quinolin-5-yl))cyclopentyl]carboxamide wwww) N-[3-(9-Chloro-3-methyl-4-oxo-5H-isoxazolo[4,3-c]quinolin-5-yl)-cyclopentyl]-2-dimethylamino-2-cyclohexylpropionamide xxxx) N-[3-(9-Chloro-3-methyl-4-oxo-5H-isoxazolo[4,3-c]quinolin-5-yl)-cyclopentyl]-2-dimethylamino-2-(3-chlorophenyl)-propionamide yyyy) N-[3-(9-Chloro-3-methyl-4-oxo-5H-isoxazolo[4,3-c]quinolin-5-yl)-cyclopentyl]-2-dimethylamino-2-pyrid-1-yl-propionamide zzzz) N-[3-(9-Chloro-3-methyl-4-oxo-5H-isoxazolo[4,3-c]quinolin-5-yl)-cyclopentyl]-2-dimethylamino-2-fur-3-yl-propionamide aaaaa) N-[3-(9-Chloro-3-methyl-4-oxo-5H-isoxazolo[4,3-c]quinolin-5-yl)-cyclopentyl]-2-(2-chlorophenyl)amino-2-(3-chlorophenyl)-propionamide bbbbb) N-[3-(9-Chloro-3-methyl-4-oxo-5H-isoxazolo[4,3-c]quinolin-5-yl)-cyclopentyl]-2-diphenylamino-2-phenylpropionamide The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I(a), wherein $R^b$, the substituent attached to the non-fused carbon, is $C_1$–$C_6$ alkyl, optionally substituted aryl, optionally substituted heterocycle, $CH_2OH$, or $CH_2O$-heterocycle may be prepared from compounds of formula II(a) as illustrated in Scheme 1 below where Y, A, $R^{10}$, het, n, and p are as described supra.

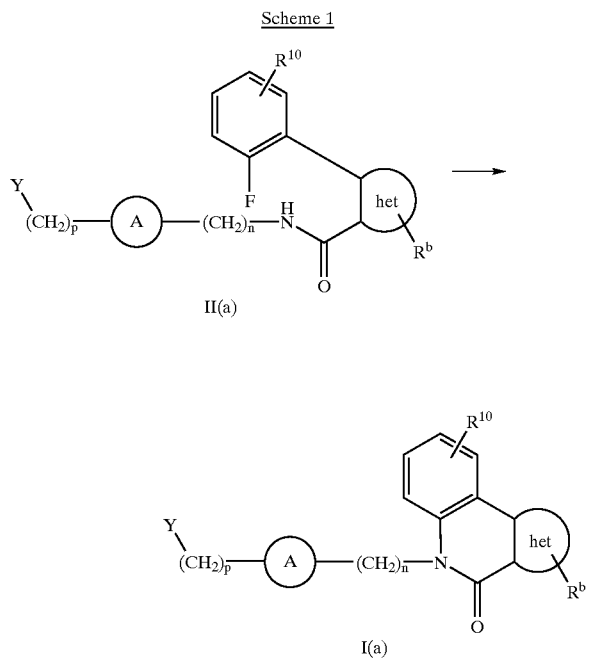

Scheme 1

II(a)

I(a)

Compounds of formula I(a) may be prepared by dissolving or suspending a compound of formula II(a) in a suitable solvent, preferably dimethylformamide, and adding a suitable base, including potassium methoxide, potassium tert-butoxide, potassium carbonate, sodium hexamethyldisilazane, and preferably potassium hexamethyldisilazane. The base is typically employed in a one to one ratio. However, as the skilled artisan would appreciate, a slight molar excess, usually in about a 1.1 to about a 3 fold molar excess relative to the compound of formula II(a), is acceptable.

The reactants are typically combined at a temperature from about 0° C. to about 100° C. When het is isoxazole, oxazole, or imidazole, the reactants are preferably combined at room temperature and the resulting solution is typically mixed for from about 5 minutes to about 18 hours, preferably from about 15 minutes to about 3 hours. When het is pyrazole the reactants are preferably combined at room temperature and the resulting solution is typically heated to about 100° C. for about 30 minutes to about 18 hours.

It is preferred, when A is cyclopentyl and the base employed is potassium hexamethyldisilazane, to combine the reactants from about 60° C. to about 100° C. for about 3 to about 6 minutes.

Any protecting groups remaining in the cyclized compound of formula I may be removed as taught in *Greene* to provide additional compounds of formula I. Preferred choices of protecting groups and methods for their removal may be found in the Preparations and Examples sections below.

Compounds of formula I(b), wherein het is substituted with halo may be prepared from compounds of formula II(b) as illustrated in Scheme 2 below where Y, A, $R^{10}$, het, n, and p are as described supra.

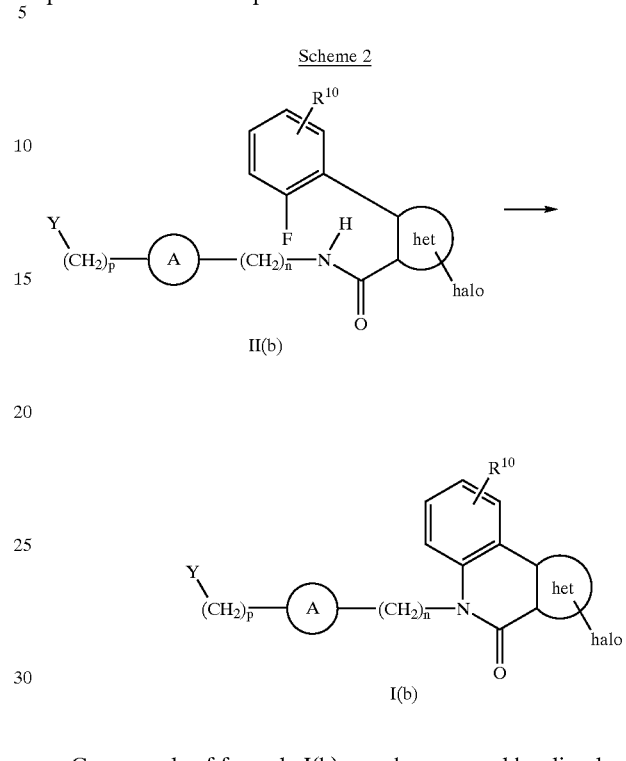

Scheme 2

II(b)

I(b)

Compounds of formula I(b) may be prepared by dissolving or suspending a compound of formula II(b) in a suitable solvent and adding a suitable base, in an inert atmosphere, preferably under $N_2$. Typically a preferred and convenient solvent is dimethylformamide. A preferred base is sodium trimethylsilanolate. The base is typically employed in a slight molar excess, usually in about a 1.05 fold molar excess relative to the compound of formula II(b). The reactants are typically combined dropwise at room temperature over a period of time from about 2 hours to about 4 hours.

The skilled artisan would appreciate that if other bases are used in the reaction of Scheme 2, the substituent of the het functionality may change. For example if sodium methylthiolate is used as the preferred base, the compound of formula II(b) will be converted into the compound of formula I wherein the bet functionality is substituted with —$SCH_3$.

Additionally, the compound of formula I(b) can be prepared according to Scheme 1 wherein the reactants are combined at about 0° C. and mixed at about –10° C. for approximately three hours. The solution is then warmed to room temperature and mixed for an additional 2 to 3 hours.

Certain compounds of formula I(c) are useful MRP1 inhibitors and are also useful intermediates for the preparation of other compounds of formula I. As is shown in Scheme 3, when $R^b$ is $CH_2O$-Pg, a derivative of formula I(c) wherein Pg is a protecting group, the compound of formula I(c) may be further reacted by methods known in the art to produce compounds of formula I(d) where $R^{b'}$ is $CH_2OH$, $CH_2N_3$, $CH_2SR^1$, or $CH_2NR^4R^6$, and Y, A, het, p, n, $R^1$, $R^4$, $R^6$, and $R^{10}$ are as described supra.

Scheme 3

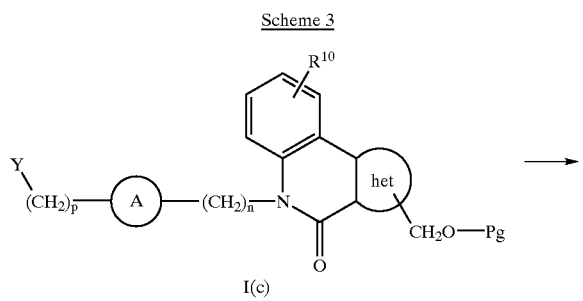

I(c)

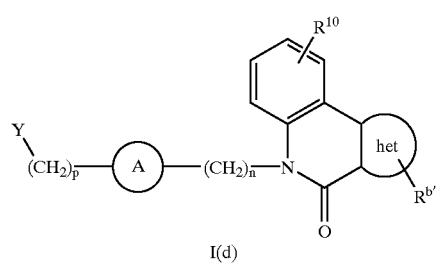

I(d)

Compounds of formula I(d) wherein het is substituted with CH$_2$OH may be prepared by dissolving or suspending a compound of formula I(c) in a suitable solvent and adding a suitable acid. Typically a preferred and convenient solvent is methanol/dichloromethane (2:1). A preferred acid is p-toluenesulfonic acid hydrate. The acid is typically employed in a slight molar excess, usually in about a 1.05 fold molar. excess relative to the compound of formula I(c). The reactants are typically combined at room temperature and mixed from about 1 hour to about 3 hours.

The skilled artisan would appreciate that the alcohol can be further converted to compounds of formula I(d) where het is substituted with CH$_2$N$_3$, CH$_2$SR$^{13}$, or CH$_2$NR$^4$R$^6$ by methods well known in the art. For general examples of these procedures, see the Preparations and Example section.

Compounds of formula I(e) when het is substituted with chloro are useful MRP1 inhibitors and are also useful intermediates for the preparation of other compounds of formula I. As is shown in Scheme 4, the compound of formula I(e) may be further reacted with a nucleophile by methods known in the art to produce compounds of formula I(q) where het is substituted with an amino acid ester, OR$^1$, SR$^{13}$, S(CH$_2$)$_k$-phenyl, NR$^4$R$^6$, or an optionally substituted heterocycle attached via a heteroatom, and Y, A, p, n, k, het, R$^1$, R$^4$, R$^6$, R$^{10}$, and R$^{13}$ are as described supra.

Scheme 4

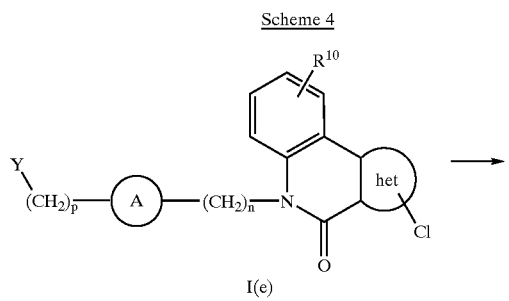

I(e)

-continued

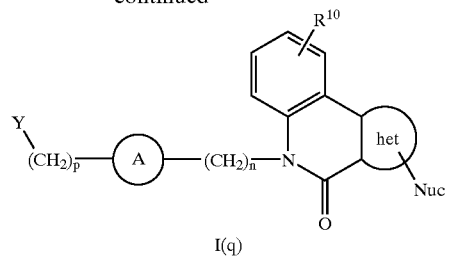

I(q)

Compounds of formula I(q) may be prepared by dissolving or suspending a compound of formula I(e) in a suitable solvent and adding an appropriate nucleophile, in an inert atmosphere, preferably under N$_2$. Typically a preferred and convenient solvent is dimethylformamide. The nucleophile is typically employed in a molar excess, usually in about a 2 to about a 4 fold molar excess relative to the compound of formula I(e).

The reactants are preferably combined at room temperature and the resulting solution is typically mixed for about 30 minutes to about 3 hours, until the reaction is complete as measured by the consumption of the substrate. The skilled artisan would appreciate that the reaction, depending on the nucleophile used, may require more time to react and may, also require heating. In these instances, it is preferred to mix the reactants for approximately 15 to approximately 20 hours, then heat the solution from about 50° C. to about 80° C. and mix for an additional 3 hours or until the reaction is complete as measured by the consumption of the compound of formula I(e).

Compounds of formula I(p) where Y is C(R$^{11'}$)(R$^{11}$) NR$^4$R$^5$ may be prepared from compounds of formula I(n) as illustrated in Scheme 5 below where R$^3$ and R$^{11}$ are equivalent, R$^{11'}$ is H, and het, n, p, A, R$^4$, R$^5$, and R$^{10}$ are as described supra.

Scheme 5

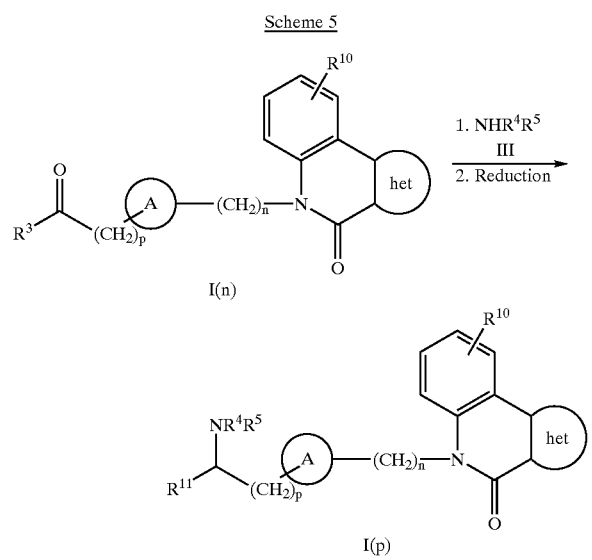

I(n)

I(p)

The compounds of formula I(n) may be reductively aminated to form the compounds of formula I(p). Reductive aminations are well known transformations, see, e.g., Larock, "Comprehensive Organic Transformations", pg. 421, VCH Publishers, New York, N.Y., 1989, hereafter referred to as "*Larock*".

Amines of formula III may be dissolved or suspended in a suitable solvent, preferably methanol, optionally in the presence of a suitable base, preferably N-methyl morpholine or triethylamine. When the compound of formula III is an acid addition salt, it is preferred to convert the salt to its free amine form. A compound of formula I(n) is then added to the mixture. Optionally, a Lewis acid catalyst, such as titanium (W) isopropoxide, may be employed. Once the compound of formula I(n) has been substantially consumed, the intermediate is typically reacted in situ with a suitable reducing agent to provide the compounds of formula I(p). The overall conversion may be performed at about 0° C. to the boiling point of the mixture, but room temperature is a preferred reaction temperature. The formation of the compounds of formula I(p) may take from 15 minutes to 24 hours as measure by the consumption of the substrate.

Suitable reducing agents include, but are not limited to, hydrogen over palladium or platinum on carbon, borane or complexes of borane, e.g., borane-pyridine, borane-t-butylamine, and borane-dimethylamine complex; and borohydride reducing agents such as sodium borohydride or sodium cyanoborohydride. Sodium cyanoborohydride is a preferred reducing agent.

Compounds of formula I(r) may be prepared from compounds of formula I(n) as illustrated below where p, n, $R^3$, $R^7$, and $R^{10}$ are as described supra.

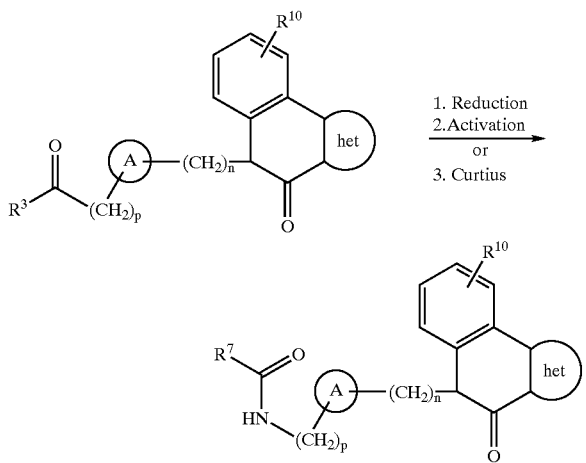

The compounds of formula I(n) may be converted to compounds of formula I(r). Such reactions are well known transformations, see, e.g., Larock, "Comprehensive Organic Transformations", pg. 421, VCH Publishers, New York, N.Y., 1989, hereafter referred to as "*Larock*".

The compound of formula I(n) may be may be reduced to the corresponding alcohol, activated (i.e. mesylation), reacted with an appropriate azide, reduced, and then acylated. Additionally, the Curtius rearrangement may be employed to give the compound of formula I(r). See the preparation/Example section for specifics.

The Curtius rearrangement is performed by converting the activated compound, in an appropriate solvent, with an appropriate azide, then an appropriate alcohol, to provide a compound of formula I(r). As the skilled artisan would appreciate, the activated compound, dissolved in an appropriate solvent, is first treated with an appropriate azide and optionally a catalyst to provide the intermediate. The intermediate is treated with an appropriate alcohol to obtain the compound of formula I(r). Once the reaction is complete, as measured by the consumption of the substrate, the resulting compound of formula I(r) may be isolated by standard extractions and filtrations. If desired, the resulting compound of formula I(r) may be further purified by chromatography or crystallization as appropriate.

Appropriate solvents must be capable of dissolving a sufficient amount of the activated compound and the azide for the reaction to proceed. Useful organic solvents include hexamethylphosphoramide, dimethylformamide, and preferably toluene.

The skilled artisan would appreciate that the Curtius rearrangement may be preformed via a number of azides and that reaction conditions may vary depending upon the azide used. For example if sodium azide, potassium azide, and the like are used the compound must first be converted to the activated acid with an appropriate activating agent, such as ethyl chloroformate or sulfuric acid. The substrate may need to be pretreated with the activating agent, such as the case with ethyl chloroformate, or may need to be added simultaneously. The skilled artisan would appreciate the potential for reaction at an ester site of the substrate, if the molecule is treated with the azide first as is the case in these circumstances.

Preferably, diphenylphosphoryl azide is used in the process of the present invention without an activating agent.

Appropriate alcohols are lower alkyl alcohols such as methanol, ethanol, propanol, isopropanol, butanol, benzyl, t-butanol, TMS-ethanol, and the like.

The reaction may be carried out over a large range of concentrations, from about 0.001 molar to about 2.0 molar of the azide, dependent upon the solubility of the particular azide in the chosen solvent. The reaction may also be performed on slurries of the azide so long as a sufficient amount of the azide is soluble in the solvent for the reaction to proceed. Preferably the process is performed at a concentration from about 0.1 molar to about 1.0 molar. A concentration of about 0.3 to about 0.4 molar is most preferred.

Reactions may be performed between about 80° C. and about 130° C., preferably between about 100° C. and about 120° C. Most preferably the reactants are combined at temperature of about 20° C. to about 30° C., then heated to about 80° C and about 120° C., the azide is then added, and the reactants are stirred for about 0.5 to about 1.5 hours at reflux. An appropriate alcohol is then added and heated to about 70° C. to about 90° C. for about 3 to about 24 hours, preferably from about 75° C. to about 85° C. for about 8 to about 12 hours.

Compounds of formula I where Y is $C(R^{11})(R^{11})NR^4R^5$ or $OR^2$, $R^2$ is $(CH_2)_2NR^4R^5$, and $R^5$ is $C_1$–$C_6$ alkyl, optionally substituted ($C_1$–$C_4$ alkyl)-aryl, optionally substituted ($C_1$–$C_4$ alkyl)-heterocycle, or $COR^7$, may be prepared from compounds of formula I(f) and I(h) as illustrated in Scheme 6 below where X is halide and het, n, p, $R^{11}$, $R^4$, $R^{10}$, and $R^{12}$ are as described supra.

Scheme 6

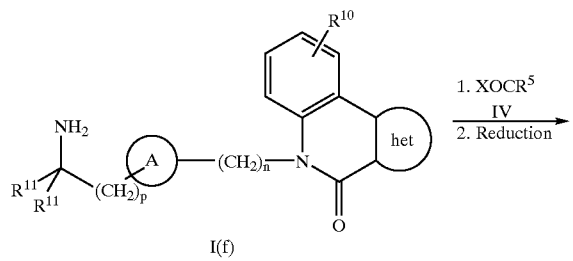

I(f)

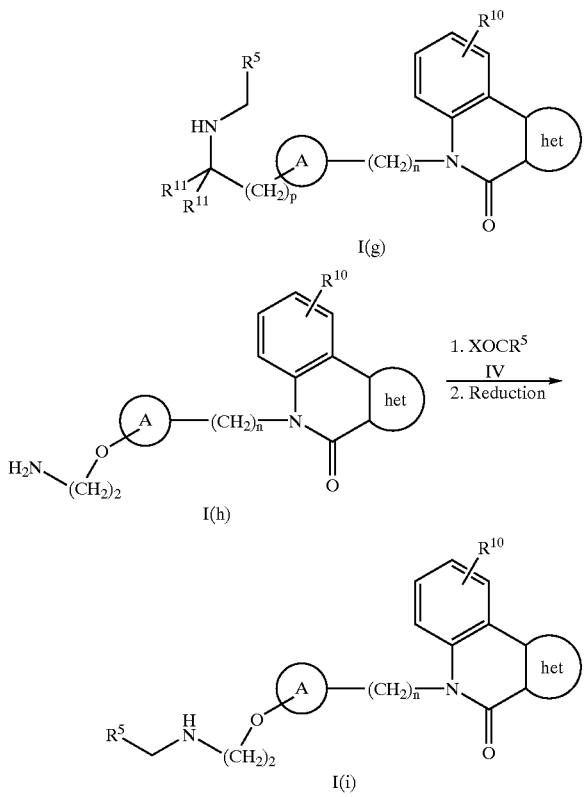

The compounds of formulas I(f) and I(h) may be reductively alkylated to form the corresponding compounds of formulas I(g) and I(i), respectively. Reductive alkylation of primary amines are well known transformations, see, e.g., *Larock*, pg. 434–435.

Once it is determined that the compound of formula IV has been substantially consumed, the intermediate is typically reacted in situ with a suitable reducing agent to provide the compounds of formula I(g) and I(i), respectively. The overall conversion may be performed at about 0° C. to the boiling point of the mixture but room temperature is a preferred reaction temperature. The formation of the compounds of formulas I(g) and I(i) may take from 15 minutes to 24 hours as measured by the consumption of the substrate.

A base is typically employed when the compound of formula I(f) or I(h) is an acid addition salt in order to convert the salt to its free amine form. Preferred bases for this purpose are N-methylmorpholine and triethylamine. A preferred Lewis acid catalyst is titanium(IV) isopropoxide. Suitable reducing agents include, but are not limited to, borane or complexes of borane, e.g., borane-pyridine, borane-t-butylamine, and borane-dimethylamine complex; and lithium aluminum hydride.

Compounds of formulas I(f) and I(h) may be converted to other compounds of the invention by methods well known in the chemical arts. Additional compounds of formula I may be prepared as follows, where Y is —E—NR$^4$R$^5$ or —E—OR$^2$, R$^2$ is (CH$_2$)$_2$NR$^4$R$^5$, R$^5$ is COR$^7$, and R$^7$ is NR$^4$R$^{6'}$ or R$^5$ is a moiety of the formula

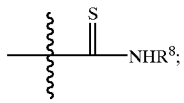

R$^{30}$ is R$^{6'}$ or R$^8$; and het, n, p, A, R$^4$, R$^{6'}$, R$^8$, R$^{10}$, and R$^{11}$ are as described supra.

Scheme 7

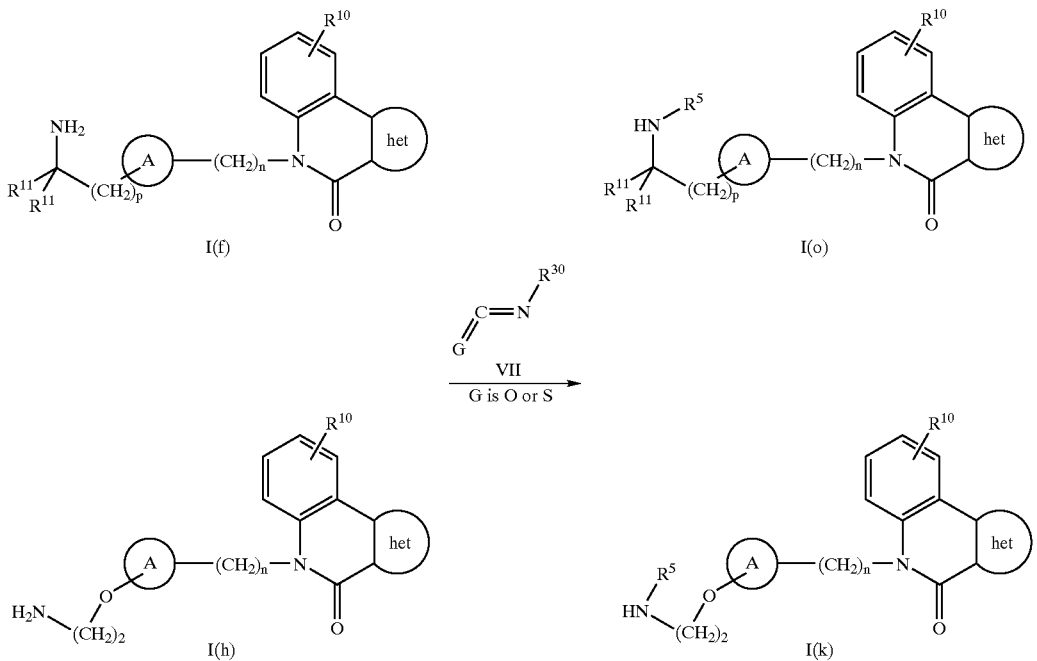

The primary amines of formulas I(h) and I(f) may be reacted, by methods well known in the art, with the isocyanates or isothiocyantes of formula VII to prepare the corresponding ureas and thioureas of formulas I(k) and I(o), see, generally, *March*, pages 802–803.

Compounds of formula I where Y is C(R$^{11}$)(R$^{11}$)NR$^4$R$^5$, and R$^5$ is SO$_2$R$^8$ can be prepared as described in Scheme 8, wherein het, n, p, A, R$^{11}$, R$^4$, R$^8$, and R$^{10}$ are as described supra.

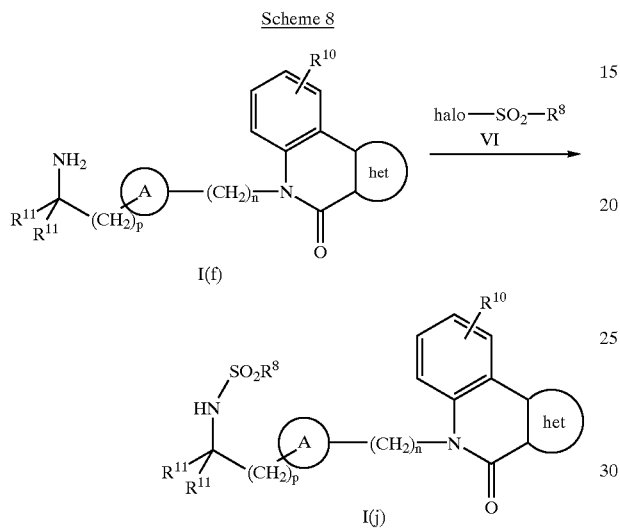

Scheme 8

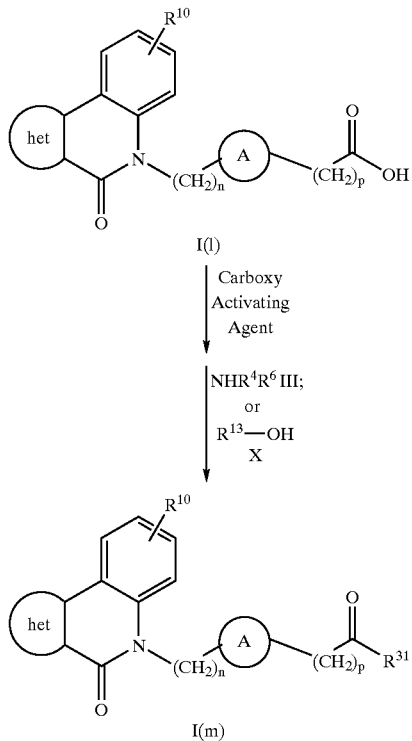

Scheme 9

Compounds of formula I(f) may be converted to other compounds of the invention via standard combinatorial synthetic techniques. For example, a compound of formula I(f) dissolved or suspended in a suitable solvent, optionally in the presence of a base, may be treated with a compound of formula VI to provide a compound of formula I(j) where R$^5$ is SO$_2$R$^8$. Typically a preferred and convenient solvent is dichloromethane. When a base is employed, triethylamine is typically preferred. Furthermore, when a base is employed, the base and compound of formula VI are typically employed in a slight stoichiometric excess. For example a 1.01 to 1.40 molar excess, relative to the compound of formula I(f), is generally employed. About 1.15 to about 1.25 fold molar excess is typically preferred. When a base is not employed, the compound of formula VI is typically employed in a relatively larger stoichiometric excess. For example, about a 1.5 to about a 3 molar excess, relative to the compound of formula I(f), is usually employed. About 1.8 to about 2.2 fold molar excess is typically preferred. The reaction is usually performed at a temperature range of about 0° C. to about the reflux temperature of the solvent for from 10 minutes to 18 hours. Preferably, the reaction is performed at about 15° C. to about 40° C. for from 5 minutes to about 1 hour.

Compounds of formula I where Y is C(O)R$^3$ and R$^3$ is OR$^{13}$ or NR$^4$R$^6$ may be prepared from compounds of formula I(l) as illustrated in Scheme 9 below wherein R$^{31}$ is NR$^4$R$^6$ or OR$^{13}$; and het, n, p, A, R$^4$, R$^6$, and R$^{13}$ are as described supra.

Compounds of formula I(l), prepared as described in Scheme 1, may also be converted to other compounds of the invention via solution or solid phase synthetic techniques. For example, acids of formula I(l) may be treated with activating agents to form the activated carboxylic acid derivatives of formula I(l) by methods well known in the chemical arts. See, e.g., *The Peptides, Peptide Synthesis* and the Examples and Preparations sections below.

Generally, preparation of compounds of formula 1(m) where R$^{31}$ is NR$^4$R$^6$ is performed in a manner similar to the reaction of compounds of formula I(f) or I(h) described in Scheme 6. Specifically, such compounds of formula I(m) may be prepared by dissolving or suspending a compound of the activated carboxylic acid derivatives of formula I(l) in a suitable solvent, optionally in the presence of a suitable base, and adding an amine of formula m. Typically a preferred and convenient solvent is dichloromethane. Preferred bases are triethylamine and piperidinylmethylpolystyrene resin. The amine is typically employed in a molar excess. For example, about a 1.5 to about a 3 molar excess, relative to the compound of the activated carboxylic acid derivatives of formula I(l) is usually employed. About 1.8 to about 2.2 fold molar excess is typically preferred. The reaction is usually performed in a temperature range of about 0° C. to about the reflux temperature of the solvent for from 10 minutes to 18 hours. Preferably, the reaction is performed at about 15° C. to about 40° C. for from 5 minutes to about 2.5 hours.

The compounds of formula I(m) where R$^{31}$ is OR$^{13}$ may be prepared by methods well known in the chemical arts. For instruction on the conversion of activated carboxylic acid derivatives to esters see, e.g., *Larock* at 978–979. Alternatively, these compounds of formula I(m) may be prepared directly from the acids of formula I(l) as taught in the *Larock* reference at pages 966–972.

The starting materials and compounds of the present invention may be obtained by a number of routes. For example, compounds of formula II may be prepared according to the routes shown in Schemes 8 and 9.

Where het, n, p, Y, A, and $R^{10}$ are as described supra, compounds of formula II may be prepared according to Scheme 10.

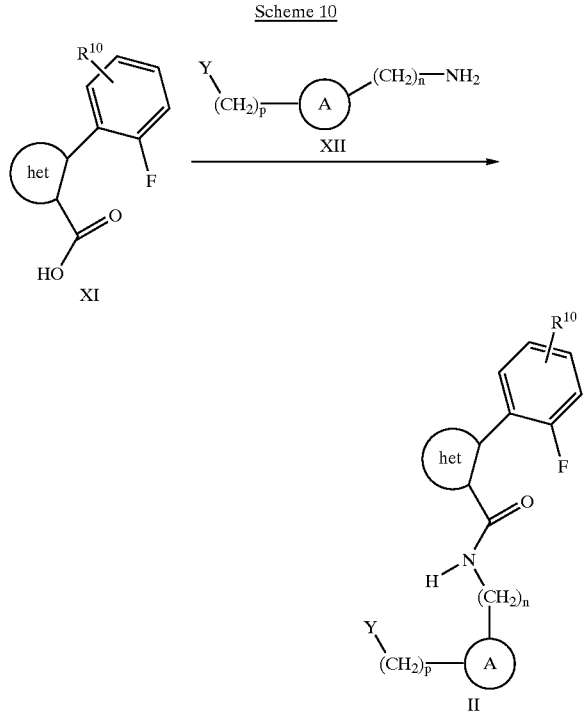

Compounds of formula XI may be converted to the corresponding acid halide by methods well known to one skilled in the art. Compounds of formula II may be prepared by dissolving or suspending an acid halide of a compound of formula XI in a suitable solvent and adding a compound of formula XII in a suitable solvent. Triethylamine or dimethylformamide is a convenient solvent and is typically preferred for the compound of formula XI. A 1:1 mixture of DMF and dichloromethane is a convenient solvent and is typically preferred for the amine of formula XII. This amide forming reaction is also preferably run in the presence of 4-dimethylaminopyridine (DMAP).

For compounds in which het is pyrazole, the addition of 1-(3-dimethyl-aminopropyl)-3-ethylcarbodiimide hydrochloride (EDCI) to the reaction is preferred. The compound of formula XI is preferably the corresponding carboxylic acid and is employed in an equimolar amount, relative to the compound of formula XII, but a slight excess (about a 0.05 to about 0.15 molar excess) is acceptable. DMAP is employed in a catalytic fashion. For example, about 5 molar percent to about 15 molar percent, relative to the compound of formula XII, is typically employed. A 10 molar percent is usually preferred.

Compounds of formula XII where Y is —E—C(O)$R^3$, —E—$NR^4$Pg, or —E—O(CH$_2$)2$NR^4$-Pg, which are used to prepare compounds of formula I(l), I(n), I(f), and I(h) are well known in the art and to the extent not commercially available, are readily synthesized-by standard procedures commonly employed in the art.

Compounds of formula XII(a) where Y is —E—$NR^4R^5$ and p, n, A, E, $R^4$, and $R^5$ are as described supra can be prepared as illustrated in Scheme 11 from compounds of formula (i) wherein Y is —E—C(O)$R^3$ and $R^3$ is hydrogen.

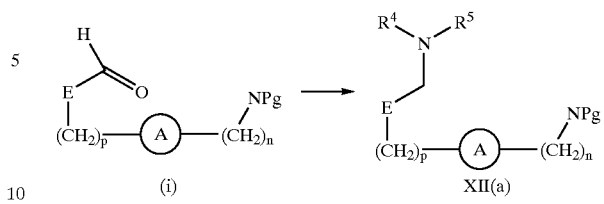

Compounds of formula XII(a) may be prepared from compounds of formula (i) in a manner similar to that as taught in the *Larock* reference at pages 421–430. For an example of this transformation, see Preparation 124. Compounds of formula (i) are well known in the art and to the extent not commercially available, are readily synthesized by standard procedures commonly employed in the art.

Compounds of formula XII(c), XII(d), and XII(e) where Y is —E—S(O)q$R^3$, and $R^3$, p, A, and E are as described supra can be prepared as illustrated in Scheme 12.

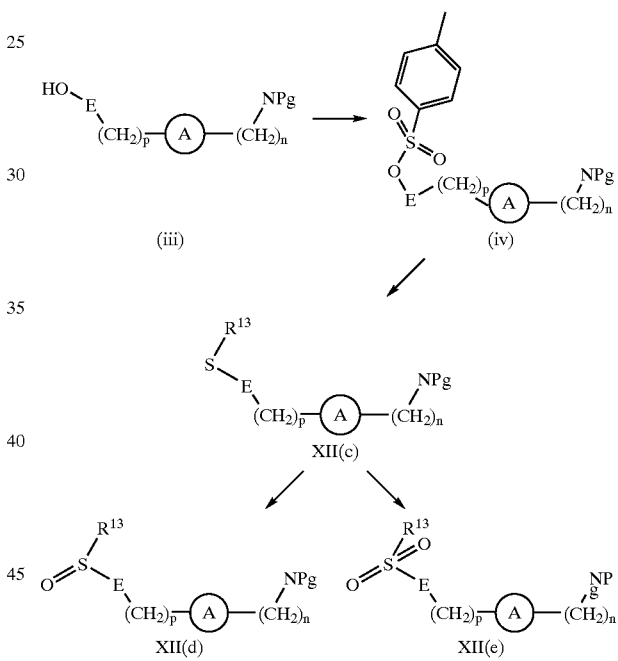

Compounds of formula XII(c) may prepared from compounds of formula (iv) by methods well known to the skilled artisan. One manner is to combine the compound of formula (iv) with sodium hydride in an appropriate solvent, preferably dimethylformamide, and combining with the appropriate thiol. The compound of formula XII(c) may be further oxidized to form the compounds of formulas XII(d) and XII(e) in a manner similar to that as taught in Preparation 175 and Examples 368, and 467–468. Compounds of formula (iii) can be converted to compounds of formula (iv) in a manner similar to that of Preparation 169. Compounds of formula (iii) are well known in the art and to the extent not commercially available, are readily synthesized by standard procedures commonly employed in the art.

Furthermore, the transformations described in Schemes 3–8 may be performed before the cyclization described in Scheme 1 and 2 to provide the compounds of formula XI with a fully elaborated R substituent. Additionally, the skilled artisan would appreciate that the transformations of Schemes 11–13 may be performed after the cyclization described in Schemes 1 and 2.

Additionally, compounds of formula XII may be prepared according to the following routes where, unless otherwise provided, $R^b$ is the substituent from the carbon atom of het, $R^a$ is the substituent from the saturated nitrogen of het, the second heteroatom is an oxygen or sulfur, and other variables are as described supra.

Compounds of formula XI(a), where het is [4,3-c] isoxazole, may be prepared in a manner similar to that described in the literature, for example, see Chen Y P, et. al, *Heterocycles,* 1995, 41, 175, and Chantegrel B, et. al, *J. Org. Chem.,* 1984, 49, 4419–4424.

Route 1

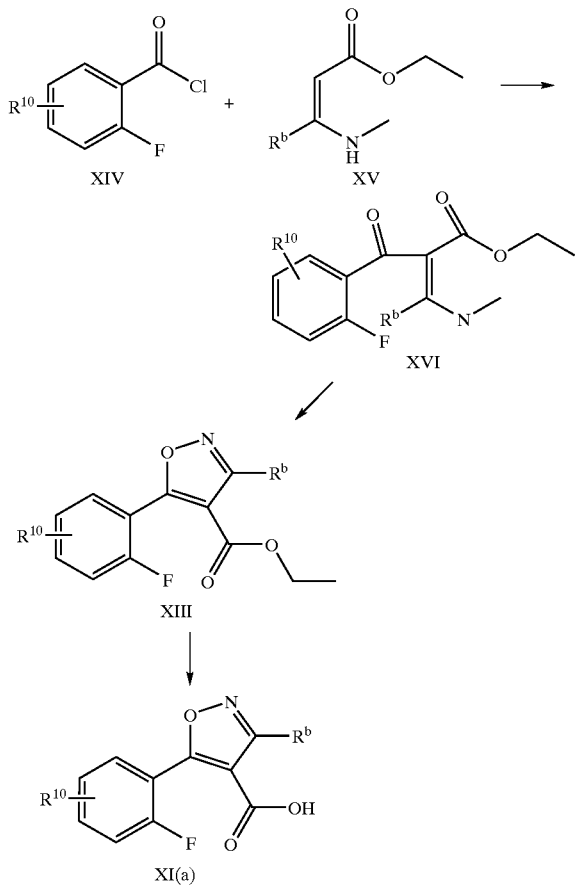

Compounds of formula XVI may be prepared by dissolving or suspending a compound of formula XV and a suitable base in a suitable solvent and adding a compound of formula XIV in a suitable solvent, dropwise. Toluene is a convenient solvent and is typically preferred. Triethylamine is the preferred base. The compound of formula XIV is typically and preferably employed in an equimolar amount, relative to the compound of formula XV, but a slight excess is acceptable.

The reactants are preferably combined at about 0° C. and the resulting solution is typically warmed to room temperature and mixed for from about 18 hours to about 24 hours.

The compound of formula XVI may then be converted to the compound of formula XIII by dissolving or suspending a compound of formula XVI in a suitable acidic solvent and adding hydroxylamine hydrochloride. Glacial acetic acid is a convenient acidic solvent and is typically preferred. The ester group is then hydrolyzed to the corresponding carboxylic acid of formula XI(a) through standard procedures commonly employed in the art, see for example, *Larock,* pgs 981–985.

The reactants are preferably combined at about room temperature then heated to reflux for from about 30 minutes to about 60 minutes. Preferably the reaction is heated to reflux from about 40 to 45 minutes.

Compounds of formula XIV and XV are known in the art and, to the extent not commercially available, are readily synthesized by standard procedures commonly employed in the art.

Compounds of formula XI(b) and (c), wherein het is [4,5-c]isoxazole, may be prepared according to route 2.

Route 2

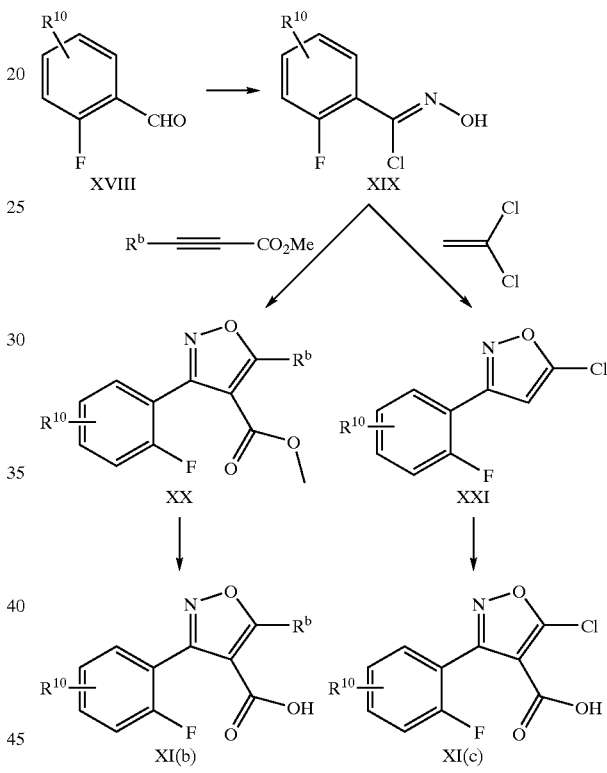

Generically, the compound of formula XVIII and hydroxylamine hydrochloride are suspended or dissolved in a suitable solvent and a suitable base is added. After the reaction is complete, the solution is acidified with a suitable acid and the resulting oxime is purified by known methods. Typically a preferred and convenient solvent is water/methanol. Typically a preferred and convenient base is sodium hydroxide.

The reactants are preferably combined at about 0° C. and the resulting solution is typically mixed for about 1 hour at about 25–30° C., until the reaction is complete. After the reaction is complete, the solution is acidified with a suitable acid, preferably hydrochloric acid, and the resulting oxime is purified by known methods.

The purified oxime is dissolved or suspended in a suitable solvent, preferably DMF, and is then reacted with N-chlorosuccinimide (NCS). Preferably, NCS is added in small portions to control the expected exotherm. The initial NCS addition results in a slight temperature decrease. If the reaction does not self-initiate within about 10 minutes, as indicated by a slight temperature rise, hydrogen chloride may be bubbled into the DMF solution. If the reaction does not begin within about 10 to 15 minutes, heating the solution to about 45–60° C. is desirable. Once the reaction begins, the temperature is preferably maintained below about 35° C. for benzaldoximes with electron-donating substituents and below about 50° C. for strong electron-withdrawing substituents. Completion of the reaction is indicated by cessation of the exotherm.

The compound of formula XIX is then converted to the compound of formula XX by methods well known to the skilled artisan. The compound of formula XIX and an appropriate methyl-2-butynoate are dissolved or suspended in a suitable solvent, preferably ethyl ether, and Et$_3$N is added. The reactants are combined at about room temperature and mixed from about 12 to 24 hours, until the reaction is complete.

The ester group of the compounds of formula XX is then hydrolyzed to the corresponding carboxylic acid of formula XI(b) through standard procedures commonly employed in the art, see for example, *Larock*, pgs 981–985.

Compounds of formula XIX may be prepared in a manner similar to that described in the literature, for example, see Liu K, Shelton B R, Howe, R K, *J. Org. Chem.*, 1980,45, 3916–3918.

Compounds of formula XXI may be prepared in a manner similar to that described in the literature, for example, see Stevens R L, Albizati K F, *Tetrahedront Lett.* 1984,25,4587. For an example of this transformation, see Preparation 3.

Compounds of formula XI(c) may be prepared from compounds of formula XXI in a manner similar to that described in the literature, for example, see Micetich R G, Chin C G, *Can. J. Chem.* 1970, 48, 1371. For an example of this transformation, see Preparation 4.

Compounds of formula XVIII are known in the art and, to the extent not commercially available, are readily synthesized by standard procedures commonly employed in the art.

The isoxazole compounds of formula XI may be converted to the isothiazole by methods well known in the art, for example see McGregor D N, Corbin U, Swigor J E, and Cheney L C, "Synthesis of isothiazoles: The transformation of isoxazoles into isothiazoles," *Tetrahedron*, 1969, 25, 389–395.

Compounds of formula XI(d) where het is pyrazolyl may be prepared as illustrated below.

Route 3

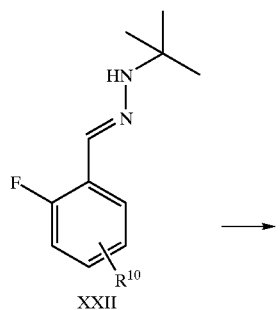

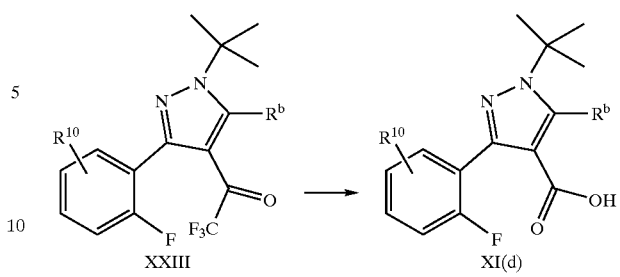

Compounds of formula XXIII may be prepared by combining the compound of formula XXII with ethyl trifluoroacetyl vinyl ether in a manner similar to that described in the literature, for example, see Kamitori et al, *J. Het. Chem.*, 1993, 30, 389. For examples of this transformation, see Preparations 7–8.

Additionally, compounds of formula XXII may be prepared from aldehyde hydrazones and ethyl propiolate as is further described by Kamitori et al, *Heterocycles*, 1994, 38, 21.

The trifluoromethyl ketone of formula XXIII may be converted to the corresponding carboxylic acid of formula M(d) in a manner similar to that described in the literature, for example, see Delgado A, Clardy J, Tetrahedron Lea. 1992, 33, 2789–2790.

Compounds of formula XXII are known in the art and, to the extent not commercially available, are readily synthesized by standard procedures commonly employed in the art.

Compounds of the invention where het is oxazolyl or imidazolyl may be prepared as illustrated below.

Route 4

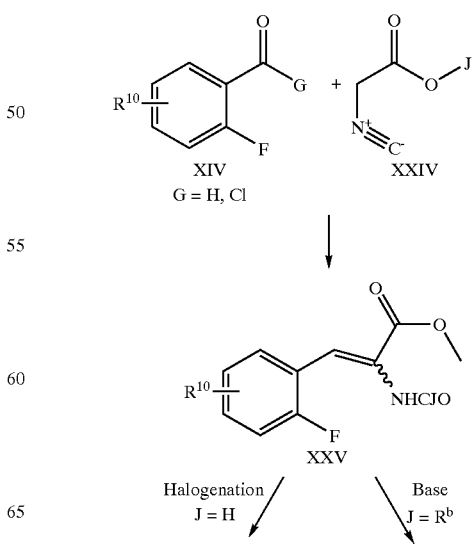

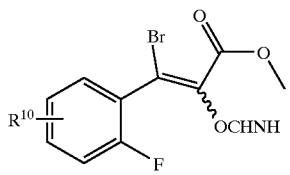

XXVI

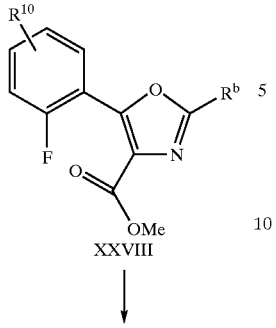

XXVIII

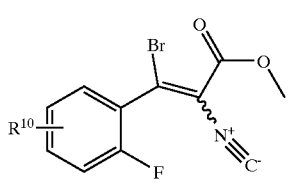

XXVII

1) $R^a$—$CH_2$—$NH_2$
2) Hydrolyze

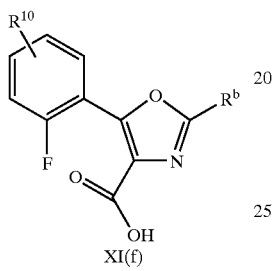

XI(f)

XI(e)

Compounds of formula XI(e) may be prepared in a manner similar to that described in the literature, for example, see Nunami et al, *J. Org. Chem.* 1994, 59, 7635–7642.

The compound of formula XXV is converted to the compound of formula XXVIII by methods well known to the skilled artisan. The compound of formula XXV is dissolved or suspended in a suitable solvent, preferably tetrahydrofuran, and a base is added, preferably $Et_3N$. The reactants are combined at about room temperature, preferably under an inert atmosphere, and mixed from about 30 minutes to 2 hours, until the reaction is complete.

The ester group of the compounds of formula XXVIII is then hydrolyzed to the corresponding carboxylic acid formula XI(f) through standard procedures commonly employed in the art, see for example, *Larock*, pgs 981–985.

Compounds of formula XIV and XXIV are known in the art and, to the extent not commercially available, are readily synthesized by standard procedures commonly employed in the art.

Compounds of the invention where het is imidazolyl may, additionally, be prepared as illustrated below:

Route 5

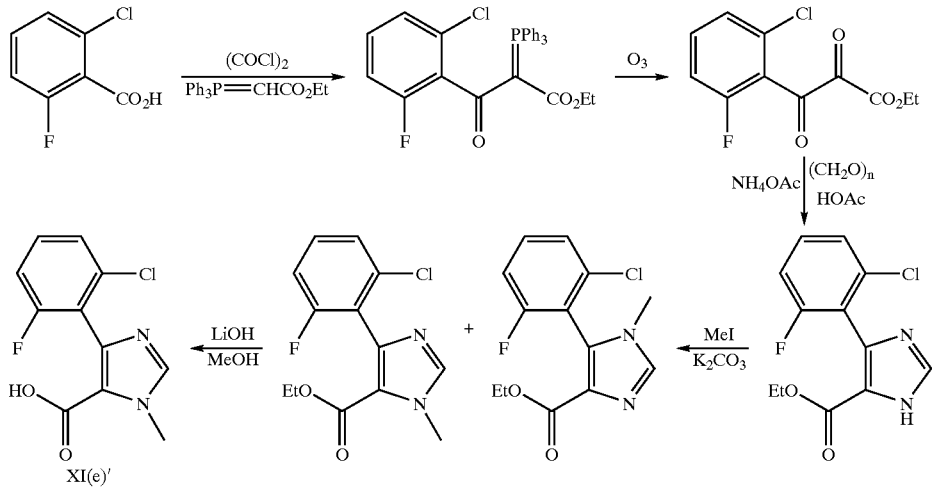

XI(e)'

The compound of formula XI(e)' may be prepared by methods well known in the art. For specific conditions, see the preparation section (preparations 400–405).

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The optimal time for performing the reactions of Schemes 1–8 and Routes 1–5 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds are preferably isolated and purified before their use in subsequent reactions. Some compounds may crystallize out of the reaction solution during their formation and then collected by filtration, or the reaction solvent may be removed by extraction, evaporation, or decantation. The intermediates and final products of formula I may be further purified, if desired by common techniques such as recrystallization or chromatography over solid supports such as silica gel or alumnina.

The skilled artisan will appreciate that not all substituents are compatible with all reaction conditions. These compounds may be protected or modified at a convenient point in the synthesis by methods well known in the art.

PREPARATION 1

2-((1R,3R)-3-Hydroxycyclohexyl)malonic Acid Dibenzyl Ester

To a −78° C. solution of 2-(1(R)-3-oxo-cyclohexyl) malonic acid dibenzyl ester (see Arai, T.; Yamada, Y. M. A.; Yamamoto, N.; Sasai, H.; Shibasaki, M. *Chem. Eur. J.* 1996, 2, 1368–1372.) (3.80 g, 10.0 mmol) in TBF (50 mL) under $N_2$ was added L-selectride (11.0 mL at 1.0 M, 11.0 mmol) dropwise and the mixture was stirred for 2 h at −78° C. EtOAc (100 mL) and $H_2O$ (100 mL) were added and the mixture was warmed to room temperature. Dilution with more EtOAc followed by washing with 1N NaOH, saturated $NH_4Cl$, brine, drying ($MgSO_4$), and column chromatography (silica gel, hexanes:EtOAc gradient) gave title compound (2.92 g, 76%). Mass spectrum (ES−)(m/z) 381.2 [M−1].

PREPARATION 2

(1R,3R)-(3-Hydroxycyclohexyl)acetic Acid Benzyl Ester

A solution of a compound from preparation 1 (2.30 g, 6.02 mmol), LiCl (0.511 g, 12.0 mmol), $H_2O$ (0.217 mL, 12.0 mmol), and DMSO (20 mL) was lowered into a 165° C. oil bath for 2 h. The reaction was cooled to room temperature and diluted with EtOAc. Washing with $H_2O$ and brine, drying ($MgSO_4$), and column chromatography (silica gel, hexanes: EtOAc gradient) gave title compound (1.12 g, 75%).

$^1H$ NMR ($CDCl_3$, 400 MHz) δ 7.34–7.25 (m, 5H), 5.06 (s, 2H), 4.02 (m, 1H), 2.21 (m, 2H), 1.71–1.59 (m, 4H), 1.50–1.40 (m, 4l), 1.30 (m, 1H), 1.00 (m, 1H) ppm.

PREPARATION 3

(1R,3S)-(3-Azidocyclohexyl)acetic Acid Benzyl Ester

To a solution of a compound from preparation 2 (1.05 g, 4.24 mmol), triphenylphosphine (1.33 g, 5.07 mmol), and hydrazoic acid (6.4 mL, at 1.0 M, 6.4 mmol) in toluene (7 mL) was added DEAD (1.0 mL, 6.4 mmol) dropwise and stirred for 20 min. The mixture was diluted with EtOAc, washed with 0.1 N NaOH, $H_2O$ and brine, dried ($MgSO_4$), and chromatographed (silica gel, hexanes: EtOAc gradient) to give the title compound (0.916 g, 80%).

PREPARATION 4

2-((1R,3S)-3-Azidocyclohexyl)-N-(3,4,5-trimethoxyphenyl)acetamide

A solution of a compound from preparation 3 (215 mg, 0.788 mmol) and NaOH (0.32 mL at SM, 1.6 mmol) in MeOH (5 mL) was heated at 50–55° C. for 3 h then cooled to room temperature. The reaction was diluted with $H_2O$ and acidified with aqueous HCl to pH 2. Extraction with EtOAc and subsequent washing (brine) and drying ($Na_2SO_4$) gave the crude carboxylic acid. A mixture of the crude acid, 3,4,5-trimethoxyaniline (288 mg, 1.58 mmol), EDCI (262 mg, 1.58 mmol), DMAP (20 mg, 0.16 mmol) in $CH_2Cl_2$ (5 mL) was stirred for 17 h. The mixture was diluted with $CH_2Cl_2$ and extracted with 1N HCl and brine then dried ($MgSO_4$). Column chromatography (silica gel, hexanes: EtOAc gradient) gave the title compound (255 mg, 93%). Mass spectrum (ES+) (m/z) 349.2 [M+1]. MS (ES+): [M+1] 349.2 m/z.

PREPARATION 5

2-((3S,1R)-3-{[3-(2-Chloro-6-fluorophenyl)-5-methylisoxazol-4-yl]carbonylamino}cyclohexyl)-N-3,4,5-trimethoxyphenyl)acetamide A mixture of a compound from preparation 4 (250 mg, 0.72 mmol), 10% palladium on carbon (76 mg, 0.07 mmol), and EtOH (5 mL) was stirred under an atmosphere of hydrogen (balloon). After 2 h the reaction was filtered through a pad of celite with the aid of MeOH and concentrated. Benzene was added to the resulting residue followed by concentration. The residue was dissolved in $CH_2Cl_2$ (5 mL) followed by addition of 3-(2-chloro-6-fluorophenyl)-5-methylisoxazole-4-carbonyl chloride (236 mg, 0.87 mmol) and DMAP (175 mg, 1.44 mmol) and stirred for 16 h. The mixture was applied to a silica gel column and elution (hexanes: EtOAc gradient) gave the title compound (256 mg, 64%). Mass spectrum (ES+) (m/z) 560.2 [M+1].

PREPARATION 6

N-(3,4,5-Trimethoxyphenyl)-2-(3-oxocyclopentyl)acetamide

To a solution of 1.0 g (7 mmol) of 3-oxocyclopentyl acetic acid in dichloromethane (18 mL) and DMP (1 mL), was added 0.68 mL (7.7 mmol) oxalyl chloride. After 30 min, the solvent was removed in vacuo. The residue was dissolved in dichloromethane (20 mL), cooled to 0–5° C., and 1.29 g of 3,4,5-trimethoxyaniline (0.63 mmol) was added followed by 0.68 mL of pyridine (8.4 mmol). After 15 min, the reaction was allowed to warm to ambient temperature. After 2 h, the reaction was rinsed with 1N HCl, followed by aq. sodium bicarbonate, and water (3×). The organic layer was dried, the solvent removed in vacuo and the residue chromatographed on a silica gel with 2% methanol in methylene chloride to yield 0.25 g of the title compound. MS(ES+)m/z=308.

PREPARATION 7

N-(3,4,5-Trimethoxyphenyl)-2-(3-hydroxycyclopentyl)acetamide

A solution of 1.07 g (3.5 mmol) of a compound from preparation 6 and 0.136 g of sodium borohydride (3.5 mmol) in methanol (60 mL) was stirred 12 h. The solvent was removed in vacuo, the residue dissolved in ethyl acetate and rinsed with 1N HCl followed by water. The organic layer was dried and concentrated in vacuo. The residue was chromatographed on silica gel and eluted with 5% methanol in dichloromethane to yield 0.45 g of the title compound. MS(ES+)m/z=310. Cis/trans racemic

PREPARATION 8

N-(3,4,5-Trimethoxyphenyl)-2-(3-methylsulfonyloxycyclopentyl)acetamide

A solution of 0.45 g (1.46 mmol) of a compound from preparation 7 and 0.135 mL (1.75 mmol) of methanesulfonyl chloride and 0.27 mL (1.9 mmol) of triethylamine in dichloromethane (15 mL) was stirred 2 h. The solvent was removed in vacuo and replaced with ethyl acetate. The organic layer was rinsed with 1N HCl followed by aq. sodium bicarbonate, then brine and dried to yield 0.115 g of the title compound. MS(ES+)m/z=387.9.

PREPARATION 9

N-(3,4,5-Trimethoxyphenyl)-2-(3-azidocyclopentyl)acetamide

A solution of 0.6 g (1.55 mmol) of a compound from preparation 8, and 0.21 g (4.3 mmol) of lithium azide in DMF (12 mL) was stirred 12 h. Water and ice were added to the reaction, and the mixture was extracted with ethyl acetate. The organic layer was washed 5 times with water, dried, concentrated in vacuo, and the residue was chromatographed on silica gel and eluted with hexane/ethyl acetate 3:2 to yield 0.13 g of cis and 0.21 g of trans of the title compound. MS(ES+) m/z=335.

PREPARATION 10 cis-N-(3,4,5-Trimethoxyphenyl)-2-(3-aminocyclopentyl)acetamide

To a solution of 0.13 g (0.39 mmol) of a cis compound from preparation 9 in ethyl acetate (30 mL) was added 0.026 g of 10% palladium on carbon and the mixture was hydrogenated at 50 psi over 1.5 h. The catalyst was removed by filtration over celite and the solvent was removed in vacuo to yield 0.128 g of the title compound. MS(ES+) m/z=309. Cis (racemic)

PREPARATION 11 trans-N-(3,4,5-trimethoxyphenyl)-2-(3-aminocyclopentyl)acetamide

In the same manner as the preparation 10, 0.21 g of a tans compound from preparation 9 was converted to 0.20 g of the title compound. MS(ES+)m/z=309. Trans (racemic)

PREPARATION 12

2-(3-{[3-(2-Chloro-6-fluorophenyl)-5-methylisoxazol-4-yl]carbonylamino}cyclopentyl)-N-(3,4,5-trimethoxyphenyl)acetamide A solution of 0.123 g (0.42 mmol)of a compound from preparation 10, 0.03 g (0.46 mmol) of 3-(2-chloro-6-fluorophenyl)-5-methylisoxazole-4-carbonyl chloride, and 0.07 mL (0.5 mmol) of triethylamine in dichloromethane (10 mL) was stirred for 12 h. The solvent was removed in vacuo and replaced with ethyl acetate. The organic layer was washed with 1N HCl, then aq. NaHCO$_3$, followed by brine and dried. The solvent was removed in vacuo to yield 0.255 g of the title compound. MS(ES+) m/z=545.8. cis (racemic)

PREPARATION 13

2-(3-{[3-(2-Chloro-6-fluorophenyl)-5-methylisoxazol-4-yl]carbonylamino}cyclopentyl)-N-(3,4,5-trimethoxyphenyl)acetarmide In the same manner as preparation 12, 0.2 g (0.65 mmol) of a compound from preparation 11 was converted to 0.324 g of the title compound. MS(ES+)m/z=545.8. Racemic

PREPARATION 14

N-((1S,3R)-3–Cyanomethylcyclopentyl)(t-butoxy)carboxamide

To a solution of 8.2 g (0.0222 mol) of N-[t-butoxycarbonyl]-2-(p-toluenesulfonyloxymethyl)cyclopentylamine in DMF (250 mL) was added 3.3 g (0.067 mmol) of NaCN and the suspension was heated at 80° C. for 4 h. The solvent was removed in vacuo at 40° C. and the residue was slurried in brine. The aqueous layer was extracted with ethyl acetate, dried and the solvent was removed in vacuo to yield 5.7 g of the title compound. MS(ES+)m/z=225. (one enantiomer)

PREPARATION 15

2-{(3S,1R)-3-[(t-Butoxy)carbonylamino]cyclopentyl}acetic Acid

A suspension of 2.0 g (8.9 mmol) of a compound from preparation 14 in 3N KOH (32 mL) and EtOH (12 mL) was heated at reflux for 6 h (solution). The alcohol was removed in vacuo and the reaction was cooled and neutralized with 3N HCl. The product was separated by filtration, rinsed with water and dried in vacuo at 40° C. to yield 1.33 g of the title compound.
MS(ES+)m/z=244.

PREPARATION 16

2-{(3S,1R)-3-[(t-Butoxy)carbonylamino]cyclopentyl-N-(3,4,5-trimethoxyphenyl)acetamide To a solution of 0.1 g (0.4 mmol) of a compound from preparation 15 in TBF/DMF 1:1 (5 mL) was added 0.061 g (0.44 mmol) of 1-hydroxy-7-azabenzotriazole and 0.086 g (0.44 mmol) of EDCI. After 40 min, 0.083 g (0.44 mmol) of 3,4,5-trimethoxyaniline was added. After 3.25 h, the solvent was removed in vacuo and replaced with ethyl acetate. The organic layer was rinsed with 1N HCl, aq. NaHCO$_3$, then 3× with water. The organic layer was dried and the solvent was removed in vacuo to yield 0.144 g of the title compound. MS(ES+)m/z=409.

PREPARATION 17

2-((3S,1R)-3-Aminocyclopentyl)-N-(3,4,5-trimethoxyphenyl)acetamide

A solution of 0.48 g (0.362 mmol) of a compound from preparation 16 in TFA (10 mL) was stirred for 1 h, after which the TFA was removed in vacuo and replaced with ethyl acetate. The organic layer was rinsed with 1N NaOH followed by brine and dried. The organic layer was removed in vacuo to yield 0.3 g of the title compound. MS(ES+)m/z=309.

PREPARATION 18

2-((3S,1R)-3-{[3-(2-Chloro-6-fluorophenyl)-5-methylisoxazol-4-yl]carbonylamino}cyclopentyl)-N-(3,4,5-trimethoxyphenyl)acetamide In the same manner as preparation 12, 0.32 g (1.04 mmol) of a compound from preparation 17 yielded 0.52 g of the title compound. MS(ES+)m/z=546.

PREPARATION 19

N-(t-Butoxycarbonyl)-3-aza-2-oxabicyclo[3.2.1]nonane

A solution of 0.59 g (4.8 mmols) of 2-oxo-3-azabicyclo-[3.2.1]nonane, 2.07 g (9.6 mmol) of (BOC)$_2$O and 1.173 g (9.6 mmol) of DMAP in CH$_2$Cl$_2$ (15 mL) was stirred 12 h. The solvent was removed in vacuo and replaced with ethyl acetate. The organic layer was rinsed with 1N HCl followed by brine, dried and the solvent removed in vacuo to yield 0.495 g of the title compound. MS(ES+)m/z=225.9

PREPARATION 20 cis-3-{[(t-Butoxy)carbonylamino]methyl}cyclopentanecarboxylic Acid

To a solution of 2.22 g (0.98 mmol) of a compound from preparation 19 in TBF (113 mL) was added H$_2$O (32 mL) and the solution cooled to 5° C. Water (30%, 11.95 mL, 9.8 mmol) was added followed by 2.08 g (4.9 mmol) of LiOH and the reaction was allowed to warm to ambient temperature. After 2 h, the reaction was quenched with sodium sulfite solution (10%) and the THF was removed in vacuo. With cooling, the reaction was acidified with 6N HCl and extracted with ethyl acetate, dried and the solvent removed in vacuo to yield 1.583 g of the title compound. MSES+)m/z=243.9.

PREPARATION 21 cis-N-(3-{[(t-Butoxy)carbonylamino]methyl}cyclopentyl)(phenylmethoxy)carboxamide To warm solution of 0.244 g (1.0 mmol) of a compound from preparation 20 in toluene (8 mL) was added 0.2 mL (1.4 mmol) of Et$_3$N followed by 0.3 mL (1.4 mmol) of diphenylphosphoryl azide. The reaction was stirred at ambient temperature for 2.5 h and refluxed for 1.5 h. The solvent was removed in vacuo and replaced with ethyl acetate which was rinsed with aq. NaHCO$_3$, aq. KHSO$_4$ and brine. The solvent was removed in vacuo and the residue was chromatographed on silica gel with 0.5–1% MeOH/CH$_2$Cl$_2$ to yield 0.264 g of the title compound. MS(ES+)m/z=349.

PREPARATION 22 cis-N-[(3-Aminocyclopentyl)methyl](t-butoxy)carboxamide

A suspension of 0.264 g (0.76 mmol) of a compound from preparation 21 and 0.034 g of Pd/C 10% in MeOH (40 mL) was reduced at 1.0 atm. of H$_2$ over 2.5 h. The catalyst was removed by filtration and the solvent was removed in vacuo to yield 0.187 g of the title compound. MS(ES+)m/z=215.

Preparation 23 cis-N-[(3-{[3-(2-chloro-6-fluorophenyl)-5-methylisoxazol-4-yl]carbonylamino}cyclopentyl)methyl](t-butoxy)carboxamide To a suspension of 0.187 g (0.873 mmol) of a compound from preparation 22 in dichloromethane (10 mL) was added 0.263 g (0.96 mmol) of 3-(2-chloro-6-fluorophenyl)-5-methylisoxazole-4-carbonyl chloride followed by 0.2 mL (1.4 mmol) of Et$_3$N. After 70 min, the solvent was removed in vacuo and replaced with ethyl acetate. The organic layer was rinsed with 1N HCl followed by aq. NaHCO$_3$, dried and the solvent was removed in vacuo to give a residue which was chromatographed on silica gel with hexane/ethyl acetate 3-1 to yield 0.156 g of the title compound. MS(ES+)m/z=452.

Preparation 24 cis-N-{[3-(9-chloro-3-methyl-4-oxo-5H-isoxazolo[4,3-c]quinolin-5-yl))cyclopentyllmethyl}(t-butoxy)carboxamide To a solution of 0.136 g (0.3 mmol) of a compound from preparation 23 in DMF (7.0 mL) at 0–5° C. was added 0.6 mL (0.3 mmol) of KHMDS (0.5N in THF). After 2 min, cooling was removed. After 3 additional min, 1N HCl was added and the mixture was extracted with ethyl acetate. The organic layer was rinsed with water, dried and concentrated to a foam in vacuo which was chromatographed on silica gel with hexane/ethyl acetate 3:1 to yield 0.057 g of the title compound. MS(ES+)m/z=432.

PREPARATION 25

2-(3-Aminocyclopentyl)ethanenitrile

In the same manner as preparation 17, 0.3 g (4.5 mmol) of a compound from preparation 14 was deprotected with TFA to yield 0.087 g of the title compound. MS(ES+)m/z=125.

PREPARATION 26

N-[(1R,3S)-3-(cyanomethyl)cyclopentyl][3-(2-chloro-6-fluorophenyl)-5-methylisoxazol-4-yl]carboxamide In the same manner as preparation 18, 0.08 g (0.65 mmol) of a compound from preparation 26 was acylated with 3-(2-chloro-6-fluorophenyl)-5-methylisoxazole-4-carbonyl chloride to yield a residue which after chromatography on silica gel with hexane/ethyl acetate 1:1 yielded 0.177 g of the title compound. MS(ES+)m/z=362.

PREPARATION 27

2-[(3S,1R)-3-(9-chloro-3-methyl4-oxo-5H-isoxazolo[4,3-c]quinolin-5-yl))cyclopentyl]ethanenitrile In the same manner as preparation 24, 0.166 g (0.46 mmol) of a compound from preparation 27 was cyclized to

PREPARATION 28

2-[(3S,1R)-3-(9-Chloro-3-methyl-4-oxo-5H-isoxazolo[4,3-c]quinolin-5-yl))cyclopentyl]acetic Acid A suspension of 0.086 g (0.25 mmol) of a compound from preparation 27 in HCl conc. (40 mL) was refluxed for 6 h, after which the reaction was concentrated to a residue in vacuo at 40° C. The residue was taken into diethyl ether, the insolubles filtered and discarded, and the filtrate was extracted with 1N NaOH. The basic layer was acidified with 1N HCl, extracted with ethyl acetate, dried and concentrated in vacuo to yield 0.059 g of the title compound. MS(ES+) n/z=361.

PREPARATION 29

N-[3(1S,3S)-3-(2-aminoethyl)cyclopentyl](t-butoxy)carboxamide 0.5 g (2.2 mmols) of a compound from preparation 14 was reduced with 0.065 g of $PtO_2$ in EtOH (50 mL) at 60 psi of $H_2$ at 40° C. over 12 h. The catalyst was removed by vacuum filtration, and the solvent was removed in vacuo to yield 0.421 g of the title compound. MS(ES+)m/z=229.

PREPARATION 30

N-{(1S,3S)-3-[2-(Phenylcarbonylaniino)ethyl]cyclopentyl}(t-butoxy)carboxamide In a manner similar to the acylation of a compound from preparation 24, 0.172 g (0.75 mmol) of a compound from preparation 29 was acylated with benzoyl chloride and the residue formed was chromatographed on silica gel with hexane/ethyl acetate 2:1 to yield 0.127 g of the title compound. MS(ES+)m/z=333.

PREPARATION 31

N-{(1S,3S)-3-[2-(Phenylcarbonylamino)ethyl]cyclopentyl }[3-(2-chloro-6-fluorophenyl)-5-methylisoxazol-4-yl]carboxamide In a manner similar to preparation 17, 0.127 g (0.36 mmol) of a compound from preparation 30 was deprotected, followed by acylation with 3-(2-chloro-6-fluorophenyl)-5-methylisoxazole-4-carbonyl chloride in the same manner as the preparation of a compound from preparation 12 to yield 0.15 g of the title compound. MS(ES+)m/z=470.

PREPARATION 32

N-((1S,3S)-3-{2-[(3,4,5-Trimethoxyphenyl)carbonylamino]ethyl}cyclopentyl)(t-butoxy)carboxamide In the same manner as preparation 30, 0.1 g (0.44 mmol) of a compound from preparation 29 was acylated with 3,4,5-trimethoxybenzoyl chloride to yield 0.16 g of the title compound. MS(ES+)m/z=423.

PREPARATION 33

N-{(1S,3S)-3-[2-((3,4,5-Trimethoxyphenyl)carbonylamino)ethyl]cyclopentyl }[3-(2-chloro-6-fluorophenyl)-5-methylisoxazol-4-yl]carboxamide In a manner similar to preparation 31, 0.16 g (0.38 mmol) of a compound from preparation 32 yielded 0.174 g of the title compound. MS(ES+)m/z=560.

PREPARATION 34

((3S,1R)-3-{[(t-Butoxy)carbonylamino]methyl)cyclopentyl)-N-(3,4,5-trimethoxyphenyl)carboxamide In a manner similar to the preparation of a compound from preparation 16, 0.224 g (0.92 mmols) of a compound from preparation 20 was converted to 0.34 g of the title compound. MS(ES+)m/z=409.

PREPARATION 35

[(3S, 1R)-3-(aminomethyl)cyclopentyl]-N-(3,4,5-trimethoxyphenyl)carboxamide In a manner similar to preparation 17, 0.049 g (0.12 mmol) of a compound from preparation 34 was deprotected with TFA to yield 0.013 g of the title compound. MS(ES+) m/z=308.

PREPARATION 36

[(3S,1R)-3-({[3-2-chloro-6-fluorophenyl)-5-methylisoxazol-4-yl]carbonylamino}methyl)cyclopentyl]-N-(3,4,5-trimethoxyphenyl)carboxamide In a manner similar to preparation 18, 0.013 g (0.042 mmol) of a compound from preparation 35 was converted to a residue which was chromatographed on silica gel with dichloromethane 100% to dichloromethane/MeOH 2% to yield 0.018 g of the title compound. MS(ES+)m/z=545.8.

PREPARATION 37

Ethyl 2-(3-{[4-(2-chloro-6-fluorophenyl)-2-methyl-3-furyl]carbonylamino}cyclohexyl)acetate To a solution of 3-nitrophenylacetic acid, 1.0 g (5.5 mmol) in 90 mL of ethanol was added 1.0 g of $PtO_2$ and 2 mL of 5N HCl. The mixture was hydrogenated overnight at 60° C. and 60 psi, filtered through celite and concentrated to dryness. To a solution of the residue in 15 mL of dichloromethane was added 3.0 mL (21.6 mmol) of triethylamine and 2.0 g (7.2 mmol) of 3-(2-chloro-6-fluorophenyl)-5-methylisoxazole-4-carbonyl chloride. The solution was stirred overnight at ambient temperature. Chloroform was added and the solution was washed with 0.5N HCl, saturated sodium bicarbonate, brine, dried over sodium sulfate, filtered and concentrated to dryness. The residue was chromatographed on silica gel using 5% acetone/dichloromethane as eluent to yield 2.0 g (66%) of the desired mixture of isomers as a white solid. $^1H$—NMR is consistent with structure. MS (ion spray) 423.2 (M+1).

PREPARATION 38

Ethyl 2-[3-(9-chloro-3-methyl-4-oxo-5H-isoxazolo[4,3-c]quinolin-5-yl)cyclohexyl]acetate To a solution of a compound from preparation 37, 1.0 g (2.4 mmol) in 20 mL of N,N-dimethylformamide was added 0.35 g (3.1 mmol) of potassium t-butoxide. After 75 min, the mixture was poured into 1N HCl/ice and extracted with ethyl acetate. The combined organics were washed with brine, dried over sodium sulfate, filtered and concentrated to dryness. The residue was chromatographed on silica gel using 5% acetone/dichloromethane as eluent to yield 0.65 g (67%) of the desired mixture of isomers as a viscous yellow oil. $^1H$—NMR is consistent with structure. MS (ion spray) 403.3 (M+1).

PREPARATION 39

2-[3-(9-chloro-3-methyl-4-oxo-5H-isoxazolo[4,3-c]quinolin-5-yl)cyclohexyl]acetic Acid To a solution of a compound from preparation 38, 0.65 g (1.5 mmol) in 10 mL of tetrahydrofuran and 10 mL of ethanol was added 3.0 mL (15.0 mmol) of 5N sodium hydroxide. After 40 min at ambient temperature, the reaction was concentrated to dryness. The residue was partitioned between ethyl acetate and water, was acidified to pH 3.0 with 1N HCl, and was extracted with ethyl acetate. The combined organics were washed with brine, dried over sodium sulfate, filtered and concentrated to dryness to yield 0.53 g (93%) of the desired mixture of isomers as a white foam. $^1$H–NMR is consistent with structure. MS (ion spray) 375.2 (M+1).

PREPARATION 40

Methyl 2-(3-nitrocyclohexyl)acetate

To a solution of m-nitrophenylacetic acid, 14.2 g (78.0 mmol) in 200 mL of methanol at 0° C. was added 20 mL of acetyl chloride dropwise. The reaction mixture was stirred overnight at ambient temperature and concentrated to dryness. The residue was chromatographed on silica gel using 50% ethyl acetate/hexanes as eluent to yield 14.7 g (97%) of the desired mixture of isomers as a yellow oil. $^1$H—NMR is consistent with structure. MS (FD) 194.8 (M−1).

PREPARATION 41

Methyl 2-(3-{[4-(2-chloro-6-fluorophenyl)-2-methyl-3-furyl]carbonylamino}cyclohexyl)acetate To a solution of methyl 2-(3-nitrocyclohexyl)acetate (13.8 g, 71.0 mmol) in 200 mL of acetic acid was added 6.9 g of PtO$_2$. The mixture was hydrogenated overnight at ambient temperature and 60 psi, then was filtered through celite and concentrated to dryness. To a solution of the residue, 8.8 g (38.0 mmol) in 200 mL of dichloromethane was added 27 mL (190 mmol) of triethylamine and 10.4 g (38.0 mmol) of 3-(2-chloro-6-fluorophenyl)-5-methylisoxazole-4-carbonyl chloride. The mixture was stirred overnight at ambient temperature then chloroform was added. The organics were washed with 0.5N HCl, saturated sodium bicarbonate, brine, dried over sodium sulfate, filtered and concentrated to dryness. The resulting residue was chromatographed on silica gel using 5% acetone/dichloromethane to yield 4.43 g (29%) of the desired mixture of isomers as a colorless, viscous oil. $^1$H—NMR is consistent with structure. MS (ion spray) 409.2 (M+1).

PREPARATION 42

2-(3-{[4-(2-Chloro-6-fluorophenyl)-2-methyl-3-furyl]carbonylamino}cyclohexyl)acetic Acid To a solution of a compound from preparation 41, 1.2 g (3.0 mmol) in 20 mL of absolute ethanol and 20 mL of tetrahydrofuran was added 6.0 mL (30.0 mmol) of 5N sodium hydroxide. The mixture was stirred 4 h, then the organics were concentrated off. The remaining aqueous phase was acidified to pH 3.0 with 1N HCl, then extracted with ethyl acetate. The combined organics were washed with brine, dried over sodium sulfate, filtered and concentrated to dryness. The residue was dissolved in chloroform and concentrated to dryness to yield 1.0 g (84%) of the desired mixture of isomers as a white foam. $^1$H—NMR is consistent with structure. MS (ion spray) 393.2 (M−1).

PREPARATION 43

[4-(2-Chloro-6-fluorophenyl)-2-methyl(3-furyl)]-N-{3-[2-(4-methylpiperidyl)-2-oxoethyl]cyclohexyl}carboxamide To a solution of a compound from preparation 42, 1.0 g (2.6 mmol) in 10 mL of N,N-dimethylformamide was added 0.34 mL (2.9 mmol) of 4-methylpiperidine, 0.43 g (3.1 mmol) of 1-hydroxy-7-azabenzotriazole and 0.6 g (3.1 mmol) of 1-(3-(dimethyl-amino)propyl)-3-ethylcarbodiimide. The mixture was stirred overnight at ambient temperature and concentrated to dryness. The resulting residue was partitioned between ethyl acetate and water and was extracted with ethyl acetate. The combined organics were washed with brine, dried over sodium sulfate, filtered and concentrated to dryness. The residue was chromatographed on silica gel using a gradient of 30% ethyl acetate/hexanes to 5% methanol/chloroform as eluent to yield 0.9 g (70%) of the desired mixture of isomers as a white foam. 1H—NMR is consistent with structure. MS (ion spray) 476.2 (M+1).

PREPARATION 44

5-[(3S,1R)-3-(Aminomethyl)cyclohexyl]-9-chloro-3-methyl-5H-isoxazolo[4,3-c]quinolin-4-one A solution of a compound from preparation 54 (enantiomer 2) (6.6 g (14.8 mmol) in 230 mL of acetic acid saturated with hydrochloric acid was stirred for 2 h at ambient temperature, then was concentrated to dryness. The resulting residue was partitioned between 20% isopropanol/chloroform and saturated sodium bicarbonate and was extracted with 20% isopropanol/chloroform. The combined organics were washed with brine, dried over sodium sulfate, filtered and concentrated to dryness to yield 4.68 g (92%) of the desired product as a yellow solid. $^1$H—NMR is consistent with structure.
MS (ion spray) 346.1 (M+1).

PREPARATION 45

Phenylmethyl-2-{(3S,1R)-3-[(t-butoxy)carbonylamino]cyclohexyl}acetate

To a solution of phenylmethyl 2-((3S,1R)-3-azidocyclohexyl)acetate, 5.0 g (18.3 mmol) in 350 mL of ethyl acetate under a nitrogen atmosphere was added 8.0 g (36.6 mmol) of BOC-anhydride and 2.0 g of Lindlar's catalyst. The nitrogen was purged with hydrogen and the reaction mixture was stirred overnight under a hydrogen balloon, then concentrated to dryness. The resulting residue was filtered through celite and chromatographed on silica gel using ethyl acetate/hexanes as eluent to yield 6.25 g (98%) of the desired product as a clear oil which solidifies upon standing. $^1$H—NMR is consistent with structure. MS (ion spray) 347 (M$^+$).

PREPARATION 46

Phenylmethyl 2-((3S,1R)-3-{[4-(2-chloro-6-fluorophenyl)-2-methyl(3-furyl)]carbonylamino }cyclohexyl)acetate To a solution of a compound from preparation 45, 5.05 g (20.4 mmol) in 80 mL of dichloromethane at 0° C. was added 3.7 mL (24.5 mmol) of triethylamine and 10 mg of 4-dimethylaminopyridine, followed by 6.15 g (22.4 mmol) of 3-(2-chloro-6-fluorophenyl)-5-methylisoxazole-4- carbonyl chloride. The reaction mixture was stirred overnight while warming to ambient temperature, and was then washed with 0.1N hydrochloric acid, washed with brine, dried over sodium sulfate, filtered and concentrated to dryness. The residue was chromatographed on silica gel using ethyl acetate/hexanes as eluent, concentrated to dryness, dissolved in chloroform and concentrated to dryness to yield 5.74 g (58%) of the desired compound as a white solid. $^1$H—NMR is consistent with structure. MS (ion spray) 485.5 (M+1).

PREPARATION 47

2-[(3S,1R)-3-(9-chloro-3-methyl-4-oxo-5H-isoxazolo[4,3-c]quinolin-5-yl))cyclohexyl]acetic Acid To a solution of a compound from Example 491 (3.91 g, 8.4 mmol) in 70 mL of dioxane was added 70 mL (350 mmol) of 5N sodium hydroxide. The mixture was refluxed for 4 h and was cooled to ambient temperature and acidified to pH 1 with 5N hydrochloric acid. The resulting mixture was extracted with 20% isopropanol/chloroform. The combined organics were washed with brine, dried over sodium sulfate, filtered and concentrated to dryness. The residue was triturated in ether, filtered and dried under vacuum to yield 1.8 g (57%) of the desired product as a tan solid. $^1$H—NMR is consistent with structure. MS (ion spray) 374.8 (M+).

PREPARATION 48 cis-N-[3-Aminomethylcyclohexyl]-9-chloro-3-methyl-5H-isoxazolo[4,3-c]quinolin-4-one A slurry of a compound from preparation 52, 1.2 g (2.7 mmol) in 20 mL of acetic acid saturated with hydrochloric acid was stirred for 4 h at ambient temperature, then concentrated to dryness. The residue was dissolved in toluene and concentrated to dryness. The residue was slurried in ether/hexanes, concentrated to dryness, and dried under vacuum to yield 750 mg (80%) of the title compound as a tan solid. $^1$H—NMR is consistent with structure. MS (ion spray) 346.2 (M+1).

PREPARATION 49

(t-Butoxy)-N-[(3-nitrophenyl)methyl]carboxamide

To a suspension of 5.00 g (26.5 mmol) of 3-nitrobenzylamine hydrochloride in 100 mL CH$_2$Cl$_2$ at room temperature was added 5.79 g (26.5 mmol) of di-t-butyl dicarbonate. To this was added 8.13 mL (58.3 mmol) of triethylamine, dropwise over 15 min. The reaction was stirred for 3 h at room temperature, after which it was diluted with 300 mL of ethyl acetate. The resulting organic solution was washed three times with 1N HCl solution, dried over sodium sulfate and concentrated in vacuo to give 6.2 g (93%) of a white solid, which was characterized as the-title compound. MS (FIA) m/z=253.

PREPARATION 50

(t-Butoxy)-N-[(3-aminocyclohexyl)methyl]carboxamide

To a solution containing 12.0 g (47.7 mmol) of a compound from preparation 49 in 300 mL ethanol was added 6.0 g of rhodium on carbon. The reaction was subjected to hydrogenation (60 psi) at 60° C. for 18 h, after with the catalyst was removed by vacuum filtration and the solvent removed in vacuo, giving 9.5 g (87%) of a clear oil. This material was characterized as the title compound and used without further purification.

PREPARATION 51

N-(3{[t-Butoxy)carbonylamino]methyl}cyclohexyl)[4-(2-chloro-6-fluorophenyl)-2-methyl(3-furyl)]carboxamide To a solution of 9.5 g (41.6 mmol) of a compound from preparation 50 in 200 mL of CH$_2$Cl$_2$ was added 11.4 g (41.6 mmol) of 3-(2-chloro-6-fluorophenyl)-5-methyl-isoxazole-4-carbonyl chloride, followed by 11.6 mL (83.2 mmol) of triethylamine at room temperature. The reaction was stirred at room temperature for 15 h, and concentrated in vacuo. The crude solid was dissolved in 200 mL of ethyl acetate and the organic solution was washed twice with 1N HCl solution, dried over sodium sulfate and concentrated in vacuo to give a yellow solid. This material was recrystallized from methanol to give 12.5 g (64%) of a white crystalline solid, which was characterized as the title compound, as an inseparable mixture of cis and trails isomers. MS(FIA) m/z =466.2.

PREPARATION 52 AND 53

(t-Butoxy)-N-{[3-(9-chloro-3-methyl-4-oxo-5H-isoxazolo[4,3-c]quinolin-5-yl))cyclohexyl]methyl}carboxamide To a stirred solution of 7.00 g (15.0 mmol) of a compound from preparation 51 in 200 mL of DMF at room temperature was added 30.0 mL (15 mmol) of a 0.5 M toluene solution of potassium bis(trimethylsilyl) amide over 10 min. The resulting dark red reaction was stirred an additional 5 min at room temperature and added to 200 mL of 1N HCl. The two phase solution was diluted with 400 mL of ethyl acetate and the organic layer was separated. The organic solution was washed four times with brine, dried over sodium sulfate and concentrated in vacuo to give an orange solid. This material was recrystallized from toluene to give 3.4 g of a light yellow solid, which was characterized as pure racemic cis material, 52: MS(FIA) m/z=446.1. Purification of the racemic trans material (53) was accomplished by concentrating the mother liquor and subjecting this material to flash chromatography on silica gel, using 50% hexane-ethyl acetate as the eluant. The major fractions were combined to give a light yellow solid, which was characterized as pure racemic trans material: MS(FIA) m/z=446.1.

PREPARATION 54

N-{3-(9-chloro-3-methyl4-oxo-5H-isoxazolo[4,3-c]quinolin-5-yl))cyclohexyl-]methyl}(t-butoxy)carboxamide The racemic cis material from a compound from preparation 52 was separated into its enantiomers by chiral HPLC chromatography using a Chiralpak AD column and 10% ethyl alcohol-heptane as the eluant at a flow of 1.0 mL/min.
Retention Time (Enantiomer 1)=10.501 min.
Retention Time (Enantiomer 2)=12.576 min.

PREPARATION 55

Methyl 3-[4-methoxyphenyl)methoxy]benzoate

To a solution containing 5.00 g (32.9 mmol) of methyl 3-hydroxybenzoate in 100 mL of DMF was added 4.77 mL (32.9 mmol) of p-methoxybenzyl chloride and 4.54 g (32.9 mmol) of anhydrous potassium carbonate. The reaction was stirred at room temperature for 16 h, followed by 1 h at 100° C. The solution was diluted with 200 mL of ethyl acetate and 200 mL of 1N HCl. The organic phase was separated and washed five times with brine, dried over sodium sulfate and concentrated in vacuo to give 8.99 g of a white amorphous solid, which was characterized as the title compound. This material was used without further purification.

PREPARATION 56

3-[(4-Methoxyphenyl)methoxy]benzoic Acid

To a solution containing 2.75 g (10.0 mmol) of a compound from preparation 55 in 50 mL of MeOH was added 10 mL of 1N NaOH solution. To aid solubility, 20 mL of THF was added and the reaction was heated at reflux for 3 h. The reaction was cooled to room temperature and diluted with 100 mL of ethyl acetate and 100 mL of 1N HCl solution. The organic layer was separated, dried over sodium sulfate and concentrated in vacuo to give 2.45 g of a white amorphous solid, which was characterized as the title compound. This material was used without further purification.

PREPARATION 57

(-)-(1R,cis)-Pinonic Acid

A solution of 1S-(-)-pinene (11.95 mL, 75 mmol) in methanol (50 mL) and chloroform (50 mL) at −78° C. was treated with ozone for 2 h via a gas dispersion tube. After purging with nitrogen for 1 h, methyl sulfide (16.5 mL, 225 mmol) was added, and the reaction was allowed to warm to room temperature overnight. The solvent was removed in vacuo and the residue dissolved in diethyl ether, washed with water, saturated aqueous brine solution, dried over magnesium sulfate and concentrated to approximately 11 g of yellow liquid. The liquid was dissolved in ethyl ether and treated with oxygen for 2 h, followed by stirring under an $O_2$ balloon overnight. The reaction was concentrated to give 12.42 g as a slightly yellow liquid, 90% yield. 1H NMR: consistent with structure.
MS (ion spray) 183 (M$^-$−1).

PREPARATION 58

(3-Acetylamino-2,2-dimethylcyclobutyl)acetic Acid

To a solution of a compound from preparation 57 (12.37 g, 67.1 mmol) in acetic acid (270 mL) was added hydroxylamine-O-sulfonic acid (11.74 g, 100.7 mmol), and the reaction was heated to reflux under nitrogen for 20 h. The reaction was concentrated and the residue dissolved in 2N HCl, followed by extraction with ethyl acetate (×4). The combined organics were washed with brine, dried over magnesium sulfate, and concentrated. The brown solution was treated with decolorizing charcoal, filtered through celite, and concentrated to 5.85 g as a light yellow oil, 44% yield. $^1$H NMR: consistent with structure. MS (ion spray) 200 (M$^+$+1), 198 (M$^+$−1).

PREPARATION 59

(3-Acetylamino-2,2-dimethylcyclobutyl)acetic Acid Methyl Ester

To a 0° C. flask of methanol (150 mL) was added thionyl chloride (10.7 mL, 146.8 mmol) dropwise via an addition funnel. To this solution was added a compound from preparation 58 (5.85 g, 29.4 mmol) dropwise as a solution in methanol (100 mL). The cooling bath was removed and the reaction allowed to stir at room temperature for 2 h. The reaction was concentrated to a brown oil, dissolved in ethyl acetate, washed with saturated aqueous sodium bicarbonate solution, brine, dried over magnesium sulfate and concentrated to a 5.5 g of a brown oil. Purification by column chromatography on silica gel (eluting with 50–100% ethyl acetate/hexane) gave 3.1 g as a brown oil, 50% yield. 1H NMR: consistent with structure. MS (ion spray) 213 (M$^+$).

PREPARATION 60

(3-Amino-2,2-dimethylcyclobutyl)acetic Acid Methyl Ester

A compound from preparation 59 (3.09 g, 14.5 mmol) was dissolved in 2N HCl (100 mL) and heated to reflux for 18 h, then concentrated. To a 0° C. flask of methanol (100 mL) was added thionyl chloride (5.3 mL, 72.4 mmol) dropwise via an addition funnel. To this solution was added the crude material dropwise as a solution in methanol (15 mL). The clear solution was allowed to warm to room temperature overnight. The solution was concentrated, and purification by SCX column (eluting with tetrahydrofuran/water then ammonia/methanol) gave 2.52 g as a brown solid, 100% yield.
$^1$H NMR: consistent with structure. MS (ion spray) 172 (M$^+$+1).

PREPARATION 61

(3-{[3-(2-Chloro-6-fluoro-phenyl)-5-methylisoxazole-4-carbonyl]amino}-2,2-dimethyl-cyclobutyl)acetic Acid Methyl Ester To a solution of a compound from preparation 60 (566 mg, 3.31 mmol) in dichloromethane (20 mL) was added 3-(2-chloro-6-fluorophenyl)-5-methylisoxazole-4-carbonyl chloride (1.09 g, 3.97 mmol), 4-dimethylaminopyridine (40 mg, 0.33 mmol), and triethylamine (1.4 mL, 9.92 mmol) dropwise via syringe. The solution was stirred under nitrogen at room temperature overnight. The solution was washed with 1.0N HCl (×3), saturated aqueous sodium bicarbonate solution, brine, dried over magnesium sulfate and concentrated. Purification by flash chromatography on silica gel (eluting with 20–40% ethyl acetate/hexane) gave 1.28 g as a yellowish oil, 95% yield. $^1$H NMR: consistent with structure. MS (ion spray) 409 (M$^+$).

PREPARATION 62

[3-(9-Chloro-3-methyl-4-oxo-5H-isoxazolo[4,3-c] quinolin-5-yl)-2,2-dimethyl-cyclobutyl]-acetic Acid Methyl Ester To a 0° C. solution of a compound from preparation 61 (2.44 g, 5.97 mmol) in dimethylformamide (100 mL) was added potassium t-butoxide (0.80 g, 7.16 mmol). After 15 min, the reaction was quenched with 1.0N HCl and extracted with 20% isopropanol/chloroform. The organic layer was then washed with 1.0N HCl (×2), saturated aqueous sodium bicarbonate solution, brine, dried over magnesium sulfate and concentrated. Purification by flash chromatography on silica gel (eluting with 15–20% ethyl acetate/hexane) gave 739 mg (32% yield) as a white solid. $^1$H NMR: consistent with structure. MS (ion spray) 389 (M$^+$).

PREPARATION 63

[3-(9-Chloro-3-methyl-4-oxo-5H-isoxazolo[4,3-c] quinolin-5-yl)-2,2-dimethyl-cyclobutyl]acetic Acid A solution of a compound from preparation 62 (737 mg, 1.89 mmol) in 5N NaOH (25 mL) was heated to reflux for 1 h. The solution was concentrated, dissolved in 20% isopropanol/chloroform, acidified to pH 2 with 5N HCl, washed with 1.0N HCl (×2), dried over magnesium sulfate and concentrated to give 519 mg as a light orange foam, 73% yield. $^1$H NMR: consistent with structure.

PREPARATION 64

[3-(9-Chloro-3-methyl4-oxo-5H-isoxazolo[4,3-c] quinolin-5-yl)-2,2-dimethyl-cyclobutylmethyl] carbamic Acid 2-trimethylsilanylethyl Ester To a mixture of a compound from preparation 63 (318.7 mg, 0.85 mmol) in toluene (15 mL) was added triethylamine (130 μL, 0.94 mmol), diphenylphosphorylazide (202 μL, 0.94 mmol), and the mixture heated to reflux for 3 h. To the reaction was added 2-(trimethylsilyl)-ethanol (183 μL, 1.28 mmol), and the mixture heated at reflux overnight. The solution was concentrated and dissolved in dichloromethane, washed with 1.0N HCl, brine, dried over magnesium sulfate and concentrated. Purification by flash chromatography on silica gel (eluting with 0–30% ethyl acetate/hexane) gave 144 mg as a white foam, 35% yield. $^1$H NMR: consistent with structure. MS (ion spray) 490 (M$^+$).

PREPARATION 65

N-3-{[3-(2-chloro-6-fluorophenyl)-5-methylisoxazol-4-yl]carbonylamino}cyclohexyl)(t-butoxy)carboxamide To a 0° C. solution of 1,3-diaminocyclohexane (50.56 g, 442.8 mmol) in chloroform (850 mL) was added a solution of di-t-butyl-dicarbonate (20.3 mL, 88.6 mmol) in chloroform (250 mL) dropwise via an addition funnel over 25 minutes. The mixture was stirred under nitrogen at room temperature overnight. The reaction was washed with saturated aqueous sodium bicarbonate solution (3×), brine, dried over magnesium sulfate, and concentrated to give 17.58 g of a white oil. To a solution of the crude material (17.58 g, 82.0 mmol) in dichloromethane (500 mL) was added 37(2-chloro-6-fluorophenyl)-5-methylisoxazole-4-carbonyl chloride (23.65 g, 86.1 mmol), dimethylaminopyridine (1.00 g, 8.2 mmol), and triethylamine (34.3 mL, 246.1 mmol) dropwise via syringe. The solution was stirred under nitrogen at room temperature overnight. The solution was washed with 0.1N HCl (2×), saturated aqueous sodium bicarbonate solution (2×), brine, dried over magnesium sulfate and concentrated. The orange solids were treated with ethyl ether, sonicated for 15 minutes, and filtered. The resulting white solids were crushed, treated with ethyl ether, sonicated for 15 minutes, filtered out, and dried on a vacuum overnight to give 16.20 g of the title racemic cis compound as a white solid, 87% yield based on a 1:1 mixture of cis:trans. This material was then separated by chiral LC on a Chiralcel OD column to yield 9 g of isomer 1: (3S,1R) and 7 g of isomer 2: (1S,3R). $^1$H NMR: consistent with structure. MS (ion spray) 352 (M$^+$–BOC+1).

PREPARATION 66

N-(1S,3R)-3-(9-Chloro-3-methyl4-oxo-5H-isoxazolo [4,3-c]quinolin-5-yl)cyclohexyl,(t-butoxy) carboxamide To a solution of a compound from preparation 65 (isomer 1) (500 mg, 1.11 mmol) in dimethylformamide (20 mL) was added KHMDS (3.3 mL, 1.66 mmol, 0.5M in toluene) rapidly via syringe. After 15 minutes, ethyl acetate (50 mL) was added to the reaction, and the solution added to a separatory funnel containing water (50 mL) and brine (30 mL). The layers were separated, and the aqueous layer was extracted with ethyl acetate (×2). The combined organics were washed with brine, dried over magnesium sulfate, and concentrated to give 709 mg red solid. Purification using flash chromatography on silica gel (eluting with 20–30% ethyl acetate/hexane) gave 205 mg of the title compound as a yellow solid, 43% yield. $^1$H NMR: consistent with structure. MS (ion spray) 332 (M$^+$–BOC).

PREPARATION 67

N-(3S,1R)-3-(9-chloro-3-methyl-4-oxo-5H-isoxazolo[4,3-c]quinolin-5-yl)cyclohexyl(t-butoxy) carboxamide To a solution of a compound from preparation 65 (isomer 2) (500 mg, 1.11 mmol) in dimethylformamide (20 mL) was added KHMDS (3.3 mL, 1.66 mmol, 0.5M in toluene) rapidly via syringe. After 4 minutes, ethyl acetate (50 mL) was added to the reaction, and the solution added to a separatory funnel containing water (50 mL) and brine (30 mL). The layers were separated, and the aqueous layer was extracted with ethyl acetate (2×). The combined organics were washed with brine, dried over magnesium sulfate, and concentrated to give 700 mg red solid. Purification using flash chromatography on silica gel (eluting with 0–0.5% methanol/chloroform) gave 372 mg of the title compound as a yellow solid, 78% yield. $^1$H NMR: consistent with structure. MS (ion spray) 332 (M$^+$–BOC).

PREPARATION 68

5-((3S,1R)-3-Aminocyclohexyl)-9-chloro-3-methyl-H-isoxazolo[4,3-c]quinolin-4-one Hydrochloride To a compound from preparation 66 (200 mg, 0.46 mmol) was added acetic acid saturated with HCl(g) (10 mL, ~3N in HCl) and the solution stirred vigorously at room temperature for 1 h. The reaction was concentrated, followed by addition of acetonitrile and concentrated to assist in the removal of acetic acid. The resulting white solid was treated with ethyl ether, sonicated, and filtered to yield 159 mg of the title compound as a white solid, 93% yield. $^1$H NMR: consistent with structure. MS (ion spray) 369 (M$^+$).

PREPARATION 69

5-((1S,3R)-3-aminocyclohexyl)-9-chloro-3-methyl-5H-isoxazolo[4,3-c]quinolin-4-one Hydrochloride To a compound from preparation 67 (368 mg, 0.85 mmol) was added acetic acid saturated with HCl$_{(g)}$ (15 mL, ~3N in HCl) and the solution stirred vigorously at room temperature for 1 h. The reaction was concentrated, followed by addition of acetonitrile and concentrated to assist in the removal of acetic acid. The resulting white solid was treated with ethyl ether, sonicated, and filtered to yield 249 mg of the title compound as a white solid, 79% yield. $^1$H NMR: consistent with structure. MS (ion spray) 369 (M$^+$).

PREPARATION 70

Ethyl 4-aminohexanecarboxylate

Thionyl chloride (3.0 mL, 0.041 mol) was added dropwise to ethanol (125 mL) at room temperature and the mixture stirred for an additional 10 min. Then, 4-amino-1-cyclohexane-carboxylic acid (5.0 g, 0.035 mol) was added and the mixture stirred overnight at ambient temperature. The mixture was then concentrated in vacuo and the resulting solid dried overnight in vacuo which resulted in the isolation of 6.84 g (94%) of the desired ester hydrochloride. MS(S): (M+1)$^+$172.2 m/z.

PREPARATION 71

Ethyl 4-{[3-(2-chloro-6-fluorophenyl)-5-methylisoxazol-4-yl]carbonylamino}cyclohexane Carboxylate A compound from preparation 70 (0.414 g, 0.002 mol) was combined with 3-(2-chloro-6-fluorophenyl)-5-methylisoxazole-4-carbonyl chloride (0.548 g, 0.002 mol) and triethylamine (0.70 mL, 0.005 mol) in CH$_2$Cl$_2$ (6.0 mL) and the mixture stirred for 5 h at ambient temperature. The mixture was diluted with CH$_2$Cl$_2$, washed with 2x water, and dried over sodium sulfate. The mixture was concentrated in vacuo. The resulting residue chromatographed over silica gel using CH$_2$Cl$_2$/MeOH as eluant which allowed for isolation of 0.790 g (97%) of the desired amide. MS(ES): (M$^+$1)$^+$409.3, 410.3, 411.2 m/z.

PREPARATION 72

Ethyl 4-(9-chloro-3-methyl4-oxo-5H-isoxazolo[4,3-c]quinolin-5-yl)cyclohexane Carboxylate A compound from preparation 71 (0.70 g, 0.0017 mol) was dissolved in DMF (10 mL) and potassium-t-butoxide (0.230 g, 0.0020 mol) was added and the mixture stirred for 2 h at ambient temperature. Water (100 mL) and aq 1N HCl (5 mL) was added and the aqueous mixture extracted with ethyl acetate. The combined extracts were dried over sodium sulfate and then concentrated in vacuo. The resulting residue was chromatographed over silica gel using CH$_2$Cl$_2$/MeOH as eluant which allowed for isolation of 0.540 g (81%) of product as a light yellow solid. MS(ES): (M+1)$^+$ 389.2, 391.2 m/z.

PREPARATION 73

3-[(t-Butoxy)carbonylamino)cyclohexanecarboxylic Acid

To 3-aminocyclohexane carboxylic acid (3.00 g, 0.021 mol) in a THF/H$_2$O mixture (50 mL/50 mL) was added potassium carbonate (2.90 g, 0.021 mol) and di-t-butyl dicarbonate (4.58 g, 0.021 mol) and the resultant mixture stirred overnight at ambient temperature. Then aqueous 5N HCl (10 mL) was added and the mixture extracted with ethyl acetate. The combined extracts were dried over sodium sulfate and concentrated in vacuo which allowed for isolation of 4.92 g (96%) of desired product as a white solid. MS(ES): (M+1)$^+$ 244.5 m/z.

PREPARATION 74

(t-Butoxy)-N-[3-(hydroxymethyl)cyclohexyl] carboxamide

A compound from preparation 73 (4.00 g, 0.0165 mol) was dissolved in dry THF (50 mL) and the mixture cooled in an ice bath under a nitrogen atmosphere. Then borane-tetrahydrofuran (1.0 M, 20 mL, 0.02 mol) was added via syringe and the mixture stirred overnight while warming to room temperature. The reaction mixture was quenched into ice water and solid NaCl was added. This mixture was extracted with ethyl acetate and the combined extracts were dried over sodium sulfate and concentrated in vacuo. The resulting residue was chromatographed over silica gel using a CH$_2$Cl$_2$/THF mixture as eluant which allowed for isolation of 2.40 g (63%) of the desired alcohol as a viscous oil. MS(ES): (+1)$^+$ 230.2 m/z.

PREPARATION 75

(t-Butoxy)-N-[3-p-toluenesulfonyloxymethyl) cyclohexyl]carboxamide

A compound from preparation 74 (0.15 g, 0.00066 mol) was combined with p-toluenesulfonyl chloride (0.125 g, 0.00066 mol), triethylamine (0.18 mL, 0.0013 mol), and DMAP (0.005 g, cat.) in dichloromethane (5.0 mL) and the resultant mixture stirred overnight at room temperature. The mixture was then concentrated in vacuo and the residue chromatographed over silica gel using a mixture of CH$_2$Cl$_2$/THF as eluant which allowed for the isolation of the desired product (0.195 g, 77%) as a thick oil that solidified upon standing. MS(ES): (M+1)$^+$ 384.2 m/z.

PREPARATION 76

(t-Butoxy)-N-[3-(phenylthiomethyl)cyclohexyl] carboxamnide

Thiophenol (0.27 mL, 0.0026 mol) was dissolved in DMF (10 mL) at ambient temperature under a nitrogen atmosphere and sodium hydride (60%, 0.115 g, 0.0029 mol) was added. After stirring for 15 min., a compound from preparation 75 was added and the mixture stirred overnight at ambient temperature. The mixture was concentrated in vacuo and the residue chromatographed over silica gel with CH$_2$Cl$_2$/THF as eluant which allowed for isolation of 0.74 g (88%) of desired product as a white solid. MS(ES): (M+1)$^+$ 322.2 m/z.

PREPARATION 77

3-(Phenylthiomethyl)cyclohexylamine

A compound from preparation 76 (0.50 g, 0.0016 mol) was dissolved in CH$_2$Cl$_2$ (10 mL) and TFA (1.0 mL) was added. After 1.5 h, deprotection was incomplete and additional TFA (1.0 mL) was added and the mixture stirred at ambient temperature for an additional 4 h. The mixture was concentrated in vacuo and the residue treated with aqueous NaHCO$_3$ and extracted with CH$_2$Cl$_2$. The combined extracts were concentrated in vacuo and the residue eluted over a short plug of silica gel (CH$_2$Cl$_2$/MeOH) which allowed for isolation of the desired amine (0.265 g, 77%). MS(ES): (M+1)$^+$ 222.2 m/z.

PREPARATION 78

[3-(2-Chloro-6-fluorophenyl)-5-methylisoxazol-4-yl]-N-[3-(phenylthiomethyl)cyclohexyl]carboxamide A compound from preparation 77 (0.26 g, 0.0012 mol) was combined with 3-(2-chloro-6-fluoro-phenyl)-5-methylisoxazole-4-carbonyl chloride (0.322 g, 0.0012 mol) and triethylamine (0.33 mL, 0.0024 mol) in CH$_2$Cl$_2$ (10 mL) and the mixture stirred overnight at ambient temperature. The reaction mixture was chromatographed over silica gel using CH$_2$Cl$_2$/THF as eluant which allowed for isolation of 0.495 g (91%) of the desired amide as a white solid. MS(ES): (+1)$^+$ 459.4 m/z.

PREPARATION 79

(t-Butoxy)-N-[3-(phenylmethylthiomethyl) cyclohexyl]carboxamide

Benzyl mercaptan (0.31 mL, 0.0026 mol) was dissolved in DMF (10 mL) at ambient temperature under a nitrogen atmosphere and sodium hydride (60%, 0.115 g, 0.0029 mol) was added. After stirring for 15 min., the compound from preparation 75 (1.00 g, 0.0026 mol) was added and the mixture stirred overnight at ambient temperature. The mixture was concentrated in vacuo and the residue chromatographed over silica gel with $CH_2Cl_2$/THF as eluant which allowed for isolation of 0.80 g (92%) of desired product as a thick oil which solidified upon standing. MS(ES): $(M+1)^+$ 336.2 m/z.

PREPARATION 80

[3-(2-Chloro-6-fluorophenyl)-5-methylisoxazol-4-yl]-N-[3-(phenylmethylthiomethyl)cyclohexyl] carboxamide The compound from preparation 73 (0.40 g, 0.0012 mol) was dissolved in $CH_2Cl_2$ (8.0 mL) and TFA (2.0 mL) and the mixture stirred at ambient temperature for 3 h. The mixture was concentrated in vacuo and the residue treated with aqueous $NaHCO_3$ and extracted with $CH_2Cl_2$. The combined extracts were dried over sodium sulfate and concentrated in vacuo which allowed for the recovery of 0.19 g (68%) of crude amine. This amine (0.19 g, 0.0008 mol) was combined with 3-(2-chloro-6-fluoro-phenyl)-5-methyl-isoxazole-4-carbonyl chloride (0.22 g, 0.0008 mol) and triethylamine (0.23 mL, 0.0016 mol) in $CH_2Cl_2$ (10 mL) and the mixture stirred overnight at ambient temperature. Water (~30 mL) was added and the mixture extracted with $CH_2Cl_2$. The combined extracts were dried over sodium sulfate and then concentrated in vacuo. The resulting residue was chromatographed over silica gel using $CH_2Cl_2$/THF as eluant which allowed for isolation of 0.29 g (77%) of the desired amide as a white solid. MS(ES): $(M+1)^+$ 473.1, 475.1 m/z.

PREPARATION 81

(t-Butoxy)-N-[3-{(benzylsulfonyl) methyl}cyclohexyl]carboxamide

A compound from preparation 79 (0.467 g, 0.0014 mol) was dissolved in a methanol/acetone (10 mL)/(10 mL) mixture and $NaHCO_3$ (0.467 g, 0.0056 mol) and water (10 mL) were added. Oxone® (1.71 g, 0.0028 mol) was then added and the mixture stirred at ambient temperature for 2.5 h. The mixture was concentrated i71 vacuo and the residue taken up in water and extracted with $CH_2Cl_2$. The combined extracts were dried over sodium sulfate and concentrated in vacuo. The resulting residue was chromatographed over silica gel using $CH_2Cl_2$/THF as eluant which allowed for isolation of 0.420 g (82%) of the desired sulfone as a white solid. MS(FD): $M^+$ 367.2 m/z.

PREPARATION 82

[3-(2-Chloro-6-fluorophenyl)-5-methylisoxazol-4-yl]-N-(3-{benzylsulfonyl]methyl}cyclohexyl) carboxamide The compound from preparation 81 (0.40 g, 0.0011 mol) and TFA (2.0 mL) were dissolved in $CH_2Cl_2$ (10.0 mL) and the mixture stirred at ambient temperature for 2 h. The mixture was concentrated in vacuo and the residue treated with aqueous $NaHCO_3$ and extracted with $CH_2Cl_2$. The combined extracts were dried over sodium sulfate and concentrated in vacuo which allowed for recovery of 0.21 g (71%) of crude amine. This amine (0.21 g, 0.0008 mol) was combined with 3-(2-chloro-6-fluoro-phenyl)-5-methyl-isoxazole-4-carbonyl chloride (0.22 g, 0.0008 mol), triethylamine (0.22 mL, 0.0016 mol) and DMAP (0.005 g, cat.) in $CH_2Cl_2$ (10 mL) and the mixture stirred overnight at ambient temperature. The mixture was concentrated in vacuo and the resulting residue chromatographed over silica gel using $CH_2Cl_2$/THF as eluant which allowed for isolation of 0.35 g (89%) of the desired amide. MS(ES): $(M+1)^+$ 505.1 m/z.

PREPARATION 83

{3-[(t-Butoxy)carbonylamino]cyclohexyl}methyl Benzoate

The compound from preparation 74 (1.00 g, 0.0044 mol) was combined with benzoyl chloride (0.56 mL, 0.0048 mol), triethylamine (1.70 mL, 0.012 mol), and DMAP (0.020 g, cat.) in $CH_2Cl_2$ (10 mL) and the mixture stirred overnight at ambient temperature. The reaction mixture was concentrated in vacuo and the residue chromatographed over silica gel using $CH_2Cl_2$/THF as eluant which allowed for isolation of 1.05 g (72%) of the desired ester as an oil. MS(ES): $(M+1)^+$ 334.1 m/z.

PREPARATION 84

(3-{[3-(2-Chloro-6-fluorophenyl)-5-methylisoxazol-4-yl]carbonylamino}cyclohexyl)methyl Benzoate The compound from preparation 83 (1.00 g, 0.003 mol) and TFA (2.0 mL) were dissolved in $CH_2Cl_2$ (10 mL) and the mixture treated in a manner similar to preparation 82, which allowed for isolation of 0.69 g (98%) of crude amine. This amine (0.69 g, 0.0029 mol) was combined with 3-(2-chloro-6-fluoro-phenyl)-5-methylisoxazole-4-carbonyl chloride (0.81 g, 0.0029 mol) and triethylamine (0.82 mL, 0.0059 mol) in $CH_2Cl_2$ (10 mL) and again treated in a manner similar to preparation 81. Purification resulted in the recovery of 1.30 g (95%) of desired amide as a white foam. MS(ES): $(M+1)^+$ 471.1 m/z.

PREPARATION 85

9-Chloro-5-[3-(hydroxymethyl)cyclohexyl]-3-methyl-5H-isoxazolo[4,3-c]quinolin4-one The compound from Example 489 (0.33 g, 0.00073 mol) was added to aqueous sodium hydroxide (1N, 1.0 mL), ethanol (2.0 mL) and THF (2.0 mL) and the mixture stirred at ambient temperature for 3 h. The mixture was diluted with water and extracted with ethyl acetate. The combined extracts were washed with 2× sat'd aq $NaHCO_3$ and dried over sodium sulfate. Concentration in vacuo netted 0.225 g (88%) of desired alcohol as a tan foam. MS(ES): 347.2, 349.3 m/z.

PREPARATION 86

2-{3-[(t-Butoxy)carbonylamino]cyclohexyl}acetic Acid

A compound from preparation 45 (1.0 g; 2.77 mmol) was dissolved in tetrahydrofuran (4 mL) and ethanol (4 mL) under a dry nitrogen atmosphere at room temperature. This cloudy white solution became clear and colorless after mixing with 2N $NaOH_{(aq)}$ (15 mL; 19.4 mmol; 11.1 equiv) for 2 h. After rotary evaporation to dryness, the white solid was dissolved in water (20 mL) and the resulting solution extracted with diethyl ether (twice). Acidification of the aqueous layer to pH 2 with 1N $HCl_{(aq)}$ produced a white solid that was extracted into ethyl acetate (thrice). The ethyl acetate was washed with saturated $NaCl_{(aq)}$, dried with $Na_2SO_{4(s)}$, and concentrated to dryness by rotary evaporation. The resulting white solid (700 mg; 98% yield) was used in subsequent reactions without further purification. MS(ES) calc'd: $[M+Na]^+$ 280.2 m/z, $[M-H]^-$=256.2 m/z. Found: 280.1 m/z; 256.2 m/z.

PREPARATION 87

2-{3-[(t-Butoxy)carbonylamino]cyclohexyl}-N-ethoxy-N-methyl Acetamide

A compound from preparation 86 (690 mg; 2.68 mmol) was dissolved in anhydrous dichloromethane (10 mL) under a dry nitrogen atmosphere at room temperature. Addition of 1,1'-carbonyldiimidazole (535 mg; 3.22 mmol; 1.2 equiv) to the clear, colorless starting material solution immediately generated a gas. After stirring the resulting solution for 30 min, triethyl amine (746 µL; 5.36 mmol; 2 equiv) and N,O-dimethylhydroxylamine hydrochloride (570 mg; 5.90 mmol; 2.2. equiv) were added and the solution stirred for 15 h. Water was added to the solution and then the solution was extracted with dichloromethane (thrice). The organic layer was washed with saturated $NaCl_{(aq)}$, dried with $Na_2SO_{4(s)}$, filtered, and concentrated to dryness by rotary evaporation. The resulting oil (850 mg) was purified by radial chromatography on a 4 mm thick silica gel rotor with a 5% tetrahydrofuran/dichloromethane (v/v) mobile phase. A clear, colorless oil (650 mg; 80%) was obtained. MS(ES) calc'd: $[M+Na]^+$=323.2 m/z. Found: 323.2 m/z.

PREPARATION 88

(t-Butoxy)-N-[3-(2-oxo-3-phenylpropyl)cyclohexyl]carboxamide

A compound from preparation 87 (4.11 g; 13.7 mmol) was dissolved in anhydrous tetrahydrofuran (100 mL) under a dry nitrogen atmosphere. The clear, colorless solution became clear and brown upon addition of 0.5 M benzylmagnesium chloride in tetrahydrofuran (15 mL; 30.1 mmol; 2.2 equiv). The reaction was quenched with water (100 mL) after 0.5 h and the product was extracted from the quenched solution with ethyl acetate. The organic layer was washed with saturated $NaCl_{(aq)}$ (once), dried with $Na_2SO_{4(s)}$, filtered, and concentrated to dryness by rotary evaporation. The resulting oil was purified by silica gel chromatography on a 6×15 cm column with a 2% acetonitrile/dichloromethane (v/v) mobile phase. A white solid (3.17 g; 70%) was obtained after concentration of appropriate fractions. TOF-MS(ES) calc'd: $[M+Na]^+$=354.2045 m/z. Found: 354.2037 m/z.

PREPARATION 89

[3-(2-Chloro-6-fluorophenyl)-5-methylisoxazol-4-yl]-N-[3-(2-oxo-3-phenylpropyl)cyclohexyl]carboxamide A compound from preparation 88 (3.0 g; 9.05 mmol) was dissolved in excess, neat acetic acid saturated with $HCl_{(g)}$ (20 mL). After 30 min of stirring at room temperature, in air, the solution was concentrated to dryness by rotary evaporation. Acetic acid was removed from the resultant solid by consecutive dissolution in, and drying from, acetonitrile (thrice) and then diethyl ether (once). The resulting white powder was dissolved in anhydrous dichloromethane (400 mL) under a nitrogen atmosphere. First was added 3-(2-chloro-6-fluoro-phenyl)-5-methylisoxazole-4-carbonyl chloride (2.74 g; 9.99 mmol; 1.1 equiv), and then 4-N,N-dimethylaminopyridine (114 mg; 0.93 mmol; 0.1 equiv) and finally triethylamine (5 mL; 36.3 mmol; 4 equiv). The reaction solution was stirred 17 h and then quenched with saturated $NaHCO_{3(aq)}$. The organic layer was washed with saturated $NaHCO_{3(aq)}$ (twice), saturated $NaCl_{(aq)}$ (once), dried with $Na_2SO_{4(s)}$, filtered, and concentrated to dryness by rotary evaporation. The resulting oil was dissolved in dichloromethane and purified by column chromatography on a 6×15 cm silica gel bed in dichloromethane. Dichloromethane (1 L) was followed by a 2% tetrahydrofuran/dichloromethane (v/v) mobile phase. A white solid (3.93 g; 95%) was obtained. TOF-MS(ES) calc'd: $[M+H]^+$= 469.1694 m/z. Found: 469.1692 m/z.

PREPARATION 90

2-{3-[(t-Butoxy)carbonylamino]cyclohexyl}acetic Acid

A compound from preparation 87 (845 mg; 2.81 mmol) was dissolved in anhydrous tetrahydrofuran (30 mL) under a dry nitrogen atmosphere. A 1 M solution of DIBAL-H in toluene (6.2 mL; 6.18 mmol; 2.2 equiv) was added dropwise to the −78° C. starting material solution over 5 min. After an additional 15 min of stirring, water quenched the cold reaction solution. Extraction with ethyl acetate produced an emulsion that was destroyed by concentration of the solution to near dryness. The resulting material was dissolved in water/diethyl ether and extracted with diethyl ether without further complication. The organic layer was washed with saturated $NaCl_{(aq)}$ (once), dried with $Na_2SO_{4(s)}$, filtered, and concentrated to dryness by rotary evaporation. The product was purified by radial chromatography on a 4 mm thick silica gel rotor with 300 mL of 1% tetrahydrofuran/dichloromethane (v/v) mobile phase followed by 300 mL of 10% tetrahydrofuran/dichloromethane (v/v) mobile phase. A white solid (535 mg; 79%) was obtained after concentration of the desired fractions. MS(ES) calc'd: $[M+H]^+$=264.1 m/z, $[M-Boc+H]^+$=142.1 m/z. Found: 264.1 m/z; 142.1 m/z.

PREPARATION 91

N-{(1S,3S)-3-[2-(Phenylamino)ethyl]cyclohexyl}(t-butoxy)carboxamide

A nitrogen sparged round bottom flask was charged with denatured ethanol (5 mL), $Ti(i-PrO)_4$ (337 µL; 1.14 mmol; 2.2 equiv), and aniline (95 µL; 1.04 mmol; 2 equiv). A compound from preparation 90 (125 mg; 0.518 mmol; 1 equiv) was then added to the clear, colorless reaction solution. The reaction solution became cloudy and then progressed to clear and light yellow over 3.3 h. $NaBH_4$ (30 mg; 0.793 mmol; 1.5 equiv) was then added and allowed to react overnight at room temperature. The clear, colorless reaction solution was quenched with 2 M $NH_{3(aq)}$ (20 mL). After a failed attempt at Celite® filtration, the product and Celite® mixture were suspended in water and extracted with $CHCl_3$ (thrice). This organic layer was washed with saturated $NaCl_{(aq)}$ (once), dried with $Na_2SO_{4(s)}$, filtered, and concentrated to dryness by rotary evaporation. The aqueous layer was decanted from the Celite® and the Celite® was suspended in 2 M $NH_{3(aq)}$ (120 mL). This suspension was extracted with $CHCl_3$ (trice) and the organic layer was treated similarly to the first organic layer. The combined extracts were purified by radial chromatography on a 2 mm thick silica gel rotor. The first chromatography with a 2% tetrahydrofuran/dichloromethane (v/v) mobile phase did not completely purify the product and was followed by a second and third radial chromatography with a 1% tetrahydrofuran/ dichloromethane (v/v) mobile phase. A white solid (55 mg; 33%) was obtained after concentration of the desired fractions. MS(ES) calc'd: [M+H]+=319.2 m/z; [M+$C_2H_3O_2$]−= 317.2 m/z. Found: 319.2 m/z; 377.2 m/z.

PREPARATION 92

N-{(1S,3S)-3-[2-(Phenylamino)ethyl]cyclohexyl}[3-(2-chloro-6-fluorophenyl)-5-methylisoxazol-4-yl] carboxamide A compound from preparation 91 (53 mg; 0.166 mmol) was dissolved in excess, neat acetic acid saturated with $HCl_{(g)}$ (2 mL). After 30 min of stirring at room temperature, in air, the solution was concentrated to dryness by rotary evaporation. Acetic acid was removed from the resultant solid by consecutive dissolution in, and drying from, acetonitrile (thrice) and then diethyl ether (twice). The resulting white powder was dissolved in anhydrous dichloromethane (8 mL) under a nitrogen atmosphere. First was added 3-(2-chloro-6-fluoro-phenyl)-5-methylisoxazole-4-carbonyl chloride (50.2 mg; 0.183 mmol; 1.1 equiv), and then 4-N, N-dimethylaminopyridine (2 mg; 0.017 mmol; 0.1 equiv) and finally triethylamine (94 μL; 0.667 mmol; 4 equiv). The reaction solution was stirred overnight, then quenched with saturated $NaHCO_{3(aq)}$, then extracted with dichloromethane (twice). The organic layer was washed with saturated $NaCl_{(aq)}$ (once), dried with $Na_2SO_{4(s)}$, filtered, and concentrated to dryness by rotary evaporation. The resulting product was dissolved in dichloromethane and purified by radial chromatography on a 2 mm thick silica gel rotor. A dichloromethane mobile phase was followed by a 5% tetrahydrofuran/dichloromethane (v/v) mobile phase. An off-white solid (66 mg; 87%) was obtained. TOF-MS(ES) calc'd: [M+H]+=456.1854 m/z.

Found: 456.1850 m/z.

PREPARATION 93

Methyl 2-(3-{[4-(2-chloro-6-fluorophenyl)-2-methyl-3-furyl]carbonylamino)}cyclohexyl)-acetate Part a: To a solution containing 15.0 g (83 mmol) of m-nitrophenylacetic acid in 200 mL ethanol was added 7.5 g 5% rhodium on carbon. The reaction was subjected to hydrogenation (60 psi) at 60° C. for 10 hours, after which the catalyst was removed by vacuum filtration and the solvent removed in vacuo, yielding 3.5 g (27%) of an oil. This material was used without further purification.

Part b: 1 mL acetyl chloride was added to 30 mL methanol. To this solution was added 3.5 g (22.3 mmol) of a compound from part a and the reaction was stirred for 1 hour. Solvents were removed in vacuo, yielding 3.24 g (70%) of an oil. This material was used without further purification.

Part c: To a solution of 1.05 g (5.06 mmol) of a compound from part b in 10 mL of methylene chloride was added 1.53 g (5.57 mmol) of 3-(2-chloro-6-fluoro-phenyl)-5-methylisoxazole-4-carbonyl chloride, followed by 2.11 mL (15.2 mmol) of triethylamine at room temperature. The reaction was stirred overnight, then concentrated in vacuo. The crude solid was dissolved in 150 mL ethyl acetate, washed 3× with 1N HCl, 3× with NaHCO3, 3× with brine, dried over sodium sulfate and concentrated iii vacuo yielding 1.8 g (87%) of a white solid. This material was an inseparable mixture of cis and trains isomers. MS(FIA) m/z=409.3

Part d: To a solution of 1.78 g (4.35 mmol) of a compound from part c in 10 mL of DMF at room temperature was added 5 mL of 2N NaOH in MeOH. The reaction was stirred for 1 hour and 0.537 g (4.78 mmol) of potassium t-butoxide was added. The resulting dark red reaction was stirred for 6 hours. The reaction was then added to 50 mL of 1N HCl and diluted with 150 mL of ethyl acetate. The organic layer was separated and washed 3× with brine, dried over sodium sulfate and concentrated in vacuo. This crude material was purified by flash chromatography, eluting with 5% MeOH ($CH_2Cl_2$. The major fractions were combined and concentrated in vacuo to give 1.15 g (71%) of a clear oil, which was characterized as the title compound. MS(FIA) m/z=375.2

PREPARATION 94

2-[3-(9-Chloro-3-methyl-4-oxo-5H-isoxazolo[4,3-c] quinolin-5-yl)cyclohexyl]acetic Acid To a solution of 1.78 g (4.35 mmol) of a product of preparation 93, in 10 mL of DMF at room temperature was added 5 mL of 2N NaOH in MeOH. The reaction was stirred for 1 h and 0.537 g (4.78 mmol) of potassium t-butoxide was added. The resulting dark red reaction was stirred for 6 h. The reaction was then added to 50 mL of 1N HCl and diluted with 150 mL of ethyl acetate. The organic layer was separated and washed 3× with brine, dried over sodium sulfate and concentrated in vacuo. This crude material was purified by flash chromatography, eluting with 5% MeOH/$CH_2Cl_2$. The major fractions were combined and concentrated in vacuo to give 1.15 g (71%) of a clear oil, which was characterized as the title compound. MS(FIA) m/z=375.2.

PREPARATION 95

2-[3-(9-Chloro-3-methyl-4-oxo-5H-isoxazolo[4,3-c] quinolin-5-yl)cyclohexyl]acetyl Chloride To an ice bath cooled solution containing 0.75 g (2.0 mmol) a compound from preparation 94 in 10 mL methylene chloride and catalytic DMF (3 drops) was added 0.262 mL (3.0 mmol) of oxalyl chloride in one portion. The ice bath was removed and the reaction stirred for 3 h. The solvents were removed in vacuo and the resulting oil azeotroped with toluene. This material was characterized as the title compound and used without further purification.

PREPARATION 96

Methyl 3-(azidomethyl)benzoate

To a solution of methyl 3-(bromomethyl)benzoate in DMF (55 ml) under $N_2$ was added sodium azide (10.39 g, 160 mmol) and stirred for 3 h. The solution was diluted with EtOAc, washed (water twice, then brine), dried (MgSO4), filtered, and concentrated to give the title compound. This material was used without further purification. MS (EI+) (m/z)=101.1 [M++1]

PREPARATION 97

Methyl 3-{[(t-butoxy)carbonylaminomethyl}benzoate

A mixture of a compound from preparation 95 (8.75 g, 45.8 mmol), (BOC)2O (11.98 g, 55 mmol), 10% Pd/C catalyst (4.76 g), and EtOAc (175 mL) was stirred under an atmosphere of hydrogen gas (balloon) for 18 h, filtered through celite, and concentrated. Column chromatography (silica gel, hexanes/EtOAc gradient) gave the title compound (5.8 g, 48%). Mass Spectrum (ES+) (m/z) 166.0 [M-BOC].

PREPARATION 98

Methyl 3-{[(t-butoxy)carbonylamino]methyl}cyclohexane Carboxylate

A mixture of a compound from preparation 97 (5.57 g, 20 mmol), 5% Rh/C (2.78 g), and MeOH (140 mL) was shaken in a PARR apparatus at 60 psi and 60° C. for 18 h, filtered through celite, and concentrated. Column chromatography (silica gel, hexanes/EtOAc gradient) gave the title compound (3.5 g, 62%). Mass Spectrum (ES+) (m/z) 166.0 [M-BOC].

PREPARATION 99

Methyl 3-{[3-(2-chloro-6-fluorophenyl)-5-methylisoxazol-5-yl]carbonylamino}cyclohexane Carboxylate To a solution of a compound from preparation 98 (0.5 g, 1.845 mmol) in dichloromethane (10 mL) was added TFA (7 mL) and stirred for 45 min. The solution was concentrated using benzene to azeotrope. The residue was dissolved in dichloromethane (20 mL) and Et$_3$N (0.77 mL, 5.54 mmol) and 3-(2-chloro-6-fluorophenyl)-5-methylisoxazole-4-carbonyl chloride (0.56 g, 2.03 mmol) were added under N$_2$. The solution was stirred overnight. The reaction was diluted with EtOAc, washed (0.1N HCl, H$_2$O, and brine), dried (MgSO$_4$), filtered, and concentrated. Column chromatography (silica gel, hexanes/EtOAc gradient) gave the title compound (0.52 g, 69%). Mass Spectrum (FIA) (m/z) 409.3 [M+1].

PREPARATION 100

Methyl 3(9-chloro-3-methyl-4-oxo-5H-isoxazolo[4,3-c]-quinolin-5-yl)cyclohexane Carboxylate A compound from preparation 99 (0.445 g, 1.09 mmol) and t-BuOK (0.135 g, 1.2 mmol), in DMF (15 mL) were allowed to react for 15 min under N$_2$. Ice water was added and extracted twice with EtOAc. The combined EtOAc layers were washed, dried, filtered, and concentrated. Column chromatography (silica gel, hexanes/EtOAc gradient) gave the title compound (0.329 g, 78%). Mass Spectrum (FIA) (m/z) 389.2 [M+1].

PREPARATION 101

Methyl 3(9-chloro-3-methyl-4-oxo-5H-isoxazolo[4,3-c]quinolin-5-yl)cyclohexane Carboxylate A compound from preparation 100 (5.17 g, 12.7 mmol) and t-BuOK (1.56 g, 13.97 mmol), in DMF (130 mL) were allowed to react for 20 min under N$_2$. Ice water was added and extracted twice with EtOAc. The combined EtOAc layers were washed, dried, filtered, and concentrated. Column chromatography (silica gel, acetone/dichloromethane gradient) gave cis (0.28 g, 7%), trans (1.08 g, 25%), and unseparated title compound (2.91 g, 68%).
Mass Spectrum (FIA) (m/z) 389.2 [M+1].
Mass Spectrum (FIA) (m/z) 389.2 [M+1].

PREPARATION 102

3-(9-Chloro-3-methyl-4-oxo-5H-isoxazolo[4,3-c] quinolin-5-yl)cyclohexane Carboxylate Racemic A cis compound from preparation 101 (1.08 g, 2.78 mmol), 1N NaOH (7 mL, 6.94 mmol), MeOH (20 mL), and THF (20 mL) were allowed to react for 5 h at 50° C. The reaction was cooled to room temperature, diluted with water, and acidified (conc. HCl) to less than pH 3. The mixture was extracted with EtOAc (2×) and the combined extracts were washed, dried, filtered, and concentrated to give the title compound (1.03 g, 98%).
Mass Spectrum (ES+) (m/z) 375.1 [M+1].

PREPARATION 103

2-{3-[(t-Butoxy)carbonylamino]cyclohexyl}acetic Acid

To a solution of a compound from preparation 45 (5.0 g, 14.4 mmol), dioxane (96 ml), and 1.0 N NaOH (28.8 ml, 28.8 mmol) was heated at 50° C. for 3 h. The reaction was cooled to room temperature, diluted with H$_2$O, and extracted with Et$_2$O. The aqueous layer was acidified (conc. HCl) to less than pH 3, and extracted with EtOAc (2×). The combined extracts were washed (brine), dried (MgSO$_4$), filtered, and concentrated to give the title compound.

PREPARATION 104

N-((1S,3R)-3-{[(Phenylmethoxy)carbonylamino]methyl}cyclohexyl)(t-butoxy)carboxamide To a solution of a compound from preparation 103 (3.43 g, 13.35 mmol), Et$_3$N (3.75 mL, 26.96 mmol) in toluene (86 mL) under N$_2$ was added DPPA (5.8 mL, 26.96 mmol) and benzyl alcohol (4.28 mL, 41.38 mmol). The solution was heated to reflux overnight. The reaction was cooled to room temperature, diluted with EtOAc, washed (1.0N NaOH then brine), dried (MgSO$_4$), filtered, and concentrated. Column chromatography (silica gel, hexanes/EtOAc gradient) gave the title compound (3.05 g, 63%). Mass Spectrum (ES+) (m/z) 263.1 [M−BOC].

PREPARATION 105

N-{(1S,3R)-3-[(phenylcarbonylamino)methyl]cyclohexyl}(t-butoxy)carboxamide

A mixture of a compound from preparation 104 (0.25 g, 0.69 mmol), benzoic anhydride (0.187 g, 0.828 mmol), 10% Pd/C catalyst (0.1 g), and EtOAc (10 mL) was stirred under an atmosphere of hydrogen gas (balloon) for 17 h. Added more benzoic anhydride (0.187 g, 0.828 mmol), and DMAP (0.025 g, 0.23 mmol), stirred for 2.5 h, filtered through celite, and concentrated. Column chromatography (silica gel, hexanes/EtOAc gradient) gave the title compound (0.208 g, 91%). Mass Spectrum (FIA) (m/z) 333.2 [M+1].

PREPARATION 106

N-{(1S,3R)-3-[(phenylcarbonylamino)methyl]cyclohexyl}[3-(2-chloro-6-fluorophenyl)-5-methylisoxazol-4-yl]carboxamide In a fashion similar to that described for preparation 46, a compound from preparation 105 (0.1 g, 0.3 mmol), TFA (2.5 mL), dichloromethane (4 mL), 3-(2,6-difluoro-phenyl)-5-methylisoxazole-4-carbonyl chloride (0.13 g, 0.5 mmol), and Et$_3$N (0.125 mL, 0.9 mmol) gave the title compound (0.109 g, 80%) after column chromatography (silica gel, hexanes/EtOAc gradient). Mass Spectrum (ES+) (m/z) 454.2 [M+1].

PREPARATION 107

N-{(1S,3R)-3-[(phenylcarbonylamino)methyl]cyclohexyl}[3-(2-chloro-6-fluorophenyl)-5-phenylisoxazol-4-yl]carboxamide In a fashion similar to that described for preparation 46, a compound from preparation 103 (0.1 g, 0.3 mmol), TFA (2.5 mL), dichloromethane (4 mL), 3-(2-chloro-6-fluoro-phenyl)-5-phenyl-isoxazole-4-carbonyl chloride (0.15 g, 0.45 mmol), and Et₃N (0.125 mL, 0.9 mmol) gave the title compound (0.14 g, 88%) after column chromatography (silica gel, acetone/dichloromethane gradient). Mass Spectrum (FIA) (m/z) 532.1 [M+1].

PREPARATION 108

N-{(1S,3R)-3-[(phenylcarbonylamino)methyl] cyclohexyl}[5–2-fluorophenyl)(1,3-oxazol-4-yl)] carboxamide A solution of a compound from preparation 105 (0.1 g, 0.3 mmol) in TFA (2 mL) was stirred for 1.5 h. The solution was concentrated using benzene to azeotrope, diluted with EtOAc, washed (1.0N NaOH), dried (Na₂SO₄), filtered, and concentrated. The residue was dissolved in dichloromethane (1.5 mL) and added to a mixture of EDCI (0.086 g, 0.45 mmol), DMAP (0.007 g, 0.06 mmol), 5-(2-fluoro-phenyl)-oxazole-4-carboxylic acid (0.087 g, 0.36 mmol) in dichloromethane (1.5 mL) under N₂. The reaction was stirred for 65 h, diluted with dichloromethane, washed (1.0N HCl, 2.0N NaOH, H₂O, and brine), dried (MgSO₄), filtered, and concentrated. Column chromatography (silica gel, acetone/dichloromethane gradient) gave the title compound (0.111 g, 81%). Mass Spectrum (FIA) (m/z) 456.2 [M+1].

PREPARATION 109

N-{(1S,3R)-3-[(phenylcarbonylamino)methyl] cyclohexyl}[3-(2-fluoro-3-iodophenyl)-5-methylisoxazol-4-yl]carboxamide In a fashion similar to that described for preparation 108, a compound from preparation 105(0.1 g, 0.3 mmol), TFA (2 mL), dichloro-methane (1.5 mL), EDCI (0.086 g, 0.45 mmol), DMAP (0.007 g, 0.06 mmol), 3-(2-fluoro-3-iodophenyl)-5-methyl-isoxazole-4-carboxylic acid (0.125 g, 0.36 mmol), and dichloromethane (1.5 mL) gave the title compound (0.104 g, 62%) after column chromatography (silica gel, acetone/dichloromethane gradient). Mass Spectrum (FIA) (m/z) 562.1 [M+1].

PREPARATION 110

N-{(1S,3R)-3-[(phenylcarbonylamino)methyl] cyclohexyl}[3-(2-fluoro-3-iodophenyl)-5-iodophenyl-4-yl]carboxamide In a fashion similar to that described for preparation 108, a compound from preparation 105 (0.1 g, 0.3 mmol), TFA (2 mL), dichloro-methane (1.5 mL), EDCI (0.125 g, 0.45 mmol), DMAP (0.007 g, 0.06 mmol), 3-(2-fluoro-5-iodo-phenyl)-5-methyl-isoxazole-4-carboxylic acid (0.125 g, 0.36 mmol), and dichloromethane (1.5 mL) gave the title compound (0.088 g, 53%) after column chromatography (silica gel, acetone/dichloromethane gradient). Mass Spectrum (FIA) (m/z) 562.1 [M+1].

PREPARATION 111

N-{(1S,3R)-3-[(phenylcarbonylamino)methyl] cyclohexyl}[3-(2,4-difluorophenyl)-5-methylisoxazol-4-yl]carboxamide In a fashion similar to that described for preparation 108, a compound from preparation 105 (0.1 g, 0.3 mmol), TFA (2 mL), dichloromethane (1.5 mL), EDCI (0.086 g, 0.45 mmol), DMAP (0.007 g, 0.06 mmol), 3-(2,4-difluorophenyl)-5-methyl-isoxazole-4-carboxylic acid (0.086 g, 0.36 mmol), and dichloromethane (1.5 mL) gave the title compound (0.123 g, 90%) after column chromatography (silica gel, acetone/dichloromethane gradient). Mass Spectrum (FIA) (m/z) 454.2 [M+1].

PREPARATION 112

N-{(1S,3R)-3-[(phenylcarbonylamino)methyl] cyclohexyl}[3-(2-chloro-6-fluorophenyl)-5-hexylisoxazol-4-yl]carboxamide In a fashion similar to that described for preparation 108, a compound from preparation 105 (0.1 g, 0.3 mmol), TFA (2 mL), dichloromethane (1.5 mL), EDCI (0.086 g, 0.45 mmol), DMAP (0.007 g, 0.06 mmol), 3-(2-chloro-6-fluorophenyl)-5-hexyl-isoxazole-4-carboxylic acid (0.117 g, 0.36 mmol), and dichloromethane (1.5 mL) gave the title compound (0.112 g, 69%) after column chromatography (silica gel, acetone/dichloromethane gradient). Mass Spectrum (FIA) (m/z) 540.5 [M+1].

PREPARATION 113

Phenylmethyl 2-((3S,1R)-3-{[5-methyl-3-(6-fluoro-2-iodophenyl)isoxazol-4-yl]carbonylamino}cyclohexyl)acetate In a fashion similar to that described for preparation 99, a compound from preparation 45 (5.1 g, 14.7 mmol), dichloromethane (30 mL), TFA (30 mL), dichloromethane (150 mL), 3-(2-fluoro-6-iodo-phenyl)-5-methylisoxazole-4-carboxylic acid (6.39 g, 17.49 mmol), and Et₃N (6.03 mL, 43.4 mmol) gave the title compound (7.15 g, 86%) after column chromatography (silica gel, hexanes/EtOAc gradient). Mass Spectrum (ES+) (m/z) 577.0 [M+1].

PREPARATION 114

Phenylmethyl 2-[(3S,1R)-3-(9-iodo-3-methyl4-oxo-5H-isoxazolo[4,3-c]quinolin-5-yl)cyclohexyl]acetate A compound from Example 499 (1.87 g, 3.35 mmol), 1.0N NaOH (6.7 mL, 6.7 mmol), and dioxane (20 mL) were allowed to react for 2 h at 50° C. in a fashion similar to that of preparation 29 to give the title compound (1.57 g, 100%). Mass Spectrum (ES+) (m/z) 467.0 [M+1].

PREPARATION 115

N-({(3S,1R)-3-aminocyclohexyl}methyl)benzamide

A solution of a compound from preparation 105 (5.3 g, 15.96 mmol) in TFA (50 mL) was stirred for 2 h. The reaction was concentrated using benzene azeotrope, diluted with EtOAc, washed (1.0N NaOH), dried (Na₂SO₄), filtered, and concentrated to give the title compound (3.41 g, 92%). Mass Spectrum (ES+) (m/z) 233.1 [M+1].

PREPARATION 116

N-[(1S,3S)-3-(3-oxo-3-phenylpropyl)cyclohexyl][5-methyl-3-(6-fluoro-2-iodophenyl)isoxazol-4-yl] carboxamide To a solution of a compound from preparation 115 (3.4 g, 14.7 mmol), Et₃N (6.14 mL, 44.1 mmol) in dichloromethane (150 mL) was added 3-(2-fluoro-6-iodo-phenyl)-5-methylisoxazole-4-carboxylic acid (6.97 g, 19.4 mmol) under N₂ and stirred for 4 h. The reaction was diluted with

PREPARATION 117

4-Amino-1-ethylcyclohexanecarboxylate Hydrochloride

Thionyl chloride (2.55 mL, 35 mmol) was added dropwise to absolute ethanol (100 mL) under a $N_2$ atmosphere. The resulting solution was stirred at room temperature for 10 min then 4-amino-1-cyclohexanecarboxylic acid (4.29 g, 30 mmol, cis, trans mixture) was added as a solid. The resulting solution was stirred at room temperature overnight. The solvent was removed in vacuo, the residue dissolved in ethanol (25 mL) and this solution was slowly added to a flask containing rapidly stirred ether (700 mL). The precipitate that formed was collected by filtration and dried in vacuo to give 5.75 g, 92% as a white solid. MS (ion spray) 172 (M+1).

PREPARATION 118

Ethyl 4-{[3-(2-chloro-6-fluorophenyl)-5-methylisoxazol-4-yl]carbonylamino}cyclohexanecarboxylate To a solution of a compound from preparation 117 (1.04 g, 5 mmol) in methylene chloride (15 mL) was added triethyl amine (0.8 mL, 5.7 mmol) followed by 3-(2-chloro-6-fluoro-phenyl)-5-methylisoxazole-4-carbonyl chloride (1.37 g, 5 mmol) in methylene chloride (10 mL), and an additional aliquot of triethyl amine (0.75 mL, 5.3 mmol). After an initial exotherm the mixture was stirred at room temperature for 4 h. The mixture was diluted with methylene chloride, washed with water, 1N aqueous hydrochloric acid solution, and brine, dried ($MgSO_4$), filtered, and concentrated in vacuo. The residue was purified by flash chromatography, eluting with 4:1 toluene: ethyl acetate, to give 2.0 g 98% of the title compound as a white solid. $^1$H—NMR was consistent with the desired structure. MS (ion spray) 409.3 (M+1).

PREPARATION 119

Ethyl 4-(9-chloro-3-methyl-4-oxo-5H-isoxazolo[4,3-c]-quinolin-5-yl)cyclohexanecarboxylate To a room temperature solution of a compound from preparation 118 (1.75 g, 4.28 mmol) in anhydrous DMF (20 mL) was added potassium t-butoxide (560 mg, 5 mmol). The resulting solution was stirred for 50 min, at which time TLC (1:1 hexane:ethyl acetate) showed the starting material had been consumed. The addition of 1N hydrochloric acid solution (5 mL) and water (95 mL) quenched the reaction. The mixture was extracted with ethyl acetate, the extracts were washed with water, and brine, dried ($MgSO_4$), filtered, and concentrated in vacuo. The residue was purified by flash chromatography, eluting with 9:1 methylene chloride: THF, to give 1.43 g 85% of the title compound, approximately 2:1 mixture of diastereoisomers, as a yellow tinted solid. $^1$H—NMR was consistent with the desired structure. MS (ion spray) 389 (M+1).

PREPARATION 120

4-(9-Chloro-3-methyl-4-oxo-5H-isoxazolo[4,3-c]quinolin-5-yl)cyclohexane carboxylic Acid To a solution of a compound from preparation 119 (390 mg, 1 mmol) in THF (7 mL) was added 0.5 M LiOH solution (5 mL). The mixture was stirred at room temperature for 3 days then acidified with of 0.1N hydrochloric acid solution (5 mL) and extracted with ethyl acetate. The extracts were washed with brine, dried ($MgSO_4$), filtered, and concentrated in vacuo to give 370 mg of the title compound as a yellow foam. NMR was consistent with the desired product.

PREPARATION 121

(3-Aminocyclohexyl)(phenylsulfonyl)amine

A solution of 1,3-diaminocyclohexane (1.14 g, 10 mmol, undetermined isomer mixture) in methylene chloride (50 mL) was cooled to 0° C. and phenylsulfonyl chloride (0.64 mL, 5 mmol) was added dropwise. The mixture was stirred at 0° C. for 4 h, then 1N sodium hydroxide solution (10 mL) was added and the mixture stirred an additional 5 min. The phases were separated, the organic phase was dried ($K_2CO_3$), filtered, and concentrated in vacuo. Toluene was added and the mixture re-concentrated to remove any remaining diamine, to give 0.77 g of a semi solid. $^1$H—NMR was consistent with the desired structure. MS (ion spray) 255 (M+1).

PREPARATION 122

[3-(2-Chloro-6-fluorophenyl)-5-methylisoxazol-4-yl]-N-{3-[(phenylsulfonyl)amino]cyclohexyl}carboxamide To a solution of a compound from preparation 121 (750 mg, 2.95 mmol theoretical) in methylene chloride (30 mL) was added triethylamine (0.6 mL, 4.3 mmol) followed by 3-(2-chloro-6-fluoro-phenyl)5-methylisoxazole-4-carbonyl chloride (822 mg, 3 mmol). The resulting mixture was stirred at room temperature for 3 h. The mixture was diluted with ethyl acetate, washed with 1N hydrochloric acid solution, saturated aqueous sodium bicarbonate solution, brine, then dried ($MgSO_4$), filtered, and concentrated in vacuo. Radial chromatography eluting with 95:5 methylene chloride: THF gave the less polar cis isomer (780 mg), mixed fractions (130 mg), and the more polar trans isomer (410 mg). The cis isomer: $^1$H—NMR was consistent with the desired structure, plus a small amount of the bis-sulfonylated diamine. MS (ion spray) 492 (M+1). For the trans isomer: 1H—NMR was consistent with the desired structure. MS (ion spray) 492 (M+1).

PREPARATION 123

2-{(3S, 1R)-3-[(t-Butoxy)carbonylamino]cyclohexyl}acetic Acid

A compound from preparation 45 (3.30 g, 0.0095 mol) was combined with aqueous 2N sodium hydroxide (35 mL), tetrahydrofuran (10 mL), and ethanol (10 mL) and the mixture stirred at room temperature for 2 h. The mixture was then concentrated in vacuo to remove volatile organics and additional water was added to the aqueous mixture. This basic aqueous mixture was then extracted with diethylether followed by careful acidification using 1N HCl. The acidic aqueous mixture was then extracted with ethyl acetate. The combined ethyl acetate extracts were dried over sodium sulfate followed by concentration in vacuo which provided the title compound (2.40 g, 98%) as a white solid. MS(ES): (M−1)⁻ 256.2 m/z.

PREPARATION 124

N-[(1S,3R)-3-(2-Hydroxyethyl)cyclohexyl](t-butoxy) Carboxamide

The compound from preparation 123 (2.10 g, 0.0082 mol) was dissolved in dry THF (35 mL) and the mixture cooled in an ice bath under a nitrogen atmosphere. Then borane-tetrahydrofuran (1.0 M, 12.25 mL, 0.0122 mol) was added via syringe and the mixture stirred overnight while slowly warming to room temperature. The reaction mixture was quenched into ice water and solid NaCl was added. This mixture was extracted with ethyl acetate and the combined extracts were dried over sodium sulfate and concentrated in vacuo. The resulting residue was chromatographed over silica gel using a $CH_2Cl_2$/THF mixture as eluant which allowed for isolation of 1.35 g (67%) of the desired alcohol. MS(ES): $(M+1)^+$ 244.5 m/z.

PREPARATION 125

N-[(1S,3R)-3-(2-p-toluenesulfonylethyl)cyclohexyl](t-butoxy)carboxamide

The compound from preparation 124 (1.30 g, 0.0054 mol) was combined with p-toluenesulfonyl chloride (1.12 g, 0.0059 mol), triethylamine (1.49 mL, 0.011 mol) and DMAP (0.02 g, cat.) in dichloromethane (30 mL) and the resultant mixture stirred overnight at room temperature. The mixture was then concentrated in vacuo and the residue chromatographed over silica gel using a mixture of $CH_2Cl_2$/THF as eluant which allowed for the isolation of the desired product (1.92 g, 90%). MS(ES): $(M+1)^+$ 398.2 m/z.

PREPARATION 126

N-{(1S,3R)-3-[2-(3-methylphenylthio)ethyl]cyclohexyl}(t-butoxy)carboxamide

3-Methylthiophenol (0.15 mL, 0.0013 mol) was dissolved in DMF (10 mL) at ambient temperature under a nitrogen atmosphere and sodium hydride (60%, 0.050 g, 0.0013 mol) was added. After stirring for 15 min., the compound from preparation 125 (0.50 g, 0.0013 mol) was added and the mixture stirred overnight at ambient temperature. The mixture was concentrated in vacuo and the residue chromatographed over silica gel using $CH_2Cl_2$/THF as eluant which allowed for isolation of 0.42 g (95%) of the desired product. MS(ES): $(M+1)^+$ 350.5 m/z.

PREPARATION 127

N-((1S,3R)-3-{2-[3-methylphenyl)sulfonyl]ethyl}cyclohexyl)(t-butoxy)carboxamide

The compound from preparation 126 (0.40 g, 0.00115 mol) was dissolved in a methanol/acetone (10 mL)/(10 mL) mixture and $NaHCO_3$ (0.40 g, 0.0048 mol) and water (5 mL) were added. Oxone® (1.46 g, 0.0024 mol) was then added and the mixture stirred at ambient temperature for 3.5 h. The mixture was concentrated in vacuo and the residue taken up in aqueous $NaHCO_3$ and extracted with $CH_2Cl_2$. The combined extracts were dried over sodium sulfate and concentrated in vacuo. The resulting residue was chromatographed over silica gel using $CH_2Cl_2$/THF as eluant which allowed for isolation of 0.420 g (96%) of the desired sulfone. MS(FD): $M^+$ 381.2, 382.2 m/z.

PREPARATION 128

N-((1S,3R)-3-{2-[(3-methylphenyl)sulfonyl]ethyl}cyclohexyl)[3-(2-chloro-6-fluorophenyl)-5-methylisoxazol-4-yl]carboxamide The compound from preparation 127 (0.385 g, 0.0010 mol) and TFA (1.0 mL) were dissolved in $CH_2Cl_2$ (5.0 mL) and the mixture stirred at ambient temperature for 2 h. The mixture was concentrated in vacuo and the residue treated with aqueous $NaHCO_3$ and extracted with $CH_2Cl_2$. The combined extracts were dried over sodium sulfate and concentrated in vacuo which allowed for recovery of crude amine. This amine was combined with 3-(2-chloro-6-fluorophenyl)-5-methylisoxazole-4-carbonyl chloride (0.302 g, 0.0011 mol), triethylamine (0.31 mL, 0.0022 mol) and DMAP (0.010 g, cat.) in $CH_2Cl_2$ (6.0 mL) and the mixture stirred overnight at ambient temperature. The mixture was concentrated in vacuo and the resulting residue chromatographed over silica gel using $CH_2Cl_2$/THF as eluant which allowed for isolation of 0.463 g (88%) of the desired amide. MS(ES): $(M+1)^+$ 519.2, 521.2 m/z.

PREPARATION 129

N-[(1S,3R)-3-(2-phenylthioethyl)cyclohexyl](t-butoxy)carboxamide

Thiophenol (0.32 mL, 0.0031 mol) was combined with sodium hydride (60%, 0.15 g, 0.0038 mol) in DMF (15 mL) and a compound from preparation 125 (1.25 g, 0.0031 mol) subsequently added in a manner similar to preparation 126. Workup and purification allowed for isolation of 1.0 g (98%) of the desired product. MS(ES): $(M+1)^+$ 335.1 m/z.

PREPARATION 130

N-[(1S,3R)-3-(2-phenylthioethyl)cyclohexyl][3-(2-chloro-6-fluorophenyl)-5-methyl]isoxazol-4-yl]carboxamide The compound from preparation 129 (0.50 g, 0.0015 mol) was combined with TFA (2 mL) in $CH_2Cl_2$ (10 mL) and treated in a manner similar to preparation 128. The resulting crude amine (0.213 g, 0.00097 mol) was combined with 3-(2-chloro-6-fluoro-phenyl)-5-methyl-isoxazole-4-carbonyl chloride (0.27 g, 0.001097 mol) and triethylamine (0.27 mL, 0.0019 mol) in $CH_2Cl_2$ (10 mL) again in a manner similar to preparation 128. Workup and purification allowed for isolation of 0.413 g (58%) of the desired amide. MS(ES): $(M+1)^+$ 473.1, 475.1 m/z.

PREPARATION 131

N-((1S,3R)-3-{2-[benzylsulfonyl]ethyl}cyclohexyl)(t-butoxy)carboxamide

Benzyl mercaptan (0.15 mL, 0.0013 mol) was combined with sodium hydride (60%, 0.05 g, 0.0013 mol) in DMF (10 mL) and the compound from preparation 125 (0.50 g, 0.0013 mol) subsequently added in a manner similar to preparation 126. Workup and purification allowed for isolation of 0.27 g (61%) of the desired sulfide. This compound (0.27 g, 0.0008 mol) was dissolved in a methanol/acetone (5 mL)/(5 mL) mixture and $NaHCO_3$ (0.27 g, 0.0032 mol) and water (5 mL) were added. Oxone® (0.98 g, 0.0016 mol) was then added and the mixture treated in a similar manner to preparation 127. Workup and purification allowed for isolation of 0.092 g (30%) of desired sulfone intermediate. MS(ES): $(M+1)^+$ 382.5 m/z.

PREPARATION 132

N-((1S,3R)-3-{2-[Benzylsulfonyl]ethyl}cyclohexyl[3-(2-chloro-6-fluorophenyl)-5-methylisoxazol-4-yl]carboxamide The compound from preparation 131 (0.090 g, 0.00024 mol) was combined with TFA (1 mL) in $CH_2Cl_2$ (3 mL) and treated in a similar manner to preparation 127. The resulting crude amine was combined with 3-(2-chloro-6-fluorophenyl)-5-methylisoxazole-4-carbonyl chloride (0.067 g, 0.00024 mol), triethylamine (4 drops), and DMAP (0.005 g, cat.) in $CH_2Cl_2$ (3 mL) again in a manner similar to preparation 126. Workup and purification allowed for isolation of 0.10 g (79%) of the desired amide.
MS(ES): $(M+1)^+$ 519.2, 521.1 m/z.

PREPARATION 133

N-{(1S,3R)-3-[2-(3-Fluorophenylthio)ethyl]cyclohexyl}(t-butoxy)carboxamide

3-Fluorothiophenol (0.14 mL, 0.0013 mol) was combined with sodium hydride (60%, 0.055 g, 0.0014 mol) in DMF (6 mL) and the compound from preparation 125 (0.50 g, 0.0013 mol) subsequently added in a manner similar to preparation 126. Workup and purification allowed for isolation of 0.40 g (89%) of the desired product. MS(ES): $(M+1)^+$ 354 m/z.

PREPARATION 134

N-((1S,3R)-3-{2-[(3-Fluorophenyl)sulfonyl]ethyl}cyclohexyl)(t-butoxy)carboxamide The compound from preparation 133 (0.38 g, 0.0011 mol) was dissolved in a methanol/acetone (10 mL)/(10 mL) mixture and $NaHCO_3$ (0.36 g, 0.0043 mol) and water (5 mL) were added. Oxone® (1.30 g, 0.0021 mol) was then added and the mixture treated in a manner similar to preparation 125. Workup and purification allowed for isolation of 0.40 g (98%) of the desired sulfone intermediate. MS(ES): $(M+1)^+$ 386.3 m/z.

PREPARATION 135

N-{(1S,3R)-3-[2-(3-Fluorophenylthioethyl]cyclohexyl}[3-(2-chloro-6-fluorophenyl)-5-methylisoxazol-4-yl]carboxamide The compound from preparation 134 (0.030 g, 0.00078 mol) was combined with TFA (1.5 mL) in $CH_2Cl_2$ (6 mL) and treated in a manner similar to preparation 126. The resulting crude amine was combined with 3-(2-chloro-6-fluorophenyl)-5-methylisoxazole-4-carbonyl chloride (0.213 g, 0.00078 mol), triethylamine (0.22 mL, 0.0016 mol) and DMAP (0.015 g, cat.) in $CH_2Cl_2$ (10 mL) again in a manner similar to preparation 126. Workup and purification allowed for isolation of 0.38 g (93%) of the desired amide.
MS(ES): $(M+1)^+$ 523.1, 525.2 m/z.

PREPARATION 136

N-{(1S,3R)-3-[2-(4-Fluorophenylthio)ethyl]cyclohexyl}(t-butoxy)carboxamide

4-Fluorothiophenol (0.16 mL, 0.0015 mol) was combined with sodium hydride (60%, 0.059 g, 0.0015 mol) in DMF (15 mL) and a compound from preparation 125 (0.59 g, 0.0015 mol) subsequently added in a manner similar to preparation 133. Workup and purification allowed for isolation of 0.52 g (98%) of the desired product. MS(ES): $(M+1)^+$ 353.6 m/z.

PREPARATION 137

N-((1S,3R)-3-{2-[(3-Fluorophenyl)sulfonyl]ethyl}cyclohexyl)(t-butoxy)carboxamide A compound from preparation 136 (0.50 g, 0.0014 mol) was dissolved in a methanol/acetone (10 mL)/(10 mL) mixture and $NaHCO_3$ (0.50 g, 0.0060 mol) and water (8 mL) were added. Oxone® (1.83 g, 0.0030 mol) was then added and the mixture treated in a manner similar to preparation 125. Workup and purification allowed for isolation of 0.50 g (92%) of the desired sulfone intermediate. MS(ES): $(M+Na)^+$ 408.1 m/z.

PREPARATION 138

N-((1S,3R)-3-{2-[(4-Fluorophenyl)sulfonyl]ethyl}cyclohexyl)-[3-(6-chloro-2-fluorophenyl)-5-methylisoxazol-4yl]-carboxamide The compound from preparation 137 (0.45 g, 0.0012 mol) was combined with TFA (2 mL) in $CH_2Cl_2$ (10 mL) and treated in a manner similar to preparation 126. The resulting crude amine (0.30 g, 0.0011 mol) was combined with 3-(2-chloro-6-fluorophenyl)-5-methylisoxazole-4-carbonyl chloride (0.29 g, 0.0011 mol), triethylamine (0.29 mL, 0.0021 mol) and DMAP (0.010 g, cat.) in $CH_2Cl_2$ (20 mL) again in a manner similar to preparation 126. Workup and purification allowed for isolation of 0.506 g (92%) of the desired amide. MS(ES): (M+1) 523.1, 525.1 m/z.

PREPARATION 139

Diphenylmethyl 2-((1R)-3-oxocyclohexyl)propane-1,3-dioate

To a flame dried flask at 0° C. was added lithium aluminum hydride (3.0 mL, 3.0 mmol, 1.0M in tetrahydrofuran) followed by (R)-(+)-1,1'-bi-2-napthol (1.71 g, 6.0 mmol) in anhydrous tetrahydrofuran (24 mL). After 30 min, the solution was allowed to warm to room temperature. A solution of sodium hydride (108 mg, 2.7 mmol, 60% in mineral oil) and dibenzylmalonate (675 µL, 2.7 mmol) in anhydrous tetrahydrofuran (30 mL) was then added to the reaction dropwise over approximately 2 min. To this mixture were then added 2-cyclohexen-1-one (2.91 mL, 30.0 mmol) and dibenzylmalonate (7.5 mL, 30 mmol), and the reaction was then stirred at room temperature, under a nitrogen atm, overnight. To the reaction was added 1N hydrochloric acid (60 mL, 60 mmol, 1N in water), followed by extraction with ethyl acetate (3×200 mL). The combined organic layers were then washed with saturated sodium bicarbonate solution, dried over magnesium sulfate and concentrated. Purification by flash chromatography on silica gel (eluting with 5–7.5% acetone/hexane) gave 10.25 g of the title compound as a opaque solid, 90% yield. $^1$H NMR: consistent with structure. MS (ion spray) 381 ($M^+$+ 1).

PREPARATION 140 cis-Diphenylmethyl 2-(3-hydroxycyclohexyl)propane-1,3-dioate

To a solution of a compound from preparation 139 (6.13 g, 16.1 mmol) in tetrahydrofuran (120 mL), methanol (10 mL), and water (10 mL) was added sodium borohydride (1.22 g, 32.2 mmol). After 10 min., the reaction was poured into 150 mL of a saturated ammonium chloride solution, and extracted with ethyl acetate. The ethyl acetate layer was washed with additional saturated ammonium chloride solution, saturated sodium bicarbonate solution, dried over magnesium sulfate, and concentrated. Purification by flash chromatography on silica gel (eluting with 5–13% acetone/hexane) gave 5.38 g of the title compound as a clear oil, 87% yield. $^1$H NMR: consistent with structure. MS (ion spray) 383 ($M^+$+ 1).

PREPARATION 141 cis-Phenylmethyl 2-(3-hydroxycyclohexyl)acetate

To a solution of a compound from preparation 140 (5.38 g, 14.07 mmol) in anhydrous methylsulfoxide was added water (0.51 mL, 28.13 mmol) and lithium chloride (1.19 g, 28.13 mmol). The reaction was placed in an oil bath at 175° C. and stirred vigorously for 2.5 h. The reaction was added to water and extracted with ethyl acetate twice. The organic layer was washed with water (×2), saturated sodium bicarbonate solution (×2), dried over magnesium sulfate and concentrated. Purification by flash chromatography on silica gel (eluting with 13% acetone/hexane) gave 1.81 g of the title compound as a yellow oil, 52% yield. $^1$H NMR: consistent with structure.

PREPARATION 142 cis-Phenylmethyl 2-(3-azidocyclohexyl)acetate

To a solution of a compound from preparation 141 (1.81 g, 7.29 mmol) in anhydrous toluene (70 mL) was added triphenylphosphine (3.82 g, 14.58 mmol), $Zn(N_3)_3 \cdot pyridine_2$ (1.68 g, 5.47 mmol), followed by dropwise addition of diethyl azodicarboxylate (2.30 mL, 14.58 mmol) over approximately 15 min., and the reaction was stirred at room temperature overnight under a nitrogen atmosphere. Filtered through Celite® to remove zinc salts, dilute with ethyl acetate, wash with 0.1N sodium hydroxide (×3), water, saturated sodium bicarbonate solution, dry over magnesium sulfate and concentrated. Purification by flash chromatography on silica gel (eluting with 3.5% ethyl acetate/hexane) gave 652 mg of the title compound as an oil, 33% yield. $^1$H NMR: consistent with structure.

PREPARATION 143 cis-Phenylmethyl 2-{3-[(t-butoxy)carbonylamino]cyclohexyl}acetate

To a solution of a compound from preparation 142 (652 mg, 2.4 mmol) and t-butoxycarbonyl anhydride (1.10 mL, 4.8 mmol) in ethyl acetate (50 mL) under a nitrogen atmosphere was added Lindlar's catalyst (270 mg, 5% by weight). The mixture was subjected to a hydrogen atmosphere at room temperature overnight. The mixture was filtered over Celite® to remove the catalyst and concentrated. Purification by flash chromatography on silica gel (eluting with 15% ethyl acetate/hexane) gave 820 mg of the title compound as a clear oil, 100% yield.

$^1$H NMR: consistent with structure.

PREPARATION 144 cis-Phenylmethyl 2-(3-{[3-(2-chloro-6-fluorophenyl)-5-methylisoxazol-4-yl]carbonylamino}cyclohexyl)acetate A solution of a compound from preparation 143 in trifluoroacetic acid was stirred at room temperature for 30 min. The solution was concentrated, followed by azeotropic removal of the remaining solvent with acetonitrile (×3). The crude product was dissolved in ethyl acetate, washed with 1N sodium hydroxide (×2), dried over magnesium sulfate and concentrated. To a solution of the resulting oil in dichloromethane (20 mL) was added 3-(2-chloro-6-fluorophenyl)-5-methylisoxazole4-carbonyl chloride (748 mg, 2.72 mmol), triethylamine (1.03 mL, 7.43 mmol), and dimethylamino pyridine (30 mg, 0.25 mmol), followed by triethylamine (1.03 mL, 7.43 mmol) dropwise via syringe. The reaction was stirred overnight under nitrogen at room temperature. The solution was washed with 0.1N HCl (×3), water, saturated sodium bicarbonate solution, dried over magnesium sulfate and concentrated. Purification by flash chromatography on silica gel (eluting with 0–30% ethyl acetate/hexane) gave 1.13 g of the title compound as a clear oil, 94% yield. $^1$H NMR: consistent with structure.

PREPARATION 145

2-[3-(9-Chloro-3-methyl4-oxo-5H-isoxazolo[4,3-c]quinolin-5-yl))cyclohexyl]acetic Acid To a solution of a compound from Example 494 (291 mg, 0.63 mmol) in dioxane (5 mL) was added 5N NaOH (5 mL) and the solution heated to reflux for 1 h. Upon cooling the reaction was quenched with 1N hydrochloric acid, and extracted with 20% isopropanol/chloroform (×3), dried over magnesium sulfate and concentrated. The resulting brown oil was treated with ethyl ether, sonicated, and a brown solid filtered out, to give 164 mg of the title compound, 70% yield. $^1$H NMR: consistent with structure.

PREPARATION 146 trans-5-[3-(Aminomethyl)cyclohexyl]-9-chloro-3-methyl-5H-isoxazolo[4,3-c]quinolin-4-one Hydrochloride To trans-racemic [3-(9-chloro-3-methyl-4-oxo-5H-isoxazolo[4,3-c]quinolin-5-yl)cyclohexyl]carbamic acid t-butyl ester (1.22 g, 2.74 mmol) was added acetic acid saturated with $HCl_{(g)}$ (30 mL, ~3N in HCl)and the solution stirred vigorously at room temperature for 10 min. The reaction was concentrated, followed by addition of acetonitrile and concentrated to assist in the removal of acetic acid. The resulting white solid was treated with ethyl ether, sonicated, and filtered to yield 985 mg of the title compound as a white solid, 94% yield. $^1$H NMR: consistent with structure. MS (ion spray) 346 ($M^+$+1).

PREPARATION 147

2-Fluoro-3-iodobenzaldehyde

To a solution of diisopropylamine (10.42 mL, 74.36) in THF (135 mL) under $N_2$ in an ice bath at 0–5° C. was added dropwise over 10 min n-BuLi (42.25 mL, 67.6 mmol) and stirred at this temperature for 10 min. Cooled the reaction mixture to −78° C. in a dry ice/acetone bath and dropwise added 1-fluoro-2-iodobenzene (7.88 mL, 67.6 mmol) over 5 min. Stirred at this temperature for 1 h, dropwise added DMF (6.26 mL, 74.36 mL) over 5 min, and stirred for 10 min. Added Acetic Acid (13.5 mL) followed by $H_2O$ and extracted with $Et_2O$ (2×). The combined organic solution was washed (0.1 N HCl then brine), dried ($MgSO_4$), filtered and concentrated. The crude benzaldehyde (16.9 g) was taken onto the next step without purification. $^1$H NMR was consistent with structure.

PREPARATION 148

2-Fluoro-3-iodobenzaldoxime

To a mixture of a compound from preparation 147 (16.9 g, 67.6 mmol) in $H_2O$ (35 mL), EtOH (35 mL), and ice (25 g) was added hydroxylamine hydrochloride (4.8 g, 74.4 mmol). Then, 169 mmol of 50% NaOH (6.76 g in 6.76 mL $H_2O$) was added with stirring. Enough ice to keep the temperature at 25–30° C. was added. Stirred for 2.5 h, acidified with conc. HCl to pH 4 (ice was added to keep the temperature at 25–30° C.), and extracted with Et$_2$O (2×). The combined organic solution was washed (brine), dried (MgSO$_4$), filtered, and concentrated. The residue was chromatographed on silica gel (EtOAc/dichloromethane gradient) to give the title compound (8.02 g, 45% over 2 steps).
Mass Spectrum (FIA) (m/z) 264.0 [M-1].

PREPARATION 149

2-Fluoro-3-iodobenzohydroximinoyl Chloride

To a stirred solution of a compound from preparation 148 (8.02 g, 30.2 mmol) in DMF (45 mL) at 25–30° C. was added about ⅕ of 30.2 mmol (4.03 g) of NCS. The initial NCS addition results in a slight temperature decrease. If the reaction does not self-initiate within 10 min., as indicated by a slight temperature rise, 5 pipettes of gas from the headspace of a conc. HCl reagent bottle was bubbled into the DMF solution. Carefully added rest of NCS and temperature rose to 45–55° C. Once reaction cooled to r.t. (about 1 h), added ice H$_2$O and extracted with Et$_2$O (2×). The combined organic solution was washed with (brine), dried (MgSO$_4$), filtered, and concentrated. The title compound (9.04 g) was taken on to the next step without purification. $^1$H NMR was consistent with structure.

PREPARATION 150

Ethyl 3-(6-fluoro-2-iodophenyl)-5-methylisoxazole-4-carboxylate

To a solution of a compound from preparation 149 (30.2 mmol) and ethyl-2-butynoate (4.23 mL, 36.24 mmol) in Et$_2$O (120 mL) under N$_2$ stirring at 0–5° C. was added dropwise a solution of Et$_3$N (5.46 mL, 39.26 mmol) in Et$_2$O (17 mL) over 1 h. Allowed to warm to room temperature and stirred overnight. Added Et$_2$O and washed (H$_2$O then brine), dried (MgSO$_4$), filtered, and concentrated. The crude residue was chromatographed on silica gel (dichloromethane) to give the title compound (6.92 g, 61%). Mass Spectrum (FIA) (m/z) 376.15 [M+1].

PREPARATION 153

N-t-Butyl-N'-(2-chloro-6-fluorobenzylidene) hydrazine Hydrochloride

A mixture of t-butyl hydrazine hydrochloride (1.24 g, 10 mmol) and 2-chloro-6-fluorobenzaldehyde (1.1 mL, 10 mmol) dissolved in acetic acid (5 mL) was stirred at 50° C. for half hour. Hexanes (10 mL) was added, filtered and washed the white solid with hexanes (20 mL). Yield: 61%. ESMS: 229 (M+1).

PREPARATION 156

3-Methyl-5-(2-chloro-6-fluorophenyl)-4-isoxazolecarboxylic Acid Ethyl Ester

To a solution of ethyl 3-aminomethyl crotonate (4.79 g, 33.5 mmol) in toluene (10 mL), was added triethylamine (3.73 g, 37 mmol). The solution was chilled using an ice bath, and then 2-chloro-6-fluorobenzoyl chloride (6.47 g, 33.5 mmol) was added dropwise over a 20 min period. The reaction was allowed to warm slowly to r.t. and stirred for 24 hr. The resulting suspension was then filtered, and the filtrate diluted with ethyl acetate (100 mL) and transferred to a separatory funnel. The organic layer was sequentially washed with water, brine, dried (sodium sulfate), and the volatiles removed under reduced pressure to provide the title compound (9.46 g) as a golden solid, and primarily one geometrical isomer. MS (ES) m/z 299.9 (M+H)$^+$.

The crude adduct was then redissolved in glacial HOAc (50 mL) to which was added NH$_2$OH.HCl (1.8 g, 1.1 eq). The solution was then heated to reflux for 40–45 min to effect isoxazole formation. The reaction mixture was concentrated to an oil, diluted with ether, and transferred to a sep. funnel. The organic phase was washed with saturated bicarbonate, brine, then dried. Filtration and concentration afforded crude isoxazole ethyl ester (7.5 g), which was used without further purification. MS (+ ES) m/z 283.9 (M+H)$^+$.

PREPARATION 157

5-(2-Chloro-6-fluorophenyl)-3-methylisoxazole-4-carboxylic Acid

Hydrolysis of the ethyl ester was accomplished by dissolving the crude ester (7.5 g, approx. 0.027 mol) in THF (250 mL), and adding aq. LiOH (1.344 g in 100 mL, 2 eq). After stirring overnight at r.t., the solution was concentrated to ⅔$^{rd}$ volume, diluted with EtOAc (200 mL) and 50 mL water, transferred to a separatory funnel, and the aqueous phase collected. The organic phase was washed twice, and the combined aqueous phase was then acidified with 5N HCl. Back extraction with three washings of EtOAc was then followed with a brine wash of the combined organics. After drying over Na$_2$SO$_4$, filtration and concentration, clean isoxazole acid was obtained (2.94 g). NMR (CDCl$_3$) δ7.13, 7.32 7.46 (3 m, 3H), 2.58 (s, CH$_3$). MS (-ES) m/z 253.8, 255.8 (M-H)$^-$.

PREPARATION 158

2-(3-{[5-(2-chloro-6-fluorophenyl)-3-methylisoxazol-4-yl]carbonylamino}cyclohexyl)-N-(3,4,5-trimethoxyphenyl)acetamide To a compound from preparation 157 (60 mg, 0.234 mmol) in benzene (4 mL) containing catalytic amount of pyridine (20 μl) was added oxalyl chloride (23 mL). After heating to reflux for 1 hr, an aliquot was concentrated under vacuum and analyzed by 1H—NMR (CDCl$_3$) for completion of acid chloride formation; 1H—NMR (CDCl$_3$) 7.53 (d of t, 1H), 7.37 (d, 1H), 7.17 (t,1 H). (racemic)

Solvent was removed under vacuum. To a solution of d,1-cis-1-amino,3-(N-3,4,5-trimethoxyphenyl)cyclohexyl-acetamide (60 mg, 0.185 mmol) in dry MeCl$_2$ (4 mL) containing catalytic DMAP (10%) and pyridine (20 μl, 0.24 mmol) was added the crude acid chloride in 0.5 mL MeCl$_2$ at r.t. Reaction was allowed to proceed for 4 hr at which time amide formation was complete by TLC. The reaction was diluted with MeCl$_2$ and transferred to a sep funnel, washed with dil.HCl (pH 1), and the aqueous fraction was separated and reextracted two more times in the same manner. The combined organics were then washed sequentially with sat'd bicarbonate, brine, dried over Na$_2$SO$_4$, filtered and concentrated under vacuum to afford crude product (69 mg). Purification was accomplished via prep TLC (Chromatotron®, 1 mm SI plate) using 70%–90% EtOAc in hexane to obtain 24 mg (24% from amine). MS (+ES) m/z 559.9 (M+H), 576.9 (M+NH$_3$).

PREPARATION 159

(3-{[5-(2-Chloro-6-fluorophenyl)-3-methylisoxazole-4-carbonyl]amino}cyclohexyl) acetic acid ethyl ester (cis)

A compound from preparation 157 (254 mg, 1 mmol) was dissolved in DMF (15 mL). EDC.HCl (211 mg, 1.1 eq) was then added, followed by DMAP (10 mg), and then cis-1,3-1(S)aminocyclohexyl-3(R)-acetic acid, methyl ester (60% ee, 188 mg, 1.1 eq) at r.t. After 18 hr, starting material was not yet fully consumed (TLC, NMR of aliquot), so the mixture was heated to 80° for 2 hr. The reaction was then cooled to r.t., and diluted with EtOAc and 0.1 N HCl. The aqueous phase was reextracted twice, and the combined organics washed with sat'd bicarbonate, brine, dried over $Na_2SO_4$. Filtration and concentration afforded crude product (207 mg). Purification using a Bond-Elut SI column (10 g, 4:3 hex/EtOAc) provided 34 mg (8%) of the title compound. MS (+ES) 411.0 (M+H)+.

PREPARATION 160

(3-{[5-(2-Chloro-6-fluorophenyl)-3-methylisoxazole-4-carbonyl]amino}cyclohexylmethyl)carbamic acid t-butyl ester Using the acid chloride method described for preparation 158, 3 mmol (0.689 g) of a cis/trans mixture of 1-amino, 3-Boc-aminomethylene cyclohexane was dissolved in $CH_2Cl_2$ (10 mL), followed by addition of $Et_3N$ (0.415 mL, 6 mmol), DMAP (cat, 20 mg), at rt. The above isoxazole acid chloride of preparation 157 (3 mmol in 10 mL $CH_2Cl_2$) was then added dropwise over 10 min. Reaction was allowed to proceed overnight. The reaction mixture was then transferred to a sep funnel, diluted with additional $CH_2Cl_2$, and washed sequentially with 5% citric acid (aq, pH 3–4), sat'd bicarbonate, brine, then dried. Filtration and concentration yielded crude product (brown oil). Purification by filtration through a pad of Silica Gel 60 in a 60 mL sintered glass funnel using 2:1 hexane/EtOAc afforded clean cis/trans product (0.830 g, 59% overall). NMR (CDCl$_3$) δ 7.2–7.6 (3 m,3H), 5.55 and 5.2 (trans/cis amide NH's), 4.5 and 4.2 (cis/trans Boc NH's), 3.8 and 2.95 (trans/cis aminomethine (CH)), 2.58 and 2.55 (trans/cis CH3), 0.6–2.9 (m's), 1.4 (2 s, cis/trans t-butyl). MS (+ES); 465.9 (N+H)$^+$; (−ES); 463.9 (M−H)$^−$, 499.9 (M+Cl−H)$^−$, 524 (M+Oac−H)$^−$.

PREPARATION 161

(cis-3(S)-Aminocyclohexylmethyl)carbamic Acid Benzyl Ester

S-amino enantiomer of N-({3-[(t-butoxy)carbonylamino]cyclohexyl}methyl) (phenylmethoxy)carboxamide (1.0 g, 2.76 mmol) was treated with TFA (5 mL) under $N_2$. After 20 min of stirring at r.t. the reaction was complete. The crude was then concentrated to an oil which was purified on a Varian Bond-Elut SCX column (10 g). The column was eluted consecutively with CHCl$_3$, MeOH, and ammonia (2.0M in MeOH). The pure product was recovered from the ammonia fractions. The solvent was removed in vacuo to afford 0.632 g (87%) as a colorless oil. MS (ES+) m/z 263.0 (M+H)$^+$.

PREPARATION 162

(3-{[5-(2-Chloro-6-fluorophenyl)-3-methylisoxazole-4-carbonyl]amino}cyclohexylmethyl)carbamic Acid Benzyl Ester A solution from preparation 157 (1.0 g, 3.9 mmol) in toluene (30 mL) was treated with a catalytic amount of pyridine (0.1 mL) and cooled to 0° C. The solution was then treated with oxalyl chloride (0.545 g, 4.3 mmol) and stirred at r.t. for 2 hr. 1H NMR showed the completion of the acid chloride formation; 7.52 (d, 1H), 7.37 (d, 1H), 7.15 (t, 1H) The solvent was removed in vacuo. A solution from preparation 161 (0.550 g, 2.09 mmol) and triethylamine (0.422 g, 4.18 mmol) in dry DMF (25 mL) was stirred at r.t. This solution was then treated with the acid chloride from preparation 158(0.859 g, 3.135 mmol) which was added dropwise over two min. The reaction was then catalyzed with DMAP (0.025 g, 0.21 mmol) and allowed to stir o.n. The reaction was diluted in EtOAc (250 mL), transferred to a sep funnel, and washed with a 5% citric acid solution (5×50 mL), sat. sodium bicarbonate solution (2×50 mL), brine (2×50 mL) and was dried over sodium sulfate. The EtOAc solution was filtered and the solvent removed in vacuo to yield an orange solid. The solid was purified using silica gel column chromatography. The column was prepared with CHCl$_3$ and the product was eluted with 10% EtOAc in CHCl$_3$. The solvent was removed in vacuo to afford 0.584 g (56%) of the title compound as a white solid. MS (ES+) m/z 500.1 (M+H)$^+$.

PREPARATION 163 cis-Octahydroquinolin-2-one

To a solution of 2-nitrocinnamic acid in 120 mL of acetic acid in a Parr shaker, was added PtO$_2$ (10 g). Hydrogen (3 atm) was then introduced, and the contents of the shaker were heated to 60° C. for 24 h. After the mixture was cooled to r.t. and filtered through Celite®, the solvent was removed in vacuo, and the residue was dissolved in EtOAc, and transferred to a sep. funnel. Treatment with sat'd HCO$_{3-}$, brine, and then drying over Na$_2$SO$_4$, filtration and concentration afforded predominantly cis lactam (<7% trans by NMR) in 55% yield (6 g). MS (+ES) m/z 254 (M+1)$^+$.

PREPARATION 164 trans-Octahydroquinolin-2-one

To a solution of 3,4,5,6,7,8-hexahydro-1H-quinoline-2-one (0.1 g, 0.66 mmol) in dioxane (10 mL) containing a catalytic quantity (40 μL) was added NaCNBH$_3$ (0.67 g). The reduction was left to stir for 20 hrs at r.t., and then diluted with EtOAc. The organic phase was treated with dilute HCl (3×), and the combined organics were washed with saturated HCO$_{3-}$, brine, dried over Na$_2$SO$_4$, filtered and concentrated to afford the mainly traits product (98 mg, 95%, 15–20% cis isomer). MS (+ES) m/z 254 (M+1)$^+$.

PREPARATION 165 cis-3-(2-{[5-(2-Chloro-6-fluorophenyl)-3-methylisoxazole-4-carbonyl]amino}cyclohexyl) propionic Acid Methyl Ester The acid chloride (0.4 mmol) of preparation 157 was prepared as described previously, and added to a MeCl$_2$ solution (10 mL) of methyl 3-((1S,2S)-2-aminocyclohexyl) propanoate (222 mg, 1.2 eq) followed by Et$_3$N (133 μl, 0.96 mmol) and DMAP (10%) at r.t. Acylation was allowed to proceed for 18 hr. Crude product was obtained by dilution of the reaction mixture with MeCl$_2$ and 0.1 N HCl, transferring to a sep funnel. The organic phase was then washed with sat'd bicarbonate, brine, then dried over Na$_2$SO$_4$. Filtration and concentration provided crude product, which was then purified using a Bond-Elut Si column (1 g, 1:1 hex/EtOAc) to generate pure methyl ester, (86 mg, 51%). MS (+ES) m/z 422.9/424.9 (M+H).

PREPARATION 166 cis-3-(2-{[5-(2-Chloro-6-fluorophenyl)-3-methylisoxazole-4-carbonyl]amino}cyclohexyl) propionic Acid To a solution of a compound from preparation 165 (86 mg, 0.2 mmol) in THF (5 mL) was added 2 mL 0.5M aq.

LiOH (5 eq), dropwise at r.t. Hydrolysis was complete at 2.5 hr. After dilution with water and EtOAc, the contents were transferred to a sep funnel, where addition of enough 1N HCl was added to maintain pH 2. The aqueous phase was back extracted 3 times with additional solvent, and the combined organics were then washed with brine, dried over $Na_2SO_4$. Filtration and concentration afforded clean acid, 80 mg (97%), which was used without further purification. MS (+ES) m/z 408.9/410.9 (M+H).

PREPARATION 167

5-(2-Chloro-6-fluorophenyl)-3-methylisoxazole-4-carboxylic acid-{2-[2-(3,4,5-trimethoxyphenylcarbamoyl)ethyl]cyclohexyl}amide To a compound from preparation 166 (40 mg, 0.1 mmol) in DMF (2 mL) was added catalytic amount of DMAP (10%, 1 mg), followed by EDC.HCl (20.6 mg, 0.11 mmol) and 3,4,5-trimethoxyaniline (20.1 mg, 0.11 mmol) at r.t. After 18 hr, the reaction was transferred to a sep funnel and diluted with EtOAc and 1N NaOH (aq. pH 9–10). The aqueous phase was extracted 3 times, and combined EtOAc fractions were then washed sequentially with 1 N HCl, sat'd bicarbonate, brine, and then dried over $Na_2SO_4$. After filtration and concentration, crude amide was obtained (33 mg). Starting material (7 mg) was also recovered from the aqueous fraction upon acidification and standard workup. The crude product was then chromatographically purified (Bond-Elut Silica column, 1 g, 2:1 EtOAc/hexanes) to afford clean amide (48 mg, 50%). MS (ES+) 573.9, 575.9 (M+H)$^+$.

PREPARATION 168 trans-3-(2-{[3-(2-Chloro-6-fluorophenyl)-5-methylisoxazole-4-carbonyl]amino}cyclohexyl) propionic Acid A solution of methyl 3-(2-{[3-(2-chloro-6-fluorophenyl)-5-methylisoxazol-4-yl]carbonylamino}cyclohexyl) propanoate (0.127 g, 0.3 mmol) in THF (5 mL) was treated with a 0.5 M sol'n of LiOH in water (3 mL). The sol'n was stirred at r.t. for 5 hr. The reaction was diluted with water (3 mL) and washed with EtOAc (2×5 mL). The pH of the aqueous was adjusted to ~3 with 0.1 M HCl and extracted with EtOAc (4×5 mL). The organic extractions were then washed with brine (2×5 mL), dried over sodium sulfate and the solvent removed to afford 0.095 g (80%) as a white solid. MS (ES+) m/z 409.0 (M+H)$^+$, (ES−) m/z 407.0 (M−H)$^−$.

PREPARATION 169 traits-3-(2-Chloro-6-fluorophenyl)-5-methylisoxazole-4-carboxylic acid{2-[2-(3,4,5-trimethoxyphenylcarbamoyl)ethyl]cyclohexyl}amide A sol'n of a compound from preparation 168 (0.095 g, 0.23 mmol) and EDC (0.115 g, 0.6 mmol) in DMF (25 mL) was treated with 3,4,5-trimethoxyaniline (0.11 g, 0.6 mmol). A catalytic amount of DMAP (4 mg, 0.03 mmol) was also added. The reaction mixture was stirred at r.t. overnight. The reaction was diluted in EtOAc (100 mL) and washed with 5% citric acid sol (3×50 mL), water (2×50 mL), and dried over sodium sulfate. The solvent was removed in vacuo to afford a crude brown oil which was purified by a Varian Bond Elut SI column (10 g) with an eluting solvent of 1:1 Hexanes: EtOAc. The solvent was removed in vacuo to afford 0.072 g (54%) as an off white solid.
MS (ES+) m/z 574.0 (M+H)$^+$, (ES−) m/z 572.1 (M−H)$^−$, 632.1 (M+CH$_3$COO$^−$)$^−$.

PREPARATION 170

{(3S, 1R)-3-[(t-butoxy)carbonylamino]cyclopentyl}-N-benzylcarboxamide

A mixture of N—BOC-1R, 3S-1 amino cyclopentane-3-carboxylic acid (229 mg, 1 mmol), EDC (286 mg, 1.5 mmol), benzyl amine (160 mg, 1.5 mmol) and DMAP (5 mg, catalytic) dissolved in DMF (20 mL) was stirred overnight at rt. The reaction mixture was diluted with ethyl acetate (200 mL) and washed with 0.2M HCl (2×50 mL), water (2×50 mL), brine (2×50 mL), dried over $Na_2SO_4$, filtered, and evaporated to yield a white solid (160 mg, 50%). ESMS: 319 (M+1)$^+$.

PREPARATION 171

(1R,3S)-1-Amino-N'-phenylmethylcyclopentane-3-carboxamide

A compound from preparation 170 (100 mg, 0.31 mmol) was dissolved in TFA reagent (9.25 mL TFA, 0.25 mL anisole, 0.25 mL TIS, 0.25 mL water) and stirred at r.t for 30 m. TFA reagent was evaporated and the residue was dissolved in chloroform (10 mL) and filtered through SCX column and eluted with ammonia (10 mL, 2 M solution in methanol) and evaporated to yield title compound (68 mg, quantitative). ESMS: 219 (M+1)$^+$, 277 (M+Ac)$^+$.

PREPARATION 172

{(3S, 1R)-3-[N-benzylcarbamoyl]cyclopentyl}[3-(2-chloro-6-fluorophenyl)-5-methylisoxazol-4-yl] carboxamide A compound from preparation 171 was dissolved in DMF (25 mL) and 2-chloro-6-fluorophenyl isoxazoyl chloride, triethylamine and DMAP were added and stirred overnight at r.t. The reaction mixture was diluted with ethyl acetate (100 mL) and washed with HCl (1M, 2×50 mL), water (2×50 mL), brine (2×50 mL), dried over sodium sulfate, filtered, and evaporated to yield title compound (248 mg, 80%, crude). ESMS: 456 (M)$^+$.

PREPARATION 173

(3S,1R)(3-Hydroxymethylcyclopentyl)carbamic Acid t-butyl Ester (1R,3S)-3-t-Butoxycarbonylaminocyclopentanecarboxylic acid (229 mg, 1 mmol) was dissolved in THF (10 mL) and borane-THF (1.5 mL, 1M solution) was added drop-wise at 0° C. and stirred overnight at r.t. The reaction mixture was poured into ice-cold water (10 mL) and extracted with ethyl acetate (2×50 mL). The ethyl acetate extract was washed with brine, dried over sodium sulfate, filtered and evaporated to yield a semi solid (160 mg, 74%). ESMS (+): 216 (M+1)$^+$, 250 (M+Cl)$^+$.

PREPARATION 174

(3R,1S)-Toluene-4-sulfonic acid 3-t-butoxycarbonylaminocyclopentylmethyl Ester

A compound from preparation 173 (150 mg, 0.69 mmol) was dissolved in methylene chloride (20 mL) and p-toluenesulfonyl chloride (131 mg, 0.69 mmol), triethylamine (268 μL, 1.86 mmol) and DMAP (10 mg) were added and stirred overnight. The methylene chloride solution was washed with 1M HCl (2×10 mL), water (2×10 mL), brine (2×10 mL), dried over sodium sulfate, filtered and evaporated to yield the title compound (223 mg, 86%). ESMS: 370 (M+1)$^+$, M+Ac)$^+$.

PREPARATION 175

(1R,3S)(3-Azidomethyl-cyclopentyl)-carbamic acid t-butyl Ester

To a solution of a compound of preparation 174 (96 mg, 0.26 mmol) dissolved in DMF (10 mL) sodium azide was added and stirred at 80° C. overnight. The reaction mixture was diluted with ethyl acetate (50 mL) and washed with water (2×25 mL), brine (2×25 mL), dried over sodium sulfate, filtered and evaporated to yield the title compound (55 mg, 88% crude). HNMR (CDCl$_3$): 1.00–1.12 (m, 1H), 1.2–1.50 (m, 2H), 1.40 (s, 9H), 1.52–1.70 (m, 1H), 1.71 (1.82 (m, 1H), 1.89–2.00 (m, 1H), 2.10–2.30 (m, 2H), 3.26–3.28 (d, 2H), 4.80 (br S, 1H).

PREPARATION 176

(1R,3S)(3-Aminomethylcyclopentyl)carbamic Acid t-butyl Ester

To a solution of a compound from preparation 175 (55 mg, 0.23 mmol) dissolved in methanol (10 mL) palladium/C (10 mg, 10%) was added and stirred under hydrogen (balloon) at for 2 h at rt. The solution was filtered off through Celite® and evaporated to yield a white solid (44 mg, 89%). ESMS: 215 (M+1)$^+$.

PREPARATION 177

(1R,3S)-[3-(Benzoylaminomethyl)cyclopentyl] carbamic Acid t-butyl Ester

To a solution of a compound from preparation 176 (44 mg, 0.2 mmol) dissolved in DMF (10 mL), benzoyl chloride (35 mg, 0.25 mmol), triethylamine (0.5 mL) and DMAP (5 mg) was added and stirred overnight at rt. The reaction mixture was diluted with ethyl acetate (50 mL), washed with 1M HCl (2×20 mL), water (2×20 mL), brine (2×20 mL), dried over sodium sulfate, filtered and evaporated to get title compound (70 mg, crude quantitative). ESMS: 319 (M+1)$^+$, 317 (M−1)$^-$, 353 (M+Cl)$^-$, 317 (M+Ac)$^-$.

PREPARATION 178

(1R,3S)—N-(3-Aminocyclopentylmethyl)benzamide

A compound from preparation 177 (70 mg, 0.22 mmol) was dissolved in TFA (5 mL) and stirred for ½ h at rt. TFA was evaporated under vacuum and the residue was dissolved in chloroform (5 mL) passed through SCX column (Varian Bond Elut, 6 cc) and eluted with 2M ammonia (methanol) to obtain title compound (34 mg, 72%). ESMS: 219 (M+1)$^+$, 277 (M+Ac)$^-$.

PREPARATION 179

(1R,3S)-3-(2-Chloro-6-fluorophenyl)-5-methylisoxazole-4-carboxylic Acid[3-(benzoylaminomethyl)cyclopentyl]amide To a solution of a compound from preparation 178 (34 mg, 0.15 mmol) in DMF (5 mL), 2-chloro-6-fluorophenyl isoxazoyl chloride (85 mg, 0.3 mmol), triethylamine (1 mL), DMAP (5 mg) were added and stirred overnight. The reaction mixture was diluted with ethyl acetate (50 mL), washed with 1M HCl (2×20 mL), water (2×25 mL), brine (2×20 mL), dried over sodium sulfate, filtered, evaporated and chromatographed (silica gel, 50% ethyl acetate in hexanes) to yield title compound (36 mg, 52%). ESMS: 456 (M)+, 514 (M+Ac)$^-$.

PREPARATION 180

(1S,4R)(4-Hydroxymethyl-cyclopent-2-enyl)-carbamic Acid t-butyl Ester

To a solution of 4-t-butoxycarbonylaminocyclopent-2-enecarboxylic acid (1 g, 4.4 mmol) dissolved in THF (100 ml) and added with borane-THF (4.5 ml, 4.5 mmol) at 0° C. and stirred overnight at r.t. The reaction mixture was poured into ice-cold water (100 ml) and extracted with ethyl acetate. The ethyl acetate extract was washed with brine, dried over sodium sulfate and evaporated to obtain the title compound (655 mg, 69%). ESMS: 214 (M+1)$^+$, 236 (M+23)$^+$, 248 (M+35)$^-$, 272 (M+59)$^-$.

PREPARATION 181

(1S,4R)-Toluene-4-sulfonic Acid 4-t-butoxycarbonylamino-cyclopent-2-enylmethyl Ester A solution of a compound from preparation 180 (655 mg, 3 mmol), p-tosyl chloride (760 mg, 4 mmol), triethyl amine (0.4 ml) and DMAP (100 mg) dissolved in dichloromethane (50 ml) was stirred at rt, overnight. The reaction mixture was washed with dilute hydrochloric acid (2×), water (2×), brine (2×), dried over sodium sulfate and evaporated to obtain the title compound (1.0 g, 90%). ESMS: 368 (M+1)$^+$, 426 (M+59)$^-$.

PREPARATION 182

(1S,4R)(4-Azidomethylcyclopent-2-enyl)carbamic Acid t-butyl Ester

To a solution of a compound from preparation 181 (2 g, 2.7 mmol) in DMF (50 mL), sodium azide (200 mg, 3 mmol) was added and stirred at 80° C. overnight. The reaction mixture was diluted with ethyl acetate (100 mL) and washed with water (2×50 mL), brine (2×50 mL), dried over sodium sulfate and evaporated to yield the title compound (quantitative). IR (chloroform): 2096.6 cm$^-$ (azide). $^1$HNMR (CDCl$_3$): δ1.27–1.30 (m, 2H), 1.43 (s, 9H), 2.51–2.56 (m, 2H), 3.27–3.35 (m, 2H), 5.76 (s, 2H).

PREPARATION 183

(1S,3R)-(3-Aminomethylcyclopentyl)carbamic Acid t-butyl Ester

To a solution of a compound from preparation 182 (300 mg, 1.25 mmol) in methanol (10 mL), Pd/C (10%, 50 mg) was added and the reaction mixture was hydrogenated (1 atm) overnight at rt. The reaction mixture was filtered through celite and evaporated to yield the title compound (222 mg, 89%). ESMS: 215 (M+1)$^+$.

PREPARATION 184

(1S,3R)[3-(Benzoylaminomethyl)cyclopentyl]carbamic Acid t-butyl Ester

A mixture of a compound from preparation 183 (222 mg, 1.03 mmol), benzoyl chloride (210 mg, 1.5 mmol), triethylamine (1 mL), and DMAP (10 mg, catalytic) in DMF (50 mL) was stirred overnight. The reaction mixture was diluted with ethyl acetate (100 mL) and washed with dilute hydrochloric acid (1M, 2×50 mL), water (2×50 mL), brine (2×50 mL), dried over sodium sulfate, filtered and evaporated to yield the title compound (395 mg). ESMS: 319 (M+1)$^+$, 377 (M+59)$^-$.

PREPARATION 185

(1S,3R)—N-(3-Aminocyclopentylmethyl)benzamide

A compound from preparation 184 (crude 390 mg) was dissolved in trifluoroacetic acid (10 mL) and stirred for half an hour at rt. The reaction mixture was evaporated and chromatographed (Varian Bond Elut 60 cc, SCX column, 2M ammonia solution in methanol) to obtain the title compound (233 mg, 87%). ESMS: 219 (M+1)$^+$.

PREPARATION 186

(1S,3R)-3-(2-Chloro-6-fluorophenyl)-3-methylisoxazole-4-carboxylic Acid[3-(benzoylaminomethyl)cyclopentyl]amide A mixture of a compound from preparation 185 (230 mg, 1.05 mmol), 3-(2-chloro, 6-fluorophenyl)-5-methyl-4-isoxazoyl chloride (328 mg, 1.2 mmol), triethyl amine (1 mL), dimethyl amino pyridine (DMAP, 50 mg) dissolved in DMF (20 mL) was stirred overnight at rt. The reaction mixture was diluted with ethyl acetate (100 mL) and washed with dilute HCl (1M, 2×50 mL), water (2×50 mL), brine (2×50 mL), dried over sodium sulfate, filtered, evaporated and then chromatographed (Varian Bond Elut, Si, 60 cc, 50% EtOAc in Hexane) to obtain the title compound (100 mg, 20%). ESMS: 456 (M)$^+$, 515 (M+59)$^-$.

PREPARATION 187

(1S,3R){3-[(4-Fluorobenzoylamino)methyl]cyclopentyl}carbamic Acid t-butyl Ester

To a solution of a compound from preparation 183 (68 mg, 0.31 mmol) and 4-fluorobenzoylchloride (60 mg, 0.38 mmol) dissolved in DMF (2 mL), triethyl amine (0.5 mL) and DMAP (10 mg) were added and stirred for four hours at rt. The reaction mixture was diluted with ethyl acetate (20 mL) and washed with dilute hydrochloric acid (2×20 mL, 0.1 M), water (2×20 mL), brine (2×20 mL), dried over sodium sulfate, filtered and evaporated to obtain 492323 (127 mg). ESMS: 337 (M+1)$^+$, 395 (M+59)$^-$.

PREPARATION 188

(1S,3R)—N-(3-Aminocyclopentylmethyl)-4-fluorobenzamide

A compound from preparation 187 (127 mg) was dissolved in trifluoroacetic acid (2 mL) and stirred for half an hour at rt. The reaction mixture was evaporated under vacuum and the residue was dissolved in methylene chloride, filtered through SCX column (Bond Elut, 60 cc) and eluted with ammonia (2M in methanol) to obtain the title compound (81 mg, 91%). ESMS: 237 (M+1)$^+$, 295 (M+59)$^-$.

PREPARATION 189

(1R,3S)-3-(2-Chloro-6-fluorophenyl)-3-methylisoxazole-4-carboxylic Acid{3-[(4-fluorobenzoylamino)methyl]cyclopentyl}amide A solution of a compound from preparation 188 (81 mg, 0.34 mmol), chloro fluoro phenyl isoxazoyl chloride (113 mg, 0.41 mmol), triethyl amine (0.5 mL) and DMAP (10 mg) in DMF (5 mL) was stirred overnight at rt. The reaction mixture was diluted with ethyl acetate (20 mL) and washed with dilute hydrochloric acid (2×20 mL, 0.1 M), water (2×20 mL), brine (2×20 mL), dried over sodium sulfate, filtered and evaporated to obtain the title compound (80 mg, crude, 50%, used directly in the next step). ESMS: 474 (M)$^+$, 475 (M+1)$^+$, 533 (M+59)$^-$.

PREPARATION 190

(1S,3R)(3-{[(Biphenyl-4-carbonyl)amino]methyl}-cyclopentyl)carbamic Acid t-butyl Ester A solution of a compound from preparation 183 (68 mg, 0.31 mmol), 4-phenyl benzoyl chloride (82 mg, 0.38 mmol), triethyl amine (0.5 mL), and DMAP (10 mg) dissolved in DMF (2 mL) was stirred for four hours at rt. The reaction mixture was diluted with ethyl acetate (20 mL) and washed with dilute hydrochloric acid (2×20 mL, 0.1 M), water (2×20 mL), brine (2×20 mL), dried over sodium sulfate, filtered and evaporated to obtain the title compound (170 mg, crude, used without purification).
ESMS:395 (M+1)$^+$, 453 (M+59)$^-$.

PREPARATION 191

(1S,3R)-Biphenyl-4-carboxylic acid (3-amino-cyclopentylmethyl)amide

A compound from preparation 190 (170 mg, crude) was dissolved in trifluoro acetic acid (2 mL) and stirred for half an hour. The reaction mixture was evaporated under vacuum and the residue was dissolved in methylene chloride and filtered through sox column (Bond Elut, 60 cc) and eluted with methanol-ammonia solution (2M) to obtain the title compound (63 mg). ESMS: 295 (M+1)$^+$, 353 (M+59)$^-$

PREPARATION 192

(1S,3R)-3-(2-Chloro-6-fluorophenyl)-5-methylisoxazole-4-carboxylic Acid (3-{[(biphenyl-4carbonyl)amino]methyl}-cyclopentyl)amide A solution a compound from preparation 191 (63 mg, 1.21 mmol), 2-chloro-6-fluoro phenyl isoxazoyl chloride (88 mg, 0.32 mmol), triethyl amine (0.5 mL), and DMAP (10 mg) dissolved in DMF (5 mL) was stirred for four hours at rt. The reaction mixture was diluted with ethyl acetate (20 mL) and washed with dilute hydrochloric acid (2×20 mL, 0.1 M), water (2×20 mL), brine (2×20 mL), dried over sodium sulfate, filtered and evaporated to obtain the title compound (61 mg, 54%, used without purification).
ESMS: 532 (M)$^+$, 533 (M+1)$^+$, 591 (M+59)$^-$.

PREPARATION 193

(1S,3R)(3-{[(Pyridine-3-carbonyl)amino]methyl}cyclopentyl)-carbamic Acid t-butyl Ester A solution of a compound from preparation 183 (68 mg, 0.31 mmol), nicotinoyl chloride (54 mg, 0.38 mmol), triethyl amine (0.5 mL), and DMAP (10 mg) dissolved in DMF (2 mL) was stirred for four hours at rt. The reaction mixture was diluted with ethyl acetate (20 mL) and washed with water (2×20 mL), brine (2×20 mL), dried over sodium sulfate, filtered and evaporated to obtain the title compound (58 mg, 59%, used without purification). ESMS: 318 (M−1)$^-$, 378 (M+59)$^+$.

PREPARATION 194

(1S,3R)—N-(3-Aminocyclopentylmethyl)nicotinamide

A compound from preparation 193 (58 mg, crude) was dissolved in trifluoroacetic acid (2 mL) and stirred for half an hour. The reaction mixture was evaporated under vacuum and the residue was dissolved in methylene chloride and filtered through scx column (Bond Elut, 60 cc) and eluted with methanol-ammonia solution (2M) to obtain the title compound (quantitative). ESMS: 220 (M+1)$^+$, 278 (M+59)$^-$.

PREPARATION 195

(1S,3R)—N-(3-{[3-(2-Chloro-6-fluorophenyl)-5-methylisoxazole-4-carbonyl]amino}cyclopentylmethyl)-nicotinamide A solution of a compound from preparation 194 (112 mg, 0.51 mmol), 2-chloro-6-fluoro phenyl isoxazoyl chloride (210 mg, 0.76 mmol), triethyl amine (0.5 mL), and DMAP (10 mg) dissolved in DMF (5 mL) was stirred for four hours at rt. The reaction mixture was diluted with ethyl acetate (20 mL) and washed water (2×20 mL), brine (2×20 mL), dried over sodium sulfate, filtered and evaporated to obtain the title compound (104 mg, 28%, used without purification). ESMS: 455 (M−1)$^-$, 515 (M+59)$^-$.

PREPARATION 196

(1S,3R)(3-{[(Furan-2-carbonyl)amino]methyl}cyclopentyl)-carbamic Acid t-butyl Ester A solution of a compound from preparation 183 (68 mg, 0.31 mmol), 2-furoyl chloride (50 mg, 0.38 mmol), triethyl amine (0.5 mL), and DMAP (5 mg) dissolved in DMF (2 mL) was stirred for four hours at rt. The reaction mixture was diluted with ethyl acetate (20 mL) and washed with water (2×20 mL), brine (2×20 mL), dried over sodium sulfate, filtered and evaporated to obtain the title compound (105 mg, crude, used without purification) ESMS: 309 (M+1)$^+$, 343 (M+35)$^-$.

PREPARATION 197

(1S,3R)-Furan-2-carboxylic Acid (3-aminocyclopentylmethyl)-amide

A compound from preparation 196 (105 mg, crude) was dissolved in trifluoroacetic acid (2 mL) and stirred for half an hour. The reaction mixture was evaporated under vacuum and the residue was dissolved in methylene chloride and filtered through SCX (Bond Elut, 60 cc) column and eluted with methanol-ammonia solution to obtain the title compound (94 mg, quantitative). ESMS: 209 (M+1)$^+$.

PREPARATION 198

(1S,3R)-3-(2-Chloro-6-fluorophenyl)-5-methylisoxazole-4-carboxylic Acid(3-{[(furan-2-carbonyl)amino]methyl}-cyclopentyl)amide A solution of a compound from preparation 197 (94 mg, 0.51 mmol), 2-chloro-6-fluoro phenyl isoxazoyl chloride (185 mg, 0.67 mmol), triethyl amine (0.5 mL), and DMAP (10 mg) dissolved in DMF (5 mL) was stirred for four hours at rt. The reaction mixture was diluted with ethyl acetate (20 mL) and washed water (2×20 mL), brine (2×20 mL), dried over sodium sulfate, filtered and evaporated to obtain the title compound (147 mg, crude, quantitative, used without purification). ESMS: 446 (M+1)$^+$, 504 (M+59)$^-$.

PREPARATION 199

(1S,3R){3-[(3,4,5-Trimethoxybenzoylamino)methyl]cyclopentyl}carbamic Acid t-butyl Ester A solution of a compound from preparation 183 (68 mg, 0.31 mmol), 3,4,5-trimethoxy benzoyl chloride (88 mg, 0.38 mmol), triethyl amine (0.5 mL), and DMAP (10 mg) dissolved in DMF (2 mL) was stirred for four hours at rt. The reaction mixture was diluted with ethyl acetate (20 mL) and washed with water (2×20 mL), brine (2×20 mL), dried over sodium sulfate, filtered and evaporated to obtain the title compound (130 mg, crude, used without purification). ESMS:409 (M+1)$^+$, 443 (M+35)$^-$.

PREPARATION 200

(1S,3R)—N-(3-Aminocyclopentylmethyl)-3,4,5-trimethoxybenzamide

A compound from preparation 199 (130 mg, crude) was dissolved in trifluoroacetic acid (2 mL) and stirred for half an hour at rt. The reaction mixture was evaporated under vacuum and the residue was dissolved in methylene chloride and filtered through SCX (Bond Elut, 60 cc) column and eluted with methanol-ammonia solution (2M) to obtain the title compound (82 mg, 83%). ESMS: 309 (M+1)$^+$, 367 (M+59)$^-$.

PREPARATION 201

(1S,3R)-3-(2-Chloro-6-fluorophenyl)-5-methylisoxazole-4-carboxylic Acid{3-[(3,4,5-trimethoxybenzoylamino)methyl]cyclopentyl}amide A solution of a compound from preparation 200 (82 mg, 0.26 mmol), 2-chloro-6-fluoro phenyl isoxazoyl chloride (109 mg, 0.39 mmol), triethylamine (0.5 mL), and DMAP (10 mg) dissolved in DMF (5 mL) was stirred for four hours at rt. The reaction mixture was diluted with ethyl acetate (20 mL) and washed water (2×20 mL), brine (2×20 mL), dried over sodium sulfate, filtered and evaporated to obtain the title compound (89 mg, 62%, used without further purification). ESMS: 546 (M+1)$^+$, 604 (M+59)$^-$.

PREPARATION 202

(1S,3R)[3-(3(Benzyloxycarbonylaminomethyl)cyclopentyl]carbamic Acid t-butyl Ester A solution of a compound from preparation 183 (1.3 g, 6 mmol), CBZ chloride (1.2 g, 7 mmol), triethyl amine (1 mL), and DMAP (50 mg) dissolved in DCM (50 mL) was stirred for four hours at rt. The reaction mixture was diluted with ethyl acetate (20 mL) and washed with water (2×20 mL), brine (2×20 mL), dried over sodium sulfate, filtered and evaporated to obtain the title compound (2.0 g, crude). ESMS: 349 (M+1)$^+$, 407 (M+59)$^-$.

PREPARATION 203

(1S,3R)(3-Aminocyclopentylmethyl)carbamic Acid Benzyl Ester

A compound from preparation 202 (2.00 g, crude) was dissolved in trifluoroacetic acid (10 mL) and DCM (10 mL) and stirred for half an hour at rt. The reaction mixture was evaporated under vacuum and the residue was dissolved in DCM and filtered through SCX (Bondesil, 20 g) column and eluted with methanol-ammonia solution (2M) to obtain the title compound (550 mg, 38%). ESMS: 249 (M+1)$^+$.

PREPARATION 204

(1S,3R)(3-{[3-(2-Chloro-6-fluorophenyl)-5-methylisoxazole-4-carbonyl]amino}cyclopentylmethyl)carbamic Acid Benzyl Ester A solution of a compound from preparation 203 (500 mg, 2 mmol), 2-chloro-6-fluorophenyl isoxazoyl chloride (600 mg, 2.2 mmol), triethylamine (1. mL), and DMAP (100 mg) dissolved in DMF (10 mL) was stirred for four hours at rt. The reaction mixture was diluted with ethyl acetate (20 mL) and washed water (2×20 ML), brine (2×20 mL), dried over sodium sulfate, filtered, evaporated and chromatographed (Si column, 12×2.5 inches, gradient −10% to 50% ethyl acetate in hexanes) to obtain the title compound (355 mg, 36%). ESMS: 486 (M+1)$^+$, 544 (M+59)$^−$.

PREPARATION 205

(1S,3R)(3-{[2-(3,4,5-Trimethoxyphenyl) acetylamino]methyl}-cyclopentyl)carbamic Acid t-butyl Ester A solution of a compound from preparation 183 (1 g, 4.6 mmol), 3,4,5-trimethoxy phenylaceticacid (1.5 g, 6.9 mmol), EDC (1.3 g, 6.9 mmol) and DMAP (100 mg) dissolved in DCM (20 mL) was stirred overnight at rt. The reaction mixture was washed with water (2×20 mL), brine (2×20 mL), dried over sodium sulfate, filtered, and evaporated to obtain the title compound (1.5 g, crude). ESMS: 423 (M+1)$^+$, 481 (M+59)$^−$.

PREPARATION 206

(1S,3R)—N-(3-Aminocyclopentylmethyl)-2-(3,4,5-trimethoxy-phenyl)acetamide

A compound from preparation 205 (1.5 g) was dissolved and stirred in a solution of hydrogen chloride in acetic acid(20 mL, 1M) for half an hour at rt. The reaction mixture was evaporated and the residue was triturated with ether to obtain the title compound (1.1 g, used without further purification). ESMS:323(M+1)$^+$, 357 (M+35)$^−$.

PREPARATION 207

(1S,3R)-3-(2-Chloro-6-fluorophenyl)-5-methylisoxazole-4-carboxylic acid (3-{[2-(3,4,5-trimethoxyphenyl)acetyl-amino]methyl}cyclopentyl) amide A solution of a compound from preparation 206 (1 g, 3.1 mmol), 2-chloro-6-fluoro phenyl isoxazoyl chloride (850 mg, 3.1 mmol), triethylamine (1 mL), and DMAP (100 mg) dissolved in DCM (20 mL) was stirred for four hours at rt. The reaction mixture was washed with water (2×20 mL), brine (2×20 mL), dried over sodium sulfate, filtered, evaporated and chromatographed (Si column, 15×6 cm, 50% ethyl acetate in hexane) to obtain the title compound (1.2 g, 70%). ESMS: 486 (M+1)$^+$, 544 (M+59)$^−$.

PREPARATION 208

(1S,3R)[3-({[3-(2-Chloro-6-fluorophenyl)-5-methylisoxazole4-carbonyl]amino}methyl) cyclopentyl]carbamic Acid t-butyl Ester A mixture of a compound from preparation 183 (215 mg, 1 mmol), 2-chloro, 6-fluoro phenyl isoxazoyl chloride (300 mg, 1.1 mmol), triethyl amine (0.1 mL) and DMAP (20 mg) dissolved in DMF (5 mL) was stirred overnight at r.t. The reaction mixture was diluted with ethyl acetate (25 mL) and washed with HCl (1M, 2×10 mL), water (2×10 mL), brine (2×10 mL), dried over sodium sulfate, filtered, and evaporated to yield the title compound (400 mg, 88%, crude). ESMS: 452 (M+1)$^+$.

PREPARATION 209

[3-({[3-(2-Chloro-6-fluorophenyl)-5-methylisoxazole-4-carbonyl]amino}methyl) cyclopentyl]carbamic Acid t-butyl Ester A mixture of a compound from preparation 176 (640 mg, 2.9 mmol), 2-chloro, 6-fluoro phenyl isoxazoyl chloride (1.22 g, 4.4 mmol), triethyl amine (0.5 mL) and DMAP (50 mg) dissolved in DCM (50 mL) was stirred overnight at rt. The reaction mixture was washed with HCl (1M, 2×10 mL), water (2×10 mL), brine (2×10 mL), dried over sodium sulfate, filtered, and evaporated to yield the title compound (1.5 g, crude, quantitative).
ESMS: 452 (M+1)$^+$.

PREPARATION 210

N-(3-aminocyclohexyl)(t-butoxy)carboxamide

To 1,3 diaminocyclohexyl (20.0 g, 175 mmol) in 400 mL CHCl$_3$ at 0° C. was added di-t-butyldicarbonate (7.65 g, 35.0 mmol), which was dissolved in 100 mL CHCl$_3$, poured rapidly. The ice bath was removed and after 0.5 h, the reaction mixture was washed with saturated NaHCO$_3$ (3×150 mL)and washed with brine (2×150 mL). The organics were concentrated to give (cis and trains, 2:1) a crude clear oil (7.50 g, 100%). The crude product was used without purification.

PREPARATION 211 and 212

N-((1S,3S)-3-{[3-(2-chloro-6-fluorophenyl)-5-methylisoxazol-4-yl]carbonyamino}cyclohexyl)(t-butoxy)carboxamide N-((3S,1R)-3-{[3-(2-chloro-6-fluorophenyl)-5-methylisoxazol-4-yl] carbonyamino}cyclohexyl)(t-butoxy)carboxamide To the crude oil from preparation 210 (7.50 g, 35.0 mmol) in 75 mL anhydrous CH$_2$Cl$_2$ at 0° C. was added Et$_3$N (7.32 mL, 52.5 mmol) followed by 3-(6-chloro-2-fluorophenyl)-5-methylisoxazole4-carbonyl chloride (10.01 g, 38.5 mmol). After 5 min. the ice bath was removed and the reaction stirred for an additional 25 minutes. The reaction was diluted with 300 mL CH$_2$Cl$_2$ and washed with saturated NaHCO$_3$ (100 mL). The organics were dried over Na$_2$SO$_4$, filtered and concentrated until a precipitate formed. The precipitate was filtered and the filtrate was concentrated a little more to give more precipitate, which was filtered. A total of 8.5 g (54%) of preparation 209 was obtained. The filtrate was concentrated and chromatographed with 20–30% EtOAc in hexanes to give 3.78 g (24%) of preparation 210.
ESIMS m/e 451 $^{35}$Cl (M$^+$+1) and 453 $^{37}$Cl (M$^+$+1).
ESIMS m/e 452 $^{35}$Cl (M$^+$+1) and 454 $^{37}$Cl (M$^+$+1).

PREPARATION 213

Cis-3-(amino)-1-(9-chloro-3-methyl-4-oxo-5H-isoxazolo[4,3-c]quinolin-5-yl)cyclohexane Hydrochloride To Example 495 (0.500 g, 1.16 mmol) at 0° C. was added 4M HCl in dioxane (5 mL) to give a suspension. The reaction was sonicated at r.t. for 2 min., then stirred at r.t. for 45 minutes. A yellow solid was obtained (0.411 g, 96%). ESIMS m/e 332 $^{35}$Cl (M$^+$+1) and 334 $^{37}$Cl (M$^+$+1).

PREPARATION 214 d,1-trans-Octahydroquinolin-2-one

Following the literature procedure of Morzycki et al (Heterocycles, (1995), 41 (12), 2729–2736) 3,4,5,6,7,8-hexahydro-1H-quinolin-2-one (100 mg, 0.66 mmol) in dioxane (10 ml) with trifluoroacetic acid (0.042 ml, catalytic) was treated with NaCNBH$_3$ (0.67 g, 10.8 mmol), and stirred for 18 hr at RT. The mixture was then diluted with EtOAc and washed with dilute HCl (0.1 N). Additional EtOAc extrac-tions (2×) were then combined with the first, and then treated with sat'd bicarbonate, brine, dried over $Na_2SO_4$, filtered and concentrated to afford the mainly trans product (98 mg, ~5:1). MS (+ES) 154 (M+H)+.

PREPARATION 215

3-(2-Amino-trans-cyclohexyl)propionic Acid Methyl Ester Hydrochloride

A compound from preparation 214 (1 g, 6.4 mmol) was dissolved in methanol (100 mL) and conc. HCl (10 ML) and refluxed for 20 h. The solvents were removed under vacuum to obtain the title compound (1.05 g, 88%). ESMS: 186 $(M)^+$, 187 $(M+1)^+$.

PREPARATION 216

3-(2-{[3-(2-Chloro-6-fluorophenyl)-5-methylisoxazole-4-carbonyl]amino}trans-cyclohexyl)propionic Acid Methyl Ester To a solution of a compound from preparation 215 (1 g, 4.5 mmol) dissolved in DMF (50 mL), was added 2-chloro-6-fluorophenyl isoxazoyl chloride (1.23 g, 4.5 mmol), triethyl amine (10 mL) and DMAP (100 mg) and stirred overnight at rt. The reaction mixture was diluted with ethyl acetate (100 mL) and washed with 1M HCl (2×50 mL), water (2×50 mL), brine (2×50 mL), dried over sodium sulfate, filtered and evaporated to yield 1.9 g. ESMS: 423 (M+1)+, 481 (M+Ac)−.

PREPARATIONS 217 and 218

Separation of Preparation 216 into Enantiomers

Preparative separation into enantiomers was achieved by column chromatography over a Chiralpak AD column using 40% isopropyl alcohol in heptane and 0.2% dimethylethylamine. Thus, the first enantiomer that eluted was designated preparation 217 (Isomer 1), and the second, preparation 218 (Isomer 2).

PREPARATION 219

3-(2-{[3-(2-Chloro-6-fluorophenyl)-5-methylisoxazole-4-carbonyl]amino}trans-cyclohexyl)propionic acid A solution from preparation 217 (0.127 g, 0.3 mmol) in THF (5 mL) was treated with a 0.5 M soln of LiOH in water (3 mL). The sol'n was stirred at r.t. for 5 hr. The reaction was diluted with water (3 mL) and washed with EtOAc (2×5 mL). The pH of the aqueous was adjusted to ~3 with 0.1 M HCl and extracted with EtOAc (4×5 mL). The organic extractions were then washed with brine (2×5 mL), dried over sodium sulfate and the solvent removed to afford 0.095 g (80%) as a white solid. MS (ES+) m/z 409.0 $(M+W)^+$, (ES−) m/z 407.0 $(M-H)^-$.

PREPARATION 220

3-(2-Chloro-6-fluorophenyl)-5-methylisoxazole-4-carboxylic Acid {2-[2-(3,4,5-trimethoxyphenylcarbamoyl)ethyl]trans-cyclohexyl}amide A sol'n from preparation 219 (0.095 g, 0.23 mmol) and EDC (0.115 g, 0.6 mmol) in DMF (25 mL) was treated with 3,4,5 trimethoxyaniline (0.11 g, 0.6 mmol). A catalytic amount of DMAP (4 mg, 0.03 mmol) was also added. The reaction mixture was stirred at r.t. overnight. The reaction was diluted in EtOAc (100 mL) and washed with 5% citric acid sol'n (3×50 mL), water (2×50 mL), and dried over sodium sulfate. The solvent was removed in vacuo to afford a crude brown oil which was purified by a Varian Bond Elut SI column (10 g) with an eluting solvent of 1:1 hexanes:EtOAc. The solvent was removed in vacuo to afford 0.072 g (54%) as an off white solid. MS (ES+) m/z 574.0 $(M+H)^+$, (ES−) m/z 572.1 $(M-H)^-$, 632.1 $(M^+CH_3COO^-)^-$.

PREPARATION 221 d,l-cis-Octahydroquinolin-2-one

2-Nitrocinnamic acid (17 g, 82 mmol) was dissolved in acetic acid (120 ml) and treated with $PtO_2$ (10 g) and $H_2$ (3 atm) for 24 hr at 60° C. The crude reaction was then cooled to r.t., filtered and concentrated. The material was then diluted with EtOAc, and sat'd bicarbonate. After reextraction of the aqueous phase with EtOAc (2×), the combined organics were washed with brine, dried over $Na_2SO_4$, filtered and concentrated to afford a 13:1 mixture of cis/trans product (10 g, 80%). Clean cis isomer eventually crystallized from residual solvent. MS (+ES) 154 (M+H)+.

PREPARATION 222

3-(2-Amino-cis-cyclohexyl)propionic Acid Methyl Ester Hydrochloride

A solution of a compound from preparation 221 (4.4 mg, 28.9 mmol) in methanol (50 mL) was treated with conc. HCl (10 mL) and refluxed overnight. The reaction mixture was evaporated to yield the title compound (7 g, crude, quantitative). ESMS+: 186 (M+1).

PREPARATION 223

3-(2-{[3-(2-Chloro-6-fluorophenyl)-5-methylisoxazole-4-carbonyl]amino}-cis-cyclohexyl) propionic Acid Methyl Ester A compound from preparation 222 (7 g, 0.038 mmol) was dissolved in $CH_2Cl_2$ (100 mL) and treated with methyl isoxazoyl chloride (11 g, 0.04 mmol) in presence of triethylamine (20 mL) at room temperature for 4 h. The reaction mixture was washed with 1 N HCl (2×100 mL), water (2×100 mL), brine (2×100 mL), dried over sodium sulfate, filtered and evaporated to give the title compound (crude gum, 10 g, 62%).
ESMS+: 430 (M), 424 (M+1).

PREPARATION 224

3-(2-{[3-(2-Chloro-6-fluorophenyl)-5-methylisoxazole-4-carbonyl]amino}-cis-cyclohexyl) propionic Acid A solution of a compound from preparation 223 (8.5 g, 20 mmol) dissolved in THF (200 mL) and LiOH (100 mL, 0.5 M solution) was stirred for 2 h at r.t. The reaction was diluted with water (50 mL) and washed with EtOAc (2×100 mL). The alkaline aqueous solution was acidified to pH 1 with conc. HCl and extracted with EtOAc (3×200 mL). The organic extract was washed with brine, dried over sodium sulfate, filtered and evaporated to yield a white solid (8 g, 97%). ESMS+: 409 (M+1).

PREPARATION 225

3-(2-Chloro-6-fluorophenyl)-5-methylisoxazole-4-carboxylic acid {2-[2-(3,4,5-trimethoxyphenylcarbamoyl)ethyl]-cis-cyclohexyl}amide A solution of a compound from preparation 224 (1 g, 2.4 mmol), EDC (955 mg, 5 mmol), trimethoxyaniline (915 mg, 5 mmol), and DMAP (50 mg, catalytic) in DMF (50 mL) was stirred at r.t. overnight. The reaction mixture was diluted with EtOAc (200 mL) and washed with dil. HCL (1 M, 3×100 mL), water (3×100 mL), brine (2×100 mL), dried over sodium sulfate, filtered and evaporated to give the title compound (1.3 g, 97%).
ESMS+: 574 (M), 576 (+2).

PREPARATION 227

3-(2-{[5-(2-Chloro-6-fluorophenyl)-3-methylisoxazole-4-carbonyl]amino}cyclohexyl) propionic Acid Methyl Ester 5-(6-Chloro-2-fluorophenyl)-3-methylisoxazole-4-carboxylic acid (0.4 mmol) was prepared as described previously, and added to a $MeCl_2$ solution (10 ml) of a compound from preparation 222 (222 mg, 1.2 eq) followed by $Et_3N$ (133 ml, 0.96 mmol) and DMAP (10%) at r.t. Acylation was allowed to proceed for 18 h. Crude product was obtained by dilution of the reaction mixture with $MeCl_2$ and 0.1 N HCl, transferring to a separatory funnel. The organic phase was then washed with sat'd bicarbonate, brine, then dried over $Na_2SO_4$. Filtration and concentration provided crude product, which was then purified using a Bond-Elut Si column (1 g, 1:1 hex/EtOAc) to generate the title compound (86 mg, 51%). MS (+ES) m/z 422.9/424.9 (M+H).

PREPARATION 227

3-(2-{[5-(2-Chloro-6-fluoro-phenyl)-3-methyl-isoxazole-4-carbonyl]-amino}-cyclohexyl)-propionic Acid To a solution of the compound from 226 (86 mg, 0.2 mmol) in THF (5 ml) was added 2 ml 0.5M aq. LiOH (5 eq), dropwise at r.t. Hydrolysis was complete at 2.5 hr. After dilution with water and EtOAc, the contents were transferred to a separatory funnel, where addition of enough 1N HCl was added to maintain pH 2. The aqueous phase was back extracted 3 times with additional solvent, and the combined organics were then washed with brine, dried over $Na_2SO_4$. Filtration and concentration afforded clean acid, 80 mg (97%), which was used without further purification. MS (+ES) m/z 408.9/410.9 (M+H).

PREPARATION 228

5-(2-Chloro-6-fluorophenyl)-3-methylisoxazole-4-carboxylic Acid-{2-[2-(3,4,5-trimethoxyphenylcarbamoyl)ethyl]-cyclohexyl}amide To the acid from preparation 227 (40 mg, 0.1 mmol) in DMF (2 ml) was added catalytic amount of DMAP (10%, 1 mg), followed by EDC.HCl (20.6 mg, 0.11 mmol) and 3,4,5-trimethoxyaniline (20.1 mg, 0.11 mmol) at r.t. After 18 hr, the reaction was transferred to a separatory funnel and diluted with EtOAc and 1N NaOH (aq. pH 9–10). The aqueous phase was extracted 3 times, and combined EtOAc fractions were then washed sequentially with 1 N HCl, sat'd bicarbonate, brine, and then dried over $Na_2SO_4$. After filtration and concentration, crude amide was obtained (33 mg). Starting material (7 mg) was also recovered from the aqueous fraction upon acidification and standard work-up. The crude product was then chromatographically purified (Bond-Elut Silica column, 1 g, 2:1 EtOAc/hexanes) to afford clean amide (48 mg, 50%). MS (ES+) 573.9, 575.9 (M+H)+.

PREPARATION 229

Methyl 3-(2-aminocyclohexyl)propanoate Hydrochloride

A solution of a compound from preparation 163 (4.4 mg, 28.9 mmol) in methanol (50 mL) was treated with conc. HCl (10 mL) and refluxed overnight. The reaction mixture was evaporated to yield the title compound (7 g, crude, quantitative). $ESMS^+$: 186 (M+1).

PREPARATION 230

Methyl 3-(2-{[3-(6-chloro-2-fluorophenyl)-5-methylisoxazol4-yl]carbonylamino}cyclohexyl) propanoate A compound from preparation 229 (7 g, 0.038 mmol) was dissolved in methylene chloride (100 mL) and treated with methyl isoxazoyl chloride (11 g, 0.04 mmol) in presence of triethylamine (20 mL) at room temperature for four hours. The reaction mixture was washed with 1 N HCl (2×100 mL), water (2×100 mL), brine (2×100 mL), dried over sodium sulfate, filtered and evaporated to give the title compound (crude gum, 10 g, 62%). ESMS+: 430 (M), 424 (M+1).

PREPARATION 231

3-(2-{[3-(6-chloro-2-fluorophenyl)-5-methylisoxazol-4-yl]carbonylamino}cyclohexyl) propanoic Acid A solution of the ester from preparation 230 (8.5 g, 20 mmol) dissolved in THF (200 mL) and LiOH (100 mL, 0.5 M solution) was stirred for 2 h at rt. LiOH solution was diluted with water (50 mL) and washed with ethyl acetate (2×100 mL). The alkaline aqueous solution was acidified to pH 1 with conc. HCl and extracted with ethyl acetate (3×200 mL). The ethyl acetate extract was washed with brine, dried over sodium sulfate, filtered and evaporated to yield a white solid (8 g, 97%). ESMS+: 409 (M+1).

PREPARATION 232

3-(2-{[3-(6-chloro-2-fluorophenyl)-5-methylisoxazol-4-yl]carbonylamino}cyclohexyl)-N-(3,4,5-trimethoxyphenyl)propanamide A solution of acid from preparation 231 (1 g, 2.4 mmol), EDC (955 mg, 5 mmol), trimethoxyaniline (915 mg, 5 mmol), and DMAP (50 mg, catalytic) in DMF (50 mL) was stirred at r.t. overnight. The reaction mixture was diluted with ethyl acetate (200 mL) and washed with dil. HCL (1 M, 3×100 mL), water (3×100 mL), brine (2×100 mL), dried over sodium sulfate, filtered and evaporated to give the title compound (1.3 g, 97%).
ESMS +: 574 (M), 576 (M+2).

PREPARATION 233

6-Fluoropyridine-2-carboxylic Acid

To a heterogeneous solution of 2-fluoro-6-methyl-pyridine (9.65 g, 86.8 mmol) in water (400 mL) was added potassium permanganate (31.6 g, 200 mmol), and the reaction was heated to approximately 100° C. After 30 minutes, additional potassium permanganate (16.5 g, 104 mmol) was added, and the reaction heated at 100° C. overnight. The reaction was filtered through celite to remove manganese salts. The mother liquor was washed with ethyl ether (200 mL×3), neutralized to pH 7, and concentrated down to approximately 100 mL total volume. The aqueous solution was acidified to pH 2 with concentrated HCl and extracted with ethyl acetate, followed by 20% i-PrOH/CHCl$_3$ (×3). The combined organic layers were dried over MgSO$_4$ and concentrated. The solids were suspended in chloroform, sonicated, then filtered to remove remaining side products. The mother liquor was concentrated to give 5.47 g as a white crystalline solid, 45% yield. $^1$H NMR: consistent with structure. MS (ion spray) 140 (M$^-$).

PREPARATION 234

6-Methoxy-pyridine-2-carboxylic Acid

To 6-hydroxypicolinic acid (1.39 g, 10.0 mmol) in toluene (35 mL) was added silver oxide (2.43 g, 10.5 mmol) and the mixture was stirred for 30 minutes. To the reaction was added iodomethane (1.31 mL, 21.0 mmol), and the reaction was heated to reflux overnight. The reaction was filtered over celite and concentrated to give 1.45 g of the methyl ester as a yellow solid. The resulting solid was dissolved in tetrahydrofuran (50 mL), and added to a solution of 5N NaOH (20 mL, 100 mmol) and water (5 mL). After one hour, the reaction was acidified to pH 3 with 5N HCl and concentrated. To the resulting white solids was added 20% MeOH/CHCl$_3$ and the mixture was sonicated for 20 minutes. The mixture was filtered, and the mother liquor was dried over MgSO$_4$ and concentrated to give 1.33 g of the title compound as a white solid, 87% yield.

$^1$H NMR: consistent with structure. MS (ion spray) 152 (M$^-$).

PREPARATION 235

5-Methoxy-nicotinic Acid

To sodium hydride (0.42 g, 10.5 mmol, washed with hexanes ×3) in dimethylformamide (15 mL) was added 5-hydroxy-nicotinic acid methyl ester (1.53 g, 10.0 mmol) in dimethylformamide (10 mL). After three minutes, iodomethane (0.65 mL, 10.5 mmol) was added dropwise while stirring at room temperature. After 1 h, the reaction was quenched with methanol and concentrated to a brown oil. The solution was dissolved in 20% isopropanol/chloroform, washed with saturated aqueous sodium bicarbonate solution, brine (×3), dried over magnesium sulfate and concentrated to give 1.46 g of 6-methoxynicotinic acid methyl ester. The resulting oil was dissolved in tetrahydrofuran (50 mL), and added to a solution of 5N NaOH (20 mL, 100 mmol) and water (5 mL). After 30 minutes, an additional 25 mL of 5N NaOH was added to the solution. After one hour, the reaction was acidified to pH 3 with 5N HCl and concentrated. To the resulting white solids was added 20% MeOH/CHCl$_3$ and the mixture was sonicated for 20 minutes. The mixture was filtered, and the mother liquor was dried over MgSO$_4$ and concentrated to give 1.38 g as a light yellow solid, 90% yield.

$^1$H NMR: consistent with structure. MS (ion spray) 152 (M$^-$).

PREPARATION 236

N-{3-[3-(1-Aminoethylidene)-5-chloro-2,4-dioxo-3,4-dihydro-2H-quinolin-1-yl]-cyclohexylmethyl}benzamide A compound from Example 125 (0.05 g, 0.1 mmol) and Mo(CO)$_6$ (0.3 g, 1.1 mmol) were combined in a solution of ACN (5 mL) and water (1 mL). The reaction mixture was heated to 60° C. while stirring. After 3 hr of stirring the reaction was complete. The reaction was concentrated to a dark brown solid under vacuum. The solid was diluted in CH$_2$Cl$_2$ (1 mL) and purified by passing through a Varian Bond Elut SI column (5 g). The product was eluted with 2% MeOH in CH$_2$Cl$_2$. The solvent was removed in vacuo to afford 0.041 g (82%) of the title compound as a light brown solid.

MS (ES+) m/z 452.0 (M+H)$^+$, (ES−) 450.0 (M−H)$^-$.

PREPARATION 237

{3-[3-(1-Aminoethylidene)-5-chloro-2,4-dioxo-3,4dihydro-2H-quinolin-1-yl]-cyclohexylmethyl}carbamic Acid Benzyl Ester A compound from Example 498 (0.25 g, 0.5 mmol) and Mo(CO)$_6$ (1.35 g, 5.2 mmol) were combined in a solution of ACN (25 mL) and water (5 mL). The reaction mixture was heated to 60° C. while stirring. After stirring overnight the reaction was complete. The reaction was concentrated to a dark brown solid under vacuum. The solid was diluted in CH$_2$Cl$_2$ (10 mL) and the solid material was filtered by passing through Celite. The yellow filtrate was purified by silica gel column chromatography using 50% EtOAc in CH$_2$Cl$_2$ to elute the product. The solvent was removed in vacuo to afford 0.24 g (98%) of the title compound as a light yellow solid. MS (ES+) m/z 481.9 (M+H)$^+$, (ES−) 479.9 (M−H)$^-$.

PREPARATION 238

N-}3-[3-(1-Aminoethylidene)-5-chloro-2,4-dioxo-3,4-dihydro-2H-quinolin-1-yl]-cyclohexylmethyl}nicotinamide A compound from Example 126 (0.02 g, 0.04 mmol) and Mo(CO)$_6$ (0.13 g, 0.5 mmol) were combined in a solution of ACN (5 mL) and water (1 mL). The reaction mixture was heated to 60° C. and stirred for 2 hr. The reaction was concentrated to a dark brown solid under vacuum. The solid was diluted in CH$_2$Cl$_2$ (10 mL) and purified by passing directly through a Bond-Elut cation exchange column. The product was eluted with 2M Ammonia in MeOH. The brown liquid was filtered using a Gelman Nylon Acrodisc to afford a yellow solution. The solvent was removed in vacuo to afford 0.018 g (90%) of the title compound as a white solid. MS (ES+) m/z 452.9 (M+H)$^+$, (ES−) m/z 450.8 (M−H)$^-$, 510.9 M+CH3COO$^-$)$^-$.

PREPARATION 239

N-{3-[3-(1-Aminoethylidene)-5-chloro-2,4-dioxo-3,4-dihydro-2H-quinolin-1-yl]-cyclohexylmethyl}-6-fluoronicotinamide A compound from Example 149 (0.05 g, 0.1 mmol) and Mo(CO)$_6$ (0.3 g, 1.1 mmol) were combined in a solution of ACN (5 mL) and water (1 mL). The reaction mixture was heated to 60° C. while stirring. After 3 hr of stirring the reaction was complete. The reaction was concentrated to a dark brown solid under vacuum. The solid was diluted in CH$_2$Cl$_2$ (1 mL) and purified by passing through a Varian Bond Elut SI column (5 g). The product was eluted with 2% MeOH in CH$_2$Cl$_2$. The solvent was removed in vacuo to afford 0.041 g (82%) of the title compound as a light brown solid.

MS (ES+) m/z 452.0 (M+H)$^+$, (ES−) 450.0 (M−H)$^{31}$.

PREPARATION 240

N-{3-[5-Chloro-3-(1-hydroxy-ethylidene)-2,4-dioxo-3,4-dihydro-2H-quinolin-1-yl]-cyclohexylmethyl}benzamide A compound from preparation 236 (0.05 g, 0.11 mmol) was stirred in a solution of acetonitrile (10 mL) and water (1 mL). The solution was treated with p-toluenesulfonic acid (0.01 g, 0.05 mmol). The reaction was heated to reflux and stirred overnight. The reaction was concentrated to a solid and diluted in EtOAc (50 mL). The organic was washed with sat'd sodium bicarbonate (2×10 mL), brine (2×10 mL), and dried over sodium sulfate. The solvent was removed to yield a crude solid that was purified using a chromatotron with a silica gel plate. The product was eluted with 50% EtOAc in $CH_2Cl_2$. The solvent was removed to afford 0.032 g (64%) of the title compound as an off-white solid. MS (ES+) m/z 452.9 $(M+H)^+$, (ES−) 450.9 $(M-H)^-$.

PREPARATION 241

(3-Aminocyclohexylmethyl)carbamic Acid Benzyl Ester

S-Amino enantiomer of a compound from preparation 104 (0.28 g, 0.77 mmol) was treated with HCl in HOAc (1.0M, 2 mL) under $N_2$. After 20 min of stirring at r.t., the reaction was complete. The crude was then concentrated to a solid using CAN to azeotrope the solvent. The white solid was taken up in ether and filtered. The white solid weighed 0.19 g (95%) and was in good purity. MS (ES+) m/z 263.0 $(M+H)^+$.

PREPARATION 242 t-Butylaminophenylacetic Acid Methyl Ester t-Butylamine (9.30 mL, 88.0 mmol) was combined with α-bromophenylacetic acid (5.0 g, 22.0 mmol) and triethylamine (3.40 mL, 22.0 mmol) in tetrahydrofuran (200 mL) and the mixture refluxed overnight. The mixture was then concentrated in vacuo and the residue taken up in 20% isopropanol/chloroform and washed 1× aqueous $NaHCO_3$, ×2 brine, and dried over sodium sulfate. Concentration left a residue which was loaded onto a silica gel column and eluted with methanol/chloroform to yield pure amine (1.34 g, 28%) as an oil. MS(ES): $(M+1)^+$ 222.2, 223.2 m/z.

PREPARATION 243 t-Butylaminophenylacetic Acid

A compound from preparation 242 (1.32 g, 6.0 mmol) was combined with aqueous 2N sodium hydroxide (20 mL), tetrahydrofuran (5 mL), and ethanol (5 mL) and the mixture stirred overnight at ambient temperature. The mixture was then adjusted to approx. pH 2.5 with aqueous hydrochloric acid and concentrated to dryness in vacuo. The resulting solids were then slurried and washed with 20% ethanol/ethyl acetate. Concentration of the filtrate left crude amino acid derivative (0.94 g, 75%) as an off white solid which was used without further purification. MS(ES): $(M+1)^+$ 208.2 m/z.

PREPARATION 244

(2,2-Dimethylpropylamino)phenylacetic Acid Methyl Ester

Neopentylamine (5.13 mL, 43.6 mmol) was combined with α-bromophenylacetic acid (5.00 g, 22.0 mmol) and triethylamine (3.65 mL, 26.2 mmol) in tetrahydrofuran (60 mL) and the mixture overnight at ambient temperature. The mixture was then diluted with ethyl acetate, washed with water, and dried over sodium sulfate. Concentration left a residue, which was loaded onto a silica gel column and eluted with methanol/chloroform to yield 3.38 g (66%) of pure amine as an oil. MS(ES): $(M+1)^+$ 236.1, 237.1 m/z.

PREPARATION 245

(2,2-Dimethylpropylamino)phenylacetic Acid

An amine from preparation 244 (3.20 g, 13.6 mmol) was combined with aqueous 2N sodium hydroxide (30 mL), tetrahydrofuran (10 mL), and ethanol (5 mL) and the mixture stirred overnight at ambient temperature. The mixture was then treated in a manner similar to that in preparation 11 which left crude amino acid derivative (0.337 g, 11%) as a white solid and was used without further purification. MS(ES): $(M+1)^+$ 222.1 m/z.

PREPARATION 246

Pyrimidine-5-carboxylic Acid Methyl Ester

A mixture of 5-bromopyrimidine (3.0 g, 18.8 mmol), 1.86 g of 1,1'-bis-(diphenylphospino)ferrocene, and 1.15 g of Pd(II)acetate in 40 mL of methanol and 40 mL of N,N-dimethylformamide was stirred under 60 psi of carbon monoxide at 85° C. for 16 hours. The reaction mixture was filtered and partitioned between ether and brine. The aqueous layer was extracted with ether. Combined organics were washed with brine, dried over sodium sulfate and was concentrated to dryness. The residue was dissolved in chloroform, filtered through celite and concentrated to dryness to yield 1.89 g (73%) of the desired crude product as a tan solid. Crude product was carried on without further purification. MS (ion spray) 123.3 (M-methyl).

PREPARATION 247

Pyrimidine-5-carboxylic Acid

To a solution of a compound from preparation 246, 1.8 g (13.0 mmol) in 60 mL of tetrahydrofuran, was added a solution of 3.0 g (130 mmol) of lithium hydroxide in 60 mL of water. The reaction mixture was stirred for five hours at ambient temperature and was then washed with ether and acidified to pH=1 with 5 N HCl. The resulting solution was extracted with 20% isopropanol/chloroform. Combined organics were washed with brine, dried over sodium sulfate, filtered and concentrated to dryness to yield 460 mg (28%) of the desired product as a crude tan oil. Crude product was carried on without further purification. MS (ion spray) 123.3 (M−) for desired product.

PREPARATION 248

2-Methoxyisonicotinic Acid Methyl Ester

To a solution of 2-methoxyisonicotinic acid methyl ester, 0.32 g (1.9 mmol) in 20 mL of tetrahydrofuran was added 1.9 mL (9.5 mmol) of 5 N sodium hydroxide in 10 mL of water. The reaction mixture was stirred for 2.5 hours at ambient temperature, acidified to pH=3.6 with 5 N HCl and concentrated to dryness. The residue was slurried in 20% isopropanol/chloroform and filtered. The solid was slurried in ethyl acetate and filtered. The combined organics were dried over sodium sulfate, filtered and concentrated to dryness to give a quantitative yield of the crude desired

PREPARATION 249

2–Cyano4-methoxypyridine

To a slurry of 4-methoxypyridine N-oxide hydrate, 50 g, in 250 mL of chloroform was added 20 g of magnesium sulfate. The slurry was stirred for 1 hour at ambient temperature, then filtered and concentrated to dryness. To a solution of the residue, 4-methoxypyridine N-oxide, 43 g (350 mmol) in 350 mL of dichloromethane was added 65 mL (490 mmol) of trimethylsilylcyanide. The solution was cooled to 10° C. and 45 mL (490 mmol) of N,N-dimethylcarbamyl chloride was added dropwise such that the reaction warmed to a gentle reflux. Upon completion of the addition, the reaction mixture was stirred overnight at ambient temperature, then carefully quenched at 0° C. dropwise with 10% aqueous potassium carbonate. The layers were separated and the aqueous layer was extracted with dichloromethane. The combined organics were washed with brine, dried over sodium sulfate, filtered and concentrated to dryness. The residue was triturated with ether. Filtration of the solid provided 31.4 g (67%) of the desired product as a white solid. $^1$H—NMR is consistent with structure; MS (ion spray) 135.1 (M+).

PREPARATION 250

4-Methoxypicolinic Acid Hydrochloride

A solution of a compound from preparation 249, 15.0 g (112 mmol) in 100 mL of 5 N HCl was refluxed overnight, cooled to ambient temperature and concentrated to dryness to yield 22 g the desired product as a crude, white solid. MS (ion spray) 153.9 (M+). Crude product was carried on without further purification.

PREPARATION 251

6-Methoxynicotinic Acid

To a solution of methyl 6-methoxynicotinate (Avacado), 0.1 g (0.6 mmol) in 5 mL of tetrahydrofuran was added a solution of 1.2 mL of 5 N sodium hydroxide in 5 mL of water. The mixture was stirred for four hours at ambient temperature, acidified to pH=3 with 5 N HCl and concentrated to dryness to yield the crude desired compound. MS (ion spray) 154.0 (M+1). The crude product was carried on without further purification.

PREPARATION 252

Dimethylaminophenylacetic Acid Methyl Ester

To a solution of α-bromophenylacetic acid methyl ester, 5.0 g (22.0 mmol) in 120 mL of tetrahydrofuran was added 12 mL (88.0 mmol) of triethylamine and 5.4 g (66.0 mmol) of dimethylamine hydrochloride. The reaction mixture was heated at 60° C. in a sealed tube for three hours, cooled to ambient temperature and concentrated to dryness. The residue was partitioned between 20% isopropanol/chloroform and water. The mixture was washed with saturated sodium bicarbonate, washed with brine, dried over sodium sulfate, filtered and concentrated to dryness. The residue was purified by chromatography using a methanol/chloroform gradient as eluent and concentrated to dryness to yield 1.86 g (44%) of the desired isomer as a yellow oil. MS (ion spray) 193.9 (M+).

PREPARATION 253

Dimethylaminophenylacetic Acid

To a solution of a compound from preparation 252, 60 mg (0.84 mmol) in 10 mL of tetrahydrofuran was added a solution of 0.5 mL (2.52 mmol) of 5 N sodium hydroxide in 5 mL of water. The mixture was stirred for two hours at ambient temperature then an additional 1 mL (5.04 mmol) of 5 N sodium hydroxide was added. The reaction mixture was stirred an additional four hours, acidified to pH=3 with 5 N HCl, and concentrated to dryness to give a quantitative yield of the crude desired mixture of isomers. Crude product was carried on without further purification. MS (ion spray) 202.1 (M+23(Na)).

PREPARATION 254

Phenylthiomorpholin-4-ylacetic Acid Methyl Ester

To a solution of racemic α-bromophenylacetic acid methyl ester, 5.0 g (22.0 mmol) in 120 mL of tetrahydrofuran was added 3.4 mL (22.0 mmol) of triethylamine and 6.7 g (66.0 mmol) of thiomorpholine. The reaction mixture was refluxed for four hours, cooled to ambient temperature and concentrated to dryness. The residue was partitioned between 20% isopropanol/chloroform and water. The mixture was washed with saturated sodium bicarbonate, washed with brine, dried over sodium sulfate, filtered and concentrated to dryness. The residue was purified by chromatography using a methanol/chloroform gradient as eluent. A second purification was performed using chloroform as eluent and was concentrated to dryness to yield 5.36 g (97%) of the desired mixture of isomers as a yellow oil. MS (ion spray) 252.1 (M+).

PREPARATION 255

Phenylthiomorpholin-4-ylacetic Acid

To a solution of a compound from preparation 254, 140 mg (0.56 mmol) in 5 mL of tetrahydrofuran was added a solution of 0.6 mL (2.8 mmol) of 5 N sodium hydroxide in 5 mL of water. The mixture was stirred for two hours at ambient temperature then an additional 0.5 mL (2.3 mmol) of 5 N sodium hydroxide was added in mL of water. The reaction mixture was stirred an additional two hours, acidified to pH=3 with 5 N HCl, and concentrated to dryness to give a quantitative yield of the crude desired mixture of isomers. Crude product was carried on without further purification. MS (ion spray) 236.1 (M+23(Na)).

PREPARATION 256

(4-Methylpiperazin-1-yl)phenylacetic Acid Methyl Ester

To a solution of racemic α-bromophenylacetic acid methyl ester, 5.0 g (22.0 mmol) in 200 mL of tetrahydrofuran was added 3.4 mL (22.0 mmol) of triethylamine and 7.3 g (66.0 mmol) of 1-methylpiperazine. The reaction mixture was refluxed for three hours, cooled to ambient temperature and concentrated to dryness. The residue was partitioned between 20% isopropano/chloroform and water. The mixture was washed with saturated sodium bicarbonate, washed with bane, dried over sodium sulfate, filtered and concentrated to dryness. The residue was purified by chromatography using a methanol/chloroform gradient as eluent. A second purification was performed using methanol/chloroform as eluent and was concentrated to dryness to

[preceding text from previous page:] product as a white solid. MS (ion spray) 154.1 (M+). Crude product was carried on without further purification.

yield 5.21 g (95%) of the desired mixture of isomers as a yellow oil. MS (ion spray) 249.1 (M+).

PREPARATION 257

(4-Methylpiperazin-1-yl)phenylacetic Acid

To a solution of racemic a compound from preparation 256, 200 mg (0.84 mmol) in 10 mL of dioxane was added a solution of 200 mg (8.4 mmol) of lithium hydroxide 8 mL of water. The mixture was stirred for six hours at ambient temperature, was acidified to pH=3 with 5 N HCl, and concentrated to dryness to give a quantitative yield of the crude desired mixture of isomers. Crude product was carried on without further purification.
MS (ion spray) 235.14 (M+).

PREPARATION 258

(4-Acetylpiperazin-1-yl)phenylacetic Acid Methyl Ester

To a solution of racemic x-bromophenylacetic acid methyl ester, 5.0 g (22.0 mmol) in 200 mL of tetrahydrofuran was added 3.4 mL (22.0 mmol) of triethylamine and 8.5 g (66.0 mmol) of 1-acetylpiperazine. The reaction mixture was refluxed for three hours, cooled to ambient temperature and concentrated to dryness. The residue was partitioned between 20% isopropanol/chloroform and water. The mixture was washed with saturated sodium bicarbonate, washed with brine, dried over sodium sulfate, filtered and concentrated to dryness. The residue was purified by chromatography using a methanol/chloroform gradient as eluent and was concentrated to dryness to give a quantitative yield of the desired mixture of isomers as a yellow, viscous oil. MS (ion spray) 277.2 (M+).

PREPARATION 259

(4-Acetylpiperazin-1-yl)phenylacetic Acid

To a solution of a racemic compound from preparation 258, 232 mg (0.84 mmol) in 10 mL of dioxane was added a solution of 200 mg (8.4 mmol) of lithium hydroxide 8 mL of water. The mixture was stirred for six hours at ambient temperature, was acidified to pH=3 with 5 N HCl, and concentrated to dryness to give a quantitative yield of the crude desired mixture of isomers. Crude product was carried on without further purification.
MS (ion spray) 269.2 (M+Li).

PREPARATION 259

(Indan-2-ylamino)phenylacetic Acid Methyl Ester

To a solution of racemic α-bromophenylacetic acid methyl ester, 5.0 g (22.0 mmol) in 200 mL of tetrahydrofuran was added 3.4 mL (22.0 mmol) of triethylamine and 8.8 g (66.0 mmol) of 2-aminoindan. The reaction mixture was refluxed for four hours, cooled to ambient temperature and concentrated to dryness. The residue was partitioned between 20% isopropanol/chloroform and water. The mixture was washed with saturated sodium bicarbonate, washed with brine, dried over sodium sulfate, filtered and concentrated to dryness. The residue was purified by chromatography using chloroform as eluent and was concentrated to dryness to give a quantitative yield of the desired mixture of isomers as a tan, viscous oil. MS (ion spray) 282.2 (M+).

PREPARATION 260

(Indan-2-ylarmino)phenylacetic Acid

To a solution of a racemic compound from preparation 259, 236 mg (0.84 mmol) in 10 mL of dioxane was added a solution of 200 mg (8.4 mmol) of lithium hydroxide 8 mL of water. The mixture was stirred for four hours at ambient temperature, was acidified to pH=3 with 5 N HCl, and concentrated to dryness to give a quantitative yield of the crude desired mixture of isomers. Crude product was carried on without further purification. MS (ion spray) 268.2 (M+1).

PREPARATION 261

Hydroxy-m-tolyl-acetic Acid

To m-methylbenzaldehyde, 21 mL (176 mmol) was added 5 mg of zinc (II) iodide and 23.4 mL (176 mmol) of trimethylsilyl cyanide dropwise. The resulting solution was stirred overnight at ambient temperature. To this solution was added 75 mL of 9 N hydrochloric acid. The mixture was stirred overnight at ambient temperature and was concentrated to dryness. The residue was partitioned between water and 20% isopropanol/chloroform and washed with brine, dried over sodium sulfate, filtered and concentrated to dryness. Crude product was recrystallized from chloroform to provide 15 g of a tan solid. NMR analysis indicates a 2:1 mixture of product to cyanohydrin intermediate. This mixture was carried on as is without further purification. MS (ion spray) 165.1 (M−1).

PREPARATION 262

(2-Fluoro-phenyl)-hydroxy-acetic Acid

To o-fluorobenzaldehyde, 18.5 mL (176 mmol) was added 5 mg of zinc (II) iodide and 23.4 mL (176 mmol) of trimethylsilyl cyanide dropwise. The resulting solution was stirred overnight at ambient temperature. To this solution was added 100 mL of 9 N hydrochloric acid. The mixture was stirred overnight at ambient temperature, then refluxed overnight. The mixture was then concentrated to dryness. The residue was partitioned between water and 20% isopropanol/chloroform and washed with brine, dried over sodium sulfate, filtered and concentrated to dryness. Crude product was recrystallized from chloroform to provide 4.57 g (15%) of a tan solid. MS (ion spray) 169.2 (M−).

PREPARATION 263

[3-(3-Acetyl-4-amino-5-chloro-2-oxo-2H-quinolin-1-yl)-cyclohexylmethyl]-carbamic Acid Benzyl Ester A solution of [3-(9-Chloro-3-methyl-4-oxo-5H-isoxazolo[4,3-c]quinolin-5-yl)-cyclohexylmethyl]-carbamic acid benzyl ester (0.5 g, 1.04 mmol) and Mo(CO)6 (3.0 g, 0.01 mmol) in Acetonitrile (50 mL) and water (5 mL) was heated to 60° C. and stirred overnight. The reaction was concentrated to a solid, diluted in $CH_2Cl_2$ and filtered through Celite to remove the black insoluble material. The filtrate was concentrated to a solid and purified using silica gel column chromatography. The product was eluted with 10% EtOAc in $CH_2Cl_2$. The solvent was removed to afford 0.520 g (quantitative) of product as a light brown oil. MS (ES+) m/z 482.0 (M+H)$^+$,(ES−) m/z 479.9 (M−H)$^-$, 540.0 (M+CH3COO$^-$)$^-$.

PREPARATION 264

N-[3-(3-Acetyl-4-amino-5-chloro-2-oxo-2H-quinolin-1-yl)-cyclohexylmethyl]-6-fluoro-nicotinamide A solution of Example 420 (0.07 g, 0.15 mmol) and Mo(CO)6 (0.43 g, 1.6 mmol) in Acetonitrile (5 mL) and water (1 mL) was heated to 60° C. and stirred overnight. The reaction was concentrated to a solid, diluted in $CHCl_3$ and filtered through Celite to remove the black insoluble material. The filtrate was concentrated to a solid and purified using silica gel column chromatography. The product was eluted with 80% EtOAc in $CHCl_3$. The solvent was removed to afford 0.04 g (57%) of product as a white solid. MS (ES+) m/z 471.1 $(M+M)^+$,(ES−) m/z 469.1 $(M-H)^-$, 529.1 $(M+CH3COO^-)^-$.

PREPARATION 265

(2–Cyano-6-fluoro-phenyl)-5-methyl-isoxazole-4-carboxylic Acid Ethyl Ester

To a mixture of ethyl 3-(2-fluoro-6-iodo-phenyl)-5-methyl-isoxazole-4-carboxylate (0.25 g, 0.67 mmol), tetrakis(triphenylphosphine)palladium (0.08 g, 0.067 mmol), and triethylamine (5 ml) under $N_2$ was added trimethylsilyl cyanide and heated at reflux overnight. The reaction was cooled to room temperature, diluted with $H_2O$, and extracted with EtOAc (2x). The combined extracts were washed ($H_2O$ then brine), dried ($MgSO_4$), filtered, and concentrated. Flash chromatography (silica gel, EtOAc/hexanes gradient) gave the title compound (0.15 g, 82%). Mass Spectrum (ES+) (m/z) 275.0 [M+1].

PREPARATION 266

3-(2–Cyano-6-fluoro-phenyl)-5-methyl-isoxazole-4-carboxylic Acid

A mixture of a compound from preparation 265 (0.14 g, 0.51 mmol), EtOH (2.5 ml), and 5 N NaOH (0.3 ml, 1.5 mmol) was heated at 50° C. for 1.5 h. The reaction was cooled to room temperature, diluted with $H_2O$, and acidified (conc. HCl) to less than pH 3. The mixture was extracted with EtOAc (2x) and the combined extracts were washed ($H_2O$ then brine), dried ($MgSO_4$), filtered, and concentrated to give the title compound (0.1 g, 80%). This material was used without further purification. Mass Spectrum (ES+) (m/z) 247.0 [M+1].

PREPARATION 267

[3-(2-cyano-6-fluorophenyl)-5-methylisoxazol-4-yl]-N-{3-[(phenylcarbonylamino)-methyl]cyclohexyl}carboxamide To a solution of a compound from preparation 265 (0.1 g, 0.41 mmol) in dichloromethane (10 ml) under $N_2$ was added oxalyl chloride (0.07 ml, 0.82 mmol) then DMF (1 drop) and stirred for 2 h. The solution was concentrated, redissolved in dichloromethane (5 ml) under $N_2$, and N-(3-Amino-cyclohexylmethyl)-benzamide (0.114 g, 0.49 mmol) was added. The reaction vessel was submerged in a water bath and triethylamine (0.17 ml, 1.23 mmol) was added dropwise. After 2.5 h of stirring, the mixture was diluted with $CH_2Cl_2$, washed (1.0 NaOH then brine), dried ($MgSO_4$), filtered, and concentrated. Flash chromatography (silica gel, Acetone/$CH_2Cl_2$ gradient) gave the title compound (0.119 g, 63%). Mass Spectrum (ES+) (m/z) 461.2 [M+1].

PREPARATION 268

(3-Amino-cyclohexylmethyl)-carbamic Acid Benzyl Ester

A solution of [3-(benzyloxycarbonylamino-methyl)-cyclohexyl]-carbamic acid tert-butyl ester (6 g, 16.6 mmol) in TFA (30 ml) was stirred for 1.5 h. The solution was concentrated using benzene to azeotrope, diluted with EtOAc, washed (1.0 N NaOH), dried ($Na_2SO_4$), filtered, and concentrated to afford the title compound (4.2 g, 97%) as a crude solid. Mass Spectrum (ES+) (m/z) 263.1 [M+1].

PREPARATION 269

(3-{[3-(2–Cyano-6-fluoro-phenyl)-5-methyl-isoxazole-4-carbonyl]-amino}-cyclohexylmethyl)-carbamic Acid Benzyl Ester In a fashion similar to that described for preparation 267, a compound from preparation 266 (3.05 g, 12.4 mmol), oxalyl chloride (2.16 ml, 24.8 mmol), dichloromethane (50 ml), DMF (0.05 ml), a compound from preparation 268 (4.2 g, 16.1 mmol), dichloromethane (125 ml), and triethylamine (5.17 ml, 37.2 mmol) gave the title compound (4.6 g, 76%) after flash chromatography (silica gel, acetone/CH2Cl2 gradient).
Mass Spectrum (ES+) (m/z) 491.2 [M+1].

PREPARATION 270

Diphenylmethyl 2-(3-oxocyclohexyl)propane-1,3-dioate (Cis Racemic)

To a solution of $LiAlH_4$ (6 ml, 6 mmol) under $N_2$ at 0° C. was added a solution of (S)-1,1'-binaphthol (3.43 g, 12 mmol) in THF (48 ml) and stirred for 30 min. The reaction was warmed to RT. To this was added a solution of sodium salt benzyl malonate in THF which was prepared by reacting benzyl malonate (14.99 ml, 60 mmol), NaH (60% by wt., 0.216 g, 5.4 mmol), and THF (60 ml) until all bubbling ceased. Next, cyclohexenone (5.82 ml, 60 mmol) and dibenzlmalonate (1.35 ml, 5.4 mmol) were added and the reaction mixture was stirred overnight. 1.0 N HCl was added and extracted with EtOAc (3x). The combined EtOAc layers were washed (brine), dried ($MgSO_4$), filtered, and concentrated. Flash chromatography (silica gel, acetone/hexanes gradient) gave the title compound (16.17 g, 71%). Mass Spectrum (FIA) (m/z) 381.3 [M+1].

PREPARATION 271

Diphenylmethyl 2-(3-oxocyclohexyl)propane-1,3-dioate (Trans Racemic)

To a −78° C. solution of a compound from preparation 270 (see Arai, T.; Yamada, Y. M. A.; Yamamoto, N.; Sasai, H.; Shibasaki, M. *Chem. Eur. J.* 1996, 2, 1368–1372.) (16.15 g, 42.5 mmol) in THF (212.5 ml) under $N_2$ was added L-selectride (46.75 ml at 1.0 M, 46.75 mmol) dropwise and the mixture was stirred for 3.5 h at −78° C. EtOAc and $H_2O$ were added and the mixture was warmed to room temperature. Dilution with more EtOAc followed by washing with 1N NaOH, saturated $NH_4Cl$, brine, drying ($MgSO_4$), and flash chromatography (silica gel, EtOAc/hexanes gradient) gave the title compound(14.29 g, 88%). Mass Spectrum (FIA) (m/z) 383.3 [M+1].

PREPARATION 272

Phenylmethyl 2-(3-hydroxycyclohexyl)acetate (Trans Racemic)

A solution of a compound from preparation 271 (19.19 g, 50.2 mmol, LiCl (4.27 g, 100.5 mmol, $H_2O$ (1.81 ml, 100.5 mmol), and DMSO (135 ml) was lowered into a 165° C. oil bath for 2 h then heated at 175° C. for 1.5 h. The reaction was cooled to room temperature and diluted with EtOAc. Washing with H₂O and brine, drying (MgSO₄), and flash chromatography (silica gel, EtOAc/hexanes gradient) gave the title compound (9.71 g, 78%). 1H NMR: consistent with structure.

PREPARATION 273

Phenylmethyl 2-(3-azidocyclohexyl)acetate (Cis Racemic)

To a solution of a compound from preparation 272 (9.71 g, 39.2 mmol), triphenylphosphine (12.32 g, 41.04 mmol), and hydrazoic acid (30.9 ml, at 1.9 M, 58.7 mmol) in toluene (120 ml) was added DEAD (9.24 ml, 58.7 mmol) dropwise and stirred for 72 h. The mixture was diluted with EtOAc, washed with 0.1 N NaOH, H₂O, and brine, dried (MgSO₄), and chromatographed (silica gel, CH₂Cl₂/hexanes gradient) to give the title compound (10.0 g, 93%). 1H NMR: consistent with structure.

PREPARATION 274

Phenylmethyl 2-{3-[(tert-butoxy)carbonylamino] cyclohexyl}acetate (Cis Racemic)

A mixture of a compound from preparation 273 (10 g, 36.6 mmol), (BOC)₂O (9.57 g, 43.9 mmol), Lindlar's catalyst (3.7 g), and EtOAc (200 ml) was stirred under an atmosphere of hydrogen gas (balloon) for 24 h, filtered through celite, and concentrated. Flash chromatography (silica gel, EtOAc/hexanes gradient) gave the title compound (7.03 g, 55%). Mass Spectrum (FD+) (m/z) 347.3 [M⁺]

PREPARATION 275

2-{3-[(t-Butoxy)carbonylamino]cyclohexyl}acetic Acid (Cis Racemic)

In a fashion similar to that described for preparation 266, a compound from preparation 274 (7 g, 20.2 mmol), 2 N NaOH (25 ml, 50 mmol), Dioxane (100 ml) were reacted for 5 h to give the title compound (5.2 g, 100%). Mass Spectrum (FD+) (m/z) 257.3 [M⁺].

PREPARATION 276

(t-Butoxy)-N-(3-{[(phenylmethoxy)carbonylamino] methyl}cyclohexyl)carboxamide (Cis Racemic)

To a solution of a compound from preparation 275 (2.6 g, 10.1 mmol), Et₃N (2.84 ml, 20.4 mmol) in toluene (100 ml) under N₂ was added DPPA (4.39 ml, 20.4 mmol) and benzyl alcohol (3.13 ml, 30.3 mmol). The solution was heated to reflux overnight. The reaction was cooled to room temperature, diluted with EtOAc, washed (1.0 N NaOH then brine), dried (MgSO₄), filtered, and concentrated. Flash chromatography (silica gel, hexanes/EtOAc gradient) gave the title compound (2.92 g, 80%). 1H NMR: consistent with structure.

PREPARATION 277

N-[3-(Aminomethyl)cyclohexyl](t-butoxy) carboxamide (Cis Racemic)

A mixture of a compound from preparation 276 (1 g, 2.76 mmol), 10% Pd/C catalyst (0.5 g), and EtOAc (30 ml) was stirred under an atmosphere of hydrogen gas (balloon) for 18 h, filtered through celite, and concentrated to give the title compound (0.48 g, 76%), which was taken on without further purification. Mass Spectrum (ES+) (m/z) 229.1 [M+1].

PREPARATION 278

N-({3-[(t-Butoxy)carbonylamino] cyclohexyl}methyl)[3-(6-chloro-2-fluorophenyl)-5-methylisoxazol-4-yl]carboxamide To a solution of a compound from preparation 277 (0.48 g, 2.1 mmol) and 3-(2-chloro-6-fluorophenyl)-5-methylisoxazole-4-carbonyl chloride (0.75 g, 2.74 mmol) in dichloromethane (20 ml) under N₂ was added dropwise triethylamine (0.73 ml, 5.25 mmol) and stirred for 4 h. The reaction was diluted with dichloromethane, washed (H₂O then brine), dried (MgSO₄), filtered, and concentrated. Flash chromatography (silica gel, hexanes/EtOAc gradient) gave the title compound (0.726 g, 74%). Mass Spectrum (ES+) (m/z) 366.1 [M–BOC].

PREPARATION 279

[5-chloro-3-(6-chloro-2-fluorophenyl)isoxazol-4-yl]-N-{3-[(phenylcarbonylamino)-methyl] cyclohexyl}carboxamide In a fashion similar to that described for preparation 267, 4-carboxy-5-chloro-3-(2-chloro-5-fluorophenyl)isoxazole acid (0.22 g, 0.84 mmol), dichloromethane (2 ml), oxalyl chloride (0.15 ml, 1.68 mmol), DMF (0.01 ml), dichloromethane (5 ml), N-(3-Amino-cyclohexylmethyl)-benzamide (0.15 g, 0.65 mmol), and triethylamine (0.35 ml, 2.52 mmol) gave the title compound (0.29 g, 90%) after flash chromatography (silica gel, Acetone/CH2Cl2 gradient). Mass Spectrum (ES+) (m/z) 490.1 [M+1].

PREPARATION 280

[5-(Diethylamino)-3-(6-chloro-2-fluorophenyl) isoxazol-4-yl]-N-{3-[(phenylcarbonylamino)methyl] cyclohexyl}carboxamide To a solution of a compound from preparation 278 (0.1 g, 0.2 mmol) in DMF (2.5 ml) under N₂ was added diethylamine (0.065 ml, 0.63 mmol)j and stirred for 2 h. The reaction was diluted with EtOAc, washed (H₂O then brine), dried (MgSO₄), filtered, and concentrated. (0.1 N HCl and brine), dried (MgSO4), filtered, and concentrated. Flash chromatography (silica gel, acetone/CH2Cl2 gradient) gave the title compound (0.1 g, 93%). Mass Spectrum (ES+) (m/z) 527.2 [M+1].

PREPARATION 281

[3-(6-Chloro-2-fluorophenyl)-5-pyrrolidinylisoxazol-4-yl]-N-{3-[(phenylcarbonylamino)methyl] cyclohexyl}carboxamide In a fashion similar to that described for preparation 280, a compound from preparation 279 (0.085 g, 0.17 mmol), DMF (2.5 ml), pyrrolidine (0.14 ml, 1.7 mmol) gave the title compound (0.089 g, 100%) which was taken on as a crude residue. Mass Spectrum (ES+) (m/z) 525.2 [M+1].

PREPARATION 282

[3-(6-Chloro-2-fluorophenyl)-5-(ethylamino) isoxazol-4-yl]-N-{3-[(phenylcarbonyl-amino) methyl]cyclohexyl}carboxamide In a fashion similar to that described for preparation 280, a compound from preparation 61 (0.085 g, 0.17 mmol), DMF (2.5 ml), ethylamine (0.85 ml, 1.7 mmol) gave the title compound (0.085 g, 100%) which was taken on as a crude residue. Mass Spectrum (ES+) (m/z) 499.2 [M+1].

PREPARATION 283

[3-(6-Chloro-2-fluorophenyl)-5-ethylthioisoxazol-4-yl]-N-{3-[(phenylcarbonyl-amino)methyl]cyclohexyl}carboxamide In a fashion similar to that described for preparation 280, a compound from preparation 279 (0.1 g, 0.2 mmol), DMF (2.5 ml), sodium ethanethiolate (0.103 g, 1.0 mmol) gave the title compound (0.85 g, 100%) which was taken on as a crude residue. 1H NMR: consistent with structure.

PREPARATION 284

4-(Methoxycarbonyl-phenyl-methyl)-piperazine-1-carboxylic Acid tert-butyl Ester

To a solution of racemic α-bromophenylacetic acid methyl ester, 5.0 g (22.0 mmol) in 200 mL of tetrahydrofuran was added 3.4 mL (22.0 mmol) of $Et_3N$ and 12.3 g (66.0 mmol) of BOC-piperazine. The reaction mixture was refluxed for 3.5 hours, cooled to rt. and concentrated to dryness. The residue was partitioned between 20% isopropanol/chloroform and water. The mixture was washed with saturated $NaHCO_3$, washed with brine, dried over $Na_2SO_4$, filtered and concentrated to dryness. The residue was purified by chromatography using chloroform as eluent and was concentrated to dryness to yield 7.73 g (100%) of the desired mixture of isomers as a colorless oil.
MS (ion spray) 335.2 (M+).

PREPARATION 285

4-(Carboxy-phenyl-methyl)-piperazine-1-carboxylic Acid tert-butyl Ester

To a solution of the compound from preparation 284, 560 mg (1.68 mmol) in 15 mL of dioxane was added a solution of 400 mg (16.8 mmol) of lithium hydroxide in 15 mL of water. The solution was stirred for five hours at rt. then acidified to pH=3.0 with 5 N HCl and concentrated to dryness to give a quantitative yield of the crude desired mixture of isomers. MS (ion spray) 319.2 (M−). Crude product was carried on without further purification.

PREPARATION 286

[4-(2-Hydroxy-ethyl)-piperazin-1-yl]-phenyl-acetic Acid Methyl Ester

To a solution of racemic a-bromophenylacetic acid methyl ester, 5.0 g (22.0 mmol) in 200 mL of tetrahydrofuran was added 3.4 mL (22.0 mmol) of $Et_3N$ and 8 mL (66.0 mmol) of 1-(hydroxyethyl)piperazine. The reaction mixture was refluxed for three hours, cooled to rt. and concentrated to dryness. The residue was partitioned between 20% isopropanol/chloroform and water. The mixture was washed with saturated $NaHCO_3$, washed with brine, dried over $Na_2SO_4$, filtered and concentrated to dryness to give a quantitative yield of the desired mixture of isomers as a yellow oil. MS (ion spray) 279.1 (M+).

PREPARATION 287

[4-(2-Hydroxy-ethyl)-piperazin-1-yl]-phenyl-acetic Acid

To a solution of the compound from preparation 286, 470 mg (1.68 mmol) in 20 mL of dioxane was added a solution of 400 mg (16.8 mmol) of lithium hydroxide in 20 mL of water. The solution was stirred for 2.5 hours at rt. then acidified to pH=3.0 with 5 N HCl and concentrated to dryness to give a quantitative yield of the crude desired mixture of isomers. Crude product was carried on without further purification.
MS (ion spray) 319.2 (M−).

PREPARATION 288

Phenyl-(4-pyridin-2-yl-piperazin-1-yl)-acetic Acid Methyl Ester

To a solution of racemic α-bromophenylacetic acid methyl ester, 5.0 g (22.0 mmol) in 200 mL of tetrahydrofuran was added 3.4 mL (22.0 mmol) of $Et_3N$ and 10 mL (66.0 mmol) of 1-(2-pyridyl)-piperazine. The reaction mixture was refluxed for five hours, cooled to rt. and concentrated to dryness. The residue was partitioned between 20% isopropanol/chloroform and water. The mixture was washed with saturated $NaHCO_3$, washed with brine, dried over $Na_2SO_4$, filtered and concentrated to dryness. The residue was purified by column chromatography using MeOH/chloroform as eluant and concentrated to dryness to give a quantitative yield of the desired mixture of isomers as a yellow oil. MS (ion spray) 312.2 (M+).

PREPARATION 289

Piperidin-1-yl-acetic Acid Ethyl Ester

To a solution of bromoethylacetate, 3.3 g (30.0 mmol) in 100 mL of tetrahydrofuran was added 4.2 mL (30.0 mmol) of $Et_3N$ and 9 mL (90.0 mmol) of piperidine. The reaction mixture stirred overnight at rt. and was concentrated to dryness. The residue was partitioned between chloroform and saturated aqueous $NaHCO_3$. The mixture was washed with saturated $NaHCO_3$, washed with brine, dried over $Na_2SO_4$, filtered and concentrated to dryness to give 4.6 g (89%) of the desired product as a tan oil.
MS (ion spray) 172.2 (M+).

PREPARATION 290

Piperidin-1-yl-acetic Acid

To a solution of the compound from preparation 289, 143 mg (0.84 mmol) in 5 mL of dioxane was added a solution of 66 mg (8.4 mmol) of lithium hydroxide in 5 mL of water. The solution was stirred for three hours at rt. then acidified to pH=2.0 with 5 N HCl and concentrated to dryness to give a quantitative yield of the crude desired product. MS (ion spray) 144.1 (M+). Crude product was carried on without further purification.

PREPARATION 291

(4-Methyl-piperazin-1-yl)-acetic Acid Ethyl Ester

To a solution of bromoethylacetate, 3.3 g (30.0 mmol) in 100 mL of tetrahydrofuran was added 4.14 g (30.0 mmol) of potassium carbonate and 3.3 mL (30.0 mmol) of 4-methylpiperazine. The reaction mixture stirred overnight at rt. and was concentrated to dryness. The residue was partitioned between 20% isopropanol/chloroform and saturated aqueous $NaHCO_3$. The mixture was washed with saturated $NaHCO_3$, washed with brine, dried over $Na_2SO_4$, filtered and concentrated to dryness to give 1.23 g (22%) of the desired product as a tan oil. MS (ion spray) 187.1 (M+).

PREPARATION 292

(4-Methyl-piperazin-1-yl)-acetic Acid

To a solution of the compound from preparation 291, 160 mg (0.84 mmol) in 5 mL of dioxane was added a solution of 66 mg (8.4 mmol) of lithium hydroxide in 5 mL of water. The solution was stirred for two hours at rt. then acidified to pH=3.0 with 5 N HCl and concentrated to dryness to give a quantitative yield of the crude desired product. MS (ion spray) 159.1 (M+). Crude product was carried on without further purification.

PREPARATION 293

(Methyl-phenyl-amino)-acetic Acid Ethyl Ester

To a solution of bromoethylacetate, 3.3 mL (30.0 mmol) in 100 mL of tetrahydrofuran was added 4.14 g (30.0 mmol) of potassium carbonate and 3.25 mL of N-methylaniline. The reaction mixture stirred overnight at rt. and was concentrated to dryness. The residue was partitioned between 20% isopropanol/chloroform and saturated aqueous $NaHCO_3$. The mixture was washed with saturated NaHCO3, washed with brine, dried over $Na_2SO_4$, filtered and concentrated to dryness. The residue was purified by column chromatography using EtOAc/hexanes as eluent and concentrated to dryness to give 4.74 g (82%) of the desired product as a tan oil. MS (ion spray) 194.1 (M+1).

PREPARATION 294

Phenyl-(pyridin-3-yloxy)-acetic Acid Methyl Ester

To a slurry of 3-hydroxypyridine sodium salt, 4.6 g (26.4 mmol) in 200 mL of tetrahydrofuran was added 5.0 g (22.0 mmol) of alpha-bromophenylacetic acid. The reaction mixture was refluxed for two hours, cooled to rt. and concentrated to dryness. The residue was partitioned between 20% isopropanol/chloroform and water. The mixture was washed with saturated $NaHCO_3$, washed with brine, dried over $Na_2SO_4$, filtered and concentrated to dryness. The residue was purified by column chromatography using MeOH/chloroform as eluent and concentrated to dryness to give 2.8 g of the desired mixture of isomers as a dark oil. MS (ion spray) 244.1 (M+).

PREPARATION 295

(Pyridin-3-yloxy)-acetic Acid Ethyl Ester

To a solution of 3-hydroxypyridine sodium salt, 6.4 g (36.0 mmol) in 200 mL of DMF was added 3.3 mL (30.0 mmol) of bromoethylacetate. The reaction mixture stirred overnight at rt. and was concentrated to dryness. The residue was partitioned between 20% isopropanol/chloroform and saturated aqueous $NaHCO_3$. The mixture was washed with saturated NaHCO3, washed with brine, dried over $Na_2SO_4$, filtered and concentrated to dryness. The residue was purified by column chromatography using MeOH/chloroform as eluent and concentrated to dryness to give 3.8 g (70%) of the desired product as a tan oil. MS (ion spray) 182.1 (M+).

PREPARATION 296

(Pyridin-3-yloxy)-acetic Acid

To a solution of the compound from preparation 295, (pyridin-3-yloxy)-acetic acid ethyl ester, 300 mg (1.68 mmol) in 15 mL of dioxane was added a solution of 400 mg (16.8 mmol) of lithium hydroxide in 15 mL of water. The solution was stirred for three hours at rt. then acidified to pH=1.0 with 5 N HCl and concentrated to dryness to give a quantitative yield of the crude desired product. MS (ion spray) 154.1 (M+). Crude product was carried on without further purification.

PREPARATION 297

1-tert-Butoxycarbonylamino-cyclohexanecarboxylic Acid

To a slurry of 1-amino-1-cyclohexane-carboxylic acid, 5.0 g (35.0 mmol) in 50 mL of tetrahydrofuran and 50 mL of water was added 14.5 g (105.0 mmol) of potassium carbonate, 7.7 g (35.0 mmol) of BOC-anhydride and 5 mg of DMAP. The mixture was stirred overnight at rt. and the organics were evaporated off in vacuo. The aqueous layer was acidified to pH=1 with 5 N HCl and extracted with 20% isopropanol/chloroform. The combined organics were washed with brine, dried over $Na_2SO_4$, filtered and concentrated to dryness to yield 1.83 g (21%) of the desired product as a white oil that solidifies upon standing. MS (IS) 244.2 (M+).

PREPARATION 298

Morpholin-4-yl-acetic Acid Ethyl Ester

To a solution of bromoethylacetate, 3.3 mL (30.0 mmol) in 100 mL of tetrahydrofuran was added 4.14 g (30.0 mmol) of potassium carbonate and 2.6 mL (30.0 mmol) of morpholine. The reaction mixture stirred overnight at rt. and was concentrated to dryness. The residue was partitioned between 20% isopropanol/chloroformn and saturated aqueous $NaHCO_3$. The mixture was washed with saturated NaHCO3, washed with brine, dried over $Na_2SO_4$, filtered and concentrated to dryness to give 2.75 g (53%) of the desired product as a tan oil. MS (ion spray) 174.2 (M+).

PREPARATION 299

Morpholin-4-yl-acetic Acid

To a solution of the compound from preparation 298, 150 mg (0.84 mmol) in 10 mL of dioxane was added a solution of 198 mg (8.4 mmol) of lithium hydroxide in 10 mL of water. The solution was stirred for two hours at rt. then acidified to pH=2.0 with 5 N HCl and concentrated to dryness to give a quantitative yield of the crude desired product. MS (ion spray) 146.0 (M+). Crude product was carried on without further purification.

PREPARATION 300

(4-Hydroxy-piperidin-1-yl)-acetic Acid Ethyl Ester

To a solution of bromoethylacetate, 3.3 mL (30.0 mmol) in 100 mL of tetrahydrofuran was added 4.2 g (30.0 mmol) of potassium carbonate and 3.0 mL (30.0 mmol) of 4-hydroxypiperidine. The reaction mixture stirred overnight at rt. and was concentrated to dryness. The residue was partitioned between 20% isopropanol/chloroform and saturated aqueous $NaHCO_3$. The mixture was washed with saturated NaHCO3, washed with brine, dried over $Na_2SO_4$, filtered and concentrated to dryness to give 4.65 g (83%) of the desired product as a tan oil. MS (ion spray) 188.0 (M+).

PREPARATION 301

(4-Hydroxy-piperidin-1-yl)-acetic Acid

To a solution of the compound from preparation 300, 158 mg (0.84 mmol) in 10 mL of dioxane was added a solution of 198 mg (8.4 mmol) of lithium hydroxide in 10 mL of water. The solution was stirred for 1.5 hours at rt. then acidified to pH=2.0 with 5 N HCl and concentrated to dryness to give a quantitative yield of the crude desired product. MS (ion spray) 160.1 (M+). Crude product was carried on without further purification.

PREPARATION 302

(2-Oxo-2H-pyridin-1-yl)-acetic Acid Ethyl Ester

To a slurry of sodium hydride, 1.73 g (43.2 mmol) in 100 mL of DMF was added 3.4 g (36.0 mmol) of 2-hydroxypyridine. The mixture was stirred 10 minutes then added to a solution of 3.3 mL (30.0 mmol) of bromoethylacetate in 100 mL DMF. The reaction mixture was stirred 72 hours at rt. then concentrated to dryness. The residue was partitioned between 20% isopropanol/chloroform and water and washed with saturated aqueous $NaHCO_3$, washed with brine, dried over $Na_2SO_4$, filtered and concentrated to dryness. The residue was purified by column chromatography using MeOH/chloroform as eluent and concentrated to dryness to yield 3.52 g (65%) of the desired product as a colorless oil. $^1$H—NMR is consistent with structure. MS (ion spray) 182.1 (M+).

PREPARATION 303

(2-Oxo-2H-pyridin-1-yl)-acetic Acid

To a solution of the compound from preparation 302, 152 mg (0.84 mmol) in 10 mL of dioxane was added a solution of 198 mg (8.4 mmol) of lithium hydroxide in 10 mL of water. The solution was stirred for two hours at rt. then acidified to pH=1.0 with 5 N HCl and concentrated to dryness to give a quantitative yield of the crude desired product. MS (ion spray) 154.1 (M+). Crude product was carried on without further purification.

PREPARATION 304

(Pyridin-4-yloxy)-acetic Acid Ethyl Ester

To a slurry of sodium hydride, 1.73 g (43.2 mmol) in 100 mL of DMF was added 3.4 g (36.0 mmol) of 4-hydroxypyridine. The mixture was stirred 10 minutes then added to a solution of 3.3 mL (30.0 mmol) of bromoethylacetate in 100 mL DMF. The reaction mixture was stirred 72 hours at rt. then concentrated to dryness. The residue was partitioned between 20% isopropanol/chloroform and water and washed with saturated aqueous $NaHCO_3$, washed with brine, dried over $Na_2SO_4$, filtered and concentrated to dryness. The residue was purified by radial chromatography using MeOH/chloroform as eluent and concentrated to dryness to yield 510 mg (9.4%) of the desired product as a tan oil. $^1$H—NMR is consistent with structure. MS (ion spray) 182.1 (M+).

PREPARATION 305 tert-Butylamino-acetic Acid

To a solution of tert-Butylamino-acetic acid methyl ester (Maybridge), 122 mg (0.84 mmol) in 10 mL of dioxane was added a solution of 60 mg (2.52 mmol) of lithium hydroxide in 10 mL of water. The reaction mixture was stirred for two hours, acidified to pH=1 with 5 N HCl and concentrated to dryness to yield the crude desired product which was carried on without further purification. MS (IS) 132.1 (M+1).

PREPARATION 306

(6-Methoxy-pyridin-3-ylamino)-acetic Acid

To a solution of (6-methoxy-pyridin-3-ylamino)-acetic acid methyl ester, 113 mg (0.58 mmol) in 10 mL of dioxane was added a solution of 70 mg (2.9 mmol) of lithium hydroxide in 10 mL of water. The reaction mixture was stirred for three hours, acidified to pH=1 with 5 N HCl and concentrated to dryness to yield the crude desired product which was carried on without further purification. MS (IS) 183.1 (M+1).

PREPARATION 307

2-(Pyridin-3-yloxy)-propionic Acid

To a solution of 2-(pyridin-3-yloxy)-propionic acid ethyl ester, 320 mg (1.6 mmol) in 10 mL of dioxane was added a solution of 190 mg (8.0 mmol) of lithium hydroxide in 10 mL of water. The reaction mixture was stirred for three hours, acidified to pH=1 with 5 N HCl and concentrated to dryness to yield the crude desired product which was carried on without further purification. MS (IS) 168.1 (M+1).

PREPARATION 308

1-Benzoyl-pyrrolidine-2-carboxylic Acid Methyl Ester

Benzoyl chloride (1.40 mL, 12.1 mmol) was added in a dropwise manner to a mixture of L-proline methyl ester hydrochloride (2.00 g, 12.1 mmol) and $Et_3N$ (4.20 mL, 30.2 mmol) in $CH_2Cl_2$ (40 mL) and the resulting mixture stirred overnight at rt. The mixture was concentrated in vacuo and the residue treated with water and extracted with EtOAc and the combined extracts dried over $Na_2SO_4$. Concentration left a residue which was loaded onto a silica gel column and eluted with MeOH/$CH_2Cl_2$ which allowed for isolation of 2.76 g (94%) of the title compound as a white solid. MS(ES): $(M+1)^+$ 234.2 m/z.

PREPARATION 309

1-Benzoyl-pyrrolidine-2-carboxylic Acid

The compound from preparation 308 (1.00 g, 4.3 mmol) was combined with aqueous 2N sodium hydroxide (4.0 mL, 8.0 mmol), tetrahydrofuran (2.0 mL) and MeOH (2.0 mL) and the mixture stirred at rt. until hydrolysis was complete. Organic solvents were removed in vacuo and the mixture was diluted with water and adjusted to pH 2.0–3.0 with aqueous hydrochloric acid. The mixture was then concentrated to dryness in vacuo. The resulting solids were then slurried (and washed) with an EtOAc/ethanol mixture followed by filtration. Concentration of the filtrate left desired acid of acceptable purity (0.52 g, 55%) as a white solid. MS(ES): $(M+1)^+$ 220.3 m/z.

PREPARATION 310

1-Phenylacetyl-pyrrolidine-2-carboxylic Acid Methyl Ester

Phenacetyl chloride (1.60 mL, 12.1 mmol) was added to a mixture of L-proline methyl ester hydrochloride (2.00 g, 12.1 mmol) and $Et_3N$ (4.20 mL, 30.2 mmol) in $CH_2Cl_2$ (40 mL) and the resulting mixture stirred overnight at rt. The mixture was treated in a manner similar to that in preparation 103, which resulted in recovery of 1.74 g (58%) of the desired ester as a clear oil. MS(ES): $(M+1)^+$ 248.2, 249.2 m/z.

PREPARATION 311

1-Phenylacetyl-pyrrolidine-2-carboxylic Acid

The compound from preparation 310 (1.00 g, 4.0 mmol) was combined with aqueous 2N sodium hydroxide (5.0 mL, 10.0 mmol), tetrahydrofuran (2.0 mL) and MeOH (2.0 mL) and the mixture stirred at rt. until hydrolysis was complete. The mixture was then treated in a manner similar to preparation 104, however when the pH was adjusted the desired acid began to precipitate. Filtration and drying of the precipitate netted 0.70 g (74%) of the title compound as a white powdery solid. MS(ES): (M+1)+ 234.3.

PREPARATION 312

N-Benzyl-L-proline

N-Benzyl-L-proline ethyl ester (1.00 g, 4.3 mmol) was combined with aqueous 2N sodium hydroxide (5.0 mL, 10.0 mmol), tetrahydrofuran (2.0 mL) and MeOH (2.0 mL) and the mixture stirred at rt. until hydrolysis was complete. The mixture was then treated in a manner similar to preparation 104. Concentration of the filtrate netted 0.79 g (90%) of crude acid as a light yellowish solid. MS(ES): (M+1)+ 206.3, 207.3.

PREPARATION 314

3-(2–Cyano-6-fluoro-phenyl)-5-methyl-isoxazole-4-carboxylic Acid Ethyl Ester

To a mixture of ethyl 3-(2-Fluoro-6-iodo-phenyl)-5-methyl-isoxazole-4-carboxylate (0.25 g, 0.67 mmol), tetrakis(triphenylphosphine)palladium (0.08 g, 0.067 mmol), and $Et_3N$ (5 mL) under $N_2$ was added TMSCN and heated at reflux overnight. The reaction was cooled to room temperature, diluted with $H_2O$, and extracted with EtOAc (2×). The combined extracts were washed ($H_2O$ then brine), dried ($MgSO_4$), filtered, and concentrated. Flash chromatography (silica gel, EtOAc/hexanes gradient) gave the title compound (0.15 g, 82%). Mass Spectrum (ES+) (m/z) 275.0 [M+1].

PREPARATION 315

3-(2–Cyano-6-fluoro-phenyl)-5-methyl-isoxazole-4-carboxylic Acid

A mixture of a compound from preparation 314, (0.14 g, 0.51 mmol), EtOH (2.5 mL), and 5 N NaOH (0.3 mL, 1.5 mmol) was heated at 50° C. for 1.5 h. The reaction was cooled to rt., diluted with $H_2O$, and acidified (conc. HCl) to less than pH 3. The mixture was extracted with EtOAc (2×) and the combined extracts were washed ($H_2O$ then brine), dried ($MgSO_4$), filtered, and concentrated to give the title compound (0.1 g, 80%). This material was used without further purification. Mass Spectrum (ES+) (m/z) 247.0 [M+1].

PREPARATION 316

3-(2–Cyano-6-fluoro-phenyl)-5-methyl-isoxazole-4-carboxylic Acid[3-(benzoylamino-methyl)-cyclohexyl]-amide To a solution of a compound from preparation 315, (0.1 g, 0.41 mmol) in $CH_2Cl_2$ (10 mL) under $N_2$ was added oxalyl chloride (0.07 mL, 0.82 mmol) then DMF (1 drop) and stirred for 2 h. The solution was concentrated, redissolved in $CH_2Cl_2$ (5 mL) under $N_2$, and N-(3-amino-cyclohexylmethyl)-benzamide (0.114 g, 0.49 mmol) was added. The reaction vessel was submerged in a water bath and $Et_3N$ (0.17 mL, 1.23 mmol) was added dropwise. After 2.5 h of stirring, the mixture was diluted with $CH_2Cl_2$, washed (1.0 NaOH then brine), dried ($MgSO_4$), filtered, and concentrated. Flash chromatography (silica gel, Acetone/$CH_2Cl_2$ gradient) gave (0.119 g, 63%). Mass Spectrum (ES+) (m/z) 461.2 [M+1].

PREPARATION 317

(3-Amino-cyclohexylmethyl)-carbamic Acid Benzyl Ester

A solution of [3-(benzyloxycarbonylamino-methyl)-cyclohexyl]-carbamic acid tert-butyl ester (6 g, 16.6 mmol) in TFA (30 mL) was stirred for 1.5 h. The solution was concentrated using benzene to azeotrope, diluted with EtOAc, washed (1.0 N NaOH), dried ($Na_2SO_4$), filtered, and concentrated to afford (4.2 g, 97%) as a crude solid. Mass Spectrum (ES+) (m/z) 263.1 [M+1].

PREPARATION 318

(3-{[3-(2–Cyano-6-fluoro-phenyl)-5-methyl-isoxazole-4-carbonyl]-amino}-cyclohexylmethyl)-carbamic Acid Benzyl Ester In a fashion similar to that described for preparation 316, a compound from preparation 315 (3.05 g, 12.4 mmol), oxalyl chloride (2.16 mL, 24.8 mmol), $CH_2Cl_2$ (50 mL), DMF (0.05 mL), (3-amino-cyclohexylmethyl)-carbamic acid benzyl ester (4.2 g, 16.1 mmol), $CH_2Cl_2$ (125 mL), and $Et_3N$ (5.17 mL, 37.2 mmol) gave the title compound (4.6 g, 76%) after flash chromatography (silica gel, acetone/$CH_2Cl_2$ gradient). Mass Spectrum (ES+) (m/z) 491.2 [M+1].

PREPARATION 319

2-(3-Oxo-cyclohexyl)-malonic Acid Dibenzyl Ester

To a solution of $LiAlH_4$ (6 mL, 6 mmol) under $N_2$ at 0° C. was added a solution of (S)-1,1'-binaphthol (3.43 g, 12 mmol) in THF (48 mL) and stirred for 30 min. The reaction was warmed to RT. To this was added a solution of sodium salt benzyl malonate in THF which was prepared by reacting benzyl malonate (14.99 mL, 60 mmol), NaH (60% by wt., 0.216 g, 5.4 mmol), and THF (60 mL) until all bubbling ceased. Next, cyclohexenone (5.82 mL, 60 mmol) and dibenzlmalonate (1.35 mL, 5.4 mmol) were added and the reaction mixture was stirred overnight. 1.0 N HCl was added and extracted with EtOAc (3×). The combined EtOAc layers were washed (brine), dried ($MgSO_4$), filtered, and concentrated. Flash chromatography (silica gel, acetone/hexanes gradient) gave the title compound (16.17 g, 71%). Mass Spectrum (FIA) (m/z) 381.3 [M+1].

PREPARATION 320

2-(3-Hydroxy-cyclohexyl)-malonic Acid Dibenzyl Ester

To a –78° C. solution of a compound from preparation 319 (see Arai, T.; Yamada, Y. M. A.; Yamamoto, N.; Sasai, H.; Shibasali, M. *Chem. Eur. J.* 1996, 2, 1368–1372.) (16.15 g, 42.5 mmol) in THF (212.5 mL) under $N_2$ was added L-selectride (46.75 mL at 1.0 M, 46.75 mmol) dropwise and the mixture was stirred for 3.5 h at –78° C. EtOAc and $H_2O$ were added and the mixture was warmed to rt. Dilution with more EtOAc followed by washing with 1N NaOH, saturated $NH_4Cl$, brine, drying ($MgSO_4$), and flash chromatography (silica gel, EtOAc/hexanes gradient) gave the title compound (14.29 g, 88%). Mass Spectrum (FIA) (m/z) 383.3 [M+1].

PREPARATION 321

(3-Hydroxy-cyclohexyl)-acetic Acid Benzyl Ester

A solution of a compound from preparation 320 (19.19 g, 50.2 mmol, LiCl (4.27 g, 100.5 mmol, $H_2O$ (1.81 mL, 100.5 mmol), and DMSO (135 mL) was lowered into a 165° C. oil bath for 2 h then heated at 175° C. for 1.5 h. The reaction was cooled to rt. and diluted with EtOAc. Washing with H$_2$O and brine, drying (MgSO$_4$), and flash chromatography (silica gel, EtOAc/hexanes gradient) gave the title compound (9.71 g, 78%). 1H NMR: consistent with structure.

PREPARATION 322

(3-Azido-cyclohexyl)-acetic Acid Benzyl Ester

To a solution of a compound from preparation 321 (9.71 g, 39.2 mmol), Ph$_3$P (12.32 g, 41.04 mmol), and hydrazoic acid (30.9 mL, at 1.9 M, 58.7 mmol) in toluene (120 mL) was added DEAD (9.24 mL, 58.7 mmol) dropwise and stirred for 72 h. The mixture was diluted with EtOAc, washed with 0.1 N NaOH, H$_2$O, and brine, dried (MgSO$_4$), and chromatographed (silica gel, CH$_2$Cl$_2$/hexanes gradient) to give the title compound (10.0 g, 93%). 1H NMR: consistent with structure.

PREPARATION 323

(3-tert-Butoxycarbonylamino-cyclohexyl)-acetic Acid Benzyl Ester

A mixture of a compound from preparation 322 (10 g, 36.6 mmol), (BOC)$_2$O (9.57 g, 43.9 mmol), Lindlar's catalyst (3.7 g), and EtOAc (200 mL) was stirred under an atmosphere of hydrogen gas (balloon) for 24 h, filtered through celite, and concentrated. Flash chromatography (silica gel, EtOAc/hexanes gradient) gave the title compound (7.03 g, 55%). Mass Spectrum (FD+) (m/z) 347.3 [M$^+$].

PREPARATION 324

(3-tert-Butoxycarbonylamino-cyclohexyl)-acetic Acid

In a fashion similar to that described for preparation 315, a compound from preparation 323 (7 g, 20.2 mmol), 2 N NaOH (25 mL, 50 mmol), Dioxane (100 mL) were reacted for 5 h to give the title compound (5.2 g, 100%). Mass Spectrum (FD+) (m/z) 257.3 [M$^+$].

PREPARATION 325

[3-(Benzyloxycarbonylamino-methyl)-cyclohexyl]-carbamic Acid tert-butyl Ester

To a solution of a compound from preparation 324 (2.6 g, 10.1 mmol), Et$_3$N (2.84 mL, 20.4 mmol) in toluene (100 mL) under N$_2$ was added DPPA (4.39 mL, 20.4 mmol) and benzyl alcohol (3.13 mL, 30.3 mmol). The solution was heated to reflux overnight. The reaction was cooled to room temperature, diluted with EtOAc, washed (1.0 N NaOH then brine), dried (MgSO$_4$), filtered, and concentrated. Flash chromatography (silica gel, hexanes/EtOAc gradient) gave the title compound (2.92 g, 80%). 1H NMR: consistent with structure.

PREPARATION 326

(3-Aminomethyl-cyclohexyl)-carbamic Acid tert-butyl Ester

A mixture of a compound from preparation 325 (1 g, 2.76 mmol), 10% Pd/C catalyst (0.5 g), and EtOAc (30 mL) was stirred under an atmosphere of hydrogen gas (balloon) for 18 h, filtered through celite, and concentrated to give (0.48 g, 76%) which was taken on without further purification. Mass Spectrum (S+) (m/z) 229.1 [M+1].

PREPARATION 327

[3-({[3-(2-Chloro-6-fluoro-phenyl)-5-methyl-isoxazole-4-carbonyl]-amino}-methyl)-cyclohexyl]-carbamic Acid tert-butyl Ester To a solution of a compound from preparation 326 (0.48 g, 2.1 mmol) and 3-(2-chloro-6-fluorophenyl)-5-methylisoxazole-4-carbonyl chloride (0.75 g, 2.74 mmol) in CH$_2$Cl$_2$ (20 mL) under N$_2$ was added dropwise Et3N (0.73 mL, 5.25 mmol) and stirred for 4 h. The reaction was diluted with CH$_2$Cl$_2$, washed (H$_2$O then brine), dried (MgSO$_4$), filtered, and concentrated. Flash chromatography (silica gel, hexanes/EtOAc gradient) gave the title compound (0.726 g, 74%). Mass Spectrum (ES+) (m/z) 366.1 [M–BOC].

PREPARATION 328

5-Chloro-3-(2-chloro-6-fluoro-phenyl)-isoxazole-4-carboxylic acid[3-(benzoylamino-methyl) cyclohexyl]amide In a fashion similar to that described for preparation 316, (0.22 g, 0.84 mmol), CH$_2$Cl$_2$ (2 mL), oxalyl chloride (0.15 mL, 1.68 mmol), DMF (0.01 mL), CH$_2$Cl$_2$ (5 mL), N-(3-Amino-cyclohexylmethyl)-benzamide (0.15 g, 0.65 mmol), and Et$_3$N (0.35 mL, 2.52 mmol) gave the title compound (0.29 g, 90%) after flash chromatography (silica gel, Acetone/CH$_2$Cl$_2$ gradient). Mass Spectrum (ES+) (m/z) 490.1 [M+1].

PREPARATION 329

3-(2-Chloro-6-fluoro-phenyl)-5-diethylamino-isoxazole-4-carboxylic Acid{3-[(2-propenyl-penta-2,-dienoylamino)-methyl]-cyclohexyl}-amide To a solution of a compound from preparation 328 (0.1 g, 0.2 mmol) in DMF (2.5 mL) under N$_2$ was added diethylamine (0.065 mL, 0.63 mmol) and stirred for 2 h. The reaction was diluted with EtOAc, washed (H$_2$O then brine), dried (MgSO$_4$), filtered, and concentrated. (0.1 N HCl and brine), dried (MgSO4), filtered, and concentrated. Flash chromatography (silica gel, acetone/CH$_2$Cl$_2$ gradient) gave the title compound (0.1 g, 93%). Mass Spectrum (ES+) (m/z) 527.2 [M+1].

PREPARATION 330

3-(2-Chloro-6-fluoro-phenyl)-5-pyrrolidin-1-yl-isoxazole-4-carboxylic Acid[3-(benzoylaminomethyl)-cyclohexyl]-amide In a fashion similar to that described for preparation 329, a compound from preparation 328 (0.085 g, 0.17 mmol), DMF (2.5 mL), pyrrolidine (0.14 mL, 1.7 mmol) gave (0.089 g, 100%) which was taken on as a crude residue. Mass Spectrum (ES+) (m/z) 525.2 [M+1].

PREPARATION 331

3-(2-Chloro-6-fluoro-phenyl)-5-ethylamino-isoxazole-4-carboxylic acid[3-(benzoylaminomethyl)-cyclohexyl]-amide In a fashion similar to that described for preparation 329, a compound from preparation 328 (0.085 g, 0.17 mmol), DMF (2.5 mL), ethylamine (0.85 mL, 1.7 mmol) gave the title compound (0.085 g, 100%) which was taken on as a crude residue. Mass Spectrum (ES+) (m/z) 499.2 [M+1].

PREPARATION 332

3-(2-Chloro-6-fluoro-phenyl)-5-ethylsulfanyl-isoxazole-4-carboxylic acid[3-(benzoylamino-methyl)-cyclohexyl]-amide In a fashion similar to that described for preparation 329, a compound from preparation 328 (0.1 g, 0.2 mmol), DMF (2.5 mL), sodium ethanethiolate (0.103 g, 1.0 mmol) gave the title compound (0.85 g, 100%) which was taken on as a crude residue. $^1$H NMR: consistent with structure.

PREPARATION 333

[3-({[3-(2-Chloro-6-fluoro-phenyl)-5-methyl-isoxazole-4-carbonyl]-amino}-methyl)-cyclohexyl]-carbamic Acid tert-butyl Ester A mixture of a compound from preparation 326 (0.85 g, 2.35 mmol), 10% Pd/C catalyst (0.5 g), and EtOAc (25 mL) was stirred under an atmosphere of hydrogen gas (balloon) for 18 h, filtered through celite, and concentrated. This residue was mixed with 3-(2-Chloro-6-fluorophenyl)-5-methylisoxazole-4-carbonyl chloride (0.772 g, 2.82 mmol) in $CH_2Cl_2$ (7 mL) under $N_2$ and to this solution was added dropwise $Et_3N$ (1.0 mL, 7.05 mmol). After stirring 48 h, the mixture was diluted with $CH_2Cl_2$, washed (0.1 N HCl then brine), dried ($MgSO_4$), filtered, and concentrated. Flash chromatography (silica gel, EtOAc/Hexanes gradient) gave the title compound (0.64 g, 58%). Mass Spectrum (ES+) (m/z) 366.3 [M−BOC].

PREPARATION 334

5-[3-(Benzoylamino-methyl)-cyclohexyl]-3-methyl-4-oxo-4,5-dihydro-isoxazolo[4,3-c]quinolin-9-yl}-carbamic Acid 2-trimethylsilanyl-ethyl Ester To a solution of 3-methyl-4-oxo-5-{3-[(phenylcarbonylamino)methyl]-cyclohexyl}-5-hydroisoxazolo[4,3-c]quinoline-9-carboxylic acid (0.25 g, 0.55 mmol), $Et_3N$ (0.118 mL, 0.845 mmol) in toluene (3.5 mL) under $N_2$ was added DPPA (0.18 mL, 0.845 mmol) and 2-(trimethylsilyl) ethanol (0.232 mL, 1.63 mmol). The solution was heated to reflux for 4 h. The reaction was cooled to rt., diluted with EtOAc, washed (1.0 N NaOH then brine), dried ($MgSO_4$), filtered, and concentrated. Column chromatography (silica gel, acetone/$CH_2Cl_2$ gradient) gave the title compound (0.285 g, 90%). Mass Spectrum (ES−) (m/z) 573.3 [M−1]

PREPARATION 335

[3-(3,4,5-Trimethoxy-phenylcarbamoyl)-cyclopentylmethyl]-carbamic Acid tert-butyl Ester To a solution of 0.224 g (0.92 mmols) of 3-[(t-butoxy)amino]cyclopentane-carboxylic acid was added 0.44 mmol of 1-hydroxy-7-azabenzotriazole and 0.44 mmol of EDCI. After 40 minutes, 0.44 mmol of 3,4,5-trimethoxyaniline was added. After 3.25 hours, the solvent was removed in vacuo and replaced with ethyl acetate. The organic layer was rinsed with 1 N HCl, aq. $NaHCO_3$, and then x3 with water. The organic layer was dried and the solvent was removed in vacuo to yield 0.34 g of the title compound. MS(ES+)m/z=409.

PREPARATION 336

3-Aminomethyl-cyclopentanecarboxylic Acid (3,4,5-trimethoxy-phenyl)-amide

A solution of 0.049 g (0.12 mmol) of a compound from preparation 335 in TFA (10 ml) was stirred for 1 hour, after which the TFA was removed in vacuo and replaced with ethyl acetate. The organic layer was rinsed with 1N NaOH followed by brine and dried. The organic layer was removed in vacuo to yield 0.013 g of the title compound. MS(ES+)m/z=308.

PREPARATION 337

3-(2-Chloro-6-fluoro-phenyl)-5-methyl-isoxazole4-carboxylic Acid[3-(3,4,5-trimethoxy-phenylcarbamoyl)-cyclopentylmethyl]-amide A solution of 0.013 g (0.042 mmol) of a compound from preparation 336, 0.03 g (0.46 mmol) of 3-(6-chloro-2-fluorophenyl)-5-methylisoxazole4-carbonyl chloride, and 0.07 ml (0.5 mmol) of triethylamine in dichloromethane (10 ml) was stirred for 12 hours. The solvent was removed in vacuo and replaced with ethyl acetate. The organic layer was washed with 1N HCl, then aq. NaHCO3, followed by brine and dried. The solvent was removed in vacuo then chromatographed on silica gel with $CH_2Cl_2$ 100% to $CH_2Cl_2$/MeOH 2% to yield 0.018 g of the title compound. MS(ES+) m/z=545.8.

PREPARATION 338

(3-{[3-(2-Chloro-6-fluoro-phenyl)-5-methyl-isoxazole-4-carbonyl]-amino}-cycloheptyl)-acetic Acid Methyl Ester A solution of 4.4 g (24 mmol) of methyl 2-(3-aminocycloheptyl)acetate, 0.03 g (0.46 mmol) of 3-(6-chloro-2-fluorophenyl)-5-methylisoxazole4-carbonyl chloride, and 0.07 ml (0.5 mmol) of triethylamine in dichloromethane (10 ml) was stirred for 12 hours. The solvent was removed in vacuo and replaced with ethyl acetate. The organic layer was washed with 1N HCl, then aq. NaHCO3, followed by brine and dried. The solvent was removed in vacuo then chromatographed on silica gel with hexane/EtOAc 3/1 to yield 1.7 g of the title compound. MS(ES+) m/z=423.

PREPARATION 339

5-(3-Aminomethyl-cycloheptyl)-9-chloro-3-methyl-5H-isoxazolo[4,3-c]quinolin-4-one To a solution of 0.43 g (1.02 mmol) of N-{[3-(9-chloro-3-methyl-4-oxo(5-hydroisoxazolo[4,3-c]quinolin-5-yl))cycloheptyl]methyl}methoxycarboxamide in $CH_2Cl_2$ (10 mL) was added 0.35 mL of trimethylsilyl iodide(2.1 mmol) and the solution was stirred for 15 hours at ambient temperature. MeOH (1.5 mL) was added and the reaction was stirred for 15 min. before the solvent was removed in vacuo. The residue was dissolved in $CH_2Cl_2$ and rinsed with 1N NaOH followed by 50% brine/water. After drying over $Na_2SO_4$, the solvent was removed to yield 0.397 g of the title compound
MS(ES+)m/z=360.1.

PREPARATION 340 tert-butylamino-pyridin-3-yl-acetic Acid Ethyl Ester

A typical synthesis of bromo-pyridin-3-yl-acetic acid ethyl ester is described: A solution of fresh lithium diisopropylamide (IDA) was prepared at −10° C. from diisopropylamine (8.54 mL; 60.5 mmol) and n-butyllithium (nBuLi) (37.8 mL of a 1.6 M hexanes solution; 12.1 mmol) and stirred for 10 min. After chilling the fresh LDA to −78° C., ethyl 3-pyridylacetate (9.21 mL; 60.5 mmol) was added and the solution was stirred another 10 min. TMSCl (7.68 mL; 60.5 mmol) was added to the resulting opaque yellow slurry and the solution was stirred 5 min. Finally a solution of 4-(dimethylamino) pyridinium tribromide (22.0 g; 60.5 mmol) in tetrahydrofuran was added and the reaction solution was stirred 10 min. After warming to rt. the reaction solution was quenched with saturated $NH_4CL$ (aq) and extracted twice with ethyl acetate. The combined organic layer was washed once with saturated NaCl (aq), dried with $Na_2SO_4$, filtered, and concentrated in vacuo. The resulting bromo-pyridin-3-yl-acetic acid ethyl ester was an unstable brown oil and was therefore used immediately by preparing aliquots of product in dichloromethane and proceeding.

Bromo-pyridin-3-yl-acetic acid ethyl ester (2.4 g; 9.8 mmol) was reacted in refluxing $CH_2Cl_2$, overnight with tert-butylamine (6.2 mL; 55.8 mmol; 6 equiv) and $Et_3N$ (2.8 mL; 19.6 mmol; 2 equiv). The reaction solution was evaporated to dryness, dissolved in $CH_2Cl_2$, washed six times with saturated $NaHCO_3$ (aq), washed once with saturated NaCl (aq), dried with $Na_2SO_4$, filtered, and concentrated in vacuo. The resulting brown oil was purified with silica gel chromatography in a 6×8 cm glass column using a 30% EtOAc/hexanes (v/v) mobile phase. A total of 955 mg desired product was isolated (41% yield). MS(ES) calc'd: $[M+H]+=$ 237.1 m/z. Found: 237.1 m/z.

PREPARATION 341

(2,2-dimethyl-propylamino)-pyridin-3-yl-acetic Acid Ethyl Ester

Bromopyridin-3-yl-acetic acid ethyl ester (2.54 g; 10.2 mmol), prepared in a manner similar to preparation 340, was reacted in refluxing $CH_2Cl_2$, overnight with neopentylamine (4.83 mL; 41.0 mmol; 4 equiv) and $Et_3N$ (5.8 mL; 41.0 mmol; 4 equiv). The reaction solution was evaporated to dryness, dissolved in $CH_2Cl_2$, washed five times with saturated $NaHCO_3$(aq), washed once with saturated NaCl (aq), dried with $Na_2SO_4$, filtered, and concentrated in vacuo. The resulting brown oil was purified with silica gel chromatography in a 3×25 cm glass column using a 0.5% methanol/chloroform (v/v) mobile phase. A second column purification with 100% chloroform followed by 1% methanol/chloroform (v/v) produced pure product as a yellow oil (1.0 g; 40% yield).
MS(ES) calc'd: $[M+M]^+=250.1$ m/z. Found: 250.1 m/z.

PREPARATION 342

Dimethylamino-pyridin-3-yl-acetic Acid Ethyl Ester

Bromopyridin-3-yl-acetic acid ethyl ester (2.54 g; 10.2 mmol) was reacted in a sealed tube, at rt., in $CH_2Cl_2$, overnight with N,N-dimethylamine hydrochloride (3.34 g; 41.0 mmol; 4 equiv) and $Et_3N$ (5.8 mL; 41.0 mmol; 4 equiv). The reaction solution was evaporated to dryness, dissolved in $CH_2Cl_2$, washed five times with saturated $NaHCO_3$ (aq), washed once with saturated NaCl (aq), dried with $Na_2SO4$, filtered, and concentrated in vacuo. The resulting brown oil was purified with silica gel chromatography in a 3×25 cm glass column using a 0.5% methanol/chloroform (v/v) mobile phase. The desired product was isolated as a yellow oil (1.12 g; 53% yield). MS(ES) calc'd: $[M+H]^+=208.1$ m/z. Found: 208.1 m/z.

PREPARATION 343

(4-methyl-piperazin-1-yl)-pyridin-3-yl-acetic Acid Ethyl Ester

Bromo-pyridin-3-yl-acetic acid ethyl ester (2.54 g; 10.2 mmol), was reacted in refluxing dichloromethane, overnight with 1-methylpiperazine (4.54 mL; 41.0 mmol; 4 equiv) and $Et_3N$ (5.8 mL; 41.0 mmol; 4 equiv). The reaction solution was evaporated to dryness, dissolved in $CH_2Cl_2$, washed five times with saturated $NaHCO_3$ (aq), washed once with saturated NaCl (aq), dried with $Na_2SO_4$, filtered, and concentrated in vacuo. The resulting brown oil was purified with silica gel chromatography in a 3×17 cm glass column using a 2% methanol/chloroform (v/v) mobile phase. A second column eluted with 30% EtOAc/hexanes (v/v) followed by a step gradient of 0.5–3% methanol/$CH_2Cl_2$ (v/v) produced the desired product as a yellow oil (756 mg; 28% yield). MS(ES) calc'd: $[M+H]^+=263.1$ m/z. Found: 263.1 m/z.

PREPARATION 344

2-{3-[(t-Butoxy)carbonylamino]cyclohexyl}acetic Acid

A compound from preparation 45 (1.0 g, 2.77 mmol) was dissolved in tetrahydrofuran (4 mL) and ethanol (4 mL) under a dry nitrogen atmosphere at room temperature. This cloudy white solution became clear and colorless after mixing with 2N $NaOH_{(aq)}$ (15 mL; 19.4 mmol, 11.1 equiv) for 2 h. After rotary evaporation to dryness, the white solid was dissolved in water (20 mL) and the resulting solution extracted with diethyl ether (twice). Acidification of the aqueous layer to pH 2 with 1N $HCl_{(aq)}$ produced a white solid that was extracted into ethyl acetate (thrice). The EtOAc was washed with saturated $NaCl_{(aq)}$, dried with $Na_2SO_{4(s)}$, and concentrated to dryness by rotary evaporation. The resulting white solid (700 mg, 98% yield) was used in subsequent reactions without further purification. MS(ES) calc'd: $[M+Na]^+=280.2$ m/z, $[M-H]^-=256.2$ m/z. Found: 280.1 m/z; 256.2 m/z.

PREPARATION 345

N-((1S,3R)-3-{[(phenylmethoxy)carbonylamino]methyl}cyclohexyl)(t-butoxy)carboxamide To a solution of a compound from preparation 344 (3.43 g, 13.35 mmol), $Et_3N$ (3.75 mL, 26.96 mmol) in toluene (86 mL) under $N_2$ was added DPPA (5.8 mL, 26.96 mmol) and benzyl alcohol (4.28 mL, 41.38 mmol). The solution was heated to reflux overnight. The reaction was cooled to rt., diluted with EtOAc, washed (1.0N NaOH then brine), dried ($MgSO_4$), filtered, and concentrated. Column chromatography (silica gel, hexanes/EtOAc gradient) gave the title compound (3.05 g, 63%). Mass Spectrum (ES+) (m/z) 263.1 [M−BOC].

PREPARATION 346

N-(cis-3(S)-Aminocyclohexylmethyl)(phenylmethoxy)carboxamide

A compound from preparation 345 (1.0 g, 2.76 mmol) was treated with TFA (5 mL) under $N_2$. After 20 min of stirring at rt. the reaction was complete. The crude was then concentrated to an oil which was purified on a Varian Bond-Elut SCX column (10 g). The column was eluted consecutively with $CHCl_3$, MeOH, and ammonia (2.0M in MeOH). The pure product was recovered from the ammonia fractions.

The solvent was removed in vacuo to afford 0.632 g (87%) as a colorless oil. MS (ES+) m/z 263.0 (M+H)$^+$.

PREPARATION 347

(3-{[3-(2-Chloro-6-fluoro-phenyl)-5-methyl-isoxazole-4carbonyl]-amino}-cyclohexylmethyl)-carbamic Acid Benzyl Ester To a mechanically stirred solution of crude compound from preparation 346 (20.1 g, 76.6 mmol) and TEA (46.9 g, 459.4 mmol) in 185 ml of dichloromethane was added a compound from preparation 344 (23.1 g, 84.2 mmol) in one portion. The solution warmed slightly and a precipitate began to form. The reaction mixture was stirred at ambient temperature for 19 hours. TLC analysis (20% EtOAc/dichloromethane) showed complete consumption of the starting material. The reaction mixture was diluted with 200 ml of dichloromethane and washed sequentially with 2×200 ml of 1N hydrochloric acid, 2×200 ml of saturated aqueous sodium bicarbonate solution, and 200 ml of half-saturated aqueous NaCl solution. The solution was dried over magnesium sulfate and concentrated to a pale yellow oil, which solidified upon standing. The solid was triturated with 150 ml of diethyl ether, stirred for one hour, filtered, washed with a small amount of diethyl ether, and dried in vacuo at 25° C. to provide 29.3 g (76%) of the title compound as a white solid. $^1$H NMR (300 MHz, CDCl$_3$) 7.48 (m, 1H), 7.35 (m, 6H), 7.17 (dt, J=8.5 Hz, 0.9 Hz, 1H), 5.08 (s, 2H), 4.98 (d, J=7.9 Hz, 1H), 4.72 (m, 1H), 3.73 (m, 1H), 3.01 (m, 2H), 2.76 (s, 3H), 1.90 (m, 1H), 1.67 (m, 3H), 1.52 (m, 1H), 1.28 (m, 1H), 0.69 (m, 2H), 0.43 (q, J=12.0 Hz, 1H).

PREPARATION 348

[3-(9-Chloro-3-methyl-4-oxo-5H-isoxazolo[4,3-c] quinolin-5-yl)-cyclohexylmethyl]-carbamic Acid Benzyl Ester To a mechanically stirred solution of compound from preparation 347 (27.6 g, 55.2 mmol) in 450 ml of DMF was added a 0.5M solution of potassium bis(trimethyl-silyl) amide in toluene (133 ml, 66.3 mmol) over 15 minutes. The resulting purple solution was stirred at ambient temperature for 5 minutes at which time TLC analysis (20% EtOAc/dichloromethane) indicated that all of the starting material had been consumed. The reaction was diluted with 1 L of EtOAc and quenched with 500 ml of water. The two layers were stirred together for 15 minutes and separated. The aqueous layer was extracted twice with 250 ml of EtOAc and the combined organic layers were washed twice with 500 ml of water and once with 500 ml of half-saturated NaCl solution. The solution was dried over magnesium sulfate and concentrated to an orange solid. The solid was slurried in a minimal amount of EtOAc, filtered, washed with a small amount of ethyl acetate, and dried in vacuo to afford 17.9 g of the title compound as an off-white solid. An additional 4.4 grams of the title compound were isolated by flash chromatography of the filtrate. Total yield was 22.3 g (84%). $^1$H NMR (300 MHz, CDCl$_3$) 7.40 (m, 2H), 7.33 (m, 6H), 5.06 (s, 2H), 4.85 (m, 1H), 3.16 (m, 2H), 2.89 (s, 3H), 2.56 (br m, 1H), 2.37 (br m, 1H), 1.98 (m, 1H), 1.81 (m, 5H), 1.46 (m, 1H), 1.07 (m, 1H).

PREPARATION 349

5-(3-Aminomethyl-cyclohexyl)-9-chloro-3-methyl-5H-isoxazolo[4,3-c]quinolin-4-one Hydroiodide To a 0° C. solution of compound from preparation 348 (5.0 g, 10.4 mmol) in dichloromethane (100 mL) was added iodotrimethylsilane (3.6 mL, 25.0 mmol) dropwise, and the solution allowed to warm to room temperature overnight. Methanol (6.1 mL, 150.0 mmol) was added dropwise over two minutes, and the reaction stirred for 30 minutes. The reaction was concentrated and suspended in ethyl ether. After 15 minutes of sonication, the solids were removed by filtration and washed with ethyl ether. The tan powder was dried on a vacuum pump to give 4.61 g of the title compound as the 1.2 HI salt, 89% yield. MS (ion spray) 346 (M$^+$).

PREPARATION 350

(t-Butoxy)-N-[(3-nitrophenyl)methyl]carboxamide

To a suspension of 5.00 g (26.5 mmol) of 3-nitrobenzylamine hydrochloride in 100 mL CH$_2$Cl$_2$ at rt. was added 5.79 g (26.5 mmol) of di-t-butyl dicarbonate. To this was added 8.13 mL (58.3 mmol) of triethylamine, dropwise over 15 min. The reaction was stirred for 3 h at rt., after which it was diluted with 300 mL of EtOAc. The resulting organic solution was washed three times with 1N HCl solution, dried over sodium sulfate and concentrated in vacuo to give 6.2 g (93%) of a white solid, which was characterized as the title compound. MS (FIA) m/z=253.

PREPARATION 351

(t-Butoxy)-N-[(3-aminocyclohexyl)methyl] carboxamide

To a solution containing 12.0 g (47.7 mmol) of a compound from preparation 350 in 300 mL ethanol was added 6.0 g of rhodium on carbon. The reaction was subjected to hydrogenation (60 psi) at 60° C. for 18 h, after with the catalyst was removed by vacuum filtration and the solvent removed in vacuo, giving 9.5 g (87%) of a clear oil. This material was characterized as the title compound and used without further purification. $^1$H—NMR is consistent with structure.

PREPARATION 352

N-(3{[t-Butoxy)carbonylamino]methyl}cyclohexyl) [4-(2-chloro-6-fluorophenyl)-2-methyl(3-furyl)] carboxamide To a solution of 9.5 g (41.6 mmol) of a compound from preparation 351 in 200 mL of CH$_2$Cl$_2$ was added 11.4 g (41.6 mmol) of a compound from preparation 344, followed by 11.6 mL (83.2 mmol) of TEA at rt. The reaction was stirred at room temperature for 15 h, and concentrated in vacuo. The crude solid was dissolved in 200 mL of ethyl acetate and the organic solution was washed twice with 1N HCl solution, dried over sodium sulfate and concentrated in vacuo to give a yellow solid. This material was recrystallized from methanol to give 12.5 g (64%) of a white crystalline solid, which was characterized as the title compound, as an inseparable mixture of cis and trans isomers. MS(FIA) m/z=466.2.

PREPARATION 353

(t-Butoxy)-N-{[3-(9-chloro-3-methyl-4-oxo-5H-isoxazolo[4,3-c]quinolin-5-yl))cyclohexyl] methyl}carboxamide To a stirred solution of 7.00 g (15.0 mmol) of a compound from preparation 352 in 200 mL of DMF at rt. was added 30.0 mL (15 mmol) of a 0.5 M toluene solution of potassium bis(trimethylsilyl) amide over 10 min. The resulting dark red reaction was stirred an additional 5 min at rt. and added to 200 mL of 1N HCl. The two phase solution was diluted with 400 mL of ethyl acetate and the organic layer was separated. The organic solution was washed four times with brine, dried over sodium sulfate and concentrated in vacuo to give an orange solid. This material was recrystallized from toluene to give 3.4 g of a light yellow solid, which was characterized as pure racemic cis material, (a). MS(FIA) m/z=446.1. Purification of the racemic trans material (b) was accomplished by concentrating the mother liquor and subjecting this material to flash chromatography on silica gel, using 50% hexane-EtOAc as the eluent. The major fractions were combined to give a light yellow solid, which was characterized as pure racemic trans material. MS(FIA) m/z= 446.1.

PREPARATION 354

N-{3-(9-chloro-3-methyl-4-oxo-5H-isoxazolo[4,3-c] quinolin-5-yl))cyclohexyl]methyl}(t-butoxy) carboxamide The racemic material of a compound from preparation 353 was separated into its enantiomers by chiral HPLC chromatography using a Chiralpak AD column and 10% ethyl alcohol-heptane as the eluent at a flow of 1.0 mL/min. Retention Time (Enantiomer 1)=10.501 min.
Retention Time (Enantiomer 2)=12.576 min.

PREPARATION 355

N-[3-(aminomethyl)cyclohexyl]-9-chloro-3-methyl-5H-isoxazolo[4,3-c]quinolin-4-one A slurry of a compound from 354 (1.2 g, 2.7 mmol) in 20 mL of acetic acid saturated with hydrochloric acid was stirred for 4 h at rt., then concentrated to dryness. The residue was dissolved in toluene and concentrated to dryness. The residue was slurried in ether/hexanes, concentrated to dryness, and dried under vacuum to yield 750 mg (80%) of the desired mixture of isomers as a tan solid. MS (ion spray) 346.2 (M+1).

PREPARATION 357

1-Methyl-piperidine-3-carboxylic Acid

To a solution of ethyl 1-methylnipecotate, 0.3 mL (1.65 mmol) in 10 mL of dioxane was added a solution of 118 mg (4.95 mmol) of lithium hydroxide in 10 mL of water. The solution was stirred for 1.5 hours at rt. then was acidified to pH=1 with 5N HCl. The mixture was concentrated to dryness and carried on without further purification. IS (MS) 144.1 (M+1).

PREPARATION 358

Piperidine-1,3-dicarboxylic Acid 1-tert-butyl Ester

To a solution of nipecotic acid, 2.0 g (16.0 mmol) in 20 mL of THF and 20 mL of water was added 4.7 g (33.6 mmol) of potassium carbonate and 3.5 g (16.0 mmol) of Boc-anhydride. The resulting solution was stirred overnight at ambient temperature then concentrated to dryness. The residue was dissolved in water, washed with ether and acidified to pH=2 with 5N HCl. The acidic aqueous layer was extracted with 20% isopropanol/chloroform. The combined organics were washed with brine, dried over sodium sulfate, filtered and concentrated to dryness to yield 3.2 g (86%) of the desired mixture of isomers as a white solid. MS (ion spray) 228.2 (M−1).

PREPARATION 359

{[3-(9-Chloro-3-methyl-4-oxo-5H-isoxazolo[4,3-c] quinolin-5-yl)-cyclohexylcarbamyl]-methyl}-carbamic Acid tert-butyl Ester To a solution of a compound from preparation 69, 130 mg (0.28 mmol) in 10 mL of DMF was added 59 mg (0.34 mmol) of N-t-butoxycarbonylglycine, 46 mg (0.34 mmol) of 1-hydroxy-7-azabenzo-triazole, 66 mg (0.34 mmol) of EDC, 5 mg of DMAP and 0.120 mL (0.84 mmol) of Et$_3$N. The reaction mixture was stirred overnight at rt. and was concentrated to dryness. The residue was dissolved in 20% isopropanol/chloroform, washed with saturated NaHCO$_3$, washed with brine, dried over Na$_2$SO$_4$, filtered and concentrated to dryness. The residue was purified by radial chromatography using a MeOH/chloroform gradient and concentrated to dryness. The residue was slurried in ether/hexanes and concentrated to dryness to yield 97 mg (71%) of the desired isomer as a white foam. MS (ion spray) 489.1 (M+).

PREPARATION 360

2-Amino-N-[3-(9-chloro-3-methyl4-oxo-5H-isoxazolo[4,3-c]quinolin-5-yl)-cyclohexyl]-acetamide Hydrochloride A solution of the compound from preparation 359, 49 mg (0.10 mmol) in 10 mL of HCl-saturated acetic acid was stirred 3 hours at rt. then concentrated to dryness. The residue was slurried 3× in toluene and concentrated to dryness. The residue was slurried in ether/hexanes and concentrated to dryness to give a quantitative yield of the desired isomer as a tan foam. MS (ion spray) 389.1 (M+).

PREPARATION 361

2-(Pyridin-3-yloxy)-hexanoic Acid Ethyl Ester

To a solution of ethyl-3-bromohexanoate, 5.0 g (22.4 mmol) in 200 mL of tetrahydrofuran was added 4.6 g (26.9 mmol) of 3-hydroxypyridine sodium salt. The mixture was refluxed for four hours and concentrated to dryness. The residue was partitioned between 20% isopropanol/chloroform and water. The organics were washed with saturated aqueous sodium bicarbonate, washed with brine, dried over sodium sulfate, filtered, and concentrated to dryness. The residue was purified by column chromatography using a methanol/chloroform gradient as eluent and concentrated to dryness to yield 1.82 g (34%) of the desired mixture of isomers as a brown liquid. MS (ion spray) 238.2 (M+1).

PREPARATION 362

2-(Pyridin-3-yloxy)-hexanoic Acid

A solution of lithium hydroxide, 200 mg (8.82 mmol) in 10 mL of water was added to a solution of compound from the preparation 361, 700 mg (2.94 mmol) in 10 mL of dioxane. The resulting solution was stirred at ambient temperature for 3 hours, acidified to pH=1 with 5 N HCl and concentrated to dryness. Crude MS (ion spray) 210.0 (M+1) for desired mix of isomers. Crude product was carried on as is without further purification.

PREPARATION 363

(Pyrimidin-2-yloxy)-acetic Acid Ethyl Ester

To a slurry of sodium hydride (60% dispersion in mineral oil), 280 mg (5.76 mmol) in 10 mL of DMF at 0° C. was added 0.52 mL (4.8 mmol) of ethyl glycolate. After 10 minutes, 0.92 g (5.76 mmol) of 2-bromopyrimidine was added. The reaction mixture was stirred 15 min at 0° C. then ice bath was removed. After four hours, reaction mixture was quenched with methanol and concentrated to dryness. The residue was partitioned between 20% isopropanol/chloroform and water, then extracted with 20% isopropanol/chloroform. The combined organics were washed with saturated aqueous sodium bicarbonate, washed with brine, dried over sodium sulfate, filtered, and concentrated to dryness. The residue was purified by radial chromatography using a methanol/chloroform gradient as eluent and concentrated to dryness to yield 0.45 g (52%) of the desired product as a colorless oil. MS (ion spray) 183.1 (M+1).

PREPARATION 364

(Pyrimidin-2-yloxy)-acetic Acid

A solution of lithium hydroxide, 260 mg (11.0 mmol) in 5 mL of water was added to a solution of 400 mg (2.2 mmol) of compound from preparation 363 in 5 mL of dioxane. The mixture was stirred for four hours at ambient temperature, then was acidified to pH=1 with 5 N HCl and concentrated to dryness. The residue was carried on without further purification. MS (ion spray) 155.1 (M+l).

PREPARATION 365

3-Methyl-5-(2-chloro-6-fluorophenyl)4-isoxazolecarboxylic Acid Ethyl Ester

To a solution of ethyl 3-aminomethyl crotonate (4.79 g, 33.5 mmol) in toluene (10 mL), was added triethylamine (3.73 g, 37 mmol). The solution was chilled using an ice bath, and then 2-chloro-6-fluorobenzoyl chloride (6.47 g, 33.5 mmol) was added dropwise over a 20 min period. The reaction was allowed to warm slowly to r.t., and stirred for 24 hr. The resulting suspension was then filtered, and the filtrate diluted with ethyl acetate (100 mL) and transferred to a separatory funnel. The organic layer was sequentially washed with water, brine, dried (sodium sulfate), and the volatiles removed under reduced pressure to provide 2-(2-chloro-6-fluorobenzoyl)-3-methylamino-but-2-enoic acid ethyl ester (9.46 g) as a golden solid, and primarily one geometrical isomer. MS (ES) m/z 299.9 (M+H)$^+$.

Crude adduct was then redissolved in glacial HOAc (50 mL) to which was added NH$_2$OH.HCl (1.8 g, 1.1 eq). The solution was then heated to reflux for 40–45 min to effect isoxazole formation. The reaction mixture was concentrated to an oil, diluted with ether, and transferred to a sep. funnel. The organic phase was washed with saturated bicarbonate, brine, then dried. Filtration and concentration afforded crude isoxazole ethyl ester (7.5 g), which could be used without further purification. MS (+ES) m/z 283.9 (M+H)$^+$.

PREPARATION 366

4-Isoxazolecarboxylic Acid, 3-Methyl, 5-(2-chloro-6-fluorophenyl)

Hydrolysis of a compound from preparation 365 was accomplished by dissolving the crude ester (7.5 g, approx. 0.027 mol) in THF (250 mL), and adding aq. LiOH (1.344 g in 100 mL, 2 eq) After stirring overnight at r.t., the solution was concentrated to ⅔$^{rd}$ volume, diluted with EtOAc (200 mL) and 50 mL water, transferred to a separatory funnel, and the aqueous phase collected. The organic phase was washed twice, and the combined aqueous phase was then acidified with 5N HCl. Back extraction with three washings of EtOAc was then followed with a brine wash of the combined organics. After drying over Na$_2$SO$_4$, filtration and concentration, clean isoxazole acid was obtained (2.94 g). MS (−ES) m/z 253.8, 255.8 (M−H)$^−$.

PREPARATION 367

5-(2-Chloro-6-fluoro-phenyl)-3-methyl-isoxazole-4-carbonyl Chloride

To a solution of a compound from preparation 366 (60 mg, 0.234 mmol) in benzene (4 mL) containing catalytic amount of pyridine (20 μl) was added oxalyl chloride (23 mL). After heating to reflux for 1 hr, an aliquot was concentrated under vacuum. 1H—NMR (CDCl$_3$) 7.53 (d of t, 1H), 7.37 (d, 1H), 7.17 (t,1 H). (racemic)

PREPARATION 368

1,3-cyclohexanedicarboxylic Acid

To a suspension of isophthalic acid (500 g, 3 mol) in methanol (2.81) was added 5% Rhodium-on-alumina catalyst (50 g) and acetic acid (150 ml). The reaction mixture was shaken under hydrogen (50 psi) at room temperature overnight. The mixture was filtered through celite. To this solution was added fresh 5% Rhodium-on-alumina catalyst (25 g), and the mixture was shaken under 50 psi of hydrogen for another 24 hours. The final reaction mixture was filtered through celite. The solution was concentrated under vacuum to give 493 g of the title compound as a white powder (96.3% yield). m.p. 163–165° C.

PREPARATION 369

3-Oxabicyclo[3.3.1]nonane-2,4-dione

A solution of dicyclohexylcarbodiimide (200 g, 1.16 mol) in CH$_2$Cl$_2$ (1000 ml) was added dropwise to a suspension of compound from preparation 368 (257 g, 1.25 mol) in CH$_2$Cl$_2$ (550 ml), and the mixture was stirred at room temperature for 4 hours. The precipitated dicyclohexylurea was filtered and washed several times with cold CH$_2$Cl$_2$ (200 ml×3). The combined organic layer was concentrated to give a white solid, which was suspended in MTBE (900 ml). This solid was collected by filtration, washed with MTBE (250 ml), and dried under house vacuum to give the title compound (137 g). The filtrate was concentrated to a residue, which was suspended in MTBE (250 ml) to give another 31 g anhydride. The total yield was 168 g (94%). m.p. 138–140° C.

PREPARATION 370 cis-1,3–Cyclohexanedicarboxylic Acid Diethyl Ester

To a solution of compound from preparation 369 (31 g, 0.2 mol) in ethanol (anhydrous, 310 ml) was added p-toluenesulfonic acid monohydrate (1.9 g, 10 mmol, 0.05 equiv.) and triethyl orthoformate (50 ml, 0.3 mol). The reaction mixture was stirred at 60° C. overnight. The volatiles were stripped and the residue was diluted with ethyl acetate (250 ml), washed with water (120 ml) and brine (100 ml), and dried over MgSO$_4$. After filtration and evaporation, the residue was purified by chromatography. Eluting the column with 10% ethyl acetate in hexane afforded the title compound (40 g, 87.7% yield).

$^1$H NMR: (500 MHz, CDCl$_3$) δ 4.11 (q, J=7.0 Hz, 4H), 2.29 (dt, 2H), 2.11 (dd, 1H), 1.97 (m, 211), 1.98 (m, 1 H), 1.53 (q, J=12.5 Hz, 2H), 1.30–1.40 (m, 2H), 1.25 (t, J=7.0 Hz, 6H).

PREPARATION 371

1,3–Cyclohexanedicarboxylic Acid, Monoethyl Ester (1R, 3S)

To a suspension of compound from preparation 370 (40 g, 17.5 mmol) in pH 7.2 phosphate buffer [0.2 M] (1.2 l) was added lipase AY30 (Amano, 16.7 g). The mixture was stirred vigorously at room temperature for 30 hours. The mixture was acidified with 10–15% HCl to pH<2, and extracted with ethyl acetate (500 ml×2). The combined organic solution was washed with aqueous 10% $Na_2CO_3$ (100 ml×2) and water (100 ml×2). The combined aqueous layers were washed again with ethyl acetate (150 ml) and then acidified with 10–15% HCl to pH<2. The acidified aqueous was then extracted with ethyl acetate (150 ml×3). The combined organic solution was dried over $MgSO_4$. After filtration and concentration the title compound (35.6 g, 100% yield) was obtained. $^1$H NMR (500 MHz, $CDCl_3$) δ 4.12 (q, J=7.0 Hz, 2H), 2.20–2.40 (m, 3H), 1.85–2.05 (m, 3H), 1.5 (q, 2H), 1.35 (m, 2 H), 1.24 (t, J=7.0 Hz, 3H), $[α]_D$3.2°, $[α]$+10.4° (c, 0.434; $CHCl_3$). $[α]_D$+3.0°, $[α]_{365}$ +9.6° (c, 0.532; $CH_3OH$).

PREPARATION 372

Ethyl-[3-N-(methylcarbamate)-cyclohexyl]-carboxylate (1R, 3S)

A solution of a compound from preparation 371 (73 g, 365 mmol) in toluene (750 ml) was heated to reflux using a Dean-Stark trap to separate trace amounts of water. After collecting about 10 ml of water, the mixture was cooled down to about 40–50° C. To this mixture was added triethylamine (56 ml, 0.4 mol), and diphenylphosphoryl azide (86.5 ml, 0.4 mol). The reaction mixture was stirred at 110° C. for 60 min, cooled to 70° C., and methanol (64 g, 2 mol ) was added with stirring. After addition, the final reaction mixture was then heated to 85° C. overnight. After cooling to room temperature, the mixture was diluted with ethyl acetate (700 ml) and washed with water (500 ml). The aqueous layer was extracted with ethyl acetate (500 ml×2). The combined organic solution was washed again with water (500 ml) and brine (500 ml). After drying over $MgSO_4$ and concentration under reduced pressure, the title compound was obtained as a colorless oil (86 g, 100%). $^1$H NMR: (300 MHz, $CDCl_3$) δ 4.60 (sb, 1H), 4.13 (q, 2H), 3.65 (s, 3H), 3.50 (sb, 1H), 2.38 (t, 1H), 2.23 (d, 1H), 2.00–1.80 (m, 3H) 1.24 (t, 3H), 1.12–0.95 (m, 1H).

PREPARATION 373

Ethyl-((1R, 3S)-3-{[3-(2-chloro-6-fluorophenyl)-5-methylisoxazol-4-yl]carbonyl-amino}cyclohexyl)-carboxylate To a solution of compound from preparation 372 (86 g, 365 mmol) in $CH_2Cl_2$ (750 ml) was added iodotrimethylsilane (100 g, 500 mmol) in one portion, at room temperature. The reaction mixture was stirred for 2 hours at ambient temperature, cooled to 0–5° C., and methanol (50 ml) was added. After stirring 15 minutes, the solution was concentrated under reduced pressure. The residue was dissolved in THF (1 l). To this solution was added water (0.5 l), potassium carbonate (138 g, 1 mol), and a solution of a compound from preparation 27 (110 g, 0.4 mol) in 250 ml THF, dropwise. After the addition, the reaction mixture was heated to room temperature and stirred for 12 hours. THF was removed under house vacuum, water (250 ml) was added, and the mixture was extracted with ethyl acetate (500 ml×3). The combined organic solution was washed with saturated sodium thiosulfate (150 ml), water (500 ml), brine (500 ml) and then dried over $MgSO_4$. After filtration and evaporation under vacuum, the residue was purified by recrystallization from MTBE (250 ml). Repeating this recrystallization procedure three times provided the title compound (122.7 g, 82.5% yield) as a white powder. M.S. m/z 409 ($M^+$, 100%).

PREPARATION 374

Ethyl [(1R,3S)-3-(9-chloro-3-methyl-4-oxo-5H-isoxazolo[4,3-c]quindin-5-yl)-cyclohexyl]-carboxylate To a solution of compound from preparation 373 (78 g, 190 mmol) in DMF (750 ml) was added a solution of KHMDS ([0.5M], 400 ml, 200 mmol). The temperature was kept at 25° C. by using an ice-bath. After the addition was complete, the reaction mixture was analyzed by TLC (silica gel, 50% EtOAc in hexane) and found to be complete. Water (1 l) was added and the mixture was extracted with EtOAc (800 ml×3). The combined organic solution was washed with 1N HCl (250 ml), water (250 ml), brine (250 ml), dried over $MgSO_4$ and concentrated to give a residue which was purified by recrystallization from MTBE (500 ml) to afford 66 g of the title compound as a light yellow powder (89.0% yield). M.S. m/z 389 ($M^+$+1, 100%).

PREPARATION 375

(1R, 3S) 3-(9-chloro-3-methyl4-oxo-5H-isoxazolo[4,3-c]quinolin-5-yl)-cyclohexyl Carboxylic Acid To a solution of compound from preparation 374 (62 g, 160 mmol) in THF (600 ml) was added 5N aqueous sodium hydroxide (120 ml) at room temperature. The reaction mixture was heated to 60° C. for 15 hours with stirring. After cooling to room temperature, water (750 ml) was added and the mixture was washed with ethyl acetate (500 ml). The aqueous phase was separated and acidified with 15% HCl to pH<2. The aqueous phase was then extracted with methylene chloride (1000 ml×3). The combined organic extracts were washed again with water (500 ml), brine (500 ml), and dried over $MgSO_4$. After filtration and evaporation under vacuum, the dark brown residue was suspended in MTBE (1000 ml), and refrigerated overnight. The mixture was filtered to afford 55.45 g (96.4%) of bright yellow product. M.S. m/e 361 ($M^+$, 50%), 225 (100%).

PREPARATION 376

2-methyl[(1R,3S)-3-(9-chloro-3-methyl4-oxo-5H-isoxazolo[4,3-c]quinolin-5-yl)-cyclohexyl]carbamate To a suspension of compound from preparation 375 (55.4 g, 154 mmol) in toluene (1 l) was added triethylamine (23.7 ml, 170 mmol), and diphenylphosphoryl azide (36.5 ml, 170 mmol). The reaction mixture was stirred at 110° C. for 2 hours during which time a solution formed. The solution was cooled to 80° C. and methanol (25 g, 0.77 mol) was added with stirring. The solution was warmed to 85° C. for 22 hours. After cooling to room temperature, the toluene was removed under reduced pressure and the residue was dissolved in dichloromethane (3 l) and washed with water (1 l). The aqueous phase was extracted with dichloromethane (1 l×2) and the combined organic solution was washed again with water (500 ml) and brine (500 ml). After drying over MgSO$_4$, the solution was concentrated under vacuum. The crude product was purified by crystallization (CH$_2$Cl$_2$/MTBE, 0.5 1/2 l) to afford the title compound (46.6 g, 78.2%). [α]$_D$+49.2°, [α]$_{365}$+263.3° (c, 0.56; CHCl$_3$). The filtrate was concentrated to a residue, which was purified by chromatography to obtain a second crop of product (5.1 g). The total yield was 86.8%. M.S. m/z 476 (M$^+$, 25%).

PREPARATION 377

[3-(3-Acetyl-4-amino-5-chloro-2-oxo-2H-quinolin-1-yl)-cyclohexyl]-carbamic Acid methyl ester A compound from preparation 376 (0.1 g, 0.26 mmol) and Mo(CO)$_6$ (0.13 g, 0.51 mmol) were combined in a solution of acetonitrile (5 mL) and water (1 mL). The reaction mixture was heated to reflux while stirring. After stirring for 2 hr the reaction was complete. A 10% aqueous EDTA solution was added and stirred for an additional 30 minutes. The reaction was then transferred to a separatory funnel and washed with water (5×10 mL). The organic solution was filtered through celite and concentrated to a dark brown solid under vacuum. The solid was diluted in EtOAc and was purified by silica gel column chromatography using 50% EtOAc in Hexanes to elute the product. The solvent was removed in vacuo to afford 0.078 g of desired product as a white solid. MS (ES+) m/z 392.2 (M+H)$^+$, (ES−) 390.2 (M−H)$^-$.

PREPARATION 378

[3-(9-Chloro-3-methyl-4-oxo-5H-isoxazolo[4,5-c] quinolin-5-yl)-cyclohexyl]-carbamic Acid Methyl Ester A solution of a compound from preparation 377 (0.05 g, 0.13 mmol) in acetic acid (5 mL) was treated with hydroxylamine hydrochloride (13 mg, 0.19 mmol). The solution was heated to reflux and stirred 5 hr. The reaction was then diluted in EtOAc (50 mL) and washed with water (3×10 mL), sat'd sodium bicarbonate (3×10 mL), and brine (2×10 mL). The organic was dried over sodium sulfate and the solvent removed. The crude product was purified by silica gel column chromatography using 50% EtOAc in Hexanes to elute the product. The solvent was removed in vacuo to afford 0.028 g (56%) of title compound as a white solid. MS (ES+) m/z 390.1 (M+H)$^+$, (ES−) 388.2 (M−H)$^-$.

PREPARATION 380

5-(3-Amino-cyclohexyl)-9-chloro-3-methyl-5H-isoxazolo[4,5-c]quinolin-4-one

A solution of a compound from preparation 378 (0.38 g, 1.0 mmol) in CH$_2$Cl$_2$ (25 mL) was treated with TMSI (0.29 g, 1.5 mmol). The solution was stirred for 2 hr at room temperature. The solution was then concentrated to a solid and the solid was diluted in EtOAc (100 mL). The organic solution was washed with 1.0 N HCl (5×20 mL) and the aqueous was adjusted to pH~12 with 5.0 N NaOH. The aqueous was then extracted with CH$_2$Cl$_2$ and the solvent was removed to afford 0.26 g (80%) of the title compound as a white solid. MS (ES+) m/z 332.1 (M+H)$^+$.

PREPARATION 390

9-Chloro-3-methyl-5-(3-methylaminomethyl-cyclohexyl)-5H-isoxazolo[4,3-c]quinolin-4-one To a solution of a compound from the preparation 48 (50 mg, 0.12 mmol) in chloroform (0.6 mL) was added trifluoroacetic acid (0.6 mL) and triethylsilane (57 μL, 0.35 mmol) dropwise. The solution was stirred at rt. under nitrogen overnight. The solution was concentrated and dissolved in chloroform (1 mL) and aqueous 1N HCl solution (1 mL). To this mixture was added dichloromethane (10 mL) and saturated sodium bicarbonate solution (10 mL). The layers were separated, and the aqueous layer was extracted with dichloromethane (×3). The combined organic layers were dried over magnesium sulfate and concentrated to give 13.7 mg of the title compound as a brown solid, 32% yield. $^1$H NMR: consistent with structure. MS (ion spray) 360 (M$^+$).

PREPARATION 391

Hydroxy-pyridin-2-yl-acetic Acid Methyl Ester

To a dry flask was added 2-pyridine-carboxaldehyde (14.4 mL, 150 mmol) and zinc iodide (5 mg, 0.02 mmol), followed by dropwise addition of trimethylsilyl cyanide (20.7 mL, 152 mmol) with rapid stirring. The solution was stirred under nitrogen at rt. overnight. The solution was treated with 9N HCl (50 mL, aqueous solution), and stirred under nitrogen at reflux overnight. The solution was partitioned between water and 20% isopropanol/chloroform, and the aqueous layer concentrated to an orange solid. Methanol was added, the mixture was sonicated, and placed in a 0° C.-freezer overnight. Ammonium chloride was removed by filtration (×2), and the solution concentrated. The solution was diluted with water (500 mL), and basified to pH 8 with aqueous 5N NaOH. The aqueous layer was extracted with 20% isopropanol/chloroform (×3), and the organic layers were washed with brine, dried over magnesium sulfate and concentrated to give 14.02 g of yellow solid. The material was sonicated as a suspension in diethyl ether and filtered to remove baseline impurities. Purification by silica gel chromatography (eluting with 0–1% methanol/chloroform) gave 4.10 g of the title compound as a yellow solid, 16% yield. $^1$H NMR: consistent with structure. MS (ion spray) 167 (M$^+$).

PREPARATION 392

(tert-Butyl-dimethyl-silanyloxy)-pyridin-2-yl-acetic Acid Methyl Ester

To a solution of a compound from preparation 391 (4.10 g, 24.5 mmol) in DMF (35 mL) was added imidazole (3.34 g, 49.0 mmol) and t-butyldimethylsilyl chloride (7.39 g, 49.0 mmol). The reaction was stirred at rt. overnight under nitrogen. The reaction was concentrated and dissolved in chloroform, washed with saturated aqueous sodium bicarbonate solution, brine, dried over magnesium sulfate and concentrated. Purification by flash chromatography on silica gel (eluting with 10–20% ethyl acetate/hexane) gave 6.07 g of the title compound as a clear oil, 88% yield. $^1$H NMR: consistent with structure. MS (ion spray) 281 (M$^+$).

PREPARATION 393

Hydroxy-pyridin-3-yl-acetic Acid Methyl Ester

To a dry flask in an ice bath was added 3-pyridine-carboxaldehyde (14.5 mL, 150 mmol) and zinc iodide (5 mg, 0.02 mmol), followed by dropwise addition of trimethylsilyl cyanide (20.7 mL, 152 mmol). The solution was stirred under nitrogen at rt. overnight. The solution was treated with 9N HCl (50 mL, in water), and stirred under nitrogen at reflux overnight. The solution was partitioned between an aqueous 1N HCl solution and chloroform, and the aqueous layer concentrated. Ethanol was added, the mixture was heated to 45° C., and ammonium chloride was removed by filtration, and the solution concentrated. To a 0° C. flask was added methanol (300 mL) followed by dropwise addition of thionyl chloride (40 ml, 548 mmol). After ten minutes, the concentrated reaction mixture was added dropwise as a solution in methanol (300 mL), and the reaction was allowed to warm to rt. overnight. The solution was concentrated, diluted with water (500 mL), and basified to pH 9 with a saturated aqueous sodium bicarbonate solution. The aqueous solution was extracted with 20% isopropanol/chloroform (×5), and the organics dried over magnesium sulfate and concentrated to give 18 g of red oil. Purification by silica gel chromatography (eluting with 0–2% methanol/chloroform) gave 11.51 g of the title compound a yellow oil, 46% yield. $^1$H NMR: consistent with structure. MS (ion spray) 167 ($M^+$).

PREPARATION 394

1-tert-Butoxycarbonylamino-cyclopentanecarboxylic Acid

To a suspension of 1-amino-1-cyclopentane carboxylic acid (4.52 g, 35.0 mmol) in THF (50 mL) and water (50 mL) was added potassium carbonate (14.51 g, 105.0 mmol), di-t-butyl-dicarbonate (7.72,g, 35.4 mmol), and DMAP (5 mg, 0.04 mmol). The reaction was stirred at rt. under nitrogen overnight. The THF was removed in vacuo, and the remaining aqueous solution was acidified to pH 5.5 with an aqueous 5N HCl solution. The aqueous solution was extracted with 20% isopropanol/chloroform (×6), dried over magnesium sulfate, and concentrated to give 1.01 g of the title compound as a white solid, 13% yield. $^1$H NMR: consistent with structure. MS (ion spray) 229 ($M^+$).

PREPARATION 395

(4-Acetyl-piperazin-1-yl)-pyridin-3-yl-acetic Acid Ethyl Ester

N-acetyl-piperazine (3.7 g; 28.8 mmol; 2.8 equiv) was combined with bromo-pyridin-3-yl-acetic acid ethyl ester (approx. 2.5 g; 10 mmol). Purification on a 3×16 cm silica column using a 30% then 40% ethyl acetate/hexanes (v/v) mobile phase followed by a 2% methanol/dichloromethane (v/v) mobile phase resulted in 1.84 g light yellow oil (approx. 60% yield). MS(ES) calc'd: $[M+H]^+$=292.2 m/z; $[M+Na]^+$=314.2 m/z.

Found: 292.1 m/z; 314.1 m/z.

PREPARATION 396

Pyridin-3-yl-(pyridin-2-yloxy)-acetic Acid Ethyl Ester

Sodium hydride (520 mg; 21.8 mmol; 1.4 equiv) was stirred with 2-hydroxypyridine (1.73 g; 18.2 mmol; 1.2 equiv) in DMF (30 mL) for 15 min. This solution was added to an aliquot of bromo-pyridin-3-yl-acetic acid ethyl ester (approx. 3.6 g; 15 mmol) in DMF (20 mL). After stirring overnight, at rt., the resulting opaque black solution was concentrated in vacuo, dissolved in 20% isopropyl alcohol/chloroform, washed 5 times with saturated $NaHCO_{3(aq)}$, washed twice with saturated $NaCl_{(aq)}$, and dried over $Na_2SO_{4(s)}$. After filtration, the solution was concentrated in vacuo and purified by $SiO_2$ column chromatography on two consecutive columns with a 1% methanol/chloroform mobile phase and then an ethyl acetate/hexanes mobile phase (30%, 40%, 50% step gradient). A light yellow oil (134 mg; approx. 3% yield) was isolated. MS(ES) calc'd: $[M+H]^+$=259.2 m/z. Found: 259.1 m/z.

PREPARATION 397

Pyridin-3-yl-(pyridin-3-yloxy)-acetic Acid Ethyl Ester

The product was prepared in a manner similar to preparation 396 using the pre-formed sodium salt of the 3-hydroxypyridine (2.13 g; 18.2 mmol; 1.2 equiv) and an aliquot of bromo-pyridin-3-yl-acetic acid ethyl ester (approx. 3.6 g; 15 mmol) in dimethylformamide (20 mL). Column purification over $SiO_2$ (0.5% then 1.5% methanol/chloroform) produced a yellow/orange oil (2.02; approx. 50% yield). MS(ES) calc'd: $[M+H]^+$=259.2 m/z; $[M-H]^-$= 257.2 m/z. Found: 259.1 m/z; 257.1 m/z.

PREPARATION 398

Pyridin-3-yl-(pyridin-4-yloxy)-acetic Acid Ethyl Ester

The product was formed in a manner similar to preparation 396 using the in situ-generated sodium salt of the 4-hydroxypyridine (2.13 g; 18.2 mmol; 1.2 equiv) and an aliquot of bromo-pyridin-3-yl-acetic acid ethyl ester (approx. 3.6 g; 15 mmol) in DMF (20 mL). Column chromatographic purification over $SiO_2$ (1% methanol/chloroform) produced a yellow/orange oil (320 mg; approx. 8% yield). MS(ES) calc'd: $[M+H]^+$=259.2 m/z. Pound: 259.1 m/z.

PREPARATION 399

5-(3-Amino-cyclohexyl)-9-chloro-3-methyl-2,5-dihydro-pyrazolo[4,3-c]quinolin4-one A solution of a compound from preparation 379 (0.150 g, 0.39 mmol) in $CH_2Cl_2$ (20 mL) was treated with TMSI (0.116 g, 0.58 mmol) and stirred at rt. for 6 hr. The reaction was then treated with MeOH (5 mL) and stirred for an additional 20 min. The solution was concentrated to an oil and then ether was added. The solid was filtered to afford 0.095 g (74%) of the title compound as an orange solid. MS (ES+) m/z 331.2 $(M+H)^+$.

PREPARATION 400

3-(2-Chloro-6-fluoro-phenyl)-3-oxo-2-(triphenyl-15-phosphanyidene)-propionic Acid ethyl ester To a solution of 20.0 g (0.115 mol) of 2-chloro-6-fluorobenzoic acid in 150 mL methylene chloride and 0.50 mL of DMF was added 11.0 mL (0.126 mol) oxalyl chloride, dropwise at rt. over 15 minutes. The reaction was stirred at rt. for one hour and concentrated in vacuo. The resulting acid chloride was redissolved in 50 mL of toluene. In a separate flask, 34.0 mL (0.138 mol) of bis(trimethylsilyl) acetamide was dissolved in 300 mL of toluene. To this was added 40.0 g (0.115 mol) of (carbethoxymethylene)-triphenylphosphorane. The resulting suspension was cooled to 10° C. and stirred as 3-(2-chloro-6-fluorophenyl)-5-methylisoxazole-4carbonyl chloride in 50 mL of toluene was added dropwise. The cold bath was removed and the reaction was allowed to stir at rt. for 18 hours. The mixture was concentrated in vacuo and to the resulting solid was added 50 mL of toluene. The white solid was collected by vacuum filtration to give 49.0 g (84%) of the title compound. MS(ES+) (m/z) 505.1 [M+1].

PREPARATION 401

3-(2-Chloro-6-fluoro-phenyl)-2,3-dioxo-propionic Acid Ethyl Ester

A solution of 25.0 g (49.5 mmol) of the compound from preparation 400 in 125 mL of methylene chloride was cooled to −78° C. Into the cooled solution was passed ozone, prepared using an ozone generator (Griffin Tech. Corp.) and oxygen at 1.8 amps. The ozone was bubbled through the cooled solution using a gas dispersion tube. The reaction was monitored visually, and determined to be completed after 45 minutes, due to the characteristic blue color that is associated with an ozone saturated solution of methylene chloride. The reaction was purged with nitrogen gas and warmed to rt. The organic solution was washed twice with brine, dried over sodium sulfate and concentrated in vacuo. This crude material was purified by flash chromatography (silica gel, 50% hexanes-ethyl acetate) to give 13.0 g (98%) of the title compound as a yellow oil. Anal. Calcd. for $C_{11}H_8O_4FCl$: C, 51.08; H, 3.12. Found: C, 50.67; H, 3.12.

PREPARATION 402

5-(2-Chloro-6-fluoro-phenyl)-3H-imidazole-4-carboxylic Acid Ethyl Ester

A solution containing 6.80 g (26.0 mmol) of a compound from preparation 401 in 50 mL of glacial acetic acid was added to a slurry of 20.3 g (260 mmol) of ammonium acetate in 100 mL of glacial acetic acid. To this mixture was added 3.95 g (130 mmol) of paraformalehyde. The mixture was stirred and heated at 80° C. for one hour and concentrated in vacuo. The resulting crude material was taken up in ethyl acetate and washed with saturated sodium bicarbonate (3×). The organic solution was dried over sodium sulfate and concentrated in vacuo to give an oily yellow solid. This crude material was precipitated out of 50% ethyl acetate-hexane to give 3.35 g (48%) of the title compound as a light yellow amorphous solid. MS (ES+) (m/z) 269.0 [M+1].

PREPARATION 403 & 404

5-(2-Chloro-6-fluorophenyl)-3-methyl-3H-imidazole-4-carboxylic Acid Ethyl Ester (isomer 1)
5-(2-Chloro-6-fluorophenyl)-1-methyl-1H-imidazole-4-carboxylic acid ethyl ester (isomer 2)

To a solution containing 2.90 g (10.8 mmol) of the compound from preparation 402 in 15 mL of DMF was added 2.98 g (21.6 mmol) of solid anhydrous potassium carbonate, followed by 1.34 mL (21.6 mmol) of methyl iodide, with stirring, at rt. The reaction was stirred at rt. for one hour, diluted with 100 mL of ethyl acetate and washed four times with brine. The resulting crude material was purified by flash chromatography (silica gel, hexanes-ethyl acetate gradient) and two main products were separated. The major product contained 1.62 g (53%) and was identified as the title compound (isomer 1). The isomeric minor product, which was identified as the title compound (isomer 2) was found to contain 933 mg (31%).
isomer 1: Mass spectrum (ES+) (m/z) 283.0 [M+1].
Anal. Calcd. for $C_{13}H_{12}N_2O_2FCl$: C, 55.23; H, 4.28; N, 9.91. Found: C, 55.14; H, 4.26; N, 9.75.
isomer 2: Mass spectrum (ES+) (m/z) 283.0 [M+1].
Anal. Calcd. for $C_{13}H_{12}N_2O_2FCl$: C, 55.23; H, 4.28; N, 9.91. Found: C, 55.08; H, 3.96; N, 9.77.

PREPARATION 405

5-(2-Chloro-6-fluoro-phenyl)-3-methyl-3H-imidazole-4-carboxylic Acid

To a solution of 95 mg (0.336 mmol) of a compound from preparation 403. in 5 mL methanol was added 5 mL of 1N sodium hydroxide solution. The reaction was stirred at rt. for 18 hours. The pH of the reaction was adjusted to pH~1 with 1N HCl and this material was concentrated in vacuo by adding 100 mL of toluene to aid in the azeotropic removal of water. The subsequent white solid, which contained the free acid. The crude title compound was used without further purification.

General Procedures, Unless Otherwise Specified a) For Condensation of a Primary Amine with a Carboxylic Acid To "Starting Material A," the primary amine of interest (1 eq.), in anhydrous DMF at 0° C. was added "Starting Material B," the carboxylic acid (3 eq.), collidine (3 eq.) and BOP (3 eq.). The cold bath was removed and after 2 h. The reaction was diluted with EtOAc (25 mL) and saturated $NaHCO_3$ (25 mL). The organic layer was washed with distilled $H_2O$ (2×25 mL), dried over $Na_2SO_4$, and chromatographed on silica gel.

b) For Acylation of Primary Amines

To a solution of "Starting Material A," the primary amine (1 eq.), in dichloromethane was added "Starting Material B," the acylating reagent (1 eq.), triethylamine (1 eq.), and 4-dimethylaminopyridine (10% mol.eq.). The mixture was stirred overnight at ambient temperature and chloroform was added. The solution was washed with 1N hydrochloric acid, saturated sodium bicarbonate, then brine; dried over sodium sulfate, filtered, and the solvent was removed in vacuo. The residue was chromatographed on silica gel to afford the desired compound.

c) For Coupling of Primary Amines and Carboxylic Acids, using 1-(3-(dimethylamino)-propyl)3-ethylcarbodiimide HCl (EDC)

To a solution of "Starting Material A," the carboxylic acid (1 eq.), in N,N-dimethylformamide was added "Starting Material B," the primary amine (1 eq.), along with EDC (1 eq.), 1-hydroxy-7-azabenzotriazole (1 eq.), 4-dimethylaminopyridine (10% mol. eq.), and triethylamine (1 eq.). The mixture was stirred overnight at ambient temperature and concentrated to dryness. The residue was partitioned between 20% isopropanol/chloroform and 1N hydrochloric acid. The mixture was washed with 1N hydrochloric acid, saturated sodium bicarbonate, brine, dried over sodium sulfate, filtered and concentrated to dryness. The residue was chromatographed on silica gel.

d) For Cyclization of 2-((1R,3S)-3-{[3-(2-chloro-6-fluorophenyl)-5-methylisoxazol-4-yl] carbonylamino}cycloalkyl Compounds using Potassium t-butoxide (KOtBu)

A solution of "Starting Material" (1 eq.) and 1 eq. of 1.0 N (in THF) KOtBu in DMF was stirred for 3 hours. The reaction was diluted with ethyl acetate and washed 5 times with water; dried and concentrated in vacuo to a residue, which was chromatographed on silica gel.

e) For Cyclization of 2-(3-}[3-(2-chloro-6-fluorophenyl)-5-methylisoxazol4yl]-carbonylamino}cycloalkly Compounds using potassium bis(trimethylsilyl)amide (KHMDS)

A solution of "Starting Material" (1 eq.) dissolved in dry DMF was stirred and cooled to 0° C. in an ice bath. The reaction was then treated with KHMDS (1.5 eq., 0.5M in THF) and was allowed to warm to room temperature. After 30 minutes the reaction was diluted in EtOAc, transferred to a separatory funnel, and washed consecutively with 1N HCl, saturated sodium bicarbonate, brine and dried over sodium sulfate. The solvent was removed in vacuo and the residue was chromatographed on silica gel to afford the desired compound.

f) For Arylation of a Primary Amine

To a stirred solution of "Starting Material A," the primary amine (1 eq.), in DMF was added $K_2CO_3$ (2 eq.) and "Starting Material B," the arylhalide (3 eq.). The reaction mixture was stirred at 50° C. for 8 hours. It was diluted with ethyl acetate, washed (brine), dried ($Na_2SO_4$), filtered and concentrated. Column chromatography on silica gel for purification was preformed.

g) Enantiomeric Separation of the 1R,3S and 1S,3R isomer Configuration of the cycloalkl Examples The racemic material was separated into its enantiomers by chiral HPLC, using a Chiralpak AD column and 30% isopropyl alcohol-heptane as the eluent at a flow of 1.0 mL/min.

a) Table for condensation using collidine:

| Ex. # | Product | Starting Material A | Starting Material B | Physical Data | Comments |
|---|---|---|---|---|---|
| 1 | cis-1-(9-chloro-3-methyl-4-oxo-5H-isoxazolo[4,3-c]quinolin-5-yl)-3-[(phenylmethylcarbonyl)-amino]cyclohexane | prep 69 | phenylacetic acid | ESIMS m/e 450 $^{35}$Cl (M$^+$ + 1) and 452 $^{37}$Cl (M$^+$ + 1) | |
| 2 | cis-1-(9-chloro-3-methyl-4-oxo-5H-isoxazolo[4,3-c]quinolin-5-yl)-3-[(3-methoxyphenyl)-methyl]carbonyl]amino]cyclohexane | prep 69 | 3-methoxy-phenylacetic acid | ESIMS m/e 480 $^{35}$Cl (M$^+$ + 1) and 482 $^{37}$Cl (M$^+$ + 1) | |
| 3 | cis-1-(9-chloro-3-methyl-4-oxo-5H-isoxazolo[4,3-c]quinolin-5-yl)-3-[(4-fluorophenyl)-methyl]carbonyl]amino]-cyclohexane | prep 69 | 2-(4-fluorophenyl)-acetic acid | ESIMS m/e 468 $^{35}$Cl (M$^+$ + 1) and 470 $^{37}$Cl (M$^+$ + 1) | |
| 4 | cis-1-(9-chloro-3-methyl-4-oxo-5H-isoxazolo[4,3-c]quinolin-5-yl)-3-[(4-methoxyphenyl)methyl]-carbonyl]amino]cyclohexane | prep 69 | 2-(4-methoxyphenyl)-acetic acid | ESIMS m/e 480 $^{35}$Cl (M$^+$ + 1) and 482 $^{37}$Cl (M$^+$ + 1) | |
| 5 | cis-1-(9-chloro-3-methyl-4-oxo-5H-isoxazolo[4,3-c]quinolin-5-yl)-3-[(2-methoxyphenyl)methyl]-carbonyl]amino]cyclohexane | prep 69 | 2-(2-methoxyphenyl)-acetic acid | ESIMS m/e 480 $^{35}$Cl (M$^+$ + 1) and 482 $^{37}$Cl (M$^+$ + 1) | |
| 6 | cis-1-(9-chloro-3-methyl-4-oxo-5H-isoxazolo[4,3-c]quinolin-5-yl)-3-[(2-fluorophenyl)methyl]-carbonyl]amino]cyclohexane | prep 69 | 2-(2-fluorophenyl)-acetic acid | ESIMS m/e 468 $^{35}$Cl (M$^+$ + 1) and 470 $^{37}$Cl (M$^+$ + 1) | |
| 7 | cis-1-(9-chloro-3-methyl-4-oxo-5H-isoxazolo[4,3-c]quinolin-5-yl)-3-[(3-fluorophenyl)methyl]-carbonyl]amino]cyclohexane | prep 69 | 2-(3-fluorophenyl)-acetic acid | ESIMS m/e 502 $^{35}$Cl (M + $^{35}$Cl$^-$) and 504 $^{37}$Cl (M+ $^{35}$Cl$^-$) | |
| 8 | cis-1-(9-chloro-3-methyl-4-oxo-5H-isoxazolo[4,3-c]quinolin-5-yl)-3-[(pyrid-2-yl)methyl]-carbonyl]amino]cyclohexane | prep 69 | 2-(2-pyridyl)acetic acid | ESIMS m/e 451 $^{35}$Cl (M$^+$ + 1) and 453 $^{37}$Cl (M$^+$ + 1) | |
| 9 | cis-1-(9-chloro-3-methyl-4-oxo-5H-isoxazolo[4,3-c]quinolin-5-yl)-3-[(pyrid-3-yl)methyl]-carbonyl]amino]cyclohexane | prep 69 | 2-(3-pyridyl)acetic acid | ESIMS m/e 451 $^{35}$Cl (M$^+$ + 1) and 453 $^{37}$Cl (M$^+$ + 1) | |
| 10 | (1S,3R)-1-(9-chloro-3-methyl-4-oxo-5H-isoxazolo[4,3-c]-quinolin-5-yl)-3-[[(2S)-2-[[(1,1-dimethylethyl)oxy)-carbonyl]-amino]-2-(pheny)acetyl]amino]-cyclohexane | prep 68 | (2S)-2-[(t-butoxy)-carbonylamino]-2-phenylacetic acid | ESIMS m/e 565 $^{35}$Cl (M$^+$ + 1) and 567 $^{37}$Cl (M$^+$ + 1) | |

-continued

| Ex. # | Product | Starting Material A | Starting Material B | Physical Data | Comments |
|---|---|---|---|---|---|
| 11 | (1R,3S)-1-(9-chloro-3-methyl-4-oxo-5H-isoxazolo[4,3-c]quinolin-5-yl)-3-[[(2R)-2-[[-(1,1-dimethylethyloxy)carbonyl]-amino]-2-(phenyl)acetyl]amino]-cyclohexane | prep 69 | (2R)-2-[(t-butoxy)-carbonylamino]-2-phenylacetic acid | ESIMS m/e 565 $^{35}$Cl (M$^+$ + 1) and 567 $^{37}$Cl (M$^+$ + 1) | |
| 12 | (1R,3S)-1-(9-chloro-3-methyl-4-oxo-5H-isoxazolo[4,3-c]-quinolin-5-yl)-3-[[(2S)-2-[[(1,1-dimethylethyloxy)-carbonyl]-amino]-2-(phenyl)acetyl]amino]-cyclohexane | prep 69 | (2S)-2-[(t-butoxy)-carbonylamino]-2-phenylacetic acid | ESIMS m/e 565 $^{35}$Cl (M$^+$ + 1) and 567 $^{37}$Cl (M$^+$ + 1) | |
| 13 | (1S,3R)-1-(9-chloro-3-methyl-4-oxo-5H-isoxazolo[4,3-c]-quinolin-5-yl)-3-[[(2R)-2-[[(1,1-dimethylethyloxy)-carbonyl]-amino]-2-(phenyl)acetyl]amino]-cyclohexane | prep 68 | (2R)-2-[(t-butoxy)-carbonylamino]-2-phenylacetic acid | ESIMS m/e 565 $^{35}$Cl (M$^+$ + 1) and 567 $^{37}$Cl (M$^+$ + 1) | | b) Table for Acylation:

| Ex. # | Product | Starting Material A | Starting Material B | Physical Data | Comments |
|---|---|---|---|---|---|
| 14 | N-[[(1S,3R)-3-(9-chloro-3-methyl-4-oxo-5H-isoxazolo[4,3-c]quinolin-5-yl)cyclohexyl]methyl]-cyclohexylcarboxamide | prep 44 | cyclohexylcarbonyl chloride | MS (ion spray) 456.2 (M + 1) | |
| 15 | N-[(1S,3R)-3-(9-chloro-3-methyl-4-oxo-5H-isoxazolo[4,3-c]-quinolin-5-yl)cyclohexylmethyl](4-phenylphenyl)-carboxamide | prep 44 | biphenylcarbonyl chloride | MS (ion spray) 526.2 (M+) | |
| 16 | N-[(1S,3R)-3-(9-Chloro-3-methyl-4-oxo-5H-isoxazolo[4,3-c]quinolin-5-yl)cyclohexyl-methyl]acetamide | prep 44 | acetic anhydride | MS (ion spray) 388 (M + 1) | |
| 17 | N-[(1S,3R)-3-(9-Chloro-3-methyl-4-oxo-5H-isoxazolo[4,3-c]quinolin-5-yl)cyclohexyl-methyl]methanesulfonamide | prep 44 | methanesulfonyl chloride | MS (ion spray) 424.0 (M + 1) | |
| 18 | N-[(1S,3R)-3-(9-chloro-3-methyl-4-oxo-5H-isoxazolo[4,3-c]quinolin-5-yl)cyclohexyl-methyl]methoxycarboxamide | prep 44 | methyl chloroformate | MS (ion spray) 404.0 (M + 1) | |
| 19 | N-[(1R,3S)-3-(methylaminothioxo-methylamino-methyl)cyclohexyl]-9-chloro-3-methyl-5H-iso-xazolo[4,3-c]quinolin-4-one | prep 44 | methyl isothiocyanate | MS (ion spray) 419.0 (M + 1) | |

| Ex. # | Product | Starting Material A | Starting Material B | Physical Data | Comments |
|---|---|---|---|---|---|
| 20 | N-[(1S,3R)-3-(9-Chloro-3-methyl-4-oxo-5H-isoxazolo[4,3-c]quinolin-5-yl)cyclohexyl-methyl]-2-methylpropanamide | prep 44 | isobutyryl chloride | MS (ion spray) 416.1 (M + 1) | |
| 21 | N-[(1S,3R)-3-(9-Chloro-3-methyl-4-oxo-5H-isoxazolo[4,3-c]quinolin-5-yl)cyclohexyl-methyl]-3-methylthiopropanamide | prep 44 | 3-methylthiopro-pionyl chloride | MS (ion spray) 448.1 (M + 1) | |
| 22 | N-[(1S,3R)-3-(9-chloro-3-methyl-4-oxo-5H-isoxazolo[4,3-c]quinolin-5-yl)cyclohexyl-methyl]pentanamide | prep 44 | valeryl chloride | MS (ion spray) 430.2 (M + 1) | |
| 23 | N-[(1S,3R)-3-(9-chloro-3-methyl-4-oxo-5H-isoxazolo[4,3-c]quinolin-5-yl)cyclohexyl-methyl]-2-phenylacetamide | prep 44 | phenacetyl chloride | MS (ion spray) 463.9 (M + 1) | |
| 24 | N-[(1S,3R)-3-(9-chloro-3-methyl-4-oxo-5H-isoxazolo[4,3-c]quinolin-5-yl)cyclohexyl-methyl]-3-phenylpropanamide | prep 44 | hydrocinnamoyl chloride | MS (ion spray) 478.1 (M + 1) | |
| 25 | 2-[(1R,3S)-3-(9-Chloro-3-methyl-4-oxo-5H-isoxazolo[4,3-c]quinolin-5-yl)-cyclohexyl]-N-pyridin-3-ylacetamide | 3-aminopyridine | prep 47 | MS (ion spray) 451 (M + 1) | prep. 47 was converted to the acid chloride using oxalyl chloride in DCM |
| 26 | 2-[(1R,3S)-3-(9-Chloro-3-methyl-4-oxo-5H-isoxazolo[4,3-c]quinolin-5-yl)-cyclohexyl]-N-pyridin-4-ylacetamide | 4-aminopyridine | prep 47 | MS (ion spray) 451.2(M + 1) | prep. 47 was converted to the acid chloride using oxalyl chloride in DCM |
| 27 | 2-[(1R,3S)-3-(9-Chloro-3-methyl-4-oxo-5H-isoxazolo[4,3-c]quinolin-5-yl)-cyclohexyl]-N-thiazol-2-ylacetamide | 2-aminothiazol | prep 47 | MS (ion spray) 457.1 (M + 1) | prep. 47 was converted to the acid chloride using oxalyl chloride in DCM |
| 28 | 2-[(1R,3S)-3-(9-Chloro-3-methyl-4-oxo-5H-isoxazolo[4,3-c]quinolin-5-yl)-cyclohexyl]-N-(3-hydroxyphenyl)acetamide | 3-aminophenol | prep 47 | MS (ion spray) 466.2 (M + 1) | prep. 47 was converted to the acid chloride using oxalyl chloride in DCM |
| 29 | N-[(1R,3S)-3-(9-Chloro-3-methyl-4-oxo-5H-isoxazolo[4,3-c]quinolin-5-yl)cyclohexyl-methyl]acetamide | prep 48 | acetic anhydride | MS (ion spray) 388 (M + 1) | |

| Ex. # | Product | Starting Material A | Starting Material B | Physical Data | Comments |
|---|---|---|---|---|---|
| 30 | N-[(1R,3S)-3-(9-chloro-3-methyl-4-oxo-5H-isoxazolo[4,3-c]-quinolin-5-yl)-cyclohexyl-methyl]-2,2-dimethyl)propionamide | prep 48 | pivaloyl chloride | MS (ion spray) 430.1 (M + 1) | |
| 31 | N-[(1R,3S)-3-(9-chloro-3-methyl-4-oxo-5H-isoxazolo[4,3-c]quinolin-5-yl)-cyclohexyl-methyl]-cyclobutyl carboxamide | prep 48 | cyclobutylcar-bonyl chloride | MS (ion spray) 428 (M + 1) | |
| 32 | [(1R,3S)-3-(9-chloro-3-methyl-4-oxo-5H-isoxazolo[4,3-c]-quinolin-5-yl)-cyclohexyl-methyl]-isoxazol-5-yl carboxamide | prep 48 | isoxazolecar-bonyl chloride | MS (ion spray) 441.1 (M + 1) | |
| 33 | 5-((1S,3R)-3-{[(Methylsulfonyl)-amino]-methyl}-9-chloro-3-methyl-4-oxo-5H-isoxazolo[4,3-c]quinolin-4-one | prep 48 | methane-sulfonyl chloride | MS (ion spray) 424.1 (M + 1) | |
| 34 | 5-((1S,3R)-3-{[(Phenylsulfonyl)-amino]-methyl}-9-chloro-3-methyl-4-oxo-5H-isoxazolo[4,3-c]quinolin-4-one | prep 48 | benzenesulfonyl chloride | MS (ion spray) 486.4 (M + 1) | |
| 35 | [(1R,3S)-3-(9-Chloro-3-methyl-4-oxo-5H-isoxazolo[4,3-c]-quinolin-5-yl)cyclohexyl-methyl]phenoxycarboxamide | prep 48 | phenyl chloroformate | MS (ion spray) 466.2 (M + 1) | |
| 36 | [(1R,3S)-3-(9-Chloro-3-methyl-4-oxo-5H-isoxazolo[4,3-c]-quinolin-5-yl)cyclohexyl-methyl](phenyl-amino)-carboxamide | prep 48 | phenyli-socyanate | MS (ion spray) 464.9 (M+) | |
| 37 | 5-[(1S,3R)-3-(Phenylaminothiomethylamino-methyl)cyclohexyl]-9-chloro-3-methyl-4-oxo-5H-isoxazolo[4,3-c]-quinolin-4-one | prep 48 | phenylthioiso-cyanate | MS (ion spray) 48 1.02 (M + 1) | |
| 38 | [(1R,3S)-3-(9-chloro-3-methyl-4-oxo-5H-isoxazolo[4,3-c]-quinolin-5-yl)-cyclohexyl-methyl]morpholin-4-yl carboxamide | prep 48 | morpholine carbonyl chloride | MS (ion spray) 459.2 (M + 1) | |
| 39 | [(1R,3S)-3-(9-chloro-3-methyl-4-oxo-5H-isoxazolo[4,3-c]-quinolin-5-yl)-cyclohexyl-methyl]cyclohexyl carboxamide | prep 48 | cyclohexyl-carbonyl chloride | MS (ion spray) 456.3 (M + 1) | |
| 40 | [(1R,3S)-3-(9-chloro-3-methyl- | prep 48 | picolinoyl | MS (ion spray) | |

-continued

| Ex. # | Product | Starting Material A | Starting Material B | Physical Data | Comments |
|---|---|---|---|---|---|
| | 4-oxo-5H-isoxazolo[4,3-c]-quinolin-5-yl)cyclohexyl-methyl]pyridin-2-yl carboxamide | | chloride HCl | 450.9 (M + 1) | |
| 41 | N-[(1R,3S)-3-(9-chloro-3-methyl-4-oxo-5H-isoxazolo[4,3-c]quinolin-5-yl)cyclohexyl-methyl]nicotinamide | prep 48 | nicotinoyl chloride HCl | MS (ion spray) 451.1 (M + 1) | |
| 42 | N-[(1R,3S)-3-(9-Chloro-3-methyl-4-oxo-5H-isoxazolo[4,3-c]quinolin-5-yl)cyclohexyl-methyl]isonicotinamide | prep 48 | isonicotinoyl chloride HCl | MS (ion spray) 451.1 (M + 1) | |
| 43 | N-[3-(9-Chloro-3-methyl-4-oxo-5H-isoxazolo[4,3-c]-quinolin-5-yl)cyclohexyl-methyl]benzamide | prep 54 | benzoyl chloride | MS(FIA) m/z = 450 | prep. 54 was converted to the primary amine using TFA in DCM |
| 44 | N-[3-(9-Chloro-3-methyl-4-oxo-5H-isoxazolo[4,3-c]-quinolin-5-yl)cyclohexylmethyl]-3,4,5-trimethoxybenzamide | prep 54 | 3,4,5-Tri-methoxybenzoyl chloride | MS(FIA) m/z = 540.4 | prep. 54 was converted to the primary amine using TFA in DCM |
| 45 | N-[3-(9-Chloro-3-methyl-4-oxo-5H-isoxazolo[4,3-c]-quinolin-5-yl)cyclohexylmethyl]-4-methoxy-benzamide | prep 54 | 4-Methoxy-benzoyl chloride | MS(FIA) m/z = 480.1 | prep. 54 was converted to the primary amine using TFA in DCM |
| 46 | N-[3-(9-Chloro-3-methyl-4-oxo-5H-isoxazolo[4,3-c]-quinolin-5-yl)cyclohexylmethyl]-3-methoxy-benzamide | prep 54 | 3-Methoxy benzoyl chloride | MS(FIA) m/z = 480.2 | prep. 54 was converted to the primary amine using TFA in DCM |
| 47 | N-[3-(9-Chloro-3-methyl-4-oxo-5H-isoxazolo[4,3-c]-quinolin-5-yl)cyclohexylmethyl]-4-nitrobenzamide | prep 54 | 4-Nitrobenzoyl chloride | MS(FIA) m/z = 493.2 | prep. 54 was converted to the primary amine using TFA in DCM |
| 48 | N-[3-(9-Chloro-3-methyl-4-oxo-5H-isoxazolo[4,3-c]-quinolin-5-yl)cyclohexyl-methyl]-3-nitrobenzamide | prep 54 | 3-Nitrobenzoyl chloride | MS(FIA) m/z = 495.1 | prep. 54 was converted to the primary amine using TFA in DCM |
| 49 | N-[3-(9-Chloro-3-methyl-4-oxo-5H-isoxazolo[4,3-c]-quinolin-5-yl)cyclohexylmethyl]-4-carbomethoxybenzamide | prep 54 | methyl 4-(chlorocarbon-yl)benzoate | MS(FIA) m/z = 508.2 | prep 54 was converted to the primary amine using TFA in DCM |
| 50 | N-[3-(9-Chloro-3-methyl-4-oxo-5H-isoxazolo[4,3-c]-quinolin-5-yl)cyclohexylmethyl]- | prep 54 | methyl 3-(chlorocarbon-yl)benzoate | MS(FIA) m/z = 508.2 | prep 54 was converted to the primary |

-continued

| Ex. # | Product | Starting Material A | Starting Material B | Physical Data | Comments |
|---|---|---|---|---|---|
|  | 3-carbomethoxybenzamide |  |  |  | amine using TFA in DCM |
| 51 | N-[3-(9-Chloro-3-methyl-4-oxo-5H-isoxazolo[4,3-c]quinolin-5-yl)cyclohexylmethyl]-3-carboxybenzamide | Ex 49 |  | MS(FIA) m/z = 492.2 | prepared by basic hydrolysis |
| 52 | N-[3-(9-Chloro-3-methyl-4-oxo-5H-isoxazolo[4,3-c]quinolin-5-yl)cyclohexylmethyl]-3-carboxybenzamide | Ex 50 |  | MS(FIA) m/z = 492.2 | prepared by basic hydrolysis |
| 53 | N-[3S-(9-Chloro-3-methyl-4-oxo-5H-isoxazolo[4,3-c]quinolin-5-yl)-R-cyclohexylmethyl]-benzamide | prep 54 | Benzoyl chloride | MS(FIA) m/z = 450 | prep. 54 was converted to the primary amine using TFA in DCM |
| 54 | N-[3S-(9-Chloro-3-methyl-4-oxo-5H-isoxazolo[4,3-c]quinolin-5-yl)-R-cyclohexylmethyl]-2-methoxybenzamide | prep 54 | 2-Methoxy-benzoyl chloride | MS(FIA) m/z = 480.1 | prep. 54 was converted to the primary amine using TFA in DCM |
| 55 | N-[3S-(9-Chloro-3-methyl-4-oxo-5H-isoxazolo[4,3-c]quinolin-5-yl)-R-cyclohexylmethyl]-3-methoxybenzamide | prep 54 | 3-Methoxy-benzoyl chloride | MS(FIA) m/z = 480.2 | prep. 54 was converted to the primary amine using TFA in DCM |
| 56 | N-[3S-(9-Chloro-3-methyl-4-oxo-5H-isoxazolo[4,3-c]quinolin-5-yl)-R-cyclohexylmethyl]-4-methoxybenzamide | prep 54 | 4-Methoxy-benzoyl chloride | MS(FIA) m/z = 480.1 | prep. 54 was converted to the primary amine using TFA in DCM |
| 57 | N-[3S-(9-Chloro-3-methyl-4-oxo-5H-isoxazolo[4,3-c]quinolin-5-yl)-R-cyclohexylmethyl]-3-ethoxybenzamide | prep 54 | 3-Ethoxy-benzoyl chloride | MS(FIA) m/z = 494.3 | prep. 54 was converted to the primary amine using TFA in DCM |
| 58 | N-[3S-(9-Chloro-3-methyl-4-oxo-5H-isoxazolo[4,3-c]quinolin-5-yl)-R-cyclohexylmethyl]-4-trifluoromethoxybenzamide | prep 54 | 4-Trifluoro-methoxybenzoyl chloride | MS(FIA) m/z = 534.2 | prep. 54 was converted to the primary amine using TFA in DCM |
| 59 | N-[3S-(9-Chloro-3-methyl-4-oxo-5H-isoxazolo[4,3-c]quinolin-5-yl)-R-cyclohexylmethyl]-4-ethoxybenzamide | prep 54 | 4-Ethoxybenzoyl chloride | MS(FIA) m/z = 494.3 | prep. 54 was converted to the primary amine using TFA in DCM |
| 60 | N-[3S-(9-Chloro-3-methyl-4-oxo-5H-isoxazolo[4,3-c]quinolin-5-yl)-R-cyclohexylmethyl]-3,4-dimethoxybenzamide | prep 54 | 3,4-Dimethoxy-benzoyl chloride | MS(FIA) m/z = 570.3 | prep. 54 was converted to the primary amine using |

| Ex. # | Product | Starting Material A | Starting Material B | Physical Data | Comments |
|---|---|---|---|---|---|
| 61 | N-[3S-(9-Chloro-3-methyl-4-oxo-5H-isoxazolo[4,3-c]quinolin-5-yl)-R-cyclohexylmethyl]-3,4-methylenedioxybenzamide | prep 54 | 3,4-methylenedioxybenzoyl chloride | MS(FIA) m/z = 494.2 | prep. 54 was converted to the primary amine using TFA in DCM |
| 62 | N-[3S-(9-Chloro-3-methyl-4-oxo-5H-isoxazolo[4,3-c]quinolin-5-yl)-R-cyclohexylmethyl]-2-fluorobenzamide | prep 54 | 2-Fluorobenzoyl chloride | MS(FIA) m/z = 468.2 | prep. 54 was converted to the primary amine using TFA in DCM |
| 63 | N-[3S-(9-Chloro-3-methyl-4-oxo-5H-isoxazolo[4,3-c]quinolin-5-yl)-R-cyclohexylmethyl]-3-fluorobenzamide | prep 54 | 3-Fluorobenzoyl chloride | MS(FIA) m/z = 468.2 | prep. 54 was converted to the primary amine using TFA in DCM |
| 64 | N-[3S-(9-Chloro-3-methyl-4-oxo-5H-isoxazolo[4,3-c]quinolin-5-yl)-R-cyclohexylmethyl]-4-fluorobenzamide | prep 54 | 4-Fluorobenzoyl chloride | MS(FIA) m/z = 468.2 | prep. 54 was converted to the primary amine using TFA in DCM |
| 65 | N-[3S-(9-Chloro-3-methyl-4-oxo-5H-isoxazolo[4,3-c]quinolin-5-yl)-R-cyclohexylmethyl]-2,3-difluorobenzamide | prep 54 | 2,3-Difluorobenzoyl chloride | MS(FIA) m/z = 486.4 | prep. 54 was converted to the primary amine using TFA in DCM |
| 66 | N-[3S-(9-Chloro-3-methyl-4-oxo-5H-isoxazolo[4,3-c]quinolin-5-yl)-R-cyclohexylmethyl]-2,4-difluorobenzamide | prep 54 | 2,4-Difluorobenzoyl chloride | MS(FIA) m/z = 486.5 | prep. 54 was converted to the primary amine using TFA in DCM |
| 67 | N-[3S-(9-Chloro-3-methyl-4-oxo-5H-isoxazolo[4,3-c]quinolin-5-yl)-R-cyclohexylmethyl]-2,5-difluorobenzamide | prep 54 | 2,5-Difluorobenzoyl chloride | MS(FIA) m/z = 486.4 | prep. 54 was converted to the primary amine using TFA in DCM |
| 68 | N-[3S-(9-Chloro-3-methyl-4-oxo-5H-isoxazolo[4,3-c]quinolin-5-yl)-R-cyclohexylmethyl]-2,6-difluorobenzamide | prep 54 | 2,6-Difluorobenzoyl chloride | MS(FIA) m/z = 486.6 | prep. 54 was converted to the primary amine using TFA in DCM |
| 69 | N-[3S-(9-Chloro-3-methyl-4-oxo-5H-isoxazolo[4,3-c]quinolin-5-yl)-R-cyclohexylmethyl]-3,4-difluorobenzamide | prep 54 | 3,4-Difluorobenzoyl chloride | MS(HA) m/z = 486.4 | prep. 54 was converted to the primary amine using TFA in DCM |
| 70 | N-[3S-(9-Chloro-3-methyl-4-oxo-5H-isoxazolo[4,3-c]quinolin-5-yl)-R-cyclohexylmethyl]-3,5-difluorobenzamide | prep 54 | 3,5-Difluorobenzoyl chloride | MS(FIA) m/z = 486.4 | prep. 54 was converted to |

| Ex. # | Product | Starting Material A | Starting Material B | Physical Data | Comments |
|---|---|---|---|---|---|
| | 5-yl)-R-cyclohexylmethyl]-3,5-difluorobenzamide | | chloride | | the primary amine using TFA in DCM |
| 71 | N-[3S-(9-Chloro-3-methyl-4-oxo-5H-isoxazolo[4,3-c]quinolin-5-yl)-R-cyclohexylmethyl]-3,4,5-trifluorobenzamide | prep 54 | 3,4,5-Trifluorobenzoyl chloride | MS(ES+) m/z = 504.1 | prep. 54 was converted to the primary amine using TFA in DCM |
| 72 | N-[3S-(9-Chloro-3-methyl-4-oxo-5H-isoxazolo[4,3-c]quinolin-5-yl)-R-cyclohexylmethyl]-2-chlorobenzamide | prep 54 | 2-Chlorobenzoyl chloride | MS(FIA) m/z = 484.4 | prep. 54 was converted to the primary amine using TFA in DCM |
| 73 | N-[3S-(9-Chloro-3-methyl-4-oxo-5H-isoxazolo[4,3-c]quinolin-5-yl)-R-cyclohexylmethyl]-3-chlorobenzamide | prep 54 | 3-Chlorobenzoyl chloride | MS(FIA) m/z = 484.4 | prep. 54 was converted to the primary amine using TFA in DCM |
| 74 | N-[3S-(9-Chloro-3-methyl-4-oxo-5H-isoxazolo[4,3-c]quinolin-5-yl)-R-cyclohexylmethyl]-4-chlorobenzamide | prep 54 | 4-Chlorobenzoyl chloride | MS(FIA)m/z = 484.4 | prep. 54 was converted to the primary amine using TFA in DCM |
| 75 | N-[3S-(9-Chloro-3-methyl-4-oxo-5H-isoxazolo[4,3-c]quinolin-5-yl-R-cyclohexylmethyl]-3-bromobenzamide | prep 54 | 3-Bromobenzoyl chloride | MS(FIA) m/z = 530.0 | prep. 54 was converted to the primary amine using TFA in DCM |
| 76 | N-[3S-(9-Chloro-3-methyl-4-oxo-5H-isoxazolo[4,3-c]quinolin-5-yl)-R-cyclohexylmethyl]-4-bromobenzamide | prep 54 | 4-Bromobenzoyl chloride | MS(FIA) m/z = 530.0 | prep. 54 was converted to the primary amine using TFA in DCM |
| 77 | N-[3S-(9-Chloro-3-methyl-4-oxo-5H-isoxazolo[4,3-c]quinolin-5-yl)-R-cyclohexylmethyl]-4-iodobenzamide | prep 54 | 4-Iodobenzoyl chloride | MS(FIA) m/z = 576.1 | prep. 54 was converted to the primary amine using TFA in DCM |
| 78 | N-[3S-(9-Chloro-3-methyl-4-oxo-5H-isoxazolo[4,3-c]quinolin-5-yl)-R-cyclohexylmethyl]-2-methylbenzamide | prep 54 | 2-Methylbenzoyl chloride | MS(FIA) m/z = 464.2 | prep. 54 was converted to the primary amine using TFA in DCM |
| 79 | N-[3S-(9-Chloro-3-methyl-4-oxo-5H-isoxazolo[4,3-c]quinolin-5-yl)-R-cyclohexylmethyl]-3-methylbenzamide | prep 54 | 3-Methylbenzoyl chloride | MS(FIA) m/z = 464.2 | prep. 54 was converted to the primary amine using TFA in DCM |

| Ex. # | Product | Starting Material A | Starting Material B | Physical Data | Comments |
|---|---|---|---|---|---|
| 80 | N-[3S-(9-Chloro-3-methyl-4-oxo-5H-isoxazolo[4,3-c]quinolin-5-yl)-R-cyclohexylmethyl]-4-methylbenzamide | prep 54 | 4-Methylbenzoyl chloride | MS(FIA) m/z = 464.2 | prep. 54 was converted to the primary amine using TFA in DCM |
| 81 | N-[3S-(9-Chloro-3-methyl-4-oxo-5H-isoxazolo[4,3-c]quinolin-5-yl)-R-cyclohexylmethyl]-3-trifluoromethylbenzamide | prep 54 | 3-Trifluoromethylbenzoyl chloride | MS(FIA) m/z = 518.2 | prep. 54 was converted to the primary amine using TFA in DCM |
| 82 | N-[3S-(9-Chloro-3-methyl-4-oxo-5H-isoxazolo[4,3-c]quinolin-5-yl)-R-cyclohexylmethyl]-4-trifluoromethylbenzamide | prep 54 | 4-Trifluoromethylbenzoyl chloride | MS(FIA) m/z = 518.2 | prep. 54 was converted to the primary amine using TFA in DCM |
| 83 | N-[3S-(9-Chloro-3-methyl-4-oxo-5H-isoxazolo[4,3-c]quinolin-5-yl)-R-cyclohexylmethyl]-4-phenylbenzamide | prep 54 | 4-phenylbenzoyl chloride | MS(ES+) m/z = 526.0 | prep. 54 was converted to the primary amine using TFA in DCM |
| 84 | N-[3S-(9-Chloro-3-methyl-4-oxo-5H-isoxazolo[4,3-c]quinolin-5-yl)-R-cyclohexylmethyl]-4-t-butylbenzamide | prep 54 | 4-t-Butylbenzoyl chloride | MS(FIA) m/z = 506.2 | prep. 54 was converted to the primary amine using TFA in DCM |
| 85 | N-[3S-(9-Chloro-3-methyl-4-oxo-5H-isoxazolo[4,3-c]quinolin-5-yl)-R-cyclohexylmethyl]-4-cyanobenzamide | prep 54 | 4-Cyanobenzoyl chloride | MS(ES+) m/z = 474.9 | prep. 54 was converted to the primary amine using TFA in DCM |
| 86 | N-[3S-(9-Chloro-3-methyl-4-oxo-5H-isoxazolo[4,3-c]quinolin-5-yl)-R-cyclohexylmethyl]-2,6-dimethylbenzamide | prep 54 | 2,6-Dimethylbenzoyl chloride | MS(FIA) m/z = 478.2 | prep. 54 was converted to the primary amine using TFA in DCM |
| 87 | N-[3S-(9-Chloro-3-methyl-4-oxo-5H-isoxazolo[4,3-c]quinolin-5-yl)-R-cyclohexylmethyl]-3-dimethylaminobenzamide | prep 54 | 3-Dimethylamino benzoyl chloride | MS(FD) m/z = 492.2 | prep. 54 was converted to the primary amine using TFAinDCM |
| 88 | N-[3S-(9-Chloro-3-methyl-4-oxo-5H-isoxazolo[4,3-c]quinolin-5-yl)-R-cyclohexylmethyl]-4-dimethylaminobenzamide | prep 54 | 4-Dimethylamihobenzoyl chloride | MS(FIA) m/z = 493.2 | prep. 54 was converted to the primary amine using TFA in DCM |
| 89 | N-[3S-(9-Chloro-3-methyl-4-oxo-5H-isoxazolo[4,3-c]quinolin-5-yl)-R-cyclohexylmethyl]-1-naphthylcarboxamide | prep 54 | naphthalene-1-carbonyl chloride | MS(FIA) m/z = 500.1 | prep. 54 was converted to the primary amine using |

| Ex. # | Product | Starting Material A | Starting Material B | Physical Data | Comments |
|---|---|---|---|---|---|
| 90 | N-[3S-(9-Chloro-3-methyl-4-oxo-5H-isoxazolo[4,3-c]quinolin-5-yl)-R-cyclohexylmethyl]-2-naphthylcarboxamide | prep 54 | naphthalene-2-carbonyl chloride | MS(FIA) m/z = 500.1 | TFA in DCM prep. 54 was converted to the primary amine using TFA in DCM |
| 91 | N-[3S-(9-Chloro-3-methyl-4-oxo-5H-isoxazolo[4,3-c]quinolin-5-yl)-R-cyclohexylmethyl]-2-furylcarboxamide | prep 54 | 2-Furoyl chloride | MS(FIA) m/z = 440.2 | prep. 54 was converted to the primary amine using TFA in DCM |
| 92 | N-[3S-(9-Chloro-3-methyl-4-oxo-5H-isoxazolo[4,3-c]quinolin-5-yl)-R-cyclohexylmethyl]-2-thiophenylcarboxamide | prep 54 | 2-Thiophene carbonyl chloride | MS(FIA) m/z = 456.3 | prep. 54 was converted to the primary amine using TFA in DCM |
| 93 | N-[3S-(9-Chloro-3-methyl-4-oxo-5H-isoxazolo[4,3-c]quinolin-5-yl)-R-cyclohexylmethyl]-3-thiophenylcarboxamide | prep 54 | 3-Thiophene carbonyl chloride | MS(FIA) m/z = 456.3 | prep. 54 was converted to the primary amine using TFA in DCM |
| 94 | N-[3-(9-Chloro-3-methyl-4-oxo-5H-isoxazolo[4,3-c]quinolin-5-yl)-cyclohexylmethyl]-3-acetylaminobenzamide | Ex 567 | acetyl chloride | MS(FIA) m/z = 507.2 | |
| 95 | N-[3-(9-Chloro-3-methyl-4-oxo-5H-isoxazolo[4,3-c]quinolin-5-yl)cyclohexylmethyl]-3-bis-(methanesulfonyl)-aminobenzamide | Ex 567 | methane-sulfonyl chloride | MS(FIA) m/z = 621.4 | |
| 96 | N-[3-(9-chloro-3-methyl-4-oxo-5H-isoxazolo[4,3-c]quinolin-5-yl)-2,2-dimethylcyclobutyl-methyl]benzamide | prep 64 | benzoyl chloride | MS (ion spray) 450 (M⁺), 448 (M⁻ − 1) | prep 64 was converted to the amine by TBAF in DCM atrt. |
| 97 | N-[3-(9-chloro-3-methyl-4-oxo-5H-isoxazolo[4,3-c]quinolin-5-yl)-2,2-dimethylcyclobutyl-methyl]-2-phenylacetamide | prep 64 | phenylacetyl chloride | MS (ion spray) 464 (M+), 462 (M⁻ − 1) | prep 64 was converted to the amine by TBAF in DCM atrt. |
| 98 | N-[3-(9-chloro-3-methyl-4-oxo-5H-isoxazolo[4,3-c]quinolin-5-yl)-2,2-dimethylcyclobutyl-methyl]-3,4,5-trimethoxybenzamide | prep 64 | 3,4,5-tri-methoxybenzoyl chloride | MS (ion spray) 540 (M⁺), 548 (M⁻ − 1) | prep 64 was converted to the amine by TBAF in DCM atrt. |

| Ex. # | Product | Starting Material A | Starting Material B | Physical Data | Comments |
|---|---|---|---|---|---|
| 99 | N-[3-(9-chloro-3-methyl-4-oxo-5H-isoxazolo[4,3-c]quinolin-5-yl)cyclohexyl]-benzamide | prep 68 | benzoyl chloride | MS (ion spray) 436 (M+) | |
| 100 | N-[3-(9-chloro-3-methyl-4-oxo-5H-isoxazolo[4,3-c]quinolin-5-yl)cyclohexyl]-benzamide | prep 69 | benzoyl chloride | MS (ion spray) 436 (M+) | |
| 101 | N-[3-(9-chloro-3-methyl-4-oxo-5H-isoxazolo[4,3-c]quinolin-5-yl)cyclohexyl]-2-phenylacetamide | prep 68 | phenacetyl chloride | MS (ion spray) 450.1 (M + 1) | |
| 102 | N-[3-(9-chloro-3-methyl-4-oxo-5H-isoxazolo[4,3-c]quinolin-5-yl)cyclohexyl]-2-phenylacetamide | prep 69 | phenacetyl chloride | MS (ion spray) 450.1 (M + 1) | |
| 103 | Phenyl-carbamic acid 3-(9-chloro-3-methyl-4-oxo-5H-isoxazolo[4,3-c]quinolin-5-yl)-cyclohexylmethyl ester | prep 85 | phenyl isocyanate | MS(ES):(M + 1)$^+$ 466.2 m/z | |
| 104 | N-{2-[3-(9-Chloro-3-methyl-4-oxo-5H-isoxazolo[4,3-c]quinolin-5-yl)cyclohexyl]-ethyl}-2,2-dimethyl-N-phenylpropionamide | prep 93 | trimethylacetyl chloride | MS(ES) [M + H]$^+$ = 520.2367 m/z | |
| 105 | 9-Chloro-5-[3-[3-chloro-1-oxo-butyl-amino)-methyl]-cyclohexyl]-3-methyl-5H-isoxazolo[4,3-c]quinolin-4-one | prep 48 | 4-chlorobutyryl chloride | MS(FIA) (m/z) 450.1 (M + 1) | |
| 106 | N-[3-(9-Iodo-3-methyl-4-oxo-5H-isoxazolo[4,3-c]quinoline-5-yl)-cyclohexyl-methyl]-benzamide | Ex 594 | benzoyl chloride | MS (FIA) (m/z) 542.3 [M + 1] | Ex 594 was converted to the primary amine using TFA in DCM |
| 107 | N-[3-(9-chloro-3-methyl-4-oxo-5H-isoxazolo[4,3-c]quinolin-5-yl)-cyclohexyl-methyl]-benzenesulfonamide | prep 146 | phenylsulfonyl chloride | MS (ion spray) 486 QVT), 484 (M − 1) | |
| 108 | N-[3-(9-chloro-3-methyl-4-oxo-5H-isoxazolo[4,3-c]quinolin-5-yl)-cyclohexyl-methyl]-nicotinamide | prep 146 | nicotinoyl chloride HCL | MS (ion spray) 451(M$^+$), 449 (M − 1) | |
| 109 | N-[3-(9-chloro-3-methyl-4-oxo-5H-isoxazolo[4,3-c]quinolin-5-yl)-cyclohexyl-methyl]-3-methoxybenzamide | prep 146 | m-anisoyl chloride | MS (ion spray) 480 (M$^+$), 478 (M − 1) | |
| 110 | Pyridine-2-carboxylic acid [3-(9-chloro-3-methyl-4-oxo-5H-isoxazolo[4,3-c]quinolin-5-yl)-cyclohexylmethyl]amide | prep 146 | picolinoyl chloride HCL | MS (ion spray) 451 (M$^+$), 449 (M − 1) | |

| Ex. # | Product | Starting Material A | Starting Material B | Physical Data | Comments |
|---|---|---|---|---|---|
| 111 | N-[3-(9-chloro-3-methyl-4-oxo-5H-isoxazolo[4,3-c]quinolin-5-yl)cyclohexyl-methyl]-4-fluorobenzamide | prep 146 | 4-fluorobenzoyl chloride | MS (ion spray) 468 (M$^+$), 466 (M$^-$ − 1) | |
| 112 | N-[3-(9-chloro-3-methyl-4-oxo-5H-isoxazolo[4,3-c]quinolin-5-yl)cyclohexyl-methyl]-3-fluorobenzamide | prep 146 | 3-fluorobenzoyl chloride | MS (ion spray) 468 (M$^+$), 466 (M$^-$ − 1) | |
| 113 | Thiophene-2-carboxylic acid [3-(9-chloro-3-methyl-4-oxo-5H-isoxazolo[4,3-c]quinolin-5-yl)cyclohexylmethyl]amide | prep 146 | 2-thiophene-carbonyl chloride | MS (ion spray) 456 (M$^+$), 454 (M$^-$ − 1) | |
| 114 | N-[3-(9-chloro-3-methyl-4-oxo-5H-isoxazolo[4,3-c]quinolin-5-yl)cyclohexylmethyl]-isonicotinamide | prep 146 | isonicotinoyl chloride HCL | MS (ion spray) 451 (M$^+$), 449 (M$^-$ − 1) | |
| 115 | N-[[(1R,3R)-3-(9-chloro-3-methyl-4-oxo-5H-isoxazolo[4,3-c]quinolin-5-yl))cyclo-hexyl]methyl]-2-furylcarboxamide | prep 146 | 2-furoyl chloride | MS (ion spray) 440 (M$^+$), 438 (M$^-$ − 1) | |
| 116 | N-[[(1R,3R)-3-(9-chloro-3-methyl-4-oxo-5H-isoxazolo[4,3-c]quinolin-5-yl))cyclo-hexyl]-methyl]-2-phenylacetamide | prep 146 | phenylacetyl chloride | MS (ion spray) 440 (M$^+$), 438 (M$^-$ − 1) | |
| 117 | cis-3-(benzoylamino)-1-(9-chloro-3-methyl-4-oxo-5H-isoxazolo[4,3-c]quinolin-5-yl)cyclohexane | prep 146 | benzoyl-chloride | ESIMS m/e 436 35Q (M$^+$ + 1) & 438 $^{37}$d (M$^+$ + 1) | |
| 118 | N-[3-Chloro-3-methyl-4-oxo-5H-isoxazolo[4,5-c]quinolin-5-yl)cyclohexyl-methyl]benzamide | Ex 612 | benzoyl chloride | MS (+ES) m/z 450.0 (M + H)$^+$ | |
| 119 | (1S,3R)-N-[3-(9-Chloro-3-methyl-4-oxo-5H-isoxazolo[4,5-c]quinolin-5-yl)-cyclohexyl-methyl]-4-fluorobenzamide | Ex 613 | 4-fluorobenzoyl chloride | MS (ES+) m/z 468.0 (M + H)$^+$ | |
| 120 | (1R,3S)-Thiophene-2-carboxylic acid [3-(9-chloro-3-methyl-4-oxo-5H-isoxazolo[4,5-c]quinolin-5-yl)cyclohexyl-methyl]-amide | Ex 613 | 2-Thiophene-carbonyl chloride | MS (ES+) m/z 456.0 (M + H)$^+$ | |
| 121 | (1S,3R)-N-[3-(9-Chloro-3-methyl-4-oxo-5H-isoxazolo[4,5-c]quinolin-5-yl)cyclohexyl-methyl]benzamide | Ex 614 | benzoyl chloride | MS (ES+) m/z 450.0 (M + H)$^+$ | |

| Ex. # | Product | Starting Material A | Starting Material B | Physical Data | Comments |
|---|---|---|---|---|---|
| 122 | (1S,3R)-H-[3-(9-Chloro-3-methyl-4-oxo-5H-isoxazolo[4,5-c]quinolin-5-yl)cyclohexyl-methyl]-4-fluorobenzamide | Ex 614 | 4-Fluorobenzoyl chloride | MS (ES+) m/z 468.0 (M + H)+ | |
| 123 | (1S,3R)-Thiophene-2-carboxylic acid [3-(9-chloro-3-methyl-4-oxo-5H-isoxazolo[4,5-c]quinolin-5-yl)cyclohexyl-methyl]-amide | Ex 614 | 2-thiophene-carbonyl chloride | MS (ES+) m/z 455.9 (M + H)+ | |
| 124 | (1S,3R)-N-[3-(9-Chloro-3-methyl-4-oxo-5H-isoxazolo[4,5-c]quinolin-5-yl)cyclohexyl-methyl]nicotinamide | Ex 614 | nicotinoyl chloride | MS (ES+) m/z 451.0 (M + H)+ | |
| 125 | (1R,3S)-N-[3-(9-Chloro-3-methyl-4-oxo-5H-isoxazolo[4,5-c]quinolin-5-yl)cyclohexyl-methyl]benzamide | Ex 615 | benzoyl chloride | MS (ES+) m/z 500.1 (M + H)+ | |
| 126 | (1R,3S)-N-[3-(9-Chloro-3-methyl-4-oxo-5H-isoxazolo[4,5-c]quinolin-5-yl)-cyclohexyl-methyl]nicotinamide | Ex 615 | nicotinyl chloride | MS (ES+) m/z 451.0 (M + H)+ | |
| 127 | N-[3-(9-Chloro-3-methyl-4-oxo-5H-isoxazolo[4,5-c]quinolin-5-yl)cyclohexyl-methyl]nicotinamide | Ex 616 | nicotinoyl chloride | MS (ES+) m/z 451.0 (M + H)+ | |
| 128 | N-[3-(9-Chloro-3-methyl-4-oxo-5H-isoxazolo[4,5-c]quinolin-5-yl)cyclohexyl-methyl]nicotinamide | Ex 617 | nicotinoyl chloride | MS (ES+) m/z 451.0 (M + H)+ | |
| 129 | N-[(1S,3R)-3-(9-Chloro-3-methyl-4-oxo-5H-isoxazolo[4,3-c]quinolin-5-yl)cyclopentyl-methyl]-3,4-difluorobenzamide | Ex 619 | 3,4-difluoro-benzoyl chloride | ESMS: 472 (M + 1)+ | |
| 130 | N-[(1S,3R)-3-(9-Chloro-3-methyl-4-oxo-5H-isoxazolo[4,3-c]quinolin-5-yl)cyclopentyl-methyl]-3-methoxybenzamide | Ex 620 | 3-methoxy-benzoyl chloride | ESMS: 466 (M + 1)+ | |
| 131 | Thiophene-2-carboxylic acid (1S,3R)-3-(9-chloro-3-methyl-4-oxo-5H-isoxazolo[4,3-c]quinolin-5-yl)-cyclopentylmethyl]-amide | Ex 620 | 2-thiophene-carbonyl chloride | ESMS: 442 (M + 1)+ | |
| 132 | (1S,3R)-3-(2-Chloro-6-fluorophenyl)-5-methylisoxazole-4-carboxylic acid [3-(9-chloro-3-methyl-4-oxo- | Ex 620 | 2-Chloro-6-fluorobenzoyl chloride | ESMS: 569 (M + 1)+ | |

| Ex. # | Product | Starting Material A | Starting Material B | Physical Data | Comments |
|---|---|---|---|---|---|
| 133 | 5H-isoxazolo[4,3-c]quinolin-5-yl)cyclopentyl-methyl]amide Pyrazine-2-carboxylic acid [(1S,3R)-3-(9-chloro-3-methyl-4-oxo-5H-isoxazolo [4,3-c]quinolin-5-yl)-cyclopentylmethyl]-amide | Ex 620 | 2-pyrazine-carbonyl chloride | ESMS: 438 (M + 1)+ | |
| 134 | N-[(1S,3R)-3-(9-Chloro-3-methyl-4-oxo-5H-isoxazolo[4,3-c]quinolin-5-yl)cyclopentyl-methyl]-carbamoyl phenylmethyl-carbamic acid t-butyl ester | Ex 620* | (2S)-2-[(t-butoxy)carbon-ylamino]-2-phenylacetic acid | ESMS: 565 (M + 1)+ | |
| 135 | 2-Amino-N-[(1S,3R)-3-(9-chloro-3-methyl-4-oxo-5H-isoxazolo[4,3-c]quinolin-5-yl)-cyclopentyl-methyl]-2-phenylacetamide | Ex 620 | (2S)-2-amino-2-phenylacetic acid | ESMS: 465 (M + 1)+ | |
| 136 | N-[(1S,3R)-3-(9-Chloro-3-methyl-4-oxo-5H-isoxazolo[4,3-c]quinolin-5-ylmethyl)cyclopentyl]benzamide | Ex 620 | benzoyl chloride | ESMS: 436 (M + 1)+ | |
| 137 | N-[(1S,3R)-3-[(9-chloro-3-methyl-4-oxo-5H-isoxazolo[4,3-c]quinolin-5-yl)-methyl]cyclopentyl](3,4,5-trimethoxyphenyl)carboxamide | Ex 620 | 3,4,5-trimethoxybenzoyl chloride | ESMS: 526 (M + 1)+ | |
| 138 | N-[(1R,3S)-3-(2-Chloro-6-fluoro-phenyl)-5-methyl-isoxazolo4-carboxylic acid [3-(9-chloro-3-methyl-4-oxo-5H-isoxazolo[4,3-c]quinolin-5-ylmethyl)cyclopentyl]amide | Ex 621 | 2-chloro-5-fluoro phenyl isoxazoyl chloride | ESMS: 570 (M + 1)+ | |
| 139 | N-[(1R,3S)-3-[(9-chloro-3-methyl-4-oxo-5H-isoxazolo[4,3-c]quinolin-5-yl)methyl] cyclopentyl]-(3,4,5-trimethoxyphenyl)carboxamide | Ex 621 | 3,4,5-trimethoxy-benzoyl chloride | ESMS: 526 (M + 1)+ | |
| 140 | N-[(1R,3S)-3-(9-Chloro-3-methyl-4-oxo-5H-isoxazolo[4,3-c]quinolin-5-ylmethyl)-cyclopentyl]-4-fluorobenzamide | Ex 621 | 4-fluorobenzoyl chloride | ESMS: 454 (M + 1)+ | |
| 141 | N-(1R,3S)-3-(9-Chloro-3-methyl-4-oxo-5H-isoxazolo[4,3-c]quinolin-5-ylmethyl)-cyclopentyl]-3,4-difluorobenzamide | Ex 621 | 3,4-difluoro-benzoyl chloride | ESMS: 472 (M + 1)+ | |
| 142 | N-[(1R,3S)-3-(9-Chloro-3-methyl-4-oxo-5H-isoxazolo[4,3-c]quinolin-5-ylmethyl)-cyclopentyl]nicotinamide | Ex 621 | pyridine-3-carbonyl chloride | ESMS: 437 (M + 1)+ | |
| 143 | N-[(1R,3S)-3-(9-Chloro-3-methyl-4-oxo-5H-isoxazolo[4,3- | Ex 621 | 3-methoxy-benzoyl | ESMS: 466 (M + 1)+ | |

| Ex. # | Product | Starting Material A | Starting Material B | Physical Data | Comments |
|---|---|---|---|---|---|
| | c]quinolin-5-ylmethyl)-cyclopentyl]-3-methoxybenzamide | | chloride | | |
| 144 | N-[[(1R,3S)-3-(9-Chloro-3-methyl-4-oxo-5H-isoxazolo[4,3-c]quinolin-5-ylmethyl)-cyclopentylcarbamoyl]-phenylmethyl]-carbamic acid t-butyl ester | Ex 621 | L-N-trifluoro-acetyl phenyl glycine | ESMS: 561 (M + 1)+ | |
| 145 | 1-Acetyl-2,3-dihydro-1H-indole-2-carboxylicacid [3-(9-chloro-3-methyl-4-oxo-5H-isoxazolo[4,3-c]quinolin-5-yl)cyclo-hexyl]amide | ((2S)indolin-2-yl)-N-[(1R,3S)-3-(9-chloro-3-methyl-4-oxo-5H-isoxazolo[4,3-c]-quinolin-5-yl)cyclo-hexyl]-carboxamide | acetic anhydride | MS (ion spray) 519 (M+). | |
| 146 | N-[3-(9-Chloro-3-methyl-4-oxo-5H-isoxazolo[4,3-c]-quinolin-5-yl)-cyclohexyl]-C-phenylmethane sulfonamide | Ex 624 | α-toluene-sulfonyl chloride | MS (ion spray) 486 (M+). | |
| 147 | (cis)-{N-[(cis)-3-(9-chloro-3-methyl-4-oxo-5H-isoxazolo[4,3-c]quinolin-5-yl))-cyclohexyl]-carbamoyl}phenylmethyl pyridine-3-carboxylate | Ex 470 | nicotinoyl HCL | MS (ion spray) 571 (M+). | |
| 148 | (trans)-{N-[(cis)-3-(9-chloro-3-methyl-4-oxo-5H-isoxazolo[4,3-c]quinolin-5-yl])-cyclohexyl]-carbamoyl]-phenylmethyl pyridine-3-carboxylate | Ex 471 | nicotinoyl HCL | MS (ion spray) 571 (M+). | |
| 149 | N-[3-(9-Chloro-3-methyl-4-oxo-5H-isoxazolo[4,5-c]-quinolin-5-yl)-cyclohexyl-methyl]-6-fluoro-nicotinamide | Ex 632 | 6-Fluoro-nicotinic acid | MS m/z (ES+) 468.8 (M + H)+ | 6-Fluoro-nicotinic acid was converted to the acid chloride by oxalyl chloride in DCM. |
| 150 | 6-Chloro-N-[3-(9-chloro-3-methyl-4-oxo-5H-isoxazolo[4,5-c]quinolin-5-yl)cyclohexyl-methyl]-nicotinamide | Ex 632 | 6-Chloro-nicotinic acid | MS m/z (ES+) 468.8 (M + H)+ | 6-Chloronicotinic acid was converted to the acid chloride by oxalyl chloride |

| Ex. # | Product | Starting Material A | Starting Material B | Physical Data | Comments |
|---|---|---|---|---|---|
| | | | | | in DCM. |
| 151 | N-[3-(9-Chloro-3-methyl-4-oxo-5H-isoxazolo[4,3-c]-quinolin-5-yl)cyclohexyl]-2-methanesulfonylamino-2-phenylacetamide | Ex 633 | methanesulfonyl chloride | MS(ES): (M + 1)+ 543.0, 545.0 m/z | |
| 152 | N-[3-(9-Chloro-3-methyl-4-oxo-5H-isoxazolo[4,3-c]-quinolin-5-yl)-cyclohexyl-methyl]-5-diacetylamino-nicotinamide | Ex 251 | acetic anhydride | MS (ion spray) 550.2 (M+). | |
| 153 | 6-Acetylamino-N-[3-(9-chloro-3-methyl-4-oxo-5H-isoxazolo[4,3-c]quinolin-5-yl)cyclohexylmethyl]-nicotinamide | Ex 245 | acetic anhydride | MS (ion spray) 508.2 (M+) | |
| 154 | N-[3-(9-Chloro-3-methyl-4-oxo-5H-isoxazolo[4,3-c]-quinolin-5-yl)cyclohexyl-methyl]-3-phenylpropionamide | Ex 632 | hydrocinnamoyl chloride | MS (ion spray) 478.1 (M+). | |
| 155 | [3-(9-Chloro-3-methyl-4-oxo-5H-isoxazolo[4,3-c]-quinolin-5-yl)cyclohexyl]-carbamic acid phenyl ester | Ex 634 | phenyl chloroformate | MS (ion spray) 451.96 (M+). | |
| 156 | 1-Benzyl-3-[3-(9-chloro-3-methyl-4-oxo-5H-isoxazolo[4,3-c]quinolin-5-yl)cyclohexyl]urea | Ex 634 | benzyl isocyanate | MS (ion spray) 465.0 (M+) | |
| 157 | 1-[3-(9-Chloro-3-methyl-4-oxo-5H-isoxazolo[4,3-c]-quinolin-5-yl)cyclohexyl]-3-phenylthiourea | Ex 634 | phenyl isothiocyanate | MS (ion spray) 467.0 (M+) | |
| 158 | 1-[3-(9-Chloro-3-methyl-4-oxo-5H-isoxazolo[4,3-c]-quinolin-5-yl)cyclohexyl]-3-phenylurea | Ex 634 | phenyl isocyanate | MS (ion spray) 451.96 (M+). | |
| 159 | N-{[3-(9-Chloro-3-methyl-4-oxo-5H-isoxazolo[4,3-c]quinolin-5-yl)cyclohexylcarbamoyl]-phenylmethyl}-2,2-dimethylpropionamide | prep 243 | pivaloyl chloride | MS(ES) exact mass [M] = 548.2190 m/z | |
| 160 | N-[3-(9-chloro-3-methyl-4-oxo-5H-isoxazolo[4,3-c]quinolin-5-yl)cyclohexyl]-2-methanesulfonylamino-2-phenyl-acetamide | Ex 638 | methanesulfonyl chloride | MS(ES) [M + H]+ = 543.1 m/z | |
| 161 | Morpholine-4-carboxylic acid {[3-(9-chloro-3-methyl-4-oxo-5H-isoxazolo[4,3-c]quinolin-5-yl)-cyclohexylcarbamoyl]-phenylmethyl}amide | Ex 638 | morpholine-4-carbonyl chloride | MS(ES) [M] = 577.2092 m/z. | |
| 162 | N-{[3-(9-chloro-3-methyl-4-oxo-5H-isoxazolo[4,3-c]- | Ex 640 (isomer 1) | pivaloyl chloride | MS(ES) [M + H]+ = 550.2253 m/z. | |

-continued

| Ex. # | Product | Starting Material A | Starting Material B | Physical Data | Comments |
|---|---|---|---|---|---|
| | quinolin-5-yl)cyclohexyl-carbamoyl]pyridin-3-ylmethyl]-2,2-dimethylpropionamide (isomer 1) | | | | |
| 163 | N-[[3-(9-chloro-3-methyl-4-oxo-5H-isoxazolo[4,3-c]quinolin-5-yl)cyclohexyl-carbamoyl]-pyridin-3-yl-methyl}-2,2-dimethylpropionamide (isomer 2) | Ex 640 (isomer 2) | pivaloyl chloride | MS(ES) exact mass [M + H]⁺ = 550.2247 m/z. | |
| 164 | N-[3-(9-Chloro-3-methyl-4-oxo-5H-isoxazolo[4,5-c]-quinolin-5-yl)cyclohexylmethyl]-6-fluoronicotinamide | Ex 632 | 6-Fluoro-nicotinic acid | MS m/z (ES+) 468.8 (M + H)⁺ | 6-Fluoronicotinic acid was converted to the acid chloride by oxalyl chloride in DCM. |
| 165 | N-[3-(9-Chloro-3-methyl-4-oxo-5H-isoxazolo[4,5-c]-quinolin-5-yl)cyclohexylmethyl]-5-fluoronicotinamide | Ex 632 | 5-Fluoro-nicotinic acid | MS m/z (ES+) 468.8 (M + H)⁺ | 5-Fluoronicotinic acid was converted to the acid chloride by oxalyl chloride in DCM. |
| 166 | N-[3-(9-Chloro-3-methyl-4-oxo-5H-isoxazolo-[4,3-c]-quinolin-5-ylmethyl)cyclohexyl]benzamide | Ex 525 | benzoyl chloride | MS(ES+) (m/z) 450.1 [M + 1] | Ex 525 was converted to the amine by TFA in DCM. |
| 167 | N-[3-(9-Chloro-3-methyl-4-oxo-5H-isoxazolo-[4,3-c]-quinolin-5-ylethyl)cyclohexyl]-4-fluorobenzamide | Ex 525 | 4-fluorobenzoyl chloride | MS(ES+) (m/z) 468.1 [M + 1] | Ex 525 was converted to the amine by TFA in DCM. |
| 168 | N-[3-(9-Chloro-3-methyl-4-oxo-5H-isoxazolo-[4,3-c]-quinolin-5-ylmethyl)cyclohexyl]benzamide | Ex 525 | 3,4-difluoro-benzoyl chloride | MS(ES+) (m/z) 486.1 [M + 1]. | Ex 525 was converted to the amine by TFA in DCM. |
| 169 | N-[3-(9-Chloro-3-methyl-4-oxo-5H-isoxazolo-[4,3-c]-quinolin-5-ylmethyl)cyclohexyl]benzamide | Ex 533 | benzoyl chloride | MS(ES+) (m/z) 450.1 [M + 1]. | Ex 533 was converted to the amine by TFA in DCM. |
| 170 | N-[3-(9-Chloro-3-methyl-4-oxo-5H-isoxazolo-[4,3-c]-quinolin-5-ylmethyl)-cyclo-hexyl]-4-fluoro-benzamide | Ex 533 | 4-fluorobenzoyl chloride | MS(ES+) (m/z) 468.1 [M + 1]. | Ex 533 was converted to the amine by TFA in DCM. |
| 171 | N-[3-(9-Chloro-3-methyl-4-oxo-5H-isoxazolo-[4,3-c]-quinolin-5-ylmethyl)cyclohexyl]-3,4-difluorobenzamide | Ex 533 | 3,4-difluorobenzoyl chloride | MS(ES+) (m/z) 486.1 [M + 1]. | Ex 533 was converted to the amine by TFA in DCM. |
| 172 | N-[3-(9-Cyano-3-methyl-4-oxo-5H-isoxazolo[4,3-c]quinolin-5- | Ex 532 | nicotinoyl chloride | MS(ES+) (m/z) 442.3 [M + 1]. | |

| Ex. # | Product | Starting Material A | Starting Material B | Physical Data | Comments |
|---|---|---|---|---|---|
| 173 | y)cyclohexyl-methyl]nicotinamide N-[3-(9-Chloro-3-methyl-4-oxo-5H-isoxazolo[4,3-c]quinolin-5-ylmethyl)cyclohexyl]benzamide | Ex 540 | HCL benzoyl chloride | MS(ES+) (m/z) 450.3 [M + 1]. | Ex 540 was converted to the amine by TFA in DCM. |
| 174 | N-[3-(9-Chloro-3-methyl-4-oxo-5H-isoxazolo[4,3-c]quinolin-5-ylmethyl)cyclohexyl]-4-fluorobenzamide | Ex 540 | 4-fluorobenzoyl chloride | MS(ES+) (m/z) 468.0 [M + 1]. | Ex 540 was converted to the amine by TFA in DCM. |
| 175 | N-[3-(9-Chloro-3-methyl-4-oxo-5H-isoxazolo[4,3-c]quinolin-5-ylmethyl)cyclohexyl]-3,4-difluorobenzamide | Ex 540 | 3,4-difluoro-benzoyl chloride | MS(ES+) (m/z) 486.2 [M + 1]. | Ex 540 was converted to the amine by TFA in DCM. |
| 176 | N-[3-(9-Chloro-3-methyl-4-oxo-5H-isoxazolo[4,3-c]-quinolin-5-yl)cyclohexyl]-bis(2-methanesulfonyl)amino-acetamide | prep 360 | mesyl chloride | MS (ion spray) 545.1 (M+) | |
| 177 | N-[3-(9-Chloro-3-methyl-4-oxo-5H-isoxazolo[4,5-c]-quinolin-5-yl)cyclohexyl]-benzamide | prep 380 | benzoyl chloride | MS (ES+) m/z 436.1 (M + H)+, (ES−) 434.1 (M − H)−. | |
| 178 | 2-[(1R,3S)-3-(9-Chloro-3-methyl-4-oxo-5H-isoxazolo[4,3-c]quinolin-5-yl)-cyclohexyl]-N-(3,4-difluoro-phenyl)-acetamide | 3,4-difluoroaniline | Prep 47 | MS (ES+) m/z = 485.8 | Prep 47 was converted to the acid chloride by oxalyl chloride in DCM. |
| 179 | 2-[(1R,3S)-3-(9-Chloro-3-methyl-4-oxo-5H-isoxazolo[4,3-c]quinolin-5-yl)-cyclohexyl]-N-(3,5-difluoro-phenyl)-acetamide | 3,5-difluoroaniline | Prep 47 | MS (ES+) m/z = 486.1 | Prep 47 was converted to the acid chloride by oxalyl chloride in DCM. |
| 180 | 2-[(1R,3S)-3-(9-Chloro-3-methyl-4-oxo-5H-isoxazolo[4,3-c]quinolin-5-yl)-cyclohexyl]-N-(2-fluoro-phenyl)-acetamide | 2-difluoroaniline | Prep 47 | MS (ES+) m/z = 468.1 | Prep 47 was converted to the acid chloride by oxalyl chloride in DCM. |
| 181 | 2-[(1R,3S)-3-(9-Chloro-3-methyl-4-oxo-5H-isoxazolo[4,3-c]quinolin-5-yl)-cyclohexyl]-N-Benzyl-acetamide | benzylamine | Prep 47 | MS (ES+) m/z = 464.1 | Prep 47 was converted to the acid chloride by oxalyl chloride in DCM. |
| 182 | 2-[(1R,3S)-3-(9-Chloro-3-methyl-4-oxo-5H-isoxazolo[4,3-c]quinolin-5-yl)cyclohexyl]-N-(3,4,5-trimethoxy-benzyl)-acetamide | 3,4,5-Trimethoxy-benzylamine | Prep 47 | MS (ES+) m/z = 554.2 | Prep 47 was converted to the acid chloride by oxalyl chloride in DCM. |

| Ex. # | Product | Starting Material A | Starting Material B | Physical Data | Comments |
|---|---|---|---|---|---|
| 183 | 2-[(1R,3S)-3-(9-Chloro-3-methyl-4-oxo-5H-isoxazolo[4,3-c]quinolin-5-yl)-cyclo-hexyl]-N-(2-methoxy-phenyl)-acetamide | 2-Methoxy-phenylamine | Prep 47 | MS (ES+) m/z = 480.1 | Prep 47 was converted to the acid chloride by oxalyl chloride in DCM. |
| 184 | 2-[(1R,3S)-3-(9-Chloro-3-methyl-4-oxo-5H-isoxazolo[4,3-c]quinolin-5-yl)-cyclo-hexyl]-N-(4-methoxy-phenyl)-acetamide | 4-Methoxy-phenylamine | Prep 47 | MS (ES+) m/z = 480.1 | Prep 47 was converted to the acid chloride by oxalyl chloride in DCM. |
| 185 | 2-[(1R,3S)-3-(9-Chloro-3-methyl-4-oxo-5H-isoxazolo[4,3-c]quinolin-5-yl)-cyclo-hexyl]-N-(2-methyl-phenyl)-acetamide | 2-Methyl-phenylamine | Prep 47 | MS (ES+) m/z = 464.2 | Prep 47 was converted to the acid chloride by oxalyl chloride in DCM. |
| 186 | 2-[(1R,3S)-3-(9-Chloro-3-methyl-4-oxo-5H-isoxazolo[4,3-c]quinolin-5-yl)-cyclo-hexyl]-N-(3-methyl-phenyl)-acetamide | 3-Methyl-phenylamine | Prep 47 | MS (ES+) m/z = 464.1 | Prep 47 was converted to the acid chloride by oxalyl chloride in DCM. |
| 187 | 2-[(1R,3S)-3-(9-Chloro-3-methyl-4-oxo-5H-isoxazolo[4,3-c]quinolin-5-yl)-cyclo-hexyl]-N-(4-methyl-phenyl)-acetamide | 4-Methyl-phenylamine | Prep 47 | MS (ES+) m/z = 464.1 | Prep 47 was converted to the acid chloride by oxalyl chloride in DCM. |
| 188 | 2-[(1R,3S)-3-(9-Chloro-3-methyl-4-oxo-5H-isoxazolo[4,3-c]quinolin-5-yl)-cyclo-hexyl]-N-(2,6-dimethyl-phenyl)-acetamide | 2,6-Methyl-phenylamine | Prep 47 | MS (ES+) m/z = 478.2 | Prep 47 was converted to the acid chloride by oxalyl chloride in DCM. |
| 189 | 2-[(1R,3S)-3-(9-Chloro-3-methyl-4-oxo-5H-isoxazolo[4,3-c]quinolin-5-yl)-cyclo-hexyl]-N-(4-carbomethoxy-phenyl)-acetamide | 4-Amino-benzoic acid methyl ester | Prep 47 | MS (ES+) m/z = 508.2 | Prep 47 was converted to the acid chloride by oxalyl chloride in DCM. |
| 190 | 2-[(1R,3S)-3-(9-Chloro-3-methyl-4-oxo-5H-isoxazolo[4,3-c]quinolin-5-yl)-cyclo-hexyl]-N-(6-methoxy-quinoline)-acetamide | 6-Methoxy-quinolin-8-ylamine | Prep 47 | MS (ES+) m/z = 531.0 | Prep 47 was converted to the acid chloride by oxalyl chloride in DCM. |
| 191 | 2-[(1R,3S)-3-(9-Chloro-3-methyl-4-oxo-5H-isoxazolo[4,3-c]quinolin-5-yl)-cyclo- | Methyl-phenyl-amine | Prep 47 | MS (ES+) m/z = 464.0 | Prep 47 was converted to the acid chloride by |

| Ex. # | Product | Starting Material A | Starting Material B | Physical Data | Comments |
|---|---|---|---|---|---|
| | hexyl]-N-phenyl-N-methyl-acetamide | | | | oxalyl chloride in DCM. |
| 192 | 2-[(1R,3S)-3-(9-Chloro-3-methyl-4-oxo-5H-isoxazolo[4,3-c]quinolin-5-yl)-cyclo-hexyl]-N-benzyl-N-methyl-acetamide | Methyl-benzyl-amine | Prep 47 | MS (ES+) m/z = 478.1 | Prep 47 was converted to the acid chloride by oxalyl chloride in DCM. |
| 193 | (3-[[5-(2-Chloro-6-fluoro-phenyl)-3-methyl-3H-imidazole-4-carbonyl]-amino]-cyclohexylmethyl)-carbamic acid benzyl ester | Ex 615 | prep 405 | MS (ES+) (m/z) 499.2 [M + 1] | Prep 405 was converted to the acid chloride by oxalyl chloride in DCM. |
| 194 | N-[3-(9-Chloro-3-methyl-4-oxo-3,4-dihydro-imidazo[4,5-c]quinolin-5-yl)-cyclohexyl-methyl]-benzamide | Ex 193 | benzoyl chloride | MS (ES+) (m/z) 449.2 [M + 1] | Example 193 was converted to the primary amine by TMSI in DCM. |
| 195 | 1R,3S-N-[3-(9-Chloro-3-methyl-4-oxo-5H-isoxazolo[4,3-c]quinolin-5-ylmethyl)-cyclopentyl]-benzamide | Ex 621 | benzoyl chloride | ESMS: 436 (M + 1)+ | |
| 196 | 1R,3S-N-[3-(9-Chloro-3-methyl-4-oxo-5H-isoxazolo[4,3-c]quinolin-5-ylmethyl)-cyclopentyl]-2-phenyl-acetamide | Ex 621 | phenylacetyl-chloride | ESMS: 450 (M + 1)+ | |
| 197 | N-[3-(9-Chloro-3-methyl-4-oxo-5H-isoxazolo[4,5-c]quinolin-5-yl)-cyclohexyl]-benzamide | prep 399 | benzoyl chloride | MS (ES+) m/z 436.1 (M + H)+, (ES−) 434.1 (M − H)− | |
| 198 | N-[3-(9-Chloro-3-methyl-4-oxo-5H-isoxazolo[4,3-c]quinolin-5-yl)-cyclohexylmethyl]-N-methyl-nicotinamide | prep 390 | nicotinoyl chloride HCL | MS (ion spray) 465 (M+) | |
| 199 | R(−)-Pyridine-2-carboxylic acid [3-(9-chloro-3-methyl-4-oxo-5H-isoxazolo[4,3-c]quinolin-5-yl)-cyclohexylcarbamoyl]-phenyl-methyl ester | Ex 471 | picolinoyl chloride HCL | MS (ion spray) 571 (M+) | |
| 200 | R(−)Isonicotinic acid [3-(9-chloro-3-methyl-4-oxo-5H-isoxazolo[4,3-c]quinolin-5-yl)-cyclohexylcarbamoyl]-phenyl-methyl ester | Ex 471 | isonicotinoyl chloride HCL | MS (ion spray) 571 (M+) | |

-continued

| Ex. # | Product | Starting Material A | Starting Material B | Physical Data | Comments |
|---|---|---|---|---|---|
| 201 | S(+)Pyridine-2-carboxylic acid [3-(9-chloro-3-methyl-4-oxo-5H-isoxazolo[4,3-c]quinolin-5-yl)-cyclohexylcarbamoyl]-phenyl-methyl ester | Ex 470 | picolinoyl chloride HCL | MS (ion spray) 571 (M⁺) | |
| 202 | S(+)Isonicotinic acid [3-(9-chloro-3-methyl-4-oxo-5H-isoxazolo[4,3-c]quinolin-5-yl)-cyclohexylcarbamoyl]-phenyl-methyl ester | Ex 470 | isonicotinoyl chloride HCL | MS (ion spray) 571 (M⁺) | |
| | | | c) EDC Coupling: | | |
| 203 | 9-Chloro-5-(3-{2-[4-(4-fluorobenzoyl)-piperidin-1-yl]-2-oxo-ethyl}cyclohexyl)-3-methyl-5H-isoxazolo[4,3-c]quinolin-4-one | prep 39 | 4-(4-fluorobenzoyl) piperidine HCL | MS (ion spray) 564.1 (M+) | |
| 204 | 9-Chloro-3-methyl-5-[3-(2-morpholin-4-yl-2-oxoethyl)cyclohexyl]-5H-isoxazolo[4,3-c]quinolin-4-one | prep 39 | Morpholine | MS (ion spray) 444.2 (M + 1) | |
| 205 | 9-Chloro-3-methyl-5-{3-[2-oxo-2-(4-phenylpiperazin-1-yl)oxoethyl]cyclo-hexyl}-5H-isoxazolo[4,3-c]quinolin-4-one | prep 39 | 1-phenyl-piperazine | MS (ion spray) 519.2(M+) | |
| 206 | 5-{3-[2-(4-Acetylpiperazin-1-yl)-2-oxoethyl]cyclohexyl}-9-chloro-3-methyl-5H-isoxazolo[4,3-c]quinolin-4-one | prep 39 | 1-acetyl-piperazine | MS (ion spray) 485.3 (M + 1) | |
| 207 | 2-[3-(9-Chloro-3-methyl-4-oxo-5H-isoxazolo[4,3-c]quinolin-5-yl)cyclohexyl]-N-cyclopropylacetamide | prep 39 | cyclopropyl-amine | MS (ion spray) 414.2 (M + 1) | |
| 208 | 2-[3-(9-Chloro-3-methyl-4-oxo-5H-isoxazolo[4,3-c]quinolin-5-yl)cyclohexyl]-N-cyclobutylacetamide | prep 39 | cyclobutyl amine | MS (ion spray) 428.2 (M + 1) | |
| 209 | 2-[3-(9-Chloro-3-methyl-4-oxo-5H-isoxazolo[4,3-c]quinolin-5-yl)cyclohexyl]-N-cyclopentylacetamide | prep 39 | Cyclopentyl-amine | MS (ion spray) 442.2 (M + 1) | |
| 210 | 2-[3-(9-Chloro-3-methyl-4-oxo-5H-isoxazolo[4,3-c]quinolin-5-yl)cyclohexyl]-N-cyclohexylacetamide | prep 39 | Cyclohexyl amine | MS (ion spray) 456.3 (M + 1) | |
| 211 | 2-[3-(9-Chloro-3-methyl-4-oxo-5H-isoxazolo[4,3- | prep 39 | Cycloheptyl-amine | MS (ion spray) 470.2 (M + 1) | |

| Ex. # | Product | Starting Material A | Starting Material B | Physical Data | Comments |
|---|---|---|---|---|---|
| | c]quinolin-5-yl)cyclohexyl]-N-cycloheptylacetamide | | | | |
| 212 | 2-[3-(9-Chloro-3-methyl-4-oxo-5H-isoxazolo[4,3-c]quinolin-5-yl)cyclohexyl]-N-cyclohexyl-N-methylacetamide | prep 39 | N-methyl,N-cyclohexyl-amine | MS (ion spray) 470.02 (M + 1) | |
| 213 | 2-[3-(9-Chloro-3-methyl-4-oxo-5H-isoxazolo[4,3-c]quinolin-5-yl)cyclohexyl]-N-indan-2-yl-acetamide | prep 39 | 2-aminoindane | MS (ion spray) 490.2 (M + 1) | |
| 214 | 2-[3-(9-Chloro-3-methyl-4-oxo-5H-isoxazolo[4,3-c]quinolin-5-yl)cyclohexyl]-N-naphthalen-1-yl-acetamide | prep 39 | 1-naphthylamine | MS (ion spray) 500.2 (M+) | |
| 215 | 9-Chloro-3-methyl-5-[3-(2-oxo-2-piperidin-1-yl-ethyl)-cyclohexyl]-5H-isoxazolo[4,3-c]quinolin-4-one | prep 39 | Piperidine | MS (ion spray) 442.2 (M + 1) | |
| 216 | N,N-Dibenzyl-2-[3-(9-chloro-3-methyl-4-oxo-5H-isoxazolo[4,3-c]quinolin-5-yl)-cyclo-hexyl]-acetamide | prep 39 | Dibenzylamine | MS (ion spray) 554.3 (M + 1) | |
| 217 | N-Benzyl-2-[3-(9-chloro-3-methyl-4-oxo-5H-isoxazolo[4,3-c]quinolin-5-yl)cyclohexyl]-N-(3,4,5-trimethoxybenzyl)acetamide | prep 39 | N-benzyl,N-(3,4,5-trimethy-oxy-benzyl)amine | MS (ion spray) 644.3 (M + 1) | |
| 218 | 2-[3-(9-Chloro-3-methyl-4-oxo-5H-isoxazolo[4,3-c]quinolin-5-yl)cyclohexyl]-N-pyridin-2-ylacetamide | prep 39 | 2-aminopyridine | MS (ion spray) 451.1 (M + 1) | |
| 219 | 2-[3-(9-Chloro-3-methyl-4-oxo-5H-isoxazolo[4,3-c]quinolin-5-yl)cyclohexyl]-N-pyridin-3-ylacetamide | prep 39 | 3-aminopyridine | MS (ion spray) 451.1 (M + 1) | |
| 220 | 2-[3-(9-Chloro-3-methyl-4-oxo-5H-isoxazolo[4,3-c]quinolin-5-yl)cyclohexyl]-N-pyridin-4-ylacetamide | prep 39 | 4-aminopyridine | MS (ion spray) 451.1 (M + 1) | |
| 221 | N-[(1S,3R)-3-(9-Chloro-3-methyl-4-oxo-5H-isoxazolo[4,3-c]quinolin-5-yl)cyclohexylmethyl]-3-cyclohexylpropanamide | cyclohexane-propionic acid | prep 44 | MS (ion spray) 484.2 (M + 1) | |
| 222 | N-[(1S,3R)-3-(9-chloro-3-methyl-4-oxo-5H-isoxazolo[4,3-c]quinolin-5-yl)cyclohexylmethyl]pyrazin-2-yl carboxamide | 2-pyrazine-carboxylic acid | prep 44 | MS (ion spray) 452.1 (M + 1) | |

| Ex. # | Product | Starting Material A | Starting Material B | Physical Data | Comments |
|---|---|---|---|---|---|
| 223 | N-[(1S,3R)-3-(9-Chloro-3-methyl-4-oxo-5H-isoxazolo[4,3-c]quinolin-5-yl)cyclohexylmethyl]-2-thiophen-2-ylacetamide | 2-thiophene-acetic acid | prep 44 | MS (ion spray) 470.1 (M + 1) | |
| 224 | N-[(1S,3R)-3-(9-Chloro-3-methyl-4-oxo-5H-isoxazolo[4,3-c]quinolin-5-yl)cyclohexylmethyl]-2-(1-methyl-1H-imidazol-4-yl)-acetamide | 1-methyl-4-iraidazoleacetic acid HCL | prep 44 | MS (ion spray) 468.1 (M + 1) | |
| 225 | N-[(1S,3R)-3-(9-Chloro-3-methyl-4-oxo-5H-isoxazolo[4,3-c]quinolin-5-yl)cyclohexylmethyl]-4-phenoxy-benzamide | 4-phenoxy-benzoic acid | prep 44 | MS (ion spray) 541.8 (M+) | |
| 226 | 4-Benzoyl-N-[(1S,3R)-3-(9-chloro-3-methyl-4-oxo-5H-isoxazolo[4,3-c]-quinolin-5-yl]-cyclohexylmethyl]benzamide | 4-benzoyl-benzoic acid | prep 44 | MS (ion spray) 554.2 (M+) | |
| 227 | 6-Fluoropyridine-2-carboxylic acid [3-(9-chloro-3-methyl-4-oxo-5H-isoxazolo[4,3-c]quinolin-5-yl)cyclohexyl]-methyl]amide | prep 1 | Ex 632 | MS (ion spray) 469 (M+) | |
| 228 | N-[3-(9-Chloro-3-methyl-4-oxo-5H-isoxazolo[4,3-c]quinolin-5-yl)cyclohexyl]-2-(4-fluorophenyl)-2-hydroxyacetamide | D(−)-mandelic acid | Ex 634 | MS (ion spray) 484 (M+) | flash chrom. (silica gel: 0-0.5% MeOH/chloroform) gave both isomers |
| 229 | Cis-N-[[3-(9-chloro-3-methyl-4-oxo-5H-isoxazolo[4,3-c]-quinolin-5-yl)cyclohexyl]methyl](5-fluoro(2-pyridyl)]carboxamide | 4-fluoro-picolinic acid | Ex 632 | MS (ion spray) 469 (NT). | |
| 230 | Cis-N-[[3-(9-chloro-3-methyl-4-oxo-5H-isoxazolo[4,3-c]quinolin-5-yl)cyclohexyl]methyl](6-methoxy(2-pyridyl)]carboxamide | 6-methoxy-pyridine-2-carboxylic acid | Ex 632 | MS (ion spray) 481 (M+). | |
| 231 | Cis-N-[3-(9-Chloro-3-methyl-4-oxo-5H-isoxazolo[4,3-c]quinolin-5-yl)cyclohexylmethyl]-5-methoxynicotinamide | prep 3 | Ex 632 | MS (ion spray) 481 (M+). | |
| 232 | cis-N-[3-(9-Chloro-3-methyl-4-oxo-5H-isoxazolo[4,3- | (d/l)-2,3-difluoroman- | Ex 634 | MS (ion spray) 502 (M+). | flash chrom. (silica gel: 0- |

| Ex. # | Product | Starting Material A | Starting Material B | Physical Data | Comments |
|---|---|---|---|---|---|
| | c]-quinolin-5-yl)cyclohexyl]-2-(2,3-difluorophenyl)-2-hydroxyacetamide | delic acid | | | 0.5% MeOH/chloroform gave both isomers |
| 234 | cis-N-[3-(9-Chloro-3-methyl-4-oxo-5H-isoxazolo[4,3-c]quinolin-5-yl)-cyclohexyl]-2-(3,4-difluorophenyl)-2-hydroxyacetamide | (dA)-3,4-difluoromandelic acid | Ex 634 | MS (ion spray) 502 (M$^+$). | flash chrom. (silica gel: 0-0.5% MeOH/chloroform) gave both isomers |
| 235 | cis {[3-(9-Chloro-3-methyl-4-oxo-5H-isoxazolo[4,3-c]quinolin-5-yl)cyclohexylcarbamoyl]phenylmethyl}-carbamic acid t-butylester | N-(t-butoxycarbonyl)-D-phenyl-glycine | Ex 634 | MS(ES): (M + Na)$^+$ 587.1 m/z, (M − BOC)$^+$ 465.1 m/z | silica gel column eluted with 30% ethylacetate/hexanes: isomer 1 R$_t$ = 33.67 min. isomer 2: R$_t$ = 23.81 min. Chiracel AD. |
| 236 | N-[[3-(9-Chloro-3-methyl-4-oxo-5H-isoxazolo[4,3-c]quinolin-5-yl)cyclohexylcarbamoyl]phenylmethyl]-2,2-dimethyl-propionamide | trimethyl-acetic acid | Ex 633 | MS(ES): (M + 1)$^+$ 549.1, 551.1 m/z. | |
| 237 | N-[[3-(9-Chloro-3-methyl-4-oxo-5H-isoxazolo[4,3-c]quinolin-5-yl)cyclohexylcarbamoyl]phenylmethyl]-nicotinamide | nicotinic acid | Ex 633 | MS(ES): (M + 1)$^+$ 570.0, 572.0 m/z | |
| 238 | Pyridine-2-carboxylic acid {[3-(9-chloro-3-methyl-4-oxo-5H-isoxazolo[4,3-c]quinolin-5-yl)cyclohexylcarbamoyl]-phenylmethyl}amide | picolinic acid | Ex 633 | MS(ES): (M + 1)$^+$ 570.2, 572.3 m/z | |
| 239 | N-[[3-(9-Chloro-3-methyl-4-oxo-5H-isoxazolo[4,3-c]quinolin-5-yl)cyclohexylcarbamoyl]phenylmethyl]-isonicotinamide | isonicotinic acid | Ex 633 | MS(ES): (M + 1)$^+$ 570.3, 572.3 m/z | |
| 240 | 2-t-Butylamino-N-[3-(9-chloro-3-methyl-4-oxo-5H-isoxazolo[4,3-c]quinolin-5-yl)cyclohexyl]-2-phenylacetamide | prep 11 | Ex 634 | MS(ES): (M + 1)$^+$ 521.2, 522.2, 523.2 m/z | Isomer 1 38% |
| 241 | 2-t-Butylamino-N-[3-(9-chloro-3-methyl-4-oxo-5H-isoxazolo[4,3-c]quinolin-5-yl)cyclohexyl]-2-phenylacetamide | prep 11 | Ex 634 | MS(ES): (M + 1)$^+$ 521.2, 522.2, 523.2 m/z | Isomer 2 30% |

| Ex. # | Product | Starting Material A | Starting Material B | Physical Data | Comments |
|---|---|---|---|---|---|
| 242 | N-[3-(9-Chloro-3-methyl-4-oxo-5H-isoxazolo[4,3-c]quinolin-5-yl)cyclohexyl]-2-(2,2-dimethylpropylamino)-2-phenylacetamide | prep 13 | Ex 634 | MS(ES): (M + 1)⁺ 535.3, 536.3, 537.3 m/z. | Isomer 1 29% |
| 243 | N-[3-(9-Chloro-3-methyl-4-oxo-5H-isoxazolo[4,3-c]quinolin-5-yl)cyclohexyl]-2-(2,2-dimethylpropylamino)-2-phenylacetamide | prep 13 | Ex 634 | MS(ES): (M + 1)⁺ 535.3, 536.3, 537.3 m/z. | Isomer 2 44% |
| 244 | N-[3-(9-Chloro-3-methyl-4-oxo-5H-isoxazolo[4,3-c]quinolin-5-yl)cyclohexylmethyl]-1-oxynicotinamide | nicotinic acid-N-oxide | Ex 619 | MS (ion spray) 467.2 (M+). | |
| 245 | 6-Amino-N-[3-(9-Chloro-3-methyl-4-oxo-5H-isoxazolo[4,3-c]quinolin-5-yl)-cyclohexylmethyl]-nicotinamide | 4-amino-nicotinic acid | Ex 619 | MS (ion spray) 466.3 (M+). | |
| 246 | N-[3-(9-Chloro-3-methyl-4-oxo-5H-isoxazolo[4,3-c]quinolin-5-yl)-cyclohexylmethyl]-2-pyridin-3-yl-acetamide | 3-pyridylacetic acid HCl | Ex 619 | MS (ion spray) 465.0 (M+). | |
| 247 | Quinoline-3-carboxylic acid [3-(9-chloro-3-methyl-4-oxo-5H-isoxazolo[4,3-c]-quinolin-5-yl)cyclohexylmethyl]amide | 3-quinoline-carboxylic acid | Ex 619 | MS (ion spray) 501 (M+). | |
| 248 | N-[3-(9-Chloro-3-methyl-4-oxo-5H-isoxazolo[4,3-c]quinolin-5-yl)-cyclohexylmethyl]-6-pyrazol-1-yl-nicotinamide | 6-(1H-pyrazol-1-yl)-nicotinic acid | Ex 619 | MS (ion spray) 517.2 (M+). | |
| 249 | N-[3-(9-Chloro-3-methyl-4-oxo-5H-isoxazolo[4,3-c]quinolin-5-yl)-cyclohexylmethyl]-3-pyridin-3-yl-propionamide | 3-pyridylpropionic acid | Ex 619 | MS (ion spray) 479.1 (M+). | |
| 250 | N-[3-(9-Chloro-3-methyl-4-oxo-5H-isoxazolo[4,3-c]quinolin-5-yl)-cyclohexylmethyl]-6-trifluoromethyl-nicotinamide | 6-trifluoromethynicotinic acid | Ex 619 | MS (ion spray) 501 (M+). | |
| 251 | 5-Amino-N-[3-(9-chloro-3-methyl-4-oxo-5H-isoxazolo[4,3-c]quinolin-5-yl)-cyclohexylmethyl]-nicotinamide | 5-aminonicotinic acid | Ex 619 | MS (ion spray) 466.2 (M+). | |
| 252 | Pyrimidine-5-carboxylic acid [3-(9-chloro-3-methyl-4-oxo-5H-isoxazolo[4,3-c]-quinolin-5-yl)-cyclohexylmethyl]-amide | prep 15 | Ex 619 | MS (ion spray) 452.2 (M+). | |

| Ex. # | Product | Starting Material A | Starting Material B | Physical Data | Comments |
|---|---|---|---|---|---|
| 253 | N-[3-(9-Chloro-3-methyl-4-oxo-5H-isoxazolo[4,3-c]quinolin-5-yl)-cyclohexylmethyl]-4-methylaminobenzamide | 4-(methylamino)benzoic acid | Ex 619 | MS (ion spray) 479.0 (M+). | |
| 254 | 6-Methyl-pyridine-2-carboxylic acid [3-(9-chloro-3-methyl-4-oxo-5H-isoxazolo[4,3-c]quinolin-5-yl)cyclohexylmethyl]amide | 6-methyl-picolinic acid | Ex 619 | MS (ion spray) 465.0 (M+). | |
| 255 | 4-Chloro-pyridine-2-carboxylic acid [3-(9-chloro-3-methyl-4-oxo-5H-isoxazolo[4,3-c]quinolin-5-yl)cyclohexylmethyl]amide | 4-chloro-picolinic acid (TCI-US) | Ex 619 | MS (ion spray) 486.9 (M+). | |
| 256 | 2,6-Dichloro-N-[3-(9-chloro-3-methyl-4-oxo-5H-isoxazolo[4,3-c]quinolin-5-yl)cyclohexylmethyl]-isonicotinamide | 2,6-dichloroisonicotinic acid | Ex 619 | MS (ion spray) 518.9 (M+). | |
| 257 | N-[3-(9-Chloro-3-methyl-4-oxo-5H-isoxazolo[4,3-c]quinolin-5-yl)-cyclohexyl-methyl]-2-fluoroisonicotinamide | 2-fluoro isonicotinic acid | Ex 619 | MS (ion spray) 469.0 (M+). | |
| 258 | Furo[3,2-b]pyridine-5-carboxylic acid[3-(9-chloro-3-methyl-4-oxo-5H-isoxazolo[4,3-c]quinolin-5-yl)cyclohexylmethyl]-amide | Furo[3,2-b]pyridine-5-carboxylic acid | Ex 619 | MS (ion spray) 491.2 (M+). | |
| 259 | 6-Chloro-pyridine-2-carboxylic acid [3-(9-chloro-3-methyl-4-oxo-5H-isoxazolo[4,3-c]quinolin-5-yl)cyclohexylmethyl]-amide | 6-chloro-2-pyridinecarboxylic acid (SALOR) | Ex 619 | MS (ion spray) 485.2 (M+). | |
| 260 | 6-Methoxy-pyridine-2-carboxylic acid [3-(9-chloro-3-methyl-4-oxo-5H-isoxazolo[4,3-c]quinolin-5-yl)cyclohexylmethyl]amide | prep 16 | Ex 619 | MS (ion spray) 481.1 (M+). | |
| 261 | 4-Methoxypyridine-2-carboxylic acid [3-(9-chloro-3-methyl-4-oxo-5H-isoxazolo[4,3-c]quinolin-5-yl)cyclohexylmethyl]amide | 4-methoxy-picolinic acid HCL | Ex 619 | MS (ion spray) 481.2 (M+). | |
| 262 | 5,6-Dichloro-N-[3-(9-chloro-3-methyl-4-oxo-5H-isoxazolo[4,3-c]quinolin-5-yl)-cyclohexymethyl]-nicotinamide | 5,6-dichloro nicotinic acid | Ex 619 | MS (ion spray) 519.0 (M+). | |
| 263 | 2-Chloro-N-[3-(9-chloro-3-methyl-4-oxo-5H-isoxazolo[4,3- | 2-chloro-6-methylpyridine- | Ex 619 | MS (ion spray) 498.8, 500.87 | |

| Ex. # | Product | Starting Material A | Starting Material B | Physical Data | Comments |
|---|---|---|---|---|---|
| | c]quinolin-5-yl)cyclohexylmethyl]-6-methylisonicotinamide | 4-carboxylic acid | | (M+). | |
| 264 | N-[3-(9-Chloro-3-methyl-4-oxo-5H-isoxazolo[4,3-c]quinolin-5-yl)cyclohexyl-methyl]-5-methyl-nicotinamide | 5-methylnicotinic acid | Ex 619 | MS (ion spray) 465.1 (M+). | |
| 265 | N-[3-(9-Chloro-3-methyl-4-oxo-5H-isoxazolo[4,3-c]quinolin-5-yl)-cyclohexyl-methyl]-6-methoxy-nicotinamide | prep 19 | Ex 619 | MS (ion spray) 481.0 (M+). | |
| 266 | 5-Chloro-N-[3-(9-chloro-3-methyl-4-oxo-5H-isoxazolo[4,3-c]quinolin-5-yl)-cyclohexylmethyl]-nicotinamide | 5-chloronicotinic acid | Ex 619 | MS (ion spray) 485.0 (M+). | |
| 267 | N-[3-(9-Chloro-3-methyl-4-oxo-5H-isoxazolo[4,3-c]quinolin-5-yl)-cyclohexylmethyl]-2-phenylacetamide | phenylacetic acid | Ex 619 | MS (ion spray) 501 (M+). | |
| 268 | 4-Fluoronaphthalene-1-carboxylic acid [3-(9-chloro-3-methyl-4-oxo-5H-isoxazolo[4,3-c]quinolin-5-yl)cyclohexylmethyl]-amide | 4-fluoro-l-naphthoic acid | Ex 619 | MS (ion spray) 518.1 (M+). | |
| 269 | N-[3-(9-Chloro-3-methyl-4-oxo-5H-isoxazolo[4,3-c]quinolin-5-yl)-cyclohexylmethyl]-3-hydroxy-2-methylbenzamide | 2-methyl-3-hydroxybenzoic acid | Ex 619 | MS (ion spray) 479.9 (M+). | |
| 270 | N-[3-(9-Chloro-3-methyl-4-oxo-5H-isoxazolo[4,3-c]quinolin-5-yl)cyclohexyl]-2-methoxy-2-phenylacetamide | .(S)-(+)-α-methoxyphenyl acetic acid | Ex 634 | MS (ion spray) 480.1 (M+). | |
| 271 | N-[3-(9-Chloro-3-methyl-4-oxo-5H-isoxazolo[4,3-c]quinolin-5-yl)cyclohexyl]-2-methoxy-2-phenylacetamide | (R)-(−)-α-methoxyphenyl acetic acid | Ex 634 | MS (ion spray) 480.1 (M+). | |
| 272 | N-[3-(9-Chloro-3-methyl-4-oxo-5H-isoxazolo[4,3-c]quinolin-5-yl)cyclohexyl]-3,3,3-trifluoro-2-methoxy-2-phenylpropionamide | (S)-(−)-α-methoxy-α-(trifluoromethyl)phenyl-acetic acid | Ex 634 | MS (ion spray) 548.1 (M+). | |
| 273 | Acetic acid [3-(9-chloro-3-methyl-4-oxo-5H-isoxazolo[4,3-c]quinolin-5-yl)cyclohexylcarbamoyl]phenylmethyl ester | (R)-(−)-O-acetylmandelic acid | Ex 634 | MS (ion spray) 508.1 (M+). | |
| 274 | Acetic acid [3-(9-chloro-3-methyl-4-oxo-5H-isoxazolo[4,3-c]quinolin-5-yl)cyclohexylcarbamoyl]phenylmethyl ester | (S)-(+)-O-acetylmandelic acid | Ex 634 | MS (ion spray) 508.1 (M+). | |

| Ex. # | Product | Starting Material A | Starting Material B | Physical Data | Comments |
|---|---|---|---|---|---|
| 275 | N-[3-(9-Chloro-3-methyl-4-oxo-5H-isoxazolo[4,3-c]quinolin-5-yl)-cyclohexyl]-2-phenoxy-2-phenylacetamide | phenoxyphenyl-acetic acid | Ex 634 | MS (ion spray) 542.1 (M+). | |
| 276 | {[3-(9-Chloro-3-methyl-4-oxo-5H-isoxazolo[4,3-c]quinolin-5-yl)cyclohexylcarbamoyl]-phenylmethyl}carbamic acid benzyl ester | CBZ-D(-)-phenylglycine | Ex 634 | MS (ion spray) 599.2 (M+). | |
| 277 | {[3-(9-Chloro-3-methyl-4-oxo-5H-isoxazolo[4,3-c]quinolin-5-yl)cyclohexylcarbamoyl]-phenylmethyl}carbamic acid benzyl ester | Z-Phg-OH | Ex 634 | MS (ion spray) 599.2 (M+) | |
| 278 | N-[3-(9-Chloro-3-methyl-4-oxo-5H-isoxazolo[4,3-c]quinolin-5-yl)cyclohexyl]-2-morpholin-4-yl-2-phenylacetamide | Morpholin-4-yl-phenylacetic acid | Ex 634 | MS (ion spray) 535.2 (M+) | |
| 279 | 2-(Acetyl-methyl-amino)-N-[3-(9-chloro-3-methyl-4-oxo-5H-isoxazolo[4,3-c]quinolin-5-yl)cyclohexyl]-2-phenylacetamide | (acetymethyl-amino)phenyl-acetic acid | Ex 634 | MS (ion spray) 521.2 (M+) | |
| 280 | N-[3-(9-Chloro-3-methyl-4-oxo-5H-isoxazolo[4,3-c]quinolin-5-yl)cyclohexyl]-2-phenyl-2-phenylaminoacetamide | phenylphenyl-aminoacetic acid | Ex 634 | MS (ion spray) 541.1 (M+) | |
| 281 | N-[3-(9-Chloro-3-methyl-4-oxo-5H-isoxazolo[4,3-c]quinolin-5-yl)-cyclohexyl]-2-dimethylamino-2-phenyl-acetamide | dimethylamino-phenylacetic acid | Ex 634 | MS (ion spray) 493.0 (M+) | diastereomers were separated |
| 282 | N-[3-(9-Chloro-3-methyl-4-oxo-5H-isoxazolo[4,3-c]quinolin-5-yl)cyclohexyl]-2-phenyl-2-thiomorpholin-4-ylacetamide | phenylthio-morpholin-4-ylacetic acid | Ex 634 | MS (ion spray) 550.9 (M+) | |
| 283 | N-[3-(9-Chloro-3-methyl-4-oxo-5H-isoxazolo[4,3-c]quinolin-5-yl)cyclohexyl]-2-(4-methylpiperazin-1-yl)-2-phenylacetamide | (4-methyl-piperazin-1-yl)phenyl-acetic acid | Ex 634 | MS (ion spray) 548.2 (M+) | |
| 284 | 2-(4-Acetylpiperazin-1-yl)-N-[3-(9-chloro-3-methyl-4-oxo-5H-isoxazolo[4,3-c]quinolin-5-yl)cyclohexyl]-2-phenyl-acetamide | (4-acetyl-piperazin-1-yl)-phenylacetic acid | Ex 634 | MS (ion spray) 576.2 (M+) | |
| 285 | N-[3-(9-Chloro-3-methyl-4-oxo-5H-isoxazolo[4,3-c]quinolin-5-yl)cyclohexyl]-2-(indan-2-ylamino)-2-phenylacetamide | (indan-2-yl-amino)-phenylacetic acid | Ex 634 | MS (ion spray) 581.0 (M+) | diastereomers were separated |

| Ex. # | Product | Starting Material A | Starting Material B | Physical Data | Comments |
|---|---|---|---|---|---|
| 286 | N-[3-(9-Chloro-3-methyl-4-oxo-5H-isoxazolo[4,3-c]quinolin-5-yl)cyclohexyl]-2-hydroxy-2-phenylpropionamide | (S)-(+)-2-hydroxy-2-phenylpropionic acid | Ex 634 | MS (ion spray) 480.13 (M+) | |
| 287 | N-[3-(9-Chloro-3-methyl-oxo-5H-isoxazolo[4,3-c]quinolin-5-yl)-cyclohexyl]-2-hydroxy-2-phenyl-propionamide | (R)-(−)-2-hydroxy-2-phenylpropionic acid | Ex 634 | MS (ion spray) 480.1 (M+) | |
| 288 | N-[3-(9-Chloro-3-methyl-4-oxo-5H-isoxazolo[4,3-c]quinolin-5-yl)cyclohexyl]-2-hydroxy-2-(3-methoxyphenyl)acetamide | m-methoxy-mandelic acid | Ex 634 | MS (ion spray) 496.1 (M+) | diastereomers were separated |
| 289 | N-[3-(9-Chloro-3-methyl-4-oxo-5H-isoxazolo[4,3-c]quinolin-5-yl)-cyclohexyl]-2-hydroxy-2-(4-methoxyphenyl)acetamide | p-methoxy-mandelic acid | Ex 634 | MS (ion spray) 496.1 (M+) | diastereomers were separated |
| 290 | N-[3-(9-Chloro-3-methyl-4-oxo-5H-isoxazolo[4,3-c]quinolin-5-yl)cyclohexyl]-2-hydroxy-2-(4-trifluoromethylphenyl)-acetamide | p-trifluoromethylmandelic acid | Ex 634 | MS (ion spray) 534.0 (M+) | diastereomers were separated |
| 291 | N-[3-(9-Chloro-3-methyl-4-oxo-5H-isoxazolo[4,3-c]quinolin-5-yl)cyclohexyl]-2-hydroxy-3-phenylpropionamide | D-3-phenyl-lactic acid | Ex 634 | MS (ion spray) 480.2 (M+) | |
| 292 | N-[3-(9-Chloro-3-methyl-4-oxo-5H-isoxazolo[4,3-c]quinolin-5-yl)-cyclohexyl]-2-hydroxy-3-phenyl-propionamide | L-3-phenyl-lactic acid | Ex 634 | MS (ion spray) 480.0 (M+) | |
| 293 | N-[3-(9-Chloro-3-methyl-4-oxo-5H-isoxazolo[4,3-c]quinolin-5-yl)-cyclohexyl]-3-hydroxy-2-phenyl-propionamide | DL-tropic acid | Ex 634 | MS (ion spray) 480.1 (M+). | diastereomers were separated |
| 294 | N-[3-(9-Chloro-3-methyl-4-oxo-5H-isoxazolo[4,3-c]quinolin-5-yl)-cyclohexyl]-2-(3-chloro-phenyl)-2-hydroxyacetamide | (R)-(−)-3-chloro-mandelic acid | Ex 634 | MS (ion spray) 500.1 (M+) | |
| 295 | N-[3-(9-Chloro-3-methyl-4-oxo-5H-isoxazolo[4,3-c]quinolin-5-yl)-cyclohexyl]-2-(3-chloro-phenyl)-2-hydroxyacetamide | racemic 3-chloromandelic acid | Ex 634 | MS (ion spray) 500.1 (M+) | diastereomers were separated by radial EDPLC |
| 296 | N-[3-(9-Chloro-3-methyl-4-oxo-5H-isoxazolo[4,3-c]quinolin-5-yl)-cyclohexyl]-2-hydroxy-2-m-tolylacetamide | hydroxy-m-tolylacetic acid | Ex 634 | MS (ion spray) 480.0 (M+) | diastereomers were separated |
| 297 | N-[3-(9-Chloro-3-methyl-4-oxo-5H-isoxazolo[4,3-c]quinolin-5-yl)-cyclohexyl]-2-(2-fluoro-phenyl)-2-hydroxyacetamide | (2-Fluoro-phenyl)-hydroxy-acetic acid | Ex 634 | MS (ion spray) 480.0 (M+) | diastereomers were separated |

| Ex. # | Product | Starting Material A | Starting Material B | Physical Data | Comments |
|---|---|---|---|---|---|
| 298 | N-[3-(9-Chloro-3-methyl-4-oxo-5H-isoxazolo[4,3-c]quinolin-5-yl)-cyclohexyl]-2-hydroxy-2,2-diphenylacetamide | benzylic acid | Ex 634 | MS (ion spray) 542 (M+) | |
| 299 | N-[3-(9-Chloro-3-methyl-4-oxo-5H-isoxazolo[4,3-c]quinolin-5-yl)cyclohexyl]-2-phenyliso-butyramide | dimethylphenyl acetic acid | Ex 634 | MS (ion spray) 478.1 (M+) | |
| 300 | 1-Phenylcyclopropanecarboxylic acid [3-(9-chloro-3-methyl-4-oxo-5H-isoxazolo[4,3-c]-quinolin-5-yl)cyclohexyl]amide | 1-phenyl-1-cyclopropyl-acetic acid | Ex 634 | MS (ion spray) 476.1 (M+) | |
| 301 | N-[3-(9-Chloro-3-methyl-4-oxo-5H-isoxazolo[4,3-c]quinolin-5-yl)cyclohexyl]-2-fluoro-2-phenylacetamide | α-fluoro-phenylacetic acid | Ex 634 | MS (ion spray) 468.1 (M+) | |
| 302 | N-[3-(9-Chloro-3-methyl-4-oxo-5H-isoxazolo[4,3-c]quinolin-5-yl)cyclohexyl]-2,2-difluoro-2-phenylacetamide | difluorophenyl-acetic acid | Ex 634 | MS (ion spray) 486.1 (M+) | |
| 303 | N-[3-(9-Chloro-3-methyl-4-oxo-5H-isoxazolo[4,3-c]quinolin-5-yl)cyclohexyl]-2-phenyl-2-phenylsulfanyl-acetamide | phenylphenylth-ioacetic acid (Lancaster) | Ex 634 | MS (ion spray) 558.0 (M+). | |
| 304 | N-[3-(9-Chloro-3-methyl-4-oxo-5H-isoxazolo[4,3-c]quinolin-5-yl)cyclohexyl]-2-phenyl-propionamide | (R)-(−)-2-phenyl-propionic acid | Ex 634 | (ion spray) 464.2 (M+) | |
| 305 | N-[3-(9-Chloro-3-methyl-4-oxo-5H-isoxazolo[4,3-c]quinolin-5-yl)cyclohexyl]-2-phenylpropionamide | (S)-(+)-2-phenylpropionic acid | Ex 634 | MS (ion spray) 464.2 (M+) | |
| 306 | 1-Phenylcyclohexanecarboxylic acid [3-(9-chloro-3-methyl-4-oxo-5H-isoxazolo[4,3-c]quinolin-5-yl)]amide | 1-phenyl-1-cyclohexane carboxylic acid (Acros) | Ex 634 | MS (ion spray) 518.2 (M+) | |
| 307 | N-[3-(9-Chloro-3-methyl-4-oxo-5H-isoxazolo[4,3-c]quinolin-5-yl)cyclohexyl]-2-methylsulfanyl-2-phenylacetamide | α-S-methyl-phenylacetic acid | Ex 634 | MS (ion spray) 495.9 (M+) | |
| 308 | Bicyclo[4.2.0]octa-1(6),2,4-triene-7-carboxylic acid [3-(9-chloro-3-methyl-4-oxo-5H-isoxazolo[4,3-c]quinolin-5-yl)-cyclohexyl]amide | 1-benzocyclo-butenecarboxylic acid | Ex 634 | MS (ion spray) 461.9 (M+) | |
| 309 | {2-[3-(9-Chloro-3-methyl-4-oxo-5H-isoxazolo[4,3-c]quinolin-5-yl)cyclohexylcarbamoyl]indan- | N-BOC-2-ardnoindane-2-carboxylic acid | Ex 634 | MS (ion spray) 491 (M − BOC) | |

-continued

| Ex. # | Product | Starting Material A | Starting Material B | Physical Data | Comments |
|---|---|---|---|---|---|
| 310 | 2-yl]carbamicacid t-butyl ester 3-oxo-indan-1-carboxylic acid [3-(9-chloro-3-methyl-4-oxo-5H-isoxazolo[4,3-c]quinolin-5-yl)cyclohexyl]amide | 3-oxo-1-indancarboxylic acid | Ex 634 | MS (ion spray) 489.9 (M+) | |
| 311 | 3-(9-Chloro-3-methyl-4-oxo-5H-isoxazolo[4,3-c]quinolin-5-yl)cyclohexylcarbamoyl]-3,4-dihydro-1H-isoquinoline-2-carboxylic acid t-butyl ester | N-t-BOC-L-1,2,3,4-tetrahydroisoquinoline-3-carboxylic acid (Sigma) | Ex 634 | MS (ion spray) 591.2 (M+) | |
| 312 | 3-(9-Chloro-3-methyl-4-oxo-5H-isoxazolo[4,3-c]quinolin-5-yl)cyclohexylcarbamoyl]-3,4-dihydro-1H-isoquinoline-2-carboxylic acid t-butyl ester | N-t-BOC-D-1,2,3,4-tetrahydroisoquinoline-3-carboxylic acid (BAChem) | Ex 634 | MS (ion spray) 591.3 (M+) | |
| 313 | N-[3-(9-Chloro-3-methyl-4-oxo-5H-isoxazolo[4,3-c]quinolin-5-yl)-cyclohexyl]-6-fluoronicotinamide | 6-fluoro-nicotinic acid | Ex 634 | MS (ion spray) 455.0 (M+) | |
| 314 | 3-[3-(9-Chloro-3-methyl-4-oxo-5H-isoxazolo[4,3-c]quinolin-5-yl)cyclohexylcarbamoyl]-azetidine-1-carboxylic acid t-butyl ester | BOC-azetidine-3-carboxylic acid | Ex 634 | MS (ion spray) 415.08 (M+−BOC). | |
| 315 | 2-[3-(9-Chloro-3-methyl-4-oxo-5H-isoxazolo[4,3-c]quinolin-5-yl)cyclohexyl-carbamoyl]-pyrrolidine-1-carboxylic acid t-butyl ester | N-t-BOC-D-proline | Ex 634 | MS (ion spray) 529.2 (M+). | |
| 316 | N-[3-(9-Chloro-3-methyl-4-oxo-5H-isoxazolo[4,3-c]quinolin-5-yl)-cyclohexyl]-2-hydroxy-3,3-dimethyl-butyramide | (S)-(+)-2-hydroxy-3,3-dimethyl-butyric acid | Ex 634 | MS (ion spray) 446.2 (M+) | |
| 317 | N-[3-(9-Chloro-3-methyl-4-oxo-5H-isoxazolo[4,3-c]quinolin-5-yl)-cyclohexyl]-2-cyclohexyl-2-hydroxyacetamide | (L)-(+)-hexahydro-mandelic acid | Ex 634 | MS (ion spray) 472.2 (M+) | |
| 318 | N-[3-(9-Chloro-3-methyl-4-oxo-5H-isoxazolo[4,3-c]quinolin-5-yl)-cyclohexyl]-2-cyclohexyl-2-hydroxyacetamide | (R)-(−)-hexahydro-mandelic acid | Ex 634 | MS (ion spray) 472.2 (M+) | |
| 319 | N-[3-(9-Chloro-3-methyl-4-oxo-5H-isoxazolo[4,3-c]quinolin-5-yl)-cyclohexyl]-3,3,3-trifluoro-2-hydroxy-propionamide | 3,3,3-trifluoro-lactic acid | Ex 634 | MS (ion spray) 480.0 (M+) | diastereomers were separated |

| Ex. # | Product | Starting Material A | Starting Material B | Physical Data | Comments |
|---|---|---|---|---|---|
| 320 | N-[3-(9-Chloro-3-methyl-4-oxo-5H-isoxazolo[4,3-c]quinolin-5-yl)-cyclohexyl]-2-hydroxy-2-methyl-propionamide | 2-methyllactic acid | Ex 634 | MS (ion spray) 417.9 (M+) | |
| 321 | [1-({[3-(9-chloro-3-methyl-4-oxo-5H-isoxazolo[4,3-c]quinolin-5-yl)-cyclohexyl-carbamoyl]-phenylmethyl}-carbamoyl)-1-methylethyl]-carbamic acid t-butylester | N-t-butyl-αx-aminoisobutyric acid | Ex 638 | MS(ES) [M + H]$^+$ = 650.2 m/z | |
| 322 | Pyridine-2-carboxylic acid {[3-(9-chloro-3-methyl-4-oxo-5H-isoxazolo[4,3-c]quinolin-5-yl)-cyclohexyl-carbamoyl]-phenyl-methyl}-amide | pyridine-2-carboxylic acid | Ex 638 | MS(ES) [M + H]$^+$ = 570.2 m/z | |
| 323 | Pyridine-3-carboxylic acid {[3-(9-chloro-3-methyl-4-oxo-5H-isoxazolo[4,3-c]-quinolin-5-yl)-cyclohexyl-carbamoyl]-phenyl-methyl}-amide | pyridine-3-carboxylic acid | Ex 638 | MS(ES) [M + H]$^+$ = 570.2 m/z | |
| 324 | Pyridine-4-carboxylic acid {[3-(9-chloro-3-methyl-4-oxo-5H-isoxazolo[4,3-c]-quinolin-5-yl)-cyclohexyl-carbamoyl]-phenyl-methyl}-amide | pyridine-4-carboxylic acid | Ex 638 | MS(ES) [M + H]$^+$ = 570.2 m/z | |
| 325 | N-[3-(9-chloro-3-methyl-4-oxo-5H-isoxazolo[4,3-c]quinolin-5-yl)-cyclohexyl]-2-[1,2,4]triazol-1-yl-isobutyramide | 2-Methyl-2-[1,2,4]-triazol-1-yl-propionic acid | Ex 634 | MS(ES) exact mass calc'd: [M + H]$^+$ = 469.1755 m/z. | |
| 326 | {[3-(9-chloro-3-methyl-4-oxo-5H-isoxazolo[4,3-c]quinolin-5-yl)-cyclohexylcarbamoyl]-pyridin-3-yl-methyl}-carbamic acid t-butyl ester | t-butoxy-carbonylamino-pyridin-3-ylacetic acid | Ex 634 | MS(ES) calc'd: [M + H]$^+$ = 565.20 m/z; [M + Na]$^+$ = 588.20 m/z. | |
| 327 | N-[3-(9-Chloro-3-methyl-4-oxo-5H-isoxazolo[4,3-c]quinolin-5-yl)-cyclohexyl]-2-hydroxy-acetamide | glycolic acid | Ex 634 | MS (ion spray) 389.9 (M+) | racemic cis |
| 328 | N-[3-(9-Chloro-3-methyl-4-oxo-5H-isoxazolo[4,3-c]quinolin-5-yl)-cyclohexyl]-2-hydroxy-3-methyl-butyramide | D-alpha-hydroxyisovaleric acid | Ex 634 | MS (ion spray) 431.9 (M+) | racemic cis |
| 329 | N-[3-(9-Chloro-3-methyl-4-oxo-5H-isoxazolo[4,3-c]quinolin-5-yl)-cyclohexyl]-3-hydroxy-3-phenyl-propionamide | (S)-3-hydroxy-3-phenyl-propionic acid | Ex 634 | MS (ion spray) 480.1 (M+) | racemic cis |

| Ex. # | Product | Starting Material A | Starting Material B | Physical Data | Comments |
|---|---|---|---|---|---|
| 330 | N-[3-(9-Chloro-3-methyl-4-oxo-5H-isoxazolo[4,3-c]quinolin-5-yl)-cyclohexyl]-3-hydroxy-3-phenyl-propionamide | (R)-3-hydroxy-3-phenyl-propionic acid | Ex 634 | MS (ion spray) 480.1 (M+) racemic cis | |
| 331 | N-[3-(9-Chloro-3-methyl-4-oxo-5H-isoxazolo[4,3-c]quinolin-5-yl)-cyclohexyl]-2-hydroxy-3-methylbutyramide | (S)-(+)-2-hydroxy-3-methyl-butyric acid | Ex 634 | MS (ion spray) 431.9 (M+) racemic cis | |
| 332 | 1-Hydroxy-cyclopropanecarboxylic acid [3-(9-chloro-3-methyl-4-oxo-5H-isoxazolo[4,3-c]quinolin-5-yl)-cyclohexyl]-amide | 1-hydroxy-1-cyclopropane-carboxylic acid | Ex 634 | MS (ion spray) 416.0 (M+) racemic cis | |
| 333 | {[3-(9-Chloro-3-methyl-4-oxo-5H-isoxazolo[4,3-c]quinolin-5-yl)-cyclohexylcarbamoyl]-methyl}-methyl-carbamic acid t-butyl ester | N-t-BOC-sarcosine | Ex 634 | MS (ion spray) 503.2 (M+) racemic cis | |
| 334 | N-[3-(9-Chloro-3-methyl-4-oxo-5H-isoxazolo[4,3-c]quinolin-5-yl)-cyclohexyl]-2-dimethylamino-acetamide | N,N-dimethyl-glycine | Ex 634 | MS (ion spray) 416.9 (M+) racemic cis | |
| 335 | {1-[3-(9-Chloro-3-methyl-4-oxo-5H-isoxazolo[4,3-c]quinolin-5-yl)-cyclohexylcarbamoyl]-1-methyl-ethyl}-carbamic acid t-butyl ester | N-t-BOC-α-aminoiso-butyric acid | Ex 634 | MS (ion spray) 516.9 (M+) racemic cis | |
| 336 | {[3-(9-Chloro-3-methyl-4-oxo-5H-isoxazolo[4,3-c]quinolin-5-yl)-cyclohexylcarbamoyl]-methyl}-carbamic acid t-butyl ester | N-t-butoxycar-bonylglycine | Ex 634 | MS (ion spray) 489.1 (M+) racemic cis | |
| 337 | 2-Hydroxy-hexanoic acid [3-(9-chloro-3-methyl-4-oxo-5H-isoxazolo[4,3-c]quinolin-5-yl)-cyclohexyl]-amide | 2-hydroxy-caproic acid | Ex 634 | MS (ion spray) 446.2 (M+) racemic cis | diastereomers were separated |
| 338 | N-[3-(9-Chloro-3-methyl-4-oxo-5H-isoxazolo[4,3-c]quinolin-5-yl)-cyclohexyl]-2-hydroxybenzamide | salicylic acid | Ex 634 | MS (ion spray) 452.0 (M+) racemic cis | |
| 339 | 4-{[3-(9-Chloro-3-methyl-4-oxo-5H-isoxazolo[4,3-c]quinolin-5-yl)-cyclohexylcarbamoyl]-phenyl-methyl}-piperazine-1-carboxylic acid t-butyl ester | prep 285 | Ex 634 | MS (ion spray) 633.9 (M+) racemic cis | |
| 340 | {[3-(9-Chloro-3-methyl-4-oxo-5H-isoxazolo[4,3-c]quinolin- | BOC-N-Me-Phg-OH | Ex 634 | MS (ion spray) 578.9 (M+) | |

-continued

| Ex. # | Product | Starting Material A | Starting Material B | Physical Data | Comments |
|---|---|---|---|---|---|
| | 5-yl)-cyclohexyl]carbamoyl]-phenyl-methyl]-methyl-carbamic acid t-butyl ester | | | racemic cis | |
| 341 | N-[3-(9-Chloro-3-methyl-4-oxo-5H-isoxazolo[4,3-c]quinolin-5-yl)-cyclohexyl]-2-[4-(2-hydroxy-ethyl)-piperazin-1-yl]-2-phenyl-acetamide | prep 287 | Ex 634 | MS (ion spray) 578.1 (M+) racemic cis | diastereomers were separated |
| 342 | N-[3-(9-Chloro-3-methyl-4-oxo-5H-isoxazolo[4,3-c]quinolin-5-yl)-cyclohexyl]-2-phenyl-2-(4-pyridin-2-yl-piperazin-1-yl)-acetamide | prep 288 | Ex 634 | MS (ion spray) 610.9 (M+) racemic cis | diastereomers were separated |
| 343 | N-[3-(9-Chloro-3-methyl-4-oxo-5H-isoxazolo[4,3-c]quinolin-5-yl)-cyclohexyl]-2-piperidin-1-yl-acetamide | prep 290 | Ex 634 | MS (ion spray) 457.1 (M+) racemic cis | |
| 344 | N-[3-(9-Chloro-3-methyl-4-oxo-5H-isoxazolo[4,3-c]quinolin-5-yl)-cyclohexyl]-2-(4-methyl-piperazin-1-yl)-acetamide | prep 292 | Ex 634 | MS (ion spray) 472.0 (M+) racemic cis | |
| 345 | N-[3-(9-Chloro-3-methyl-4-oxo-5H-isoxazolo[4,3-c]quinolin-5-yl)-cyclohexyl]-2-diethylamino-acetamide | N,N-diethyl-glycine sodium salt | Ex 634 | MS (ion spray) 445.0 (M+) | |
| 346 | N-[3-(9-Chloro-3-methyl-4-oxo-5H-isoxazolo[4,3-c]quinolin-5-yl)-cyclohexyl]-2-(methyl-phenyl-amino)-acetamide | prep 293 | Ex 634 | MS (ion spray) 479.0 (M+) racemic cis | |
| 347 | N-[3-(9-Chloro-3-methyl-4-oxo-5H-isoxazolo[4,3-c]quinolin-5-yl)-cyclohexyl]-2-phenyl-2-(pyridin-3-yloxy)-acetamide | prep 294 | Ex 634 | MS (ion spray) 543.0 (M+) | |
| 348 | N-[3-(9-Chloro-3-methyl-4-oxo-5H-isoxazolo[4,3-c]quinolin-5-yl)-cyclohexyl]-2-(pyridin-3-yloxy)-acetamide | prep 296 | Ex 634 | MS (ion spray) 467.1 (M+) | |
| 349 | {1-[3-(9-Chloro-3-methyl-4-oxo-5H-isoxazolo[4,3-c]quinolin-5-yl)-cyclohexyl]carbamoyl]-cyclohexyl}-carbamic acid t-butyl ester | prep 297 | Ex 634 | MS (ion spray) 557.2 (M+) | |
| 350 | N-[3-(9-Chloro-3-methyl-4-oxo-5H-isoxazolo[4,3-c]quinolin-5-yl)-cyclohexyl]-2-morpholin-4-yl-acetamide | prep 299 | Ex 634 | MS (ion spray) 459.0 (M+) | |
| 351 | N-[3-(9-Chloro-3-methyl-4-oxo- | prep 301 | Ex 634 | MS (ion spray) | |

-continued

| Ex. # | Product | Starting Material A | Starting Material B | Physical Data | Comments |
|---|---|---|---|---|---|
|  | 5H-isoxazolo[4,3-c]quinolin-5-yl)-cyclohexyl]-2-(4-hydroxy-piperidin-1-yl)-acetamide |  |  | 473.1 (M+) |  |
| 352 | N-[3-(9-Chloro-3-methyl-4-oxo-5H-isoxazolo[4,3-c]quinolin-5-yl)-cyclohexyl]-2-(2-oxo-2H-pyridin-1-yl)-acetamide | prep 303 | Ex 634 | MS (ion spray) 467.1 (M+) |  |
| 353 | N-[3-(9-Chloro-3-methyl-4-oxo-5H-isoxazolo[4,3-c]quinolin-5-yl)-cyclohexyl]-2-(pyridin-4-yloxy)-acetamide | prep 304 | Ex 634 | MS (ion spray) 467.0 (M+) |  |
| 354 | N-[3-(9-Chloro-3-methyl-4-oxo-5H-isoxazolo[4,3-c]quinolin-5-yl)-cyclohexyl]-2-(pyridin-4-ylsulfanyl)-acetamide | (4-pyridyl-thio)-acetic acid | Ex 634 | MS (ion spray) 483.1 (M+) |  |
| 355 | {[3-(9-Chloro-3-methyl-4-oxo-5H-isoxazolo[4,3-c]quinolin-5-yl)-cyclohexylcarbamoyl]-cyclohexyl-methyl}-carbamic acid t-butyl ester | N-t-BOC-D-α-cyclohexyl-glycine | Ex 634 | MS (ion spray) 571.2 (M+) |  |
| 356 | {[3-(9-Chloro-3-methyl-4-oxo-5H-isoxazolo[4,3-c]quinolin-5-yl)-cyclohexylcarbamoyl]-cyclohexyl-methyl}-carbamic acid t-butyl ester | N-t-BOC-L-α-cyclohexyl-glycine | Ex 634 | MS (ion spray) 571.2 (M+) |  |
| 357 | Thieno[3,2-b]pyridine-2-carboxylic acid[3-(9-chloro-3-methyl-4-oxo-5H-isoxazolo[4,3-c]quinolin-5-yl)-cyclohexyl]-amide | thieno[3,2-b]pyridine-2-carboxylic acid | Ex 634 | MS (ion spray) 493.0 (M+). |  |
| 358 | N-[3-(9-Chloro-3-methyl-4-oxo-5H-isoxazolo[4,3-c]quinolin-5-yl)-cyclohexyl]-2-(2-chloro-pyridin-4-yloxy)-acetamide | thieno[3,2-b]pyridine-2-carboxylic acid | Ex 634 | MS (ion spray) 501.0 (M+) |  |
| 359 | N-[3-(9-Chloro-3-methyl-4-oxo-5H-isoxazolo[4,3-c]quinolin-5-yl)-cyclohexyl]-2-(quinolin-3-yloxy)-acetamide | (quinolin-3-yloxy)acetic acid HCl (SALOR) prep 305 | Ex 634 | MS (ion spray) 517.2 (M+) |  |
| 360 | 2-t-Butylamino-N-[3-(9-chloro-3-methyl-4-oxo-5H-isoxazolo[4,3-c]quinolin-5-yl)-cyclohexyl]-acetamide |  | Ex 634 | MS (ion spray) 445.1 (M+) |  |
| 361 | N-[3-(9-Chloro-3-methyl-4-oxo-5H-isoxazolo[4,3-c]quinolin-5-yl)-cyclohexyl]-2-(pyridin-2-ylsulfanyl)-acetamide | (pyridin-2-ylsulfanyl)-acetic acid (Maybridge) | Ex 634 | MS (ion spray) 483.1 (M+) |  |
| 362 | N-[3-(9-Chloro-3-methyl-4-oxo-5H-isoxazolo[4,3-c]quinolin- | trans-3-(3-pyridyl)- | Ex 634 | MS (ion spray) 463.1 (M+) |  |

-continued

| Ex. # | Product | Starting Material A | Starting Material B | Physical Data | Comments |
|---|---|---|---|---|---|
| 363 | N-[3-(9-Chloro-3-methyl-4-oxo-5H-isoxazolo[4,3-c]quinolin-5-yl)-cyclohexyl]-3-pyridin-2-yl-acrylamide | trans-3-Pyridin-2-yl-acrylic acid | Ex 634 | MS (ion spray) 463.1 (M+) | |
| 364 | N-[3-(9-Chloro-3-methyl-4-oxo-5H-isoxazolo[4,3-c]quinolin-5-yl)-cyclohexyl]-3-pyridin-4-yl-acrylamide | trans-3-(4-pyridyl)-acrylic acid | Ex 634 | MS (ion spray) 463.0 (M+) | |
| 365 | {1-[3-(9-Chloro-3-methyl-4-oxo-5H-isoxazolo[4,3-c]quinolin-5-yl)-cyclohexylcarbamoyl]-2-hydroxy-ethyl}-carbamic acid t-butyl ester | N-t-BOC-L-Serine | Ex 634 | MS (ion spray) 519.0 (M+) | |
| 366 | {1-[3-(9-Chloro-3-methyl-4-oxo-5H-isoxazolo[4,3-c]quinolin-5-yl)-cyclohexylcarbamoyl]-2-hydroxy-ethyl}-carbamic acid t-butyl ester | N-t-BOC-D-Serine | Ex 634 | MS (ion spray) 519.0 (M+) | |
| 367 | N-[3-(9-Chloro-3-methyl-4-oxo-5H-isoxazolo[4,3-c]quinolin-5-yl)-cyclohexyl]-2(6-methoxy-pyridin-3-yl)amino)-acetamide | prep 306 | Ex 634 | MS (ion spray) 496.2 (M+) | |
| 368 | N-[3-(9-Chloro-3-methyl-4-oxo-5H-isoxazolo[4,3-c]quinolin-5-yl)-cyclohexyl]-2-(pyridin-3-yloxy)-propionamide | prep 307 | Ex 634 | MS (ion spray) 481.2 (M+) | |
| 369 | N-[3-(9-Chloro-3-methyl-4-oxo-5H-isoxazolo[4,3-c]quinolin-5-yl)-cyclohexyl]-2-(pyridin-2-yloxy)-acetamide | (pyridin-2-yloxy) acetic acid | Ex 634 | MS (ion spray) 467.0 (M+) | |
| 370 | {1-[3-(9-Chloro-3-methyl-4-oxo-5H-isoxazolo[4,3-c]quinolin-5-yl)-cyclohexylcarbamoyl]-2-phenyl-ethyl}-carbamic acid t-butyl ester | N-BOC-L-phenyl-alanine | Ex 634 | MS (ion spray) 579.2 (M+) | |
| 371 | N-[3-(9-Chloro-3-methyl-4-oxo-5H-isoxazolo[4,3-c]quinolin-5-yl)-cyclohexyl]-2-hydroxy-2,2-diphenyl-acetamide | benzylic acid | Ex 634 | MS (ion spray) 542 (M+) | |
| 372 | N-[3-(9-Chloro-3-methyl-4-oxo-5H-isoxazolo[4,3-c]quinolin-5-yl)-cyclohexyl]-2-(9H-fluoren-9-yl)-2-hydroxy-acetamide | 9-hydroxy-9-fluorene-carboxylic acid | Ex 634 | MS (ion spray) 540.1 (M+) | |
| 373 | N-[3R-Chloro-3-methyl-4-oxo-5H-isoxazolo[4,3-c]quinolin-5-yl)R-cycloheptyl-methyl]-6-fluoro-nicotinamide | 6-fluoro-nicotinic acid | prep 137 | MS(ES+)m/z = 483.1 | |

| Ex. # | Product | Starting Material A | Starting Material B | Physical Data | Comments |
|---|---|---|---|---|---|
| 374 | 2-(Benzenesulfonyl-pyridin-2-yl-amino)-N-[3-(9-chloro-3-methyl-4-oxo-5H-isoxazolo[4,3-c]quinolin-5-yl)-cyclohexyl]-acetamide | (benzenesulf-onylpyridin-2-yl-amino) acetic acid (Bionet) | prep 137 | MS (ion spray) 606.1 (M+) | |
| 375 | 2-Chloro-N-[3-(9-chloro-3-methyl-4-oxo-5H-isoxazolo[4,3-c]quinolin-5-yl)-cyclohexylmethyl]-6-methoxy-isonicotinamide | prep 355 | 2-chloro-6-meth-oxy-pyridine-4-carboxylic acid | MS (ion spray) 514.8 (M+) | |
| 376 | 1-Methyl-piperidine-3-carboxylic acid [3-(9-chloro-3-methyl-4-oxo-5H-isoxazolo[4,3-c]quinolin-5-yl)-cyclohexylmethyl]-amide | prep 355 | prep 357 | MS (ion spray) 471.2 (M+) | |
| 377 | 3-[[3-(9-Chloro-3-methyl-4-oxo-5H-isoxazolo[4,3-c]quinolin-5-yl)-cyclohexylmethyl]-carbamoyl]-piperidine-1-carboxylic acid tert-butyl ester | prep 355 | prep 358 | MS (ion spray) 557.2 (M+) | |
| 378 | N-[3-(9-Chloro-3-methyl-4-oxo-5H-isoxazolo[4,3-c]quinolin-5-yl)-cyclohexyl]-2-(1-methyl-7H-indol-3-yl)-acetamide | prep 69 | 1-methyl-3-indoleacetic acid | MS (ion spray) 503.3 (M+) | |
| 379 | 2-(Pyridin-3-yloxy)-hexanoic acid [3-(9-chloro-3-methyl-4-oxo-5H-isoxazolo[4,3-c]quinolin-5-yl)-cyclohexyl]-amide | prep 362 | prep 357 | MS (ion spray) 523.3 (M+) | |
| 380 | N-[3-(9-Chloro-3-methyl-4-oxo-5H-isoxazolo[4,5-c]quinolin-5-yl)-cyclohexyl]-2-hydroxy-2-phenyl-acetamide | prep 380 | R-Madelic acid | MS (ES+) m/z 466.1 (M + H)+, (ES−) 464.2 (M − H)− | |
| 381 | N-[3-(9-Chloro-3-methyl-4-oxo-5H-isoxazolo[4,5-c]quinolin-5-yl)-cyclohexyl]-2-(3-fluorophenyl)acetamide | prep 380 | 3-Fluoro-phenylacetic acid | MS (ES+) m/z 468.1 (M + H)+, (ES−) 466.2 (M − H)− | |
| 382 | N-[(1S,3R)-3-(9-Chloro-3-methyl-4-oxo-5H-isoxazolo[4,3-c]quinolin-5-yl)-cyclohexyl-methyl]-4-phenyl-butanamide | phenyl-butyric acid | Prep 44 | MS (ion spray) 492.2 (M+) | |
| 383 | N-[(1S,3R)-3-(9-Chloro-3-methyl-4-oxo-5H-isoxazolo[4,3-c]quinolin-5-yl)-cyclohexyl-methyl]-4-oxo-4-phenyl-butanamide | 3-benzoyl-propionic acid | Prep 44 | MS (ion spray) 506.2 (M+) | |
| 384 | N-[(1S,3R)-3-(9-Chloro-3-methyl-4-oxo-5H-isoxazolo[4,3-c]quinolin-5-yl)-cyclohexyl-methyl]-3-(4-hydroxy-phenyl)- | 3-(4-hydroxy-phenyl)-propionic acid | Prep 44 | MS (ion spray) 494.2 (M + 1) | |

| Ex. # | Product | Starting Material A | Starting Material B | Physical Data | Comments |
|---|---|---|---|---|---|
| 385 | N-[(1S,3R)-3-(9-chloro-3-methyl-4-oxo-5H-isoxazolo[4,3-c]quinolin-5-yl)cyclohexyl-methyl]-3-(1H-indol-3-yl)-propanamide | 3-indole-propionic acid | Prep 44 | MS (ion spray) 516.9 (M+) | |
| 386 | N-[(1S,3R)-3-(9-chloro-3-methyl-4-oxo-5H-isoxazolo[4,3-c]quinolin-5-yl)cyclohexyl-methyl]-2-dimethylamino-acetamide | N,N-dimethyl-glycine HCL | Prep 44 | MS (ion spray) 431.2 (M + 1) | |
| 387 | (2R)-N-[(1S,3R)-3-(9-chloro-3-methyl-4-oxo-5H-isoxazolo[4,3-c]quinolin-5-yl)cyclohexyl-methyl]-2-[t-butoxycarbonyl-amino]-3-(phenylmethoxy)-propanamide | (D)-BOC-benzyloxy-serine | Prep 44 | MS (ion spray) 523.2 (M − 100(M − BOC) | |
| 388 | (2S)-N-[(1S,3R)-3-(9-chloro-3-methyl-4-oxo-5H-isoxazolo[4,3-c]quinolin-5-yl)-cyclohexylmethyl]-2-[t-butoxycarbonyl-amino]-3-(phenylmethoxy)propanamide | (L)-BOC-benzyloxy-serine | Prep 44 | MS (ion spray) 523.0 (M − 100(M − BOC) | |
| 389 | 2-[(1R,3S)-3-(9-Chloro-3-methyl-4-oxo-5H-isoxazolo[4,3-c]quinolin-5-yl)-cyclo-hexyl]-N-cyclohexyl-acetamide | Prep 47 | cyclohexylamine | MS (ion spray) 456.2 (M + 1) | |
| 390 | 2-[(1R,3S)-3-(9-Chloro-3-methyl-4-oxo-5H-isoxazolo[4,3-c]quinolin-5-yl)-cyclo-hexyl]-N-phenyl-acetamide | Prep 47 | aniline | MS (ion spray) 448.1 (M + 1) | |
| 391 | 2-[(1R,3S)-3-(9-Chloro-3-methyl-4-oxo-5H-isoxazolo[4,3-c]quinolin-5-yl)-cyclohexyl]-N-pyridin-2-yl-acetamide | Prep 47 | 2-amino-pyridine | MS (ion spray) 451.2 (M + 1) | |
| 392 | 2-[(1R,3S)-3-(9-chloro-3-methyl-4-oxo-5H-isoxazolo[4,3-c]quinolin-5-yl)-cyclo-hexyl]-N-(3-acetyl-phenyl)acetamide | Prep 47 | 3-amino-aceto-phenone | MS (ion spray) 492.2 (M + 1) | |
| 393 | 2-[(1R,3S)-3-(9-Chloro-3-methyl-4-oxo-5H-isoxazolo[4,3-c]quinolin-5-yl)cyclohexyl]-N-(3-methanesulfonylphenyl)-acetamide | Prep 47 | 3-methane-sulf-onylaniline HCL | MS (ion spray) 528.2 (M+) | |
| 394 | 2-[(1R,3S)-3-(9-Chloro-3-methyl-4-oxo-5H-isoxazolo[4,3-c]quinolin-5-yl)-cyclohexyl]-N-(4-fluoro-phenyl)-acetamide | Prep 47 | 4-fluoro-aniline | MS (ion spray) 468.2 (M + 1) | |
| 395 | 2-[(1R,3S)-3-(9-Chloro-3-methyl-4-oxo-5H-isoxazolo[4,3- | Prep 47 | 3-fluoro-aniline | MS (ion spray) 468.2 (M + 1) | |

-continued

| Ex. # | Product | Starting Material A | Starting Material B | Physical Data | Comments |
|---|---|---|---|---|---|
| | c]quinolin-5-yl)-cyclohexyl]-N-(3-fluoro-phenyl)-acetamide | | | | |
| 396 | 2-[(1R,3S)-3-(9-Chloro-3-methyl-4-oxo-5H-isoxazolo[4,3-c]quinolin-5-yl)-cyclohexyl]-N-(3-methoxy-phenyl)-acetamide | Prep 47 | 3-methoxy-aniline | MS (ion spray) 480.2 (M + 1) | |
| 397 | N-[(1R,3S)-3-(9-chloro-3-methyl-4-oxo-5H-isoxazolo[4,3-c]quinolin-5-yl)-cyclohexyl]-3,5-dimethoxy-4-methyl-benzamide | (3,5-dimethoxy-4-methyl)-benzoic acid | Prep 48 | MS (ion spray) 524.3 (M + 1) | |
| 398 | N-[(1R,3S)-3-(9-chloro-3-methyl-4-oxo-5H-isoxazolo[4,3-c]quinolin-5-yl)-cyclohexyl-methyl]-1-methylpiperid-4-ylcarboxamide | 1-methyl-piperidine-4-carboxylic acid HCL | Prep 48 | MS (ion spray) 471.2 (M + 1) | |
| 399 | N-[(1R,3S)-3-(9-chloro-3-methyl-4-oxo-5H-isoxazolo[4,3-c]quinolin-5-yl)-cyclohexyl-methyl]-[1,2,3]thiadiazol-4-ylcarboxamide | 1,2,3-thiadiazole-4-carboxylic acid | Prep 48 | MS (ion spray) 458.1 (M + 1) | |
| 400 | 6-Chloro-N-[(1R,3S)-3-(9-chloro-3-methyl-4-oxo-5H-isoxazolo[4,3-c]quinolin-5-yl)-cyclohexyl-methyl]-nicotinamide | 6-chloroni-cotinic acid | Prep 48 | MS (ion spray) 485.1 (M+) | |
| 401 | 6-Methyl-N-[(1R,3S)-3-(9-chloro-3-methyl-4-oxo-5H-isoxazolo[4,3-c]quinolin-5-yl)-cyclohexyl-methyl]-nicotinamide | 6-methyl-nicotinic acid | Prep 48 | MS (ion spray) 465.1 (M + 1) | |
| 402 | 2-Methyl-N-[(1R,3S)-3-(9-chloro-3-methyl-4-oxo-5H-isoxazolo[4,3-c]quinolin-5-yl)-cyclohexyl-methyl]nicotinamide | 2-methylnicotinic acid | Prep 48 | MS (ion spray) 465.1 (M + 1) | |
| 403 | 2-Fluoro-N-[(1R,3S)-3-(9-chloro-3-methyl-4-oxo-5H-isoxazolo[4,3-c]quinolin-5-yl)-cyclohexyl-methyl]nicotinamide | 2-fluoroni-cotinic acid. | Prep 48 | MS (ion spray) 469.1 (M + 1) | |
| 404 | N-[(1R,3S)-3-(9-Chloro-3-methyl-4-oxo-5H-isoxazolo[4,3-c]quinolin-5-yl)-cyclohexyl-methyl]-5-fluoro-nicotinamide | 5-fluoroni-cotinic acid | Prep 48 | MS (ion spray) 469.1 (M + 1) | |
| 405 | N-[(1R,3S)-3-(9-Chloro-3-methyl-4-oxo-5H-isoxazolo[4,3-c]quinolin-5-yl)cyclohexylmethyl]-2-methylsulfanyl-nicotinamide | 2-(methylthio)-nicotinic acid | Prep 48 | MS (ion spray) 497.0 (M+) | |
| 406 | 2-Chloro-N-[(1R,3S)-3-(9-chloro-3-methyl-4-oxo-5H-isoxazolo[4,3-c]quinolin-5-yl)-cyclohexyl-methyl]isonicotine | 2-chloroiso-nicotinic acid | Ex 615 | MS (ion spray) 485.1,487.1 (M+) | |

-continued

| Ex. # | Product | Starting Material A | Starting Material B | Physical Data | Comments |
|---|---|---|---|---|---|
| 407 | N-[(1R,3S)-3-(9-chloro-3-methyl-4-oxo-5H-isoxazolo[4,3-c]quinolin-5-yl)-cyclohexylmethyl]-pyrazin-2-yl carboxamide | pyrazinecarboxylic acid | Ex 615 | MS (ion spray) 452.1 (M + 1) | |
| 408 | N-[(1R,3S)-3-(9-chloro-3-methyl-4-oxo-5H-isoxazolo[4,3-c]quinolin-5-yl)-cyclohexyl-methyl]-cinnolin-4-yl carboxamide | cinnoline-4-carboxylic acid | Ex 615 | MS (ion spray) 502.2 (M + 1) | |
| 409 | N-[(1R,3S)-3-(9-chloro-3-methyl-4-oxo-5H-isoxazolo[4,3-c]quinolin-5-yl)cyclohexylmethyl]-1-methyl-1H-pyrrol-3-yl carboxamide | M-methyl-pyrrrole-2-carboxylic acid | Ex 615 | MS (ion spray) 453.2 (M + 1) | |
| 410 | N-[(1R,3S)-3-(9-chloro-3-methyl-4-oxo-5H-isoxazolo[4,3-c]quinolin-5-yl)-cyclohexyl-methyl]-1H-pyrazol-4-yl carboxamide | 4-pyrazole-carboxylic acid | Ex 615 | MS (ion spray) 440.1 (M + 1) | |
| 411 | N-[(1R,3S)-3-(9-chloro-3-methyl-4-oxo-5H-isoxazolo[4,3-c]quinolin-5-yl)-cyclohexyl-methyl]-1H-indol-3-yl carboxamide | indole-3-carboxylic acid | Ex 615 | MS (ion spray) 489.1 (M+) | |
| 412 | N-[(1R,3S)-3-(9-chloro-3-methyl-4-oxo-5H-isoxazolo[4,3-c]quinolin-5-yl)-cyclohexyl-methyl]-1H-indol-2-yl carboxamide | indole-2-carboxylic acid | Ex 615 | MS (ion spray) 488.1 (M+) | |
| 413 | N-[(1R,3S)-3-(9-chloro-3-methyl-4-oxo-5H-isoxazolo[4,3-c]quinolin-5-yl)-cyclohexyl-methyl]-1-methyl-1H-indol-2-yl carboxamide | 1-methyl-indole-2-carboxylic acid | Ex 615 | MS (ion spray) 503.1 (M+) | |
| 414 | N-[(1R,3S)-3-(9-Chloro-3-methyl-4-oxo-5H-isoxazolo[4,3-c]quinolin-5-yl)-cyclohexyl-methyl]-1H-indol-4-yl carboxamide | indole-4-carboxylic acid | Ex 615 | MS (ion spray) 489.1 (M+) | |
| 415 | N-[(1R,3S)-3-(9-chloro-3-methyl-4-oxo-5H-isoxazolo[4,3-c]quinolin-5-yl)cyclohexylmethyl]-2-(1-methyl-1H-imidazol-4-yl)acetamide | 1-methyl-4-imidazole acetic acid hydrochloride | Ex 615 | MS (ion spray) 468 (M+), 466 (M− − 1) | |
| 416 | 3-Benzoyl-N-[(1R,3S)-3-(9-chloro-3-methyl-4-oxo-5H-isoxazolo[4,3-c]quinolin-5-yl)-cyclohexylmethyl]-benzamide | 3-benzoyl-benzoic acid | Ex 615 | MS (ion spray) 554 (M+), 552 (M− − 1) | |
| 417 | N-[(1R,3S)-3-(9-chloro-3-methyl-4-oxo-5H-isoxazolo[4,3-c]quinolin-5-yl)-cyclo-hexylmethyl]-3-phenoxy-benzamide | 3-phenoxy-benzoic acid | Ex 615 | MS (ion spray) 542 (M+), 540 (M− − 1) | |

-continued

| Ex. # | Product | Starting Material A | Starting Material B | Physical Data | Comments |
|---|---|---|---|---|---|
| 418 | N-[(1R,3S)-3-(9-chloro-3-methyl-4-oxo-5H-isoxazolo[4,3-c]quinolin-5-yl)-cyclohexylmethyl]-4-methoxythiophen-3-yl carboxamide | 4-methoxythio-phene-3-carboxylic acid | Ex 615 | MS (ion spray) 486 (M+), 484 (M− − 1) | |
| 419 | 1,2,5-Trimethyl-1H-pyrrole-3-carboxylic acid [(1R,3S)-3-(9-chloro-3-methyl-4-oxo-5H-isoxazolo[4,3-c]quinolin-5-yl)-cyclohexylmethyl]-amide | 1,2,5-trimethyl-pyrrole-3-carboxylic acid | Ex 615 | MS (ion spray) 481 (M+) | |
| 420 | N-[(1R,3S)-3-(9-chloro-3-methyl-4-oxo-5H-isoxazolo[4,3-c]quinolin-5-yl)cyclo-hexylmethyl]-6-fluoronicotinamide | 6-Fluoro-nicotinic acid | Ex 615 | MS (ion spray) 469 (M+) | |
| 421 | 2-[3-(9-chloro-3-methyl-4-oxo-5H-isoxazolo[4,3-c]quinolin-5-yl)-2,2-dimethyl-cyclobutyl]-N-(3,4,5-trimethoxyphenyl)-acetamide | Prep 63 | 3,4,5,-trimethoxy aniline | MS (ion spray) 450 (M+), 448 (M− − 1) | |
| 422 | 2-[3-(9-chloro-3-methyl-4-oxo-5H-isoxazolo[4,3-c]quinolin-5-yl)-2,2-dimethyl-cyclobutyl]-N-phenylacetamide | Prep 63 | aniline | MS (ion spray) 540 (M+), 538 (M− − 1) | |
| 423 | 2-[3-(9-Chloro-3-methyl-4-oxo-5H-isoxazolo[4,3-c]quinolin-5-yl)-2,2-dimethyl-cyclobutyl]-N-pyridin-3-ylacetamide | Prep 63 | 3-amino-pyridine | MS (ion spray) 451 (M+),449 (M− − 1) | |
| 424 | N-[3-(9-Chloro-3-methyl-4-oxo-5H-isoxazolo[4,3-c]quinolin-5-yl)cyclohexyl]-2-(3-fluorophenyl)acetamide | 3-fluoro-phenyl-acetic acid | Prep 68 | MS (ion spray) 468 (M+), 466 (M− − 1) | |
| 425 | N-[3-(9-Chloro-3-methyl-4-oxo-5H-isoxazolo[4,3-c]quinolin-5-yl)cyclohexyl]-2-(3-fluorophenyl)acetamide | 3-fluoro-phenyl-acetic acid | prep 69 | MS (ion spray) 468 (M+), 466 (M− − 1) | |
| 426 | N-[3-(9-Chloro-3-methyl-4-oxo-5H-isoxazolo[4,3-c]quinolin-5-yl)cyclohexyl]-2-pyridin-3-ylacetamide | 3-pyridyl-acetic acid HCl | prep 69 | MS (ion spray) 451 (M+),449 (M− − 1) | |
| 427 | N-[3-(9-Chloro-3-methyl-4-oxo-5H-isoxazolo[4,3-c]quinolin-5-yl)cyclohexyl]-2-pyridin-4-ylacetamide | 4-pyridyl-acetic acid HCl | prep 69 | MS (ion spray) 451 (M+),449 (M− − 1) | |
| 428 | N-[3-(9-chloro-3-methyl-4-oxo-5H-isoxazolo[4,3-c]quinolin-5-yl)cyclohexyl]-2-(1-methyl-3H-imidazol-4-yl)acetamide | 1-methyl-4-imidazol-eacetic acid HCl | prep 69 | MS (ion spray) 454 (M+), 452 (M− − 1) | |
| 429 | 2-[3-(9-chloro-3-methyl-4-oxo-5H-isoxazolo[4,3-c]quinolin- | N-BOC-(S)-(−)-indoline-2- | prep 69 | MS (ion spray) 477 (M+ − BOC + | |

| Ex. # | Product | Starting Material A | Starting Material B | Physical Data | Comments |
|---|---|---|---|---|---|
| | 5-yl)cyclohexylcarbamoyl]-2,3-dihydroindole-1-carboxylic acid t-butyl ester | carboxylic acid | | 1) | |
| 430 | [[3-(9-chloro-3-methyl-4-oxo-5H-isoxazolo[4,3-c]quinolin-5-yl)cyclohexyl-carbamoyl]-(4-fluorophenyl)methyl]carbamic acid t-butyl ester | N-BOC-L-4-fluoro-phenyl-glycine | prep 69 | MS (ion spray) 483 (M$^+$ − BOC + 1) | |
| 431 | N-[3-(9-Chloro-3-methyl-4-oxo-5H-isoxazolo[4,3-c]quinolin-5-yl)cyclohexyl]-2,2-diphenylacetamide | diphenylacetic acid | prep 69 | MS (ES) 526.2 m/z[M + H]$^+$ | |
| 432 | 2-[3-(9-Chloro-3-methyl-4-oxo-5H-isoxazolo[4,3-c]quinolin-5-yl]-N-3,4,5-trimethoxy-phenylacetamide | prep 94 | 3,4,5-trimethoxy aniline | MS (HA) m/z = 540.5 | diastereomers were separated |
| 433 | 3-(9-Chloro-3-methyl-4-oxo-5H-isoxazolo[4,3-c]quinolin-5-ylmethyl)-cyclohexane-carboxylic acid cyclobutylamide | prep 102 | cyclobutylamine | MS (ES+) (m/z) 428.1 [M + 1] | |
| 434 | 3-(9-Chloro-3-methyl-4-oxo-5H-isoxazolo[4,3-c]quinolin-5-ylmethyl)-cyclohexane-carboxylic acid cyclohexylamide | prep 102 | cyclohexylamine | Mass Spectrum (FIA) (m/z) 456.3 [M + 1] | |
| 435 | 3-(9-Chloro-3-methyl-4-oxo-5H-isoxazolo[4,3-c]quinolin-5-ylmethyl)-cyclohexane-carboxylic acid phenylamide | prep 102 | aniline | MS (FIA) (m/z) 448.1 [M − 1] | |
| 436 | 3-(9-Chloro-3-methyl-4-oxo-5H-isoxazolo[4,3-c]quinolin-5-ylmethyl)-cyclohexanecarboxylic acid pyridin-2-ylamide | prep 102 | 3-aminopyridine | Mass Spectrum (FIA) (m/z) 451.1 [M + 1] | |
| 437 | N-(3,4,5-trimethoxyphenyl)[3-methyl-4-oxo-9-chloro-5H-isoxazolo[4,3-c]quinolin-5-yl)cyclohexyl]amide | prep 120 | trimethoxyaniline | MS (ion spray) 526.2 (M + 1) | diastereomers were separated |
| 438 | 2-[3-(9-chloro-3-methyl-4-oxo-5H-isoxazolo[4,3-c]quinolin-5-yl)-cyclohexyl]-N-phenyl-acetamide | prep 145 | aniline | MS (ion spray) 450 (M$^+$) | |
| 439 | 2-[3-(9-chloro-3-methyl-4-oxo-5H-isoxazolo[4,3-c]quinolin-5-yl)-cyclohexyl]-N-pyridin-3-yl-acetamide | prep 145 | 3-amino-pyridine | MS (ion spray) 450 (M$^+$) | |
| 440 | 2-[3-(9-chloro-3-methyl-4-oxo-5H-isoxazolo[4,3-c]quinolin-5-yl)-cyclohexyl]-N-(3-methoxy-phenyl)-acetamide | prep 145 | 3-Methoxy-phenylamine | MS (ion spray) 480 (M$^+$) | |

| Ex. # | Product | Starting Material A | Starting Material B | Physical Data | Comments |
|---|---|---|---|---|---|
| 441 | N-[3-(9-Chloro-3-methyl-4-oxo-5H-isoxazolo[4,3-c]quinolin-5-yl)-cyclohexyl]-2-hydroxy-2-phenyl-pyridin-3-yl-acetamide | Hydroxy-phenyl-pyridin-3-yl-acetic acid | prep 48 | MS (ion spray) 543.1 (M+) | |
| 442 | N-[3-(9-Chloro-3-methyl-4-oxo-5H-isoxazolo[4,5-c]quinolin-5-yl)-cyclohexyl]-2-hydroxy-2-phenyl-acetamide | R-Madelic acid | prep 380 | MS (ES+) m/z 466.1 (M + H)+, (ES−) 464.2 (M − H)− | |
| 443 | N-[3-(9-Chloro-3-methyl-4-oxo-5H-isoxazolo[4,5-c]quinolin-5-yl)-cyclohexyl]-2-hydroxy-2-phenyl-acetamide | S-Madelic acid | prep 380 | MS (ES+) m/z 466.1 (M + H)+, (ES−) 464.2 (M − H)− | |
| 444 | N-[3-(9-Chloro-3-methyl-4-oxo-5H-isoxazolo[4,5-c]quinolin-5-yl)-cyclohexyl]-2-(3-fluoro-phenyl)-acetamide | 3-F-Phenylacetic acid | prep 380 | MS (ES+) m/z 468.1 (M + H)+, (ES−) 466.2 (M − H)− | |
| 445 | N-[3-(9-Chloro-3-methyl-4-oxo-2,4-dihydro-pyrazolo[4,3-c]quinolin-5-yl)-cyclohexyl]-2-hydroxy-2-phenyl-acetamide | R-Madelic acid | prep 399 | MS (ES+) m/z 465.2 (M + H)+ | |
| 446 | N-[3-(9-Chloro-3-methyl-4-oxo-2,4-dihydro-pyrazolo[4,3-c]quinolin-5-yl)-cyclohexyl]-2-hydroxy-2-phenyl-acetamide | S-Madelic acid | prep 399 | MS (ES+) m/z 465.2 (M + H)+ | |
| 447 | 6-Hydroxy-pyridine-2-carboxylic acid [3-(9-chloro-3-methyl-4-oxo-5H-isoxazolo[4,3-c]quinolin-5-yl)cyclohexyl]-methyl]-amide | 6-hydroxy-picolinic acid | prep 48 | MS (ion spray) 467 (M+) | |
| 448 | N-[3-(9-Chloro-3-methyl-4-oxo-5H-isoxazolo[4,3-c]quinolin-5-yl)-cyclohexyl]-2-hydroxy-2-pyridin-2-yl-acetamide | Ex 615 | prep 69 | MS (ion spray) 467 (M+) | Prep 69 was hydro-lized by LiOH in dioxane at rt. |
| 449 | N-[3-(9-Chloro-3-methyl-4-oxo-5H-isoxazolo[4,3-c]quinolin-5-yl)-cyclohexyl]-2-hydroxy-2-pyridin-3-yl-acetamide | Ex 615 | prep 69 | MS (ion spray) 467 (M+) | Prep 69 was hydro-lized by LiOH in dioxane at rt. |
| 450 | {1-[3-(9-Chloro-3-methyl-4-oxo-5H-isoxazolo[4,3-c]quinolin-5-yl)-cyclohexylcarbamoyl]-cyclopentyl}-carbamic acid tert-butyl ester | Ex 615 | prep 69 | MS (ion spray) 543 (M+) | |
| 451 | {1-[3-(9-Chloro-3-methyl-4-oxo-5H-isoxazolo[4,3-c]quinolin-5-yl)-cyclohexylcarbamoyl]-cyclopropyl}-carbamic acid tert-butyl ester | Ex 615 | prep 69 | MS (ion spray) 515 (M+) | |

-continued

| Ex. # | Product | Starting Material A | Starting Material B | Physical Data | Comments |
|---|---|---|---|---|---|
| 452 | 2-Amino-bicyclo[2,2,1]heptane-2-carboxylicacid [3-(9-chloro-3-methyl-4-oxo-5H-isoxazolo[4,3-c]quinolin-5-yl)-cyclohexyl]-amide | Ex 615 | prep 69 | MS (ion spray) 469 (M⁺) | |
| 453 | N-[3-(9-Chloro-3-methyl-4-oxo-5H-isoxazolo[4,3-c]quinolin-5-yl)cyclohexyl]-4-dimethylamino-2-phenoxy-2-phenyl-butyramide | Ex 615 | prep 69 | MS (ion spray) 613 (M⁺) | Prep 69 was hydrolized by LiOH in dioxane at rt. |
| 454 | S(+)1R,3S-N-[3-(9-Chloro-3-methyl-4-oxo-5H-isoxazolo[4,3-c]quinolin-5-ylmethyl)-cyclopentyl]-2-hydroxy-2-phenyl-acetamide | (S)(+) Mandelic acid | Ex 621 | ESMS: 466 (M + 1)⁺ | |
| 455 | R(−)1R,3S-N-[3-(9-Chloro-3-methyl-4-oxo-5H-isoxazolo[4,3-c]quinolin-5-ylmethyl)cyclopentyl]-2-hydroxy-2-phenyl-acetamide | (R)(−) Mandelic acid | Ex 621 | ESMS: 466 (M + 1)⁺ | |
| 456 | S(+)tert-Butoxycarbonylamino-acetic acid [3-(9-chloro-3-methyl-4-oxo-5H-isoxazolo[4,3-c]quinolin-5-yl)-cyclohexylcarbamoyl]-phenyl-methyl ester | S(+)N-t-BOC-glycine | prep 69 | MS (ion spray) 623 (M⁺) | |
| 457 | R(−)tert-Butoxycarbonylamino-acetic acid [3-(9-chloro-3-methyl-4-oxo-5H-isoxazolo[4,3-c]quinolin-5-yl)-cyclohexylcarbamoyl]-phenyl-methyl ester | R(−)N-t-BOC-glycine | prep 69 | MS (ion spray) 623 (M⁺) | |
| 458 | 2-(4-Acetyl-piperazin-1-yl)-N-[3-(9-chloro-3-methyl-4-oxo-5H-isoxazolo[4,3-c]quinolin-5-yl)cyclohexyl]-2-pyridin-3-yl-acetamide | prep 395 | prep 69 | MS (exact mass) [M + H]⁺ = 577.2340 m/z | Prep 69 was hydrolized by LiOH in dioxane at rt. |
| 459 | N-[3-(9-Chloro-3-methyl-4-oxo-5H-isoxazolo[4,3-c]quinolin-5-yl)-cyclohexyl]-2-pyridin-3-yl-2-(pyridin-2-yloxy)-acetamide | prep 396 | prep 69 | MS(ES) [M + H]⁺ = 544.4 m/z; [M − H]⁻ = 542.3 m/z | Prep 69 was hydrolized by LiOH in dioxane at rt. |
| 460 | N-[3-(9-Chloro-3-methyl-4-oxo-5H-isoxazolo[4,3-c]quinolin-5-yl)-cyclohexyl]-2-(pyridin-3-yloxy)-2-pyridin-3-yl-acetamide | prep 397 | prep 69 | MS(ES) [M + H]⁺ = 544.3 m/z; [M − H]⁻ = 542.5 m/z | Prep 69 was hydrolized by LiOH in dioxane at rt. |
| 461 | N-[3-(9-Chloro-3-methyl-4-oxo-5H-isoxazolo[4,3-c]quinolin-5-yl)-cyclohexyl]-2-(pyridin-4-yloxy)-2-pyridin-3-yl-acetamide | prep 398 | prep 69 | MS(ES) [M + H]⁺ = 544.3 m/z; [M − H]⁻ = 542.4 m/z | Prep 69 was hydrolized by LiOH in dioxane at rt. |

| Ex. # | Product | Starting Material A | Starting Material B | Physical Data | Comments |
|---|---|---|---|---|---|
| 462 | 4-tert-Butoxycarbonylamino-butyric acid [3-(9-chloro-3-methyl-4-oxo-5H-isoxazolo[4,3-c]quinolin-5-yl)-cyclohexyl-carbamoyl]-phenyl-methyl ester | Ex 471 | prep 69 | MS[ES][M + H]$^+$ = 651.2 m/z | |
| 463 | N-[3-(9-Chloro-3-methyl-4-oxo-5H-isoxazolo[4,3-c]quinolin-5-yl)-cyclohexyl]-2-hydroxy-2-phenyl-2-pyridin-3-yl-acetamide | Hydroxy-phenyl-pyridin-3-yl-acetic acid | prep 69 | MS (ion spray) 543.1 (M$^+$) | |
| 465 | N-[3-(9-Chloro-3-methyl-4-oxo-5H-isoxazolo[4,3-c]quinolin-5-yl)-cyclohexyl]-2-(4-fluorophenyl)acetamide | 4-fluoro-phenyl-acetic acid | Ex 634 | MS (ion spray) 468 (M$^+$) | noDMAP |
| 466 | N-[3-(9-Chloro-3-methyl-4-oxo-5H-isoxazolo[4,3-c]quinolin-5-yl)-cyclohexyl]-2-oxo-2-phenylacetamide | benzoyl-formic acid | Ex 634 | MS(ion spray) 464 (M$^+$) | |
| 467 | 3-(9-Chloro-3-methyl-4-oxo-5H-isoxazolo[4,3-c]quinolin-5-yl)-cyclohexanecarboxylic acid benzylamide | Prep 43 | benzylamine | MS (ion spray) 450 (M$^+$) | |
| 468 | 3-(9-Chloro-3-methyl-4-oxo-5H-isoxazolo[4,3-c]quinolin-5-yl)-cyclohexanecarboxylic acid (pyridin-3-ylmethyl)-amide | Prep 43 | 3-(aminoethyl)-pyridine | MS (ion spray) 451 (M$^+$) | |
| 469 | 3-(9-Chloro-3-methyl-4-oxo-5H-isoxazolo[4,3-c]quinolin-5-yl)-cyclohexanecarboxylic acid (pyridazin-3-ylmethyl)-amide | Prep 43 | 3-(aminoethyl)-pyridine | MS (ion spray) 452 (M$^+$) | |
| 470 | N-[3-(9-Chloro-3-methyl-4-oxo-5H-isoxazolo[4,3-c]quinolin-5-yl)-cyclohexyl]-2-hydroxy-2-phenylacetamide | L-(+)-mandelic acid | Ex 634 | MS (ion spray) 466 (M$^+$) | |
| 471 | N-[3-(9-Chloro-3-methyl-4-oxo-5H-isoxazolo[4,3-c]quinolin-5-yl)-cyclohexyl]-2-hydroxy-2-phenylacetamide | D-(−)-mandelic acid | Ex 634 | MS (ion spray) 466 (M$^+$) | |
| 472 | N-[3-(9-Chloro-3-methyl-4-oxo-5H-isoxazolo[4,3-c]quinolin-5-yl)-cyclohexyl]-2-phenyl-2-piperidin-1-ylacetamide | phenyl-piperidin-1-yl-acetic acid | Ex 634 | MS (ion spray) 533 (M$^+$) | isomer 1 = 15.1 mg isomer 2 = 8.8 mg |
| 473 | N-[3-(9-Chloro-3-methyl-4-oxo-5H-isoxazolo[4,3-c]quinolin-5-yl)-cyclohexyl]-2-dimethylamino-2-phenyl-propionamide | d/1-2-dimethyl-amino-3-phenyl-propionic acid | Ex 634 | MS (ion spray) 507 (M$^+$) | |

| Ex. # | Product | Starting Material A | Starting Material B | Physical Data | Comments |
|---|---|---|---|---|---|
| 474 | N-[3-(9-Chloro-3-methyl-4-oxo-5H-isoxazolo[4,3-c]quinolin-5-yl)-cyclohexyl]-2-methoxy-2-phenylpropionamide | 2-methoxy-2-phenyl-propionic acid | Ex 634 | MS (ion spray) 494 (M+) | | d) Table for Cyclization using KOtBu

| Ex. # | Product | Starting Material A | Starting Material B | Physical Data | Comments |
|---|---|---|---|---|---|
| 475 | 2-[3-(9-Chloro-3-methyl-4-oxo-5H-isoxazolo[4,3-c]quinolin-5-yl)cyclohexyl]-N-(3,4,5-trimethoxyphenyl)acetamide | prep 5 | | | Racemic-68% yield |
| 476 | 2-[3-(9-Chloro-3-methyl-4-oxo-5H-isoxazolo[4,3-c]quinolin-5-yl)cyclopentyl]-N-(3,4,5-trimethoxyphenyl)acetamide | prep 12 | | MS(ES+) m/z = 525.8 Racemic | |
| 477 | 2-[3-(9-Chloro-3-methyl-4-oxo-5H-isoxazolo[4,3-c]quinolin-5-yl)cyclopentyl]-N-(3,4,5-trimethoxyphenyl)acetamide | prep 13 | | MS(ES+)m/z = 525.9 Racemic | |
| 478 | 9-Chloro-3-methyl-5-{3-[2-(4-methyl-piperidin-1-yl)-2-oxo-ethyl]-cyclohexyl}-5H-isoxazolo[4,3-c]quinolin-4-one | prep 43 | | MS (ion spray) 456.2 (M + 1) Racemic | |
| 479 | Cis-2-[3-(9-Chloro-3-methyl-4-oxo-5H-isoxazolo[4,5-c]quinolin-5-yl)-cyclohexyl]-N-(3,4,5-trimethoxyphenyl)-acetamide | prep 158 | | MS (−ES) m/z 536.9 (M − H), 597.9 (M + OAc). | | e) Table for Cyclization using KHMDS

| Ex. # | Product | Starting Material A | Starting Material B | Physical Data | Comments |
|---|---|---|---|---|---|
| 480 | 2-[(1R,3S)-3-(9-Chloro-3-methyl-4-oxo-5H-isoxazolo[4,3-c]quinolin-5-yl)cyclopentyl]-N-(3,4,5-trimethoxyphenyl)-acetamide | prep 18 | | MS(ES+)m/z = 526. (single enantiomer) | |
| 481 | 2-[(1R,3S)-3-(9-Chloro-3-methyl-4-oxo-5H-isoxazolo[4,3-c]quinolin-5-yl)cyclopentyl]-N-(phenyl)acetamide | prep 28 | | MS(ES+)m/z = 436. Single enantiomer | |
| 482 | 2-[(1R,3S)-3-(9-Chloro-3-methyl-4-oxo-5H-isoxazolo[4,3-c]quinolin-5-yl)cyclopentyl]acetamide | prep 28 | | MS(ES+)m/z = 454. Single enantiomer | |
| 483 | 2-[(1R,3S)-3-(9-Chloro-3-methyl-4-oxo-5H-isoxazolo[4,3-c]quinolin-5-yl)-cyclopentyl]-N-(4-fluorophenyl)acetamide | prep 28 | | MS(ES+)m/z = 437. Single enantiomer | |
| 484 | 2-[(1R,3S)-3-(9-Chloro-3-methyl-4-oxo-5H-isoxazolo[4,3-c]quinolin-5-yl)-cyclopentyl]-N-(pyrid-3-yl)acetamide | prep 31 | | MS(ES+)m/z = 450 Single enantiomer | |
| | N-{2-[3-(9-chloro-3-methyl-4,3-c]quinolin-5-yl)cyclopentyl]ethyl}benzamide | | | | |

-continued

| Ex. # | Product | Starting Material A | Starting Material B | Physical Data | Comments |
|---|---|---|---|---|---|
| 485 | N-[(1S,3R)-3-(9-Chloro-3-methyl-4-oxo-5H-isoxazolo[4,3-c]quinolin-5-yl)cyclopentyl-ethyl]-N-(3,4,5-trimethoxyphenyl)-acetamide | prep 33 | | MS(ES+)m/z = 540. Single enantiomer | |
| 486 | {3-(9-Chloro-3-methyl-4-oxo-5H-isoxazolo[4,3-c]quinolin-5-ylmethyl)cyclopentyl-ethyl]-N-(3,4,5-trimethoxy-phenyl)-carboxamide | prep 36 | | MS(ES+)m/z = 525.8 Racemic | |
| 487 | 9-Chloro-3-methyl-5H-(3-phenyl-sulfanylmethyl-cyclohexyl)-5H-isoxazolo[4,3-c]-quinolin-4-one | prep 78 | | MS(FD): M+ 438.3 m/z Racemic | |
| 488 | 9-Chloro-3-methyl-5-(3-phenyl-methane-sulfonylmethylcyclohexyl)-5H-isoxazolo[4,3-c]quinolin-4-one Racemic | prep 82 | | MS(ES): (M + 1)+ 485.5, 487.5 m/z | |
| 489 | [3-(9-chloro-3-methyl-4-oxo-5H-isoxazolo[4,3-c]quinolin-5-yl)cyclohexyl]-methyl benzoate Racemic | prep 84 | | MS(ES): (M + 1)+ 450.4, 542.4 m/z | |
| 490 | 9-Chloro-3-methyl-5-[3-(2-oxo-3-phenyl-propyl)cyclohexyl]-5H-isoxazolo[4,3-c]quinolin-4-one (cis) | prep 89 | | MS(ES): [M + H]+ = 449.1 m/z, [M − H]− = 447.1 m/z | |
| 491 | [3-(9-Chloro-3-methyl-4-oxo-5H-isoxazolo[4,3-c]quinolin-5-yl)-cyclohexyl]-acetic acid benzyl ester (cis) | prep 84 | | MS (FIA) (m/z) 465.2 [M + 1] | |
| 492 | N-[3-(9-Fluoro-3-methyl-4-oxo-5H-isoxazolo[4,3-c]quinolin-5-yl)-cyclohexylmethyl]benzamide (cis) | prep 106 | | MS (FIA) (m/z) 434.3 [M + 1] | |
| 493 | N-[3-(9-Chloro-4-oxo-3-phenyl-5H-isoxazolo[4,3-c]quinolin-5-yl)-cyclohexyl-methyl]benzamide (cis) | prep 107 | | MS (FIA) (m/z) 512.4 [M + 1] | |
| 494 | N-[3-(9-Chloro-4-oxo-5H-isoxazolo[4,5-c]quinolin-5-yl)-cyclohexylmethyl]-benzamide (cis) | prep 108 | | MS (ES+) (m/z) 436.2 [M + 1] | |
| 495 | N-[3-(6-Iodo-3-methyl-4-oxo-5H-isoxazolo[4,3-c]quinolin-5-yl)-cyclohexylmethyl]-benzamide (cis) | prep 109 | | MS (FIA) (m/z) 540.3 [M − 1] | |
| 496 | N-[3-(8-Iodo-3-methyl-4-oxo-5H-isoxazolo[4,3-c]quinolin-5-yl)-cyclohexylmethyl]- | prep 110 | | MS (FIA) (m/z) 542.2 [M + 1] | |

| Ex. # | Product | Starting Material A | Starting Material B | Physical Data | Comments |
|---|---|---|---|---|---|
| | benzamide (cis) | | | | |
| 497 | N-[3-(7-Fluoro-3-methyl-4-oxo-5H-isoxazolo[4,3-c]quinolin-5-yl)-cyclohexylmethyl]-benzamide (cis) | prep 111 | | MS (FIA) (m/z) 434.3 [M + 1] | |
| 498 | N-[3-(9-Chloro-3-hexyl-4-oxo-5H-isoxazolo[4,3-c]quinolin-5-yl)-cyclohexylmethyl]-benzamide (cis) | prep 112 | | MS (FIA) (m/z) 520.3 [M + 1] | |
| 499 | Phenylmethyl 2-[3-(9-iodo-3-methyl-4-oxo-5H-isoxazolo[4,3-c]quinolin-5-yl)cyclo-hexyl]acetate (cis) | prep 113 | | MS (FIA) (m/z) 557.0 [M + 1] | |
| 500 | 9-Chloro-3-methyl-5-{3-[2-(toluene-3-sulfonyl)-ethyl]-cyclohexyl}-5H-isoxazolo[4,3-c]quinolin-4-one (cis) | prep 128 | | MS (ES): (M + 1)$^+$ 499.2, 501.2 m/z | |
| 501 | 9-Chloro-3-methyl-5-{(3-phenyl-thioethyl)-cyclohexyl}-5H-isoxazolo[4,3-c]-quinolin-4-one (cis) | prep 131 | | MS (FD): M$^+$ 452.4 m/z | |
| 502 | 9-Chloro-3-methyl-5-[3-(2-phenylmethane-sulfonyl-ethyl)-cyclohexyl]-5H-isoxazolo[4,3-c]quinolin-4-one (cis) | prep 132 | | MS (ES): (M + 1)$^+$ 499.2, 501.2 m/z | |
| 503 | 9-Chloro-5-{3-[2-(4-fluoro-benzene-sulfonyl)-ethyl]-cyclohexyl}-3-methyl-5H-isoxazolo[4,3-c]quinolin-4-one (cis) | prep 138 | | MS (ES): (M + 1)$^+$ 503.1, 505.1 m/z | |
| 504 | phenylmethyl 2-((3R,1R)-3-[[3-(2-chloro-6-fluorophenyl)-5-methylisoxazol-4-yl]carbonyl-amino]cyclohexyl)acetate (cis) | prep 144 | | MS (ion spray) 465 (M$^+$) | |
| 505 | cis-1-(9-chloro-3-methyl-4-oxo-5H-isoxazolo[4,3-c]quinolin-5-yl)-3-[[(1,1-dimethyl-ethyloxy)carbonyl]amino]-cyclohexane | prep 160 | | ESMS m/e 432 $^{35}$Cl (M$^+$ + 1); 434 $^{37}$Cl (M$^+$ + 1) | |
| 506 | [3-(9-Chloro-3-methyl-4-oxo-5H-isoxazolo[4,5-c]quinolin-5-yl)-cyclohexylmethyl]carbamic acid t-butyl ester(trans) | prep 160 | | MS (ES+) m/z 446.1 (M + H)$^+$ | |
| 507 | [3-(9-Chloro-3-methyl-4-oxo-5H-isoxazolo[4,5-c]quinolin-5-yl)-cyclohexylmethyl]carbamic acid t-butyl ester(cis) | prep 160 | | MS (ES+) m/z 446.1 (M + H)$^+$ | |

-continued

| Ex. # | Product | Starting Material A | Starting Material B | Physical Data | Comments |
|---|---|---|---|---|---|
| 508 | [3-(9-Chloro-3-methyl-4-oxo-5H-isoxazolo[4,5-c]quinolin-5-yl)-cyclohexyl-methyl]carbamic acid benzyl ester (cis) | prep 162 | | MS (ES+) m/z 500.1 (M + H)⁺ | |
| 509 | 3-[2-(9-Chloro-3-methyl]-4-oxo-5H-isoxazolo[4,3-c]quinolin-5-yl)-cyclohexyl]-N-(3,4,5-trimethoxy-phenyl)propionamide | prep 167 | | MS (ES+) m/z 554.0 (M + H)⁺ | |
| 510 | (1R,3S)3-(9-Chloro-3-methyl-4-oxo-5H-isoxazolo[4,3-c]quinolin-5-yl)cyclopentane-carboxylic acid benzylamide | prep 170 | | ESMS: 436 (M)⁺, 437 (M + 2)⁺ | |
| 511 | (1R,3S)-N-[3-(9-Chloro-3-methyl-4-oxo-5H-isoxazolo[4,3-c]quinolin-5-yl)-cyclopentylmethyl]benzamide | prep 179 | | ESMS: 436 (M)⁺, 437 (M + 1)⁺ | |
| 512 | (1S,3R)-N-[3-(9-Chloro-3-methyl-4-oxo-5H-isoxazolo[4,3-c]quinolin-5-yl)-cyclopentylmethyl]benzamide | prep 179 | | ESMS: 436 (M)+, 437 (M + 1)⁺ | |
| 513 | (1S,3R)-N-[3-(9-Chloro-3-methyl-4-oxo-5H-isoxazolo[4,3-c]quinolin-5-yl)-cyclopentylmethyl]-4-fluorobenzamide | prep 189 | | ESMS: 454 (M)⁺, 455 (M + 1)⁺, 513 (M + 59)⁻ | |
| 514 | (1S,3R)-Biphenyl-4-carboxylic acid [3-(9-chloro-3-methyl-4-oxo-5H-isoxazolo[4,3-c]quinolin-5-yl)cyclopentylmethyl]amide | prep 192 | | ESMS: 512 (M + 1)⁺, 570 (M + 59)⁻ | |
| 515 | (1S,3R)-N-[3-(9-Chloro-3-methyl-4-oxo-5H-isoxazolo[4,3-c]quinolin-5-yl)-cyclopentylmethyl]-nicotinamide | prep 195 | | ESMS: 435 (M − 1)⁻, 495 (M + 59)⁻ | |
| 516 | (1S,3R)-Furan-2-carboxylic acid [3-(9-chloro-3-methyl-4-oxo-5H-isoxazolo[4,3-c]quinolin-5-yl)-cyclopentylmethyl]amide | prep 198 | | ESMS: 426 (M + 1)⁺, 460 (M + 35)⁻, 484(M + 59)⁻ | |
| 517 | (1S,3R)-N-[3-(9-Chloro-3-methyl-4-oxo-5H-isoxazolo[4,3-c]quinolin-5-yl)-cyclopentylmethyl]-3,4,5-trimethoxybenzamide | prep 201 | | ESMS: 526 (M + 1)⁺, 584 (M + 59)⁻ | |
| 518 | (1S,3R)-N-[3-(9-Chloro-3-methyl-4-oxo-5H-isoxazolo[4,3-c]quinolin-5-yl)-cyclopentylmethyl]carbamic acid benzyl ester | prep 204 | | ESMS: 466 (M + 1)⁺, 524 (M + 59)⁻ | |
| 519 | N-[3-(9-Chloro-3-methyl-4-oxo- | prep 207 | | ESMS: 540 | |

| Ex. # | Product | Starting Material A | Starting Material B | Physical Data | Comments |
|---|---|---|---|---|---|
| | 5H-isoxazolo[4,3-c]quinolin-5-yl)-cyclopentyl-methyl]-2-(3,4,5-trimethoxyphenyl)-acetamide | | | (M + 1)+, 574 (M + 35)-, 598 (M + 59)- | |
| 520 | N-[3-(9-Chloro-3-methyl-4-oxo-5H-isoxazolo[4,3-c]quinolin-5-ylmethyl)-cyclopentyl]carbamic acid t-butyl ester | prep 208 | | ESMS: 432 (M + 1)+ | |
| 521 | [3-(9-Chloro-3-methyl-4-oxo-5H-isoxazolo[4,3-c]quinolin-5-ylmethyl)-cyclopentyl]carbamic acid t-butyl ester | prep 209 | | ESMS: 432 (M + 1)+ | |
| 522 | trans-[1-(9-chloro-3-methyl-4-oxo-5H-isoxazolo[4,3-c]quinolin-5-yl)-3-[[(1,1-dimethylethyloxy)carbonyl]amino]]-cyclohexane | prep 22 | | ESMS m/e 432 $^{35}$Cl (M$^+$ + 1); 434 $^{37}$Cl (M$^+$ + 1) | |
| 523 | N-[3-(9-Cyano-3-methyl-4-oxo-5H-isoxazolo[4,3-c]quinolin-5-yl)-cyclohexylmethyl]-benzamide | prep 267 | | MS(ES+) (m/z) 441.2 [M + 1] | |
| 524 | [3-(9-Cyano-3-methyl-4-oxo-5H-isoxazolo[4,3-c]quinolin-5-yl)-cyclohexylmethyl]-carbamic acid benzyl ester | prep 269 | | MS(ES+) (m/z) 471.2 [M + 1] | |
| 525 | [3-(9-Chloro-3-methyl-4-oxo-5H-isoxazolo[4,3-c]quinolin-5-ylmethyl)-cyclohexyl]-carbamic acid tert-butyl ester | prep 278 | | MS(ES+) (m/z) 346.1 [M − BOC] | |
| 526 | N-[3-(9-Chloro-3-diethylamino-4-oxo-5H-isoxazolo[4,3-c]quinolin-5-yl)-cyclohexylmethyl]-benzamide | prep 280 | | MS(ES+) (m/z) 507.2 [M + 1] | |
| 527 | N-[3-(9-Chloro-4-oxo-3-pyrroldin-1-yl-5H-isoxazolo[4,3-c]quinolin-5-yl)-cyclohexylmethyl]-benzamide | prep 281 | | MS(ES+) (m/z) 505.1 [M + 1] | |
| 528 | N-[3-(9-Chloro-3-ethylamino-4-oxo-5H-isoxazolo[4,3-c]quinolin-5-yl)-cyclohexylmethyl]-benzamide | prep 280 | | MS(ES+) (m/z) 479.1 [M + 1] | |
| 529 | N-[3-(9-Chloro-3-ethylsulfanyl-4-oxo-5H-isoxazolo[4,3-c]quinolin-5-yl)-cyclohexylmethyl]-benzamide | prep 283 | | MS(ES+) (m/z) 496.1 [M + 1] | |
| 530 | N-[3-(9-Chloro-4-oxo-3-phenylamino-5H-isoxazolo[4,3-c]quinolin-5-yl)-cyclo-hexyl-methyl]-benzamide | prep 278 | | MS(ES+) (m/z) 527.2 [M + 1] | |
| 531 | N-[3-(9-Cyano-3-methyl-4-oxo- | prep 316 | | MS(ES+) | |

| Ex. # | Product | Starting Material A | Starting Material B | Physical Data | Comments |
|---|---|---|---|---|---|
| 532 | 5H-isoxazole-[4,3-c]quinolin-5-yl)-cyclohexylmethyl]-benzamide | prep 318 | | (m/z) 441.2 [M + 1]. MS(ES+) (m/z) 471.2 [M + 1]. | |
| 533 | [3-(9-Cyano-3-methyl-4-oxo-5H-isoxazole-[4,3-c]quinolin-5-yl)-cyclohexylmethyl]-carbamic acid benzyl ester | prep 327 | | MS(ES+) (m/z) 346.1 [M − BOC]. | |
| 534 | [3-(9-Chloro-3-methyl-4-oxo-5H-isoxazole-[4,3-c]quinolin-5-ylmethyl)-cyclohexyl]-carbamic acid tert.-butyl ester | prep 329 | | MS(ES+) (m/z) 507.2 [M + 1]. | |
| 535 | N-[3-(9-Chloro-3-diethylamino-4-oxo-5H-isoxazole[4,3-c]quinolin-5-yl)-cyclohexylmethyl]-benzamide | prep 330 | | MS(ES+) (m/z) 505.1 [M + 1]. | |
| 536 | N-[3-(9-Chloro-4-oxo-3-pyrrolidin-1-yl-5H-isoxazole[4,3-c]quinolin-5-yl)-cyclohexylmethyl]-benzamide | prep 331 | | MS(ES+) (m/z) 479.1 [M + 1] | |
| 537 | N-[3-(9-Chloro-3-ethylamino-4-oxo-5H-isoxazole[4,3-c]quinolin-5-yl)-cyclohexylmethyl]-benzamide | prep 332 | | MS(ES+) (m/z) 496.1 [M + 1]. | |
| 538 | N-[3-(9-Chloro-3-ethylsulfanyl-4-oxo-5H-isoxazole[4,3-c]quinolin-5-yl)-cyclohexylmethyl]-benzamide | prep 328 | | MS(ES+) (m/z) 544.2 [M + 1]. | Prep 328 was initially treated with Na thiophenoxide (5eq) in DMF. |
| 539 | N-[3-(9-Chloro-4-oxo-3-phenylsulfanyl-5H-isoxazole[4,3-c]quinolin-5-yl)-cyclohexylmethyl]-benzamide | prep 328 | | MS(ES+) (m/z) 527.2 [M + 1]. | Prep 328 was initially treated with aniline (20eq) in DMF. |
| 540 | N-[3-(9-Chloro-4-oxo-3-phenylamino-5H-isoxazole[4,3-c]quinolin-5-yl)-cyclohexylmethyl]-benzamide | Prep 333 | | MS(ES+) (m/z) 346.3 [M − BOC]. | |
| 541 | [3-(9-Chloro-3-methyl-4-oxo-5H-isoxazole[4,3-c]quinolin-5-ylmethyl)-cyclohexyl]-carbamic acid tert.-butyl ester | Prep 33 | | MS(ES+) m/z = 540. Single enantiomer | |
| 541a | N-{2-[3-(9-Chloro-3-methyl-4-oxo-5H-isoxazolo[4,3-c]-quinolin-5-yl)-cyclopentyl]-ethyl}-3,4,5-trimethoxy-benzamide | Prep 337 | | MS(ES+) m/z = 525.8 | |
| | {3-[(9-chloro-3-methyl-4-oxo-5H-isoxazolo[4,3-c]quinolin-5-yl)]methyl]cyclopentyl}-N-(3,4,5-trimethoxyphenyl)-carboxamide | | | | |

-continued

| Ex. # | Product | Starting Material A | Starting Material B | Physical Data | Comments |
|---|---|---|---|---|---|
| 542 | [3-(9-Chloro-3-methyl-4-oxo-5H-isoxazolo[4,3-c]quinolin-5-yl)-cycloheptyl]-acetic acid methyl ester | Prep 338 | | MS(ES+) m/z = 402.9. | |
| 543 | N-{2-[3-(9-Chloro-3-methyl-4-oxo-5H-isoxazolo[4,3-c]quinolin-5-yl)-cyclopentyl]-ethyl}-benzamide | Prep 31 | | MS(ES+) m/z = 450. | |
| 544 | 2-[3-(9-Chloro-3-methyl-4-oxo-5H-isoxazolo[4,3-c]quinolin-5-yl)-cyclopentyl]-N-(3,4,5-trimethoxyphenyl)-acetamide | Prep 337 | | MS(ES+) m/z = 526. (Single enantiomer) | |
| 545 | [3-(9-Chloro-3-methyl-4-oxo-3,4-dihydro-imidazo[4,5-c]quinolin-5-yl)-cyclohexylmethyl]-carbamic acid benzyl ester | Ex 405 | | MS (ES+) (m/z) 479.3 [M + 1] | | f) Table for Arylation:

| 546 | 9-Chloro-3-methyl-5-[3-(quinolin-2-ylaminomethyl)-cyclohexyl]-5H-isoxazolo[4,3-c]quinolin-4-one | Ex 619 | 2-chloro-quinoline | MS(FIA) (m/z) 473.1 (M + 1) | |
| 547 | 9-Chloro-3-methyl-5-{3-[(5-nitro-pyridin-2-ylamino)-methyl]-cyclohexyl}-5H-isoxazolo[4,3-c]quinolin-4-one | Ex 619 | 2-chloro-6-nitro-pyridine | MS(FIA) (m/z) 466.1 (M − 1) | |
| 548 | 2-{[3-(9-Chloro-3-methyl-4-oxo-5H-isoxazolo[4,3-c]quinolin-5-yl)cyclohexyl]methyl}-amino}-nicotinonitrile | Ex 619 | 2-chloro-3-nitrile-pyridine | MS(FIA) (m/z) 448.1 (M + 1) | |
| 549 | 9-Chloro-3-methyl-5-{3-[(5-nitropyridin-2-ylamino)methyl]-cyclohexyl}-5H-isoxazolo[4,3-c]quinolin-4-one | Ex 619 | 2-chloro-pyrimidine | MS(FIA) (m/z) 424.1 (M + 1) | |
| 550 | 9-Chloro-5-{3-[4-chloro-pyrimidin-2-ylamino)-methyl]cyclohexyl}-3-methyl-5H-isoxazolo[4,3-c]quinolin-4-one and 9-Chloro-5-{3-[2-chloro-pyrimidin-4-ylamino)-methyl]-cyclohexyl}-3-methyl-5H-isoxazolo[4,3-c]quinolin-4-one (racemic) | Ex 619 | 2,4-dichloropyrimidine | MS(FIA) (m/z) 458.4 (M + 1) isomers were separated | |
| 551 | 9-Chloro-5-{3-[(6-chloro-benzothiazol-2-ylamino)methyl]-cyclohexyl}-3-methyl-5H- | Ex 619 | 2,6-dichlorobenzo-thiazole | MS(FIA) (m/z) 515.2 (M + 1) | |

-continued

| Ex. # | Product | Starting Material A | Starting Material B | Physical Data | Comments |
|---|---|---|---|---|---|
| 552 | isoxazolo[4,3-c]quinolin-4-one 5-[3-(Benzothiazol-2-ylamino-methyl)-cyclohexyl]-9-chloro-3-methyl-5H-isoxazolo[4,3-c]quinolin-4-one | Ex 619 | 2-chlorobenzothiazole | MS(FIA) (m/z) 479.1 (M + 1) | |
| 553 | 5-[3-(Benzooxazol-2-ylamino-methyl)cyclohexyl]-9-chloro-3-methyl-5H-isoxazolo[4,3-c]quinolin-4-one | Ex 619 | 2-chlorobenzooxazole | MS(FIA) (m/z) 463.3 (M + 1) | | g) Table for Chiral Separation:

| 554 | 2-[(1S,3R)-3-(9-chloro-3-methyl-4-oxo-5H-isoxazolo[4,3-c]quinolin-5-yl)cyclohexyl]-N-(3,4,5-trimethoxyphenyl)acetamide | Ex 432 | | Retention Time = 8.56 minutes | |
| 555 | 2-[(1R,3S)-3-(9-chloro-3-methyl-4-oxo-5H-isoxazolo[4,3-c]quinolin-5-yl)cyclohexyl]-N-(3,4,5-trimethoxyphenyl)acetamide | Ex 432 | | Retention Time = 16.08 minutes | |
| 556 | N-{[(1R,3S)-3-(9-chloro-3-methyl-4-oxo(5-hydroisoxazolo[4,3-c]quinolin-5-yl))cyclohexyl]methyl}benzamide | Ex 116 | | Retention Time = 9.232 min | |
| 557 | N-{[(1S,3R)-3-(9-chloro-3-methyl-4-oxo-5H-isoxazolo[4,3-c]quinolin-5-yl)cyclohexyl]methyl}benzamide | Ex 116 | | Retention Time = 12.704 min | |
| 558 | 2-[(1R,3S)-3-(9-chloro-3-methyl-4-oxo-5H-isoxazolo[4,5-c]quinolin-5-yl)cyclohexyl]-N-(3,4,5-trimethoxyphenyl)acetamide | Ex 479 | | MS (−ES) m/z 536.9 (M − H), 597.9 (M + OAc) | |
| 559 | 2-[(1S,3R)-3-(9-chloro-3-methyl-4-oxo-5H-isoxazolo[4,5-c]quinolin-5-yl)cyclohexyl]-N-(3,4,5-trimethoxyphenyl)acetamide | Ex 479 | | MS (−ES) m/z 536.9 (M − H), 597.9 (M + OAc) | |
| 560 | N-{[(1S,3S)-3-(9-chloro-3-methyl-4-oxo-5H-isoxazolo[4,5-c]quinolin-5-yl)cyclohexyl]methyl}(t-butoxy)carboxamide | Ex 506 | | MS (+ES) m/z 446 (M + H)+, 463(M + NH3)+, (−ES)480 (M − H + Cl)−, 504 (M − H + OAc)− | |
| 561 | N-{[(1R,3R)-3-(9-chloro-3-methyl-4-oxo-5H-isoxazolo[4,5-c]quinolin-5-yl)cyclohexyl]methyl}(t-butoxy)carboxamide | Ex 506 | | MS (+ES) m/z 446 (M + H)+, 463 (M + NH3)+, (−ES)480 (M − H + Cl)−, 504 (M − H + OAc)− | |
| 562 | N-{[(1R,3S)-3-(9-chloro-3-methyl-4-oxo-5H-isoxazolo[4,5- | Ex 507 | | MS (+ES) m/z 446 (M + H)+, | |

| Ex. # | Product | Starting Material A | Starting Material B | Physical Data | Comments |
|---|---|---|---|---|---|
|  | c]quinolin-5-yl)cyclohexyl]-methyl}(t-butoxy)carboxamide |  |  | 463 (M + NH3)+, (−ES)480 (M − H + Cl)−, 504 (M − H + OAc) |  |
| 563 | N-{[(1S,3R)-3-(9-chloro-3-methyl-4-oxo-5H-isoxazolo[4,5-c]quinolin-5-yl)cyclohexyl]methyl}(t-butoxy)carboxamide | Ex 507 |  | MS (+ES) m/z 446 (M + H)+, 463 (M + NH3)+, (−ES)480 (M − H + Cl)−, 504 (M − H + OAc)− |  |
| 564 | 3-[(1S,2S)-2-(9-chloro-3-methyl-4-oxo-5H-isoxazolo[4,5-c]quinolin-5-yl)cyclohexyl]-N-(3,4,5-trimethoxyphenyl)propanamide | Ex 618 |  | MS (+ES) 553.9, 555.9 (M + H)+ |  |
| 565 | 3-[(2S,1R)-2-(9-chloro-3-methyl-4-oxo-5H-isoxazolo[4,5-c]quinolin-5-yl)cyclohexyl]-N-(3,4,5-trimethoxyphenyl)propanamide | Ex 618 |  | MS (+ES) 553.9, 555.9 (M + H)+ |  |

EXAMPLE 566

(2R)-N-[(1S,3R)-3-(9-chloro-3-methyl-4-oxo-5H-isoxazolo[4,3-c]quinolin-5-yl)cyclo-hexylmethyl]-2-amino-3-(phenylmethoxy)propanamide A solution of (2R)-N-{[(1S,3R)-3-(9-chloro-3-methyl-4-oxo-5H-isoxazolo[4,3-c]quinolin-5-yl))cyclohexyl]methyl}-2-[(t-butoxy)carbonylamino]-3-(phenylmethoxy)-propanamide, 80 mg (0.13 mmol) in 10 mL of acetic acid saturated with hydrochloric acid was stirred for 2 h at ambient temperature and concentrated to dryness. The residue was dissolved in toluene and concentrated to dryness and dried under vacuum to yield a quantitative yield of the desired product as a white foam. $^1$H—NMR is consistent with structure. MS (ion spray) 523.2 (M+).

EXAMPLE 567

N-[3-(9-Chloro-3-methyl-4-oxo-5H-isoxazolo[4,3-c]quinolin-5-yl)-cyclohexylmethyl]-3-aminobenzamide To a solution containing 620 mg (1.25 mmol) of a compound from Example 48 in 15 mL of THF was added 848 mg (3.75 mmol) of $SnCl_2.2H_2O$ at room temperature. To the resulting suspension was added 1.0 mL of concentrated HCl and the reaction was stirred for 15 hours at room temperature. The reaction was diluted with 100 mL of ethyl acetate and washed once with brine. The organic solution was separated, dried and concentrated to give a white foam. This crude material was purified by flash chromatography, using ethyl acetate as the eluent. The major fractions were combined and concentrated in vacuo to give 400 mg of a white amorphous solid. MS(FIA) m/z=465.2.

EXAMPLE 568

N-[3-(9-Chloro-3-methyl-4-oxo-5H-isoxazolo[4,3-c]quinolin-5-yl)cyclohexylmethyl]-4-aminobenzamide The title compound was prepared from the compound from Example 110 according to the conditions for the preparation of Example 567. MS(FIA) m/z=465.2.

EXAMPLE 569

N-[3S-(9-Chloro-3-methyl-4-oxo-5H-isoxazolo[4,3-c]quinolin-5-yl)-R-cyclohexylmethyl]-3-(4methyoxy)benzyloxybenzamide To a suspension of 150 mg (0.581 mmol) of a compound from preparation 56 in 10 mL of $CH_2Cl_2$ was added 2 drops of DMF, followed by the addition of 51 μL (0.581 mmol) of oxalyl chloride. The reaction was stirred at room temperature and evolution of CO gas was noted. The reaction was stirred an additional 30 minutes at room temperature and then concentrated in vacuo. The resulting acid chloride was dissolved in 10 mL of $CH_2Cl_2$. In a separate flask, 250 mg (0.528 mmol) of the compound from Example 302, was suspended in 10 mL of $CH_2Cl_2$. To this was added 110 μL of triethylamine and the resulting solution was added to the flask containing the acid chloride, followed by the addition of an additional 110 μL of triethylamine. The reaction was stirred at room temperature for 15 hours, diluted with 50 mL of ethyl acetate and washed twice with 1N HCl, twice with 1N NaOH, dried over sodium sulfate and concentrated in vacuo to give a white amorphous solid. This material was recrystallized from toluene to give 190 mg of a white amorphous solid. MS(ES+) m/z=586.19.

EXAMPLE 570

N-[3S-(9-Chloro-3-methyl-4-oxo-5H-isoxazolo[4,3-c]quinolin-5-yl)-R-cyclohexylmethyl]-3-hydroxybenzamide To a solution containing 50 mg (0.0853 mmol) of a compound from Example 569 in 2 mL of $CH_2Cl_2$ was added 2 mL of TFA. The reaction was stirred at room temperature for 18 hours and concentrated in vacuo. The resulting crude solid was recrystallized from toluene to give a white amorphous solid. MS(ES+) m/z=466.1.

EXAMPLE 571

N-[3S-(9-Chloro-3-methyl-4-oxo-5H-isoxazolo[4,3-c]quinolin-5-yl)-R-cyclohexylmethyl]-4-(4-methoxy)benzyloxybenzamide The title compound was prepared from methyl 4-hydroiybenzoate according to the conditions for the preparation of Example 569. MS(ES+) m/z=586.19.

EXAMPLE 572

N-[3S-(9-Chloro-3-methyl-4-oxo-5H-isoxazolo[4,3-c]quinolin-5-yl)-R-cyclohexylmethyl]-4-hydroxybenzamide The title compound was prepared from a compound of Example 571 according to the conditions for the preparation of Example 570. MS(ES+) m/z=466.1.

EXAMPLE 573

N-[3-(9-Chloro-3-methyl-4-oxo-5H-isoxazolo[4,3-c]quinolin-5-yl)cyclohexyl]-benzenesulfonamide N-[3-(9-Chloro-3-methyl-4-oxo-5H-isoxazolo[4,3-c]quinolin-5-yl)-cyclohexyl]benzenethioamide (0.78 g; 1.59 mmol) was dissolved in anhydrous dimethylformamide (16 mL), chilled to −20° C. for 10 min, and mixed with 0.5 M potassium bis(trimethylsilyl)amide in toluene (7.0 mL; 3.5 mmol; 2.2 equiv). The reaction solution was stirred 10 min at −20° C. and another 35 min at room temperature. After quenching the reaction with 1 M HCl (50 mL), the solution was extracted with ethyl acetate (twice). The organic layer was washed with saturated $NaCl_{(aq)}$ (twice), then dried with $Na_2SO_{4(s)}$, filtered, and concentrated to dryness by rotary evaporation. The resulting white solid was purified by radial chromatography (three consecutive times) on a 4 mm thick silica gel rotor with a 5% tetrahydrofuran/dichloromethane (v/v) mobile phase and then twice with a 50% ethyl acetate/hexanes (v/v) mobile phase. Concentration of product-containing fractions produced 11 mg (2% yield) of a white solid. MS(ES) calc'd: [M+H]$^+$=472.0 m/z, [M−H]$^−$=470.0 m/z. Found: 471.9 m/z, 470.0 m/z.

EXAMPLE 574

N-[3-(9-Chloro-3-methyl-4-oxo-5H-isoxazolo[4,3-c]quinolin-5-yl)cyclohexyl]benzenesulfonamide N-[3-(9-Chloro-3-methyl-4-oxo-5H-isoxazolo[4,3-c]quinolin-5-yl)cyclohexyl]benzenethioamide (0.41 g; 0.83 mmol) was dissolved in anhydrous dimethylformamide (8 mL), chilled to −20° C. for 10 min, and mixed with 0.5 M potassium bis(trimethylsilyl)amide in toluene (4 mL; 1.83 mmol; 2.2 equiv). The reaction solution was stirred 10 min at −20° C. and another 35 min at room temperature. After quenching the reaction with 1 M HCl (50 mL), the solution was extracted with ethyl acetate (twice). The organic layer was washed with saturated $NaCl_{(aq)}$ (twice), then dried with $Na_2SO_{4(s)}$, filtered, and concentrated to dryness by rotary evaporation. The resulting white solid was purified by radial chromatography on a 4 nm thick silica gel rotor with a 40% ethyl acetate/hexanes (v/v) mobile phase. Product containing fractions were combined, concentrated and further purified by radial chromatography (twice) on a 2 mm thick silica gel rotor with a 50% ethyl acetate/hexanes (v/v) mobile phase. Concentration of product-containing fractions produced 53 mg (14% yield) of a white solid. MS(ES) calc'd: $[M+H]^+$=472.0 m/z, $[M-H]^-$=470.0 m/z. Found: 472.0 m/z, 470.2 m/z.

EXAMPLE 575

4-(9-Chloro-3-methyl-4-oxo-5H-isoxazolo[4,3-c] quinolin-5-yl)-cyclohexanecarboxylic acid 3,4,5-trimethoxybenzylamide The compound from preparation 72 (0.40 g, 0.00098 mol) was combined with THF (5 mL), MeOH (2 mL), water (5 mL) and 2N NaOH (5 mL) and the mixture stirred at ambient temperature until hydrolysis was complete. The mixture was concentrated in vacuo and the residue taken up in water and carefully acidified using aq 1N HCl. The aqueous mixture was extracted with ethyl acetate and the combined extracts were dried over sodium sulfate. Concentration in vacuo left the crude acid which was combined with 1-(3-dimethyl-aminopropyl-3-ethylcarbodiimide hydrochloride (0.186 g, 0.00097 mol), 1-hydroxy-7-azabenzotriazole (0.133 g, 0.00098 mol) and 3,4,5-trimethoxybenzylamine (0.193 g, 0.00098 mol) in DMF (15 mL) and the resulting mixture stirred overnight at ambient temperature. The mixture was concentrated in vacuo and the residue taken up in water. The aqueous mixture was extracted with $CH_2Cl_2$ and the combined extracts dried over sodium sulfate and concentrated in vacuo. The resulting residue was chromatographed over silica gel using $CH_2Cl_2$/THF as eluent which allowed for isolation of 0.120 g (40%) of the desired product as a yellowish solid. MS(ES): $(M+1)^+$ 540.4 m/z.

EXAMPLE 576–577

5-(3-Benzenesulfinylmethylcyclohexyl)-9-chloro-3-methyl-5H-isoxazolo[4,3-c]quinolin4-one & 5-(3-Benzenesulfonylmethylcyclohexyl)-9-chloro-3-methyl-5H-isoxazolo[4,3-c]quinolin-4-one The compound from Example 487 (0.20 g, 0.00046 mol) was dissolved in $CH_2Cl_2$ (30 mL) and the mixture cooled under a nitrogen atmosphere in a dry ice/acetone bath. Then 3-chloroperoxybenzoic acid (50%, 0.16 g, 0.00046 mol) was added and the mixture stirred for 2 h while warming near ambient temperature. The mixture was concentrated and the residue chromatographed over silica gel using $CH_2Cl_2$/MeOH as eluent which allowed for isolation of both the sulfoxide (0.132 g, 63%). MS(ES): $(M+1)^+$ 455.1, 457.3 m/z, and the sulfone (0.078 g, 36%) MS(ES): $(M+1)^+$ 471.2 m/z.

EXAMPLE 578

9-Chloro-5-[3-(2-methoxyimino-3-phenylpropyl) cyclohexyl]-3-methyl-5H-isoxazolo[4,3-c]quinolin-4-one To a solution of the compound from Example 490 in denatured ethanol (6 mL) was added a solution of methoxyamine hydrochloride (74.5 mg; 0.892 mmol; 4 equiv) and sodium acetate (73.1 mg; 0.892 mmol; 4 equiv) in water (1 mL). The cloudy reaction mixture became clear and colorless when heated to reflux. After 1.6 h the reaction solution was concentrated to dryness by rotary evaporation. The resulting solid was dissolved in dichloromethane and the organic layer was washed with water (once), washed with saturated $NaCl_{(aq)}$ (once), dried with $Na_2SO_{4(s)}$, filtered, and concentrated to dryness by rotary evaporation. The product was isolated as a mixture of oxime isomers by radial chromatography on a 2 mm thick silica gel rotor with a 2% acetonitrile/dichloromethane (v/v) mobile phase. A clear, colorless oil (92 mg; 86%) was obtained after concentration of the appropriate fractions. TOF-MS(ES) calc'd: $[M+M]^+$=478.1897 m/z. Found: 478.1891 m/z.

EXAMPLE 579

2-[3-(9-Chloro-3-methyl-4-oxo-5H-isoxazolo[4,3-c] quinolin-5-yl]-N4-methoxyphenylacetamide To a 7 mL scintillation vial containing 0.10 g (0.254 mmol) of a compound from preparation 95 in 3 mL of methylene chloride was added 0.086 g (0.509 mmol) p-anisidine followed by 0.10 mL of triethylamine. The reaction was shaken overnight, passed through a 2 g SCX column, eluting with methylene chloride and the racemic cis product crystallized out of one of the fractions giving 0.054 g (44%). MS(FIA) m/z=480.1.

EXAMPLE 580

2-[3-(9-Chloro-3-methyl-4-oxo-5H-isoxazolo[4,3-c] quinolin-5-yl]-N-2-methoxy-5-nitrophenylacetamide The title compound was prepared from a compound of preparation 95 and 2-methoxy-5-nitroaniline triethylamine in a manner similar to that of Example 579 to yield 0.051 g (38%). MS(FIA) m/z=525.2.

EXAMPLE 581

9-Chloro-3-methyl-5-[3-(2-oxo-pyrrolidin-1-ylmethylcyclohexyl]-5H-isoxazolo[4,3-c]quinolin-4-one To a stirred solution of the compound of Example 105 (148 mg, 0.33 mmol) in DMF (3 mL) and THF (4 mL) was added NaH (41 mg, 1.0 mmol, 60% in mineral oil) and stirred at r.t. for 1.5 hours. The reaction mixture was diluted with ethyl acetate, washed (brine), dried ($Na_2SO_4$), filtered and concentrated. Column chromatography (silica gel, ethyl acetate) gave 82 mg, 60%. MS(FIA) (m/z) 414.2 (M+1).

EXAMPLE 582

N-[3-(9-Chloro-3-methyl-4-oxo-5H-isoxazolo[4,3-c] quinolin-5-yl)cyclopentyl-2-(3,4,5-trimethoxyphenylmethyl)]acetamide To a stirred solution of N-[(1S,4R)-4-(9-chloro-3-methyl-4-oxo(5-hydroisoxazolo[4,3-c]quinolin-5-yl))cyclopent-2-enyl]-2-(3,4,5-trimethoxyphenyl)-acetamide (55 mg, 0.11 mmol) in DMF (5 mL) was added Rh/C (5%) and treated with $H_2$ and stirred at r.t. for 18 hours. The mixture was filtered. The filtrate was diluted with EtOAc, washed (brine), dried ($Na_2SO_4$), filtered and concentrated. Column chromatography (silica gel, hexanes/ethyl acetate, gradient) gave the title compound 38 mg, 69%. MS(FIA) (m/z) 526.3 (M+1).

EXAMPLE 583

N-[3-(9-chloro-3-methyl-4-oxo-5H-isoxazolo[4,3-c]
quinolin-5-yl)-cyclopentyl-2-(3-
fluorophenylmethyl)]acetamide To a stirred solution of N-[(1S,4R)-4-(9-chloro-3-methyl-4-oxo(5-hydroisoxazolo[4,3-c]quinolin-5-yl))cyclopent-2-enyl]-2-(3,4,5-trimethoxyphenyl)-acetamide (49 mg, 0.11 mmol) in EtOAc (5 mL) was added Rh/C (5%, catalytic amount) and treated with $H_2$ and stirred at r.t. for 18 hours. The mixture was filtered. The filtrate was diluted with EtOAc, washed (brine), dried ($Na_2SO_4$), filtered and concentrated. Column chromatography (silica gel, hexanes/ethyl acetate, gradient) gave the title compound 48 mg, 97%. MS(FIA) (m/z) 454.1 (M+1).

EXAMPLE 584 and 585

3-(9-Chloro-3-methyl-4-oxo-5H-isoxazolo[4,3-c]
quinolin-5-ylmethyl)cyclohexane-carboxylic acid
(3,4,5-trimethoxyphenyl)

A compound from preparation 101 (0.2 g, 0.54 mmol), 1 N NaOH (1.32 ml, 1.32 mmol), and MeOH (8 ml) were heated at 50° C. for 2 h. The reaction was cooled to r.t., acidified to pH<3, and concentrated using benzene to azeotrope. The residue, EDCI (0.2 g, 1.07 mmol), 3,4,5-trimethoxyaniline (0.119 g, 0.65 mmol), DMAP (0.013 g, 0.11 mmol), and dichloromethane (5.5 ml) were mixed under $N_2$. The mixture was diluted with EtOAc, washed, dried, filtered, and concentrated to give 585 (0.05 g, 17%) and 584 (0.07 g, 24%) after radial chromatography (silica gel, 5% acetone/dichloromethane). 585: MS(FIA) (m/z) 540.4 [M+1]. 584: MS(FIA) (m/z) 540.4 [M+1].

EXAMPLE 586

3-(9-Chloro-3-methyl-4-oxo-5H-isoxazolo[4,3-c]
quinolin-5-ylmethyl)cyclohexane-carboxylic Acid
(2-methoxy-5-nitrophenyl)

In a fashion similar to that described for Example 585, methyl 3-(9-chloro-3-methyl-4-oxo-5H-isoxazolo[4,3-c]quinolin-5-yl)cyclohexane carboxylate (0.2 g, 0.54 mmol), 1 N NaOH (1.32 ml, 1.32 mmol), MeOH (8 ml), EDCI (0.2 g, 1.07 mmol), 2-methoxy-5-nitroaniline (0.11 g, 0.65 mmol), DMAP (0.013 g, 0.11 mmol), dichloromethane (5.5 ml) gave b (0.052 g, 18%) and a (0.068 g, 24%) after radial chromatography (silica gel, 2% acetone/dichloromethane).
b: MS(FIA) (m/z) 523.1 [M−1].
a: MS(FIA) (m/z) 523.1 [M−1].

EXAMPLE 587

9-Chloro-5-[3-(4,4-dimethyl-4,5-dihydro-oxazol-2-
ylmethyl)cyclohexyl]-3-methyl-5H-isoxazolo[4,3-c]
quinolin-4one The compound from preparation 43 (0.2 g, 0.54 mmol) was dissolved in dichloromethane (3.6 ml) followed by addition of oxalyl chloride (0.108 ml, 1.08 mmol) and DMF (0.005 ml). After 1 h of stirring, the volatiles were removed. The residue was dissolved in dichloromethane (1.5 ml) and 2-amino-2-methyl-1-propanol (0.1 ml, 1.08 mmol) was added. The reaction was stirred for 3 h then concentrated. The reaction was dissolved in thionyl chloride (2 ml) and stirred for 40 min. The reaction was concentrated, added 0.1 N NaOH, and extracted with EtOAc (3×). The combined organic layers were washed (brine), dried ($MgSO_4$), filtered, and concentrated. Column chromatography (silica gel, hexanes/EtOAc gradient) gave the title compound (0.06 g, 26%). MS(FIA) (m/z) 428.2 [M+1].

EXAMPLE 588 & 589

5-(3-Benzooxazol-2-ylmethyl-cyclohexyl)-9-chloro-
3-methyl-5H-isoxazolo[4,3-c]-quinolin-4-one & 2-
[3-(9-Chloro-3-methyl-4-oxo-5H-isoxazolo[4,3-c]
quinolin-5-yl)-cyclohexyl]-N-(2-hydroxyphenyl)
acetamide In a fashion similar to that described for Example 587, compound from preparation 43 (0.159 g, 0.423 mmol), oxalyl chloride (0.073 ml, 0.84 mmol), dichloromethane (2.8 ml), DMF (0.005 ml), 2-aminophenol (0.2 g, 1.07 mmol), dichloromethane (1.5 ml), and thionyl chloride (2 ml) gave the title compounds 5-(3-benzooxazol-2-ylmethyl-cyclohexyl)-9-chloro-3-methyl-5H-isoxazolo[4,3-c]quinolin-4-one, 588, (0.089 g, 47%) and 2-[3-(9-chloro-3-methyl-4-oxo-5H-isoxazolo[4,3-c]quinolin-5-yl)-cyclohexyl]-N-(2-hydroxy-phenyl)-acetamide, 589, (0.031 g, 16%) after column chromatography (silica gel, acetone/dichloromethane gradient).
588: MS(FIA) (m/z) 448.1 [M+1]. 589: MS(FIA) (m/z) 466.2 [M+1].

EXAMPLE 590

9-Chloro-3-methyl-5-[3-(4-phenyl-4,5-dihydro-
oxazol-2-ylmethyl)cyclohexyl]-5H-isoxazolo[4,3-c]
quinolin-4-one In a fashion similar to that described for Example 587, a compound from preparation 43 (0.159 g, 0.423 mmol), oxalyl chloride (0.073 ml, 0.84 mmol), dichloromethane (2.8 ml), DMF (0.005 ml), R-(−)-2-phenylglycinol (0.115 g, 0.84 mmol), dichloromethane (1.5 ml), and thionyl chloride (2 ml) gave the title compound (0.105 g, 52%) after column chromatography (silica gel, acetone/dichloromethane gradient). MS(FIA) (m/z) 476.1 [M+1].

EXAMPLE 591

9-Chloro-3-methyl-5-[3-(4-phenyl-4,5-dihydro-
oxazol-2-ylmethyl)cyclohexyl]-5H-isoxazolo[4,3-c]
quinolin-4-one In a fashion similar to that described for Example 587, compound from preparation 43 (0.159 g, 0.423 mmol), oxalyl chloride (0.073 ml, 0.84 mmol), dichloromethane (2.8 ml), DMF (0.005 ml), S-(+)-2-phenylglycinol (0.115 g, 0.84 mmol), dichloromethane (1.5 ml), and thionyl chloride (2 ml) gave the title compound (0.07 g, 35%) after column chromatography (silica gel, acetone/dichloromethane gradient). MS(FIA) (m/z) 476.1 [M+1].

EXAMPLE 592

5-[3-(Benzoylaminomethyl)cyclohexyl]-3-methyl-4-
oxo-4,5-dihydroisoxazolo[4,3-c]-quinoline-8-
carboxylic Acid Methyl Ester To a mixture of Example 496 (0.034 g, 0.063 mmol), acetonitrile (8 ml), MeOH (3 ml), $Et_3N$ (0.15 ml, 0.2 mmol) submerged in a 65° C. oil bath was added $PdCl_2$(dppf) (0.003 g, 0.003 mmol) under CO atmosphere (balloon). The reaction was stirred for 5 h. The reaction was cooled to room temperature and concentrated. The residue was diluted with EtOAc, washed ($H_2O$ then brine), dried ($MgSO_4$), filtered, and concentrated. Column chromatography (silica gel, acetone/dichloromethane gradient) gave the title compound (0.021 g, 70%).
MS(ES+) (m/z) 474.2 [M+1].

EXAMPLE 593

5-[3-(Benzoylaminomethyl)cyclohexyl]-3-methyl-4-oxo-4,5-dihydroisoxazolo[4,3-c]-quinoline-6-carboxylic Acid Methyl Ester In a fashion similar to that described for Example 592, N-[3-(6-Iodo-3-methyl-4-oxo-5H-isoxazolo[4,3-c]quinolin-5-yl)-cyclohexylmethyl]-benzamide (0.048 g, 0.089 mmol), acetonitrile (10 ml), MeOH (5 ml), Et$_3$N (0.04 ml, 0.267 mmol), and PdCl$_2$(dppf) (0.004 g, 0.004 mmol) gave the title compound (0.035 g, 83%) after column chromatography (silica gel, acetone/dichloromethane gradient). MS(FIA) (m/z) 472.3 [M−1].

EXAMPLE 594

[3-(9-Iodo-3-methyl-4-oxo-5H-isoxazolo[4,3-c]quinoline-5-yl)cyclohexylmethyl]-carbamic Acid t-butyl Ester To a solution of phenylmethyl 2-[(1R,3S)-3-(9-iodo-3-methyl-4-oxo-5H-isoxazolo[4,3-c]quinolin-5-yl))cyclohexyl]acetate (1 g, 2.14 mmol) and t-BuOH (15 ml) submerged in a 50° C. oil bath was added Et$_3$N (0.386 ml, 2.78 mmol) and DPPA (0.6 ml, 2.78 mmol) under N$_2$. This solution was heated at reflux overnight. The solvents were removed in vacuum and the residue was chromatographed (silica gel, EtOAc/hexanes gradient) to give the title compound (0.47 g, 40%). MS(FIA) (m/z) 538.3 [M+1], 438.0 [M−BOC].

EXAMPLE 595

N-[3-(3-Methyl-4-oxo-5H-isoxazolo[4,3-c]quinolin-5-yl)cyclohexylmethyl]benzamide To a mixture of Example 106 (0.07 g, 0.129 mmol) and tetrakis(triphenyl-phosphine)palladium (0.015 g, 0.0129 mmol) in toluene (1.3 ml) under N$_2$ was added tributyltin hydride (0.042 ml, 0.155 mmol) and heated at 80° C. for 17 h. Added more tributyltin hydride (0.069 ml, 0.258 mmol) to the mixture and heated at this temperature for 24 h. The reaction was cooled to room temperature, applied to a silica gel column, and elution (acetone/dichloromethane gradient) gave the title compound (0.02 g, 38%).
MS(BS+) (m/z) 416.2 [M+1].

EXAMPLE 596

N-{3-[9-(4-Methoxyphenyl)-3-methyl-4-oxo-5H-isoxazolo[4,3-c]quinolin-5-yl)-cyclohexylmethyl]benzamide To a mixture of Example 106 (0.1 g, 0.185 mmol), tetrakis(triphenyl-phosphine)palladium (0.043 g, 0.037 mmol), and 4-methoxyphenylboronic acid (0.7 g, 0.46 mmol) in dioxane (2 ml) under N2 was added Na2CO3(aq) (0.185 ml, 0.37 mmol) and heated at reflux for 72 h. The reaction was cooled to room temperature, diluted with EtOAc, washed (H2O then brine), dried (MgSO4), filtered, and concentrated. Radial chromatography (silica gel, 33.3% EtOAc/hexanes) gave the title compound (0.057 g, 59%). MS(FIA) (m/z) 522.2 [M+1].

EXAMPLE 597

5-[3-(Benzoylamino-methyl)-cyclohexyl]-3-methyl-4-oxo-5-hydro-isoxazolo[4,3-c]quinoline-9-carboxylic Acid Methyl Ester In a fashion similar to that described for Example 272, a compound from Example 106 (0.88 g, 1.63 mmol), aceto-nitrile (60 ml), MeOH (20 ml), Et$_3$N (0.68 ml, 4.89 mmol), and PdCl$_2$(dppf) (0.066 g, 0.08 mmol) gave the title compound (0.687 g, 89%) after column chromatography (silica gel, acetone/dichloromethane gradient).
MS(FIA) (m/z) 474.1 [M+1].

EXAMPLE 598

5-[3-(Benzoylaminomethyl)cyclohexyl]-3-methyl-4-oxo-5H-isoxazolo[4,3-c]quinoline-9-carboxylic Acid A compound from Example 597 (0.35 g, 0.74 mmol), 5.0 N NaOH (2.4 ml, 11.84 mmol), and dioxane (7 ml) were allowed to react for 3 h at 90° C. in a fashion similar to that of Example 472, give the title compound (0.28 g, 85%).
MS(ES+) (m/z) 460.2 [M+1].

EXAMPLE 599

5-[3-(Benzoylaminomethyl)cyclohexyl]-3-methyl-4-oxo-5H-isoxazolo[4,3-c]quinoline-9-carboxylic Acid Amide To a solution of Example 598, (0.05 g, 0.11 mmol), EDCI (0.032 g, 0.165 mmol), and HOBt (0.023 g, 0.165 mmol) in DMF (1.5 ml) under N$_2$ was added NH$_4$Cl (0.009 g, 0.165 mmol) and diisopropylamine (0.046 ml, 0.33 mmol). The reaction was stirred overnight. The mixture was diluted with EtOAc, washed (1.0 N HCl saturated with NaCl), dried (MgSO$_4$), filtered, and concentrated. Column chromatography (silica gel, hexanes/EtOAc gradient) gave the title compound (0.024 g, 48%). MS(ES+) (m/z) 459.1 [M+1].

EXAMPLE 600

5-[3-(Benzoylaminomethyl)cyclohexyl]-3-methyl-4-oxo-5H-isoxazolo[4,3-c]quinoline-9-carboxylic Acid diethylamide In a fashion similar to that described for Example 596, a compound from Example 598 (0.05 g, 0.11 mmol), EDCI (0.032 g, 0.165 mmol), HOBt (0.023 g, 0.165 mmol), DMF (1.5 ml), and diethylamine (0.017 ml, 0.165 mmol) gave the title compound (0.039 g, 68%) after column chromatography (silica gel, acetone/dichloromethane gradient).
MS(ES+) (m/z) 515.2 [M+1].

EXAMPLE 601

5-[3-(Benzoylaminomethyl)cyclohexyl]-3-methyl-4-oxo-5H-isoxazolo[4,3-c]quinoline-9-carboxylic Acid Ethyl Ester To a solution of Example 598, (0.05 g, 0.11 mmol) in DMF (1 ml) under N$_2$ was added iodoethane (0.062 ml, 0.33 mmol) and Cs$_2$CO$_3$ (0.036 g, 0.11 mmol). The mixture was stirred overnight, diluted with EtOAc, washed (H$_2$O then brine), dried (MgSO$_4$), filtered, and concentrated. Column chromatography (silica gel, acetone/dichloromethane gradient) gave the title compound (0.043 g, 80%). MS(FIA) (m/z) 488.4 [M+1].

EXAMPLE 602

5-[3-(Benzoylaminomethyl)cyclohexyl]-3-methyl-4-oxo-5H-isoxazolo[4,3-c]quinoline-9-carboxylic Acid Benzyl Ester In a fashion similar to that described for Example 601, a compound from Example 598 (0.05 g, 0.11 mmol), benzyl bromide (0.039 ml, 0.33 mmol), $Cs_2CO_3$ (0.036 g, 0.11 mmol), and DMF (1 ml) gave the title compound (0.051 g, 85%) after column chromatography (silica gel, acetone/ dichloromethane gradient). MS(FIA) (m/z) 548.3 [M-1].

EXAMPLE 603

5-[3-(Benzoylaminomethyl)cyclohexyl]-3-methyl-4-oxo-5H-isoxazolo[4,3-c]quinoline-9-carboxylic Acid Ethoxycarbonylmethyl Ester In a fashion similar to that described for Example 601, a compound from Example 598 (0.05 g, 0.11 mmol), ethyl bromoacetate (0.036 ml, 0.33 mmol), $Cs_2CO_3$ (0.036 g, 0.11 mmol), and DMF (1 ml) gave the title compound (0.054 g, 90%) after column chromatography (silica gel, acetone/ dichloromethane gradient). MS(FIA) (m/z) 546.2 [M+1].

EXAMPLE 604

5-[3-(Benzoylaminomethyl)cyclohexyl]-3-methyl-4-oxo-5H-isoxazolo[4,3-c]quinoline-9-carboxylic Acid Isopropyl Ester In a fashion similar to that described for Example 601, a compound from Example 598 (0.05 g, 0.11 mmol), 2-iodopropane (0.033 ml, 0.33 mmol), $Cs_2CO_3$ (0.036 g, 0.11 mmol), and DMF (1 ml) gave the title compound (0.021 g, 38%) after column chromatography (silica gel, acetone/ dichloromethane gradient). MS(ES+) (m/z) 502.2 [M+1].

EXAMPLE 605

5-[3-(Benzoylamino-methyl)-cyclohexyl]-3-methyl-4oxo-5H-isoxazolo[4,3-c]quinoline-9-carboxylic Acid Ethylamide In a fashion similar to that described for Example 599, a compound from Example 598 (0.05 g, 0.11 mmol), EDCI (0.032 g, 0.165 mmol), HOBt (0.023 g, 0.165 mmol), DMF (1.5 ml), ethylamine (0.55 ml, 1.1 mmol), and diisopropylethylamine (0.06 ml, 0.33 mmol) gave the title compound (0.003 g, 6%) after column chromatography (silica gel, acetone/dichloromethane gradient). MS(ES+) (m/z) 487.3 [M+1].

EXAMPLE 606

5-[3-(Benzoylaminomethyl)cyclohexyl]-3-methyl-4-oxo-5H-isoxazolo[4,3-c]quinoline-9-carboxylic Acid Methyl Amide To a solution of Example 598 (0.05 g, 0.11 mmol) in toluene (1.5 ml) under $N_2$ was added thionyl chloride (0.5 ml) and heated at reflux for 3 h. The solution was concentrated using toluene to azeotrope. The residue was dissolved in dichloromethane (2 ml) under $N_2$ and added methylamine (0.55 ml, 1.1 mmol) and DMAP (0.025 g, 0.22 mmol). The reaction was stirred overnight, diluted with dichloromethane, washed (0.1 N HCl, $H_2O$, and brine), dried ($MgSO_4$), filtered, and concentrated. Column chromatography (silica gel, acetone/$CH_2Cl_2$ gradient) gave the title compound (0.029 g, 56%). MS(ES+) (m/z) 473.2 [M+1].

EXAMPLE 607

N-{3-[9-(4,5-Dihydro-oxazol-2-yl)-3-methyl{3oxo-H-isoxazolo[4,3-c]quinolin-5-yl]-cyclohexylmethyl}benzamide To a solution of Example 598 (0.1 g, 0.22 mmol) in toluene (4 ml) under $N_2$ was added thionyl chloride (1 ml) and heated at reflux for 3 h. The solution was concentrated using toluene to azeotrope and the residue was dissolved in dichloromethane (4 ml) under $N_2$. Ethanolamine (0.131 ml, 2.2 mmol) and DMAP were added to the reaction and stirred overnight. The mixture was diluted with dichloromethane, washed (5% $NaHCO_3$, $H_2O$, and brine), dried ($MgSO_4$), filtered, and concentrated. The residue was dissolved in thionyl chloride (2 ml), stirred overnight, and concentrated. The crude material was purified by column chromatography (silica gel, acetone/$CH_2Cl_2$ gradient) to give the title compound (0.01 g, 10%). MS(ES+) (m/z) 485.2 [M+1], 521.2 [M+HCl].

EXAMPLE 608

N-[3-(9-Hydroxymethyl-3-methyl-4-oxo-5H-isoxazolo[4,3-c]quinolin-5-yl)-cyclohexylmethyl] benzamide To a solution of Example 598 (0.01 g, 0.022 mmol) in toluene (0.4 ml) under $N_2$ was added thionyl chloride (0.1 ml) and heated at reflux for 3 h. The solution was concentrated using toluene to azeotrope and the residue was dissolved in dichloromethane (0.5 ml). To this solution was added $NaBH_4$ (0.008 g, 0.22 mmol) in THF (0.5 ml) and stirred overnight. The mixture was diluted with MeOH (1 ml) and EtOAc, washed (0.1 N NaOH, $H_2O$, and brine), dried ($MgSO_4$), filtered, and concentrated to give the title compound (0.005 g, 53%) without further purification. MS(ES+) (m/z) 446.2 [M+1].

EXAMPLE 609

N-[3-(3-Methyl-4-oxo-9-propionyl-5H-isoxazolo[4, 3-c]quinolin-5-yl)-cyclohexylmethyl]benzamide To a solution of Example 598 (0.05 g, 0.011 mmol) in toluene (2 ml) under $N_2$ was added thionyl chloride (1 ml) and heated at reflux for 3 h. The solution was concentrated using toluene to azeotrope. To a solution of diethylzinc (1 ml, 1 mmol) under $N_2$ stirring at −20° C. was added a solution of CuCN (0.093 g, 1.04 mmol) and LiCl (0.086 g, 2.02 mmol) in THF (1.5 ml). This mixture was gradually allowed to warm to 0° C., stirred for 15 min at this temperature, and cooled to −25° C. To this solution was added the acid chloride residue in THF (0.5 ml) and stirred for 1.5 h gradually allowing to warm to 0° C. The reaction was diluted with $NH4Cl_{(aq)}$ and extracted with dichloromethane (2×). The combined organic layers were washed (brine), dried ($MgSO_4$), filtered, and concentrated. Column chromatography (silica gel, acetone/dichloromethane gradient) gave the title compound (0.013 g, 28%). MS(ES+) (m/z) 472.2 [M+1].

EXAMPLE 610 & 611

5-[3-(2-Benzenesulfinyl-ethyl)-cyclohexyl]-9-chloro-3-methyl-5H-isoxazolo[4,3-c]quinolin4one & 5-[3-(2-Benzenesulfonyl-ethyl)-cyclohexyl]-9-chloro-3-methyl-5H-isoxazolo[4,3-c]quinolin-4-one A compound from Example 501 (0.20 g, 0.00044 mol) was dissolved in $CH_2Cl_2$ (30 mL) and the mixture cooled under a nitrogen atmosphere in an ice bath. Then 3-chloroperoxy-benzoic acid (50%, 0.15 g, 0.00044 mol) was added and the mixture stirred for 6 h while warming to ambient temperature. The mixture was quenched with aq $NaHCO_3$ and extracted with $CH_2Cl_2$. The combined extracts were dried over sodium sulfate and concentrated in vacuo.

The resulting residue was chromatographed over silica gel using CH$_2$Cl$_2$/THF as eluent which allowed for isolation of both the pure sulfoxide (0.075 g, 36%), MS(ES): (M+1)$^+$ 469.1, 471.2 m/z, and pure sulfone (0.025 g, 12%). MS(ES): (M+1)$^+$ 485.4, 487.3 m/z.

EXAMPLE 612

5-(3-Aminomethyl-cyclohexyl)-9-chloro-3-methyl-5H-isoxazolo[4,5-c]quinolin-4-one (d,l)

To 41.5 mg (0.093 mmol) of Example 507 was added 0.75 ml trifluoroacetic acid. After 10 min stirring at rt, starting material (via TLC) was consumed. The crude reaction mixture was diluted with EtOAc and sat'd aq. bicarbonate and transferred to a sep funnel. The aqueous phase was reextracted two add'l times with EtOAc, and the combined organics were washed with brine, dried over Na$_2$SO$_4$, filtered and concentrated to afford clean amine (28 mg, 87%) which was used without further purification. MS (+ES) m/z 345.9 (M+H)+.

EXAMPLE 613

(1R,3S)-5-(3-Aminomethylcyclohexyl)-9-chloro-3-methyl-5H-isoxazolo[4,5-c]quinolin-4-one The product from Example 562 (0.069 g, 0.16 mmol) was treated with TFA (2 mL) and stirred at room temperature for 15 min. The reaction was added dropwise to sat HCO$_3^-$ (10 mL) and the product was extracted with CH$_2$Cl$_2$ (5×10 mL). The solvent was removed in vacuo to afford 0.05 g (94%) of the title compound as a white solid. MS (ES+) m/z 346.0 (M+H)$^+$.

EXAMPLE 614

(1S,3R)-5-(3-Aminomethylcyclohexyl)-9-chloro-3-methyl-5H-isoxazolo[4,5-c]quinolin-4-one The product of Example 553 (0.08 g, 0.18 mmol) was treated with TFA (2 mL) and stirred at room temperature for 20 min. The reaction was added dropwise to sat HCO$_3^-$ (10 mL) and the product was extracted with CH$_2$Cl$_2$ (5×10 mL). The solvent was removed in vacuo to afford 0.047 g (76%) of title compound as a white solid. MS (ES+) m/z 346.0 (M+H)$^+$.

EXAMPLE 615

(1R,3S)-5-(3-Aminomethylcyclohexyl)-9-chloro-3-methyl-5H-isoxazolo[4,5-c]quinolin-4-one A solution of the product from Example 508 (0.40 g, 0.83 mmol) in dry CH$_2$Cl$_2$ (5 mL) was treated with iodotrimethylsilane (0.25 g, 1.25 mmol) and stirred at r.t. After 3 hr the reaction was quenched with MeOH (2 mL) and stirred for an additional 30 min. The solution was then concentrated to an orange solid and taken up in EtOAc (20 mL) and 1 N HCl (20 mL) and transferred to a sep funnel. The organic layer was extracted and the aqueous layer was washed with additional EtOAc (2×10 mL). The pH of the aqueous layer was then adjusted to ph~12 with 5 M NaOH. The product was extracted with EtOAc (3×25 mL). The EtOAc extractions were dried over sodium sulfate, filtered, and the solvent removed in vacuo to afford 0.240 g (84%) as a white solid which was used without further purification. MS (ES+) m/z 346.0 (M+H)$^+$.

EXAMPLE 616

5-(3-Aminomethylcyclohexyl)-9-chloro-3-methyl-5H-isoxazolo[4,5-c]quinolin-4-one

The product from Example 560 (30 mg, 0.067 mmol) was treated with HCl-1.0 M in HOAc (2 mL). The reaction was stirred at r.t. for 20 minutes. Acetonitrile (2 mL) was added and the solution was concentrated to a white solid. The white solid was suspended in ether and filtered to afford 15 mg (70%) as a white solid. MS (ES+) m/z 346.0 (M+H)$^+$.

EXAMPLE 617

5-(3-Aminomethylcyclohexyl)-9-chloro-3-methyl-5H-isoxazolo[4,5-c]quinolin-4-one

The product of Example 561 (30 mg, 0.067 mmol) was treated with HCl-1.0 M in HOAc (2 mL). The reaction was stirred at r.t. for 20 minutes. Acetonitrile (2 mL) was added and the solution was concentrated to a white solid. The white solid was suspended in ether and filtered to afford 13 mg (60%) as a white solid. MS (MS+) m/z 346.0 (M+H)$^+$.

EXAMPLE 618

3-[2-(9-Chloro-3-methyl-4-oxo-5H-isoxazolo[4,5-c]quinolin-5-yl)cyclohexyl]-N-(3,4,5-trimethoxyphenyl)propionamide The amide from preparation 165 (24 mg, 0.042 mmol) was dissolved in anhydrous DMF (0.5 ml). NaHMDS (1 M in THF, 0.046 ml, 1.1 eq) was added dropwise. After 1 hr, sm still present, and additional base (1.1 eq) was added, followed by a third volume (1.1 eq) an hour later. The reaction was then allowed to proceed o.n. The reaction was then quenched with 0.1 N HCl and EtOAc, transferred to a sep funnel, and the aqueous phase was reextracted two additional times. the combined organics were washed with sat'd bicarbonate, then with brine, dried over Na$_2$SO$_4$, filtered and concentrated to afford 21 mg of crude product. Purification over silica (1 g Bond-Elut cartridge, 2:1 EtOAc/hexanes) afforded 21 mg of product (40%).
MS (+Es) 553.9, 555.9 (M+H)$^+$.

EXAMPLE 619

5-(3-Aminomethylcyclopentyl)-9-chloro-3-methyl-5H-isoxazolo[4,3-c]quinolin4-one

A mixture of Example 518 (240 mg, 0.5 mmol) and trimethyl silyl iodide (154, 077 mmol) dissolved in methylene chloride (10 mL) was stirred overnight at rt. The reaction mixture was passed through Bond Elut SCX column (20 cc, 5 g), eluted with ammonia solution in methanol (1M, 20 mL) and evaporated to obtain the title compound (150 mg, 90%). ESMS: 332 (M+1)$^+$.

EXAMPLE 620

5-[((1R,3S)-3-Aminocyclopentyl)methyl]-9-chloro-3-methyl-5H-isoxazolo[4,3-c]quinolin-4-one N-{(1S,3R)-3-[(9-chloro-3-methyl-4-oxo-5H-isoxazolo[4,3-c]quinolin-5-yl))methyl]cyclopentyl}(tert-butoxy)carboxamide was converted to the amine by TFA in DCM at rt. for three hours. ESMS: 332 (M+1)+.

EXAMPLE 621

5-[((1S,3R)-3-Aminocyclopentyl)methyl]-9-chloro-3-methyl-5H-isoxazolo[4,3-c]quinolin4-one N-{(1R,3S)-3-[(9-chloro-3-methyl-4-oxo-5H-isoxazolo-[4,3-c]quinolin-5-yl))methyl]cyclopentyl}(tert-butoxy)carboxamide was converted to the amine as described in Example 620. ESMS: 332 (M+1)+.

EXAMPLE 622 cis-1-(9-Chloro-3-methyl-4-oxo-5H-isoxazolo[4,3-c] quinolin-5-yl)-3-(3-phenyluriedo)-cyclohexane To the suspension of cis-1-(9-chloro-3-methyl-4-oxo-5H-isoxazolo[4,3-c]quinolin-5-yl)-3-amino-cyclohexane (0.0446 g, 0.121 mmol) in 1 mL anhydrous THF at RT was added 2N NaOH (0.60 mL, 0.121 mmol). After 5 min. the phenylisocyanate (0.013 mL, 0.121 mmol). After 20 min. the reaction was diluted with EtOAc, washed with water and concentrated to near dryness. After sonication and filtration a white solid (0.0412, 75%) was obtained. ESIMS m/e 451 $^{35}$Cl (M$^+$+1) and 453 $^{37}$Cl (M$^+$+1).

EXAMPLE 623 cis-1-(9-chloro-3-methyl-4-oxo-5H-isoxazolo[4,3-c] quinolin-5-yl)-3-[3-(phenylmethyl)-uriedo] cyclohexane A procedure similar to that for Example 622 was used to prepare the title compound as a yellow solid (0.110 g, 87%). ESIMS m/e 465 $^{35}$Cl (M$^+$+1) and 467 $^{37}$Cl (M$^+$+1).

EXAMPLE 624 cis-1-(9-chloro-3-methyl-4-oxo5H-isoxazolo[4,3-c] quinolin-5-yl)-3-(3-cyclohexyluriedo) Cyclohexane A procedure similar to that for Example 622 was used to prepare the title compound as a yellow solid (0.106 g, 86%). ESIMS m/e 457 $^{35}$Cl (M$^+$+1) and 459 $^{37}$Cl (M$^+$+1).

EXAMPLE 625

Preparation of racemic cis-1-(9-chloro-3-methyl-4-oxo-5H-isoxazolo[4,3-c]quinolin-5-yl)-3-(3-ethyluriedo) Cyclohexane A procedure similar to that for Example 622 was used to prepare the title compound as a yellow solid (0.102 g, 94%). ESIMS m/e 403 $^{35}$Cl (M$^+$+1) and 405 $^{37}$Cl (M$^+$+1).

EXAMPLE 626 cis-1-(9-chloro-3-methyl-4-oxo-5H-isoxazolo[4,3-c] quinolin-5-yl)-3-(3-propyluriedo)cyclohexane A procedure similar to that for Example 622 was used to prepare the title compound as a yellow solid (0.106 g, 94%). ESIMS m/e 417 $^{35}$Cl (M$^+$+1) and 419 $^{37}$Cl (M$^+$+1).

EXAMPLE 627

(1S,3R)-1-(9-chloro-3-methyl-4-oxo-5H-isoxazolo [4,3-c]quinolin-5-yl)-3-[((2S)-2-amino-2-phenylacetyl)amino]cyclohexane Hydrochloride To the product from Example 11 (0.015 g, 0.027 mmol) in 1 mL CH$_2$Cl$_2$ was added 1 mL 4M HCl in dioxane. After 3 h the mixture was stipped to dryness to give the title compound as a white solid (0.0131 g, 98%). ESIMS m/e 465 $^{35}$Cl (M$^+$+1) and 467 $^{37}$Cl (M$^+$+1).

EXAMPLE 628

(1R,3S)-1-(9-chloro-3-methyl-4-oxo-5H-isoxazolo [4,3-c]quinolin-5-yl)-3-[((2S)-2-amino-2-phenylacetyl)amino]cyclohexane Hydrochloride To the product from Example 11 (0.013 g, 0.023 mmol) in 1 mL CH$_2$Cl$_2$ was added 1 mL 4M HCl in dioxane. After 3 h the mixture was stipped to dryness to give, a white solid (0.0115 g, 100%). ESIMS m/e 465 $^{35}$Cl (M$^+$+1) and 467 $^{37}$Cl (M$^+$+1).

EXAMPLE 629

(1S,3R)-1-(9-chloro-3-methyl-4-oxo-5H-isoxazolo [4,3-c]quinolin-5-yl)-3-[((2R)-2-amino-2-phenylacetyl) amino]cyclohexane Hydrochloride To the product from Example 11 (0.013 g, 0.019 mmol) in 1 mL CH$_2$Cl$_2$ was added 1 mL 4M HCl in dioxane. After 3 h the mixture was stipped to dryness to give a white solid (0.0098 g, 100%). ESIMS m/e 465 $^{35}$Cl (M$^+$+1) and 467 $^{37}$Cl (M$^+$+1).

EXAMPLE 630 AND 631

N-[3-(9-Chloro-3-methyl-4-oxo-5H-isoxazolo[4,3-c] quinolin-5-yl)cyclohexyl]-2-(5-methyltetrazol-2-yl)-2-phenylacetamide & N-[3-(9-Chloro-3-methyl-4-oxo-5H-isoxazolo[4,3-c]quinolin-5-yl)cyclohexyl]-2-(5-methyltetrazol-1-yl)-2-phenylacetamide To a 0° C. solution of N-[3-(9-Chloro-3-methyl-4-oxo-5H-isoxazolo[4,3-c]quinolin-5-yl)-cyclohexyl]-2-hydroxy-2-phenyl (30 mg, 0.06 mmol) in toluene (4 mL) was added triphenylphosphine (20 mg, 0.08 mmol), 5-methyltetrazole (8 mg, 0.10 mmol), and diethylazodicarboxylate (16 μL, 0.10 mmol) dropwise. After 30 minutes the reaction was allowed to warm to room temperature overnight. Purification gave 4.4 mg and 10.2 mg, respectively as white solids, 43% combined yield. $^1$H NMR: consistent with structures. MS (ion spray) 532 (M$^+$).

EXAMPLE 632

5-(3-Aminomethyleyclohexyl)-9-chloro-3-methyl-5H-isoxaolo[4,3-c]quinolin-4-one Hydroiodide To a 0° C. solution of [3-(9-chloro-3-methyl-4-oxo-5H-isoxazolo[4,3-c]quinolin-5-yl)-cyclohexylmethyl]-carbamic acid be (5.0 g, 10.4 mmol) in dichloromethane (100 mL) was added iodotrimethylsilane (3.6 mL, 25.0 mmol) dropwise, and the solution allowed to warm to room temperature overnight. Methanol (6.1 mL, 150.0 mmol) was added dropwise over two minutes, and the reaction stirred for 30 minutes. The reaction was concentrated and suspended in ethyl ether. After 15 minutes of sonication, the solids were removed by filtration and washed with ethyl ether. The tan powder was dried on a vacuum pump to give 4.61 g as the 1.2 HI salt, 89% yield. $^1$H NMR: consistent with structure. MS (ion spray) 346 (M$^+$).

EXAMPLE 633

2-Amino-N-[3-(9-chloro-3-methyl-4-oxo-5H-isoxazolo[4,3-c]quinolin-5-yl)cyclohexyl]-2-phenylacetamide A compound from Example 235 (180 mg, 0.32 mmol) was combined with trifluoroacetic acid (0.75 mL) in dichloromethane (4.0 mL) and the mixture stirred at ambient temperature until deprotection was complete. The mixture was then concentrated in vacuo and the residue treated with aqueous NaHCO$_3$ and extracted with ethyl acetate. Concentration left a residue, which was chromatographed over silica (methanol/dichloro-methane) allowing for isolation of the desired product (145 mg, 97%) as a white solid. MS(ES): (M+1)$^+$ 465.2, 467.2 m/z.

EXAMPLE 634

5-(3-Aminocyclohexyl)-9-chloro-3-methyl-5H-isoxazolo[4,3-c]quinolin-4-one Hydroiodide To a solution of [3-(9-chloro-3-methyl-4-oxo-5H-isoxazolo[4,3-c]quinolin-5-yl)cyclohexyl]carbamic acid methyl ester, 2.0 g (5.1 mmol) in 50 mL of dichloromethane was added 1.74 mL (12.2 mmol) of trimethylsilyliodide. The reaction mixture was stirred overnight at ambient temperature and was quenched dropwise with 3.0 mL (73.4 mmol) of methanol. The mixture was stirred 30 minutes at ambient temperature and was concentrated to dryness. The residue was triturated with ether, filtered and dried to provide a quantitative yield of the desired isomer as a tan solid. $^1$H—NMR is consistent with structure. MS (ion spray) 332.1 (M+ for free base).

EXAMPLE 635

Pyridazine-4-carboxylic acid [3-(9-chloro-3-methyl-4-oxo-5H-isoxazolo[4,3-c]quinolin-5-yl)cyclohexylmethyl]amide 4-Methylpyridazine, 4.0 mL (44.6 mmol) was dissolved in 200 mL of water and 16.2 g (103 mmol) of potassium permanganate was added. The resulting slurry was refluxed for 30 min, then an additional 8.5 g (54 mmol) of potassium permanganate was added. The resulting slurry was refluxed for 24 h, then filtered hot through celite. The resulting solution was washed with ether, acidified to pH=7 with 5 N HCl, and concentrated to a volume of 80 mL. This solution was acidified to pH=2 with 1 N HCl and extracted with ethyl acetate and with 20% isopropanol/chloroform. The combined organics were dried over sodium sulfate, filtered and concentrated to dryness to yield 320 mg of a tan foam. 1H NMR indicated a 2:1 mixture of 4-pyridazine carboxylic acid: starting material 4-methylpyridazine.

This mixture, 40 mg, was added to a solution of 66 mg (0.14 mmol) of a compound from Example 632 in 5 mL of N,N-dimethylformamide. To this solution was added 23 mg (0.17 mmol) of 1-hydroxy-7-azabenzotriazole, 33 mg (0.17 mmol) of 1-(3-dimethyl-aminopropyl)-3-ethylcarbodiimide hydrochloride, 5 mg of 4-dimethylaminopyridine and 60 μL (0.42 mmol) of triethylamine. Yield=33 mg (53%) of the desired isomer as a white foam. $^1$H—NMR is consistent with structure. MS (ion spray) 452.2 (M+).

EXAMPLE 636

1,2,3,4-Tetrahydroisoquinoline-3-carboxylic acid [3-(9-chloro-3-methyl-4-oxo-5H-isoxazolo[4,3-c]quinolin-5-yl)cyclohexyl]amide Hydrochloride A solution of 3-(9-Chloro-3-methyl-4oxo-5H-isoxazolo[4,3-c]quinolin-5-yl)-cyclohexylcarbamoyl]-3,4-dihydro-1H-isoquinoline-2-carboxylic acid tert-butyl ester, 74 mg (0.125 mmol) in 5 mL of acetic acid saturated with HCl gas was stirred for three hours at ambient temperature, then was concentrated to dryness. The residue was slurried 3× in toluene and concentrated to dryness to give a quantitative yield of the desired isomer as a white solid. $^1$H—NMR is consistent with structure. MS (ion spray) 491.0 (M+).

EXAMPLE 637

1,2,3,4-Tetrahydro-isoquinoline-3-carboxylic acid [3-(9chloro-3-methyl-4-oxo-5H-isoxazolo[4,3-c]quinolin-5-yl)-cyclohexyl]-amide Hydrochloride A solution of 3-(9-chloro-3-methyl-4-oxo-5H-isoxazolo[4,3-c]quinolin-5-yl)-cyclohexylcarbamoyl[-3,4-dihydro-1H-isoquinoline-2-carboxylic acid tert-butyl ester, 74 mg (0.125 mmol) in 5 mL of acetic acid saturated with HCl gas was stirred for four hours at ambient temperature, then was concentrated to dryness. The residue was slurried 3× in toluene and concentrated to dryness to give a quantitative yield of the desired isomer as a white solid. $^1$H—NMR is consistent with structure. MS (ion spray) 491.3 (M+).

EXAMPLE 638

2-Amino-N-[3-(9-chloro-3-methyl-4-oxo-5H-isoxazolo[4,3-c]quinolin-5-yl)cyclohexyl]-2-phenylacetamide {[3-(9-Chloro-3-methyl-4-oxo-5H-isoxazolo[4,3-c]quinolin-5-yl)-cyclohexylcarbamoyl]-phenyl-methyl}-carbamic acid tert-butyl ester (1.24 g; 2.2 mmol) was dissolved in excess, neat acetic acid saturated with $HCl_{(g)}$ (20 mL). After stirring 30 min at room temperature, the solution was concentrated to dryness by rotary evaporation. Acetic acid was removed from the resulting solid by consecutive dissolution in, and drying from, acetonitrile (thrice) and then diethyl ether (once). The solid was dissolved in 25% (v/v) isopropyl alcohol in chloroform, washed with saturated $NaHCO_{3(aq)}$, and dried by rotary evaporation to yield the desired product in 97% isolated yield.
MS(ES) calc'd: [M+H]$^+$=465.2 m/z. Found: 465.2 m/z.

EXAMPLE 639

2-Amino-N-{[3-(9-chloro-3-methyl-4-oxo-5H-isoxazolo[4,3-c]quinolin-5-yl)-cyclohexylcarbamoyl]-phenylmethyl}-2-methylpropionamide Hydrochloride A compound from Example 321 was deprotected in a manner similar to Example 638 and kept as the hydrochloride salt. MS(ES) calc'd: [M+H]$^+$=550.2 m/z; [M–H]$^-$=548.2 m/z; [M+Cl]$^-$=584.2 m/z. Found: 550.0 m/z; 548.0 m/z; 584.0 m/z.

EXAMPLE 640

2-Amino-N-[3-(9-chloro-3-methyl-4-oxo-5H-isoxazolo[4,3-c]quinolin-5-yl)cyclohexyl]-2-pyridin-3-ylacetamide A compound from Example 326 was deprotected in a manner similar to Example 638. The free base was separated into individual diastereomers by radial chromatography on a 2 mm thick silica gel rotor with a 2% methanol/dichloromethane (v/v) mobile phase (300 mL) followed by increasing methanol to 10% in step gradients (each mobile phase now containing 1% triethylamine). The desired product was isolated as 13 mg of isomer 1, 18 mg of isomer 2, and 7 mg mixed product.
Isomer 1 MS(ES) exact mass calc'd: [M+H]$^+$=466.1646 m/z. Found: 466.1648 m/z.
Isomer 2 MS(ES) exact mass calc'd: [M+H]$^+$=466.1646 m/z. Found: 466.1663 m/z.

EXAMPLE 641

N-[3-(9-Chloro-3-methyl-4-oxo-5H-isoxazolo[4,5-c]quinolin-5-yl)cyclohexylmethyl]-thiobenzamide A solution of cis-N-{[3-(9-chloro-3-methyl-4-oxo-5H-isoxazolo[4,5-c]quinolin-5-yl))cyclohexyl]methyl}benzamide (0.1 g, 0.2 mmol) in pyridine (10 mL) was treated with P$_2$S$_5$ (0.37 g, 1.7 mmol) and heated to reflux. The reaction was stirred for 1 hour at reflux and then allowed to cool to r.t. The reaction was quenched with water (150 mL) A white precipitate formed and was filtered to afford a light yellow solid. This solid was taken up in $CH_2Cl_2$ (15 mL) and purified by silica gel column chromatography. The product was eluted with 1% MeOH in $CH_2Cl_2$. The solvent was removed to afford 0.082 g (81%) of a yellow solid. MS m/z (ES+) 465.8 (M+H)$^+$, (ES−) 463.8 (M−H)$^−$.

EXAMPLE 642

N-[3-(9-Chloro-3-methyl-4-oxo-2,4-dihydropyrazolo[4,3-c]quinolin-5-yl)-cyclohexylmethyl]benzamide Cis-N-({3-[3-(aminoethylidene)-5-chloro-2,4-dioxohydroquinolyl]-cyclohexyl}methyl)benzamide (0.15 g, 0.3 mmol) and hydrazine hydrate-85% (0.016 g, 0.49 mmol) in EtOH (20 mL). The reaction was heated to reflux and stirred for 6 hr. The reaction was then concentrated to a solid and taken up in $CH_2Cl_2$. This solution was purified by silica gel column chromatography using 50% EtOAc in $CH_2Cl_2$ to elute the product. The solvent was removed to afford 0.095 g (64%) as a yellow solid. MS (ES+) m/z 448.9 (M+H)$^+$, (ES−) m/z 446.9 (M−H)$^−$, 506.9 (M+CH3COO$^−$)$^−$.

EXAMPLE 643

N-[3-(9-Chloro-3-methyl-4-oxo-2,4-dihydropyrazolo[4,3-c]quinolin-5-yl)-cyclohexylmethyl]-6-fluoronicotinamide cis-N-({3-[3-(Aminoethylidene)-5-chloro-2,4-dioxohydroquinolyl]-cyclohexy}methyl)(6-fluoro(3-pyridyl))carboxamide (0.92 g, 0.2 mmol) and hydrazine hydrate-85% (0.063 g, 0.3 mmol) in EtOH (20 mL). The reaction was heated to reflux and stirred for 1 hr. The reaction was then concentrated to a solid and taken up in $CHCl_3$. This solution was purified by silica gel column chromatography using 5% MeOH in $CHCl_3$ to elute the product. The solvent was removed to afford 0.02 g (22%) as a white solid. MS (ES+) m/z 468.1 (M+H)$^+$, (ES−) m/z 466.1 (M−H)$^−$, 526.2 (M+CH3COO$^−$)$^−$.

EXAMPLE 644

[3-(9-Chloro-3-methyl-4-oxo-5H-isoxazolo[4,5-c]quinolin-5-yl)cyclohexylmethyl]-carbamic Acid Benzyl Ester A solution of N-{[3-(3-acetyl-4-amino-5-chloro-2-oxohydroquinolyl)-cyclohexyl]-methyl}(phenylmethoxy)carboxamide (0.02 g, 0.04 mmol) in acetic acid (2 mL) was treated with hydroxylamine hydrochloride (3 mg, 0.046 mmol). The solution was heated to reflux and stirred 4 hr. The reaction was then diluted in $CH_2Cl_2$ (50 mL) and washed with 5M NaOH (3×10 mL) and brine (2×10 mL). The organic was dried over sodium sulfate and the solvent removed. The crude product was purified by silica gel column chromatography using 10% EtOAc in $CH_2Cl_2$ to elute the product. The solvent was removed in vacuo to afford 0.014 g (70%) of the title compound as an off-white solid.
MS (ES+) m/z 500.1 (M+H)$^+$.

EXAMPLE 645

N-[3-(9-Chloro-3-methyl-4-oxo-5H-isoxazolo[4,5-c]quinolin-5-yl)cyclohexylmethyl]-6-fluoronicotinamide A solution of N-{[3-(3-acetyl-4-amino-5-chloro-2-oxohydroquinolyl)cyclohexyl]-methyl}(6-fluoro(3-pyridyl))carboxamide (0.035 g, 0.07 mmol) in acetic acid (5 mL) was treated with hydroxylamine hydrochloride (7.8 mg, 0.11 mmol). The solution was heated to reflux and stirred 3 hr. The reaction was then diluted in $CHCl_3$ (50 mL) and washed with sat'd sodium bicarbonate (3×10 mL) and brine (2×10 mL). The organic was dried over sodium sulfate and the solvent removed. The crude product was purified by silica gel column chromatography using 50% EtOAc in $CHCl_3$ to elute the product. The solvent was removed in vacuo to afford 0.025 g (72%) of the title compound as a white solid. MS m/z (ES+) 468.8 (M+H)$^+$, (ES−) 466.8 (M−H)$^−$, 526.8 (M+CH3COO$^−$)$^−$.

EXAMPLE 646

N-[3-(9–Cyano-3-methyl-4-oxo-5H-isoxazole[4,3-c]quinolin-5-yl)-cyclohexylmethyl]-4-fluoro-benzamide To a solution of a compound from Example 524 (0.106 g, 0.23 mmol) in $CH_2Cl_2$ (10 ml) under $N_2$ was added TMSI (0.36 ml, 2.52 mmol) and stirred overnight. Added MeOH (5 ml) and stirred for 1 h to quench the reaction. The mixture was concentrated, triturated with toluene and dried to obtain a crude solid. This was mixed with 4-fluorobenoyl chloride (0.093 ml, 0.8 mmol)in $CH_2Cl_2$ (5 ml)under $N_2$ and triethylamine (0.22 ml, 1.6 mmol) was added dropwise. After stirring overnight, the mixture was diluted with $CH_2Cl_2$, washed (0.1N HCl then brine), dried (MgSO$_4$), filtered, and concentrated. Flash chromatography (silica gel, acetone/$CH_2Cl_2$ gradient) gave the title compound (0.085 g, 88%). Mass Spectrum (ES+) (m/z) 459.1 [M+1].

EXAMPLE 647

N-[3-(9–Cyano-3-methyl-4-oxo-5H-isoxazole[4,3-c]quinolin-5-yl)cyclohexylmethyl]-3,4-difluorobenzamide In a fashion similar to that described for Example 527, a compound from Example 524 (0.106 g, 0.23 mmol), $CH_2Cl_2$ (10 ml), TMSI (0.36 ml, 2.52 mmol), 3,4-difluorobenzoyl chloride (0.093 ml, 0.8 mmol), $CH_2Cl_2$ (5 ml), and triethyamine (0.22 ml, 1.6 mmol) gave the title compound (0.087 g, 87%) after flash chromatography (silica gel, acetone/$CH_2Cl_2$ gradient). Mass Spectrum (ES+) (m/z) 477.1 [M+1].

EXAMPLE 648

N-[3-(9-Chloro-4-oxo-3-phenylsulfanyl-5H-isoxazole[4,3-c]quinolin-5-yl)-cyclohexylmethyl]benzamide To a solution of N-{[3-(3-acetyl-4-amino-5-chloro-2-oxohydroquinolyl)-cyclohexyl]methyl}(6-fluoro(3-pyridyl))carboxamide (0.1 g, 0.2 mmol) in DMF (2.5 ml) under $N_2$ was added sodium thiophenoxide (0.132 g, 1.0 mmol) and stirred for 2 h. The reaction was diluted with EtOAc, washed ($H_2O$ then brine), dried (MgSO$_4$), filtered, and concentrated. The residue was dissolved in DMF (2 ml) under $N_2$, cooled to 0 degrees C., and KHMDS (0.566 ml, 0.28 mmol) was added over 15 min. After 30 min, the solution was diluted with EtOAc, washed (H20 and brine), dried (MgSO$_4$), filtered, and concentrated. Flash chromatography (silica gel, Acetone/$CH_2Cl_2$ gradient) gave the title compound (0.045 g, 41%). Mass Spectrum (ES+) (m/z) 544.2 [M+1].

EXAMPLE 649

N-[3-(9-Chloro-3-ethoxy4-oxo-5H-isoxazole[4,3-c]quinolin-5-yl)cyclohexylmethyl]-benzamide To a solution of 278 (0.1 g, 0.2 mmol) in DMF (2.5 ml) under $N_2$ was added sodium ethoxide (0.33 ml at 21% wt., 1.0 mmol) and stirred for 2 h. The reaction was diluted with EtOAc, washed ($H_2O$ then brine), dried ($MgSO_4$), filtered, and concentrated. Purification by flash chromatography gave the title compound (0.025 g, 26%) (silica gel, acetone/$CH_2Cl_2$ gradient). Mass Spectrum (ES+) (m/z) 480.2 [M+1].

EXAMPLE 650

N-[3-(9-Chloro-3-methyl-4-oxo-5H-isoxazolo[4,3-c]quinolin-5-yl)-cyclohexyl]-2-methylamino-acetamide Hydrochloride A solution of the compound from Example 333, 66 mg (0.13 mmol) in 10 mL of HCl-saturated acetic acid was stirred 4 hours at rt., then concentrated to dryness. The residue was slurried 3× in toluene and concentrated to dryness to give a quantitative yield of the desired isomer as a white foam. $^1H$—NMR is consistent with structure. MS (ion spray) 403.2 (M+).

EXAMPLE 651

2-Amino-N-[3-(9-chloro-3-methyl-4-oxo-5H-isoxazolo[4,3-c]quinolin-5-yl)cyclohexyl]-2-methyl-propionamide Hydrochloride A solution of the compound from Example 335, 64 mg (0.12 mmol) in 10 mL of HCl-saturated acetic acid was stirred 3 hours at rt. then concentrated to dryness. The residue was slurried 3× in toluene and concentrated to dryness. The residue was slurried in ether/hexanes and concentrated to dryness to give a quantitative yield of the desired isomer as a white foam. MS (ion spray) 417.1 (M+).

EXAMPLE 652

2-Amino-N-[3-(9-chloro-3-methyl-4-oxo-5H-isoxazolo[4,3-c]quinolin-5-yl)cyclohexyl]-acetamide Hydrochloride A solution of the compound from Example 336,49 mg (0.10 mmol) in 10 mL of HCl-saturated acetic acid was stirred 3 hours at rt. then concentrated to dryness. The residue was slurried 3× in toluene and concentrated to dryness. The residue was slurried in ether/hexanes and concentrated to dryness to give a quantitative yield of the desired isomer as a tan foam. MS (ion spray) 389.1 (M+).

EXAMPLE 653

N-[3-(9-Chloro-3-methyl-4-oxo-5H-isoxazolo[4,3-c]quinolin-5-yl)cyclohexyl]-2-phenyl-2-piperazin-1-ylacetamide Dihydrochloride A solution of the compound from Example 339, 171 mg (0.27 mmol) in 10 mL of HCl-saturated acetic acid was stirred 2 hours at rt. then concentrated to dryness. The residue was slurried 3× in toluene and concentrated to dryness. The residue was slurried in ether/hexanes and concentrated to dryness to give a quantitative yield of the desired mixture of isomers as a tan foam. $^1H$—NMR is consistent with structure. MS (ion spray) 389.1 (M+). The isomers were separated by chiral chromatography in a similar fashion to that described for Example 554 to yield 31.5 mg (19%) of isomer 1 as a white foam and 32.9 mg (20%) of isomer 2 as a white foam. I.S. (534.2) M+.

EXAMPLE 654

N-[3-(9-Chloro-3-methyl-4-oxo-5H-isoxazolo[4,3-c]quinolin-5-yl)cyclohexyl]-2-methylamino-2-phenylacetamide Hydrochloride A solution of the compound from Example 340, 130 mg (0.22 mmol) in 10 mL of HCl-saturated acetic acid was stirred 2 hours at rt. then concentrated to dryness. The residue was slurried 3× in toluene and concentrated to dryness. The residue was slurried in ether/hexanes and concentrated to dryness to give a quantitative yield of the desired mixture of isomers as a white foam. MS (ion spray) 479.2 (M+).

EXAMPLE 655

1-Aminocyclohexanecarboxylic acid [3-(9-chloro-3-methyl-4-oxo-5H-isoxazolo[4,3-c]quinolin-5-yl)cyclohexyl]amide Hydrochloride A solution of the compound from preparation 229a, 198 mg (0.35 mmol) in 15 mL of HCl-saturated acetic acid was stirred three hours at rt. then concentrated to dryness. The residue was slurried 3× in acetonitrile and concentrated to dryness to give 160 mg (93%) of the desired isomer as a white solid. MS (ion spray) 457.2 (M+1).

EXAMPLE 656

2-Amino-N-[3-(9-chloro-3-methyl-4-oxo-5H-isoxazolo[4,3-c]quinolin-5-yl)cyclohexyl]-2-cyclohexylacetamide Hydrochloride A solution of the compound from Example 355, 80 mg (0.14 mmol) in 30 mL of HCl-saturated acetic acid was stirred four hours at rt. then concentrated to dryness. The residue was slurried 3× in toluene and concentrated to dryness to give 60 mg (85%) of the desired isomer as a tan solid. MS (ion spray) 471.2 (M+).

EXAMPLE 657

2-Amino-N-[3-(9-chloro-3-methyl-4-oxo-5H-isoxazolo[4,3-c]quinolin-5-yl)cyclohexyl]-2-cyclohexylacetamide Hydrochloride A solution of the compound from Example 356, 100 mg (0.17 mmol) in 30 mL of HCl-saturated acetic acid was stirred four hours at rt. then concentrated to dryness. The residue was slurried 3× in toluene and concentrated to dryness to give 47 mg (55%) of the desired isomer as a tan solid. $^1H$—NMR is consistent with structure. MS (ion spray) 471.2 (M+).

EXAMPLE 658

2-Aminoindan-2-carboxylic acid [3-(9-chloro-3-methyl-4-oxo-5H-isoxazolo[4,3-c]quinolin-5-yl)cyclohexyl]amide Hydrochloride A solution of a compound from Example 634, 220 mg (0.37 mmol) in 40 mL of HCl-saturated acetic acid was stirred three hours at rt., then concentrated to dryness. The residue was slurried 3× in toluene and concentrated to dryness give a quantitative yield of the desired isomer as a white solid. MS (ion spray) 491.2 (M+).

EXAMPLE 659

2-Amino-N-[3-(9-chloro-3-methyl-4-oxo-5H-isoxazolo[4,3c]quinolin-5-yl)cyclohexyl]-3-phenylpropionamide A solution of the compound from Example 370, 84 mg (0.14 mmol) in 10 mL of HCl-saturated acetic acid was stirred four hours at rt., then concentrated to dryness. The residue was slurried 3× in acetonitrile and concentrated to dryness give a quantitative yield of the desired isomer as a tan foam. MS (ion spray) 479.1 (M+).

EXAMPLE 660

5-(3-Amino-cyclohexyl)-9-chloro-3-methyl-5H-isoxazolo[4,3-c]quinolin4-one

A compound from Example 634 (350 mg,0.95 mmol) was treated with excess aqueous $NaHCO_3$ and the mixture extracted with EtOAc. The combined extracts were dried over $Na_2SO_4$ and concentrated in vacuo to yield 309 mg (98%) of the title compound.

EXAMPLE 661

N-[3-(9–Cyano-3-methyl-4-oxo-5H-isoxazole[4,3-c]quinolin-5-yl)cyclohexylmethyl]-4-fluorobenzamide To a solution of a compound from Example 532 (0.106 g, 0.23 mmol) in $CH_2Cl_2$ (2 mL) under $N_2$ was added TMSI (0.046 mL, 0.32 mmol) and stirred overnight. Added MeOH (1 mL) and stirred for 1 h to quench the reaction. The mixture was concentrated, triturated with toluene and dried to obtain a crude solid. This was mixed with 4-fluorobenoyl chloride (0.093 mL, 0.8 mmol) in $CH_2Cl_2$ (5 mL) under $N_2$ and $Et_3N$ (0.22 mL, 1.6 mmol) was added dropwise. After stirring overnight, the mixture was diluted with $CH_2Cl_2$, washed (0.1N HCl then brine), dried ($MgSO_4$), filtered, and concentrated. Flash chromatography (silica gel, Acetone/CH2C12 gradient) gave the title compound (0.085 g, 88%). Mass Spectrum (ES+) (m/z) 459.1 [M+1].

EXAMPLE 662

N-[3-(9–Cyano-3-methyl-4-oxo-5H-isoxazole[4,3-c]quinolin-5-yl)cyclohexylmethyl]-3,4-difluorobenzamide In a fashion similar to that described for Example 542, a compound from Example 413 (0.1 g, 0.21 mmol), $CH_2Cl_2$ (2 mL), TMSI (0.046 mL, 0.32 mmol), 3,4-difluorobenzoyl chloride (0.093 mL, 0.8 mmol), $CH_2Cl_2$ (5 mL), and $Et_3N$ (0.22 mL, 1.6 mmol) gave the title compound (0.087 g, 87%) after flash chromatography (silica gel, acetone/$CH_2Cl_2$ gradient). Mass Spectrum (ES+) (m/z) 477.1 [M+1].

EXAMPLE 663

N-[3-(9-Chloro-3-ethoxy-4-oxo-5H-isoxazole[4,3-c]quinolin-5-yl)cyclohexylmethyl]-benzamide To a solution of a compound from preparation 328 (0.1 g, 0.2 mmol) in DMF (2.5 mL) under $N_2$ was added sodium ethoxide (0.33 mL at 21% wt., 1.0 mmol) and stirred for 2 h. The reaction was diluted with EtOAc, washed ($H_2O$ then brine), dried ($MgSO_4$), filtered, and concentrated. Purification by flash chromatography gave the title compound (0.025 g, 26%) (silica gel, acetone/$CH_2Cl_2$ gradient). Mass Spectrum (ES+) (m/z) 480.2 [M+1].

EXAMPLE 664

N-[3-(9–Cyano-3-methyl-4-oxo-5H-isoxazolo[4,3-c]quinolin-5-yl)cyclohexylmethyl]-6-fluoronicotinamide To a solution of N-{[3-(9-cyano-3-methyl-4-oxo(5-hydroisoxazolo[4,3-c]quinolin-5-yl))cyclohexyl]methyl}(phenylmethoxy)carboxamide (0.27 g, 0.58 mmol) in $CH_2Cl_2$ (7 mL) under $N_2$ was added TMSI (0.2 mL, 1.4 mmol) and stirred overnight. Added MeOH (3 mL) and stirred for 1 h to quench the reaction. The mixture was concentrated, triturated with toluene and dried to obtain a crude solid. This was mixed with 6-fluoronicontic acid (0.114 g, 0.81 mmol) in DMF (5 mL) under $N_2$ and to this solution was added EDCI (0.16 g, 0.81 mmol) and DMAP (0.131 g, 1.08 mmol). After stirring overnight, the mixture was diluted with EtOAc, washed ($H_2O$ then brine), dried ($MgSO_4$), filtered, and concentrated. Flash chromatography (silica gel, Acetone/$CH_2Cl_2$ gradient) gave the title compound (0.198 g, 80%). Mass Spectrum (ES+) (m/z) 460.3 [M+1].

EXAMPLE 665

6-Chloro-N-[3-(9-cyano-3-methyl-4-oxo-5H-isoxazolo[4,3-c]quinolin-5-yl)-cyclohexylmethyl]nicotinamide In a fashion similar to that described for Example 664, a compound from Example 532 (0.1 g, 0.21 mmol), $CH_2Cl_2$ (2 mL), TMSI (0.046 mL, 0.32 mmol), 6-chloronicotinic acid (0.068 g, 0.43 mmol), DMF (4 mL), EDCI (0.62 g, 0.32 mmol) and DMAP (0.052 g, 0.43 mmol) gave the title compound (0.045 g, 44%) after flash chromatography (silica gel, EtOAc/Hexanes gradient). Mass Spectrum (ES+) (m/z) 476.2 [M+1].

EXAMPLE 666

N-[3-(9–Cyano-3-methyl-4-oxo-5H-isoxazolo[4,3-c]quinolin-5-yl)cyclohexylmethyl]-6-methylnicotinamide In a fashion similar to that described for Example 664, a compound from Example 532 (0.1 g, 0.21 mmol), $CH_2Cl_2$ (2 mL), TMSI (0.046 mL, 0.32 mmol), 6-methyl-nicotinic acid (0.059 g, 0.43 mmol), DMP (4 mL), EDCI (0.62 g, 0.32 mmol) and DMAP (0.131 g, 1.08 mmol) gave the title compound (0.045 g, 44%) after flash chromatography (silica gel, EtOAc/Hexanes gradient). Mass Spectrum (ES+) (m/z) 456.2 [M+1].

EXAMPLE 667

N-[3-(9-Amino-3-methyl-4-oxo-5H-isoxazolo[4,3-c]quinolin-5-yl)cyclohexylmethyl]-benzamide To a solution of a compound from preparation 333 (0.24 g, 0.42 mmol) in THF (4.2 mL) under $N_2$ was added TBAF (0.84 mL, 0.84 mmol, 1.0M in THF) dropwise and stirred for 4 h. The reaction was applied directly to a silica gel column and eluted with EtOAc which gave the title compound (0.18 g, 99%). Mass Spectrum (ES–) (m/z) 429.3 [M–1]

EXAMPLES 668 & 669

9-Chloro-5-[3-(2-hydroxy-2-phenylethylamino) cyclohexyl]-3-methyl-5H-isoxazolo[4,3-c]quinolin-4-one & 9-Chloro-5-[3-(2-hydroxy-1-phenylethylamino)cyclohexyl]-3-methyl-5H-isoxazolo[4,3-c]quinolin-4-one To a stirred solution of a compound from Example 634 (440 mg, 1.33 mmol) in abs. EtOH (60 mL) was added S-styrene oxide (159.2 mg, 1.33 mmole) under $N_2$ atmosphere. The reaction mixture was refluxed for 22 h. The solvent was removed on Buchi and the crude was chromatographed by Elution solution systems (40L column, $NH_3$ in MeOH: EtOAc, gradient). The title compounds were yielded (A, 201 mg; B, 41 mg, 40.3% yield). Mass Spectrum(FIA); A(m/z) 452.2 (M+1); B(m/z) 452.2 (M+1).

EXAMPLES 670 & 671

9-Chloro-5-[3-(2-hydroxy-2-phenylethylamino) cyclohexyl]-3-methyl-5H-isoxazolo[4,3-c]quinolin-4-one & 9-Chloro-5-[3-(2-hydroxy-1-phenylethylamino)cyclohexyl]-3-methyl-5H-isoxazolo[4,3-c]quinolin4-one To a stirred solution of a compound from Example 634 (441 mg, 1.33 mmole) in abs. EtOH (60 mL) was added R-styrene oxide (160 mg, 1.33 mmole) under $N_2$ atmosphere. The reaction mixture was refluxed for 202 h. The solvent was removed on Buchi and the crude was chromatographed by Elution solution systems (40L column, $NH_3$ in MeOH: EtOAc, gradient). The title compounds were yielded (A, 161 mg; B. 40 mg, 33.4% yield). Mass Spectrum (FIA) A(m/z) 452.2 (M+1); B(m/z) 452.2 (M+1).

EXAMPLE 672

9-Chloro-3-methyl-5-[3-(2-oxo-5-phenyloxazolidin-3-yl)cyclohexyl]-5H-isoxazolo[4,3-c]quinolin-4-one To a stirred solution of a compound from Example 668 (41 mg, 0.091 mmole) in THF (2 mL) was added DCC (15 mg, 0.091 mmole) and $Et_3N$ (0.013 mL, 0.091 mmole). The reaction mixture was stirred at rt. under $N_2$ atmosphere for 18 h. It was diluted with EtOAc, washed with brine, dried over $Na_2SO_4$ and concentrated. The resulted crude oil was chromatographed (gradient, hexanes: EtOAc) and the desired product was yielded as white foam solid (23 g, 54%). Mass Spectrum: m/z calcd. 478.1533, Found 478.1544

EXAMPLE 673

9-Chloro-3-methyl-5-[3-(2-oxo-5-phenyloxazolidin-3-yl)cyclohexyl]-5H-isoxazolo[4,3-c]quinolin-4-one To a stirred solution of a compound from Example 670 (50 mg, 0.11 mmol) in THF (2 mL) was added DCC (18 mg, 0.11 mmol), $Et_3N$ (0.016 mL, 0.11 mmol) and DMAP (catalytic amount). The reaction mixture was stirred at rt. under $N_2$ atmosphere for 48 h. It was diluted with EtOAc, washed with brine, dried over $Na_2SO_4$ and concentrated. The resulted crude oil was chromatographed (gradient, hexanes: EtOAc) and the desired product was yielded as white foam solid (21 g, 40%). Mass Spectrum: m/z calcd. 478.1533, Found 478.1565.

EXAMPLE 674

9-Chloro-3-methyl-5-[3-(2-oxo-4-phenyloxazolidin-3-yl)cyclohexyl]-5H-isoxazolo[4,3-c]quinolin-4-one To a stirred solution of a compound from Example 669 (97 mg, 0.21 mmole) in THF (4 mL) was added DCC (34.1 mg, 0.21 mmole), $Et_3N$ (0.03 mL, 0.21 mmole) and DMAP (catalytic amount). The reaction mixture was stirred at rt. under $N_2$ atmosphere for 18 h. It was diluted with EtOAc, washed with brine, dried over $Na_2SO_4$ and concentrated. The resulted crude oil was chromatographed (gradient, hexanes: EtOAc) and the desired product was yielded as white foam solid (40 g, 40%). Mass Spectrum(FIA)(m/z) 478.1 (M+1).

EXAMPLE 675

9-Chloro-3-methyl-5-[3-(2-oxo-4phenyloxazolidin-3-yl)cyclohexyl]-5H-isoxazolo[4,3-c]quinolin-4-one To a stirred solution of a compound from Example 671 (64 mg, 0.14 mmole) in $CH_2Cl_2$ (5 mL) was added DCC (115 mg, 0.7 mmole), $Et_3N$ (0.02 mL, 0.14 mmole) and DMAP (catalytic amount). The reaction mixture was stirred at rt. under $N_2$ atmosphere for 48 h. It was diluted with $CH_2Cl_2$, washed with brine, dried over $Na_2SO_4$ and concentrated. The resulted crude oil was chromatographed (gradient, hexanes: EtOAc) and the desired product was yielded as white foam solid (51 g, 76%). Mass Spectrum (FIA) (m/z) 478.0 (M+1).

EXAMPLE 676

9-Chloro-5-{3-[2-(6-chloropyridin-3-yl)-2-hydroxyethylamino]cyclohexyl}-3-methyl-5H-isoxazolo[4,3-c]quinolin4one To a stirred solution of 6-chloronicotinic acid (900 mg, 5.7 mmol) in THF (7 mL) was added $BH_3$ (16 mL, 17.1 mmol, 1M in THF) under $N_2$ atmosphere. The reaction mixture was stirred for 5 h. It was quenched with methanol (5 mL) and then concentrated. The crude was dissolved in EtOAc (30 mL), washed with 1N NaOH (15 mL×3), brine, dried and concentrated. Yield: 615 mg (75%) of 6-chloro-pyridin-3-yl-methanol. To this alcohol (615 mg, 4.28 mmol) solution in $CH_2Cl_2$ (8 mL) was added Dess-Martin reagent (5.4 mg, 12.8 mmol). It was stirred at rt. for 2 h and then diluted with $CH_2Cl_2$. The resulting solution was washed with NaOH (1N, 2×5 mL), brine, dried and concentrated. 516 mg (85%) of yellow solid as the desired 6-chloro-pyridine-3-carbaldehyde. To a solution of above aldehyde (401 mg, 2.82 mmol) in $CH_2Cl_2$ (10 mL) was added 50% NaOH solution (9.3 mL), trimethylsulfonium iodide (1.15 g, 5.64 mmol) and tetrabutylammonium iodide (11 mg). It was refluxed for 48 h and poured onto ice water. The organic layer was extracted with $CH_2Cl_2$, washed with brine, dried and concentrated. The crude epoxide was chromatographed (gradient, hexanes: EtOAc) and 190 mg (43%) yellow oil was yielded as desired 2-Chloro-5-oxiranyl-pyridine. To the solution of 2-chloro-5-oxiranyl-pyridine (118.4 mg, 0.76 mmol) in absolute ethanol (40 mL) was added a compound from Example 660 (252 mg, 0.76 mmol). The reaction mixture was refluxed for 24 h and concentrated.

EXAMPLE 677

[3-(9-Chloro-3-methyl-4-oxo-5H-isoxazolo[4,3-c] quinolin-5-yl)cycloheptylmethyl]-carbamic Acid 2-trimethylsilanylethyl Ester To a warm solution of 0.2 g (0.52 mmol) of a compound from Example 680 in toluene (4 mL) was added 0.154 mL (0.72 mmol) of DPPA followed by 0.1 mL (0.72 mmol) of $Et_3N$. After heating the solution at 80° C. for 2 hours, 0.11 mL (0.78 mmol) of the silyl alcohol was added and the reaction was heated at 85° C. for 12 hours. The reaction was cooled, diluted with EtOAc, rinsed with water followed by brine, and dried over $Na_2SO_4$. The solvent was removed in vacuo and the residue was chromatographed on silica gel with 2/1 hexanes/EtOAc to yield 0.127 g of the title compound.
MS(ES+)m/z=504.

EXAMPLE 678

N-[3S-(9-Chloro-3-methyl-4-oxo-5H-isoxazolo[4,3-c]quinolin-5-yl)R-cycloheptylmethyl]benzamide A solution of 0.052 g (0.2 mmol) of a compound from Example 677 in THF (6 mL), and 4.5 mL of TBAF (1.OM in THF)(4.5 mmol) was heated at 60° C. for 4 hours. The solution was cooled to ambient temperature and water (2 mL) then 0.028 g of anhydrous $K_2CO_3$ (0.2 mmol) were added followed by 0.016 g (0.11 mmol) of benzoyl chloride. The reaction was stirred 12 hours, after which the THF was replaced with EtOAc and rinsed with 1N HCl and dried over $Na_2SO_4$. The organic layer was concentrated in vacuo to a residue, which was chromatographed on silica gel with 2/1 hexanes/EtOAc to yield 0.011 g of the title compound. MS(ES+)m/z=464.

EXAMPLE 679

N-[3S-(9-Chloro-3-methyl-4-oxo-5H-isoxazolo [4,3-c] quinolin-5-yl)-R-cycloheptylmethyl]-4-fluorobenzamide In a manner similar to the preparation of Example 678, 0.052 g (0.1 mmol) of a compound from Example 678 yielded 0.012 g of the title compound. MS(ES+)m/z=482.

EXAMPLE 680

[3-(9-Chloro-3-methyl-4-oxo-5H-isoxazolo[4,3-c] quinolin-5-yl)cycloheptyl]acetic Acid A suspension of 0.82 g (2.0 mmol) of a compound from Example 424 in 1N NaOH (45 mL) and MeOH (125 mL) was stirred for 16 hrs. at ambient temperature. The MeOH was removed in vacuo and the reaction was cooled and neutralized with 3N HCl. The acidic aqueous layer was extracted with EtOAc, rinsed with water and concentrated in vacuo at 40° C. to yield 0.78 g of the title compound. MS ES+)m/z=388.9.

EXAMPLE 681

[3-(9-Chloro-3-methyl-4-oxo-5H-isoxazolo[4,3-c] quinolin-5-yl)cycloheptylmethyl]-carbamic Acid Methyl Ester In a manner similar to the preparation of Example 677 (except the intermediate isocyanate was trapped with MeOH instead of TMS ethanol) 0.68 g (1.8 mmols) of a compound from Example 680 was converted to 0.43 g of the title compound.
MS(ES+)m/z=418.1.

EXAMPLE 682

N-[3R-(9-Chloro-3-methyl-4-oxo-5H-isoxazolo[4,3-c]quinolin-5-yl)R-cycloheptylmethyl]benzamide A suspension of 0.036 g (0.1 mmol) of a compound from Example 632, 0.028 g (2.0 mmol) of anhydrous $K_2CO_3$, and 0.013 mL (1.1 mmol) of benzoyl chloride in 3 mL of THF/$H_2O$ 2/1 was stirred 15 hours. The solvent was removed in vacuo and the residue was taken into EtOAc and rinsed with $NaHCO_3$ sat., 1N HCl, and brine. The organic layer was dried over anhyd. $Na_2SO_4$ and the solvent was removed in vacuo. The residue was crystallized from MeOH to yield 0.28 g of the title compound.
MS(ES+)m/z=464.1.

EXAMPLE 683

2-Amino-N-[3-(9-chloro-3-methyl-4-oxo-5H-isoxazolo[4,3-c]quinolin-5-yl)cyclohexyl]-3-phenylpropionamide A solution of {1-[3-(9-chloro-3-methyl-4-oxo-5H-isoxazolo[4,3-c]quinolin-5-yl)-cyclohexylcarbamoyl]-2-phenyl-ethyl}-carbamic acid tert-butyl ester, 82 mg (0.14 mmol) in 15 mL of HCl-saturated acetic acid was stirred three hours at rt., then concentrated to dryness. The residue was slurried 3× in acetonitrile and concentrated to dryness to give a quantitative yield of the title compound as a tan foam. MS (ion spray) 479.2. (M+).

EXAMPLE 684

2-Amino-N-[3-(9-chloro-3-methyl-4-oxo-5H-isoxazolo[4,3-c]quinolin-5-yl)cyclohexyl]-3-hydroxypropionamide A solution of {1-[3-(9-Chloro-3-methyl-4-oxo5H-isoxazolo[4,3-c]quinolin-5-yl)-cyclohexylcarbamoyl]-2-hydroxy-ethyl}-carbamic acid tert-butyl ester, 73 mg (0.14 mmol) in 8 mL of 25% TFA in $CH_2Cl_2$ was stirred rt. for three hours then concentrated to dryness. The residue was partitioned between 20% isopropanol/chloroform and saturated aqueous $NaHCO_3$. The organics were washed with saturated $NaHCO_3$, washed with brine, dried over $Na_2SO_4$, filtered and concentrated to dryness. The residue was purified by radial chromatography using MeOH/chloroform as eluent and concentrated to dryness to yield 40 mg (69%) of the title compound as a white solid. $^1$H—NMR is consistent with structure. MS (IS) 419.1 (M+).

EXAMPLE 685

2-Amino-N-[3-(9-chloro-3-methyl-4-oxo-5H-isoxazolo[4,3-c]quinolin-5-yl)cyclohexyl]-3-hydroxypropionamide A solution of {1-[3-(9-Chloro-3-methyl-4-oxo-5H-isoxazolo[4,3-c]quinolin-5-yl)-cyclohexylcarbamoyl]-2-hydroxy-ethyl }-carbamic acid tert-butyl ester, 92.3 mg (0.18 mmol) in 8 mL of 25% TFA in $CH_2Cl_2$ was stirred rt. for three hours then concentrated to dryness. The residue was partitioned between 20% isopropanol/chloroform and saturated aqueous $NaHCO_3$. The organics were washed with saturated $NaHCO_3$, washed with brine, dried over Na2SO4, filtered and concentrated to dryness. The residue was purified by radial chromatography using MeOH/chloroform as eluent and concentrated to dryness to yield 37 mg (50%) of the title compound as a white solid. MS (IS) 419.2 (M+).

EXAMPLE 686

N-[3-(9-Chloro-3-methyl-4-oxo-5H-isoxazolo[4,3-c] quinolin-5-yl)-cyclohexylmethyl]-6-dimethylaminonicotinamide A solution of compound from Example 245, 50 mg, (0.10 mmol) in 2.0 mL (4.0 mmol) of 2N N,N-dimethylamine in THF was stirred 24 H in a sealed tube at 90° C. then concentrated to dryness. The residue was dissolved in 20% isopropanol/chloroform and washed with saturated aqueous sodium bicarbonate, washed with brine, dried over sodium sulfate, filtered and concentrated to dryness. The residue was purified by radial chromatography using a methanol/chloroform gradient as eluent and was concentrated to dryness. The residue was slurried in ether/hexanes and concentrated to dryness to yield 48 mg (96%) of the desired isomer as a white foam.
$^1$H—NMR is consistent with structure.
MS (ion spray) 494.2 (M+).

EXAMPLE 687

N-[3-(9-Chloro-3-methyl-4-oxo-5H-isoxazolo[4,3-c] quinolin-5-yl)-cyclohexylmethyl]-6-methylaminonicotinamide A solution of a compound from Example 245, 50 mg, (0.10 mmol) in 2.0 mL (4.0 mmol) of 2N methylamine in tetrahydrofuran was stirred 24 H in a sealed tube at 100° C. then concentrated to dryness. Some mechanical loss occurred. The residue was dissolved in 20% isopropanol/chloroform and washed with saturated aqueous sodium bicarbonate, washed with brine, dried over sodium sulfate, filtered and concentrated to dryness. The residue was purified by radial chromatography using a methanol/chloroform gradient as eluent and was concentrated to dryness. The residue was slurried in ether/hexanes and concentrated to dryness to yield 30 mg (62%) of the desired isomer as a white foam. MS (ion spray) 480.1 (M+).

EXAMPLE 688

N-[3-(9-Chloro-3-methyl-4-oxo-5H-isoxazolo[4,3-c] quinolin-5-yl)cyclohexyl]-2-(pyridin-3-yloxy) propionamide (Isomers 1 & 2)

The isomers of N-[3-(9-Chloro-3-methyl-4oxo-5H-isoxazolo[4,3-c]quinolin-5-yl)-cyclohexyl]-2-(pyridin-3-yloxy)-propionamide (mixture of isomers, 142 mg (0.29 mmol) was separated via chiral chromatography to yield 63.5 mg of crude isomer 1 and 60.2 mg of crude isomer 2. Isomer 1 was purified by radial chromatography (methanol/chloroform gradient) and concentrated to dryness to yield 55.7 mg (39%) of the desired isomer as a tan foam. 1H—NMR is consistent with structure.
MS (ion spray) 481.2 M+.
Isomer 2 was purified by radial chromatography (methanol/chloroform gradient) and concentrated to dryness to yield 51.3 mg (36%) of the desired isomer as a white foam.
$^1$H—NMR is consistent with structure.
MS (ion spray) 481.2 M+.

EXAMPLE 689

N-{[3-(9-chloro-3-methyl-4-oxo-5H-isoxazolo[4,3-c]quinolin-5-yl)cyclopentyl]methyl }benzamide In the same manner as preparation 17, N-(t-butoxycarbonyl)2-(9-chloro-3-methyl-4-oxo-5H-isoxazolo[4,3-c]quinolin-5-yl)cyclopentylamine (0.06 g, 0.14 mmol) of was deprotected to yield 0.044 g (0.133 mmol) of the free amine MS(ES+)m/z=332, which was dissolved in dichloromethane (2.5 mL). To the solution was added 0.0222 mL (0.16 mmol) of Et$_3$N followed by 0.019 mL (0.16 mmol) of benzoyl chloride. After 45 min, the solvent was removed in vacuo, replaced with ethyl acetate and the organic layer was rinsed with 1N HCl followed by 1N NaOH, then water. The organic layer was dried and the solvent was removed in vacuo to give a residue which was chromatographed on silica gel with ethyl acetate/hexane 1:1 to yield 0.035 g of the title compound. MS(ES+)m/z436. Cis (racemic)

EXAMPLE 690

Phenylmethyl 2-[(1R,3S)-3-(9-chloro-3-methyl-4-oxo-5H-isoxazolo[4,3-c]quinolin-5-yl))cyclohexyl] acetate To a solution of phenylmethyl 2-((1R,3S)-3-{[4-(2-chloro-6-fluorophenyl)-2-methyl(3-furyl)]carbonylamino}cyclohexyl)acetate, 5.71 g (11.8 mmol) in 100 mL of N,N-dimethylformamide at ambient temperature was added 47 mL (23.6 mmol) of 0.5 M potassium bis(trimethylsilyl)amide in toluene dropwise. After 10 min., the reaction was quenched with saturated ammonium chloride and extracted with ethyl acetate. The combined organics were washed with brine, dried over sodium sulfate, filtered and concentrated to dryness. The residue was chromatographed on silica gel using ethyl acetate/hexanes as eluent to yield 3.8 g (70%) of the desired product as a green oil.
$^1$H—NMR is consistent with structure.
MS (ion spray) 465.2 (M+1).

EXAMPLE 691

5-{(1S,3S)-3-[2-(phenylamino)ethyl]cyclohexyl }-9-chloro-3-methyl-5H-isoxazolo[4,3-c]quinolin-4-one N-{(1S,3S)-3-[2-(phenylamino)ethyl]cyclohexyl }[3-(2-chloro-6-fluorophenyl)-5-methylisoxazol-4-yl]carboxamide (54 mg; 0.118 mmol) was dissolved in anhydrous DMF (2 mL) under a dry nitrogen atmosphere at room temperature. When potassium bis(trimethylsilyl)amide (0.5 M in toluene; 572 μL; 2.2 equiv) was added dropwise to this solution, a clear orange color formed. After 5 min, the reaction was chilled in an ice bath, quenched with 1N HCl$_{(aq)}$ (10 mL), and extracted with ethyl acetate (twice). The organic layer was washed with saturated NaCl$_{(aq)}$ (once), dried with Na$_2$SO$_{4(s)}$, filtered, and concentrated to dryness by rotary evaporation. The product was purified by radial chromatography on a 2 mm thick silica gel rotor. A dichloromethane mobile phase was ineffective at purifying the product. Re-chromatography with a 100% hexanes mobile phase followed by a 20% ethyl acetate/hexanes (v/v) mobile phase separated product from impurities. After drying from diethyl ether, an off-white foam (43 mg; 84%) was obtained.
TOF-MS(ES) calc'd: [M+H]$^+$=436.1792 m/z. Found: 436.1797 m/z.

EXAMPLE 692

5-[3-(2-Aza-bicyclo[2.2.1]hept-5-en-2-ylmethyl)-cyclohexyl]-9-chloro-3-methyl-5H-isoxazolo[4,3-c] quinolin-4-one To a suspension of a compound from preparation 48 (500 mg, 1.0 mmol) in water (5 mL) was added formaldehyde (0.24 mL, 3.0 mmol) dropwise, and the mixture stirred rapidly under nitrogen. After 5 minutes, freshly cracked cyclopentadiene (0.41 mL, 5.0 mmol) was added dropwise. The solution was stirred under nitrogen at rt. overnight. The solution was diluted with a saturated aqueous sodium bicarbonate solution, extracted with dichloromethane (×3), and the organics dried over magnesium sulfate and concentrated. Purification by flash chromatography on silica gel (eluting with 1–4% methanol/chloroform/0.5% NH$_4$OH) gave 183.7 mg of the title compound as a white foam, 43% yield. MS (ion spray) 424 (M$^+$).

EXAMPLE 693

1-Amino-cyclopentanecarboxylic acid [3-(9-chloro-3-methyl-4-oxo-4H-isoxazolo[4,3-c]quinolin-5-yl)-cyclohexyl]-amide Hydrochloride A compound from Example 460 (89.9 mg, 0.17 mmol) was dissolved in HCl$_{(g)}$/AcOH (5 mL, ~3N) and stirred at rt. After 1 h, additional HCl$_{(g)}$/AcOH (5 mL, ~3N) was added. After 5 h, the mixture was concentrated, followed by azeotropic removal of water with acetonitrile in vacuo (×3). To the white solid was added diethyl ether, and the mixture was sonicated, and filtered. The resulting material was dried on a vacuum pump to give 52.9 mg of the title compound as a white solid, 67% yield. $^1$H NMR: consistent with structure. MS (ion spray) 479 (M$^+$).

EXAMPLE 694

1-Amino-cyclopropanecarboxylic acid [3-(9-chloro-3-methyl-4-oxo4H-isoxazolo[4,3-c]quinolin-5-yl)-cyclohexyl]-amide Hydrochloride A compound from Example 461 (94.3 mg, 0.18 mmol) was dissolved in HCl$_{(g)}$/AcOH (5 mL, ~3N) and stirred at rt.

After 1 h, additional HCl$_{(g)}$/AcOH (5 mL, ~3N) was added. After 5 h, the mixture was concentrated, followed by azeotropic removal of water with acetonitrile in vacuo (×3). To the white solid was added diethyl ether, and the mixture was sonicated, and filtered. The resulting material was dried on a vacuum pump to give 70.2 mg of the title compound as a white solid, 85% yield. 1H NMR: consistent with structure. MS (ion spray) 451 (M$^+$).

EXAMPLE 695

N-[3-(4,10-Dichloro-5-oxo-5H-benzo[h][1,6]naphthyridin-6-yl)-cyclohexylmethyl]-benzamide To 0.045 g (0.1 mmols)of N-{[(1R,3S)-3-(3-acetyl-4-amino-5-chloro-2-oxohydroquinolyl)cyclohexyl]methyl}benzamide and 0.03 ml (0.3 mmols) of POCl$_3$ were dissolved in DMF (2 ml) at 0–5° C. The reaction was allowed to warm to rt. and stirred for 30 minutes. The reaction was then heated at 45° C. over 12 hours. The solvent was removed in vacuo and the residue was chromatographed on silica and eluted with EtOAc/Hexane 1:1 to 2:1 to yield 0.002 g of the title compound.
MS(ES+)m/z=480.

EXAMPLE 696

N-[3-(10-Chloro-4-methoxy-5-oxo-5H-benzo[h][1,6]naphthyridin-6-yl)-cyclohexylmethyl]-benzamide To 0.045 g (0.1 mmols) of N-{[(1R,3S)-3-(3-acetyl-4-amino-5-chloro-2-oxyhydroquinolyl)cyclohexyl}methyl}benzamide and 0.03 ml (0.3 mmols) of POCl$_3$ were dissolved in DMF (2 ml) at 0–5° C. The reaction was allowed to warm to rt. and stirred for 30 minutes. The reaction was then heated at 45° C. over 12 hours. The reaction was cooled to rt. and NaOMe in MeOH (0.4 mmols) was added. The reaction was heated at 60° C. for 6 hours. The solvent was removed in vacuo. The residue was dissolved in CH$_2$Cl$_2$ and rinsed 1 time with 1N HCl, followed by 3 times with water. The solvent was removed in vacuo and the residue was chromatographed on silica and eluted with EtOAc/Hexane 1:1 to 2:1 to yield 0.011 g of the title compound.
MS(ES+)m/z=476.

EXAMPLE 697

N-[3-(10-Chloro-4-methylamino-5-oxo-5H-benzo[h][1,6]naphthyridin-6-yl)-cyclohexylmethyl]-benzamide To 0.005 g (0.01 mmols) of a compound from Example 696 was combined with 1.0 ml of aqueous methylamine 40% (excess) in ethanol (5 ml). The reaction was refluxed for 30 minutes. MS(ES+)m/z475.

EXAMPLE 698

R(–)Amino-acetic Acid [3-(9-chloro-3-methyl-4oxo4H-isoxazolo[4,3-c]quinolin-5-yl)-cyclohexylcarbamoyl]-phenyl-methyl Ester Hydrochloride To a compound from Example 472 (96.7 mg, 0.16 mmol) was added acetic acid saturated with HCl$_{(g)}$ (10 mL, ~3N in HCl) and the solution stirred vigorously at rt. for 1 hour. The reaction was concentrated, followed by addition of acetonitrile and concentration to assist in the removal of acetic acid (×2). The resulting white solid was treated with ethyl ether, sonicated, and filtered to yield 68.4 mg of the title compound as a white solid, 79% yield. $^1$H NMR: consistent with structure. MS (ion spray) 523 (M$^+$).

EXAMPLE 699

S(+)Amino-acetic Acid [3-(9-chloro-3-methyl-4-oxo-4H-isoxazolo[4,3-c]quinolin-5-yl)-cyclohexylcarbamoyl]-phenyl-methyl Ester Hydrochloride To a compound from Example 467 (70.0 mg, 0.11 mmol) was added acetic acid saturated with HCl$_{(g)}$ (10 mL, ~3N in HCl) and the solution stirred vigorously at rt. for 1 hour. The reaction was concentrated, followed by addition of acetonitrile and concentration to assist in the removal of acetic acid (×2). The resulting white solid was treated with ethyl ether, sonicated, and filtered to yield 37.84 mg of the title compound as a white solid, 60% yield. $^1$H NMR: consistent with structure. MS (ion spray) 523 (M$^+$).

EXAMPLE 700

{[3-(9-Chloro-3-methyl-4oxo-5H-isoxazolo[4,3-c]quinolin-5-ylmethyl)-cyclopentylcarbamoyl]-phenyl-methyl}-carbamic Acid tert-butyl Ester A compound from Example 621 was converted to obtain the title compound with L-N-boc phenyl glycine as described for Example 515. ESMS: 565 (M+1)+.

EXAMPLE 701

{[3-(9-Chloro-3-methyl-4-oxo-5H-isoxazolo[4,3-c]quinolin-5-ylmethyl)-cyclopentylcarbamoyl]-phenyl-methyl}-trifluoroacetamide A compound from Example 621 was converted to obtain the title compound with L-N-trifluoroacetyl phenyl glycine as described for Example 515. ESMS: 561 (M+1)+.

EXAMPLE 703 cis-1-(9-chloro-3-methyl-4-oxo-5H-isoxazolo[4,3-c]quinolin-5-yl)-3-(3-phenylureido)cyclohexane To the suspension of cis-1-(9-chloro-3-methyl-4-oxo-5H-isoxazolo[4,3-c]quinolin-5-yl)-3-amino-cyclohexane (0.0446 g, 0.121 mmol) in 1 mL anhydrous THF at RT was added 2N NaOH (0.60 mL, 0.121 mmol). After 5 min. the phenylisocyanate (0.013 mL,0.121 mmol). After 20 min. the reaction was diluted with EtOAc, washed with water and concentrated to near dryness. After sonication and filtration a white solid (0.0412, 75%) was obtained.
ESIMS m/e 451 $^{35}$Cl (M$^+$+1) and 453 $^{37}$Cl (M$^+$+1).

EXAMPLE 704

2-[(3S,1R)-3-(9-Chloro-3-methyl-4-oxo-5H-isoxazolo[4,3-c]quinolin-5-yl)-cyclohexylmethyl]-5H-isoquinoline-1,3-dione To 5-[(1S,3R)-3-(aminomethyl)cyclohexyl]-9-chloro-3-methyl-5-hydroisoxazolo[4,3-c]quinolin4-one (60 mg, 0.17 mmol) and homophthalic acid (38 mg, 0.21 mmol) was added xylenes (10 mL), and the reaction heated to reflux under nitrogen overnight with a Dean-Stark trap attached to effect removal of water. The solution was concentrated and dissolved in 20% isopropanol/chloroform, washed with 1.0N HCl (×2), saturated aqueous sodium bicarbonate solution, brine, dried over sodium sulfate and concentrated. Purification by flash chromatography on silica gel (eluting with 20–25% ethyl acetate/hexane) gave 26 mg of the title compound as a clear oil, 31% yield. $^1$H NMR: consistent with structure. MS (ion spray) 490 (M$^+$), 488 (M–1).

EXAMPLE 705

3-(2-Chloro-6-fluoro-phenyl)-5-methyl-isoxazole-4-carboxylic Acid [3-(9-chloro-3-methyl-4-oxo-5H-isoxazolo[4,3-c]quinolin-5-ylmethyl)-cyclopentyl]-amide A compound from Example 620 was acylated with 2chloro-5-fluoro phenyl isoxazoyl chloride to obtain the title compound as described for Example 515. ESMS: 570 (M+1)$^+$.

EXAMPLE 706

1-tert-Butyl-3-(2-chloro-6-fluoro-phenyl)-1H-pyrazole-4-carboxylic Acid [3-(9-chloro-3-methyl-4-oxo-5H-isoxazolo[4,3-c]quinolin-5-ylmethyl)-cyclopentyl]-amide A compound from Example 620 was converted to obtain the title compound with 4-(2-chloro-5-fluoro phenyl)-1-t-butyl-pyrazole-3-carboxylic acid as described for Example 515. ESMS: 610 (M+1)+.

EXAMPLE 707

{[3-(9-Chloro-3-methyl-4-oxo-5H-isoxazolo[4,3-c]quinolin-5-ylmethyl)-cyclopentylcarbamoyl]-phenyl-methyl}-carbamic Acid tert-Butyl Ester A compound from Example 621 was converted to obtain the title compound with L-N-boc phenyl glycine as described for Example 515. ESMS: 565 (M+1)+.

EXAMPLE 708

1R, 3S—N-[3-(9-Chloro-3-methyl-4-oxo-5H-isoxazolo[4,3-c]quinolin-5-ylmethyl)-cyclopentyl]-2-(3,4,5-trimethoxy-phenyl)-acetamide A mixture of 1R, 3S-5-(3-amino-cyclopentylmethyl)-9-chloro-3-methyl-5H-isoxazolo[4,3-c]quinolin-4one (15 mg, 0.045 mmol), 3,4,5-trimethoxyphenyl acetic acid (14 mg, 0.06 mmol), EDC (12 mg, 0.06 mmol) and DMAP (2 mg) dissolved in DCM (10 mL) was stirred overnight at rt. The reaction mixture was diluted with additional DCM (10 mL), washed with aq. NaHCO$_3$ (sat'd, 2×20 mL), water (2×20 mL), brine (2×20 mL), dried over sodium sulfate, filtered, evaporated, and chromatographed (Bond Elut, Si, 60 cc, 50% EtOAc in hexanes) to yield the desired product (10 mg, 41%). ESMS: 540 (M+1)+.

EXAMPLE 709

N-[3-(9-Chloro-3-methyl-4-oxo-5H-isoxazolo[4,3-c]quinolin-5-yl-cyclopentyl]-2-(3,4,5-trimethoxy-phenyl)-acetamide To a stirred solution of racemic 5-(3-aminocyclopentyl)-9-chloro-3-methyl-5H-isoxazolo[4,3-c]quinolin-4-one (81 mg, 0.26 mmol) in CH$_2$Cl$_2$ (3 mL) was added 3,4,5-trimethoxy phenyl acetic acid (114 mg, 0.52 mmol), Et$_3$N (0.1 mL, 0.50 mmol), HOBt (41 mg, 0.3 mmol), DMAP (catalytic amount) and EDCI (72 mg, 0.38 mmol). The reaction mixture was stirred at r.t. for 18 hours. The mixture was diluted with CH$_2$Cl$_2$, washed (brine), dried (Na$_2$SO$_4$), filtered and concentrated. Column chromatography (silica gel, hexanes/ethyl acetate, gradient) gave the racemic title compound (89 mg, 66%). Mass Spectrum (FIA) (m/z) 454.0 (M+1)

EXAMPLE 710

2-[3S-(9-Chloro-3-methyl-4-oxo-5H-isoxazolo[4,3-c]quinolin-5yl)-R-cycloheptyl]-N-(3,4,5-trimethoxyphenyl)-acetamide To a solution of 0.038 g (0.1 mmol) of 2-[3-(9-chloro-3-methyl-4-oxo-5H-isoxazolo[4,3-c]quinolin-5-yl) cycloheptyl]acetic acid in THF/DMF 1-1 (5 mL) was added 0.061 g (0.44 mmol) of 1-hydroxy-7-azabenzotriazole and 0.86 g (0.44 mmol) of EDCI. After 40 minutes, 0.083 g (0.44 mmol) of 3,4,5-trimethoxyaniline was added. After 3.25 hours, the solvent was removed in vacuo and replaced with EtOAc. The organic layer was rinsed with 1N HCl, aq. NaHCO$_3$, then ×3 with water. The organic layer was dried and the solvent was removed in vacuo to yield 0.026 g of the title compound. MS(ES+)m/z=554.

EXAMPLE 711

2-Acetylamino-N-[3-(9-chloro-3-methyl-4-oxo-5H-isoxazolo[4,3-c]quinolin-5-yl)cyclohexyl]-2-phenylacetamide A compound as described in Example 633 (75 mg, 0.16 mmol) was combined with 1,3-dicyclohexylcarbodiimide (50 mg, 0.24 mmol), 1-hydroxybenzotriazole hydrate (33 mg, 0.24 mmol), and glacial acetic acid (0.015 mL, 0.24 mmol) in tetrahydrofuran (6 mL) and the mixture stirred over the weekend at ambient temperature. The mixture was then concentrated in vacuo and the residue loaded onto a silica gel column and eluted with methanol/ dichloromethane, which allowed for isolation of 82 mg (99%) of product as an off white solid. MS(ES): (M+1)$^+$ 507.1, 509.1 m/z.

EXAMPLE 712

2-[3-(9-Chloro-3-methyl-4-oxo-5H-isoxazolo[4,3-c]quinolin-5-yl)-cyclohexylcarbamoyl]-pyrrolidine-1-carboxylic Acid Benzyl Ester A compound as described in Example 660 (60 mg, 0.18 mmol) was combined with DCC (56 mg, 0.27 mmol), HOBT (37 mg, 0.27 mmol), and N-carbobenzyloxy-L-proline (68 mg, 0.27 mmol) in tetrahydrofuran (6 mL) and the mixture stirred overnight at rt. The mixture was then concentrated in vacuo and the residue loaded onto a silica gel column and eluted with MeOH/CH$_2$Cl$_2$, which allowed for isolation of 71 mg (70%) of product as a white solid. MS(ES): (M+1)$^+$ 563.0, 565.0 m/z.

EXAMPLE 713

2-[3-(9-Chloro-3-methyl-4-oxo-5H-isoxazolo[4,3-c]quinolin-5-yl)-cyclohexylcarbamoyl]-pyrrolidine-1-carboxylic Acid Benzyl Ester A compound as described in Example 660 (40 mg, 0.12 mmol) was combined with DCC (37 mg, 0.18 mmol), HOBT (24 mg, 0.18 mmol), and N-carbobenzyloxy-D-proline (45 mg, 0.18 mmol) in tetrahydrofuran (4 mL) and the mixture stirred overnight at rt. The mixture was then concentrated in vacuo and the residue loaded onto a silica gel column and eluted with MeOH/CH$_2$Cl$_2$, which allowed for isolation of 27 mg (40%) of product as a white solid. MS(ES): (M+1)$^+$ 563.0, 565.0 m/z.

EXAMPLE 714

1-Benzoyl-pyrrolidine-2-carboxylic acid [3-(9-chloro-3-methyl-4-oxo-5H-isoxazolo[4,3-c]quinolin-5-yl)-cyclohexyl]-amide A compound as described in Example 660 (40 mg, 0.12 mmol) was combined with EDC, HOBT (25 mg, 0.18 mmol), and the compound from preparation 104 (40 mg, 0.18 mmol) in tetrahydrofuran (6 mL) and the mixture stirred overnight at rt. The mixture was then concentrated in vacuo and the residue loaded onto a silica gel column and eluted with EtOAc, which allowed for isolation of 58 mg (90%) of product as a white solid. MS(ES): (M+1)$^+$ 533.3, 5535.3 m/z.

EXAMPLE 715

1-Phenylacetyl-pyrrolidine-2-carboxylic acid [3-(9-chloro-3-methyl-4-oxo-5H-isoxazolo[4,3-c]quinolin-5-yl)-cyclohexyl]-amide A compound as described in Example 660 (40 mg, 0.12 mmol) was combined with EDC (37 mg, 0.18 mmol), HOBT (25 mg, 0.18 mmol), and the compound from preparation 8R (42 mg, 0.18 mmol) in tetrahydrofuran (5 mL) and the mixture stirred over the weekend at rt. The mixture was then concentrated in vacuo and the residue loaded onto a silica gel column and eluted with EtOAc, which allowed for isolation of 54 mg (82%) of product as a white solid. MS(ES): (M+1)$^+$ 547.1 m/z.

EXAMPLE 716

1-Benzyl-pyrrolidine-2-carboxylic Acid [3-(9-chloro-3-methyl-4-oxo-5H-isoxazolo[4,3-c]quinolin-5-yl)-cyclohexyl]-amide A compound as described in Example 660 (40 mg, 0.12 mmol) was combined with DCC (37 mg, 0.18 mmol), HOBT (25 mg, 0.18 mmol), and the compound from preparation 107 (49 mg, 0.24 mmol) in tetrahydrofuran (5 mL) and the mixture stirred over the weekend at rt. The mixture was then concentrated in vacuo and the residue loaded onto a silica gel column and eluted with MeOH/CH$_2$Cl$_2$. A repeat of the chromatography yielded the title compound (56 mg, 89%). MS(ES): (M+1)$^+$ 519.3, 520.3 m/z.

EXAMPLE 717

N-{[3-(9-Chloro-3-methyl-4-oxo-5H-isoxazolo[4,3-c]quinolin-5-yl)-cyclohexylcarbamoyl]-methyl}-2-phenyl-acetamide 5-(3-Amino-cyclohexyl)-9-chloro-3-methyl-5H-isoxazolo[4,3-c]quinolin-4-one hydroiodide (70 mg, 0.19 mmol) was combined with EDC (47 mg, 0.25 mmol), 1-hydroxy-7-azabenzo-triazole (34 mg, 0.25 mmol), N,N-diisopropylethyl amine (0.10 mL, 0.58 mmol), DMAP (5 mg, cat.), and N-benzylglycine hydrochloride (50 mg, 0.25 mmol) in DMF(6 mL) and the mixture stirred overnight at rt. The mixture was then concentrated in vacuo and the residue taken up in chloroform/MeOH and the organic solution washed with aqueous NaHCO$_3$. The organic solution was dried over Na$_2$SO$_4$ and concentrated in vacuo. The residue was loaded onto a silica gel column and eluted with MeOH/CH$_2$Cl$_2$, which allowed for the recovery of 32 mg (35%) of the free base. This material was dissolved in minimal EtOAc and treated with excess diethyl ether/hydrochloric acid. Concentration of this mixture to dryness allowed for quantitative recovery of the hydrochloride salt as an off white solid. MS(ES): (M+1)$^+$ 479.1, 481.2.

EXAMPLE 718

1-methyl-piperidine-4-carboxylic Acid {[3-(9-chloro-3-methyl-4-oxo-5H-isoxazolo[4,3-c]quinolin-5-yl)-cyclohexylcarbamoyl]-phenyl-methyl }-amide A product from Example 638 (50 mg; 0.108 mmol) was dissolved in anhydrous dimethylformamide (10 mL) under a nitrogen atmosphere, mixed with 1-methyl-piperidine-4-carboxylic acid hydrochloride (58.0 mg; 0.323 mmol; 3 equiv), 1-[3-(dimethylamino)propyl]-3-ethylcarbodiimide hydrochloride (61.8 mg; 0.323 mmol; 3 equiv), 2,4,6-trimethylpyridine (86 μL; 0.645 mmol; 6 equiv), and 1-hydroxy-7-azabenzotriazole (43.9 mg; 0.323 mmol; 3 equiv), and stirred overnight at room temperature. The reaction solution was diluted with 2 volumes ethyl acetate, 10 volumes water, and 1 volume saturated NaHCO$_{3(aq)}$. The organic layer was separated and then washed with saturated NaCl$_{(aq)}$, dried over Na$_2$SO$_{4(S)}$, filtered, and concentrated in vacuo. The resulting material was purified by radial chromatography on a 2 mm thick silica gel rotor with a 2% then 4% methanol/dichloromethane (v/v) mobile phase and finally a 2% methanol/0.5% triethylamine/dichloromethane (v/v/v) mobile phase. The desired product was isolated as a white solid in 74% yield (47 mg).

EXAMPLE 719

N-[3-(9-Acetylamino-3-methyl-4-oxo-5H-isoxazolo[4,3-c]quinolin-5-yl)-cyclohexylmethyl]-benzamide To a solution of a compound from Example 667 (0.025 g, 0.06 mmol) and AcOH (0.02 mL, 0.36 mmol) in DMF (1 mL) under N$_2$ was added EDCI (0.023 g, 0.12 mmol) and DMAP (0.002 g, 0.01 mmol). The solution was stirred overnight, diluted with EtOAc, washed (H$_2$O then brine), dried (MgSO$_4$), filtered, and concentrated. Flash chromatography (silica gel, acetone/CH$_2$Cl$_2$ gradient) gave the title compound (0.023 g, 82%). Mass Spectrum (ES+) (m/z) 473.3 [M+1]

EXAMPLE 720

N-[3-(9-chloro-3-methyl-4-oxo-5H-isoxazolo[4,3-c]quinolin-5-yl)-cyclohexyl]-2-phenylamino-acetamide Anhydrous dimethylformamide (10 mL) in a nitrogen atmosphere was used to dissolve 5-(3-aminocyclohexyl)-9-chloro-3-methyl-5H-isoxazolo[4,3-c]quinolin4-one (50 mg; 0.151 mmol), N-phenylglycine (29.6 mg; 0.196 mmol; 1.3 equiv), 1-hydroxy-7-azabenzotriazole (26.7 mg; 0.196 mmol; 1.3 equiv), 1-[3-(dimethylamino)propyl[-3-ethylcarbodiimide hydrochloride (37.6 mg; 0.196 mmol; 1.3 equiv), and 2,4,6-trimethylpyridine (199 μL; 1.51 mmol; 10 equiv). After overnight stirring at room temperature, the reaction solution was treated in a manner similar to Example 159. The resulting material was purified by three consecutive radial chromatography runs on a 2 mm thick silica gel rotor with a 1% methanol/dichloromethane (v/v) mobile phase, a 1% methanol/0.25% triethylamine/ dichloromethane (v/v/v) mobile phase, and a 5% acetonitrile/dichloromethane mobile phase. The desired product was isolated as a white solid 56% yield (30 mg). MS(ES) calc'd: [M+M]$^+$=465.16 m/z; [M−H]$^-$=463.16 m/z; [M+OAc]$^-$=523.16 m/z. Found: 465.1 m/z; 463.2 m/z; 523.2 m/z.

EXAMPLE 721

2-[3R-(9-Chloro-3-methyl-4-oxo-5H-isoxazolo[4,3-c]quinolin-5-yl)-R-cycloheptyl]-N-(3,4,5-trimethoxyphenyl)-acetamide In a manner similar to the preparation of Example 710, 0.055 g (0.14 mmol) of a compound from Example 680 was converted to a residue which was chromatographed on silica with EtOAc/hexanes 1/1 to yield 0.044 g of the title compound. MS(ES+)m/z=553.9.

EXAMPLE 722

6-Chloro-N-[3-(9-chloro-3-methyl-4-oxo-5H-isoxazolo[4,5-c]quinolin-5-yl)-cyclohexylmethyl]-nicotinamide A solution of cis-5-[3-(aminomethyl)cyclohexyl]-9-chloro-3-methyl-5-hydroisoxazolo[4,5-c]quinolin4-one (0.188 g, 0.54 mmol) and 6-chloro-nicotinic acid (0.103 g, 0.65 mmol) in DMF (10 mL) was treated with EDCI (0.125 g, 0.65 mmol) and HOAt (0.089 g, 0.65 mmol). The reaction was then treated with excess Et$_3$N (0.167 g, 1.62 mmol) and DMAP (6 mg, 0.05 mmol) and stirred at room temperature overnight. The reaction was concentrated to a solid and then taken up in 20% isopropanol in CHCl$_3$ (100 mL). This solution was transferred to a separatory funnel and washed with a saturated sodium bicarbonate solution (3×50 mL) and brine (2×50 mL). The organic solution was dried over sodium sulfate, filtered, and the solvent removed to afford a crude yellow solid. The solid was purified using silica gel column chromatography. The product was eluted using 50% EtOAc in CHCl$_3$. The solvent was removed in vacuo to afford 0.150 g (57%) of product as an off white solid. MS m/z (ES+) 484.8 (M+H)$^+$, (ES−) 482.8 (M—H), 542.8 (M+CH3COO$^-$)$^-$.

EXAMPLE 723

2-tert-butylamino-N-[3-(9-chloro-3-methyl-4-oxo-5H-isoxazolo[4,3-c]quinolin-5-yl)-cyclohexyl]-2-pyridin-3-yl-acetamide A compound from preparation 341 was saponified over 2 h with LiOH (1.5 equiv in water subsequently mixed with 1,4-dioxane). The carboxylic acid was isolated by rotary evaporation of the solution to dryness, acidification to pH 2 with 1 N HCl (aq), rotary evaporation of the solution to dryness, and overnight drying at 0.1 torr. This material (1.3 equiv) was mixed with the free base of material from Preparation 210 (100 mg; 0.301 mmol) in anhydrous DMF. Diisopropylethylamine (262 µL; 0.392 mmol; 5 equiv), 1-[3-(dimethylamino)propyl]-3-ethylcarbodiimide hydrochloride (75.1 mg; 0.392 mmol; 1.3 equiv), and 1-hydroxy-7-azabenzotriazole (53.3 mg; 0.392 mmol; 1.3 equiv) were then added and the solution was stirred overnight, at rt. EtOAc (70 mL) and saturated NaHCO$_3$ (aq)(10 volumes) were added and the organic layer was separated, washed with saturated NaCl (aq)(once), dried with Na$_2$SO$_4$ filtered, and concentrated in vacuo. After purification by radial chromatography, 34 mg off-white solid was isolated (22% yield). MS(ES) calc'd: [M+H]$^+$=522.2 m/z; [M−H]$^-$=520.2 m/z. Found: 522.2 m/z; 520.3 m/z.

EXAMPLE 724

N-[3-(9-chloro-3-methyl-4-oxo-5H-isoxazolo[4,3-c]quinolin-5-yl)-cyclohexyl]-2-(2,2-dimethyl-propylamino)-2-pyridin-3-yl-acetamide A compound from preparation 341 was used in a manner similar to Example 723 (substituting triethylamine for diisopropylethylamine) to prepare the title compound (24 mg white solid; 15% yield). MS(ES) calc'd: [M+H]$^+$=536.2 m/z. Found: 536.2 m/z.

EXAMPLE 725

N-[3-(9-chloro-3-methyl-4-oxo-5H-isoxazolo[4,3-c]quinolin-5-yl)-cyclohexyl]-2-(4-methyl-piperazin-1-yl)-2-pyridin-3-yl-acetamide A compound from preparation 343 was used in a manner similar to Example 723 (substituting Et$_3$N for diisopropylethylamine) to prepare the desired product A 1% then 2% then 3% methanol/chloroform/trace Et$_3$N (v/v/v) mobile phase on a 2 mm chromatotron rotor was used to purify the desired product (129 mg white solid; 78% yield). MS(exact mass) calc'd: [M+H]$^+$=594.2381 m/z. Found: 594.2385 m/z.

EXAMPLE 726

2-(Benzenesulfonyl-pyridin-2-yl-amino)-N-[3-(9-chloro-3-methyl-4-oxo-5H-isoxazolo[4,3-c]quinolin-5-yl)-cyclohexyl]-acetamide To a solution of 5-(3-amino-cyclohexyl)-9-chloro-3-methyl-5H-isoxazolo[4,3-c]quinolin-4-one hydroiodide, 130 mg (0.28 mmol) in 10 mL of DMF was added 82 mg (0.28 mmol) of (benzenesulfonyl-pyridin-2-yl-amino)-acetic acid (Bionet), 46 mg (0.34 mmol) of 1-hydroxy-7-azabenzo-triazole, 66 mg (0.34 mmol) of EDC, 5 mg of DMAP and 120 µL (0.84 mmol) of TEA. The reaction mixture was stirred six days at rt. and was concentrated to dryness. The residue was dissolved in 20% isopropanol/chloroform, washed with saturated NaHCO$_3$, washed with brine, dried over Na$_2$SO$_4$, filtered and concentrated to dryness. The residue was purified by radial chromatography using a MeOH/chloroform gradient and concentrated to dryness. The residue was slurried in ether/hexanes and concentrated to dryness to yield 79 mg (47%) of the title compound as a tan foam. MS (ion spray) 606.1 (M+).

EXAMPLE 727

N-[3-(9-Chloro-3-methyl-4-oxo-5H-isoxazolo[4,5-c]quinolin-5-yl)-cyclohexyl]-2-hydroxy-2-phenyl-acetamide A solution of a compound from preparation 380 (0.08 g, 0.24 mmol), R-Mandelic acid (0.04 g, 0.29 mmol), EDCI (0.06 g, 0.29 mmol), HOAt (0.04 g, 0.29 mmol) in DMF (10 mL) was treated with Et$_3$N (0.07 g, 0.7 mmol) and DMAP (3.0 mg, 0.02 mmol) and stirred overnight at room temperature. The solution was then diluted in EtOAc (50 mL) and washed with 5% citric acid (3×10 mL), sat'd sodium bicarbonate (3×10 mL), and brine (2×10 mL). The solution was dried over sodium sulfate and purified by silica gel column chromatography. The solvent was removed in vacuo to afford 0.08 g (74%) as a white solid.

EXAMPLE 728

N-{[3-(9-Chloro-3-methyl-4oxo-5H-isoxazolo[4,3-c]quinolin-5-yl)-cyclohexylcarbamoyl]-methyl}-nicotinamide 5-(3-Amino-cyclohexyl)-9-chloro-3-methyl-5H-isoxazolo[4,3-c]quinolin4-one hydroiodide (70 mg, 0.19 mmol) was combined with EDC (47 mg, 0.25 mmol), 1-hydroxy-7-azabenzo-triazole (34 mg, 0.25 mmol), N,N-diisopropylethyl amine (0.10 mL, 0.58 mmol), (5 mg, cat.), and nicotinuric acid (44 mg, 0.24 mmol) in DMF(6 mL) and the mixture stirred overnight at rt. The mixture was then concentrated in vacuo and the residue taken up in water and extracted with EtOAc. The combined extracts were dried over $Na_2SO_4$ and concentrated in vacuo. The residue was loaded onto a silica gel column and eluted with MeOH/$CH_2Cl_2$ which allowed for the recovery of 87 mg (92%) of the title compound as a white solid.
MS(ES): $(M+1)^+$ 494.1, 496.1.

EXAMPLE 729

N-[3-(9-chloro-3-methyl-4-oxo-5H-isoxazolo[4,3-c]quinolin-5-yl)-cyclohexyl]-2-dimethylamino-2-pyridin-3-yl-acetamide A compound from preparation 342 was used in a manner similar to Example 723 (substituting $Et_3N$ for diisopropylethylamine) to prepare the desired product. A 1% methanol/chloroform/trace triethylamine (v/v/v) mobile phase on a 2 mm chromatotron rotor was used to purify the desired product (112 mg white solid; 76% yield). MS(exact mass) calc'd: $[M+H]^+$=494.1959 m/z. Found: 494.1978 m/z.

PREPARATION 406

Pyridin-3-yl-(pyridin-2-yloxy)-acetic Acid Ethyl Ester

A typical synthesis of bromopyridin-3-ylacetic acid ethyl ester is described: A solution of fresh lithium diisopropylamide (LDA) was prepared at −10° C. from diisopropylamine (8.54 mL; 60.5 mmol) and n-butyllithium (37.8 mL of a 1.6 M hexanes solution; 12.1 mmol) and stirred for 10 min. After chilling the fresh LDA to −78° C., ethyl 3-pyridylacetate (9.21 mL; 60.5 mmol) was added and the solution was stirred another 10 min. Chlorotrimethylsilane (7.68 mL; 60.5 mmol) was added to the resulting opaque yellow slurry and the solution was stirred 5 min. Finally a solution of 4-(dimethylamino)pyridinium tribromide (22.0 g; 60.5 mmol) in tetrahydrofuran was added and the reaction solution was stirred 10 min. After warming to room temperature the reaction solution was quenched with saturated $NH4Cl_{(aq)}$ and extracted twice with ethyl acetate. The combined organic layer was washed once with saturated $NaCl_{(aq)}$, dried with $Na_2SO_{4(S)}$, filtered, and concentrated in vacuo. The resulting bromopyridin-3-ylacetic acid ethyl ester was an unstable brown oil and was therefore used immediately.

Silver carbonate (2.79 g; 10.1 mmol; 0.5 equiv) was refluxed in toluene (40 mL) for 0.5 h with 2-hydroxypyridine (1.92 g; 20.2 mmol; 1.0 equiv) and an aliquot of bromo-pyridin-3-yl-acetic acid ethyl ester (approx. 4.9 g; 20.2 mmol), prepared as described above. After cooling to room temperature and filtration of the reaction mixture, the supernatant was washed with saturated $NaHCO_{3(aq)}$ (1×), water (1×), and saturated $NaCl_{(aq)}$ (1×). The organic layer was dried over $Na_2SO_{4(S)}$, filtered, and concentrated in vacuo. Silica chromatography with a 35% ethyl acetate/hexanes mobile phase produced a yellow oil (1.14 g; 22% yield) that solidified upon standing. MS(ES) calc'd: $[M+H]^+$=259.2 m/z; $[M-M]^-$=257.2 m/z. Found: 259.1 m/z; 257.2 m/z. REFERENCE: U. Schöllkopf, I. Hoppe, Justus Liebigs Ann. Chem. (1972) 765, 153–170.

EXAMPLE 730

PREPARATION a

1,3-cyclohexanedicarboxylic Acid

To a suspension of isophthalic acid (500 g, 3 mol) in methanol (2.8) was added 5% Rhodium-on-alumina catalyst (50 g) and acetic acid (150 ml). The reaction mixture was shaken under hydrogen (50 psi) at room temperature overnight. The mixture was filtered through celite. To this solution was added fresh 5% Rhodium-on-alumina catalyst (25 g), and the mixture was shaken under 50 psi of hydrogen for another 24 hours. The final reaction mixture was filtered through celite. The solution was concentrated under vacuum to give 493 g of the title compound as a white powder (96.3% yield). m.p. 163–165° C.

PREPARATION b

3-Oxabicyclo[3.3.1]nonane-2,4-dione

A solution of dicyclohexylcarbodiimide (200 g, 1.16 mol) in $CH_2Cl_2$ (1000 ml) was added dropwise to a suspension of compound from preparation a (257 g, 1.25 mol) in $CH_2Cl_2$ (550 ml), and the mixture was stirred at room temperature for 4 hours. The precipitated dicyclohexylurea was filtered and washed several times with cold $CH_2Cl_2$ (200 ml×3). The combined organic layer was concentrated to give a white solid, which was suspended in MTBE (900 ml). This solid was collected by filtration, washed with MTBE (250 ml), and dried under house vacuum to give the title compound (137 g). The filtrate was concentrated to a residue, which was suspended in MTBE (250 ml) to give another 31 g anhydride. The total yield was 168 g (94%). m.p. 138–140° C.

PREPARATION c cis-1,3–Cyclohexanedicarboxylic Acid Diethyl Ester

To a solution of compound from preparation b (31 g, 0.2 mol) in ethanol (anhydrous, 310 ml) was added p-toluenesulfonic acid monohydrate (1.9 g, 10 mmol, 0.05 equiv.) and triethyl orthoformate (50 ml, 0.3 mol). The reaction mixture was stirred at 60° C. overnight. The volatiles were stripped and the residue was diluted with ethyl acetate (250 ml), washed with water (120 ml) and brine (100 ml), and dried over $MgSO_4$. After filtration and evaporation, the residue was purified by chromatography. Eluting the column with 10% ethyl acetate in hexane afforded the title compound (40 g, 87.7% yield).

$^1$H NMR: (500 MHz, $CDCl_3$) δ 4.11 (q, J=7.0 Hz, 4H), 2.29 (dt, 2H), 2.11 (dd, 1H) 1.97 (m, 2H), 1.98 (m, 1 H), 1.53 (q, J=12.5 Hz, 2H), 1.30–1.40 (m, 2H), 1.25 (t, J=7.0 Hz, 6H).

PREPARATION d

1,3–Cyclohexanedicarboxylic Acid, Monoethyl Ester (1R, 3S)

To a suspension of compound from preparation c (40 g, 17.5 mmol) in pH 7.2 phosphate buffer [0.2 M](1.21) was added lipase AY30 (Amano, 16.7 g). The mixture was stirred vigorously at room temperature for 30 hours. The mixture was acidified with 10–15% HCl to pH<2, and extracted with ethyl acetate (500 ml×2). The combined organic solution was washed with aqueous 10% $Na_2CO_3$ (100 ml×2) and water (100 ml×2). The combined aqueous layers were washed again with ethyl acetate (150 ml) and then acidified with 10–15% HCl to pH<2. The acidified aqueous was then extracted with ethyl acetate (150 ml×3). The combined organic solution was dried over $MgSO_4$. After filtration and concentration the title compound (35.6 g, 100% yield) was obtained.

$^1$H NMR (500 MHz, $CDCl_3$) δ 4.12 (q, J=7.0 Hz, 2H), 2.20–2.40 (m, 3H), 1.85–2.05 (m, 3H), 1.5 (q, 2H), 1.35 (m, 2H), 1.24 (t, J=7.0 Hz, 3H).

PREPARATION e

Ethyl-[3-N-(methylcarbamate)-cyclohexyl]-carboxylate (1R, 3S)

A solution of a compound from preparation d (73 g, 365 mmol) in toluene (750 ml) was heated to reflux using a Dean-Stark trap to separate trace amounts of water. After collecting about 10 ml of water, the mixture was cooled down to about 40–50° C. To this mixture was added triethylamine (56 ml, 0.4 mol), and diphenylphosphoryl azide (86.5 ml, 0.4 mol). The reaction mixture was stirred at 110° C. for 60 min, cooled to 70° C., and methanol (64 g, 2 mol ) was added with stirring. After addition, the final reaction mixture was then heated to 85° C. overnight. After cooling to room temperature, the mixture was diluted with ethyl acetate (700 ml) and washed with water (500 ml). The aqueous layer was extracted with ethyl acetate (500 ml×2). The combined organic solution was washed again with water (500 ml) and brine (500 ml). After drying over $MgSO_4$ and concentration under reduced pressure, the title compound was obtained as a colorless oil (86 g, 100%).

$^1$H NMR: (300 MHz, $CDCl_3$) δ 4.60 (sb, 1H), 4.13 (q, 2H), 3.65 (s, 3H), 3.50 (sb, 1H), 2.38 (t, 1H), 2.23 (d, 1H), 2.00–1.80 (m, 3H), 1.24 (t, 3H), 1.12–0.95 (m, 1H).

PREPARATION f

Ethyl-((1R, 3S)-3-{[3-(2-chloro-6-fluorophenyl)-5-methylisoxazol-4-yl]carbonyl-amino}cyclohexyl)-carboxylate To a solution of compound from preparation e (86 g, 365 mmol) in $CH_2Cl_2$ (750 ml) was added iodotrimethylsilane (100 g, 500 mmol) in one portion, at room temperature. The reaction mixture was stirred for 2 hours at ambient temperature, cooled to 0–5° C., and methanol (50 ml) was added. After stirring 15 minutes, the solution was concentrated under reduced pressure. The residue was dissolved in THF (1l). To this solution was added water (0.5l), potassium carbonate (138 g, 1 mol), and a solution of 3-(6-fluoro-2-chlorophenyl)-5-methylisooxazole-4-carboxyl chloride (10 g, 0.4 mol) in 250 ml THF, dropwise. After the addition, the reaction mixture was heated to room temperature and stirred for 12 hours. THF was removed under house vacuum, water (250 ml) was added, and the mixture was extracted with ethyl acetate (500 ml×3). The combined organic solution was washed with saturated sodium thiosulfate (150 ml), water (500 ml), brine (500 ml) and then dried over $MgSO_4$. After filtration and evaporation under vacuum, the residue was purified by recrystallization from ABE (250 ml). Repeating this recrystallization procedure three times provided the title compound (122.7 g, 82.5% yield) as a white powder.

IR: $\nu_{max}$ (film) 3429, 3011, 2940, 1725, 1662, 1187 $cm^{-1}$.

PREPARATION g

Ethyl [(1R,3S)-3-(9-chloro-3-methyl-4-oxo-5H-isoxazolo[4,3-c]quinolin-5-yl)-cyclohexyl]-carboxylate To a solution of compound from preparation f (78 g, 190 mmol) in DMF (750 ml) was added a solution of KHMDS ([0.5M], 400 ml, 200 mmol). The temperature was kept at 25° C. by using an ice-bath. After the addition was complete, the reaction mixture was analyzed by TLC (silica gel, 50% EtOAc in hexane) and found to be complete. Water (1 l) was added and the mixture was extracted with EtOAc (800 ml×3). The combined organic solution was washed with 1N HCl (250 ml), water (250 ml), brine (250 ml), dried over $MgSO_4$ and concentrated to give a residue which was purified by recrystallization from MTBE (500 ml) to afford 66 g of the title compound as a light yellow powder (89.0% yield).

IR: $\nu_{max}$ (film) 3030, 1720, 1670, 1220 $cm^{-1}$.

PREPARATION h

(1R, 3S) 3-(9-chloro-3-methyl-4oxo-5H-isoxazolo[4,3-c]quinolin-5-yl)-cyclohexyl Carboxylic Acid To a solution of compound from preparation g (62 g, 160 mmol) in THF (600 ml) was added 5N aqueous sodium hydroxide (120 ml) at room temperature. The reaction mixture was heated to 60° C. for 15 hours with stirring. After cooling to room temperature, water (750 ml) was added and the mixture was washed with ethyl acetate (500 ml). The aqueous phase was separated and acidified with 15% HCl to pH<2. The aqueous phase was then extracted with methylene chloride (1000 ml×3). The combined organic extracts were washed again with water (500 ml), brine (500 ml), and dried over $MgSO_4$. After filtration and evaporation under vacuum, the dark brown residue was suspended in MTBE (1000 ml), and refrigerated overnight. The mixture was filtered to afford 55.45 g (96.4%) of bright yellow product.

IR: $\nu_{max}$ (Film) 3200, 2936, 1726, 1643, 1595, 1173 $cm^{-1}$.

PREPARATION i

2-methyl [(1R,3S)-3-(9-chloro-3-methyl-4-oxo-5H-isoxazolo[4,3-c]quinolin-5-yl)-cyclohexyl] carbamate To a suspension of compound from preparation 8 (55.4 g, 154 mmol) in toluene (1l) was added triethylamine (23.7 ml, 170 mmol), and diphenylphosphoryl azide (36.5 ml, 170 mmol). The reaction mixture was stirred at 110° C. for 2 hours during which time a solution formed. The solution was cooled to 80° C. and methanol (25 g, 0.77 mol) was added with stirring. The solution was warmed to 85° C. for 22 hours. After cooling to room temperature, the toluene was removed under reduced pressure and the residue was dissolved in dichloromethane (3l) and washed with water (1l). The aqueous phase was extracted with dichloromethane (1l×2) and the combined organic solution was washed again with water (500 ml) and brine (500 ml). After drying over $MgSO_4$, the solution was concentrated under vacuum. The crude product was purified by crystallization ($CH_2Cl_2$/MTBE, 0.5 ½ l) to afford the title compound (46.6 g, 78.2%). $[\alpha]_D$+49.2°, $[\alpha]_{365}$+263.3° (c, 0.56; $CHCl_3$). The filtrate was concentrated to a residue, which was purified by chromatography to obtain a second crop of product (5.1 g). The total yield was 86.8%.

IR $v_{max}$ (Film) 3410, 3020, 2950, 1710, 1670, 1220 cm$^{-1}$.

PREPARATION j (1R, 3S) 3-(9-Chloro-3-methyl-4-oxo-5H-isoxazolo [4,3-c]quinolin-5-yl)-cyclohexyl Methyl Alcohol To a solution of compound from preparation h (4.4 g, 12.2 mmol) in THF (45 ml) was added borane-methyl sulfide complex (2.0 M solution in THF, 12.5 ml, 25 mmol) dropwise at 0° C. When the addition was complete, the reaction mixture was allowed to warm to room temperature and was stirred for one hour. Methanol (10 ml) was added slowly (gas generated) with stirring. The reaction mixture was then poured into ice-water (60 ml) and extracted with ethyl acetate (100 ml×3). The combined organic solution was washed with 1N HCl (50 ml), brine (50 ml), and dried over MgSO$_4$. After filtration and evaporation under vacuum, the yellow title compound (4.34 g, 100%) was obtained.

M.S.: m/z 347 (M$^+$+1).

PREPARATION k (1R, 3S) 3-(9-chloro-3-methyl-4-oxo-5H-isoxazolo [4,3-c]quinolin-5-yl)-cyclohexyl Methyl Alcohol Mesylate To a stirred solution of compound from preparation j (4.32 g. 12.5 mol) in pyridine (25 ml) was added DMAP (10 mg) and methanesulfonyl chloride (1.16 ml, 15 mmol, 1.2 equiv) and the resulting mixture was stirred at room temperature for 1.5 h. Water (100 ml) was added, and the mixture was extracted with ethyl acetate (150 ml×2). The combined organic extracts were washed again with brine (100 ml), dried (MgSO$_4$) and concentrated. The residue was suspended in MTBE (25 ml) and filtered to obtain the title compound as a solid (4.65 g, 87.8%).

$[\alpha]_D$+8.71°, $[\alpha]_{365}$+58.7° (c, 0.358; CHCl$_3$).

PREPARATION m (1R, 3S) 3-(9-chloro-3-methyl-4-oxo-5H-isoxazolo [4,3-c]quinolin-5-yl)-cyclohexyl Methyl Azide A mixture of a compound from preparation k (4.6 g, 10.8 mmol), sodium azide (2.15 g, 33 mmol) and DMF (45 ml) was heated to 60° C. and stirred for 24 h. After cooling to room temperature, the mixture was poured into 150 ml of ice-water and extracted with MTBE (200 ml×2). The combined organic extracts were washed with brine (150 ml) and dried over MgSO$_4$. After filtration and concentration, the residue was chromatographed on silica gel using 30% ethyl acetate/hexane to give the title compound as a white powder (3.82 g, 95%).

$[\alpha]_D$+17.2°, $[\alpha]_{365}$+105.7° (c, 0.864; CHCl$_3$).

PREPARATION n (1R, 3S) 3-(9-chloro-3-methyl-4-oxo-5H-isoxazolo [4,3-c]quinolin-5-yl)-cyclohexyl Methyl Amine To a solution of a compound from preparation m (2.0 g, 5.4 mmol) in ethyl acetate (25 ml) was added 5% Pd/C catalyst (200 mg). The reaction mixture was shaken under hydrogen (50 psi) at room temperature for 2 days. The mixture was filtered through celite and the filtrate was concentrated under vacuum to give the title compound as a solid (1.85 g, 99.2%).

$^1$H NMR: (300 MHz, CDCl$_3$) δ 7.45 (t, 1.5H), 7.34 (d, 1.5H), 2.90 (s, 3H), 2.62 (m, 2H), 2.59 (br s, 1H), 2.42 (br s, 1H), 2.00 (m, 1H), 1.84 (m, 4H), 1.50 (m, 2), 1.12 (m, 1H).

PREPARATION o

Ethyl-((1R, 3S)-3-{[5-(2-chloro-6-fluorophenyl)-3-methylisoxazol-4-yl]carbonyl-amino}cyclohexyl)-carboxylate To a solution of a compound from preparation d (42 g, 182 mmol) in CH$_2$Cl$_2$ (400 ml) was added iodotrimethylsilane (36.5 ml, 255 mmol) in one portion at room temperature. The reaction mixture was stirred for 2 hours at ambient temperature and then cooled down to 0–5° C. To this mixture was added methanol (50 ml) and the mixture was stirred 15 minutes and concentrated under reduced pressure. The residue was dissolved in THF (300 ml), and water (150 ml) and potassium carbonate (62 g, 0.45 mol) were added. To the resulting mixture was slowly added a solution of 5-(2-chloro-6-fluorophenyl)-3-methyl-isooxazole-4-carboxyl chloride (50 g, 182 mmol) in 50 ml of THF. After the addition, the reaction mixture was allowed to warm to room temperature and was stirred for 12 hours. THF was removed under house vacuum, water (150 ml) was added and the mixture was extracted with ethyl acetate (500 ml×2). The combined organic solution was washed with water (250 ml), brine (250 ml) and dried over MgSO$_4$. After filtration and evaporation under vacuum, the residue was purified by silica gel chromatography (30% ethyl acetate in hexane) to obtain the title compound (62.57 g, 84.3% yield) as a white powder.

M.S.: m/z 409 (M$^+$, 100%).

PREPARATION p

Ethyl [(1R,3S)-3-(9-chloro-3-methyl-4-oxo-5H-isoxazolo[4,5-c]quinolin-5-yl)-cyclohexyl]-carboxylate To a 0–5° C. solution of a compound from preparation o (61.5 g, 0.15 mol) in DMF (500 ml) was added a solution of KHMDS (340 ml, [0.5M], 0.17 mol) in toluene. After the addition was complete, the mixture was stirred at ambient temperature for 15 minutes and analyzed by TLC (silica gel, 50% EtOAc in hexane), which indicated completion of the reaction (TLC showed a minor by-product spot along with the major product spot). Water (1 l) was added and the mixture was extracted with EtOAc (800 ml×3). The combined organic extracts were washed with water (250 ml), brine (250 ml), dried over MgSO$_4$ and concentrated to a residue. The residue was purified by recrystallization from MTBE (200 ml) to obtain 28.12 g of the title compound. The filtrate was concentrated and purified by silica gel chromatography to obtain an additional 12.4 g of the title compound (40.52 g total, 69.3% yield).

M.S.: m/z 389 (M$^+$+1, 100%).

PREPARATION q (1R, 3S) 3-(9-chloro-3-methyl-4oxo-5H-isoxazolo [4,5-c]quinolin-5-yl)-cyclohexyl Carboxylic Acid To a solution of a compound from preparation p (40 g, 103 mmol) in THF (350 ml) was added 5N aqueous sodium hydroxide (88 ml) at room temperature. The reaction mixture was warmed to 60° C. and stirred for 15 hours. After cooling to room temperature, water (500 ml) was added and the mixture was washed with ethyl acetate (500 ml). The aqueous phase was separated and acidified with 15% HCl to pH<2. The precipitate was collected by filtration and washed with ethyl acetate (250 ml). The filtrate was extracted with ethyl acetate (500 ml) and the combined organic solution was washed again with water (200 ml), brine (200 ml), and dried over $MgSO_4$. After filtration and evaporation under vacuum, the residue was combined with the precipitate obtained from acidification of the reaction mixture and suspended in MTBE (500 ml). The suspension was filtered to afford the title compound as a bright yellow product (36.0 g, 100%).

M.S.: m/e 361 ($M^+$+1, 100%);

PREPARATION r (1R, 3S) 3-(9-chloro-3-methyl-4-oxo-5H-isoxazolo [4,5-c]quinolin-5-yl)-cyclohexyl Methyl Alcohol To a suspension of a compound from preparation q (37.52 g, 0.104 mmol) in THF (350 ml) was added borane-methyl sulfide complex in 140 ml of THF (26 ml, 0.27 mol) dropwise at 0° C. After the addition, the reaction mixture was stirred at 0–5° C. for one hour. TLC (3:1 EtOAc/hexane) indicated the completion of the reaction. Methanol (50 ml) was added slowly (gas generated) with stirring, followed by aqueous 10% HCl (50 ml). After stirring for 15 minutes, the reaction mixture was poured into ice water (250 ml) and extracted with ethyl acetate (350 ml×2). The combined organic solution was washed with brine (300 ml), dried over $MgSO_4$ and concentrated under vacuum. The crude product was purified by silica gel chromatography (EtOAc/hexane, 1:1) to give the title compound (32.5 g, 90%).

M.S.: m/e 347 ($M^+$+1).

PREPARATION s (1R, 3S) 3-(9-chloro-3-methyl-4-oxo-5H-isoxazolo [4,5-c]quinolin-5-yl)-cyclohexyl Methyl Alcohol Mesylate To a stirred solution of a compound from preparation r (32.25 g. 93.2 mmol) in pyridine (270 ml) was added DMAP (20 mg) and methanesulfonyl chloride (7.9 ml, 102 mmol, 1.1 equiv.). The mixture was stirred at room temperature for 1.5 hours. Water (500 ml) and EtOAc/MTBE (500 ml, 1:1) were added causing the product to precipitate. The solid was collected by filtration, washed with MTBE (150 ml) and dried under vacuum to provide 29.35 g as a white powder. The filtrate was washed again with brine (300 ml), dried ($MgSO_4$), and concentrated. The residue was suspended in MTBE (50 ml) and filtered to give a second crop of the title compound (9.5 g, total yield: 38.8 g, 99.3%).

M.S.: m/e 425 ($M^+$+1).

PREPARATION t (1R, 3S) 3-(9-chloro-3-methyl-4-oxo-5H-isoxazolo [4,5-c]quinolin-5-yl)-cyclohexyl Methyl Azide A mixture of a compound from preparation s (38.2 g, 90 mmol), sodium azide (21 g, 0.32 mol), and DMF (350 ml) was heated to 60° C. with stirring for 20 hours. After cooling to room temperature, the mixture was poured into ice-water (500 ml) and extracted with EtOAc (500 ml×2). The combined organic phases were washed with brine (250 ml) and dried over $MgSO_4$. After filtration and evaporation, the residue was chromatographed on silica gel using 30% ethyl acetate/hexane to give the title compound as a white powder (28.2 g, 84.4%).

M.S.: m/e 372 ($M^+$+1).

PREPARATION u 1,3-cyclohexanedicarboxylic Acid

To a suspension of isophthalic acid (5.0 g, 30.1 mmol) in 45 ml of acetic acid was added a slurry of 0.1 g of platinum oxide in 5 ml of acetic acid. The resulting mixture was stirred under 50 psi of hydrogen at 25° C. for 16 hours. NMR analysis (DMSO-$d_6$) at this time showed complete reduction of starting material. The reaction mixture was filtered through Celite and the filter cake was rinsed with methanol. The combined filtrate and washes were concentrated under reduced pressure, using heptane to azeotropically remove residual acetic acid. Trituration of the resultant semi-solid with heptane and filtration of the precipitate provided 4.92 g (95%) of the title compound as a white powder. mp: 163–165° C.

PREPARATION v

3-Oxabicyclo[3.3.1]nonane-2,4-dione

A suspension of 1,3-cyclohexanedicarboxylic acid (490 g, 2.88 mol) in acetic anhydride (1500 ml) was heated to 140° C., refluxing for 2 hours. Acetic anhydride was then removed with distillation (oil bath 180° C). To the residue was added acetic anhydride (1000 ml) and refluxed at 140° C. for 1 hour. The acetic anhydride was removed again with distillation (under house vacuum, about 50° C.). After crystals appeared, the mixture was cooled to room temperature and MTBE (400 ml) was added. The mixture was then cooled to 0–5° C. The crystals were filtered, washed with MTBE (250 ml), and dried under house vacuum to give the title compound (382 g). The filtrate was concentrated to a residue and suspended in MTBE (100 ml) to give the second crop of the title compound (14.0 g). The total yield was 396 g (90.5%). Mp 138–140° C.

EXAMPLE A

Benzoyl [(1R,3S)-3-(9-chloro-3-methyl-4-oxo-5H-isoxazolo[4,3-c]quinolin-5-yl)-cyclohexyl] amide To a solution of the compound from preparation i (160 mg, 0.41 mmol) in $CH_2Cl_2$ (3 ml) was added iodotrimethylsilane (124 mg, 0.62.mmol) in one portion, at room temperature. The reaction mixture was stirred for 2 hours at ambient temperature and cooled to 0–5° C. Methanol (1 ml) was added and the mixture was stirred for 15 minutes and concentrated under reduced pressure. The residue was dissolved in THF (2 ml). To this solution was added water (1 ml), potassium carbonate (210 mg, 1.5 mmol), and benzoyl chloride (60 ml, 0.5 mmol). The resultant mixture was stirred at room temperature for 2 hours. THF was removed under house vacuum, water (15 ml) was added, and the mixture was extracted with ethyl acetate (15 ml×2). The combined organic extracts were washed with saturated sodium thiosulfate (10 ml), brine (10 ml) and dried over $MgSO_4$. After filtration and evaporation under vacuum, the residue was purified by silica gel chromatography (35% EtOAc/hexane) to obtain the title compound (145 mg, 81.0% yield) as an off-white powder.

$^1$H NMR: (300 MHz, DMSO-$d_6$) δ 8.40 (d, 1H), 7.82 (m, 4H), 7.62 (t, 1H), 7.43 (m, 4H), 4.5 (br s, 1H), 4.05 (m, 1H), 2.82 (s, 3H), 2.78 (m, 1H), 1.88 (m, 4H), 1.71 (m, 2H), 1.60 (m, 1H), 1.41 (m, 1H).

EXAMPLE B

4-Fluoro-3-pyridyl-carboxyl-(1R, 3S) 3-(9-chloro-3-methyl-4-oxo-5H-isoxazolo[4,3-c]quinolin-5-yl)-cyclohexyl Methyl Amide To a solution of a compound from preparation n (466 mg, 1.35 mmol) in THF/$H_2O$ (5 ml/2.5 ml) was added potassium carbonate (690 mg, 5 mmol) and 2-fluoro-pyridin-4-carboxyl chloride (240 mg, 1.5 mmol) at room temperature. After the addition, the reaction mixture was stirred for 2 hours at ambient temperature. Water (50 ml) was added and the mixture was extracted with dichloromethane (50 ml×2). The combined organic extracts were washed with water (35 ml), brine (35 ml) and dried over MgSO$_4$. After filtration, the filtrate was concentrated to a residue (720 mg) which was purified by silica gel chromatography (ethyl acetate/dichloromethane, 1:2) to give the title compound (450 mg, 71.0%) as a white powder.

M.S.: m/z 469 (M$^+$+1, 100%).

EXAMPLE C 4-fluoro-3-pyridyl-carboxyl-(1R, 3S) 3-(9-chloro-3-methyl-4-oxo-5H-isoxazolo[4,5-c]quinolin-5-yl)-cyclohexyl Methyl Amide To a solution of the compound from preparation t (2.0 g, 5.4 mmol) in THF (120 ml) was added triphenylphosphine (10.5 g, 40 mmol) and water (25 ml). The mixture was stirred under nitrogen at room temperature overnight. To the reaction mixture was added 15% aqueous HCl (15 ml) and the mixture was stirred for 30 minutes. The mixture was then poured into water (200 ml) and washed with ethyl acetate/MTBE (150 ml/50 ml). Some product precipitated and was suspended in the aqueous layer. The organic layer was separated and washed with water (70 ml). The combined aqueous phases (about 270 ml) were washed again with ethyl acetate/MTBE (100 ml/50 ml). To the aqueous suspension was added THF (270 ml), K$_2$CO$_3$ (41 g, 0.3 mol) and 2-fluoropyridine-4-carboxyl chloride (6.4 g, 40 mmol) at room temperature. After the addition, the reaction mixture was stirred for 20 hours. The mixture was extracted with ethyl acetate (250 ml×2) and the combined organic extracts were washed with brine (200 ml), and dried over MgSO$_4$. After filtration, the filtrate was concentrated to give (16.5 g, 99.7%) of a white powder. The product was further purified by recrystallization from methanol to afford the title compound (14.0 g, 85%).

M.S.: m/e 469 (M$^+$+1).

EXAMPLE D

N-[(1R,3S)-3-(9-chloro-3-methyl-4-oxo-5H-isoxazolo[4,3-c]quinolin-5-yl)-cyclohexylmethyl]-nicotinamide To a solution of (1R, 3S) 3-(9-chloro-3-methyl-4-oxo-5H-isoxazolo[4,3-c]quinolin-5-yl)-cyclohexyl methyl amide (700 mg, 2.0 mmol) in 35 mL of dichloromethane was added 440 mg (2.4 mmol) of nicotinoyl chloride hydrochloride, 0.85 mL (6.0 mmol) of triethylamine and 5 mg of 4-dimethylaminopyridine. The reaction mixture was stirred overnight at ambient temperature, then washed with 1 N hydrochloric acid. The aqueous layer was extracted with 20% isopropanol/chloroform. The combined organics were washed with saturated sodium carbonate, brine, dried over sodium sulfate, filtered and concentrated to dryness. The residue was chromatographed on silica gel using methanol/chloroform as eluent to yield 740 mg (82%) of the desired isomer as a white solid. MS (ion spray) 451.1 (M+1).

EXAMPLE E

6-Chloro-N-[(1R,3S)-3-(9-chloro-3-methyl-4-oxo-5H-isoxazolo[4,3-c]quinolin-5-yl)-cyclohexylmethyl]-nicotinamide To a solution of 5-[3-(aminomethyl)cyclohexyl]-9-chloro-3-methyl-5-hydroisoxazolo[4,3-c]quinolin4-one HCl (86 mg, 0.22 mmol) in 20 mL of N,N-dimethylformamide was added 62 µL (0.45 mmol) of triethylamine, 43 mg (0.27 mmol) of 6-chloronicotinic acid, 36 mg (0.27 mmol) of 1-hydroxy-7-azabenzo-triazole, 51 mg (0.27 mmol) of 1-(3-dimethylamino-propyl)-3-ethyl-carbodiimide hydrochloride and 5 mg of 4-dimethylaminopyridine. The reaction mixture was stirred overnight at ambient temperature and concentrated to dryness. The residue was partitioned between chloroform and saturated sodium bicarbonate. The mixture was washed with saturated sodium bicarbonate, water, brine, dried over sodium sulfate, filtered and concentrated to dryness. The residue was chromatographed on silica gel using methanol/chloroform as eluent and concentrated to dryness. The residue was slurried in ether/hexanes and concentrated to dryness to yield 77 mg (71%) of the desired isomer as a white foam. MS (ion spray) 485.1 (M+).

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Camptosar, melphalan, paclitaxel, vinorelbine, mitoxantrone, doxorubicin, daunorubicin, epirubicin, vincristine, and etopsoside are oncolytics that are substrates of MRP1. See Cole, et. al., "Pharmacological Characterization of Multidrug Resistant MRP-transfected Human Tumor Cells", *Cancer Research,* 54:5902–5910, 1994. Since MRP1 is ubiquitous in mammals, particularly humans, Nooter, K, et. al., "Expression of the Multidrug Resistance-Associated Protein (MRP) Gene in Human Cancers", *Clin. Can. Res.,* 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay which rapidly and accurately measured the activity of the tested compound in inhibiting MRP1 or MDR1. Assays useful for evaluating this reversing capability are well known in the art. See, e.g., T. McGrath, et al., *Biochemical Pharmacology,* 38:3611, 1989; D. Marquardt and M. S. Center, *Cancer Research,* 52:3157, 1992; D. Marquardt, et al., *Cancer Research,* 50:1426, 1990; and Cole, et. al., *Cancer Research,* 54: 5902–5910, 1994.

Assay for Reversal of MRP1-Mediated Doxorubicin Resistance and MDR1-Mediated Vincristine Resistance HL60/Adr and HL60/Vinc are continuous cell lines, which were selected for doxorubicin and vincristine resistance respectively by culturing HL60, a human acute myeloblastic leukemia cell line, in increasing concentrations of doxorubicin or vincristine until a highly resistant variant was attained.

HL60/Adr and HL60/Vinc cells were grown in RPMI 1640 (Gibco) containing 10% fetal bovine serum (FBS) and 50 µg/ml GENTAMICIN™ (Sigma). Cells were harvested;

washed twice with assay medium (same as culture media); counted; and diluted to 1×10$^5$ cells/ml in assay medium. One hundred microliters of cells were aliquoted into wells of a 96 well tissue culture plate. Two columns of each 96 well plate served as a negative control and received assay medium containing no cells.

Test compounds and reference compounds were dissolved in dimethyl sulfoxide (DMSO) at a concentration of 5 mM. Samples were diluted in assay medium and 25 µl of each test compound was added to 8 wells. Assay standards were run in quadruplicate. Assay media was added to half of the wells and doxorubicin to the other half of the wells to achieve a final volume of 150 µl per well.

The plates were incubated at 37° C. for 72 hours in a humidified incubator with a 5% carbon dioxide atmosphere. Cell viability and vitality was measured by oxidation of a alamarBlue™ fluorescent dye using standard conditions. The plates were incubated for 3 hours at 37° C. Fluorescence was determined using 550 nm excitation and 590 nm emission using a microtitre plate reader.

The ability of a test compound to reverse the resistance of HL60/Adr and HL60/Vinc cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration minimally inhibits the growth of HL60/Adr or HL60/Vinc cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/Adr cell line over the HL60/Vinc cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645-1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in combination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices which deliver the formulation in an appropriate manner.

The following formulation examples are illustrative only and are not intended to limit the scope of the invention in any way. "Active ingredient(s)" means a compound according to formula I or a pharmaceutical salt or solvate thereof optionally with one or more oncolytics.

FORMULATION EXAMPLE 1

Hard gelatin capsules containing the following ingredients are prepared:

| Ingredient | Quantity (mg/capsule) |
| --- | --- |
| Active ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active ingredient | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 ml dose are made as follows:

| Ingredient | Amount |
| --- | --- |
| Active ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

Capsules, each containing 15 mg of medicament, are made as follows:

| Ingredient | Quantity (mg/capsule) |
| --- | --- |
| Active ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
| --- | --- |
| Active ingredient | 250.0 mg |
| Isotonic saline | 1000 ml |

FORMULATION EXAMPLE 10

A topical formulation may be prepared as follows:

| Ingredient | Quantity |
| --- | --- |
| Active ingredient | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

FORMULATION EXAMPLE 11

Sublingual or buccal tablets, each containing 10 mg of active ingredient, may be prepared as follows:

| Ingredient | Quantity Per Tablet |
| --- | --- |
| Active ingredient | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C.

When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions, which can transiently open the blood-brain barrier.

We claim:

1. A compound of formula I:

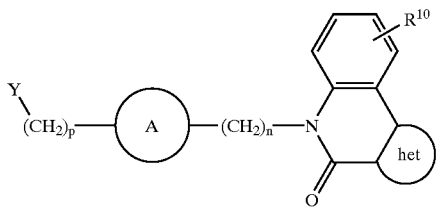

where:
A is a $C_3$–$C_8$ cycloalkyl, optionally substituted 1–3 times with a $C_1$–$C_4$ alkyl;
het is isoxazole;
  wherein the non-fused carbon atom of the isoxazole may be optionally substituted with $R^b$, wherein $R^b$ is $C_1$–$C_6$ alkyl, optionally substituted aryl, optionally substituted heterocycle, an amino acid ester, $CH_2OH$, $CH_2O$-heterocycle, halo, $CH_2N_3$, $CH_2SR^1$, $CH_2NR^4R^6$, $OR^1$, $SR^{13}$, $S(CH_2)_k$-phenyl, or $NR^4R^6$;
k is 0, 1, 2, 3, or 4;
n is 0, 1, or 2;
p is 0 or 1;
q is 0, 1, or 2;
r is 0, 1, or 2;
t is 0, 1, 2, 3, or 4;
u is 0, 1, 2, 3, or 4;
Y is —$EC(O)R^3$, —E—CH=$CHR^{13}$, —E—$C(OH)R^{13}$, —E—$NR^4R^5$, —E—$OR^2$, —E—$S(O)_qR^{13}$, —E—$SO_2NR^4R^6$, —$C(R^{11})$=$NR^6$, or an optionally substituted heterocycle;
E is a bond or —$C(R^{11})(R^{11})$—;
$R^1$ is independently at each occurrence hydrogen or $C_1$–$C_6$ alkyl;
$R^2$ is independently at each occurrence hydrogen, $C_1$–$C_6$ alkyl, optionally substituted $C_3$–$C_8$ cycloalkyl, optionally substituted ($C_1$–$C_4$ alkyl)-aryl, optionally substituted aryl, optionally substituted heterocycle, C(O)-aryl, C(O)N-phenyl, or $(CH_2)_2NR^4R^5$;
$R^3$ is independently at each occurrence hydrogen, $C_1$–$C_6$ alkyl, optionally substituted $C_3$–$C_8$ cycloalkyl, optionally substituted ($C_1$–$C_4$ alkyl)-aryl, optionally substituted aryl, optionally substituted heterocycle, $OR^{13}$, or $NR^4R^6$;
$R^4$ is independently at each occurrence hydrogen, $C_1$–$C_6$ alkyl, optionally substituted ($C_1$–$C_6$ alkyl)-aryl, $SO_2CH_3$, or optionally substituted aryl; or $R^5$, $R^6$, or $R^{6'}$ combine with $R^4$ to form =$CR^1R^{14}$;
$R^5$ is independently at each occurrence hydrogen, $C_1$–$C_6$ alkyl, $C_1$–$C_4$ alkoxy, optionally substituted heterocycle, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted ($C_1$–$C_4$ alkyl)-heterocycle, $C(O)C(O)R^{13}$, $C(O)R^7$, $CH_2R^7$, $SO_2R^8$, or a moiety of the formula

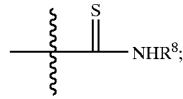

or $R^4$ and $R^5$ together with the nitrogen to which they are attached combine to form an optionally substituted N-heterocycle;
$R^6$ is independently at each occurrence hydrogen, $C_1$–$C_6$ alkyl, $C_1$–$C_4$ alkoxy, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted ($C_1$–$C_4$ alkyl)-heterocycle, or optionally substituted heterocycle; or $R^4$ and $R^6$ together with the nitrogen to which they are attached combine to form an optionally substituted N-heterocycle;
$R^{6'}$ is independently at each occurrence hydrogen, $C_1$–$C_6$ alkyl, $C_1$–$C_4$ alkoxy, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted ($C_1$–$C_4$ alkyl)-heterocycle, optionally substituted heterocycle, $C_1$–$C_4$ alkyl)-$OR^{13}$:
  wherein the ($C_1$–$C_4$ alkyl) of the $C_1$–$C_4$ alkyl)-$OR^{13}$ may be optionally substituted from 1 to 2 times with $C_1$–$C_4$ alkyl, optionally substituted aryl, or optionally substituted heterocycle;
or $R^4$ and $R^{6'}$ together with the nitrogen to which they are attached combine to form an optionally substituted N-heterocycle;
$R^7$ is independently at each occurrence optionally substituted $C_1$–$C_6$ alkyl, $C_1$–$C_6$ alkoxy, $C_1$–$C_4$ alkoxy)-aryl, $C_1$–$C_4$ alkoxy)-heterocycle, $C_1$–$C_4$ alkoxy)-Si($CH_3$)$_3$, optionally substituted ($C_3$–$C_8$ cycloalkyl), optionally substituted ($C_1$–$C_4$ alkyl)-($C_3$–$C_8$ cycloalkyl), optionally substituted $C_1$–$C_4$ alkyl)-aryl, optionally substituted aryl, diphenylmethyl, optionally substituted $C_1$–$C_4$ alkyl)-CO-aryl, optionally substituted CO-aryl, optionally substituted $C_1$–$C_4$ alkyl)-heterocycle, 3-oxoindanyl, fluoren-9-yl substituted with hydroxy, optionally substituted CH=CH-heterocycle, optionally substituted phenoxy, optionally substituted heterocycle, optionally substituted $C_1$–$C_4$ alkyl)-phenoxy, $(CH_2)_tS(O)_rR^1$, $(CH_2)_tC(R^{12})(R^9)N(R^{16})(R^{15})$, $(CH_2)_tC(R^{12})(R^9)O(R^{17})$, $(CH_2)_tC(R^{12})(R^9)S(R^{17})$, or $NR^4R^{6'}$;

$R^8$ is independently at each occurrence optionally substituted $C_1$–$C_6$ alkyl, optionally substituted aryl, optionally substituted $C_1$–$C_4$ alkyl)-aryl, optionally substituted $C_1$–$C_4$ alkyl)-heterocycle, or optionally substituted heterocycle;

$R^9$ is independently at each occurrence hydrogen, optionally substituted $C_1$–$C_6$ alkyl, optionally substituted $C_3$–$C_8$ cycloalkyl, optionally substituted ($C_1$–$C_4$ alkyl)-aryl, optionally substituted aryl, optionally substituted heterocycle, $(CH_2)_u$-($C_1$–$C_6$ alkoxy), optionally substituted $(CH_2)_u$-O-($C_3$–$C_8$ cycloalkyl), optionally substituted $(CH_2)_u$-($C_1C_4$ alkoxy)-aryl, optionally substituted $(CH_2)_u$-O-aryl, optionally substituted $(CH_2)_u$-O-heterocycle, ($C_1$–$C_4$ alkyl)-$CO_2$-($C_1$–$C_6$ alkyl), optionally substituted ($C_1$–$C_4$ alkyl)-$CO_2$-($C_3$–$C_8$ cycloalkyl), optionally substituted $C_1$–$C_4$ alkyl)-$CO_2$-($C_1$–$C_4$ alkyl)-aryl, optionally substituted ($C_1$–$C_4$ alkyl)-$CO_2$-aryl, or optionally substituted ($C_1$–$C_4$ alkyl)-$CO_2$-heterocycle; or $R^9$ and $R^{12}$ combine to form a $C_3$–$C_8$ cycloalkyl;

$R^{10}$ is 0 to 4 substituents from the aryl ring independently at each occurrence hydrogen, halo, $C(O)R^3$, cyano, optionally substituted heterocycle, optionally substituted aryl C≡C—$R^1$, $C_1$–$C_4$ alkoxy, ($C_1$–$C_4$ alkyl)-phenyl, $NR^{19}R^{20}$, $CH_2OH$, $C_2CH_2CO_2CH_2CH_3$, or $C_2$–$C_6$ alkenyl;

$R^{11}$ is independently at each occurrence hydrogen, $C_1$–$C_6$ alkyl, optionally substituted heterocycle, optionally substituted ($C_1$–$C_4$ alkyl)-heterocycle, optionally substituted aryl, or optionally substituted ($C_1$–$C_4$ alkyl)-aryl;

$R^{12}$ is independently at each occurrence hydrogen, optionally substituted $C_1$–$C_6$ alkyl, optionally substituted $C_3$–$C_8$ cycloalkyl, optionally substituted ($C_1$–$C_4$ alkyl)-aryl, optionally substituted aryl, optionally substituted $C_1$–$C_4$ alkyl)-heterocycle or optionally substituted heterocycle;

$R^{13}$ is independently at each occurrence hydrogen, optionally substituted $C_1$–$C_6$ alkyl, methoxy, hydroxy, optionally substituted $C_3$–$C_8$ cycloalkyl, optionally substituted ($C_1$–$C_4$ alkyl)-aryl, optionally substituted aryl, $CO_2CH_2CO_2CH_2CH_3$, or optionally substituted heterocycle;

$R^{14}$ is independently at each occurrence $C_1$–$C_6$ alkyl or optionally substituted ($C_1$–$C_4$ alkyl)-aryl;

$R^{15}$ is independently at each occurrence hydrogen, $C_1$–$C_6$ alkyl, optionally substituted $C_3$–$C_8$ cycloalkyl, optionally substituted $C_6$–$C_{10}$ bicycloalkyl, optionally substituted ($C_1$–$C_4$ alkyl)-aryl, optionally substituted aryl, optionally substituted $C_1$–$C_4$ alkyl)-heterocycle, optionally substituted heterocycle, $C(O)OR^{13}$, $SO_2R^8$, $C(O)R^{18}$, or a moiety of the formula

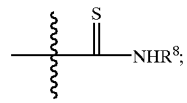

$R^{16}$ is independently at each occurrence hydrogen, optionally substituted $C_1$–$C_6$ alkyl, optionally substituted aryl, optionally substituted heterocycle, $SO_2CH_3$ or —$COR^8$; or $R^{16}$ and $R^{15}$ together with the nitrogen to which they are attached combine to form an optionally substituted N-heterocycle;

$R^{17}$ is independently at each occurrence hydrogen, optionally substituted $C_1$–$C_6$ alkyl, optionally substituted $C_3$–$C_8$ cycloalkyl, optionally substituted $C_1$–$C_4$ alkyl)-aryl, optionally substituted aryl, $COR^{18}$, optionally substituted heterocycle, optionally substituted ($C_1$–$C_4$ alkyl)-heterocycle, optionally substituted $C_1$–$C_6$ alkoxy, optionally substituted ($C_1$–$C_4$ alkoxy)-aryl, optionally substituted ($C_1$–$C_4$ alkoxy)-heterocycle, ($C_1$–$C_4$ alkyl)-N($R^1$)($R^1$), or an amino acid ester;

$R^{18}$ is independently at each occurrence hydrogen, optionally substituted $C_1$–$C_6$ alkyl, optionally substituted $C_3$–$C_8$ cycloalkyl, optionally substituted $C_1$–$C_4$ alkyl)-aryl, optionally substituted aryl, optionally substituted heterocycle, $C_1$–$C_4$ alkyl)-$NHCO_2$-($C_1$–$C_4$ alkyl), or optionally substituted ($C_1$–$C_4$ alkyl)-heterocycle;

$R^{19}$ is independently at each occurrence hydrogen, CO—($C_1$–$C_4$ alkyl), or optionally substituted $C_1$–$C_6$ alkyl;

$R^{20}$ is independently at each occurrence hydrogen, optionally substituted $C_1$–$C_6$ alkyl, $CH_2OH$, or CO—($C_1$–$C_4$ alkyl);

or a pharmaceutical salt thereof;

wherein:

optionally substituted $C_1$–$C_4$ alkyl and optionally substituted $C_1$–$C_6$ alkyl refers to a $C_1$–$C_4$ alkyl or $C_1$–$C_6$ alkyl, respectively, unsubstituted or substituted from 1 to 3 times with halo, $C_1$–$C_4$ alkanol, $NH_2$, or hydroxy;

optionally substituted $C_3$–$C_8$ cycloalkyl refers to a $C_3$–$C_8$ cycloalkyl unsubstituted or substituted once with a phenyl, substituted phenyl, hydroxy, or $CO_2R^1$ group;

optionally substituted ($C_1$–$C_4$ alkyl)-($C_3$–$C_8$ cycloalkyl) refers to optionally substituted $C_3$–$C_8$ cycloalkyl linked through an optionally substituted $C_1$–$C_4$ alkyl;

optionally substituted O—($C_3$–$C_8$ cycloalkyl) refers to an optionally substituted $C_3$–$C_8$ cycloalkyl linked through an oxygen atom;

optionally substituted $C_6$–$C_{10}$ bicycloalkyl refers to a $C_6$–$C_{10}$ bicycloalkyl unsubstituted or substituted once with a phenyl, substituted phenyl. or $CO_2R^1$ group;

optionally substituted aryl refers to a phenyl and naphthyl group, respectively, unsubstituted or substituted from 1 to 5 times independently with $C_1$–$C_6$ alkyl, halo, hydroxy, trifluoromethyl, phenyl, phenoxy, $SO_2R^1$, $OR^{11}$; $NR^4R^5$, $SO_2N(R^{13})_2$, NH-Pg, $C_1$–$C_6$ alkoxy, benzyloxy, $C(O)R^{13}$, $C_5$–$C_7$ cycloalkyl, trifluoromethoxy, $SR^1$, cyano, or nitro;

optionally substituted ($C_1$–$C_4$ alkyl)-aryl refers to optionally substituted aryl linked through an optionally substituted $C_1$–$C_4$ alkyl;

optionally substituted O-aryl refers to an optionally substituted aryl linked through an oxygen atom;

optionally substituted phenoxy refers to a phenoxy group unsubstituted or substituted from 1 to 3 times independently with $C_1$–$C_6$ alkyl, halo, hydroxy, trifluoromethyl, $NR^4R^6$, $SO_2N(R^{13})_2$, NH-Pg, $C_1$–$C_6$ alkoxy, benzyloxy, $C(O)R^{13}$, $C_5$–$C_7$ cycloalkyl, trifluoromethoxy, cyano, or nitro;

optionally substituted $C_1$–$C_4$ alkyl)-phenoxy refers to unsubstituted or substituted phenoxy linked through an optionally substituted $C_1$–$C_4$ alkyl;

heterocycle is taken to mean stable unsaturated and saturated 3 to 6 membered rings containing from 1 to 4 heteroatoms selected from the group consisting of nitrogen, oxygen and sulfur, said rings being optionally benzofused, All of these rings may be substituted with up to three substituents independently selected from the group consisting of halo, $C_1$–$C_4$ alkoxy, $C_1$–$C_4$ alkyl, cyano, nitro, hydroxy, —$S(O)_m$-($C_1C_4$ alkyl) and —$S(O)_m$-phenyl where m is 0, 1 or 2;

optionally substituted heterocycle refers to a heterocyclic ring unsubstituted or substituted 1 or 3 times independently with a $C_1$–$C_6$ alkyl, halo, benzyl, optionally substituted phenyl, $SR^1$, $C_1$–$C_4$ alkoxy, $CO_2R^1$, nitro, cyano, $C_1$–$C_4$ alkyl)-cyano, heterocycle. $NR^{19}R^{20}$, $COR^{12}$, $C_1$–$C_6$ alkanol, benzyloxy, phenoxy, trifluoromethyl, Heterocyclic rings may be additionally substituted 1 or 2 times with an oxo group;

optionally substituted O-heterocycle refers to an optionally substituted heterocycle linked through an oxygen atom;

optionally substituted ($C_1$–$C_4$ alkyl)-heterocycle refers to optionally substituted heterocycle linked through an optionally substituted $C_1$–$C_4$ alkyl;

N-heterocycle refers to a nitrogen containing heterocycle linked through a nitrogen atom; and optionally substituted N-heterocycle refers to a N-heterocycle, optionally substituted 1 or 3 times independently with a $C_1$–$C_6$ alkyl, halo, benzyl, optionally substituted phenyl, $SR^1$, $C_1$–$C_4$ alkoxy, $CO_2R^1$, nitro, cyano, ($C_1$–$C_4$ alkyl)-cyano, heterocycle, $NR^{19}R^{20}$, $COR^{12}$, $C_1$–$C_6$ alkanol, benzyloxy, phenoxy, trifluoromethyl; and additionally substituted 1 or 2 times with an oxo group.

2. The compound of claim 1 where the isoxazole is

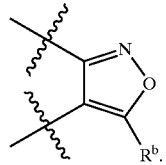

3. The compound of claim 1 where the isoxazole is

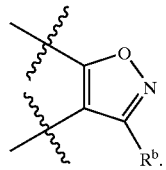

4. The compound of any one of claims 1–3 where A is 1,3-cyclohexyl.

5. The compound of claim 4 where n is 0.

6. The compound of claim 4 where p is 0 or 1.

7. The compound of claim 4 where Y is E—$NR^4R^5$.

8. The compound of claim 7 where $R^5$ is $COR^7$.

9. The compound of claim 8 where $R^7$ is optionally substituted heterocycle.

10. The compound of claim 8 where $R^7$ is optionally substituted CO-aryl.

11. The compound of claim 8 where $R^7$ is optionally substituted CO-heteroaryl.

12. The compound of claim 8 where $R^7$ is $(CH_2)_t C(R^{12})(R^9)N(R^{16})(R^{15})$.

13. The compound of claim 4 where $R^b$ is $C_1$–$C_6$ alkyl.

14. The compound of claim 13 where $R^b$ is methyl.

15. The compound of claim 4 where $R^{10}$ is halo.

16. The compound of claim 15 where $R^{10}$ is chloro.

17. The compound of claim 16 where $R^{10}$ is 9-chloro.

18. The compound of claim 1 selected from the group consisting of N-[(3S,1R)-3-(9-chloro-3-methyl-4-oxo-5H-isoxazolo[4,3-c]quinolin-5-yl))cyclohexyl]-2-piperidylacetamide, N-[(3S,1R)-3-(9-chloro-3-methyl-4-oxo-5H-isoxazolo[4,3-c]quinolin-5-yl))cyclohexyl]-2-(2-chloro(4-pyridyloxy))acetamide, N-{[(1S,3R)-3-(9-chloro-3-methyl-4-oxo-5H-isoxazolo[4,3-c]quinolin-5-yl))cyclohexyl]methyl }benzamide, N-[(3S,1R)-3-(9-chloro-3-methyl-4-oxo-5H-isoxazolo[4,3-c]quinolin-5-yl))cyclohexyl]-2-hydroxy-2-phenylacetamide, N-[(3S,1R)-3-(9-chloro-3-methyl-4-oxo-5H-isoxazolo[4,3-c]quinolin-s-yl))cyclohexyl-2(4-fluorophenyl)-2-hydroxyacetamide, N-{[(3S,1R)-3-(9-chloro-3-methyl-4-oxo-5H-isoxazolo[4,3-c]quinolin-5-yl))cyclohexyl]methyl}-3-pyridylcarboxamide, N-[(3S,1R)-3-(9-chloro-3-methyl-4-oxo-5H-isoxazolo[4,3-c]quinolin-5-yl))cyclohexyl]-2-(4-acetylpiperazinyl)-2-phenylacetamide, and N-[(1S,3R)-3-(9-chloro-3-methyl-4-oxo-5H-isoxazolo[4,3-c]quinolin-5-yl))cyclohexyl]-2-(4-acetylpiperazinyl)-2-phenylacetamide.

19. A method of inhibiting MRP1 in a mammal which comprises administering to a mammal in need thereof an amount effective to inhibit MRP1 of a compound of formula I, as defined in claim 1, or a pharmaceutical salt thereof.

20. The method according to claim 19 where the mammal is a human.

21. The method of claim 19 where het is

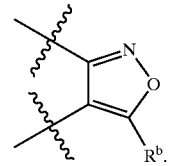

22. The method of claim 19 where het is

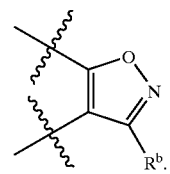

23. The method of any one of claims 19–22 where A is 1,3-cyclohexyl.

24. The method of claim 23 where n is 0.

25. The method of claim 23 where p is 0 or 1.

26. The method of claim 23 where Y is E—NR$^4$R$^5$.

27. The method of claim 26 where R$^5$ is COR$^7$.

28. The method of claim 27 where R$^7$ is optionally substituted heterocycle.

29. The method of claim 27 where R$^7$ is optionally substituted CO-aryl.

30. The method of claim 27 where R$^7$ is optionally substituted CO-heteroaryl.

31. The method of claim 27 where R$^7$ is (CH$_2$)$_t$C(R$^{12}$)(R$^9$)N(R$^{16}$)(R$^{15}$).

32. The method of claim 23 where R$^b$ is C$_1$–C$_6$ alkyl.

33. The method of claim 32 where R$^b$ is methyl.

34. The method of claim 23 where R$^{10}$ is halo.

35. The method of claim 34 where R$^{10}$ is chloro.

36. The method of claim 35 where R$^{10}$ is 9-chloro.

37. The method of claim 19 wherein the compound is selected from the group consisting of N-[(3S,1R)-3-(9-chloro-3-methyl-4-oxo-5H-isoxazolo[4,3-c]quinolin-5-yl))cyclohexyl]-2-piperidylacetamide, N-[(3S,1R)-3-(9-chloro-3-methyl-4-oxo-5H-isoxazolo[4,3-c]quinolin-5-yl))cyclohexyl]-2-(2-chloro(4-pyridyloxy))acetamide, N-{[(1S,3R)-3-(9-chloro-3-methyl-4-oxo-5H-isoxazolo[4,3-c]quinolin-5-yl))cyclohexyl]methyl}benzamide, N-[(3S,1R)-3-(9-chloro-3-methyl-4-oxo-5H-isoxazolo[4,3-c]quinolin-5-yl))cyclohexyl]-2-hydroxy-2-phenylacetamide, N-[(3S,1R)-3-(9-chloro-3-methyl-4-oxo-5H-isoxazolo[4,3-c]quinolin-5-yl))cyclohexyl]-2-(4-fluorophenyl)-2-hydroxyacetamide, N-{[(3S,1R)-3-(9-chloro-3-methyl-4-oxo-5H-isoxazolo[4,3-c]quinolin-5-yl))cyclohexyl]methyl}-3-pyridylcarboxamide, N-[(3S,1R)-3-(9-chloro-3-methyl-4-oxo-5H-isoxazolo[4,3-c]quinolin-5-yl))cyclohexyl]-2-(4-acetylpiperazinyl)-2-phenylacetamide, and N-[(1S,3R)-3-(9-chloro-3-methyl-4-oxo-5H-isoxazolo[4,3-c]quinolin-5-yl))cyclohexyl]-2-(4-acetylpiperazinyl)-2-phenylacetamide.

38. A pharmaceutical formulation comprising a compound of formula I, as defined in claim 1, or a pharmaceutical salt thereof; in combination with one or more pharmaceutical carriers, diluents, or excipients therefor.

39. A pharmaceutical composition for inhibiting MRP1 in a mammal which comprises an effective amount of a compound of formula I, as defined in claim 1, or a pharmaceutical salt thereof.

* * * * *